(12) United States Patent
Kubo et al.

(10) Patent No.: US 7,803,822 B2
(45) Date of Patent: Sep. 28, 2010

(54) TRIAZOLE DERIVATIVE AND USE THEREOF

(75) Inventors: Keiji Kubo, Osaka (JP); Mamoru Tobisu, Minoh (JP); Eiji Honda, Osaka (JP); Takahiko Taniguchi, Osaka (JP); Yoshiyuki Fukase, Osaka (JP); Masaki Kawamura, Osaka (JP); Masaharu Nakayama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 69 days.

(21) Appl. No.: 11/887,936

(22) PCT Filed: Apr. 6, 2006

(86) PCT No.: PCT/JP2006/307797

§ 371 (c)(1),
(2), (4) Date: Oct. 5, 2007

(87) PCT Pub. No.: WO2006/109846

PCT Pub. Date: Oct. 19, 2006

(65) Prior Publication Data

US 2009/0105253 A1  Apr. 23, 2009

(30) Foreign Application Priority Data

Apr. 6, 2005 (JP) .............................. 2005-110391

(51) Int. Cl.
  A61K 31/41 (2006.01)
  C07D 249/00 (2006.01)
(52) U.S. Cl. ....................................... 514/359; 548/255
(58) Field of Classification Search ................. 514/359; 548/255
See application file for complete search history.

(56) References Cited

U.S. PATENT DOCUMENTS

| | | | |
|---|---|---|---|
| 5,523,310 A * | 6/1996 | Maehr | 514/359 |
| 2002/0045581 A1 | 4/2002 | D'Andrea et al. | |
| 2002/0103138 A1 | 8/2002 | D'Andrea et al. | |
| 2004/0102492 A1* | 5/2004 | Cogan et al. | 514/359 |
| 2004/0242627 A1 | 12/2004 | Suzuki et al. | |
| 2004/0254376 A1 | 12/2004 | Suzuki et al. | |
| 2005/0004197 A1 | 1/2005 | Suzuki et al. | |
| 2005/0004204 A1 | 1/2005 | Suzuki et al. | |
| 2005/0153972 A1 | 7/2005 | Cogan et al. | |

FOREIGN PATENT DOCUMENTS

| | | |
|---|---|---|
| DE | 103 15 570 | 10/2004 |
| WO | 98/28269 | 7/1998 |
| WO | 99/32454 | 7/1999 |
| WO | 01/00576 | 1/2001 |
| WO | 01/00657 | 1/2001 |
| WO | 02/085850 | 10/2002 |
| WO | 02/085855 | 10/2002 |
| WO | 02/088092 | 11/2002 |
| WO | 02/088094 | 11/2002 |
| WO | 2004/050642 | 6/2004 |
| WO | 2005/056535 | 6/2005 |

OTHER PUBLICATIONS

International Search Report issued in the International (PCT) Application of which the present application is the U.S. National Stage.

* cited by examiner

*Primary Examiner*—Susannah Chung
(74) *Attorney, Agent, or Firm*—Wenderoth, Lind & Ponack, L.L.P.

(57) ABSTRACT

The present invention relates to a thrombin receptor antagonist containing a compound represented by the formula (I)

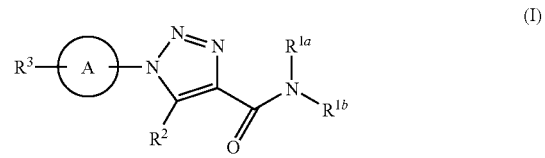

wherein $R^{1a}$, $R^{1b}$ and $R^2$ are each a hydrogen atom, an optionally substituted hydrocarbon group, an optionally substituted heterocyclic group, or an optionally substituted alkoxy, $R^3$ is a group represented by the formula —NHCOR$^4$, —NHSO$_2$R$^5$, —NHCON(R$^{6a}$)(R$^{6b}$), —NHCOOR$^7$ or —CONHR$^8$ wherein $R^4$, $R^5$, $R^{6a}$, $R^{6b}$, $R^7$ and $R^8$ are each a hydrogen atom, an optionally substituted hydrocarbon group, an optionally substituted heterocyclic group and the like), ring A is monocyclic aromatic ring optionally further having substituent(s), $R^{1a}$ and $R^{1b}$ are optionally bonded to each other to form an optionally substituted nitrogen-containing non-aromatic heterocycle, or a salt thereof or a prodrug thereof. The thrombin receptor antagonist of the present invention has a thrombin receptor (particularly PAR-1) antagonistic action and is useful for the prophylaxis or treatment of PAR-1 mediated pathological condition or disease.

10 Claims, No Drawings

TRIAZOLE DERIVATIVE AND USE THEREOF

This application is a U.S. national stage of International Application No. PCT/JP2006/307797 filed Apr. 6, 2006.

TECHNICAL FIELD

The present invention relates to a novel triazole derivative having a thrombin receptor antagonistic action and useful for the prophylaxis or treatment of thrombosis, vascular restenosis, cerebral infarction, heart disease, disseminated intravascular coagulation syndrome, neurologic disease and/or malignant tumor and the like and use thereof.

BACKGROUND ART

It has long been recognized that thrombin not only functions as a final protease of coagulation cascade, which catalyzes the decomposition of fibrinogen to produce fibrin, but is also a multifunctional molecule that acts on various cells including platelet. While involvement of a "thrombin receptor" in such cell response has been presumed, and biochemical investigations relating to receptor characteristics in the platelet have been continued, the substance of the molecule has remained unknown. In 1990, a report documented thrombin receptor expression and receptor signaling by injecting human umbilical vein endothelial mRNA into Rana catesbeiana oocyte, showing the similarity to vascular endothelial expression thrombin receptor that had been reported. In 1991, the following year, two groups simultaneously reported cDNA cloning of PAR-1 in human and hamster (Cell, 1991, Vol. 64, pp. 1057-1068; FEBS, 1991, Vol. 288, pp. 123-128). A homology search of cDNA clarified that these receptors belong to G protein-coupled receptor superfamily and the report by the former showed that a limited decomposition of R41-S42 peptide bond in the PAR-1 N-terminal extracellular domain was necessary for receptor activation. In addition, it was demonstrated that 5-6 amino acid residue peptide corresponding to a new receptor N-terminal sequence could be a PAR-1 activating agonist (thrombin receptor agonist: TRAP). From a research using the TRAP, a wide variety of physiological actions of PAR-1 such as platelet activation, vascular, bronchial and gastrointestinal smooth muscle contraction and the like have been confirmed (Journal of the Pharmaceutical Society of Japan, 2001, Vol. 121, pp. 1-7). As mentioned earlier, expression of PAR-1 has been confirmed in almost all organs of living organisms including platelet, vascular smooth muscle, gastrointestinal tract smooth muscle, vascular endothelium, monocyte, T cells, fibroblast, renal glomerular mesangial cell and the like, strongly suggesting its involvement in various pathologies. Therefore, a PAR-1 antagonist is considered to be useful as a drug for the prophylaxis or treatment of various diseases.

Heretofore, compounds having a PAR-1 antagonistic action have been disclosed, for example, in WO01/00576, WO01/00657, WO01/00659, WO02/68425, WO02/85850, WO02/88092, WO02/88094, U.S. Pat. No. 6,544,982, Bioorg. Med. Chem. Lett., 2001, Vol. 11, pp. 2691-2696, Bioorg. Med. Chem. Lett., 2001, Vol. 11, pp. 2851-2853 and the like.

Moreover, a triazole derivative having a particular structure is described to have, for example, an FXa inhibitory action in WO99/32454, a glycine transporter inhibitory action in DE10315570A1, and a cytokine inhibitory activity in WO2004/050642. However, the derivative is not described or suggested to have a thrombin receptor antagonistic action, and is different from the triazole derivative of the present invention in the structural characteristics.

DISCLOSURE OF THE INVENTION

As mentioned above, since activation of PAR-1 is involved in various physiological actions, and a compound having an antagonistic action thereto is expected to show a superior action and effect in the treatment or prophylaxis of a disease involving PAR-1, the provision of a PAR-1 antagonist having a pharmacological activity, particularly high affinity for PAR-1, which meets safety, oral absorbability and the like, has been demanded. However, conventional PAR-1 antagonists are not satisfactory in terms of receptor selectivity, oral absorbability and the like, and the development of a novel compound useful as a pharmaceutical agent has been desired.

The present inventors have conducted intensive studies predicated on the thought that a 1,2,3-triazole derivative having a particular structure has high affinity for a thrombin receptor (particularly PAR-1) and a strong antagonistic action thereon, can exhibit a sustained and sufficient effect by oral administration, and is useful as a pharmaceutical agent for the prophylaxis and/or treatment of a disease involving PAR-1 (for example, thrombosis, vascular restenosis, cerebral infarction, heart disease, disseminated intravascular coagulation syndrome, neurologic disease, malignant tumor and the like) and the like.

As a result, they have found that a 1,2,3-triazole derivative represented by the following formula (I) and a salt thereof have a strong thrombin receptor (particularly PAR-1) antagonistic action, high safety, and a sustained and sufficient effect by oral administration, which resulted in the completion of the present invention.

Accordingly, the present invention relates to (1) a thrombin receptor antagonist comprising a compound represented by the formula (I)

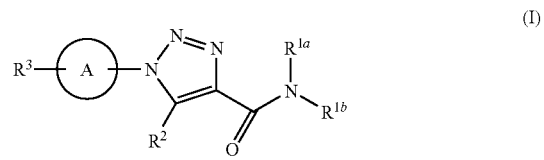

wherein $R^{1a}$ and $R^{1b}$ are each independently a hydrogen atom, an optionally substituted hydrocarbon group, an optionally substituted heterocyclic group, or an optionally substituted alkoxy, $R^2$ is a hydrogen atom, an optionally substituted hydrocarbon group, an optionally substituted heterocyclic group, or an optionally substituted alkoxy, $R^3$ is a group represented by the formula —NHCOR$^4$, —NHSO$_2$R$^5$, —NHCON(R$^{6a}$)(R$^{6b}$), —NHCOOR$^7$ or —CONHR$^8$ wherein $R^4$ and $R^7$ are each independently a hydrogen atom, an optionally substituted hydrocarbon group, or an optionally substituted heterocyclic group, $R^5$, $R^{6a}$, $R^{6b}$ and $R^8$ are each independently a hydrogen atom, an optionally substituted hydrocarbon group, an optionally substituted heterocyclic group, or an optionally substituted alkoxy, $R^{6a}$ and $R^{6b}$ are optionally bonded to each other to form an optionally substituted nitrogen-containing non-aromatic heterocycle, ring A is a monocyclic aromatic ring optionally further having substituent(s), $R^2$ and the substituent on ring A other than $R^3$ are optionally bonded to each other to form an optionally substituted ring, $R^8$ and the substituent on ring A are optionally bonded to each other to form an optionally substituted ring, $R^{1a}$ and $R^2$ are optionally bonded to each other to form an optionally substituted ring, $R^{1a}$ and $R^{1b}$ are optionally bonded to each other to form an optionally substituted nitrogen-containing non-aromatic heterocycle, or a salt thereof or a prodrug thereof;

(2) a compound represented by the formula (I')

wherein $R^{1a}$ and $R^{1b}$ are each independently a hydrogen atom, an optionally substituted hydrocarbon group, an optionally substituted heterocyclic group, or an optionally substituted alkoxy, $R^2$ is a hydrogen atom, an optionally substituted hydrocarbon group, an optionally substituted heterocyclic group, or an optionally substituted alkoxy, $R^3$ is a group represented by the formula —NHCOR$^4$, —NHSO$_2$R$^5$, —NHCON(R$^{6a}$)(R$^{6b}$), —NHCOOR$^7$ or —CONHR$^8$ wherein $R^4$ and $R^7$ are each independently a hydrogen atom, an optionally substituted hydrocarbon group, or an optionally substituted heterocyclic group, $R^5$, $R^{6a}$, $R^{6b}$ and $R^8$ are each independently a hydrogen atom, an optionally substituted hydrocarbon group, an optionally substituted heterocyclic group, or an optionally substituted alkoxy, $R^{6a}$ and $R^{6b}$ are optionally bonded to each other to form an optionally substituted nitrogen-containing non-aromatic heterocycle, ring A' is a benzene ring optionally further having substituent(s) or a 6-membered nitrogen-containing aromatic heterocycle optionally further having substituent(s), $R^2$ and the substituent on ring A' other than $R^3$ are optionally bonded to each other to form an optionally substituted ring, $R^8$ and the substituent on ring A' are optionally bonded to each other to form an optionally substituted ring, $R^{1a}$ and $R^2$ are optionally bonded to each other to form an optionally substituted ring, $R^{1a}$ and $R^{1b}$ are optionally bonded to each other to form an optionally substituted nitrogen-containing non-aromatic heterocycle, provided that when ring A' is a benzene ring optionally further having substituent(s), $R^4$ is not methyl, or a salt thereof;

(3) the compound of the aforementioned (2), wherein $R^{1a}$ is a hydrogen atom;

(4) the compound of the aforementioned (3), wherein $R^{1b}$ is a hydrogen atom, an optionally substituted alkyl, or an optionally substituted cycloalkyl;

(5) the compound of the aforementioned (2), wherein $R^2$ is an optionally substituted chain hydrocarbon group;

(6) the compound of the aforementioned (5), wherein the chain hydrocarbon group is alkyl or alkenyl;

(7) the compound of the aforementioned (2), wherein $R^3$ is a group represented by the formula —CONHR$^8$ wherein $R^8$ is as defined in the aforementioned (2);

(8) the compound of the aforementioned (7), wherein $R^8$ is an optionally substituted chain hydrocarbon group;

(9) the compound of the aforementioned (2), wherein ring A' is a benzene ring optionally further having substituent(s) or a pyridine ring optionally further having substituent(s);

(10) the compound of the aforementioned (2), which is a compound selected from the group consisting of N-cyclopropyl-1-{4-[(ethylamino)carbonyl]phenyl}-5-propyl-1H-1,2, 3-triazole-4-carboxamide (Example 43), N-cyclopropyl-5-propyl-1-(4-{[(2,2,2-trifluoroethyl)amino]carbonyl}phenyl)-1H-1,2,3-triazole-4-carboxamide (Example 46), N-cyclopropyl-1-{4-[(ethylamino)carbonyl]phenyl}-5-(4-fluorobutyl)-1H-1,2,3-triazole-4-carboxamide (Example 108), N-cyclopropyl-5-[(1E)-prop-1-en-1-yl]-1-(4-{[(2,2,2-trifluoroethyl)amino]carbonyl}phenyl)-1H-1,2,3-triazole-4-carboxamide (Example 399), and N-cyclopropyl-1-{4-[(ethylamino)carbonyl]phenyl}-5-[(3-fluorophenoxy)methyl]-1H-1,2,3-triazole-4-carboxamide (Example 414), or a salt thereof;

(11) a prodrug of the compound of the aforementioned (2);

(12) a pharmaceutical agent comprising the compound of the aforementioned (2) or a prodrug thereof;

(13) the pharmaceutical agent of the aforementioned (12), which is a thrombin receptor antagonist;

(14) the pharmaceutical agent of the aforementioned (13), wherein the thrombin receptor is PAR-1;

(15) the pharmaceutical agent of the aforementioned (14), which is an agent for the prophylaxis or treatment of a PAR-1 mediated pathological condition or disease;

(16) the pharmaceutical agent of the aforementioned (15), wherein the PAR-1 mediated pathological condition or disease is arterial and/or venous thrombosis;

(17) the pharmaceutical agent of the aforementioned (16), wherein the arterial and/or venous thrombosis is selected from the group consisting of cerebral infarction, ischemic cerebrovascular disorder, acute cerebral thrombosis, cerebrovascular contraction, transient ischemic attack (TIA), cerebrovascular dementia, asymptomatic/multiple cerebral infarction, lacunar infarction;

thrombus after an extracranial-intracranial artery bypass surgery;

acute coronary artery disease, myocardial infarction, ischemic coronary artery disease, unstable angina pectoris, cardiomyopathy, acute heart failure, congestive chronic heart failure, vascular reocclusion and restenosis after coronary artery intervention;

vascular reocclusion and restenosis after coronary artery bypass surgery;

chronic arterial occlusive disease, arteriosclerosis obliterans, peripheral circulatory failure; and thrombus after peripheral vascular bypass surgery or artificial blood vessel or vena cava filter indwelling;

(18) A production method of a compound represented by the formula (I')

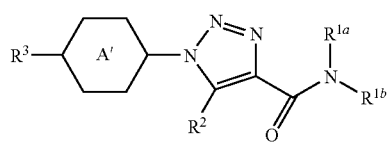

(I')

wherein $R^{1a}$ and $R^{1b}$ are each independently a hydrogen atom, an optionally substituted hydrocarbon group, an optionally substituted heterocyclic group, or an optionally substituted alkoxy, $R^2$ is a hydrogen atom, an optionally substituted hydrocarbon group, an optionally substituted heterocyclic group, or an optionally substituted alkoxy, $R^3$ is a group represented by the formula —NHCOR$^4$, —NHSO$_2$R$^5$, —NHCON(R$^{6a}$)(R$^{6b}$), —NHCOOR$^7$ or —CONHR$^8$ wherein $R^4$ and $R^7$ are each independently a hydrogen atom, an optionally substituted hydrocarbon group, or an optionally substituted heterocyclic group, $R^5$, $R^{6a}$, $R^{6b}$ and $R^8$ are each independently a hydrogen atom, an optionally substituted hydrocarbon group, an optionally substituted heterocyclic group, or an optionally substituted alkoxy, $R^{6a}$ and $R^{6b}$ are optionally bonded to each other to form an optionally substituted nitrogen-containing non-aromatic heterocycle, ring A' is a benzene ring optionally further having substituent(s) or a 6-membered nitrogen-containing aromatic heterocycle optionally further having substituent(s), $R^2$ and the substituent on ring A' other than $R^3$ are optionally bonded to each other to form an optionally substituted ring, $R^8$ and the substituent on ring A' are optionally bonded to each other to form an optionally substituted ring, $R^{1a}$ and $R^2$ are optionally bonded to each other to form an optionally substituted ring, $R^{1a}$ and $R^{1b}$ are optionally bonded to each other to form an optionally substituted nitrogen-containing non-aromatic heterocycle, provided that when ring A' is a benzene ring optionally further having substituent(s), $R^4$ is not methyl, or a salt thereof, which comprises (A) reacting a compound represented by the formula (II')

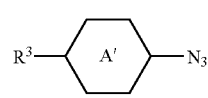

(II')

wherein $R^3$ and ring A' are as defined above, or a salt thereof, with a compound represented by the formula (III)

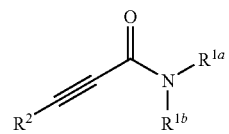

(III)

wherein $R^{1a}$, $R^{1b}$ and $R^2$ are as defined above, provided that $R^2$ and the substituent on ring A' other than $R^3$ are not bonded to each other to form an optionally substituted ring, and $R^{1a}$ and $R^2$ are not bonded to each other to form an optionally substituted ring, or a salt thereof, to give a compound represented by the formula (I') or a salt thereof, or (B) reacting a compound represented by the formula (II')

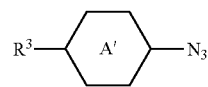

(II')

wherein $R^3$ and ring A' are as defined above, or a salt thereof, with a compound represented by the formula (IV)

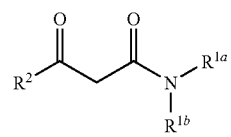

(IV)

wherein $R^{1a}$, $R^{1b}$ and $R^2$ are as defined above, provided that $R^2$ and the substituent on ring A' other than $R^3$ are not bonded to each other to form an optionally substituted ring, or a salt thereof, to give a compound represented by the formula (I') or a salt thereof, or (C) treating a compound represented by the formula (V')

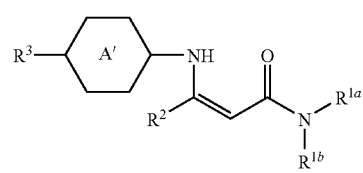

(V')

wherein $R^{1a}$, $R^{1b}$, $R^2$, $R^3$ and ring A' are as defined above, or a salt thereof, with a diazotizating reagent to give a compound represented by the formula (I') or a salt thereof;

(19) use of the compound of the aforementioned (2) or a prodrug thereof for the production of a thrombin receptor antagonist;

(20) use of the compound of the aforementioned (2) or a prodrug thereof for the production of an agent for the prophylaxis or treatment of a PAR-1 mediated pathological condition or disease;

(21) the use of the aforementioned (20), wherein the PAR-1 mediated pathological condition or disease is arterial and/or venous thrombosis;

(22) the use of the aforementioned (21), wherein the arterial and/or venous thrombosis is selected from the group consisting of cerebral infarction, ischemic cerebrovascular disorder, acute cerebral thrombosis, cerebrovascular contraction, transient ischemic attack (TIA), cerebrovascular dementia, asymptomatic/multiple cerebral infarction, lacunar infarction;

thrombus after an extracranial-intracranial artery bypass surgery;

acute coronary artery disease, myocardial infarction, ischemic coronary artery disease, unstable angina pectoris, cardiomyopathy, acute heart failure, congestive chronic heart failure, vascular reocclusion and restenosis after coronary artery intervention;

vascular reocclusion and restenosis after coronary artery bypass surgery;

chronic arterial occlusive disease, arteriosclerosis obliterans, peripheral circulatory failure; and thrombus after peripheral vascular bypass surgery or artificial blood vessel or vena cava filter indwelling;

(23) a method of antagonizing a thrombin receptor in a mammal, which comprises administering an effective amount of the compound of the aforementioned (2) or a prodrug thereof to the mammal;

(24) a method for the prophylaxis or treatment of a PAR-1 mediated pathological condition or disease in a mammal, which comprises administering an effective amount of the compound of the aforementioned (2) or a prodrug thereof to the mammal;

(25) the method of the aforementioned (24), wherein the PAR-1 mediated pathological condition or disease is arterial and/or venous thrombosis;

(26) the method of the aforementioned (25), wherein the arterial and/or venous thrombosis is selected from the group consisting of cerebral infarction, ischemic cerebrovascular disorder, acute cerebral thrombosis, cerebrovascular contraction, transient ischemic attack (TIA), cerebrovascular dementia, asymptomatic/multiple cerebral infarction, lacunar infarction;

thrombus after an extracranial-intracranial artery bypass surgery;

acute coronary artery disease, myocardial infarction, ischemic coronary artery disease, unstable angina pectoris, cardiomyopathy, acute heart failure, congestive chronic heart failure, vascular reocclusion and restenosis after coronary artery intervention;

vascular reocclusion and restenosis after coronary artery bypass surgery;

chronic arterial occlusive disease, arteriosclerosis obliterans, peripheral circulatory failure; and thrombus after peripheral vascular bypass surgery or artificial blood vessel or vena cava filter indwelling; and the like.

The thrombin receptor antagonist of the present invention is advantageously used for the prophylaxis or treatment of a thrombin receptor (particularly PAR-1) mediated pathological condition or disease, for example, thrombosis such as cerebral infarction, myocardial infarction, peripheral arterial occlusive disease and the like, vascular restenosis, disseminated intravascular coagulation syndrome, neurodegenerative disease, malignant tumor and the like. Particularly, it is promising as an antithrombotic agent because, different from an anticoagulant, it can suppress activation of platelet by thrombin without directly influencing the blood coagulation system. In addition, since the thrombin receptor antagonist can inhibit a thrombin receptor expressed in various tissues, it can also be used advantageously for the prophylaxis or treatment of a thrombin receptor mediated pathological condition or disease other than thrombosis without directly influencing the blood coagulation system.

DETAILED DESCRIPTION OF THE INVENTION

In the aforementioned formulas, $R^{1a}$ and $R^{1b}$ are each independently a hydrogen atom, an optionally substituted hydrocarbon group, an optionally substituted heterocyclic group, or an optionally substituted alkoxy.

Examples of the "hydrocarbon group" in the "optionally substituted hydrocarbon group" for $R^{1a}$ or $R^{1b}$ include alkyl, alkenyl, alkynyl, aromatic hydrocarbon group, cycloalkyl, cycloalkenyl, aralkyl, cycloalkylalkyl, arylalkenyl, cycloalkyl condensed with benzene ring, bridged cyclic hydrocarbon group and the like.

Examples of the "alkyl" include $C_{1-6}$ alkyl such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 2-ethylpropyl, etc., and the like.

Examples of the "alkenyl" include $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., and the like.

Examples of the "alkynyl" include $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., and the like.

Examples of the "aromatic hydrocarbon group" include monocyclic or condensed polycyclic aromatic hydrocarbon group, such as $C_{6-14}$ aromatic hydrocarbon group (e.g., phenyl, naphthyl, anthryl, phenanthryl, acenaphthylenyl, etc.) and the like.

Examples of the "cycloalkyl" include $C_{3-7}$ cycloalkyl such as cyclopropyl, cyclobutyl, cyclopentyl, cyclohexyl, cycloheptyl, etc., and the like.

Examples of the "cycloalkenyl" include $C_{3-7}$ cycloalkenyl such as cyclopropenyl, cyclobutenyl, cyclopentenyl, cyclohexenyl, cycloheptenyl, etc., and the like.

Examples of the "aralkyl" include $C_{7-16}$ aralkyl such as phenyl-$C_{1-6}$ alkyl (e.g., benzyl, phenethyl, 3-phenylpropyl, 4-phenylbutyl, 5-phenylpentyl, etc.), naphthyl-$C_{1-6}$ alkyl (e.g., (1-naphthyl)methyl, (2-naphthyl)methyl, 2-(1-naphthyl)ethyl, 2-(2-naphthyl)ethyl, etc.) and the like, and the like.

Examples of the "cycloalkylalkyl" include $C_{3-7}$ cycloalkyl-$C_{1-6}$ alkyl such as cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, etc., and the like.

Examples of the "arylalkenyl" include $C_{6-14}$ aryl-$C_{2-6}$ alkenyl such as phenyl-$C_{2-6}$ alkenyl (e.g., 2-phenylvinyl, 3-phenyl-1-propenyl, 3-phenyl-2-propenyl, etc.), naphthyl-$C_{2-6}$ alkenyl (e.g., 2-(1-naphthyl)vinyl, 2-(2-naphthyl)vinyl, 3-(1-naphthyl)-1-propenyl, 3-(1-naphthyl)-2-propenyl, 3-(2-naphthyl)-1-propenyl, 3-(2-naphthyl)-2-propenyl, etc.) and the like, and the like.

Examples of the "cycloalkyl condensed with benzene ring" include $C_{5-7}$ cycloalkyl condensed with benzene ring such as indanyl, 1,2,3,4-tetrahydronaphthyl, etc., and the like.

Examples of the "bridged cyclic hydrocarbon group" include $C_{7-10}$ bridged cyclic hydrocarbon group such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantly, etc., and the like, As the substituent that the "hydrocarbon group" optionally has, for example, (i) nitro, (ii) hydroxy, oxo, (iii) cyano, (iv) carbamoyl, (v) mono- or di-$C_{1-4}$ alkyl-carbamoyl (e.g., N-methylcarbamoyl, N-ethylcarbamoyl, N,N-dimethylcarbamoyl, N,N-diethylcarbamoyl and the like; the alkyl is optionally substituted by halogen atom, hydroxy, $C_{1-4}$ alkoxy or the like), mono- or di-$C_{2-4}$ alkenyl-carbamoyl (e.g., N-allylcarbamoyl and the like; the alkenyl is optionally substituted by halogen atom, hydroxy, $C_{1-4}$ alkoxy or the like), mono- or di-$C_{3-7}$ cycloalkyl-carbamoyl, mono- or di-phenyl-carbamoyl, mono- or di-(phenyl-$C_{1-4}$ alkyl)-carbamoyl (e.g., benzylcarbamoyl, phenethylcarbamoyl; the phenyl is optionally substituted by halogen atom, hydroxy, $C_{1-4}$ alkoxy or the like), $C_{1-4}$ alkoxy-carbonyl-carbamoyl, $C_{1-4}$ alkylsulfonyl-carbamoyl, $C_{1-4}$ alkoxy-carbamoyl, amino-carbamoyl, mono- or di-$C_{1-4}$ alkylamino-carbamoyl, mono- or di-phenylamino-carbamoyl, (vi) carboxyl, (vii) $C_{1-4}$ alkoxy-carbonyl (e.g., methoxycarbonyl, ethoxycarbonyl, propoxycarbonyl, isopropoxycarbonyl and the like), (viii) sulfo, (ix) a halogen atom (e.g., fluorine, chlorine, bromine, iodine), (x) optionally halogenated $C_{1-6}$ alkoxy (preferably optionally halogenated $C_{1-4}$ alkoxy, for example, methoxy, ethoxy, propoxy, isopropoxy and the like), $C_{1-6}$ alkoxy optionally substituted by hydroxy, $C_{1-6}$ alkoxy optionally substituted by carboxyl, $C_{1-6}$ alkoxy optionally substituted by $C_{1-4}$ alkoxy-carbonyl, $C_{1-4}$ alkoxy-$C_{1-6}$ alkoxy, $C_{1-4}$ alkoxy-$C_{1-6}$ alkoxy-$C_{1-4}$ alkoxy, $C_{3-7}$ cycloalkyloxy-$C_{1-6}$ alkoxy, $C_{2-6}$ alkenyloxy, $C_{2-6}$ alkynyloxy, (xi) phenoxy, phenoxy-$C_{1-4}$ alkyl, optionally halogenated phenoxy-$C_{1-4}$ alkoxy, $C_{1-4}$ alkyl-carbonyl-oxy (the alkyl is optionally substituted by 1 to 3 substituents selected from carboxyl, mono- or di-$C_{1-4}$ alkylamino and the like), $C_{1-4}$ alkoxy-carbonyl-oxy, carbamoyloxy, mono- or di-$C_{1-4}$ alkyl-carbamoyloxy, phenyl-carbamoyloxy (the phenyl is optionally substituted by 1 to 3 substituents selected from halogen atom, hydroxy, $C_{1-4}$ alkoxy and the like), phenyl-$C_{1-4}$ alkyl-carbamoyloxy (the phenyl is optionally substituted by 1 to 3 substituents selected from halogen atom, hydroxy, $C_{1-4}$ alkoxy and the like), (xii) phenyl optionally substituted by 1 to 5 substituents selected from halogen atom, hydroxy, $C_{1-4}$ alkoxy and the like, optionally halogenated phenyl-$C_{1-4}$ alkyl, optionally halogenated phenyl-$C_{2-4}$ alkenyl, optionally halogenated phenyl-$C_{1-4}$ alkoxy, optionally halogenated phenyl-$C_{1-4}$ alkyl-$C_{1-4}$ alkoxy, pyridyloxy (the pyridyloxy is optionally substituted by 1 to 3 substituents selected from halogen atom and $C_{1-4}$ alkyl; for example, 2-, 3- or 4-chloropyridyloxy, 2-, 3- or 4-methylpyridyloxy and the like), benzothiazolyloxy, $C_{3-10}$ cycloalkyl, $C_{3-10}$ cycloalkyl-$C_{1-4}$ alkoxy, $C_{3-10}$ cycloalkyl-$C_{1-4}$ alkyl, 1-oxo-2,3-dihydro-1H-indenyloxy, (xiii) phenoxy optionally substituted by 1 to 3 substituents selected from the following (e.g., o-, m- or p-chlorophenoxy, o-, m- or p-bromophenoxy and the like)

(a) halogen atom;

(b) cyano;

(c) $C_{1-4}$ alkyl optionally substituted by 1 to 3 substituents selected from halogen atom, cyano, $C_{1-4}$ alkoxy-carbonyl, $C_{1-6}$ alkanoyl, hydroxyimino and mono- or di-$C_{1-4}$ alkylamino;

(d) $C_{2-6}$ alkynyl;

(e) optionally halogenated $C_{1-4}$ alkoxy;

(f) carbamoyl;

(g) —C(=S)NH$_2$;

(h) $C_{1-4}$ alkoxy-carbonyl;

(i) phenoxy;

(j) optionally halogenated phenyl;

(k) $C_{1-4}$ alkylthio;

(l) $C_{1-6}$ alkanoylamino;

(m) phenylamino;

(n) $C_{1-6}$ alkanoyl optionally substituted by $C_{1-4}$ alkoxycarbonyl;

(o) a 5- to 10-membered heterocyclic group (preferably 5- or 6-membered monocyclic heterocyclic group containing 1 to 4 heteroatoms of one or two kinds selected from oxygen atom, sulfur atom and nitrogen atom, such as imidazolyl, morpholinyl, pyrazolyl, imidazolidinyl and the like) optionally substituted by 1 to 3 substituents selected from halogen atom, $C_{1-4}$ alkyl, $C_{1-4}$ alkoxy and oxo; and (p) optionally halogenated straight chain or branched $C_{1-4}$ alkylenedioxy (e.g., methylenedioxy), (xiv) optionally halogenated $C_{1-4}$ alkyl (e.g., methyl, ethyl, propyl, isopropyl, butyl and the like), optionally halogenated $C_{2-6}$ alkenyl (e.g., vinyl, allyl, 2-butenyl, 3-butenyl and the like), optionally halogenated $C_{2-6}$ alkynyl (e.g., ethynyl, 1-propynyl, 2-propynyl, 1-butynyl, 2-butynyl, 3-butynyl and the like), optionally halogenated $C_{1-4}$ alkylthio (e.g., methylthio, ethylthio, n-propylthio, isopropylthio, n-butylthio and the like), $C_{1-4}$ alkyl optionally substituted by hydroxy, $C_{1-4}$ alkylthio optionally substituted by hydroxy, $C_{1-4}$ alkoxy-$C_{1-4}$ alkyl, (xv) mercapto, thioxo, (xvi) benzyloxy or benzylthio each optionally substituted by 1 to 3 substituents selected from halogen atom, optionally halogenated $C_{1-4}$ alkyl, $C_{1-4}$ alkoxy, carboxyl, $C_{1-4}$ alkoxycarbonyl, a 5- to 10-membered heterocyclic group (e.g., imidazolyl and the like) and 4- to 7-membered cyclic amino (e.g., morpholino and the like), (xvii) optionally halogenated phenylthio, pyridylthio, phenylthio-$C_{1-4}$ alkyl, pyridylthio-$C_{1-4}$ alkyl, (xviii) optionally halogenated $C_{1-4}$ alkylsulfinyl (e.g., methylsulfinyl, ethylsulfinyl and the like), phenylsulfinyl, phenylsulfinyl-$C_{1-4}$ alkyl, (xix) optionally halogenated $C_{1-4}$ alkylsulfonyl (e.g., methylsulfonyl, ethylsulfonyl and the like), phenylsulfonyl, phenylsulfonyl-$C_{1-4}$ alkyl, (xx) amino, aminosulfonyl, mono- or di-$C_{1-4}$ alkylaminosulfonyl (e.g., methylaminosulfonyl, ethylaminosulfonyl, N,N-dimethylaminosulfonyl, N,N-diethylaminosulfonyl and the like; the alkyl is optionally substituted by 1 to 3 substituents selected from halogen atom, hydroxy, $C_{1-4}$ alkoxy and the like), (xxi) $C_{1-10}$ acyl-amino (e.g., $C_{1-6}$ alkanoylamino (e.g., formylamino, acetylamino, trifluoroacetylamino, propionylamino, pivaloylamino and the like), benzoylamino, $C_{1-6}$ alkylsulfonylamino (e.g., methanesulfonylamino, trifluoromethanesulfonylamino and the like), $C_{6-10}$ arylsulfonylamino (e.g., benzenesulfonylamino, toluenesulfonylamino and the like);

the $C_{1-10}$ acyl is optionally substituted by 1 to 3 substituents selected from halogen atom, hydroxy, carboxyl and the like), benzyloxycarbonylamino, optionally halogenated $C_{1-6}$ alkoxy-carbonylamino, carbamoylamino, mono- or di-$C_{1-4}$ alkyl-carbamoylamino (the alkyl is optionally substituted by 1 to 3 substituents selected from halogen atom, hydroxy, $C_{1-4}$ alkoxy and the like), phenyl-carbamoylamino (the phenyl is optionally substituted by 1 to 3 substituents selected from halogen atom, hydroxy, $C_{1-4}$ alkoxy and the like), phenyl-$C_{1-4}$ alkyl-carbamoylamino (the phenyl is optionally substituted by 1 to 3 substituents selected from halogen atom, hydroxy, $C_{1-4}$ alkoxy and the like), (xxii) mono- or di-$C_{1-4}$ alkylamino (e.g., methylamino, ethylamino, dimethylamino, diethylamino and the like; the alkyl is optionally substituted by 1 to 3 substituents selected from halogen atom, hydroxy, $C_{1-4}$ alkoxy and the like), phenylamino, phenyl-$C_{1-4}$ alkyl-amino (e.g., benzylamino, phenethylamino, 3-phenylpropylamino; the phenyl is optionally substituted by 1 to 3 substituents selected from halogen atom, hydroxy, $C_{1-4}$ alkoxy and the like), N—$C_{1-4}$ alkyl-N-(phenyl-$C_{1-4}$ alkyl)amino, (xxiii) 4- to 7-membered cyclic amino (e.g., 1-azetidinyl, 1-pyrrolidinyl, piperidino, morpholino, thiomorpholino, 1-piperazinyl, 3-thiazolidinyl, 1-imidazolidinyl, 1-perhydroazepinyl and the like; the 4- to 7-membered cyclic amino is optionally substituted by 1 to 5 substituents selected from $C_{1-4}$ alkyl, oxo and the like), 4- to 7-membered cyclic amino-carbonyl (e.g., 1-azetidinylcarbonyl, 1-pyrrolidinylcarbonyl, piperidinocarbonyl, morpholinocarbonyl, thiomorpholinocarbonyl, 1-piperazinylcarbonyl and the like), 4- to 7-membered cyclic amino-carbonyl-oxy (e.g., 1-pyrrolidinylcarbonyloxy, piperidinocarbonyloxy, morpholinocarbonyloxy, thiomorpholinocarbonyloxy, 1-piperazinylcarbonyloxy and the like), 4- to 7-membered cyclic amino-carbonyl-amino (e.g., 1-pyrrolidinylcarbonylamino, piperidinocarbonylamino, morpholinocarbonylamino, thiomorpholinocarbonylamino, 1-piperazinylcarbonylamino and the like), 4- to 7-membered cyclic amino-sulfonyl (e.g., 1-pyrrolidinylsulfonyl, piperidinosulfonyl, morpholinosulfonyl, thiomorpholinosulfonyl, 1-piperazinylsulfonyl and the like), 4- to 7-membered cyclic amino-$C_{1-4}$ alkyl, (xxiv) $C_{1-6}$ acyl (e.g., optionally halogenated $C_{1-6}$ alkanoyl such as formyl, acetyl, etc., and the like) or benzoyl each optionally substituted by 1 to 3 substituents selected from halogen atom, carboxyl and $C_{1-4}$ alkoxy-carbonyl, (xxv) benzoyl optionally substituted by halogen atom, (xxvi) 5- to 10-membered heterocyclic group (e.g., 2- or 3-thienyl, 2- or 3-furyl, 1-, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 2-, 3- or 4-pyridyl, 2-, 4- or 5-pyrimidinyl, 3- or 4-pyridazinyl, 2-pyrazinyl, quinolyl, isoquinolyl, indolyl, tetrahydrofuran-2-yl, tetrahydrofuran-3-yl, pyrrolyl, imidazolyl, benzo[b]thienyl, benzothiazolyl, benzimidazolyl, 1H-benzotriazolyl, imidazo[1,2-a]pyridyl, 4,5-dihydro-1,2,4-oxadiazolyl, 1,3-dihydroisoindolyl, pyrazolo[4,3-d]pyrimidinyl, 1,3-benzoxathiolyl, 1,2,3,4-tetrahydroquinolyl, 2H-chromenyl, tetrahydropyran-4-ylidene and the like; the heterocyclic group is optionally substituted by 1 to 5 (preferably 1 to 3) substituents selected from $C_{1-4}$ alkyl optionally substituted by 1 to 3 substituents selected from halogen atom and hydroxy; halogen atom; nitro; $C_{1-4}$ alkoxy; $C_{1-4}$ alkylthio; $C_{1-4}$ alkoxy-carbonyl; mono- or di-$C_{1-4}$ alkylamino; benzyloxy; optionally halogenated phenyl; 5- to 10-membered heterocyclic group (e.g., thienyl and the like); 5- to 10-membered heterocyclyl-$C_{1-4}$ alkyl (e.g., tetrahydropyran-4-ylmethyl and the like); trityl; oxo and the like), (xxvii) 5- to 10-membered heterocyclyl-carbonyl (e.g., 2- or 3-thienylcarbonyl, 2- or 3-furylcarbonyl, 1-, 3-, 4- or 5-pyrazolylcarbonyl, 2-, 4- or 5-thiazolylcarbonyl, 3-, 4- or 5-isothiazolylcarbonyl, 2-, 4- or 5-oxazolylcarbonyl, 1,2,3- or 1,2,4-triazolylcarbonyl, 1H- or 2H-tetrazolylcarbonyl, 2-, 3- or 4-pyridylcarbonyl, 2-, 4- or 5-pyrimidinylcarbonyl, 3- or 4-pyridazinylcarbonyl, 2-pyrazinylcarbonyl, quinolylcarbonyl, isoquinolylcarbonyl, indolylcarbonyl, tetrahydrofuran-2-ylcarbonyl, tetrahydrofuran-3-ylcarbonyl, pyrrolylcarbonyl, imidazolylcarbonyl, benzo[b]thienylcarbonyl, benzothiazolylcarbonyl, benzimidazolylcarbonyl, 1H-benzotriazolylcarbonyl, imidazo[1,2-a]pyridylcarbonyl, 4,5-dihydro-1,2,4-oxadiazolylcarbonyl, 1,3-dihydroisoindolylcarbonyl, pyrazolo[4,3-d]pyrimidinylcarbonyl, 1,3-benzoxathiolylcarbonyl, 1,2,3,4-tetrahydroquinolylcarbonyl, 2H-chromenylcarbonyl and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxviii) 5- to 10-membered heterocyclyl-oxy (e.g., 2- or 3-thienyloxy, 2- or 3-furyloxy, 1-, 3-, 4- or 5-pyrazolyloxy, 2-, 4- or 5-thiazolyloxy, 3-, 4- or 5-isothiazolyloxy, 2-, 4- or 5-oxazolyloxy, 1,2,3- or 1,2,4-triazolyloxy, 1H- or 2H-tetrazolyloxy, 2-, 3- or 4-pyridyloxy, 2-, 4- or 5-pyrimidinyloxy, 3- or 4-pyridazinyloxy, 2-pyrazinyloxy, quinolyloxy, isoquinolyloxy, indolyloxy, tetrahydrofuran-2-yloxy, tetrahydrofuran-3-yloxy, pyrrolyloxy, imidazolyloxy, benzo[b]thienyloxy, benzothiazolyloxy, benzimidazolyloxy, 1H-benzotriazolyloxy, imidazo[1,2-a]pyridyloxy, 4,5-dihydro-1,2,4-oxadiazolyloxy, 1,3-dihydroisoindolyloxy, pyrazolo[4,3-d]pyrimidinyloxy, 1,3-benzoxathiolyloxy, 1,2,3,4-tetrahydroquinolyloxy, 2H-chromenyloxy and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxix) 5- to 10-membered heterocyclyl-amino (e.g., 2- or 3-thienylamino, 2- or 3-furylamino, 1-, 3-, 4- or 5-pyrazolylamino, 2-, 4- or 5-thiazolylamino, 3-, 4- or 5-isothiazolylamino, 2-, 4- or 5-oxazolylamino, 1,2,3- or 1,2,4-triazolylamino, 1H- or 2H-tetrazolylamino, 2-, 3- or 4-pyridylamino, 2-, 4- or 5-pyrimidinylamino, 3- or 4-pyridazinylamino, 2-pyrazinylamino, quinolylamino, isoquinolylamino, indolylamino, tetrahydrofuran-2-ylamino, tetrahydrofuran-3-ylamino, pyrrolylamino, imidazolylamino, benzo[b]thienylamino, benzothiazolylamino, benzimidazolylamino, 1H-benzotriazolylamino, imidazo[1,2-a]pyridylamino, 4,5-dihydro-1,2,4-oxadiazolylamino, 1,3-dihydroisoindolylamino, pyrazolo[4,3-d]pyrimidinylamino, 1,3-benzoxathiolylamino, 1,2,3,4-tetrahydroquinolylamino, 2H-chromenylamino and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxx) 5- to 10-membered heterocyclyl-carbonylamino (e.g., 2- or 3-thienylcarbonylamino, 2- or 3-furylcarbonylamino, 1-, 3-, 4- or 5-pyrazolylcarbonylamino, 2-, 4- or 5-thiazolylcarbonylamino, 3-, 4- or 5-isothiazolylcarbonylamino, 2-, 4- or 5-oxazolylcarbonylamino, 1,2,3- or 1,2,4-triazolylcarbonylamino, 1H- or 2H-tetrazolylcarbonylamino, 2-, 3- or 4-pyridylcarbonylamino, 2-, 4- or 5-pyrimidinylcarbonylamino, 3- or 4-pyridazinylcarbonylamino, 2-pyrazinylcarbonylamino, quinolylcarbonylamino, isoquinolylcarbonylamino, indolylcarbonylamino, tetrahydrofuran-2-ylcarbonylamino, tetrahydrofuran-3-ylcarbonylamino, pyrrolylcarbonylamino, imidazolylcarbonylamino, benzo[b]thienylcarbonylamino, benzothiazolylcarbonylamino, benzimidazolylcarbonylamino, 1H-benzotriazolylcarbonylamino, imidazo[1,2-a]pyridylcarbonylamino, 4,5-dihydro-1,2,4-oxadiazolylcarbonylamino, 1,3-dihydroisoindolylcarbonylamino, pyrazolo[4,3-d]pyrimidinylcarbonylamino, 1,3-benzoxathiolylcarbonylamino, 1,2,3,4-tetrahydroquinolylcarbonylamino, 2H-chromenylcarbonylamino and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxxi) 5- or 10-membered heterocyclyl-$C_{1-4}$ alkyl-amino (e.g., 2- or 3-thienylmethylamino, 2- or 3-furylmethylamino, 1-, 3-, 4- or 5-pyrazolylmethylamino, 2-, 4- or 5-thiazolylmethylamino, 3-, 4- or 5-isothiazolylmethylamino, 2-, 4- or 5-oxazolylmethylamino, 1,2,3- or 1,2,4-triazolylmethylamino, 1H- or 2H-tetrazolylmethylamino, 2-, 3- or 4-pyridylmethylamino, 2-, 4- or 5-pyrimidinylmethylamino, 3- or 4-pyridazinylmethylamino, 2-pyrazinylmethylamino, quinolylmethylamino, isoquinolylmethylamino, indolylmethylamino, tetrahydrofuran-2-ylmethylamino, tetrahydrofuran-3-ylmethylamino, pyrrolylmethylamino, imidazolylmethylamino, benzo[b]thienylmethylamino, benzothiazolylmethylamino, benzimidazolylmethylamino, 1H-benzotriazolylmethylamino, imidazo[1,2-a]pyridylmethylamino, 4,5-dihydro-1,2,4-oxadiazolylmethylamino, 1,3-dihydroisoindolylmethylamino, pyrazolo[4,3-d]pyrimidinylmethylamino, 1,3-benzoxathiolylmethylamino, 1,2,3,4-tetrahydroquinolylmethylamino, 2H-chromenylmethylamino and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxxii) 5- to 10-membered heterocyclyl-$C_{1-4}$ alkyl-thio (e.g., 2- or 3-thienylmethylthio, 2- or 3-furylmethylthio, 1-, 3-, 4- or 5-pyrazolylmethylthio, 2-, 4- or 5-thiazolylmethylthio, 3-, 4- or 5-isothiazolylmethylthio, 2-, 4- or 5-oxazolylmethylthio, 1,2,3- or 1,2,4-triazolylmethylthio, 1H- or 2H-tetrazolylmethylthio, 2-, 3- or 4-pyridylmethylthio, 2-, 4- or 5-pyrimidinylmethylthio, 3- or 4-pyridazinylmethylthio, 2-pyrazinylmethylthio, quinolylmethylthio, isoquinolylmethylthio, indolylmethylthio, tetrahydrofuran-2-ylmethylthio, tetrahydrofuran-3-ylmethylthio, pyrrolylmethylthio, imidazolylmethylthio, benzo[b]thienylmethylthio, benzothiazolylmethylthio, benzimidazolylmethylthio, 1H-benzotriazolylmethylthio, imidazo[1,2-a]pyridylmethylthio, 4,5-dihydro-1,2,4-oxadiazolylmethylthio, 1,3-dihydroisoindolylmethylthio, pyrazolo[4,3-d]pyrimidinylmethylthio, 1,3-benzoxathiolylmethylthio, 1,2,3,4-tetrahydroquinolylmethylthio, 2H-chromenylmethylthio and the like; the heterocyclyl is optionally substituted by 1 to 5 (preferably 1 to 3) substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl, oxo and the like), (xxxiii) $C_{3-7}$ cycloalkylidene (e.g., cyclobutylidene, cyclopentylidene, cyclohexylidene), (xxxiv) hydroxyimino, $C_{1-4}$ alkoxyimino, $C_{6-14}$ aryl (e.g., 1- or 2-naphthyl and the like), (xxxv) optionally halogenated straight chain or branched $C_{1-4}$ alkylenedioxy (e.g., methylenedioxy, ethylenedioxy, propylenedioxy, tetrafluoroethylenedioxy and the like), (xxxvi) azido and the like can be used.

Examples of the "5- to 10-membered heterocyclic group" include a 5- to 10-membered heterocyclic group containing 1 to 4 heteroatoms of one or two kinds selected from oxygen atom, sulfur atom and nitrogen atom and the like.

Examples of the "5- to 10-membered heterocyclyl" include 5- to 10-membered heterocyclyl containing 1 to 4 heteroatoms of one or two kinds selected from oxygen atom, sulfur atom and nitrogen atom and the like.

The "hydrocarbon group" optionally has 1 to 5 (preferably, 1 to 3) of these substituents at substitutable position(s), and when 2 or more substituents are present, the substituents may be the same or different.

Examples of the "heterocyclic group" of the "optionally substituted heterocyclic group" for $R^{1a}$ or $R^{1b}$ include aromatic heterocyclic group, saturated or unsaturated non-aromatic heterocyclic group (aliphatic heterocyclic group) and the like containing, as a ring-constituting atom (ring atom), at least one (preferably 1 to 4, more preferably 1 or 2) heteroatoms of one to three kinds (preferably one or two kinds) selected from oxygen atom, sulfur atom and nitrogen atom and the like.

Examples of the "aromatic heterocyclic group" include 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and 8- to 16-membered (preferably, 8- to 12-membered) aromatic fused heterocyclic group such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like. Preferred are the aforementioned 5- or 6-membered aromatic monocyclic heterocyclic groups, and particularly preferred are pyridyl, pyrimidinyl, thienyl, thiazolyl and the like.

Examples of the "non-aromatic heterocyclic group" include a heterocyclic group wherein 3- to 8-membered (preferably 5- or 6-membered) saturated or unsaturated (preferably saturated) non-aromatic monocyclic heterocyclic group (aliphatic monocyclic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, perhydroazepinyl, oxazolidinyl, isoxazolidinyl, thiazolidinyl, isothiazolidinyl and the like; a heterocyclic group wherein the aforementioned 1 or 2 (preferably 1) non-aromatic monocyclic heterocyclic groups are condensed with 1 or 2 (preferably 1) benzene ring such as 1,3-dihydroisoindolyl and the like; a heterocyclic group wherein the aforementioned 1 or 2 (preferably 1) non-aromatic monocyclic heterocyclic groups are condensed with 1 or 2 (preferably 1) heterocycles of the aforementioned 5- or 6-membered aromatic monocyclic heterocyclic group; or non-aromatic heterocyclic group wherein a part of or all of the double bonds of the aforementioned aromatic monocyclic heterocyclic group or aromatic fused heterocyclic group is saturated, such as 1,2,3,4-tetrahydroquinolyl, 1,2,3,4-tetrahydroisoquinolyl, 1,3-dihydroisobenzofuranyl and the like; and the like.

As the substituent that the "heterocyclic group" of the "optionally substituted heterocyclic group" optionally has, groups similar to the substituents that the aforementioned hydrocarbon group of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

Examples of the "alkoxy" of the "optionally substituted alkoxy" for $R^{1a}$ or $R^{1b}$ include $C_{1-6}$ alkoxy such as methoxy, ethoxy, propoxy, isopropoxy, butoxy, isobutoxy, sec-butoxy, tert-butoxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy, 2-ethylpropyloxy and the like.

As the substituent that the "alkoxy" optionally has, groups similar to the substituents that the hydrocarbon group of the "optionally substituted hydrocarbon group" for $R^{1a}$ or $R^{1b}$ optionally has (preferably, halogen atom, hydroxy, oxo, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, optionally halogenated phenyl and the like) can be mentioned, and 1 to 5 (preferably 1 to 3) of these optional substituents may be present at substitutable position(s).

In the aforementioned formulas, $R^{1a}$ and $R^{1b}$ are optionally bonded to each other to form an optionally substituted nitrogen-containing non-aromatic heterocycle.

As the "nitrogen-containing non-aromatic heterocycle" of the "optionally substituted nitrogen-containing non-aromatic heterocycle" optionally formed by $R^{1a}$ and $R^{1b}$ bonded to each other, for example, 3- to 8-membered (preferably 4- to 6-membered) saturated or unsaturated (preferably saturated) nitrogen-containing non-aromatic monocyclic heterocycle (nitrogen-containing aliphatic monocyclic heterocycle) such as aziridine, azetidine, pyrrolidine, piperidine, morpholine, thiomorpholine, perhydroazepine, piperazine, oxazolidine, thiazolidine and the like, and the like can be mentioned. The nitrogen-containing non-aromatic heterocycle may be nitrogen-containing non-aromatic fused heterocycle (e.g., 1,3,4,9-tetrahydro-2H-β-carboline) wherein the aforementioned nitrogen-containing non-aromatic monocyclic heterocycle is condensed with other ring such as benzene ring, pyridine ring, indole ring and the like.

As the substituent that the "nitrogen-containing non-aromatic heterocycle" optionally has, groups similar to the substituents that the hydrocarbon group of the "optionally substituted hydrocarbon group" for $R^{1a}$ or $R^{1b}$ optionally has (preferably, halogen atom, hydroxy, oxo, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, phenyl (the phenyl is optionally substituted by 1 to 5 substituents selected from halogen atom, hydroxy, $C_{1-4}$ alkoxy and the like), $C_{1-4}$ alkyl optionally substituted by hydroxy, $C_{1-4}$ alkoxy-$C_{1-4}$ alkyl, optionally halogenated $C_{1-4}$ alkylsulfonyl, 4- to 7-membered cyclic amino (e.g., piperidino), 5- to 10-membered heterocyclyl-carbonylamino (e.g., 2- or 3-thienylcarbonylamino; the heterocyclyl is optionally substituted by 1 to 3 substituents selected from halogen atom, $C_{1-4}$ alkyl, $C_{1-4}$ alkoxy and the like) and the like) and the like can be mentioned, and 1 to 5 (preferably 1 to 3) of these optional substituents may be present at substitutable position(s).

As the "hydrocarbon group" of the "optionally substituted hydrocarbon group" for $R^{1a}$ or $R^{1b}$, $C_{1-6}$ alkyl, $C_{2-6}$ alkenyl, $C_{2-6}$ alkynyl, $C_{6-14}$ aromatic hydrocarbon group, $C_{3-7}$ cycloalkyl, $C_{3-7}$ cycloalkenyl, $C_{7-16}$ aralkyl, $C_{3-7}$ cycloalkyl-$C_{1-6}$ alkyl, $C_{5-7}$ cycloalkyl condensed with benzene ring or $C_{7-10}$ bridged cyclic hydrocarbon group is preferable.

Preferable examples of the substituent that the "$C_{1-6}$ alkyl", "$C_{2-6}$ alkenyl" and "$C_{2-6}$ alkynyl" optionally have include 1 to 5 (preferably 1 to 3) substituents selected from (1) halogen atom, (2) hydroxy, (3) $C_{1-6}$ alkoxy optionally substituted by 1 to 3 substituents selected from halogen atom and hydroxy, (4) carbamoyl, (5) mono- or di-$C_{3-7}$ cycloalkyl-carbamoyl, (6) mono- or di-benzyl-carbamoyl (the benzyl is optionally substituted by 1 to 3 substituents selected from halogen atom, hydroxy and $C_{1-4}$ alkoxy), (7) carboxyl, (8) $C_{1-4}$ alkoxy-carbonyl, (9) phenoxy optionally substituted by 1 to 3 halogen atoms,

(10) $C_{1-4}$ alkyl-carbonyl-oxy (the alkyl is optionally substituted by 1 to 3 substituents selected from carboxyl and mono- or di-$C_{1-4}$ alkylamino),

(11) $C_{1-4}$ alkoxy-carbonyl-oxy,

(12) phenyl-carbamoyloxy (the phenyl is optionally substituted by 1 to 3 substituents selected from halogen atom, hydroxy and $C_{1-4}$ alkoxy),

(13) phenyl-$C_{1-4}$ alkyl-carbamoyloxy (the phenyl is optionally substituted by 1 to 3 substituents selected from halogen atom, hydroxy and $C_{1-4}$ alkoxy),

(14) optionally halogenated $C_{1-4}$ alkylthio,

(15) benzyloxy or benzylthio each optionally substituted by 1 to 3 halogen atoms,

(16) optionally halogenated $C_{1-4}$ alkylsulfonyl,

(17) amino,

(18) $C_{1-6}$ alkanoylamino,

(19) optionally halogenated $C_{1-4}$ alkylsulfonylamino,

(20) benzyloxycarbonylamino,

(21) optionally halogenated $C_{1-6}$ alkoxy-carbonylamino,

(22) carbamoylamino,

(23) mono- or di-$C_{1-4}$ alkyl-carbamoylamino (the alkyl is optionally substituted by 1 to 3 substituents selected from halogen atom, hydroxy and $C_{1-4}$ alkoxy),

(24) phenyl-carbamoylamino (the phenyl is optionally substituted by 1 to 3 substituents selected from halogen atom, hydroxy and $C_{1-4}$ alkoxy),

(25) phenyl-$C_i$ alkyl-carbamoylamino (the phenyl is optionally substituted by 1 to 3 substituents selected from halogen atom, hydroxy and $C_{1-4}$ alkoxy),

(26) mono- or di-$C_{1-4}$ alkylamino,

(27) phenylamino,

(28) 4- to 7-membered cyclic amino (e.g., 1-pyrrolidinyl, piperidino, morpholino, thiomorpholino, 1-piperazinyl, 3-thiazolidinyl, 1-imidazolidinyl, 1-perhydroazepinyl and the like; the 4- to 7-membered cyclic amino is optionally substituted by 1 to 5 substituents selected from $C_{1-4}$ alkyl and oxo),

(29) 5- to 10-membered heterocyclic group (e.g., pyridyl, pyrazinyl, indolyl, tetrahydrofuryl, thienyl, pyrazolyl, thiazolyl, pyrrolyl, 1,2,3-triazolyl, 1,2,4-triazolyl, imidazolyl, benzo[b]thienyl, benzimidazolyl, 1H-benzotriazolyl, imidazo[1,2-a]pyridyl and the like; the heterocyclic group is optionally substituted by 1 to 3 substituents selected from halogen atom; $C_{1-4}$ alkyl optionally substituted by hydroxy; $C_{1-4}$ alkoxy; benzyloxy; optionally halogenated phenyl; 5- to 10-membered heterocyclic group (e.g., thienyl); 5- to 10-membered heterocyclyl-$C_{1-4}$ alkyl (e.g., tetrahydropyran-4-ylmethyl); oxo and the like),

(30) 5- to 10-membered heterocyclyl-oxy (e.g., pyridyloxy, thienyloxy and the like; the heterocyclyl is optionally substituted by 1 to 3 substituents selected from halogen atom, $C_{1-4}$ alkyl, $C_{1-4}$ alkoxy and the like),

(31) 5- to 10-membered heterocyclyl-amino (e.g., pyridylamino, thienylamino and the like; the heterocyclyl is optionally substituted by 1 to 3 substituents selected from halogen atom, $C_{1-4}$ alkyl, $C_{1-4}$ alkoxy and the like),

(32) 5- to 10-membered heterocyclyl-carbonylamino (e.g., pyridylcarbonylamino, thienylcarbonylamino and the like; the heterocyclyl is optionally substituted by 1 to 3 substituents selected from halogen atom, $C_{1-4}$ alkyl, $C_{1-4}$ alkoxy and the like),

(33) 5- to 10-membered heterocyclyl-$C_{1-4}$ alkyl-thio (e.g., pyridylmethylthio, thienylmethylthio, imidazo[1,2-a]pyridylmethylthio and the like; the heterocyclyl is optionally substituted by 1 to 3 substituents selected from halogen atom, $C_{1-4}$ alkyl, $C_{1-4}$ alkoxy, etc.) and the like.

Preferable examples of the substituent that the "$C_{6-14}$ aromatic hydrocarbon group", "$C_{3-7}$ cycloalkyl", "$C_{3-7}$ cycloalkenyl", "$C_{7-16}$ aralkyl", "$C_{3-7}$ cycloalkyl-$C_{1-6}$ alkyl", "$C_{5-7}$ cycloalkyl condensed with benzene ring" and "$C_{7-10}$ bridged cyclic hydrocarbon group" optionally have include 1 to 5 (preferably 1 to 3) substituents selected from the substituents (1)-(33) exemplified as the substituents that the aforementioned "$C_{1-6}$ alkyl", "$C_{2-6}$ alkenyl" and "$C_{2-6}$ alkynyl" optionally have,

(34) optionally halogenated phenyl,

(35) optionally halogenated $C_{1-4}$ alkyl,

(36) optionally halogenated $C_{2-6}$ alkenyl,

(37) optionally halogenated $C_{2-6}$ alkynyl,

(38) optionally halogenated straight chain or branched $C_{1-4}$ alkylenedioxy (e.g., methylenedioxy and the like), and the like.

As the "optionally substituted hydrocarbon group" for $R^{1a}$ or $R^{1b}$, $C_{1-6}$ alkyl, $C_{2-6}$ alkenyl, $C_{3-7}$ cycloalkyl, $C_{3-7}$ cycloalkenyl, $C_{7-16}$ aralkyl or $C_{5-7}$ cycloalkyl condensed with benzene ring (the $C_{1-6}$ alkyl, $C_{2-6}$ alkenyl, $C_{3-7}$ cycloalkyl, $C_{3-7}$ cycloalkenyl, $C_{7-16}$ aralkyl and $C_{5-7}$ cycloalkyl condensed with benzene ring are each optionally substituted by 1 to 3 substituents selected from halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, 5- to 10-membered heterocyclic group (e.g., pyridyl, pyrazinyl, indolyl, tetrahydrofuryl and the like; the heterocyclic group is optionally substituted by 1 to 3 substituents selected from $C_{1-4}$ alkyl, $C_{1-4}$ alkoxy and the like), optionally halogenated straight chain or branched $C_{1-4}$ alkylenedioxy and the like) is preferable, and $C_{1-6}$ alkyl, $C_{3-7}$ cycloalkyl, phenyl-$C_{1-6}$ alkyl or $C_{5-7}$ cycloalkyl condensed with benzene ring (the $C_{1-6}$ alkyl, $C_{3-7}$ cycloalkyl, phenyl-$C_{1-6}$ alkyl and $C_{5-7}$ cycloalkyl condensed with benzene ring are each optionally substituted by 1 to 3 substituents selected from halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, 5- to 10-membered heterocyclic group (e.g., pyridyl, pyrazinyl, indolyl, tetrahydrofuryl and the like; the heterocyclic group is optionally substituted by 1 to 3 substituents selected from $C_{1-4}$ alkyl, $C_{1-4}$ alkoxy and the like), optionally halogenated straight chain or branched $C_{1-4}$ alkylenedioxy) is more preferable.

As the "heterocyclic group" of the "optionally substituted heterocyclic group" for $R^{1a}$ or $R^{1b}$, 5- or 6-membered aromatic monocyclic heterocyclic group containing 1 to 4 heteroatoms of one or two kinds selected from oxygen atom, sulfur atom and nitrogen atom (e.g., isoxazolyl, pyridyl);

3- to 8-membered saturated or unsaturated non-aromatic monocyclic heterocyclic group containing 1 to 4 heteroatoms of one or two kinds selected from oxygen atom, sulfur atom and nitrogen atom (e.g., pyrrolidinyl, tetrahydrofuryl, thiolanyl, piperidyl, tetrahydropyranyl, perhydroazepinyl, isoxazolidinyl);

8- to 12-membered aromatic fused heterocyclic group containing 1 to 4 heteroatoms of one or two kinds selected from oxygen atom, sulfur atom and nitrogen atom, or non-aromatic fused heterocyclic group wherein a part of or all of the double bonds of the aforementioned aromatic fused heterocyclic group is saturated (e.g., 1,3-dihydroisobenzofuranyl) and the like are preferable.

Preferable examples of the substituent that the "heterocyclic group" optionally has include 1 to 5 (preferably 1 to 3) substituents selected from $C_{1-4}$ alkyl, phenyl-$C_{1-4}$ alkyl, phenoxy optionally substituted by 1 to 3 halogen atoms, oxo and the like.

As the "nitrogen-containing non-aromatic heterocycle" of the "optionally substituted nitrogen-containing non-aromatic heterocycle" optionally formed by $R^{1a}$ and $R^{1b}$ bonded to each other, 1,3,4,9-tetrahydro-2H-β-carboline, pyrrolidine, piperidine, piperazine, thiazolidine and the like are preferable.

Preferable examples of the substituents that the "nitrogen-containing non-aromatic heterocycle" optionally has include 1 to 5 (preferably 1 to 3) substituents selected from hydroxy, oxo, carbamoyl, phenyl (the phenyl is optionally substituted by 1 to 5 substituents selected from halogen atom, hydroxy, $C_{1-4}$ alkoxy and the like), $C_{1-4}$ alkyl optionally substituted by hydroxy, $C_{1-4}$ alkoxy-$C_{1-4}$ alkyl, optionally halogenated $C_{1-4}$ alkylsulfonyl, 4- to 7-membered cyclic amino (e.g., piperidino), 5- to 10-membered heterocyclyl-carbonylamino (e.g., 2- or 3-thienylcarbonylamino; the heterocyclyl is optionally substituted by 1 to 3 substituents selected from halogen atom, $C_{1-4}$ alkyl, $C_{1-4}$ alkoxy, etc.) and the like.

As the "alkoxy" of the "optionally substituted alkoxy" for $R^{1a}$ or $R^{1b}$, $C_{1-6}$ alkoxy is preferable.

Preferable examples of the substituent that the "alkoxy" optionally has include optionally halogenated phenyl (e.g., phenyl, fluorophenyl, chlorophenyl, bromophenyl, pentafluorophenyl, etc.) and the like.

As the $R^{1a}$, a hydrogen atom and $C_{1-6}$ alkyl are preferable, and a hydrogen atom is more preferable.

As the $R^{1b}$, optionally substituted cycloalkyl is preferable, $C_{3-7}$ cycloalkyl (the $C_{3-7}$ cycloalkyl is optionally substituted by 1 to 3 substituents selected from halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino and the like) is particularly preferable, and cyclopropyl is especially preferable.

In the aforementioned formulas, $R^2$ is a hydrogen atom, an optionally substituted hydrocarbon group, an optionally substituted heterocyclic group, or an optionally substituted alkoxy.

As the "hydrocarbon group" of the "optionally substituted hydrocarbon group" for $R^2$, a group similar to the "hydrocarbon group" of the "optionally substituted hydrocarbon group" for $R^{1a}$ or $R^{1b}$ and the like can be mentioned.

As the substituent that the "hydrocarbon group" optionally has, groups similar to the substituents that the "hydrocarbon group" of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

As the "heterocyclic group" of the "optionally substituted heterocyclic group" for $R^2$, groups similar to the "heterocyclic group" of the "optionally substituted heterocyclic group" for $R^{1a}$ or $R^{1b}$ and the like can be mentioned.

As the substituent that the "heterocyclic group" optionally has, groups similar to the substituents that the "hydrocarbon group" of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

As the "alkoxy" of the "optionally substituted alkoxy" for $R^2$, groups similar to the "alkoxy" of the "optionally substituted alkoxy" for $R^{1a}$ or $R^{1b}$ and the like can be mentioned.

As the substituent that the "alkoxy" optionally has, groups similar to the substituents that the "hydrocarbon group" of the "optionally substituted hydrocarbon group" for $R^{1a}$ or $R^{1b}$ optionally has (preferably halogen atom, hydroxy, oxo, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, optionally halogenated phenyl and the like) can be mentioned, and 1 to 5 (preferably 1 to 3) of these optional substituents may be present at substitutable position(s).

As the $R^2$, a hydrogen atom, "optionally substituted chain hydrocarbon group", aromatic hydrocarbon group, aralkyl, cycloalkylalkyl or arylalkenyl is preferable, a hydrogen atom or "optionally substituted chain hydrocarbon group" is more preferable, and "optionally substituted chain hydrocarbon group" is particularly preferable. Examples of the "chain hydrocarbon group" of the "optionally substituted chain hydrocarbon group" include alkyl, alkenyl, alkynyl and the like.

As the "alkyl", groups similar to the "alkyl" exemplified as the "hydrocarbon group" of the "optionally substituted hydrocarbon group" for $R^{1a}$ or $R^{1b}$ and the like can be used, and $C_{1-6}$ alkyl is preferable.

As the "alkenyl", groups similar to the "alkenyl" exemplified as the "hydrocarbon group" of the "optionally substituted hydrocarbon group" for $R^{1a}$ or $R^{1b}$ and the like can be used, and $C_{2-6}$ alkenyl is preferable.

As the "alkynyl", groups similar to the "alkynyl" exemplified as the "hydrocarbon group" of the "optionally substituted hydrocarbon group" for $R^{1a}$ or $R^{1b}$ and the like can be used, and $C_{2-6}$ alkynyl is preferable.

As the "aromatic hydrocarbon group", groups similar to the "aromatic hydrocarbon group" exemplified as the "hydrocarbon group" of the "optionally substituted hydrocarbon group" for $R^{1a}$ or $R^{1b}$ and the like can be used, and phenyl is preferable.

As the "aralkyl", groups similar to the "aralkyl" exemplified as the "hydrocarbon group" of the "optionally substituted hydrocarbon group" for $R^{1a}$ or $R^{1b}$ and the like can be used, and phenyl-$C_{1-6}$ alkyl is preferable.

As the "cycloalkylalkyl", groups similar to the "cycloalkylalkyl" exemplified as the "hydrocarbon group" of the "optionally substituted hydrocarbon group" for $R^{1a}$ or $R^{1b}$ and the like can be used, and $C_{3-7}$ cycloalkyl-$C_{1-6}$ alkyl is preferable.

As the "arylalkenyl", groups similar to the "arylalkenyl" exemplified as the "hydrocarbon group" of the "optionally substituted hydrocarbon group" for $R^{1a}$ or $R^{1b}$ and the like can be used, and phenyl-$C_{2-6}$ alkenyl is preferable.

Preferable examples of the substituent that the "chain hydrocarbon group", "aromatic hydrocarbon group", "aralkyl", "cycloalkylalkyl" and "arylalkenyl" optionally have include 1 to 5 (preferably 1 to 3) substituents selected from (1) halogen atom, (2) hydroxy, (3) cyano, (4) optionally halogenated $C_{1-4}$ alkoxy, (5) benzyloxy optionally substituted by 1 to 3 halogen atoms, (6) carbamoyl, (7) carboxyl, (8) $C_{1-4}$ alkoxy-carbonyl, (9) $C_{1-4}$ alkyl-carbonyl-oxy,

(10) mono- or di-$C_{1-4}$ alkyl-carbamoyloxy,

(11) phenyl-carbamoyloxy (the phenyl is optionally substituted by 1 to 3 substituents selected from halogen atom, hydroxy and $C_{1-4}$ alkoxy),

(12) 1-oxo-2,3-dihydro-1H-indenyloxy,

(13) phenoxy optionally substituted by 1 to 3 substituents selected from
  (a) halogen atom;
  (b) cyano;
  (c) $C_{1-4}$ alkyl optionally substituted by 1 to 3 substituents selected from halogen atom, cyano, $C_{1-4}$ alkoxy-carbonyl, $C_{1-6}$ alkanoyl, hydroxyimino and mono- or di-$C_{1-4}$ alkylamino;
  (d) $C_{2-6}$ alkynyl;
  (e) optionally halogenated $C_{1-4}$ alkoxy;
  (f) carbamoyl;
  (g) —C(=S)NH$_2$;
  (h) $C_{1-4}$ alkoxy-carbonyl;
  (i) phenoxy;
  (j) optionally halogenated phenyl;
  (k) $C_{1-4}$ alkylthio;
  (l) $C_{1-6}$ alkanoylamino;
  (m) phenylamino;
  (n) $C_{1-6}$ alkanoyl optionally substituted by $C_{1-4}$ alkoxy-carbonyl;
  (o) a 5- to 10-membered heterocyclic group (e.g., imidazolyl, morpholinyl, pyrazolyl, imidazolidinyl and the like) optionally substituted by 1 to 3 substituents selected from halogen atom, $C_{1-4}$ alkyl, $C_{1-4}$ alkoxy and oxo; and
  (p) optionally halogenated straight chain or branched $C_{1-4}$ alkylenedioxy (e.g., methylenedioxy),

(14) optionally halogenated $C_{1-4}$ alkylthio,

(15) optionally halogenated phenylthio,

(16) phenylsulfinyl,

(17) optionally halogenated $C_{1-4}$ alkylsulfonyl,

(18) phenylsulfonyl,

(19) amino,

(20) carbamoylamino,

(21) mono- or di-$C_{1-4}$ alkyl-carbamoylamino (the alkyl is optionally substituted by 1 to 3 substituents selected from halogen atom, hydroxy, $C_{1-4}$ alkoxy and the like),

(22) mono- or di-$C_{1-4}$ alkylamino,

(23) phenylamino,

(24) phenyl-$C_{1-4}$ alkyl-amino (e.g., benzylamino, phenethylamino, 3-phenylpropylamino; the phenyl is optionally substituted by 1 to 3 substituents selected from halogen atom, hydroxy, $C_{1-4}$ alkoxy and the like),

(25) N—$C_{1-4}$ alkyl-N-(phenyl-$C_{1-4}$ alkyl)amino,

(26) 4- to 7-membered cyclic amino (e.g., 1-pyrrolidinyl, morpholino and the like),

(27) 5- to 10-membered heterocyclic group (e.g., oxazolyl, thiazolyl, imidazolyl, pyrazolyl, 1,2,4-triazolyl, tetrazolyl, pyridyl, pyrimidinyl, indolyl, benzothiazolyl, quinolyl, pyrazolo[4,3-d]pyrimidinyl, 4,5-dihydro-1,2,4-oxadiazolyl, 1,3-dihydroisoindolyl, 1,3-benzoxathiolyl, 1,2,3,4-tetrahydroquinolyl, 2H-chromenyl, tetrahydro-4H-pyran-4-ylidene; the heterocyclic group is optionally substituted by 1 to 3 substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl and oxo)

(28) 5- to 10-membered heterocyclyl-oxy (e.g., oxazolyloxy, thiazolyloxy, imidazolyloxy, pyrazolyloxy, 1,2,4-triazolyloxy, tetrazolyloxy, pyridyloxy, pyrimidinyloxy, indolyloxy, benzothiazolyloxy, quinolyloxy, pyrazolo[4,3-d]pyrimidinyloxy, 4,5-dihydro-1,2,4-oxadiazolyloxy, 1,3-dihydroisoindolyloxy, 1,3-benzoxathiolyloxy, 1,2,3,4-tetrahydroquinolyloxy, 2H-chromenyloxy; the heterocyclyl is optionally substituted by 1 to 3 substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl and oxo)

(29) 5- to 10-membered heterocyclyl-$C_{1-4}$ alkylamino (e.g., oxazolylmethylamino, thiazolylmethylamino, imidazolylmethylamino, pyrazolylmethylamino, 1,2,4-triazolylmethylamino, tetrazolylmethylamino, pyridylmethylamino, pyrimidinylmethylamino, indolylmethylamino, benzothiazolylmethylamino, quinolylmethylamino; the heterocyclyl is optionally substituted by 1 to 3 substituents selected from halogen atom, nitro, optionally halogenated $C_{1-4}$ alkyl, $C_{1-4}$ alkoxy, $C_{1-4}$ alkylthio, $C_{1-4}$ alkoxy-carbonyl, mono- or di-$C_{1-4}$ alkylamino, trityl and oxo)

(30) $C_{3-7}$ cycloalkylidene (e.g., cyclobutylidene, cyclopentylidene, cyclohexylidene),

(31) hydroxyimino and the like.

As the "chain hydrocarbon group", alkyl or alkenyl is preferable, and $C_{1-6}$ alkyl or $C_{2-6}$ alkenyl is more preferable.

As the substituent that the "chain hydrocarbon group" optionally has, groups similar to the substituents that the hydrocarbon group of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

As the substituent that the "chain hydrocarbon group" optionally has, 1 to 3 substituents selected from halogen atom; hydroxy; optionally halogenated $C_{1-4}$ alkoxy; benzyloxy optionally substituted by 1 to 3 halogen atoms; carbamoyl; carboxyl; $C_{1-4}$ alkoxy-carbonyl; amino; mono- or di-$C_{1-4}$ alkylamino; phenoxy optionally substituted by 1 to 3 substituents selected from halogen atom, optionally halogenated $C_{1-4}$ alkyl, $C_{1-4}$ alkoxy, imidazolyl and morpholinyl; pyridyloxy optionally substituted by 1 to 3 substituents selected from halogen atom and $C_{1-4}$ alkyl; benzothiazolyloxy; 1-oxo-2,3-dihydro-1H-indenyloxy; optionally halogenated $C_{1-4}$ alkylthio; optionally halogenated phenylthio; benzylamino; and 4- to 6-membered cyclic amino (e.g., 1-pyrrolidinyl, morpholino and the like) are preferable.

As the "heterocyclic group" of the "optionally substituted heterocyclic group" for $R^2$, a 5- or 6-membered aromatic monocyclic heterocyclic group containing 1 to 4 heteroatoms of one or two kinds selected from oxygen atom, sulfur atom and nitrogen atom (e.g., thienyl, thiazolyl) is preferable.

Preferable examples of the substituent that the "heterocyclic group" optionally has include 1 to 5 (preferably 1 to 3) substituents selected from halogen atom, $C_{1-4}$ alkyl and the like.

As the "alkoxy" of the "optionally substituted alkoxy" for $R^2$, $C_{1-6}$ alkoxy is preferable.

Preferable examples of the substituent that the "alkoxy" optionally has include optionally halogenated phenyl (e.g., phenyl, fluorophenyl, chlorophenyl, bromophenyl, pentafluorophenyl and the like) and the like.

As the $R^2$, hydrogen atom, $C_{1-6}$ alkyl or $C_{2-6}$ alkenyl (the $C_{1-6}$ alkyl and the $C_{2-6}$ alkenyl are each optionally substituted by halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, optionally halogenated phenoxy and the like) is preferable, and a hydrogen atom, optionally halogenated $C_{1-6}$ alkyl or $C_{2-6}$ alkenyl is particularly preferable.

In the aforementioned formulas, $R^3$ is a group represented by the formula —NHCOR$^4$, —NHSO$_2$R$^5$, —NHCON(R$^{6a}$)(R$^{6b}$), —NHCOOR$^7$ or —CONHR$^8$, wherein $R^4$ and $R^7$ are each independently a hydrogen atom, an optionally substituted hydrocarbon group, or an optionally substituted heterocyclic group, and $R^5$, $R^{6a}$, $R^{6b}$ and $R^8$ are each a hydrogen atom, an optionally substituted hydrocarbon group, an optionally substituted heterocyclic group, or an optionally substituted alkoxy.

As the "hydrocarbon group" of the "optionally substituted hydrocarbon group" for $R^4$, $R^5$, $R^{6a}$, $R^{6b}$, $R^7$ or $R^8$, a group similar to the "hydrocarbon group" of the "optionally substituted hydrocarbon group" for $R^{1a}$ or $R^{1b}$ and the like can be mentioned.

As the substituent that the "hydrocarbon group" optionally has, groups similar to the substituents that the "hydrocarbon group" of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

As the "heterocyclic group" of the "optionally substituted heterocyclic group" for $R^4$, $R^5$, $R^{6a}$, $R^{6b}$, $R^7$ or $R^8$, a group similar to the "heterocyclic group" of the "optionally substituted heterocyclic group" for $R^{1a}$ or $R^{1b}$ and the like can be mentioned.

As the substituent that the "heterocyclic group" optionally has, groups similar to the substituents that the "heterocyclic group" of the "optionally substituted heterocyclic group" for $R^{1a}$ or $R^{1b}$ optionally has and the like can be mentioned, and 1 to 5 (preferably 1 to 3) of these optional substituents may be present at substitutable position(s).

As the "alkoxy" of the "optionally substituted alkoxy" for $R^5$, $R^{6a}$, $R^{6b}$ or $R^8$, for example, $C_{1-6}$ alkoxy such as methoxy, ethoxy, propoxy, isopropoxy, butoxy, isobutoxy, sec-butoxy, tert-butoxy, pentyloxy, isopentyloxy, neopentyloxy, etc., and the like can be used. Of these, $C_{1-3}$ alkoxy such as methoxy, ethoxy, propoxy and isopropoxy is preferable.

As the substituent that the "alkoxy" optionally has, groups similar to the substituents that the "hydrocarbon group" of the "optionally substituted hydrocarbon group" for $R^{1a}$ or $R^{1b}$ optionally has and the like can be mentioned, and 1 to 5

(preferably 1 to 3) of these optional substituents may be present at substitutable position(s).

In the aforementioned formulas, $R^8$ and the substituent on ring A (or ring A') are optionally bonded to each other to form an optionally substituted ring. As the ring formed by $R^8$ and the substituent on ring A (or ring A') bonded to each other, 5- to 8-membered (preferably 5- or 6-membered) heterocycle which contains one nitrogen atom, and further may contain 1 or 2 heteroatoms selected from nitrogen atom, sulfur atom and oxygen atom can be mentioned.

In the formula (I), as the ring formed by $R^9$ and the substituent on ring A bonded to each other, for example,

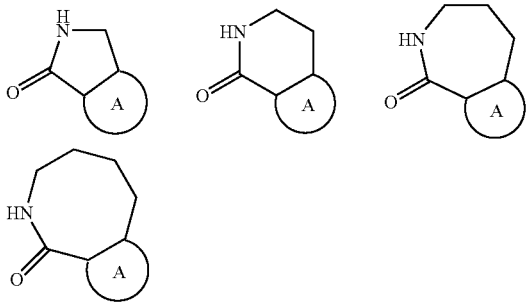

and the like can be mentioned.

In the formula (I'), as the ring formed by $R^8$ and the substituent on ring A' bonded to each other, for example,

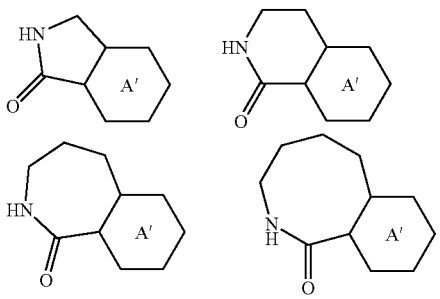

and the like can be mentioned.

As the substituent that the ring formed by $R^8$ and the substituent on ring A (or ring A') bonded to each other optionally has, a group similar to the substituent that the "hydrocarbon group" of the "optionally substituted hydrocarbon group" for $R^{1a}$ or $R^{1b}$ optionally has (preferably, halogen atom, hydroxy, oxo, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino and the like) can be mentioned, and 1 to 5 (preferably 1 to 3) of these optional substituents may be present at substitutable position(s).

In the aforementioned formulas, $R^{6a}$ and $R^{6b}$ are optionally bonded to each other to form an optionally substituted nitrogen-containing non-aromatic heterocycle.

As the "nitrogen-containing non-aromatic heterocycle" of the "optionally substituted nitrogen-containing non-aromatic heterocycle" that can be formed by $R^{6a}$ and $R^{6b}$ bonded to each other, a ring similar to the "nitrogen-containing non-aromatic heterocycle" of the "optionally substituted nitrogen-containing non-aromatic heterocycle" that can be formed by $R^{1a}$ and $R^{1b}$ bonded to each other and the like can be used.

As the substituent that the "nitrogen-containing non-aromatic heterocycle" optionally has, groups similar to the substituents that the "hydrocarbon group" of the "optionally substituted hydrocarbon group" for $R^{1a}$ or $R^{1b}$ optionally has (preferably, halogen atom, hydroxy, oxo, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino and the like) and the like can be mentioned, and 1 to 5 (preferably 1 to 3) of these optional substituents may be present at substitutable position(s).

As the "optionally substituted nitrogen-containing non-aromatic heterocycle" that can be formed by $R^{6a}$ and $R^{6b}$ bonded to each other, pyrrolidine or morpholine is preferable.

$R^4$ and $R^7$ are each preferably hydrogen atom, $C_{1-6}$ alkyl, $C_{2-6}$ alkenyl, phenyl, $C_{3-7}$ cycloalkyl or phenyl-$C_{1-6}$ alkyl (the $C_{1-6}$ alkyl, $C_{2-6}$ alkenyl, phenyl, $C_{3-7}$ cycloalkyl and phenyl-$C_{1-6}$ alkyl are each optionally substituted by 1 to 5 (preferably 1 to 3) substituents selected from halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, 4- to 6-membered cyclic amino (the 4- to 6-membered cyclic amino is optionally substituted by $C_{1-4}$ alkyl), $C_{1-6}$ alkanoylamino, optionally halogenated $C_{1-6}$ alkoxy-carbonylamino, optionally halogenated $C_{1-4}$ alkylthio, optionally halogenated $C_{1-4}$ alkylsulfinyl, optionally halogenated $C_{1-4}$ alkylsulfonyl, 5- to 10-membered heterocyclic group (preferably, thienyl, furyl and the like) and the like).

As $R^5$, $R^{6a}$, $R^{6b}$ and $R^8$ are each preferably hydrogen atom, $C_{1-6}$ alkyl, $C_{2-6}$ alkenyl, phenyl, $C_{3-7}$ cycloalkyl, phenyl-$C_{1-6}$ alkyl or $C_{1-6}$ alkoxy (the $C_{1-6}$ alkyl, $C_{2-6}$ alkenyl, phenyl, $C_{3-7}$ cycloalkyl, phenyl-$C_{1-6}$ alkyl and $C_{1-6}$ alkoxy are each optionally substituted by 1 to 5 (preferably 1 to 3) substituents selected from halogen atom, hydroxy, optionally halogenated $C_{1-4}$ alkoxy, optionally halogenated benzyloxy, carbamoyl, carboxyl, $C_{1-4}$ alkoxy-carbonyl, amino, mono- or di-$C_{1-4}$ alkylamino, 4- to 6-membered cyclic amino (the 4- to 6-membered cyclic amino is optionally substituted by $C_{1-4}$ alkyl), $C_{1-6}$ alkanoylamino, optionally halogenated $C_{1-6}$ alkoxy-carbonylamino, optionally halogenated $C_{1-4}$ alkylthio, optionally halogenated $C_{1-4}$ alkylsulfinyl, optionally halogenated $C_{1-4}$ alkylsulfonyl, 5- to 10-membered heterocyclic group (preferably, thienyl, furyl and the like) and the like).

As the $R^4$, $C_{1-6}$ alkyl, $C_{2-6}$ alkenyl, phenyl or $C_{3-7}$ cycloalkyl (the $C_{1-6}$ alkyl, $C_{2-6}$ alkenyl, phenyl and $C_{3-7}$ cycloalkyl are each optionally substituted by 1 to 5 (preferably 1 to 3) substituents selected from halogen atom, hydroxy, optionally halogenated $C_{1-4}$ alkoxy, carboxyl, $C_{1-4}$ alkoxy-carbonyl, amino, mono- or di-$C_{1-4}$ alkylamino, $C_{1-6}$ alkanoylamino, optionally halogenated $C_{1-6}$ alkoxy-carbonylamino, optionally halogenated $C_{1-4}$ alkylthio, optionally halogenated $C_{1-4}$ alkylsulfinyl, optionally halogenated $C_{1-4}$ alkylsulfonyl, thienyl and the like) is more preferable. As the $R^4$, trifluoromethyl, 2,2,2-trifluoroethyl, cyclopropyl and isopropyl are particularly preferable.

As the $R^{6a}$, a hydrogen atom or $C_{1-6}$ alkyl is more preferable, and a hydrogen atom is particularly preferable.

As the $R^{6b}$, a hydrogen atom, $C_{1-6}$ alkyl, phenyl, phenyl-$C_{1-6}$ alkyl or $C_{1-6}$ alkoxy (the $C_{1-6}$ alkyl, phenyl and phenyl-$C_{1-6}$ alkyl are each optionally substituted by 1 to 5 (preferably 1 to 3) substituents selected from halogen atom and optionally halogenated $C_{1-4}$ alkoxy and the like) is more preferable.

As the $R^7$, the "optionally substituted alkyl" is preferable, and $C_{1-6}$ alkyl is more preferable.

As the $R^3$, a group represented by the formula —$CONHR^8$ is preferable, and as the $R^8$, the "optionally substituted chain hydrocarbon group" is preferable. As the "chain hydrocarbon group" of the "optionally substituted chain hydrocarbon group", a group similar to the "chain hydrocarbon group" as a preferable example of the "optionally substituted chain hydrocarbon group" for $R^2$ and the like can be mentioned.

As $R^8$, $C_{1-6}$ alkyl, $C_{2-6}$ alkenyl, $C_{3-7}$ cycloalkyl, phenyl-$C_{1-6}$ alkyl or $C_{1-6}$ alkoxy (the $C_{1-6}$ alkyl, $C_{2-6}$ alkenyl, $C_{3-7}$ cycloalkyl, phenyl-$C_{1-6}$ alkyl and $C_{1-6}$ alkoxy are each optionally substituted by 1 to 5 (preferably 1 to 3) substituents selected from halogen atom, hydroxy, optionally halogenated $C_{1-4}$ alkoxy, carbamoyl, carboxyl, $C_{1-4}$ alkoxy-carbonyl, amino, mono- or di-$C_{1-4}$ alkylamino, 4- to 6-membered cyclic amino (e.g., piperidino, morpholino, 1-piperazinyl and the like; the 4- to 6-membered cyclic amino is optionally substituted by $C_{1-4}$ alkyl), furyl and the like) is preferable, $C_{1-6}$ alkyl optionally substituted by 1 to 3 substituents selected from halogen atom, hydroxy, optionally halogenated $C_{1-4}$ alkoxy, carbamoyl, carboxyl, $C_{1-4}$ alkoxy-carbonyl, amino, mono- or di-$C_{1-4}$ alkylamino, 4- to 6-membered cyclic amino (e.g., piperidino, morpholino, 1-piperazinyl and the like; the 4- to 6-membered cyclic amino is optionally substituted by $C_{1-4}$ alkyl) and furyl is more preferable, and $C_{1-6}$ alkyl optionally substituted by 1 to 3 substituents selected from halogen atom, hydroxy, optionally halogenated $C_{1-4}$ alkoxy, carbamoyl, carboxyl, $C_{1-4}$ alkoxy-carbonyl, amino and mono- or di-$C_{1-4}$ alkylamino is particularly preferable. As $R^8$, $C_{1-6}$ alkyl optionally substituted by 1 to 3 halogen atoms is most preferable.

In the aforementioned formulas, ring A is a monocyclic aromatic ring optionally having further substituent(s).

As the "monocyclic aromatic ring" of the "monocyclic aromatic ring optionally further having substituent(s)" for ring A, for example, (i) benzene ring and (ii) aromatic monocyclic heterocycle containing, besides carbon atom, preferably 1 to 3 heteroatoms of one or two kinds selected from nitrogen atom, sulfur atom and oxygen atom and the like can be mentioned.

Examples of the "aromatic monocyclic heterocycle" include 5- to 6-membered aromatic monocyclic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc., and the like.

As the substituent that the "monocyclic aromatic ring" optionally has, groups substitutable on the aromatic ring among the substituents that the "hydrocarbon group" of the "optionally substituted hydrocarbon group" for $R^{1a}$ or $R^{1b}$ optionally has and the like can be mentioned, and 1 to 5 (preferably 1 to 3) of these optional substituents may be present at substitutable position(s).

Examples of the substituent that the "monocyclic aromatic ring" optionally has include (1) halogen atom, (2) hydroxy, (3) amino, (4) mono- or di-$C_{1-4}$ alkylamino, (5) optionally substituted $C_{1-6}$ alkyl, (6) optionally substituted $C_{2-6}$ alkenyl, (7) optionally substituted $C_{2-6}$ alkynyl, (8) optionally substituted $C_{1-6}$ alkoxy, (9) optionally substituted $C_{2-6}$ alkenyloxy,

(10) optionally substituted $C_{2-6}$ alkynyloxy,

(11) $C_{5-7}$ cycloalkyl-oxy condensed with benzene ring (e.g., 2,3-dihydro-1H-indenyloxy) optionally having substituent(s), and the like.

As the substituent that the "$C_{1-6}$ alkyl", "$C_{2-6}$ alkenyl" and "$C_{2-6}$ alkynyl" optionally have, 1 to 5 (preferably 1 to 3) substituents selected from (1) halogen atom, (2) hydroxy, (3) optionally halogenated phenyl, (4) 5- to 10-membered heterocyclic group (e.g., pyridyl) and the like can be mentioned.

Examples of the substituent that the "$C_{1-6}$ alkoxy", "$C_{2-6}$ alkenyloxy" and "$C_{2-6}$ alkynyloxy" optionally have include 1 to 5 (preferably 1 to 3) substituents selected from (1) a halogen atom, (2) hydroxy, (3) cyano, (4) $C_{1-4}$ alkylthio, (5) mono- or di-(phenyl-$C_{1-4}$ alkyl)-carbamoyl (e.g., benzylcarbamoyl, phenethylcarbamoyl), (6) $C_{1-4}$ alkoxy-carbonyl, (7) optionally halogenated $C_{1-4}$ alkoxy, (8) $C_{1-4}$ alkoxy-$C_{1-6}$ alkoxy, (9) phenoxy-$C_{1-4}$ alkoxy, (9) $C_{3-7}$ cycloalkyloxy,

(10) benzyloxy,

(11) benzoyloxy,

(12) phenyl optionally substituted by 1 to 5 substituents selected from
    (a) halogen atom;
    (b) cyano;
    (c) optionally halogenated $C_{1-4}$ alkyl;
    (d) optionally halogenated $C_{1-4}$ alkoxy;
    (e) $C_{1-4}$ alkoxy-carbonyl;
    (f) optionally halogenated phenoxy;
    (g) phenyl optionally substituted by 1 to 5 substituents selected from halogen atom and cyano;
    (h) $C_{1-4}$ alkylsulfonyl;
    (i) optionally halogenated benzyl;
    (j) optionally halogenated benzoyl; and
    (k) benzyloxy-carbonyl-$C_{1-4}$ alkyl,

(13) phenoxy optionally substituted by 1 to 5 substituents selected from
    (a) halogen atom;
    (b) optionally halogenated $C_{1-4}$ alkyl;
    (c) optionally halogenated $C_{1-4}$ alkoxy;
    (d) mono- or di-$C_{1-4}$ alkyl-carbamoyl; and
    (e) 5- to 10-membered heterocyclic group (e.g., 1,2,3-triazolyl) optionally substituted by 1 to 3 substituents selected from $C_{1-4}$ alkyl and mono- or di-$C_{3-7}$ cycloalkyl-carbamoyl,

(14) optionally halogenated phenyl-$C_{1-4}$ alkyl,

(15) $C_{6-14}$ aryl-carbonyl (e.g., benzoyl, naphthoyl) optionally substituted by 1 to 5 substituents selected from
    (a) halogen atom;
    (b) cyano;

(c) optionally halogenated $C_{1-4}$ alkyl;
(d) optionally halogenated $C_{1-4}$ alkoxy;
(e) $C_{1-4}$ alkoxy-carbonyl;
(f) phenyl; and
(g) straight chain or branched $C_{1-4}$ alkylenedioxy (e.g., methylenedioxy, ethylenedioxy),

(16) 5- to 10-membered heterocyclic group (e.g., pyridyl, 1,2-dihydropyridyl, indolyl, pyrrolyl, benzothiazolyl, isoxazolyl, oxazolyl, 1,3-dihydroisoindolyl, imidazo[1,2-a]pyridyl, 2,3-dihydrobenzo[d]isothiazolyl) optionally substituted by 1 to 5 substituents selected from
(a) halogen atom;
(b) $C_{1-4}$ alkyl optionally substituted by 1 to 3 substituents selected from halogen atom and hydroxy;
(c) $C_{1-4}$ alkoxy-carbonyl;
(d) phenyl-$C_{2-4}$ alkenyl; and
(e) oxo,

(17) 5- to 10-membered heterocyclyl-oxy (e.g., pyridyloxy, 2-tetrahydropyranyloxy) optionally substituted by 1 to 5 substituents selected from
(a) halogen atom; and
(b) oxo,

(18) 5- to 12-membered (preferably 5- to 10-membered) heterocyclyl-carbonyl (e.g., thiazolylcarbonyl, indolylcarbonyl, spiro[cyclopropyl-1,2'-2,3-dihydrobenzofuran]carbonyl) optionally substituted by 1 to 5 substituents selected from
(a) halogen atom;
(b) optionally halogenated $C_{1-4}$ alkyl;
(c) phenyl; and
(d) oxo and the like.

Examples of the substituent that the "$C_{5-7}$ cycloalkyl-oxy condensed with benzene ring" optionally has include 1 to 5 (preferably 1 to 3) substituents selected from hydroxy, oxo and the like.

As the substituent that the "monocyclic aromatic ring" optionally has, halogen atom, hydroxy, optionally halogenated $C_{1-4}$ alkyl, optionally halogenated $C_{1-6}$ alkoxy, $C_{2-6}$ alkenyloxy, amino, mono- or di-$C_{1-4}$ alkylamino, optionally halogenated phenyl-$C_{1-4}$ alkoxy, optionally halogenated phenoxy-$C_{1-4}$ alkoxy, optionally halogenated phenyl-$C_{1-4}$ alkyl-$C_{1-4}$ alkoxy and the like are more preferable, and 1 to 5 (preferably 1 to 3) of these optional substituents may be present at substitutable position(s).

In the aforementioned formulas, ring A' is a benzene ring optionally further having substituent(s) or 6-membered nitrogen-containing aromatic heterocycle (e.g., pyridine, pyridazine, pyrimidine, pyrazine, triazine etc.) optionally further having substituent(s).

As the ring A, ring A' is preferable (that is, as a compound represented by the formula (I), a compound represented by the formula (I') is preferable). Of these, benzene ring optionally further having substituent(s) or pyridine ring optionally further having substituent(s) is particularly preferable, and benzene ring optionally further having substituent(s) is particularly preferable. As the substituent that the benzene ring and pyridine ring optionally further have, 1 to 3 (preferably 1 or 2) substituents selected from halogen atom, hydroxy, optionally halogenated $C_{1-4}$ alkyl, optionally halogenated $C_{1-4}$ alkoxy, amino, mono- and di-$C_{1-4}$ alkylamino and the like are preferable.

In the aforementioned formulas, $R^2$ and the substituent on ring A (or ring A') other than $R^3$ are optionally bonded to each other to form an optionally substituted ring. As the ring optionally formed by $R^2$ and the substituent on ring A (or ring A') other than $R^3$ bonded to each other, 5- to 8-membered (preferably 6- to 8-membered) heterocycle which contains one nitrogen atom, and further may contain 1 or 2 heteroatoms selected from nitrogen atom, sulfur atom and oxygen atom can be mentioned.

As a compound of the formula (I) wherein $R^2$ and the substituent on ring A other than $R^3$ are bonded to each other to form an optionally substituted ring, for example,

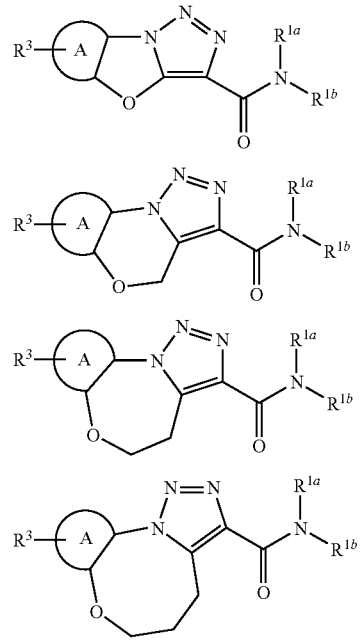

and the like can be mentioned.

As a compound of the formula (I') wherein $R^2$ and the substituent on ring A' other than $R^3$ are bonded to each other to form an optionally substituted ring, for example,

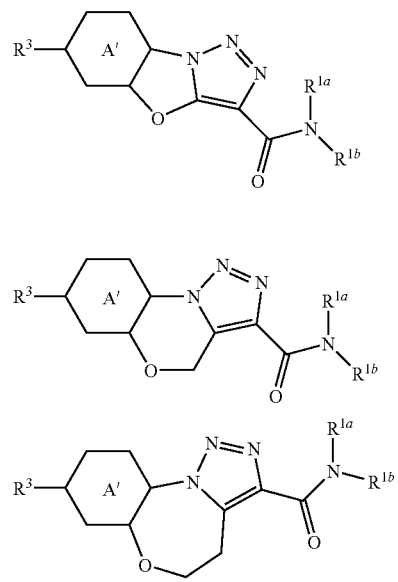

-continued

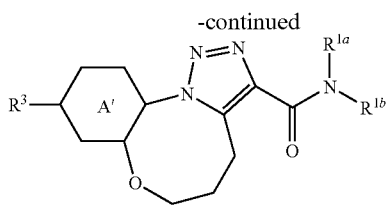

and the like can be mentioned.

As the substituent that a ring optionally formed by $R^2$ and the substituent on ring A (or ring A') other than $R^3$ bonded to each other optionally has, groups similar to the substituents that the "hydrocarbon group" of the "optionally substituted hydrocarbon group" for $R^{1a}$ or $R^{1b}$ optionally has (preferably halogen atom, hydroxy, oxo, optionally halogenated $C_{1-4}$ alkyl, optionally halogenated $C_{1-6}$ alkoxy, carbamoyl, carboxyl, $C_{1-6}$ alkoxy-carbonyl, amino, mono- or di-$C_{1-4}$ alkylamino and the like) can be mentioned, and 1 to 5 (preferably 1 to 3) of these optional substituents may be present at substitutable position(s).

In the aforementioned formulas, $R^{1a}$ and $R^2$ are optionally bonded to each other to form an optionally substituted ring. As the ring optionally formed by $R^{1a}$ and $R^2$ bonded to each other, 5- to 8-membered (preferably 6- to 8-membered) heterocycle which contains one nitrogen atom, and further may contain 1 or 2 heteroatoms selected from nitrogen atom, sulfur atom and oxygen atom can be mentioned.

As the ring optionally formed by $R^{1a}$ and $R^2$ bonded to each other, for example,

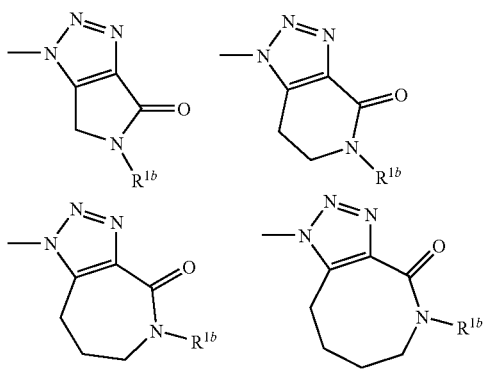

and the like can be mentioned.

As the substituent that the ring formed by $R^{1a}$ and $R^2$ bonded to each other optionally has, groups similar to the substituents that the "hydrocarbon group" of the "optionally substituted hydrocarbon group" for $R^{1a}$ or $R^{1b}$ optionally has (preferably halogen atom, hydroxy, oxo, optionally halogenated $C_{1-4}$ alkyl, optionally halogenated $C_{1-6}$ alkoxy, carbamoyl, carboxyl, $C_{1-6}$ alkoxy-carbonyl, amino, mono- or di-$C_{1-4}$ alkylamino and the like) can be mentioned, and 1 to 5 (preferably 1 to 3) of these optional substituents may be present at substitutable position(s).

In the formula (I'), when ring A' is a benzene ring optionally further having substituent(s), $R^4$ is not methyl, in other words, $R^3$ is not —NHCOCH$_3$. In the formula (I'), when ring A' is a benzene ring optionally further having substituent(s), $R^4$ is preferably substituted methyl, optionally substituted $C_{2-6}$ alkyl, optionally substituted $C_{2-6}$ alkenyl, optionally substituted phenyl or optionally substituted $C_{3-7}$ cycloalkyl. The methyl is substituted by 1 to 5 (preferably 1 to 3) substituents selected from halogen atom, hydroxy, optionally halogenated $C_{1-4}$ alkoxy, carboxyl, $C_{1-4}$ alkoxy-carbonyl, amino, mono- or di-$C_{1-4}$ alkylamino, $C_{1-6}$ alkanoylamino, optionally halogenated $C_{1-6}$ alkoxy-carbonylamino, optionally halogenated $C_{1-4}$ alkylthio, optionally halogenated $C_{1-4}$ alkylsulfinyl, optionally halogenated $C_{1-4}$ alkylsulfonyl, thienyl and the like. The $C_{2-6}$ alkyl, $C_{2-6}$ alkenyl, phenyl and $C_{3-7}$ cycloalkyl are each optionally substituted by 1 to 5 (preferably 1 to 3) substituents selected from halogen atom, hydroxy, optionally halogenated $C_{1-4}$ alkoxy, carboxyl, $C_{1-4}$ alkoxy-carbonyl, amino, mono- or di-$C_{1-4}$ alkylamino, $C_{1-6}$ alkanoylamino, optionally halogenated $C_{1-6}$ alkoxy-carbonylamino, optionally halogenated $C_{1-4}$ alkylthio, optionally halogenated $C_{1-4}$ alkylsulfinyl, optionally halogenated $C_{1-4}$ alkylsulfonyl, thienyl and the like.

In the formula (I'), when ring A' is a benzene ring optionally further having substituent(s), as the $R^4$, methyl substituted by 1 to 3 substituents selected from halogen atom, $C_{1-4}$ alkoxy, carboxyl, $C_{1-4}$ alkoxy-carbonyl, amino, mono- or di-$C_{1-4}$ alkylamino, $C_{1-6}$ alkanoylamino, $C_{1-6}$ alkoxy-carbonylamino and thienyl; $C_{2-6}$ alkyl optionally substituted by 1 to 3 substituents selected from halogen atom, carboxyl, $C_{1-4}$ alkylthio, $C_{1-4}$ alkylsulfinyl and $C_{1-4}$ alkylsulfonyl; $C_{2-6}$ alkenyl; phenyl optionally substituted by 1 to 3 substituents selected from halogen atom and $C_{1-4}$ alkoxy; or $C_{3-7}$ cycloalkyl is more preferable, and trifluoromethyl, 2,2,2-trifluoroethyl, cyclopropyl or isopropyl is particularly preferable.

As a salt of a compound represented by the formula (I) (including a compound represented by the formula (I')), a pharmacologically acceptable salt and the like can be mentioned. For example, an acid addition salt with acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydriodic acid, sulfamic acid, sulfuric acid and the like; for example, a salt with a metal such as sodium, potassium, magnesium, calcium and the like; for example, a salt with organic base such as trimethylamine, triethylamine, pyridine, picoline, N-methylpyrrolidine, N-methylpiperidine, N-methylmorpholine, etc., and the like can be mentioned.

A prodrug of a compound represented by the formula (I) or a salt thereof (hereinafter sometimes to be referred to as compound (I), including a compound represented by the formula (I') or a salt thereof) means a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxol-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

When compound (I) has isomers such as optical isomer, stereoisomer, positional isomer, rotational isomer and the like, and any isomers and mixtures of the isomers are encompassed in the compound (I). For example, when compound (I) has an optical isomer, an optical isomer separated from a racemate is also encompassed in the compound (I). These isomers can be obtained as independent products by a synthesis means or a separation means (concentration, solvent extraction, column chromatography, recrystallization and the like) known per se.

The compound (I) may be a crystal or amorphous form. When compound (I) is a crystal, both a single crystal and a crystal mixture are both encompassed in compound (I). Crystals can be produced by crystallization by applying a crystallization method known per se.

The compound (I) may be a solvate (e.g., hydrate etc.) or a non-solvate, both of which are encompassed in compound (I).

The compound (I) may be labeled with an isotope (e.g., $^3$H, $^{14}$C, $^{35}$S, $^{125}$I and the like) and the like.

A compound represented by the formula (I) or a salt thereof can be produced by a method according to a method known per se (e.g., methods described in A. R. Katritzky et al., Heterocycles, 60, 1225, 2003; A. Da Settimo et al., Il Farmaco-Ed. Sci., 38, 725, 1983; G. A. Romerio et al., Tetrahedron Letters, 38, 5103, 1997 and the like), for example, methods A —C shown below. Each compound described in the following schemes may form a salt as long as it does not inhibit the reaction, and as such salt, those similar to the salt of compound (I) and the like can be mentioned.

Method A

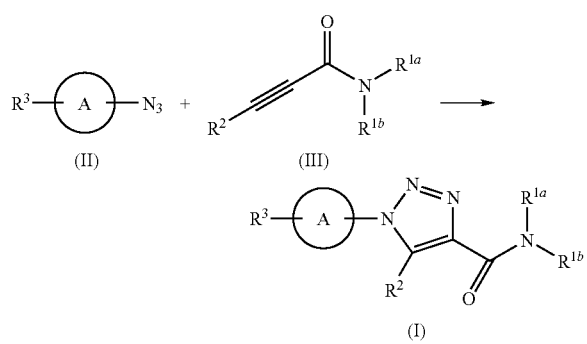

wherein $R^{1a}$, $R^{1b}$, $R^2$, $R^3$ and ring A are as defined for $R^{1a}$, $R^{1b}$, $R^2$, $R^3$ and ring A in compound (I), provided that $R^2$ and the substituent on ring A other than $R^3$ are not bonded to each other to form an optionally substituted ring, and $R^{1a}$ and $R^2$ are not bonded to each other to form an optionally substituted ring.

Method B

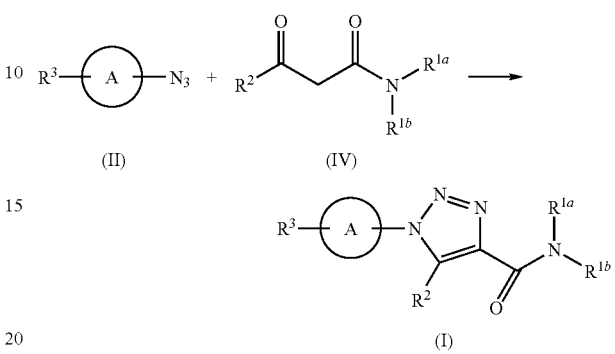

wherein $R^{1a}$, $R^{1b}$, $R^2$, $R^3$ and ring A are as defined for $R^{1a}$, $R^{1b}$, $R^2$, $R^3$ and ring A in compound (I), provided that $R^2$ and the substituent on ring A other than $R^3$ are not bonded to each other to form an optionally substituted ring.

Method C

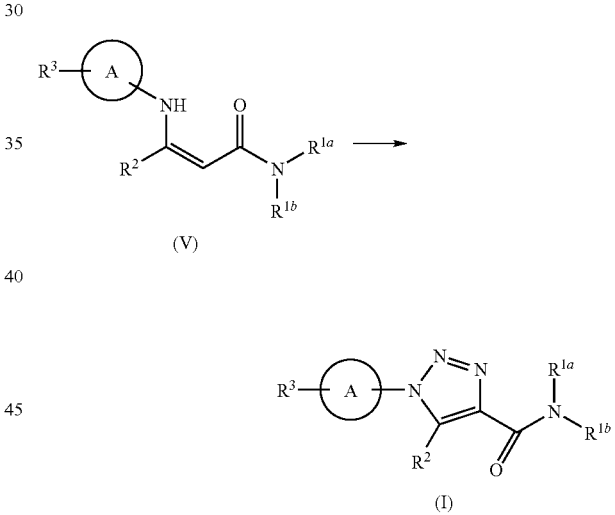

wherein $R^{1a}$, $R^{1b}$, $R^2$, $R^3$ and ring A are as defined for $R^{1a}$, $R^{1b}$, $R^2$, $R^3$ and ring A in compound (I).

Method A

Compound (I) or a salt thereof can be produced by reacting a compound (II) represented by the formula (II)

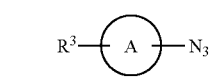

wherein $R^3$ and ring A are as defined for $R^3$ and ring A in the aforementioned compound (I), or a salt thereof, with a compound (III) represented by the formula (III)

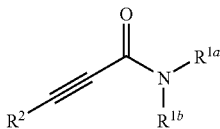

wherein $R^{1a}$, $R^{1b}$ and $R^2$ are as defined for $R^{1a}$, $R^{1b}$ and $R^2$ in the aforementioned compound (I), provided that $R^2$ and the substituent on ring A other than $R^3$ are not bonded to each other to form an optionally substituted ring, and $R^{1a}$ and $R^2$ are not bonded to each other to form an optionally substituted ring, or a salt thereof. As a salt of compound (II) or compound (III), those similar to the salt of compound (I) and the like can be mentioned.

This reaction is generally performed in a solvent, and a solvent that does not inhibit the reaction is appropriately selected. As such solvent, alcohols (e.g., methanol, ethanol, propanol, isopropanol, butanol, tert-butanol etc.), ethers (e.g., dioxane, tetrahydrofuran, diethyl ether, tert-butyl methyl ether, diisopropyl ether, ethylene glycol dimethyl ether, ethylene glycol monomethyl ether etc.), esters (e.g., ethyl formate, ethyl acetate, n-butyl acetate etc.), carboxylic acids (e.g., formic acid, acetic acid, propionic acid etc.), halogenated hydrocarbons (e.g., dichloromethane, chloroform, carbon tetrachloride, trichloroethylene, 1,2-dichloroethane, chlorobenzene etc.), hydrocarbons (e.g., n-hexane, benzene, toluene etc.), amides (e.g., formamide, N,N-dimethylformamide, N,N-dimethylacetamide etc.), ketones (e.g., acetone, methyl ethyl ketone, methyl isobutyl ketone etc.), nitriles (e.g., acetonitrile, propionitrile etc.) and the like, as well as dimethyl sulfoxide, sulfolane, hexamethylphosphoramide, water and the like are used alone or as a mixed solvent.

For the reaction, 0.5 to 5 equivalents, preferably 0.8 to 2 equivalents, of compound (II) is used relative to compound (III).

The reaction temperature is $-20°$ C. to 200° C., and preferably 0° C. to 170° C.

While the reaction time varies depending on the kind of compound (II) or (III), the kind of the solvent, reaction temperature and the like, it is generally about 1 min to about 2 weeks, preferably about 30 min to about 72 hr.

Method B

Compound (I) or a salt thereof can be produced by reacting a compound (II) represented by the formula (II)

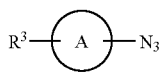

wherein $R^3$ and ring A are as defined for $R^3$ and ring A in compound (I), or a salt thereof with a compound (IV) represented by the formula (IV)

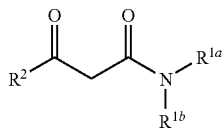

wherein $R^{1a}$, $R^{1b}$ and $R^2$ are as defined for $R^{1a}$, $R^{1b}$ and $R^2$ in compound (I), provided that $R^2$ and the substituent on ring A other than $R^3$ are not bonded to each other to form an optionally substituted ring, or a salt thereof. As a salt of compound (II) or compound (IV), those similar to the salt of compound (I) and the like can be mentioned.

This reaction is generally performed in the presence of a base, and as such base, for example, metal alcoholates such as sodium methoxide, sodium ethoxide, potassium t-butoxide and the like; inorganic bases such as lithium hydroxide, potassium hydroxide, sodium hydroxide, calcium hydroxide, sodium carbonate, potassium carbonate, sodium hydrogen carbonate, potassium hydrogen carbonate and the like; alkali metal salts of $C_{1-6}$ lower fatty acid such as sodium formate, sodium acetate, potassium acetate and the like; tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine and the like are used. The amount of the base to be used is 1 to 10 equivalents, preferably 1 to 5 equivalents, relative to compound (IV).

This reaction is generally performed in a solvent, and a solvent that does not inhibit the reaction is appropriately selected. As such solvent, alcohols (e.g., methanol, ethanol, propanol, isopropanol, butanol, tert-butanol etc.), ethers (e.g., dioxane, tetrahydrofuran, diethyl ether, tert-butyl methyl ether, diisopropyl ether, ethylene glycol dimethyl ether, ethylene glycol monomethyl ether etc.), esters (e.g., ethyl formate, ethyl acetate, n-butyl acetate etc.), carboxylic acids (e.g., formic acid, acetic acid, propionic acid etc.), halogenated hydrocarbons (e.g., dichloromethane, chloroform, carbon tetrachloride, trichloroethylene, 1,2-dichloroethane, chlorobenzene etc.), hydrocarbons (e.g., n-hexane, benzene, toluene etc.), amides (e.g., formamide, N,N-dimethylformamide, N,N-dimethylacetamide etc.), ketones (e.g., acetone, methyl ethyl ketone, methyl isobutyl ketone etc.), nitriles (e.g., acetonitrile, propionitrile etc.) and the like, as well as dimethyl sulfoxide, sulfolane, hexamethylphosphoramide, water and the like are used alone or as a mixed solvent.

For the reaction, 0.5 to 5 equivalents, preferably 0.8 to 2 equivalents, of compound (II) is used relative to compound (IV).

The reaction temperature is $-20°$ C. to 200° C., preferably 0° C. to 170° C.

While the reaction time varies depending on the kind of compound (II) or (IV), the kind of the solvent, reaction temperature and the like, it is generally about 1 min to about 1 week, preferably about 15 min to about 48 hr.

Method C

Compound (I) or a salt thereof can be produced by treating a compound (V) represented by the formula (V)

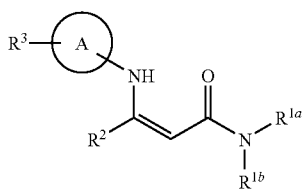

wherein $R^{1a}$, $R^{1b}$, $R^2$, $R^3$ and ring A are as defined for $R^{1a}$, $R^{1b}$, $R^2$, $R^3$ and ring A in compound (I), or a salt thereof with a diazotizating reagent. As a salt of compound (V), those similar to the salt of compound (I) and the like can be mentioned.

As the diazotizating reagent to be used for this reaction, for example, arylsulfonyl azides such as benzenesulfonyl azide, p-toluenesulfonyl azide, p-dodecylbenzenesulfonyl azide and the like; alkylsulfonyl azides such as methanesulfonyl azide and the like; and the like are used. The amount of the diazotizating reagent to be used is 1 to 10 equivalents, preferably 1 to 5 equivalents, relative to compound (V). In addition, polymer-supported benzenesulfonyl azide (e.g., polystyrene-supported benzenesulfonyl azide described in G. M. Green et al., 66, 2509, 2001 and the like) can also be used.

This reaction is generally performed in a solvent, and a solvent that does not inhibit the reaction is appropriately selected. As such solvent, alcohols (e.g., methanol, ethanol, propanol, isopropanol, butanol, tert-butanol etc.), ethers (e.g., dioxane, tetrahydrofuran, diethyl ether, tert-butyl methyl ether, diisopropyl ether, ethylene glycol dimethyl ether, ethylene glycol monomethyl ether etc.), esters (e.g., ethyl formate, ethyl acetate, n-butyl acetate etc.), carboxylic acids (e.g., formic acid, acetic acid, propionic acid etc.), halogenated hydrocarbons (e.g., dichloromethane, chloroform, carbon tetrachloride, trichloroethylene, 1,2-dichloroethane, chlorobenzene etc.), hydrocarbons (e.g., n-hexane, benzene, toluene etc.), amides (e.g., formamide, N,N-dimethylformamide, N,N-dimethylacetamide etc.), ketones (e.g., acetone, methyl ethyl ketone, methyl isobutyl ketone etc.), nitriles (e.g., acetonitrile, propionitrile etc.) and the like, as well as dimethyl sulfoxide, sulfolane, hexamethylphosphoramide and the like are used alone or as a mixed solvent.

Where necessary, this reaction may be performed in the presence of a base, and as such base, for example, metal alcoholates such as sodium methoxide, sodium ethoxide, potassium t-butoxide and the like; metal hydrides such as sodium hydride, potassium hydride, calcium hydride and the like; inorganic bases such as lithium hydroxide, potassium hydroxide, sodium hydroxide, calcium hydroxide, sodium carbonate, potassium carbonate, sodium hydrogen carbonate, potassium hydrogen carbonate and the like; alkali metal salts of $C_{1-6}$ lower fatty acid such as sodium formate, sodium acetate, potassium acetate and the like; tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine and the like are used. The amount of the base to be used is 1 to 10 equivalents, preferably 1 to 5 equivalents, relative to compound (V).

The reaction temperature is −20° C. to 200° C., preferably 0° C. to 170° C.

While the reaction time varies depending on the kind of compound (V), the kind of the solvent, reaction temperature and the like, it is generally about 1 min to about 1 week, preferably about 15 min to about 48 hr.

In methods A-C, a ring formation reaction may be performed using a compound containing halogen atom (e.g., chlorine, bromine, iodine etc.), protected amino group, nitro group, $Cl_6$ lower alkoxy-carbonyl group (e.g., methoxycarbonyl, ethoxycarbonyl, t-butoxycarbonyl etc.) and the like instead of $R^3$ in compound (II) or (V), after which the halogen atom, protected amino group, nitro group, $C_{1-6}$ lower alkoxy-carbonyl group and the like may be converted to $R^3$ by a method known per se.

Similarly, in methods A-C, a ring formation reaction may be performed using a compound containing cyano group, $C_{1-6}$ lower alkoxy-carbonyl group (e.g., methoxycarbonyl, ethoxycarbonyl, t-butoxycarbonyl etc.) and the like instead of $CONR^{1a}R^{1b}$ of compound (III), compound (IV) or compound (V), after which the cyano group, $C_{1-6}$ lower alkoxy-carbonyl group (e.g., methoxycarbonyl, ethoxycarbonyl, t-butoxycarbonyl etc.) and the like may be converted to $CONR^{1a}R^{1b}$ by a method known per se.

Furthermore, when $R^{1a}$, $R^{1b}$, $R^2$, $R^3$ and ring A has a substituent, the substituent can be introduced before or after the ring formation reaction shown in methods A-C by a reaction according to the kind of the substituent. When the reactions of methods A-C and the like are performed, the substituent is preferably protected as necessary and, as the protecting group, those known per se can be used.

A compound represented by the formula (I') or a salt thereof (hereinafter sometimes referred to as compound (I')) can be produced in the same manner as in the aforementioned methods A-C.

Method A'

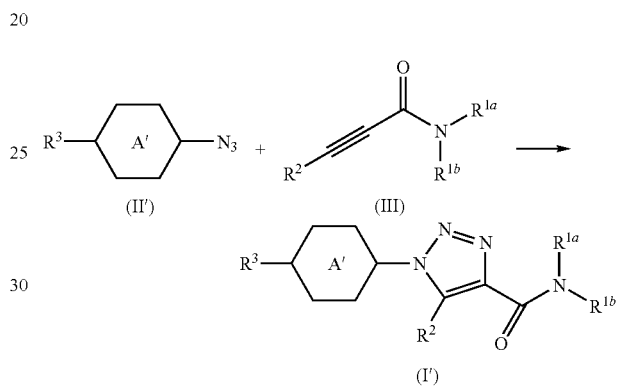

wherein $R^{1a}$, $R^{1b}$, $R^2$, $R^3$ and ring A' are as defined for $R^{1a}$, $R^{1b}$ $R^2$, $R^3$ and ring A' in compound (I'), provided that $R^2$ and the substituent on ring A' other than $R^3$ are not bonded to each other to form an optionally substituted ring, and $R^{1a}$ and $R^2$ are not bonded to each other to form an optionally substituted ring.

Compound (I') or a salt thereof can be produced by reacting compound (II') or a salt thereof with compound (III) or a salt thereof. As a salt of compound (II') or compound (III), those similar to the salt of compound (I) and the like can be mentioned.

This reaction can be performed in the same manner as in method A.

Method B'

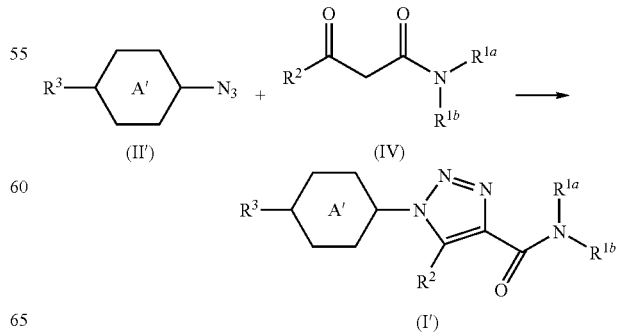

wherein $R^{1a}$, $R^{1b}$, $R^2$, $R^3$ and ring A' are as defined for $R^{1a}$, $R^{1b}$, $R^2$, $R^3$ and ring A' in compound (I'), provided that $R^2$ and the substituent on ring A' other than $R^3$ are not bonded to each other to form an optionally substituted ring.

Compound (I') or a salt thereof can be produced by reacting compound (II') or a salt thereof with compound (IV) or a salt thereof. As a salt of compound (II') or compound (IV), those similar to the salt of compound (I) and the like can be mentioned.

This reaction can be performed in the same manner as in method B.

Method C'

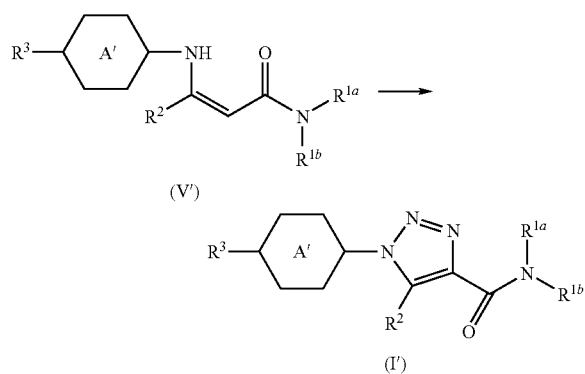

wherein $R^{1a}$, $R^{1b}$, $R^2$, $R^3$ and ring A' are as defined for $R^{1a}$, $R^{1b}$, $R^2$, $R^3$ and ring A' in compound (I').

Compound (I') or a salt thereof can be produced by treating a compound (V') or a salt thereof with a diazotiating reagent. As a salt of compound (V'), those similar to the salt of compound (I) and the like can be mentioned.

This reaction can be performed in the same manner as in method C.

The compound (I) of the present invention or a salt thereof is low toxic and safe (e.g., superior as a pharmaceutical agent from the aspects of acute toxicity, chronic toxicity, genetic toxicity, reproductive toxicity, cardiotoxicity, drug interaction, carcinogenicity etc.), and is preferably used for the prophylaxis or treatment of various arterial and/or venous thromboses, for example, myocardial infarction, cerebral infarction, arteriosclerosis obliterans and the like, in an animal, particularly mammals (e.g., human, monkey, cat, pig, horse, bovine, mouse, rat, guinea pig, dog, rabbit, etc.). The compound (I) of the present invention or a salt thereof can be used, for example, for the prophylaxis or treatment of the following diseases and the like.

Brain:

Prevention or treatment of cerebral infarction, ischemic cerebrovascular disorder, acute cerebral thrombosis, cerebrovascular contraction after subarachnoid hemorrhage, Alzheimer's disease, transient ischemic attack (TIA), mixed dementia, cerebrovascular dementia, asymptomatic/multiple cerebral infarction, lacunar infarction and the like, prognosis improvement or secondary onset prevention of cerebral infarction, prevention or treatment of thrombus after an extracranial-intracranial artery bypass surgery, combination use or supplemental use with a thrombolytic agent against cerebral infarction (among them, ischemic cerebrovascular disorder), combination therapy with warfarin, heparin, low-molecular-weight heparin, thrombin inhibitor, FXa inhibitor or the like in preventing onset of cerebral infarction.

Heart:

Prevention or treatment of acute coronary artery disease such as acute coronary syndrome or acute myocardial infarction, myocardial infarction, ischemic coronary artery disease, unstable angina pectoris, cardiomyopathy, acute heart failure, congestive chronic heart failure, vascular reocclusion and restenosis after coronary artery intervention such as stent indwelling or PTCA (percutaneous transluminal coronary angioplasty) or atherectomy, prevention or treatment of vascular reocclusion and restenosis after coronary artery bypass surgery, combination use or supplemental use with a thrombolytic agent against acute coronary artery disease, combination therapy with warfarin, heparin, low-molecular-weight heparin, thrombin inhibitor, FXa inhibitor or the like in preventing onset of myocardial infarction.

Periphery:

Prevention or treatment of chronic arterial occlusive disease, arteriosclerosis obliterans, peripheral circulatory failure such as Buerger's disease, peripheral circulatory failure after frostbite, aneurysm, varix, adult respiratory distress syndrome, acute renal failure, chronic renal disease (e.g. diabetic nephropathy, chronic glumerular nephritis, IgA nephropathy etc.), diabetic circulatory disorder, pain, neuropathy, diabetic complication such as diabetic retinopathy and the like, prevention or treatment of thrombus after peripheral vascular bypass surgery or artificial blood vessel or vena cava filter indwelling, prevention or treatment of reocclusion and restenosis after peripheral vascular intervention such as stent indwelling or PTA (percutaneous transluminal angioplasty) or atherectomy, combination therapy with warfarin, heparin, low-molecular-weight heparin, thrombin inhibitor, FXa inhibitor or the like in therapy of peripheral circulatory failure such as arteriosclerosis obliterans.

Others:

Prevention or treatment of thrombocytopenia on a major surgery, thrombocytopenic purpura, disseminated intravascular coagulation syndrome (DIC) developed in a patient suffering from progression of arteriosclerosis or cancer metastasis or systemic inflammatory reaction syndrome (SIRS) or pancreatitis or cancer or leukemia or a major surgery or sepsis or the like, various organ disorders such as liver function disorder caused by oligemia or ischemia or retention of blood, various organ failures (e.g. lung failure, liver failure, renal failure, heart failure etc.) caused by progression of shock or DIC, systemic lupus erythematosus, collagen disease, hyperthyroidism, parturient paralysis and the like, inhibition of rejection reaction on transplantation, organ protection or function improvement on transplantation, promotion of healing of bedsore or wound, and the like.

Thrombin produced by an increased activity of the blood coagulation system acts on thrombin receptors (particularly PAR-1) on the platelet to cause platelet activation and subsequent adhesion and aggregation reaction of the platelet. On the other hand, anticoagulants such as heparin, warfarin, FXa inhibitor and the like, namely, pharmaceutical agents inhibiting thrombin production, inhibit not only PAR-1-mediated platelet activation but also the blood coagulation system, frequently causing a serious hemorrhagic side effect.

Unlike anticoagulants, since the thrombin receptor antagonist of the present invention does not directly influence the blood coagulation system and can suppress activation of platelet by thrombin, it is promising as an antithrombotic agent. Moreover, since the pharmaceutical agent can inhibit thrombin receptors (particularly PAR-1) expressed in various tissues, it can effectively act in a thrombin receptor mediated pathological condition or disease other than thrombosis without directly influencing the blood coagulation system.

In the pharmaceutical agent of the present invention, the compound (I) can be administered orally or parenterally as it is or after mixing with a pharmacologically acceptable carrier.

The dosage form of a pharmaceutical agent containing compound (I) of the present invention when used for oral administration include tablet (including sugar-coated tablet, film-coated tablet), pill, granule, powder, capsule (including soft capsule, microcapsule), syrup, emulsion, suspension and the like, and the dosage form thereof for parenteral administration is, for example, injection, injecting agent, instillation, suppository and the like. In addition, it is effective to make a sustained release preparation by combining with a suitable base (e.g., polymer of butyric acid, polymer of glycolic acid, copolymer of butyric acid-glycolic acid, a mixture of polymer of butyric acid and polymer of glycolic acid, polyglycerol fatty acid ester etc.).

The content of the compound (I) in the preparation of the present invention varies depending on the form of a preparation, and is usually from 2 to 85 wt %, preferably from 5 to 70 wt %, based on the whole preparation.

As a method to produce the compound (I) in the above-mentioned dosage form, a known production method generally used in the pertinent field can be applied. When the above-mentioned dosage form is produced, suitable amounts of additives such as an excipients, a binder, a disintegrant, a lubricant, a sweetener, a surfactant, a suspending agent, an emulsifier and the like generally used in the pertinent field are appropriately added as necessary, and produced.

When the compound (I) is prepared into a tablet, for example, it can be produced by adding an excipient, a binder, a disintegrant, a lubricant and the like, and when a pill and a granule are to be prepared, they can be produced by adding an excipient, a binder, a disintegrant and the like. When a powder and a capsule are to be prepared, they can be produced by adding an excipient and the like, and when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, saccharose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound (I) is produced in the above-mentioned dosage form, a suitable amount of a colorant, a preservative, an aromatic, a corrigent, a stabilizer, a thickening agent and the like typically used in the field of preparation can be added on demand.

The pharmaceutical agent of the present invention is stable and low toxic, and can be used safely. While the daily dose varies depending on the condition and body weight of patients, the kind of compound, administration route and the like, in the case of, for example, oral administration to patients of thrombosis, the daily dose to an adult (body weight about 60 kg) is about 1 to 2000 mg, preferably about 3 to 1000 mg, more preferably about 10 to 500 mg, as an active ingredient (the compound (I)), which can be given in a single administration or administered in 2 or 3 portions a day.

When the compound (I) is administered parenterally, it is generally administered in the form of a liquid formulation (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, or by dissolving, suspending or emulsifying the compound (I) in a sterilized aqueous solution or oily liquid. As an aqueous solution for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), non-ionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like may be mixed therewith. A prepared injection is generally filled in an ampoule.

The compound (I) can be used in combination with suitable pharmaceutical agents (hereinafter abbreviated as concomitant drugs) such as thrombolytic agent (e.g., TPA, urokinase etc.), therapeutic agent for Alzheimer's disease (for example, Avan, Calan etc.), therapeutic agent for hyperlipidemia (e.g., HMG-CoA reductase inhibitor such as simvastatin, pravastatin etc.; nicotinic acid preparation such as nicomol etc.; cholesterol absorption inhibitor such as ezetimibe etc.; squalene synthase inhibitor and the like), TG lowering agent (e.g., clofibrate etc.), AII antagonist (e.g., candesartan cilexetil, losartan, telmisartan, olmesartan medoxomil etc.), antiplatelet agent (e.g., clopidogrel, aspirin, cilostazol etc.), Ca antagonist (e.g., calslot, amlodipine etc.), ACE inhibitor (e.g., enalapril, captopril etc.), diuretic (e.g., benzylhydrochlorothiazide, cyclopenthiazide, ethiazide, chlortalidone, clofenamide, indapamide, mefruside, meticrane, sotolazone, spironolactone, eplerenone etc.), β-blocker (e.g., metoprolol, carvedilol etc.), antiarrhythmic agent (e.g., procainamide etc.), anticoagulant (e.g., antithrombin III, warfarin, unfractionated heparin, low-molecular-weight heparin etc.), thrombin inhibitor (e.g., ximelagatran etc.), FXa inhibitor (e.g., rivaroxaban, razaxaban etc.), thrombolytic agent (e.g., tPA, urokinase etc.), GPIIb/IIIa antagonist (e.g., abciximab etc.) and the like. The concomitant drug may be a low-molecular-weight compound or a high-molecular-weight protein, polypeptide, antibody or vaccine etc. In this case, the administration mode of the compound of the present invention and the concomitant drug is not particularly restricted, and it is sufficient that the compound of the present invention and the concomitant drug are combined in administration. Examples of such administration mode include the following methods:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like can be mentioned. The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01 to 100 parts by weight relative to 1 part by weight of the compound of the present invention.

EXAMPLES

The present invention is further described in detail in reference to Examples, Preparation Examples and Experimental Examples, but they are not intended to limit the invention and may be modified in the range not to be construed to limit the scope thereof.

The elution in column chromatography of Examples was carried out under observation by means of TLC (Thin Layer Chromatography). In the TLC observation, 60F$_{254}$ (manufactured by Merck & Co., Inc.) or NH (manufactured by Fuji Silysia Chemical, Ltd.) were adopted as a TLC plate, the solvent used for the elution in column chromatography was adopted as an eluent, a UV detector was adopted as the means for detection. As the silica gel for column, Kieselgel 60 (70 to 230 meshes) or Kieselgel 60 (230 to 400 meshes) manufactured by Merck & Co., Inc. was used. As the basic silica gel for column, NH-DM 1020 (manufactured by Fuji Silysia Chemical, Ltd.; 100 to 200 mesh) was used. NMR spectra were measured with a Varian Gemini 200 or Mercury 300 spectrometer by using tetramethylsilane as internal or external standard. The chemical shift was indicated by δ, and a coupling constant was indicated by Hz. IR spectra were measured with a Shimadzu FTZR-8200 spectrometer. The numeric value in parenthesis with regard to a mixed solvent is a volumetric mixing ratio of each solvent. Moreover, "%" in the solution represents the number of grams in 100 ml of a solution. Abbreviations employed in Examples are described below.

| | |
|---|---|
| s | singlet |
| d | doublet |
| t | triplet |
| q | quartet |
| dd | double doublet |
| m | multiplet |
| br | broad |
| brs | broad singlet |
| J | coupling constant |
| WSC | water soluble carbodiimide |
| THF | tetrahydrofuran |
| DMF | dimethylformamide |
| DMSO | dimethyl sulfoxide |
| HOBt | 1-hydroxybenzotriazole monohydrate |
| DBU | 1,8-diazabicyclol[5.4.0]-7-undecene |
| DMAP | 4-dimethylaminopyridine |
| ADDP | 1,1'-(azodicarbonyl)dipiperidine |
| DAST | diethylaminosulfur trifluoride |
| AcOEt | ethyl acetate |
| IPE | diisopropyl ether |
| Et$_2$O | diethyl ether |
| $^i$Pr$_2$O | diisopropyl ether |
| HPLC | high performance liquid chromatography |
| LC/MS | liquid chromatography/mass spectrometry |

Example 1

1-[4-(benzoylamino)phenyl]-N-cyclopropyl-5-propyl-1H-1,2,3-triazole-4-carboxamide

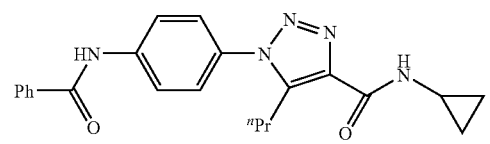

1a) 1-azido-4-nitrobenzene

To a solution of 4-nitroaniline (27.6 g) in 0.4N hydrochloric acid (500 ml) was added 1M aqueous sodium nitrite solution (200 ml) under ice-cooling, and the mixture was stirred for 30 min and then at room temperature for 20 min. An aqueous solution (100 ml) of sodium azide (13.0 g) was added to the obtained reaction mixture under ice-cooling, and the mixture was stirred for 30 min. The precipitated crystals were collected by filtration, washed with 1N hydrochloric acid and water and air-dried to give the title compound as a brown powder (28.2 g, 86%).

NMR (CDCl$_3$) δ: 7.12-7.17 (2H, m), 8.22-8.27 (2H, m).

1b) 1-(4-nitrophenyl)-5-propyl-1H-1,2,3-triazole-4-carboxylic acid

To a solution of 1-azido-4-nitrobenzene (16.4 g) obtained in Example 1a) and ethyl 3-keto-n-hexanoate (17.0 ml) in methanol (200 ml) was added 28% sodium methoxide in methanol solution (21 ml) under ice-cooling, and the mixture was stirred for 30 min and then at 50° C. overnight. Then, 1N aqueous sodium hydroxide solution (100 ml) was added, and the mixture was stirred at 50° C. for 1.5 hr, and cooled to room temperature. The solvent was evaporated under reduced pressure, and the residual aqueous solution was diluted with water and washed with ethyl acetate. Then, the mixture was acidified with 1N hydrochloric acid and extracted with ethyl acetate. The extract was dried over anhydrous magnesium sulfate, and the solvent was evaporated under reduced pressure to give the title compound as a brown solid (13.4 g, 49%). The obtained crude product was used for the next reaction without further purification.

1c) N-cyclopropyl-1-(4-nitrophenyl)-5-propyl-1H-1,2,3-triazole-4-carboxamide To a solution of 1-(4-nitrophenyl)-5-propyl-1H-1,2,3-triazole-4-carboxylic acid (1.38 g) obtained in Example 1b) in acetonitrile (50 ml) were successively added cyclopropylamine (0.38 ml), HOBt (0.84 g) and WSC (1.05 g), and the reaction mixture was stirred overnight at room temperature. The solvent was evaporated under reduced pressure, and the residue was dissolved in ethyl acetate and washed with aqueous sodium hydrogen carbonate solution. The organic layer was dried over anhydrous magnesium sulfate, and the solvent was evaporated under reduced pressure. The residue was purified by silica gel column (ethyl acetate/hexane=1/1) to give the title compound as a pale-yellow solid (1.29 g, 82%).

NMR (CDCl$_3$) δ: 0.66-0.71 (2H, m), 0.86-0.93 (5H, m), 1.57-1.68 (2H, m), 2.88-2.94 (1H, m), 3.05-3.11 (2H, m), 6.90 (1H, s), 7.68 (2H, d, J=9.0), 8.47 (2H, d, J=9.0).

1d) 1-(4-aminophenyl)-N-cyclopropyl-5-propyl-1H-1,2,3-triazole-4-carboxamide To a solution of N-cyclopropyl-1-(4-nitrophenyl)-5-propyl-1H-1,2,3-triazole-4-carboxamide (1.2 g) obtained in Example 1c) in ethanol (38 ml) was added 10% Pd/C (50% wet) (0.12 g) and the mixture was stirred overnight under a hydrogen atmosphere. The reaction mixture was filtered through celite, and the filtrate was evaporated under reduced pressure. The residue was purified by silica gel column (methanol/ethyl acetate=1/10) to give the title compound as a white powder (0.91 g, 84%).

NMR (CDCl$_3$) δ: 0.63-0.69 (2H, m), 0.83-0.89 (5H, m), 1.51-1.63 (2H, m), 2.85-2.97 (3H, m), 3.97 (2H, s), 6.75-6.80 (2H, m), 7.12-7.17 (2H, m), 7.34 (1H, s).

1e) 1-[4-(benzoylamino)phenyl]-N-cyclopropyl-5-propyl-1H-1,2,3-triazole-4-carboxamide To a solution of 1-(4-aminophenyl)-N-cyclopropyl-5-propyl-1H-1,2,3-triazole-4-carboxamide (0.34 g) obtained in Example 1d) in dichloromethane (24 ml) was added benzoyl chloride (0.14 ml) under ice-cooling, and the mixture was stirred for 30 min and at room temperature for 3 hr. The reaction mixture was washed with saturated aqueous sodium hydrogen carbonate solution, and dried over anhydrous magnesium sulfate. The solvent was evaporated under reduced pressure, and the precipitated solid was washed with ethyl acetate to give the title compound as a white powder (0.36 g, 78%).

NMR (CDCl$_3$) δ: 0.65-0.70 (2H, m), 0.85-0.90 (5H, m), 1.55-1.58 (2H, m), 2.87-2.93 (1H, m), 2.98-3.03 (2H, m), 7.84 (1H, s), 7.43 (2H, d, J=8.7), 7.50-7.63 (3H, m), 7.87-7.92 (4H, m), 8.03 (1H, s).

Elemental analysis for C$_{22}$H$_{23}$N$_5$O$_2$.0.5H$_2$O.0.25DMF
Calcd. (%): C, 65.57; H, 6.23; N, 17.65.
Found (%): C, 65.31; H, 5.96; N, 18.01.

Example 2

N-cyclopropyl-1-[4-(propionylamino)phenyl]-5-propyl-1H-1,2,3-triazole-4-carboxamide

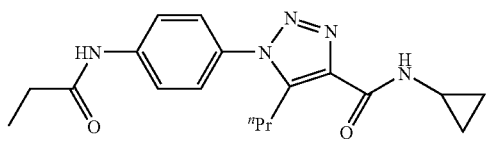

To a solution of 1-(4-aminophenyl)-N-cyclopropyl-5-propyl-1H-1,2,3-triazole-4-carboxamide (0.29 g) obtained in Example 1d) in dichloromethane (10 ml) was added propionyl chloride (0.09 ml) under ice-cooling, and the mixture was stirred for 1 hr. The reaction mixture was diluted with dichloromethane, and washed with saturated aqueous sodium hydrogen carbonate solution. The organic layer was dried over anhydrous magnesium sulfate, and the solvent was evaporated under reduced pressure. The residue was purified by silica gel column (ethyl acetate/hexane=1/4 to 1/1) to give the title compound as a white powder (0.11 g, 31%).

NMR (CDCl$_3$) δ: 0.64-0.70 (2H, m), 0.83-0.90 (5H, m), 1.28 (3H, t, J=7.5), 1.50-1.63 (2H, m), 2.46 (2H, q, J=7.5), 2.85-2.92 (1H, m), 2.95-3.00 (2H, m), 7.33-7.38 (3H, m), 7.56 (1H, s), 7.74-7.77 (2H, m).

Elemental analysis for C$_{18}$H$_{23}$N$_5$O$_2$
Calcd. (%): C, 63.32; H, 6.79; N, 20.51.
Found (%): C, 63.18; H, 6.90; N, 20.20.

Example 3

N-cyclopropyl-1-[4-(isobutyrylamino)phenyl]-5-propyl-1H-1,2,3-triazole-4-carboxamide

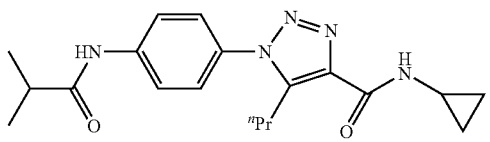

To a solution of 1-(4-aminophenyl)-N-cyclopropyl-5-propyl-1H-1,2,3-triazole-4-carboxamide (0.29 g) obtained in Example 1d) and pyridine (0.09 ml) in dichloromethane (3 ml) was added 2-methylpropanoyl chloride (0.1 ml) under ice-cooling, and the mixture was stirred at room temperature overnight. The reaction mixture was diluted with dichloromethane, and washed successively with diluted hydrochloric acid, saturated aqueous sodium hydrogen carbonate solution, and saturated brine. The organic layer was dried over anhydrous magnesium sulfate, and the solvent was evaporated under reduced pressure. The residue was purified by silica gel column (ethyl acetate/hexane=1/1 to ethyl acetate), and the obtained product was washed with diisopropyl ether to give the title compound as a pale-yellow powder (0.21 g, 60%).

NMR (CDCl$_3$) δ: 0.64-0.69 (2H, m), 0.83-0.90 (5H, m), 1.30 (6H, d, J=7.0), 1.53-1.60 (2H, m), 2.52-2.61 (1H, m), 2.86-3.00 (3H, m), 7.33-7.38 (4H, m), 7.74-7.77 (2H, m).

Elemental analysis for $C_{19}H_{25}N_5O_2 \cdot 0.1H_2O$
Calcd. (%): C, 63.88; H, 7.11; N, 19.60.
Found (%): C, 63.59; H, 7.00; N, 19.91.

Example 4

N-cyclopropyl-1-{4-[(cyclopropylcarbonyl)amino]phenyl}-5-propyl-1H-1,2,3-triazole-4-carboxamide

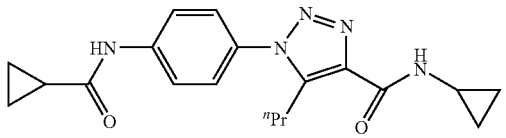

In the same manner as in Example 3, the title compound was obtained as a white powder (0.34 g, 69%) from 1-(4-aminophenyl)-N-cyclopropyl-5-propyl-1H-1,2,3-triazole-4-carboxamide (0.4 g) obtained in Example 1d) and cyclopropanecarbonyl chloride (0.14 ml).
NMR (CDCl$_3$) δ: 0.64-0.69 (2H, m), 0.83-0.94 (6H, m), 1.11-1.15 (2H, m), 1.52-1.61 (4H, m), 2.87-3.00 (3H, m), 7.34-7.37 (3H, m), 7.73-7.76 (3H, m).
Elemental analysis for $C_{19}H_{23}N_5O_2 \cdot 0.5H_2O$
Calcd. (%): C, 62.97; H, 6.67; N, 19.32.
Found (%): C, 63.15; H, 6.52; N, 19.15.

Example 5

1-[4-(butyrylamino)phenyl]-N-cyclopropyl-5-propyl-1H-1,2,3-triazole-4-carboxamide

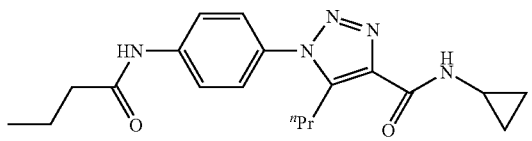

In the same manner as in Example 3, the title compound was obtained as a white powder (0.4 g, 81%) from 1-(4-aminophenyl)-N-cyclopropyl-5-propyl-1H-1,2,3-triazole-4-carboxamide (0.4 g) obtained in Example 1d) and butanoyl chloride (0.15 ml).
NMR (CDCl$_3$) δ: 0.64-0.69 (2H, m), 0.83-0.90 (5H, m), 1.03 (3H, t, J=7.4), 1.51-1.62 (2H, m), 1.73-1.86 (2H, m), 2.40 (2H, t, J=7.2), 2.85-3.00 (3H, m), 7.34-7.38 (3H, m), 7.48 (1H, s), 7.73-7.76 (2H, m).
Elemental analysis for $C_{19}H_{25}N_5O_2 \cdot 0.25H_2O$
Calcd. (%): C, 63.40; H, 7.14; N, 19.46.
Found (%): C, 63.28; H, 7.02; N, 19.40.

Example 6

N-cyclopropyl-1-{4-[(4-methoxybenzoyl)amino]phenyl}-5-propyl-1H-1,2,3-triazole-4-carboxamide

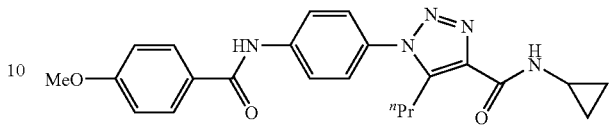

In the same manner as in Example 3, the title compound was obtained as a white powder (0.46 g, 79%) from 1-(4-aminophenyl)-N-cyclopropyl-5-propyl-1H-1,2,3-triazole-4-carboxamide (0.4 g) obtained in Example 1d) and 4-methoxybenzoyl chloride (0.21 ml).
NMR (CDCl$_3$) δ: 0.64-0.69 (2H, m), 0.84-0.90 (5H, m), 1.51-1.64 (2H, m), 2.85-2.93 (1H, m), 2.96-3.01 (2H, m), 3.89 (3H, s), 6.96-7.01 (2H, m), 7.36 (1H, d, J=3.0), 7.31-7.42 (2H, m), 7.85-7.91 (4H, m), 8.15 (1H, s).
Elemental analysis for $C_{23}H_{25}N_5O_3 \cdot 0.75H_2O$
Calcd. (%): C, 63.80; H, 6.17; N, 16.17.
Found (%): C, 63.87; H, 5.79; N, 15.95.

Example 7

N-cyclopropyl-1-{4-[(4-fluorobenzoyl)amino]phenyl}-5-propyl-1H-1,2,3-triazole-4-carboxamide

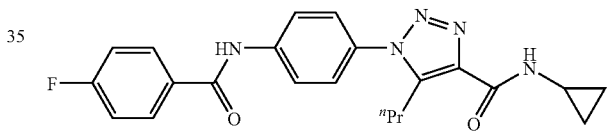

In the same manner as in Example 3, the title compound was obtained as a white powder (0.46 g, 81%) from 1-(4-aminophenyl)-N-cyclopropyl-5-propyl-1H-1,2,3-triazole-4-carboxamide (0.40 g) obtained in Example 1d) and 4-fluorobenzoyl chloride (0.18 ml).
NMR (DMSO-d$_6$) δ: 0.63-0.69 (4H, m), 0.75 (3H, t, J=7.2), 1.37-1.49 (2H, m), 2.83-2.97 (3H, m), 7.38-7.45 (2H, m), 7.55-7.60 (2H, m), 8.01-8.11 (4H, m), 8.62 (1H, d, J=4.7), 10.60 (1H, s).
Elemental analysis for $C_{22}H_{22}N_5O_2F \cdot 0.2H_2O$
Calcd. (%): C, 64.28; H, 5.49; N, 17.04.
Found (%): C, 64.28; H, 5.40; N, 17.20.

Example 8

1-{4-[(4-chlorobenzoyl)amino]phenyl}-N-cyclopropyl-5-propyl-1H-1,23-triazole-4-carboxamide

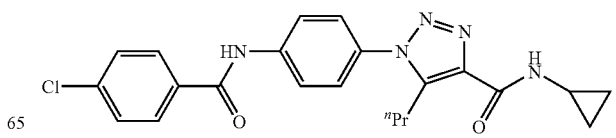

In the same manner as in Example 3, the title compound was obtained as a white powder (0.42 g, 70%) from 1-(4-aminophenyl)-N-cyclopropyl-5-propyl-1H-1,2,3-triazole-4-carboxamide (0.40 g) obtained in Example 1d) and 4-chlorobenzoyl chloride (0.19 ml).

NMR (DMSO-d$_6$) δ: 0.63-0.69 (4H, m), 0.74 (3H, t, J=7.3), 1.39-1.46 (2H, m), 2.85-2.97 (3H, m), 7.56-7.60 (2H, m), 7.63-7.67 (2H, m), 8.00-8.04 (4H, m), 8.62 (1H, d, J=4.7), 10.65 (1H, s).

Elemental analysis for C$_{22}$H$_{22}$N$_5$O$_2$Cl

Calcd. (%): C, 62.34; H, 5.23; N, 16.52.

Found (%): C, 62.06; H, 5.17; N, 16.76.

Example 9

1-{4-[(4-bromobutanoyl)amino]phenyl}-N-cyclopropyl-5-propyl-1H-1,2,3-triazole-4-carboxamide

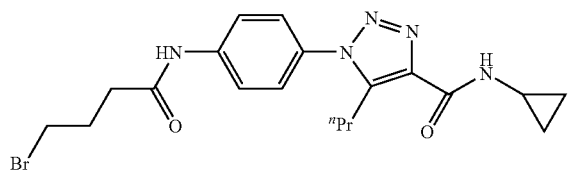

In the same manner as in Example 3, the title compound was obtained as white needle crystals (0.42 g, 97%) from 1-(4-aminophenyl)-N-cyclopropyl-5-propyl-1H-1,2,3-triazole-4-carboxamide (0.29 g) obtained in Example 1d) and 4-bromobutyryl chloride (0.12 ml).

NMR (DMSO-d$_6$) δ: 0.62-0.76 (5H, m), 1.36-1.44 (2H, m), 2.10-2.19 (2H, m), 2.53-2.57 (4H, m), 3.62 (3H, t, J=6.6), 7.48-7.52 (2H, m), 7.81-7.85 (2H, m), 8.60 (1H, d, J=4.5), 10.34 (1H, s).

Elemental analysis for C$_{19}$H$_{24}$N$_5$O$_2$Br

Calcd. (%): C, 52.54; H, 5.57; N, 16.12.

Found (%): C, 52.71; H, 5.67; N, 16.41.

Example 10

N-cyclopropyl-1-(4-{[3-(methylthio)propanoyl]amino}phenyl)-5-propyl-1H-1,2,3-triazole-4-carboxamide

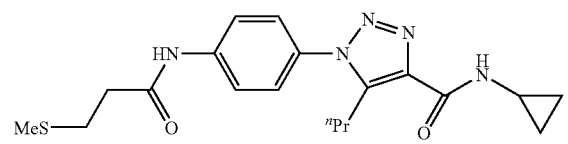

In the same manner as in Example 3, the title compound was obtained as a white powder (0.62 g, 80%) from 1-(4-aminophenyl)-N-cyclopropyl-5-propyl-1H-1,2,3-triazole-4-carboxamide (0.57 g) obtained in Example 1d) and 3-(methylthio)propanoyl chloride (0.24 ml).

NMR (CDCl$_3$) δ: 0.64-0.70 (2H, m), 0.84-0.91 (5H, m), 1.53-1.61 (2H, m), 2.20 (3H, s), 2.70-2.74 (2H, m), 2.87-3.00 (5H, m), 7.34-7.39 (3H, m), 7.74-7.77 (2H, m), 7.91 (1H, brs).

Elemental analysis for C$_{19}$H$_{25}$N$_5$O$_2$S

Calcd. (%): C, 58.89; H, 6.50; N, 18.07.

Found (%): C, 59.01; H, 6.41; N, 18.30.

Example 11

1-[4-(acryloylamino)phenyl]-N-cyclopropyl-5-propyl-1H-1,2,3-triazole-4-carboxamide

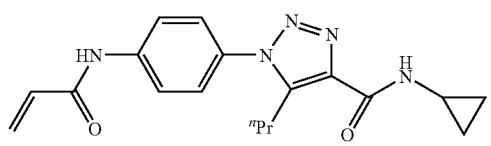

In the same manner as in Example 1e), the title compound was obtained as a colorless powder (0.25 g, 21%) from 1-(4-aminophenyl)-N-cyclopropyl-5-propyl-1H-1,2,3-triazole-4-carboxamide (1.00 g) obtained in Example 1d) and 3-chloropropionyl chloride (0.41 ml).

NMR (CDCl$_3$) δ: 0.64-0.70 (2H, m), 0.70-0.90 (5H, m), 1.50-1.63 (2H, m), 2.85-2.91 (1H, m), 2.92-3.00 (2H, m), 5.83 (1H, dd, J=10.1, 1.4), 6.32 (1H, dd, J=16.8, 10.1), 6.50 (1H, dd, J=16.8, 1.4), 7.34-7.38 (3H, m), 7.80-7.85 (2H, m), 8.01 (1H, brs).

Elemental analysis for C$_{18}$H$_{21}$N$_5$O$_2$

Calcd. (%): C, 63.70; H, 6.24; N, 20.64.

Found (%): C, 63.45; H, 6.36; N, 20.55.

Example 12 ethyl 3-[(4-{4-[(cyclopropylamino)carbonyl]-5-propyl-1H-1,2,3-triazol-1-yl}phenyl)amino]-3-oxopropanoate

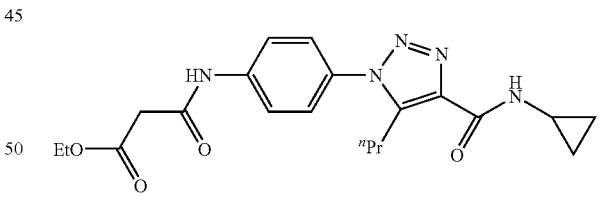

In the same manner as in Example 1e), the title compound was obtained as a colorless powder (2.70 g, 96%) from 1-(4-aminophenyl)-N-cyclopropyl-5-propyl-1H-1,2,3-triazole-4-carboxamide (2.00 g) obtained in Example 1d) and ethyl 3-chloro-3-oxopropanoate (1.10 ml).

NMR (CDCl$_3$) δ: 0.64-0.70 (2H, m), 0.84-0.90 (5H, m), 1.35 (3H, t, J=7.2), 1.53-1.63 (2H, m), 2.86-2.92 (1H, m), 2.95-3.00 (2H, m), 3.52 (2H, s), 4.28 (2H, q, J=7.2), 7.33 (1H, brs), 7.34-7.39 (2H, m), 7.76-7.81 (2H, m), 9.64 (1H, brs).

Elemental analysis for C$_{20}$H$_{25}$N$_5$O$_4$

Calcd. (%): C, 59.07; H, 6.39; N, 17.22.

Found (%): C, 59.32; H, 6.40; N, 16.95.

Example 13

N-cyclopropyl-1-(4-{[3-(methylsulfinyl)propanoyl]amino}phenyl)-5-propyl-1H-1,2,3-triazole-4-carboxamide

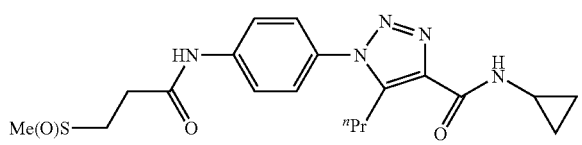

To a solution of N-cyclopropyl-1-(4-{[3-(methylthio)propanoyl]amino}phenyl)-5-propyl-1H-1,2,3-triazole-4-carboxamide (0.10 g) obtained in Example 10 in methanol (6 ml) was added an aqueous solution (2 ml) of Oxone (0.10 g) at room temperature, and the mixture was stirred for 1 hr. The solvent was evaporated under reduced pressure, and the residue was diluted with ethyl acetate and washed with saturated brine. The organic layer was dried over magnesium sulfate, and the solvent was evaporated under reduced pressure. The residue was recrystallized from methanol-diethyl ether to give the title compound as a white powder (0.09 g, 82%).

NMR (CDCl$_3$) δ: 0.67-0.68 (2H, m), 0.82-0.90 (5H, m), 1.51-1.62 (2H, m), 2.71 (3H, s), 2.87-3.07 (6H, m), 3.21-3.33 (1H, m), 7.33-7.37 (3H, m), 7.75-7.79 (2H, m), 9.20 (1H, s).

Elemental analysis for $C_{19}H_{25}N_5O_3S$

Calcd. (%): C, 56.56; H, 6.25; N, 17.36.

Found (%): C, 56.30; H, 6.28; N, 17.37.

Example 14

N-cyclopropyl-1-(4-{[3-(methylsulfonyl)propanoyl]amino}phenyl)-5-propyl-1H-1,2,3-triazole-4-carboxamide

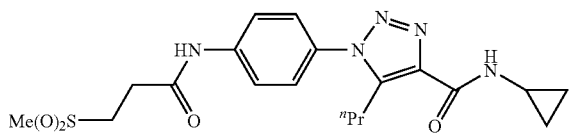

In the same manner as in Example 13, the title compound was obtained as a white powder (0.15 g, 73%) from N-cyclopropyl-1-(4-{[3-(methylthio)propanoyl]amino}phenyl)-5-propyl-1H-1,2,3-triazole-4-carboxamide (0.19 g) obtained in Example 10 and Oxone (0.37 g).

NMR (CDCl$_3$) δ: 0.65-0.70 (2H, m), 0.84-0.89 (5H, m), 1.53-1.61 (2H, m), 2.87-3.06 (8H, m), 7.35-7.38 (3H, m), 7.70-7.73 (2H, m), 8.01 (1H, s).

Elemental analysis for $C_{19}H_{25}N_5O_4S$

Calcd. (%): C, 54.40; H, 6.01; N, 16.69.

Found (%): C, 54.11; H, 6.02; N, 16.66.

Example 15

3-[(4-{4-[(cyclopropylamino)carbonyl]-5-propyl-1H-1,2,3-triazol-1-yl}phenyl)amino]-3-oxopropanoic acid

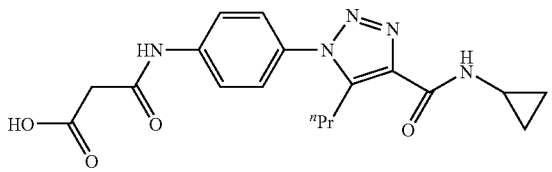

A solution of ethyl 3-[(4-{4-[(cyclopropylamino)carbonyl]-5-propyl-1H-1,2,3-triazol-1-yl}phenyl)amino]-3-oxopropanoate obtained in Example 12 and sodium carbonate (0.80 g) in methanol (10 ml)—water (10 ml) was heated under reflux for 2 hr, and the reaction mixture was concentrated under reduced pressure. The concentrate was acidified with 1N hydrochloric acid and extracted with ethyl acetate. The extract was washed with saturated brine and dried over magnesium sulfate. The solvent was evaporated under reduced pressure, and the residue was washed with diethyl ether to give the title compound as a colorless powder (0.83 g, 89%).

NMR (CDCl$_3$) δ: 0.64-0.75 (7H, m), 1.37-1.44 (2H, m), 2.85-2.91 (3H, m), 3.41 (2H, s), 7.51 (2H, d, J=9.0), 7.81 (2H, d, J=9.0), 8.59 (1H, d, J=4.5), 10.51 (1H, brs).

Elemental analysis for $C_{18}H_{21}N_5O_4 \cdot 0.1H_2O$

Calcd. (%): C, 57.93; H, 5.73; N, 18.77.

Found (%): C, 57.80; H, 5.75; N, 18.66.

Example 16

N-cyclopropyl-5-propyl-1-{4-[(trifluoroacetyl)amino]phenyl}-1H-1,2,3-triazole-4-carboxamide

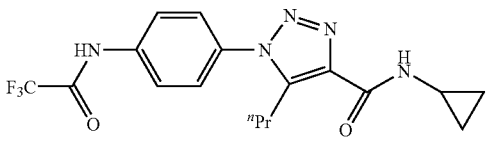

To a solution of 1-(4-aminophenyl)-N-cyclopropyl-5-propyl-1H-1,2,3-triazole-4-carboxamide (0.40 g) obtained in Example 1d) in dichloromethane (7 ml) were added triethylamine (0.21 ml) and trifluoroacetic anhydride (0.21 ml), and the mixture was stirred at room temperature for 3 days. The reaction mixture was diluted with dichloromethane, and washed with saturated aqueous sodium hydrogen carbonate solution and saturated brine. The organic layer was dried over magnesium sulfate, and the solvent was evaporated under reduced pressure. The residue was purified by high performance liquid chromatography and recrystallized from ethyl acetate-hexane to give the title compound as white needle crystals (0.23 g, 42%).

NMR (CDCl$_3$) δ: 0.65-0.70 (2H, m), 0.81-0.91 (5H, m), 1.51-1.61 (2H, m), 2.87-2.94 (1H, m), 2.97-3.03 (2H, m), 7.34-7.35 (1H, m), 7.46-7.50 (2H, m), 7.81-7.85 (2H, m), 8.18 (1H, s).

Elemental analysis for $C_{17}H_{18}N_5O_2F_3 \cdot 0.2H_2O$

Calcd. (%): C, 53.04; H, 4.82; N, 18.19.

Found (%): C, 53.04; H, 4.70; N, 18.19.

Example 17

4-[(4-{4-[(cyclopropylamino)carbonyl]-5-propyl-1H-1,2,3-triazol-1-yl}phenyl)amino]-4-oxobutanoic acid

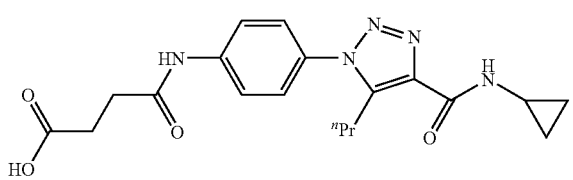

To a solution of 1-(4-aminophenyl)-N-cyclopropyl-5-propyl-1H-1,2,3-triazole-4-carboxamide (0.14 g) obtained in Example 1d) in chloroform (10 ml) was added succinic anhydride (0.06 mg), and the mixture was stirred at room temperature for 3 days. Diethyl ether was added to the reaction mixture, and the precipitated crystals were collected by filtration and washed with diethyl ether to give the title compound as a pale-brown powder (0.12 g, 63%).

NMR (DMSO-$d_6$) δ: 0.62-0.68 (4H, m), 0.72 (3H, t, J=7.4), 1.36-1.44 (2H, m), 2.53-2.64 (4H, m), 2.82-2.93 (3H, m), 7.47-7.51 (2H, m), 7.80-7.85 (2H, m), 8.60 (1H, d, J=4.7), 10.33 (1H, s), 12.17 (1H, brs).

Elemental analysis for $C_{19}H_{23}N_5O_4$

Calcd. (%): C, 59.21; H, 6.01; N, 18.17.

Found (%): C, 58.93; H, 5.99; N, 18.07.

Example 18

N-cyclopropyl-1-{4-[(N,N-dimethylglycyl)amino]phenyl}-5-propyl-1H-1,2,3-triazole-4-carboxamide

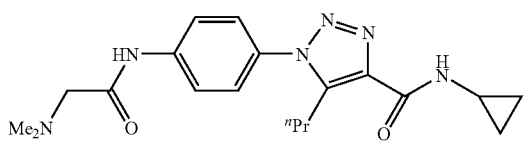

To a solution of N,N-dimethylglycine hydrochloride (0.17 mg), triethylamine (0.17 ml) and HOBt (0.18 g) in dichloromethane (10 ml) was added WSC (0.23 g), and the mixture was stirred at room temperature for 20 min. 1-(4-Aminophenyl)-N-cyclopropyl-5-propyl-1H-1,2,3-triazole-4-carboxamide (0.29 g) obtained in Example 1d) was added to the reaction mixture, and the mixture was stirred at room temperature for 3 days. The reaction mixture was diluted with dichloromethane, and washed with aqueous sodium hydrogen carbonate solution. The organic layer was dried over anhydrous magnesium sulfate, and the solvent was evaporated under reduced pressure. The residue was purified by high performance liquid chromatography to give the title compound as a white powder (0.09 g, 24%).

NMR (CDCl$_3$) δ: 0.63-0.71 (2H, m), 0.83-0.93 (5H, m), 1.48-1.76 (2H, m), 2.42 (6H, s), 2.84-3.02 (3H, m), 3.13 (2H, s), 7.36-7.41 (3H, m), 7.78-7.86 (2H, m), 9.40 (1H, s).

Elemental analysis for $C_{19}H_{26}N_6O_2$

Calcd. (%): C, 61.60; H, 7.07; N, 22.69.

Found (%): C, 60.94; H, 7.13; N, 22.31.

Example 19

N-cyclopropyl-1-{4-[(methoxyacetyl)amino]phenyl}-5-propyl-1H-1,2,3-triazole-4-carboxamide

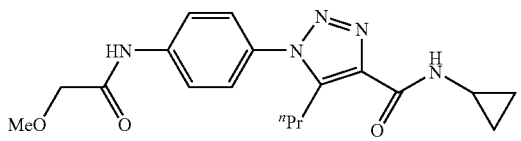

To a solution of 1-(4-aminophenyl)-N-cyclopropyl-5-propyl-1H-1,2,3-triazole-4-carboxamide (0.29 g) obtained in Example 1d) in acetonitrile (10 ml) were successively added methoxyacetic acid (0.08 ml), triethylamine (0.17 ml), HOBt (0.18 g) and WSC (0.23 g), and the mixture was stirred overnight at room temperature. The solvent was evaporated under reduced pressure, and the residue was dissolved in ethyl acetate and washed with saturated aqueous sodium hydrogen carbonate solution. The organic layer was dried over anhydrous magnesium sulfate, and the solvent was evaporated under reduced pressure. The residue was purified by silica gel column (ethyl acetate/hexane=1/1 to ethyl acetate), and the obtained product was recrystallized from ethanol-water to give the title compound as colorless needle crystals (0.16 g, 44%).

NMR (CDCl$_3$) δ: 0.63-0.71 (2H, m), 0.83-0.93 (5H, m), 1.52-1.63 (2H, m), 2.85-3.02 (3H, m), 3.55 (3H, s), 4.07 (2H, s), 7.37-7.42 (3H, m), 7.78-7.85 (2H, m), 8.50 (1H, brs).

Elemental analysis for $C_{18}H_{23}N_5O_3$

Calcd. (%): C, 60.49; H, 6.49; N, 19.59.

Found (%): C, 60.41; H, 6.43; N, 19.56.

Example 20

N-cyclopropyl-5-propyl-1-{4-[(2-thienylacetyl)amino]phenyl}-1H-1,2,3-triazole-4-carboxamide

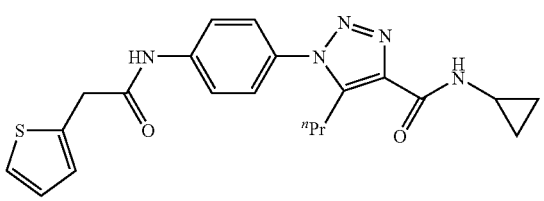

In the same manner as in Example 19, the title compound was obtained as a pale-yellow powder (0.08 g, 32%) from 1-(4-aminophenyl)-N-cyclopropyl-5-propyl-1H-1,2,3-triazole-4-carboxamide (0.17 g) obtained in Example 1d) and 2-thienylacetic acid (0.10 mg).

NMR (CDCl$_3$) δ: 0.64-0.69 (2H, m), 0.82-0.90 (5H, m), 1.48-1.61 (2H, m), 2.85-2.98 (3H, m), 4.01 (2H, s), 7.07-7.09 (2H, m), 7.33-7.36 (4H, m), 7.62 (1H, s), 7.68-7.70 (2H, m).

Elemental analysis for $C_{21}H_{23}N_5O_2S \cdot 0.5H_2O$

Calcd. (%): C, 60.27; H, 5.78; N, 16.73.

Found (%): C, 60.09; H, 5.55; N, 16.38.

Example 21

N-cyclopropyl-5-propyl-1-{4-[(3-thienylacetyl)amino]phenyl}-1H-1,2,3-triazole-4-carboxamide

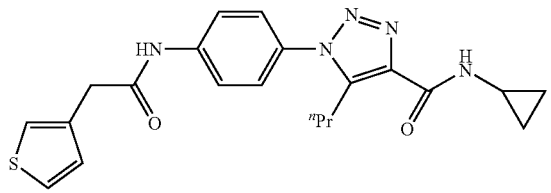

In the same manner as in Example 19, the title compound was obtained as a pale-yellow powder (0.06 g, 24%) from 1-(4-aminophenyl)-N-cyclopropyl-5-propyl-1H-1,2,3-triazole-4-carboxamide (0.17 g) obtained in Example 1d) and 3-thienylacetic acid (0.10 mg).

NMR (CDCl$_3$) δ: 0.64-0.69 (2H, m), 0.82-0.90 (5H, m), 1.51-1.59 (2H, m), 2.86-2.98 (3H, m), 3.83 (2H, s), 7.10 (1H, dd, J=1.3, 4.9), 7.27-7.28 (1H, m), 7.31-7.36 (3H, m), 7.43 (1H, dd, J=3.0, 4.9), 7.48 (1H, brs), 7.64-7.69 (2H, m).

Elemental analysis for $C_{21}H_{23}N_5O_2S \cdot 0.25H_2O$
Calcd. (%): C, 60.92; H, 5.72; N, 16.92.
Found (%): C, 60.93; H, 5.61; N, 16.98.

Example 22 tert-butyl {2-[(4-{4-[(cyclopropylamino)carbonyl]-5-propyl-1H-1,2,3-triazol-1-yl}phenyl)amino]-2-oxoethyl}carbamate

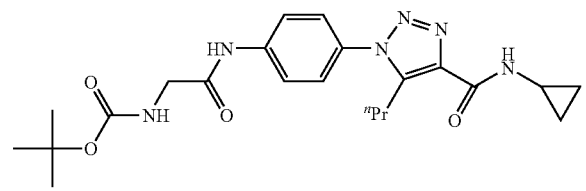

In the same manner as in Example 19, the title compound was obtained as a white powder (0.83 g, 58%) from 1-(4-aminophenyl)-N-cyclopropyl-5-propyl-1H-1,2,3-triazole-4-carboxamide (0.91 g) obtained in Example 1d) and N-(tert-butoxycarbonyl)glycine (0.67 g).

NMR (CDCl$_3$) δ: 0.64-0.70 (2H, m), 0.84-0.90 (5H, m), 1.50 (9H, s), 1.53-1.63 (2H, m), 2.85-3.00 (3H, m), 3.97 (2H, d, J=6.2), 5.25 (1H, brs), 7.35-7.39 (3H, m), 7.72-7.76 (2H, m), 8.59 (1H, brs).

Elemental analysis for $C_{22}H_{30}N_6O_4$
Calcd. (%): C, 59.71; H, 6.83; N, 18.99.
Found (%): C, 59.42; H, 6.74; N, 18.68.

Example 23

1-{4-[(N-acetylglycyl)amino]phenyl}-N-cyclopropyl-5-propyl-1H-1,2,3-triazole-4-carboxamide

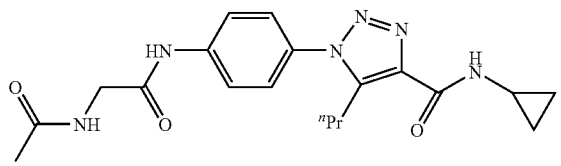

23a) N-cyclopropyl-1-[4-(glycylamino)phenyl]-5-propyl-1H-1,2,3-triazole-4-carboxamide To a suspension of tert-butyl {2-[(4-{4-[(cyclopropylamino)carbonyl]-5-propyl-1H-1,2,3-triazol-1-yl}phenyl)amino]-2-oxoethyl}carbamate (0.76 g) obtained in Example 22 in ethanol (5 ml) was added 6N hydrochloric acid in isopropyl alcohol solution (6 ml) at room temperature, and the mixture was stirred for 2 hr. The solvent was evaporated under reduced pressure to give the title compound as a white powder (0.64 g, 100%).

NMR (DMSO-d$_6$) δ: 0.64-0.75 (7H, m), 1.34-1.46 (2H, m), 2.83-2.95 (3H, m), 3.87 (2H, d, J=4.9), 7.57 (2H, d, J=8.9), 7.88 (2H, d, J=8.9), 8.30 (2H, brs), 8.62 (1H, d, J=4.5), 11.20 (1H, s).

23b) 1-{4-[(N-acetylglycyl)amino]phenyl}-N-cyclopropyl-5-propyl-1H-1,2,3-triazole-4-carboxamide In the same manner as in Example 3, the title compound was obtained as a white powder (0.12 g, 79%) from N-cyclopropyl-1-[4-(glycylamino)phenyl]-5-propyl-1H-1,2,3-triazole-4-carboxamide (0.15 g) obtained in Example 23a) and acetyl chloride (0.03 ml).

NMR (CDCl$_3$) δ: 0.63-0.75 (2H, m), 0.81-0.91 (5H, m), 1.50-1.63 (2H, m), 2.15 (3H, s), 2.87-2.93 (1H, m), 2.95-3.00 (2H, m), 4.17 (2H, d, J=5.3), 6.48 (1H, t, J=5.1), 7.34-7.38 (3H, m), 7.76-7.79 (2H, m), 9.11 (1H, s).

Elemental analysis for $C_{19}H_{24}N_6O_3$
Calcd. (%): C, 59.36; H, 6.29; N, 21.86.
Found (%): C, 59.21; H, 6.38; N, 21.89.

Example 24

N-cyclopropyl-1-{4-[(ethoxyacetyl)amino]phenyl}-5-propyl-1H-1,2,3-triazole-4-carboxamide

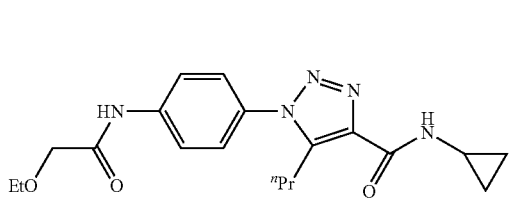

In the same manner as in Example 19, the title compound was obtained as a white powder (0.08 g, 31%) from 1-(4-aminophenyl)-N-cyclopropyl-5-propyl-1H-1,2,3-triazole-4-carboxamide (0.20 g) obtained in Example 1d) and ethoxyacetic acid (0.08 ml).

NMR (CDCl$_3$) δ: 0.65-0.71 (2H, m), 0.84-0.91 (5H, m), 1.33 (3H, t, J=7.0), 1.51-1.63 (2H, m), 2.86-2.93 (1H, m), 2.95-3.01 (2H, m), 3.70 (2H, q, J=7.0), 4.11 (2H, s), 7.31-7.41 (3H, m), 7.79-7.84 (2H, m) 8.53 (1H, s).

Elemental analysis for C$_{19}$H$_{25}$N$_5$O$_3$

Calcd. (%): C, 61.44; H, 6.78; N, 18.85.

Found (%): C, 61.07; H, 6.83; N, 18.63.

Example 25

N-cyclopropyl-5-propyl-1-{4-[(3,3,3-trifluoropropanoyl)amino]phenyl}-1H-1,2,3-triazole-4-carboxamide

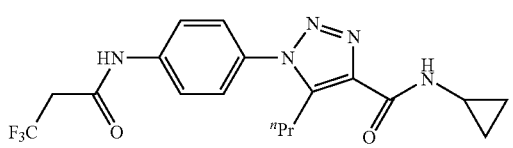

In the same manner as in Example 19, the title compound was obtained as a white powder (0.12 g, 43%) from 1-(4-aminophenyl)-N-cyclopropyl-5-propyl-1H-1,2,3-triazole-4-carboxamide (0.20 g) obtained in Example 1d) and 3,3,3-trifluoropropanoic acid (0.07 ml).

NMR (CDCl$_3$) δ: 0.65-0.70 (2H, m), 0.83-0.91 (5H, m), 1.52-1.60 (3H, m), 2.86-2.93 (1H, m), 2.94-3.00 (2H, m), 3.32 (2H, q, J=10.4), 7.34 (1H, s), 7.37-7.40 (2H, m), 7.71-7.74 (2H, m), 7.78 (1H, s).

Elemental analysis for C$_{18}$H$_{20}$N$_5$O$_2$F$_3$

Calcd. (%): C, 54.68; H, 5.10; N, 17.71.

Found (%): C, 54.30; H, 5.07; N, 17.66.

Example 26

1-[6-(acetylamino)pyridin-3-yl]-N-cyclopropyl-5-propyl-1H-1,2,3-triazole-4-carboxamide

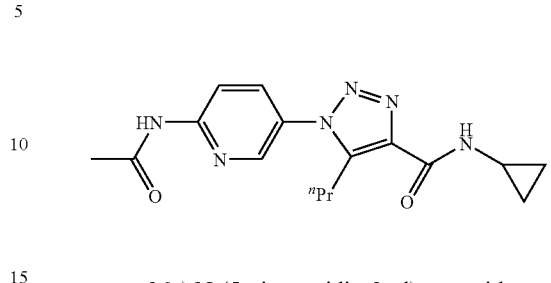

26a) N-(5-nitropyridin-2-yl)acetamide

In the same manner as in Example 17, the title compound was obtained as a pale-brown powder (2.4 g, 44%) from 2-amino-5-nitropyridine (4.2 g) and acetic anhydride (3.4 ml).

NMR (CDCl$_3$) δ: 2.29 (3H, s), 8.32 (1H, brs), 8.40 (1H, dd, J=0.6, 9.2), 8.50 (1H, ddd, J=0.4, 2.6, 9.2), 9.14 (1H, dd, J=0.6, 2.6).

26b) N-(5-aminopyridin-2-yl)acetamide

In the same manner as in Example 1d), the title compound was obtained as a yellow powder (2.0 g, 99%) from N-(5-nitropyridin-2-yl)acetamide (2.4 g) obtained in Example 26a).

NMR (DMSO-d$_6$) δ: 1.99 (3H, s), 5.01 (2H, s), 6.94 (1H, dd, J=3.0, 8.4), 7.65 (1H, d, J=2.6), 7.72 (1H, d, J=8.8), 9.96 (1H, s).

26c) N-(5-azidopyridin-2-yl)acetamide

In the same manner as in Example 1a), the title compound was obtained as a yellow powder (0.80 g, 75%) from N-(5-aminopyridin-2-yl)acetamide (0.91 g) obtained in Example 26b).

NMR (CDCl$_3$) δ: 2.21 (3H, s), 7.39 (1H, dd, J=2.8, 8.9), 8.00 (1H, d, J=2.7), 8.25 (1H, d, J=8.7), 8.44 (1H, brs).

26d) methyl 1-[6-(acetylamino)pyridin-3-yl]-5-propyl-1H-1,2,3-s triazole-4-carboxylate To a solution of N-(5-azidopyridin-2-yl)acetamide (1.42 g) obtained in Example 26c) and ethyl 3-keto-n-hexanoate (1.5 ml) in methanol (40 ml) was added 28% sodium methoxide in methanol solution (1.7 ml), and the mixture was stirred at room temperature for 4 hr. The reaction mixture was diluted with ethyl acetate and washed with saturated brine. The organic layer was dried over anhydrous magnesium sulfate, and the solvent was evaporated under reduced pressure. The residue was purified by silica gel column (ethyl acetate/hexane=1/1) to give the title compound as a pale-yellow oil (0.55 g, 23%).

NMR (CDCl$_3$) δ: 0.88 (3H, t, J=7.4), 1.51-1.63 (2H, m), 2.31 (3H, s), 2.92-2.98 (2H, m), 4.00 (3H, s), 7.78-7.83 (1H, m), 8.38-8.39 (1H, m), 8.46-8.49 (1H, m), 8.88 (1H, brs).

26e) 1-[6-(acetylamino)pyridin-3-yl]-N-cyclopropyl-5-propyl-1H-1,2,3-triazole-4-carboxamide To a solution of methyl 1-[6-(acetylamino)pyridin-3-yl]-5-propyl-1H-1,2,3-triazole-4-carboxylate (0.55 g) obtained in Example 26d) in ethanol (5 ml) was added 8N aqueous sodium hydroxide solution (0.45 ml), and the mixture was stirred at room temperature for 2 hr. The solvent was evaporated under reduced pressure, toluene (5 ml) was added to the residue. The solvent was evaporated under reduced pressure. To a solution of the residue in acetonitrile (10 ml) was added 4N hydrochloric acid-ethyl acetate solution (0.9 ml) to give a solution of 1-[6-(acetylamino)pyridin-3-yl]-5-propyl-1H-1,2,3-triazole-4-carboxylic acid in acetonitrile. Then, cyclopropylamine (0.15 ml), triethylamine (0.31 ml), HOBt (0.34 g) and WSC (0.42 g) were successively added, and the mixture was stirred overnight at room temperature. The solvent was evaporated under reduced pressure, the residue was dissolved in ethyl acetate and washed with aqueous sodium hydrogen carbonate solution. The organic layer was dried over anhydrous magnesium sulfate, and the solvent was evaporated under reduced pressure. The residue was purified by silica gel column (ethyl acetate/hexane=1/1 to ethyl acetate) to give the title compound as a pale-green powder (0.22 g, 41%).

NMR (CDCl$_3$) δ: 0.65-0.70 (2H, m), 0.85-0.91 (5H, m), 1.53-1.63 (2H, m), 2.29 (3H, s), 2.86-2.94 (1H, s), 2.96-3.01 (2H, m), 7.35 (1H, brs), 7.77 (1H, dd, J=2.5, 8.9), 8.24 (1H, brs), 8.36-8.37 (1H, m), 8.46 (1H, d, J=8.9).

Elemental analysis for C$_{16}$H$_{20}$N$_6$O$_2$·0.1AcOEt

Calcd. (%): C, 58.42; H, 6.22; N, 24.92.

Found (%): C, 58.73; H, 5.94; N, 24.72.

Example 27

N-cyclopropyl-1-(4-{[(ethylamino)carbonyl]amino}phenyl)-5-propyl-1H-1,2,3-triazole-4-carboxamide

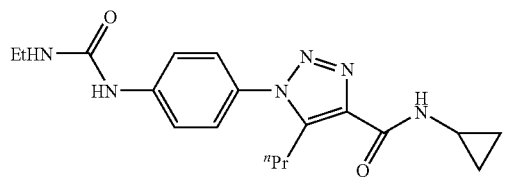

To a solution of 1-(4-aminophenyl)-N-cyclopropyl-5-propyl-1H-1,2,3-triazole-4-carboxamide (0.40 g) obtained in Example 1d) and DMAP (0.34 g) in dichloromethane (14 ml) was added ethyl isocyanate (0.79 ml) at room temperature and the mixture was stirred for 3 hr. The reaction mixture was diluted with dichloromethane, and washed with saturated aqueous sodium hydrogen carbonate solution. The organic layer was dried over magnesium sulfate, and the solvent was evaporated under reduced pressure. The residue was purified by silica gel column (ethyl acetate/hexane=1/1 to ethyl acetate), and the obtained product was recrystallized from ethyl acetate-diethyl ether to give the title compound as a white powder (0.12 g, 49%).

NMR (CDCl$_3$) δ: 0.64-0.70 (2H, m), 0.81-0.91 (5H, m), 1.19 (3H, t, J=7.2), 1.49-1.59 (2H, m), 2.87-2.98 (3H, m), 3.29-3.38 (2H, m), 5.02 (1H, t, J=5.5), 7.03 (1H, s), 7.27-7.31 (2H, m), 7.36 (1H, d, J=3.0), 7.52-7.57 (2H, m).

Elemental analysis for C$_{18}$H$_{24}$N$_6$O$_2$

Calcd. (%): C, 60.66; H, 6.79; N, 23.58.

Found (%): C, 60.37; H, 6.82; N, 23.34.

Example 28

1-(4-{[(benzylamino)carbonyl]amino}phenyl)-N-cyclopropyl-5-propyl-1H-1,2,3-triazole-4-carboxamide

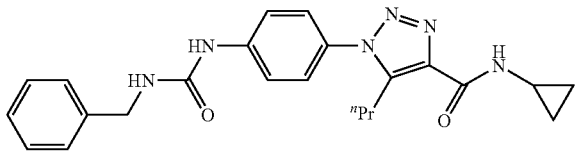

To a solution of triphosgene (0.08 g) in dichloromethane (7 ml) was added dropwise a solution of 1-(4-aminophenyl)-N-cyclopropyl-5-propyl-1H-1,2,3-triazole-4-carboxamide (0.21 g) obtained in Example 1d) and N,N-diisopropylethylamine (0.13 ml) in dichloromethane (3 ml) under ice-cooling, and the mixture was stirred under ice-cooling for 30 min. A solution of benzylamine (0.12 ml) and N,N-diisopropylethylamine (0.13 ml) in dichloromethane (3 ml) was added. The mixture was stirred at room temperature for 20 hr and diluted with ethyl acetate. The ethyl acetate solution was washed with water and saturated brine and dried over anhydrous magnesium sulfate. The solvent was evaporated under reduced pressure, and the residue was purified by silica gel column (hexane/ethyl acetate=1/1 to ethyl acetate). The resultant product was recrystallized from diethyl ether/methanol to give the title compound as a colorless powder (0.16 g, 52%).

NMR (CDCl$_3$) δ: 0.63-0.68 (4H, m), 0.84 (3H, t, J=7.3), 1.51-1.59 (2H, m), 2.83-2.90 (2H, m), 2.95 (1H, t, J=7.9), 4.49 (2H, d, J=5.6), 5.14 (1H, t, J=5.6), 6.72 (1H, s), 7.26-7.34 (6H, m), 7.53 (2H, d, J=8.9).

Elemental analysis for C$_{23}$H$_{26}$N$_6$O$_2$·0.1AcOEt

Calcd. (%): C, 65.77; H, 6.32; N, 19.67.

Found (%): C, 66.08; H, 6.08; N, 19.57.

Example 29

N-cyclopropyl-5-propyl-1-(4-{[(propylamino)carbonyl]amino}phenyl)-1H-1,2,3-triazole-4-carboxamide

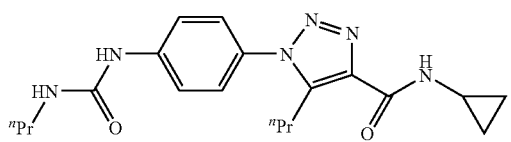

In the same manner as in Example 28, the title compound was obtained as a colorless powder (0.14 g, 54%) from 1-(4-aminophenyl)-N-cyclopropyl-5-propyl-1H-1,2,3-triazole-4-carboxamide (0.20 g) obtained in Example 1d).

NMR (CDCl$_3$) δ: 0.64-0.69 (2H, m), 0.85 (2H, t, J=7.3), 0.97 (6H, t, J=7.5), 1.50-1.65 (4H, m), 2.85-2.92 (2H, m), 2.96 (1H, t, J=7.9), 3.26 (2H, dd, J=7.0, 5.8), 4.87 (1H, t, J=5.5), 6.74 (1H, s), 7.29 (2H, d, J=8.9), 7.54 (2H, d, J=8.9).

Elemental analysis for C$_{19}$H$_{26}$N$_6$O$_2$

Calcd. (%): C, 61.60; H, 7.09; N, 22.36.

Found (%): C, 61.49; H, 7.09; N, 22.36.

Example 30

N-cyclopropyl-1-[4-({[(4-methoxyphenyl)amino]carbonyl}amino)phenyl]-5-propyl-1H-1,2,3-triazole-4-carboxamide

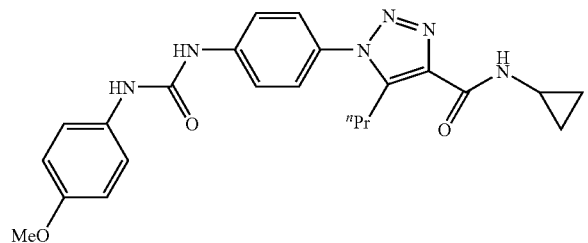

In the same manner as in Example 28, the title compound was obtained as a colorless powder (0.06 g, 20%) from 1-(4-aminophenyl)-N-cyclopropyl-5-propyl-1H-1,2,3-triazole-4-carboxamide (0.21 g) obtained in Example 1d).

NMR (CDCl$_3$) δ: 0.64-0.69 (2H, m), 0.85 (3H, t, J=7.4), 0.87 (2H, q, J=5.3), 1.50-1.62 (2H, m), 2.85-2.92 (2H, m), 2.96 (1H, t, J=7.9), 3.84 (3H, s), 6.44 (1H, s), 6.79 (1H, s), 6.94 (2H, d, J=8.9), 7.28 (2H, d, J=8.9), 7.31 (2H, d, J=8.9), 7.57 (2H, d, J=8.9).

Elemental analysis for C$_{23}$H$_{26}$N$_6$O$_3$
Calcd. (%): C, 63.06; H, 6.07; N, 19.18.
Found (%): C, 62.76; H, 5.77; N, 19.26.

Example 31

N-cyclopropyl-1-(4-{[(methylamino)carbonyl]amino}phenyl)-5-propyl-1H-1,2,3-triazole-4-carboxamide

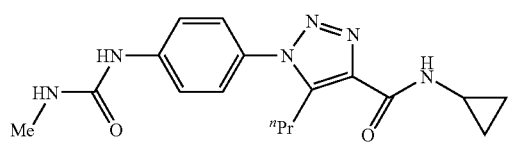

In the same manner as in Example 28, the title compound was obtained as a colorless powder (0.10 g, 34%) from 1-(4-aminophenyl)-N-cyclopropyl-5-propyl-1H-1,2,3-triazole-4-carboxamide (0.24 g) obtained in Example 1d).

NMR (CDCl$_3$) δ: 0.65-0.71 (2H, m), 0.82-0.88 (5H, m), 1.52-1.60 (2H, m), 2.90 (5H, d, J=4.9), 2.94-3.01 (1H, m), 4.85 (1H, d, J=4.7), 6.77 (1H, s), 7.30 (2H, d, J=8.7), 7.55 (2H, d, J=8.7), 7.93 (1H, s).

Elemental analysis for C$_{17}$H$_{22}$N$_6$O$_2$
Calcd. (%): C, 59.63; H, 6.48; N, 24.54.
Found (%): C, 59.69; H, 6.38; N, 24.35.

Example 32

1-{4-[(anilinocarbonyl)amino]phenyl}-N-cyclopropyl-5-propyl-1H-1,2,3-triazole-4-carboxamide

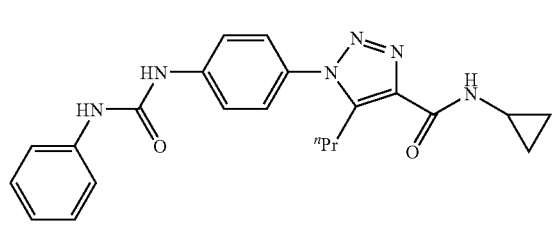

In the same manner as in Example 28, the title compound was obtained as a colorless powder (0.10 g, 23%) from 1-(4-aminophenyl)-N-cyclopropyl-5-propyl-1H-1,2,3-triazole-4-carboxamide (0.32 g) obtained in Example 1d).

NMR (CDCl$_3$) δ: 0.65-0.70 (2H, m), 0.82 (3H, t, J=7.5), 0.85-0.91 (2H, m), 1.55 (2H, q, J=7.5), 2.86-2.95 (1H, m), 2.95 (2H, t, J=7.7), 7.13 (1H, t, J=7.0), 7.28 (2H, d, J=8.9), 7.31-7.40 (5H, m), 7.54 (1H, d, J=6.6), 7.55 (2H, d, J=8.9).

Elemental analysis for C$_{22}$H$_{24}$N$_6$O$_2$·0.1AcOEt
Calcd. (%): C, 65.10; H, 6.05; N, 20.34.
Found (%): C, 64.91; H, 6.05; N, 20.36.

Example 33

N-cyclopropyl-1-(4-{[(methoxyamino)carbonyl]amino}phenyl)-5-propyl-1H-1,2,3-triazole-4-carboxamide

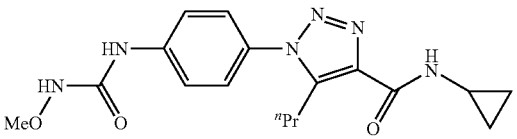

In the same manner as in Example 28, the title compound was obtained as a colorless powder (0.28 g, 44%) from 1-(4-aminophenyl)-N-cyclopropyl-5-propyl-1H-1,2,3-triazole-4-carboxamide (0.50 g) obtained in Example 1d).

NMR (CDCl$_3$) δ: 0.65-0.70 (2H, m), 0.87 (3H, t, J=7.3), 0.85-0.91 (2H, m), 1.58-1.60 (2H, m), 2.86-2.94 (1H, m), 2.98 (2H, t, J=7.9), 3.84 (3H, s), 7.38 (2H, d, J=8.7), 7.48 (1H, s), 7.72 (2H, d, J=8.7), 7.77 (1H, s).

Elemental analysis for C$_{17}$H$_{22}$N$_6$O$_3$
Calcd. (%): C, 56.97; H, 6.19; N, 23.45.
Found (%): C, 56.93; H, 6.17; N, 23.17.

Example 34

N-cyclopropyl-5-propyl-1-[4-({[(2,2,2-trifluoroethyl)amino]carbonyl}amino)phenyl]-1H-1,2,3-triazole-4-carboxamide

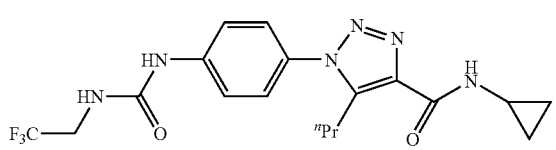

In the same manner as in Example 28, the title compound was obtained as a colorless powder (0.58 g, 90%) from 1-(4-aminophenyl)-N-cyclopropyl-5-propyl-1H-1,2,3-triazole-4-carboxamide (0.45 g) obtained in Example 1d).

NMR (CDCl$_3$) δ: 0.65-0.70 (2H, m), 0.82 (3H, t, J=7.4), 0.85-0.91 (2H, m), 1.47-1.60 (2H, m), 2.85-2.93 (1H, m), 2.94 (2H, t, J=7.7), 3.96 (2H, qd, J=9.0, 6.6), 5.85 (1H, t, J=6.6), 7.28 (2H, d, J=8.7), 7.89 (1H, d, J=3.0), 7.55 (2H, d, J=8.7), 7.78 (1H, s).

Elemental analysis for C$_{18}$H$_{21}$N$_6$O$_2$F$_3$
Calcd. (%): C, 52.68; H, 5.16; N, 20.48.
Found (%): C, 52.54; H, 5.33; N, 20.20.

Example 35

N-cyclopropyl-1-(4-{[(dimethylamino)carbonyl]amino}phenyl)-5-propyl-1H-1,2,3-triazole-4-carboxamide

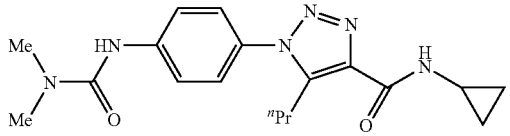

To a solution of 1-(4-aminophenyl)-N-cyclopropyl-5-propyl-1H-1,2,3-triazole-4-carboxamide (0.32 g) obtained in Example 1d) and triethylamine (1.5 ml) in dichloromethane (7 ml) was added dimethylcarbamoyl chloride (0.15 g) under ice-cooling. The mixture was stirred at room temperature for 4 hr, N,N-dimethylpyridin-4-amine (0.14 g) was added, and the mixture was further stirred at room temperature for 15 hr. The reaction mixture was concentrated under reduced pressure, and the residue was dissolved in ethyl acetate. The ethyl acetate solution was washed with 1N hydrochloric acid and saturated brine and dried over anhydrous magnesium sulfate. The solvent was evaporated under reduced pressure, the residue was purified by silica gel column (hexane/ethyl acetate=7/3 to ethyl acetate), and the resultant product was recrystallized from ethanol to give the title compound as a colorless powder (0.26 g, 64%).

NMR (CDCl$_3$) δ: 0.64-0.69 (2H, m), 0.82-0.90 (5H, m), 1.56 (2H, q, J=7.5), 2.86-2.92 (1H, m), 2.96 (2H, t, J=8.1), 3.07 (6H, s), 6.89 (1H, s), 7.29 (2H, d, J=8.7), 7.38 (1H, s), 7.62 (2H, d, j=8.7).

Elemental analysis for C$_{18}$H$_{24}$N$_6$O$_2$.0.1AcOEt
Calcd. (%): C, 60.51; H, 6.84; N, 23.01.
Found (%): C, 60.43; H, 7.17; N, 22.90.

Example 36

N-(4-{4-[(cyclopropylamino)carbonyl]-5-propyl-1H-1,2,3-triazol-1-yl}phenyl)morpholine-4-carboxamide

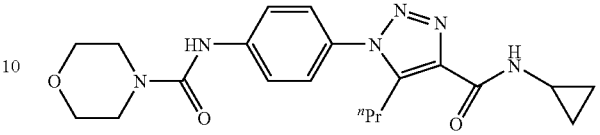

In the same manner as in Example 35, the title compound was obtained as a colorless powder (0.39 g, 88%) from 1-(4-aminophenyl)-N-cyclopropyl-5-propyl-1H-1,2,3-triazole-4-carboxamide (0.32 g) obtained in Example 1d).

NMR (CDCl$_3$) δ: 0.64-0.69 (2H, m), 0.80-0.90 (5H, m), 1.48-1.61 (2H, m), 2.84-2.91 (1H, m), 2.95 (2H, t, J=8.1), 3.55 (4H, t, J=4.5), 3.74 (4H, t, J=4.5), 7.28 (2H, d, J=8.5), 7.86 (1H, s), 7.43 (1H, d, J=3.0), 7.61 (2H, d, J=8.5).

Elemental analysis for C$_{20}$H$_{26}$N$_6$O$_3$
Calcd. (%): C, 60.29; H, 6.58; N, 21.09.
Found (%): C, 60.15; H, 6.73; N, 22.02.

Example 37

N-cyclopropyl-5-propyl-1-{4-[(pyrrolidin-1-ylcarbonyl)amino]phenyl}-1H-1,2,3-triazole-4-carboxamide

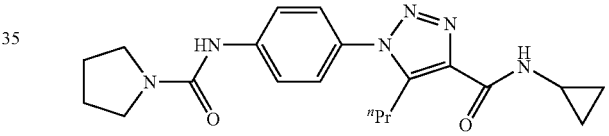

In the same manner as in Example 35, the title compound was obtained as a colorless powder (0.29 g, 88%) from 1-(4-aminophenyl)-N-cyclopropyl-5-propyl-1H-1,2,3-triazole-4-carboxamide (0.34 g) obtained in Example 1d).

NMR (CDCl$_3$) δ: 0.64-0.69 (2H, m), 0.86 (5H, t, J=7.4), 1.57 (2H, q, J=7.7), 2.01 (4H, t, J=6.6), 2.85-2.93 (1H, m), 2.96 (2H, t, J=7.9), 3.51 (4H, t, J=6.6), 6.40 (1H, s), 7.31 (2H, d, J=8.9), 7.83 (1H, s), 7.64 (2H, d, J=8.9).

Elemental analysis for C$_{20}$H$_{26}$N$_6$O$_2$
Calcd. (%): C, 62.81; H, 6.85; N, 21.97.
Found (%): C, 62.63; H, 6.83; N, 22.02.

Example 38

N-cyclopropyl-1-(4-{[(diethylamino)carbonyl]amino}phenyl)-5-propyl-1H-1,2,3-triazole-4-carboxamide

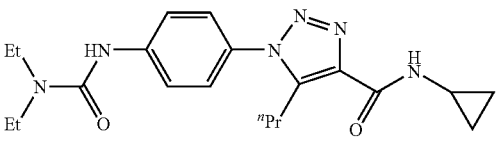

In the same manner as in Example 35, the title compound was obtained as a colorless powder (0.12 g, 24%) from 1-(4-aminophenyl)-N-cyclopropyl-5-propyl-1H-1,2,3-triazole-4-carboxamide (0.38 g) obtained in Example 1d).

NMR (CDCl$_3$) δ: 0.64-0.69 (2H, m), 0.85 (5H, t, J=7.4), 1.26 (6H, t, J=7.2), 1.50-1.62 (2H, m), 2.85-2.92 (1H, m), 2.96 (2H, t, J=7.9), 3.42 (4H, q, J=7.2), 6.62 (1H, s), 7.30 (2H, d, J=8.9), 7.84 (1H, s), 7.62 (2H, d, J=8.9).

Elemental analysis for C$_{20}$H$_{28}$N$_6$O$_2$.0.1EtOH
Calcd. (%): C, 62.24; H, 7.48; N, 21.35.
Found (%): C, 61.94; H, 7.45; N, 21.59.

Example 39

1-{4-[(aminocarbonyl)amino]phenyl}-N-cyclopropyl-5-propyl-1H-1,2,3-triazole-4-carboxamide

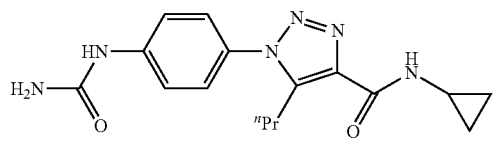

To a solution of 4-nitrophenyl chloroformate (1.06 g) in dichloromethane (15 ml) was added dropwise a solution of 1-(4-aminophenyl)-N-cyclopropyl-5-propyl-1H-1,2,3-triazole-4-carboxamide (1.0 g) obtained in Example 1d) and N,N-dimethylpyridin-4-amine (0.65 g) in dichloromethane (15 ml) under ice-cooling. The reaction mixture was stirred at room temperature for 7 hr, a solution (2M, 18 ml) of ammonia in methanol was added, and the mixture was further stirred for 10 hr. Ethyl acetate was added to the reaction mixture, and the resulting insoluble material was collected by filtration and recrystallized from methanol/ethyl acetate to give the title compound as a colorless powder (0.91 g, 80%).

NMR (DMSO-d$_6$) δ: 0.64-0.69 (4H, m), 0.74 (3H, t, J=7.3), 1.41 (2H, qt, J=7.7, 7.3), 2.82-2.92 (3H, m), 6.12 (2H, br), 7.38 (2H, d, J=8.9), 7.65 (2H, d, J=8.9), 8.57 (1H, d, J=4.7), 9.31 (1H, br).

Elemental analysis for C$_{16}$H$_{20}$N$_6$O$_2$
Calcd. (%): C, 58.52; H, 6.14; N, 25.59.
Found (%): C, 58.81; H, 5.98; N, 25.75.

Example 40 tert-butyl 4-{5-(3-buten-1-yl)-4-[(cyclopropylamino)carbonyl]-1H-1,2,3-triazol-1-yl}phenylcarbamate

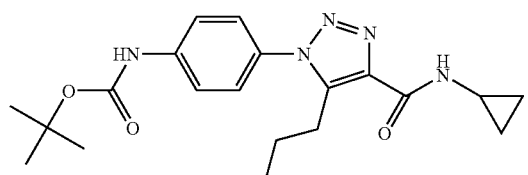

40a) tert-butyl (4-aminophenyl)carbamate

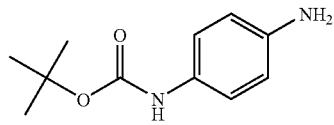

To a solution of p-phenylenediamine (16.2 g) and triethylamine (20.8 ml) in DMF (80 ml) was added di-tert-butyl carbonate (34.4 ml). The reaction mixture was stirred at room temperature for 8 hr and diluted with ethyl acetate. The ethyl acetate solution was washed with water and saturated brine and dried over anhydrous magnesium sulfate, and the solvent was evaporated. The residue was purified by silica gel column (hexane/ethyl acetate=4/1 to ethyl acetate), and the resultant product was recrystallized from ethyl acetate/hexane to give the title compound as a colorless powder (29.2 g, 95%).

NMR (CDCl$_3$) δ: 1.51 (9H, s), 6.60 (2H, d, J=6.0), 7.29 (2H, d, J=6.0).

40b) methyl 3-oxo-6-heptenoate

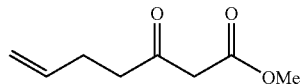

To a solution of Meldrum's acid (22.0 g) and pyridine (25.0 ml) in dichloromethane (100 ml) was added dropwise pent-4-enoyl chloride (18.5 ml) under ice-cooling. The reaction mixture was stirred at room temperature for 10 hr, and washed with water and 1M hydrochloric acid. The organic layer was dried over anhydrous magnesium sulfate, and the solvent was evaporated. The residue was dissolved in methanol (150 ml), and the mixture was stirred with heating under reflux for 8 hr. After cooling the reaction mixture to room temperature, the solvent was evaporated under reduced pressure. The residue was purified by silica gel column (hexane/ethyl acetate=10/1 to hexane/ethyl acetate=5/1) to give the title compound as a pale-yellow liquid (4.57 g, 40%).

NMR (CDCl$_3$) δ: 2.32-2.39 (2H, m), 2.65 (2H, t, J=6.9), 3.46 (2H, s), 3.74 (3H, s), 4.98-5.08 (2H, m), 5.76-5.85 (1H, m).

40c) butyl 5-(3-buten-1-yl)-1-{4-[(tert-butoxycarbonyl)amino]phenyl}-1H-1,2,3-triazole-4-carboxylate

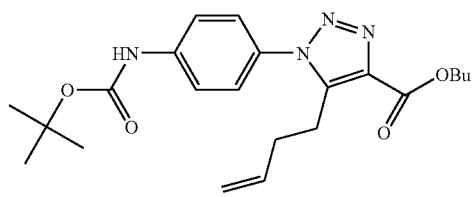

To a solution of tert-butyl (4-aminophenyl)carbamate (6.00 g) obtained in Example 40a) and methyl 3-oxo-6-heptenoate (4.57 g) obtained in Example 40b) in n-butanol (80 ml) was added concentrated sulfuric acid (3 drops). The reaction mixture was stirred with heating under reflux for 6 hr while dehydrating by a Dean-Stark trap. The reaction mixture was cooled to room temperature, and the solvent was evaporated under reduced pressure. To a solution of the residue and triethylamine (6.0 ml) in acetonitrile (80 ml) was added p-dodecylbenzenesulfonyl azide (15.0 g), and the reaction mixture was stirred with heating under reflux for 6 hr. The reaction mixture was cooled to room temperature, 10% aqueous sodium nitrite solution (100 ml) was added, and the mixture was extracted with ethyl acetate. The extract was dried over anhydrous magnesium sulfate, and the solvent was evaporated. The residue was purified by basic silica gel column (hexane/ethyl acetate=9/1 to hexane/ethyl acetate=6/4) to give the title compound as a pale-yellow powder (9.98 g, 86%).

NMR (CDCl$_3$) δ: 0.98 (3H, t, J=7.5), 1.42-1.53 (2H, m), 1.54 (9H, s), 1.80 (2H, q, J=6.9), 2.28 (2H, q, J=6.8), 3.05 (2H, t, J=7.8), 4.40 (2H, t, J=6.0), 4.88-4.95 (2H, m), 5.57-5.71 (1H, m), 6.84 (1H, br), 7.34 (2H, d, J=8.7), 7.58 (2H, d, J=8.7).

40d) tert-butyl 4-{5-(3-buten-1-yl)-4-[(cyclopropylamino)carbonyl]-1H-1,2,3-triazol-1-yl}phenylcarbamate A solution of butyl 5-(3-buten-1-yl)-1-{4-[(tert-butoxycarbonyl)amino]phenyl}-1H-1,2,3-triazole-4-carboxylate obtained in Example 40c) and 8M aqueous sodium hydroxide solution (15 ml) in tetrahydrofuran (50 ml)—methanol (80 ml)—water (15 ml) was stirred at room temperature for 4 hr, and the mixture was acidified with 1M hydrochloric acid. The reaction mixture was extracted with ethyl acetate, the extract was washed with saturated brine, and dried over anhydrous magnesium sulfate, and the solvent was evaporated. The residue was recrystallized from ethyl acetate/hexane to give a brown powder (5.72 g, 70%). To a solution of the obtained powder, cyclopropylamine (1.32 ml), HOBt (2.91 g) and triethylamine (2.65 ml) in dichloromethane (100 ml) was added WSC (3.70 g) under ice-cooling. The reaction mixture was stirred at room temperature for 8 hr, and washed with saturated brine. The organic layer was dried over anhydrous magnesium sulfate, and the solvent was evaporated. The residue was purified by silica gel column (hexane/ethyl acetate=1/1) to give the title compound as a colorless solid (5.85 g, 93%).

NMR (CDCl$_3$) δ: 0.64-0.70 (2H, m), 0.84-0.91 (2H, m), 1.54 (9H, s), 2.31 (2H, td, J=7.7, 6.8), 2.86-2.94 (1H, m), 3.10 (2H, t, J=7.9), 4.88-4.89 (1H, m), 4.91-4.95 (1H, m), 5.59-5.73 (1H, m), 6.74 (1H, br), 7.33 (2H, d, J=8.9), 7.33-7.35 (1H, m), 7.58 (2H, d, J=8.9).

Example 41

5-(3-buten-1-yl)-N-cyclopropyl-1-(4-{[(ethylamino)carbonyl]amino}phenyl)-1H-1,2,3-triazole-4-carboxamide

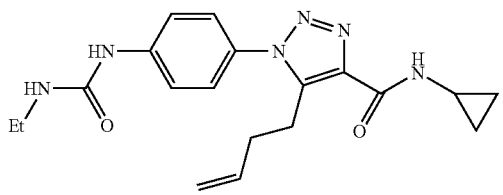

To a solution of tert-butyl 4-{5-(3-buten-1-yl)-4-[(cyclopropylamino)carbonyl]-1H-1,2,3-triazol-1-yl}phenylcarbamate (1.58 g) obtained in Example 40d) in dichloromethane (20 ml) was added trifluoroacetic acid (5.0 ml). The reaction mixture was stirred at room temperature for 11 hr and the solvent was evaporated under reduced pressure. The residue was dissolved in chloroform, and washed with 1M aqueous sodium hydroxide solution. The organic layer was dried over anhydrous sodium sulfate, and the solvent was evaporated to give a brown solid. A solution of the obtained solid residue and N,N-dimethylpyridin-4-amine (0.60 g) in dichloromethane (15 ml) was added dropwise to a solution of 4-nitrophenyl chloroformate (1.17 g) in dichloromethane (15 ml) under ice-cooling. The reaction mixture was stirred at room temperature for 8 hr, and a solution (2M, 9.7 ml) of ethylamine in tetrahydrofuran was added. After further stirring for 1 hr, the reaction mixture was diluted with ethyl acetate, washed with 1M aqueous sodium hydroxide solution and saturated brine, and dried over anhydrous magnesium sulfate. The solvent was evaporated. The residue was purified by silica gel column (hexane/ethyl acetate=2/3 to ethyl acetate), and the resultant product was recrystallized from ethyl acetate/hexane to give the title compound as colorless crystals (1.03 g, 73%).

NMR (CDCl$_3$) δ: 0.63-0.71 (2H, m), 0.83-0.93 (2H, m), 1.19 (3H, t, J=6.8), 2.24-2.35 (2H, m), 2.86-2.94 (1H, m), 3.08 (2H, t, J=5.0), 3.33 (2H, q, J=6.8), 4.84-4.85 (1H, m), 4.91-4.93 (1H, m), 5.14 (1H, t, J=5.4), 5.53-5.70 (1H, m), 7.23 (1H, d, J=7.6), 7.27 (2H, d, J=8.8), 7.37 (1H, d, J=3.2), 7.55 (2H, d, J=8.8).

Elemental analysis for C$_{19}$H$_{24}$N$_6$O$_2$
Calcd. (%): C, 61.94; H, 6.57; N, 22.81.
Found (%): C, 62.00; H, 6.60; N, 22.89.

Example 42

N-cyclopropyl-5-(3,4-dihydroxybutyl)-1-(4-{[(ethylamino)carbonyl]amino}phenyl)-1H-1,2,3-triazole-4-carboxamide

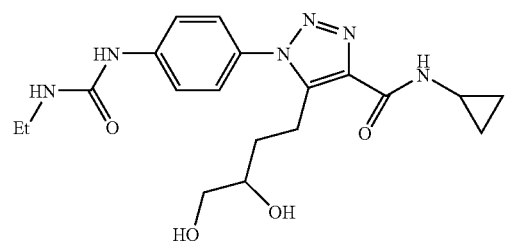

To a solution of 5-(3-buten-1-yl)-N-cyclopropyl-1-(4-{[(ethylamino)carbonyl]amino}phenyl)-1H-1,2,3-triazole-4-carboxamide obtained in Example 41 in acetone (3 ml)-acetonitrile (3 ml)—water (3 ml) were added N-methylmorpholine N-oxide (0.18 g) and microencapsulated osmium tetroxide (containing 10%, 0.5 g). The reaction mixture was stirred at room temperature for 4 days, and the insoluble material was filtered off. The solvent was evaporated under reduced pressure, and the residue was purified by silica gel column (ethyl acetate/methanol=9/1 to ethyl acetate/methanol=7/3). The resultant product was recrystallized from ethyl acetate/hexane to give the title compound as colorless crystals (0.12 g, 23%).

NMR (CDCl$_3$) δ: 0.63-0.70 (4H, m), 1.07 (3H, t, J=7.2), 1.28-1.40 (1H, m), 1.56-1.67 (1H, m), 2.83-2.92 (1H, m), 2.94-3.00 (2H, m), 3.09-3.24 (3H, m), 4.41 (1H, t, J=5.5), 4.53 (1H, d, J=4.7), 6.26 (1H, t, J=5.5), 7.39 (2H, d, J=9.1), 7.61 (2H, d, J=9.1), 8.60 (1H, d, J=4.7), 8.83 (1H, s).

Elemental analysis for $C_{19}H_{26}N_6O_4 \cdot 0.1H_2O$
Calcd. (%): C, 56.45; H, 6.53; N, 20.79.
Found (%): C, 56.22; H, 6.48; N, 20.57.

Example 43

N-cyclopropyl-1-{4-[(ethylamino)carbonyl]phenyl}-5-propyl-1H-1,2,3-triazole-4-carboxamide

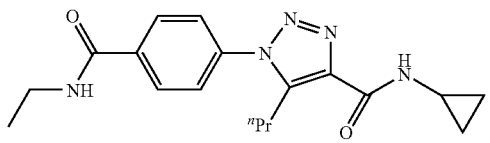

43a) 4-azido-N-ethylbenzamide

To a solution of 4-azidobenzoic acid (0.65 g) in acetonitrile-DMF (2:1, 15 ml) were successively added 2M ethylamine in THF solution (2.4 ml), triethylamine (0.67 ml), HOBt (0.79 g) and WSC (0.92 g), and the mixture was stirred overnight at room temperature. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure to give the title compound as a pale-yellow powder (0.73 g, 96%).

NMR (CDCl$_3$) δ: 1.26 (3H, t, J=7.4), 3.50 (2H, dq, J=5.7, 7.3), 6.07 (1H, brs), 7.04-7.09 (2H, m), 7.75-7.79 (2H, m).

43b) 1-{4-[(ethylamino)carbonyl]phenyl}-5-propyl-1H-1,2,3-triazole-4-carboxylic acid To a solution of 4-azido-N-ethylbenzamide (0.73 g) obtained in Example 43a) and ethyl 3-keto-n-hexanoate (0.77 ml) in ethanol (20 ml) was added 20% sodium ethoxide in ethanol solution (1.85 ml) at room temperature, and the mixture was stirred overnight at 60° C. The reaction mixture was cooled to room temperature, and the solvent was evaporated under reduced pressure. The residue was diluted with water, and washed with ethyl acetate. The aqueous layer was acidified with 1N hydrochloric acid, and extracted with ethyl acetate. The extract was dried over anhydrous magnesium sulfate, and the solvent was evaporated under reduced pressure to give the title compound as a white solid (1.13 g, 98%).

NMR (DMSO-d$_6$) δ: 0.75 (3H, t, J=7.4), 1.18 (3H, t, J=7.4), 1.38-1.50 (2H, m), 2.07 (2H, t, J=7.4), 3.31-3.40 (2H, m), 7.75 (2H, d, J=8.5), 8.12 (2H, d, J=8.3), 8.74 (1H, t, J=5.3), 13.24 (1H, s).

43c) N-cyclopropyl-1-{4-[(ethylamino)carbonyl]phenyl}-5-propyl-1H-1,2,3-triazole-4-carboxamide To a solution of 1-{4-[(ethylamino)carbonyl]phenyl}-5-propyl-1H-1,2,3-triazole-4-carboxylic acid (0.40 g) obtained in Example 43b) in acetonitrile-DMF (7:2, 9 ml) were successively added cyclopropylamine (0.11 ml), triethylamine (0.22 ml), HOBt (0.24 g) and WSC (0.30 g), and the reaction mixture was stirred overnight at room temperature. The solvent was evaporated under reduced pressure, the residue was dissolved in ethyl acetate and washed with saturated aqueous sodium hydrogen carbonate solution. The organic layer was dried over anhydrous sodium sulfate, and the solvent was evaporated under reduced pressure. The residue was purified by silica gel column (ethyl acetate/hexane=1/1 to ethyl acetate) to give the title compound as a white powder (0.20 g, 44%).

NMR (CDCl$_3$) δ: 0.65-0.70 (2H, m), 0.81-0.90 (5H, m), 1.25-1.30 (3H, m), 1.49-1.61 (2H, m), 2.86-2.92 (1H, m), 2.97-3.02 (2H, m), 3.48-3.57 (2H, m), 6.87 (1H, brs), 7.38-7.39 (1H, m), 7.47-7.50 (2H, m), 8.00-8.04 (2H, m).

Elemental analysis for $C_{18}H_{23}N_5O_2$
Calcd. (%): C, 63.32; H, 6.79; N, 20.51.
Found (%): C, 63.11; H, 6.64; N, 20.46.

Example 44

N-cyclopropyl-1-{4-[(methylamino)carbonyl]phenyl}-5-propyl-1H-1,2,3-triazole-4-carboxamide

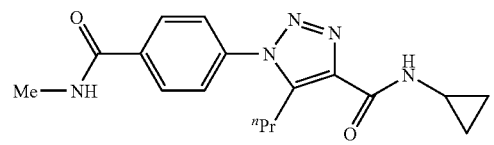

44a) 4-azido-N-methylbenzamide

In the same manner as in Example 43a), the title compound was obtained as a yellow solid (2.01 g, 46%) from 4-azidobenzoic acid (4.08 g) and 2M methylamine in THF solution (12.5 ml).

NMR (CDCl$_3$) δ: 3.01 (3H, d, J=4.9), 6.18 (1H, brs), 7.04-7.08 (2H, m), 7.74-7.79 (2H, m).

44b) 1-{4-[(methylamino)carbonyl]phenyl}-5-propyl-1H-1,2,3-triazole-4-carboxylic acid In the same manner as in Example 43b), the title compound was obtained as a white powder (1.3 g, 79%) from 4-azido-N-methylbenzamide (1.0 g) obtained in Example 44a) and ethyl 3-keto-n-hexanoate (1.1 ml).

NMR (DMSO-d$_6$) δ: 0.72 (3H, t, J=7.5), 1.35-1.47 (2H, m), 2.83 (3H, d, J=4.5), 2.91-2.96 (2H, m), 7.70-7.73 (2H, m), 8.06-8.09 (2H, m), 8.69-8.72 (1H, m), 13.21 (1H, s).

44c) N-cyclopropyl-1-{4-[(methylamino)carbonyl]phenyl}-5-propyl-1H-1,2,3-triazole-4-carboxamide In the same manner as in Example 43c), the title compound was obtained as a white powder (0.28 g, 84%) from 1-{4-[(methylamino)carbonyl]phenyl}-5-propyl-1H-1,2,3-triazole-4-carboxylic acid (0.29 g) obtained in Example 44b) and cyclopropylamine (0.08 ml).

NMR (CDCl$_3$) δ: 0.65-0.70 (2H, m), 0.84-0.91 (5H, m), 1.51-1.62 (2H, m), 2.86-2.94 (1H, m), 2.99-3.04 (2H, m), 3.06-3.10 (3H, m), 6.30 (1H, brs), 7.34 (1H, brs), 7.50-7.54 (2H, m), 7.96-7.99 (2H, m).

Elemental analysis for $C_{17}H_{21}N_5O_2 \cdot 0.2H_2O$
Calcd. (%): C, 61.69; H, 6.52; N, 21.16.
Found (%): C, 61.60; H, 6.32; N, 21.69.

Example 45

N-cyclopropyl-1-(4-{[(2-hydroxyethyl)amino]carbonyl}phenyl)-5-propyl-1H-1,2,3-triazole-4-carboxamide

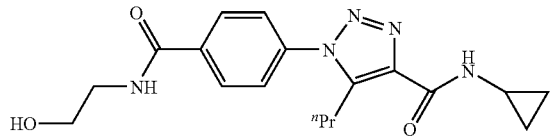

45a) 4-azido-N-(2-hydroxyethyl)benzamide

In the same manner as in Example 43a), the title compound was obtained as a yellow solid (5.6 g, 90%) from 4-azidobenzoic acid (4.1 g) and 2-aminoethanol (1.8 ml).

NMR (CDCl$_3$) δ: 3.59-3.64 (2H, m), 3.80-3.84 (2H, m), 6.95 (1H, brs), 7.02-7.05 (2H, m), 7.79-7.83 (2H, m), 8.00 (1H, brs).

45b) 1-(4-{[(2-hydroxyethyl)amino]carbonyl}phenyl)-5-propyl-1H-1,2,3-triazole-4-carboxylic acid In the same manner as in Example 43b), the title compound was obtained as a white powder (3.6 g, 64%) from 4-azido-N-(2-hydroxyethyl)benzamide (3.6 g) obtained in Example 45a) and ethyl 3-keto-n-hexanoate (3.4 ml).

NMR (DMSO-d$_6$) δ: 0.72 (3H, t, J=7.2), 1.35-1.47 (2H, m), 2.92-2.97 (2H, m), 3.33-3.40 (2H, m), 3.52-3.56 (2H, m), 4.77 (1H, brs), 7.70-7.74 (2H, m), 8.07-8.11 (2H, m), 8.68 (1H, t, J=5.5), 13.24 (1H, brs).

45c) N-cyclopropyl-1-(4-{[(2-hydroxyethyl)amino]carbonyl}phenyl)-5-propyl-1H-1,2,3-triazole-4-carboxamide In the same manner as in Example 43c), the title compound was obtained as white needle crystals (0.13 g, 46%) from 1-(4-{[(2-hydroxyethyl)amino]carbonyl}phenyl)-5-propyl-1H-1,2,3-triazole-4-carboxylic acid (0.26 g) obtained in Example 45b) and cyclopropylamine (0.07 ml).

NMR (CDCl$_3$) δ: 0.65-0.70 (2H, m), 0.84-0.92 (5H, m), 1.51-1.61 (2H, m), 2.33 (1H, t, J=4.9), 2.87-2.93 (1H, m), 2.99-3.04 (2H, m), 3.67-3.72 (2H, m), 3.87-3.92 (2H, m), 6.72 (1H, brt, J=5.1), 7.35 (1H, brd, J=2.6), 7.50-7.54 (2H, m), 7.98-8.02 (2H, m).

Elemental analysis for $C_{18}H_{23}N_5O_3$
Calcd. (%): C, 60.49; H, 6.49; N, 19.59.
Found (%): C, 60.52; H, 6.47; N, 19.59.

Example 46

N-cyclopropyl-5-propyl-1-(4-{[(2,2,2-trifluoroethyl)amino]carbonyl}phenyl)-1H-1,2,3-triazole-4-carboxamide

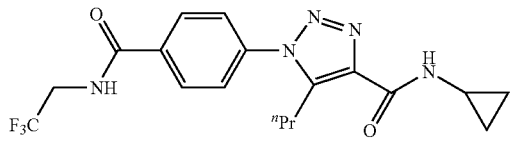

46a) 4-azido-N-(2,2,2-trifluoroethyl)benzamide

To a solution of 4-azidobenzoic acid (0.65 g) in acetonitrile-DMF (2:1, 15 ml) were successively added 2,2,2-trifluoroethanamine (0.38 ml), triethylamine (0.67 ml), HOBt (0.79 g) and WSC (0.92 g), and the reaction mixture was stirred overnight at room temperature. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure to give the title compound as a white powder (0.98 g, 100%).

NMR (CDCl$_3$) δ: 4.13 (2H, dq, J=6.5, 9.0), 6.33 (1H, brs), 7.08-7.12 (2H, m), 7.19-7.83 (2H, m).

46b) 5-propyl-1-(4-{[(2,2,2-trifluoroethyl)amino]carbonyl}phenyl)-1H-1,2,3-triazole-4-carboxylic acid To a solution of 4-azido-N-(2,2,2-trifluoroethyl)benzamide (0.98 g) obtained in Example 46a) and ethyl 3-keto-n-hexanoate (0.77 ml) in ethanol (20 ml) was added 20% sodium ethoxide in ethanol solution (1.85 ml) at room temperature, and the mixture was stirred overnight at 60° C. The reaction mixture was cooled to room temperature, and the solvent was evaporated under reduced pressure. The residue was diluted with water, and washed with ethyl acetate. The aqueous layer was acidified with 1N hydrochloric acid, and extracted with ethyl acetate. The extract was dried over anhydrous magnesium sulfate, and the solvent was evaporated under reduced pressure to give the title compound as a pale-brown amorphous solid (1.4 g, 100%).

NMR (CDCl$_3$) δ: 0.88 (3H, t, J=7.4), 1.52-1.62 (2H, m), 2.99-3.04 (2H, m), 4.16-4.25 (2H, m), 6.48 (1H, t, J=6.2), 7.57-7.62 (2H, m), 8.03-8.07 (2H, m).

46c) N-cyclopropyl-5-propyl-1-(4-{[(2,2,2-trifluoroethyl)amino]carbonyl}phenyl)-1H-1,2,3-triazole-4-carboxamide In the same manner as in Example 43c), the title compound was obtained as pale-yellow plate crystals (0.52 g, 69%) from 5-propyl-1-(4-{[(2,2,2-trifluoroethyl)amino]carbonyl}phenyl)-1H-1,2,3-triazole-4-carboxylic acid (0.67 g) obtained in Example 46b) and cyclopropylamine (0.16 ml).

NMR (CDCl$_3$) δ: 0.65-0.70 (2H, m), 0.83-0.91 (5H, m), 1.50-1.63 (2H, m), 2.85-2.93 (1H, m), 2.99-3.04 (2H, m), 4.18 (2H, dq, J=6.4, 9.0), 6.84 (1H, t, J=6.2), 7.34 (1H, d, J=2.8), 7.52-7.56 (2H, m), 8.01-8.06 (2H, m).

Elemental analysis for $C_{18}H_{20}N_5O_2F_3$
Calcd. (%): C, 54.68; H, 5.10; N, 17.71.
Found (%): C, 54.76; H, 4.92; N, 17.75.

Example 47

N-cyclopropyl-1-(4-{[(2-furylmethyl)amino]carbonyl}phenyl)-5-propyl-1H-1,2,3-triazole-4-carboxamide

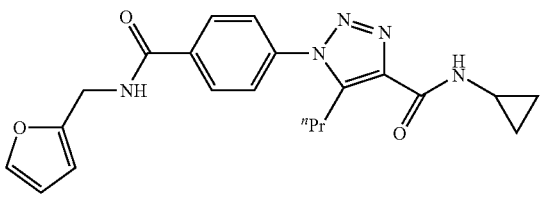

47a) 4-azido-N-(2-furylmethyl)benzamide

In the same manner as in Example 43a), the title compound was obtained as a yellow powder (0.97 g, 100%) from 4-azidobenzoic acid (0.65 g) and 1-(2-furyl)methanamine (0.42 ml).
NMR (CDCl$_3$) δ: 4.64 (1H, d, J=5.5), 6.30-6.31 (1H, m), 6.35 (1H, dd, J=1.9, 3.2), 6.89 (1H, brs), 7.04-7.09 (2H, m), 7.38-7.39 (1H, m), 7.77-7.81 (2H, m).

47b) 1-(4-{[(2-furylmethyl)amino]carbonyl}phenyl)-5-propyl-1H-1,2,3-triazole-4-carboxylic acid In the same manner as in Example 43b), the title compound was obtained as a pale-yellow solid (1.3 g, 92%) from 4-azido-N-(2-furylmethyl)benzamide (0.97 g) obtained in Example 47a) and ethyl 3-keto-n-hexanoate (0.77 ml).
NMR (DMSO-d$_6$) δ: 0.72 (3H, t, J=7.4), 1.35-1.48 (2H, m), 2.94 (2H, t, J=7.4), 4.52 (2H, d, J=5.7), 6.33-6.34 (1H, m), 6.41-6.43 (1H, m), 7.60-7.61 (1H, m), 7.74 (2H, d, J=8.7), 8.12 (2H, d, J=8.5), 9.23 (1H, t, J=5.7), 13.21 (1H, s).

47c) N-cyclopropyl-1-(4-{[(2-furylmethyl)amino]carbonyl}phenyl)-5-propyl-1H-1,2,3-triazole-4-carboxamide In the same manner as in Example 43c), the title compound was obtained as colorless needle crystals (0.54 g, 72%) from 1-(4-{[(2-furylmethyl)amino]carbonyl}phenyl)-5-propyl-1H-1,2,3-triazole-4-carboxylic acid (0.66 g) obtained in Example 47b) and cyclopropylamine (0.16 ml).
NMR (CDCl$_3$) δ: 0.64-0.70 (2H, m), 0.83-0.91 (5H, m), 1.50-1.63 (2H, m), 2.85-2.94 (1H, m), 2.98-3.03 (2H, m), 4.68 (2H, d, J=5.5), 6.33-6.37 (2H, m), 6.63 (1H, t, J=5.3), 7.35 (1H, d, J=2.6), 7.39-7.40 (1H, m), 7.49-7.53 (2H, m), 7.99-8.01 (2H, m).
Elemental analysis for $C_{21}H_{23}N_5O_3$
Calcd. (%): C, 64.11; H, 5.89; N, 17.80.
Found (%): C, 64.20; H, 5.92; N, 17.86.

Example 48

N-cyclopropyl-1-(4-{[(2-methoxyethyl)amino]carbonyl}phenyl)-5-propyl-1H-1,2,3-triazole-4-carboxamide

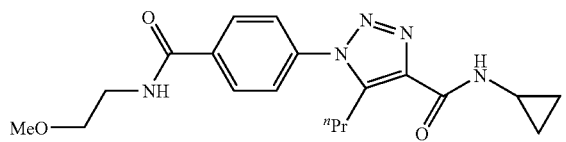

48a) 4-azido-N-(2-methoxyethyl)benzamide

In the same manner as in Example 43a), the title compound was obtained as a pale-yellow powder (0.88 g, 100%) from 4-azidobenzoic acid (0.65 g) and 2-methoxyethanamine (0.42 ml).
NMR (CDCl$_3$) δ: 3.40 (3H, s), 3.54-3.59 (2H, m), 3.63-3.68 (2H, m), 6.49 (1H, brs), 7.05-7.09 (2H, m), 7.77-7.81 (2H, m).

48b) 1-(4-{[(2-methoxyethyl)amino]carbonyl}phenyl)-5-propyl-1H-1,2,3-triazole-4-carboxylic acid In the same manner as in Example 43b), the title compound was obtained as a white powder (1.1 g, 84%) from 4-azido-N-(2-methoxyethyl)benzamide (0.88 g) obtained in Example 48a) and ethyl 3-keto-n-hexanoate (0.77 ml).
NMR (CDCl$_3$) δ: 0.83-0.88 (3H, m), 1.53-1.62 (2H, m), 2.99 (2H, t, J=7.7), 3.44 (3H, s), 3.64-3.76 (4H, m), 7.06 (1H, brs), 7.53 (2H, d, J=7.9), 8.06 (2H, d, J=7.9).

48c) N-cyclopropyl-1-(4-{[(2-methoxyethyl)amino]carbonyl}phenyl)-5-propyl-1H-1,2,3-triazole-4-carboxamide In the same manner as in Example 43c), the title compound was obtained as a white solid (0.46 g, 84%) from 1-(4-{[(2-methoxyethyl)amino]carbonyl}phenyl)-5-propyl-1H-1,2,3-triazole-4-carboxylic acid (0.50 g) obtained in Example 48b) and cyclopropylamine (0.12 ml).
NMR (CDCl$_3$) δ: 0.65-0.70 (2H, m), 0.84-0.91 (5H, m), 1.51-1.64 (2H, m), 2.86-2.92 (1H, m), 2.99-3.05 (2H, m), 3.41 (3H, s), 3.58-3.65 (2H, m), 3.67-3.73 (2H, m), 6.64-6.68 (1H, m), 7.35-7.36 (1H, m), 7.50-7.54 (2H, m), 7.98-8.02 (2H, m).
Elemental analysis for $C_{19}H_{25}N_5O_3$
Calcd. (%): C, 61.44; H, 6.78; N, 18.85.
Found (%): C, 61.14; H, 6.82; N, 18.72.

Example 49

N-cyclopropyl-1-{4-[(isopropylamino)carbonyl]phenyl}-5-propyl-1H-1,2,3-triazole-4-carboxamide

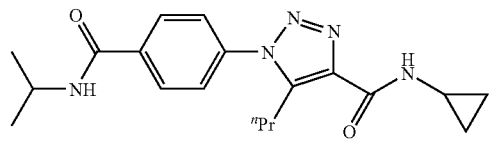

49a) 4-azido-N-isopropylbenzamide

In the same manner as in Example 43a), the title compound was obtained as a pale-yellow powder (0.93 g, 91%) from 4-azidobenzoic acid (0.82 g) and propan-2-amine (0.51 ml).
NMR (CDCl$_3$) δ: 1.27 (6H, d, J=6.0), 4.22-4.34 (1H, m), 5.86 (1H, brs), 7.04-7.08 (2H, m), 7.73-7.78 (2H, m).

49b) 1-{4-[(isopropylamino)carbonyl]phenyl}-5-propyl-1H-1,2,3-triazole-4-carboxylic acid In the same manner as in Example 43b), the title compound was obtained as a crude product (0.91 g, 63%) of yellow powder from 4-azido-N-isopropylbenzamide (0.93 g) obtained in Example 49a) and ethyl 3-keto-n-hexanoate (0.87 ml). The obtained crude product was used for the next reaction without further purification.

49c) N-cyclopropyl-1-{4-[(isopropylamino)carbonyl]phenyl}-5-propyl-1H-1,2,3-triazole-4-carboxamide In the same manner as in Example 43c), the title compound was obtained as colorless plate crystals (0.80 g, 77%) from 1-{4-[(isopropylamino)carbonyl]phenyl}-5-propyl-1H-1,2,3-triazole-4-carboxylic acid (0.91 g) obtained in Example 49b) and cyclopropylamine (0.08 ml).
NMR (CDCl$_3$) δ: 0.65-0.70 (2H, m), 0.82-0.91 (5H, m), 1.31 (6H, d, J=6.6), 1.51-1.63 (2H, m), 2.86-2.93 (1H, m), 2.99-3.04 (2H, m), 4.27-4.38 (1H, m), 6.04 (1H, d, J=7.5), 7.34 (1H, brs), 7.48-7.53 (2H, m), 7.94-7.99 (2H, m).
Elemental analysis for C$_{19}$H$_{25}$N$_5$O$_2$
Calcd. (%): C, 64.20; H, 7.09; N, 19.70.
Found (%): C, 64.18; H, 7.07; N, 19.79.

Example 50

1-{4-[(sec-butylamino)carbonyl]phenyl}-N-cyclopropyl-5-propyl-1H-1,2,3-triazole-4-carboxamide

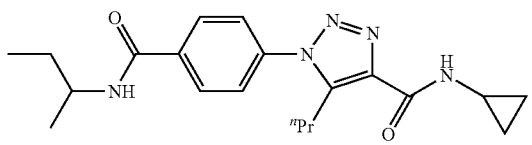

50a) 4-azido-N-(sec-butyl)benzamide

In the same manner as in Example 43a), the title compound was obtained as a pale-yellow powder (0.91 g, 83%) from 4-azidobenzoic acid (0.82 g) and butan-2-amine (0.61 ml).
NMR (CDCl$_3$) δ: 0.97 (3H, t, J=7.4), 1.24 (3H, d, J=6.6), 1.58 (2H, quintet, J=7.4), 4.07-4.17 (1H, m), 5.82 (1H, brs), 7.04-7.09 (2H, m), 7.74-7.78 (2H, m).

50b) 1-{4-[(sec-butylamino)carbonyl]phenyl}-5-propyl-1H-1,2,3-triazole-4-carboxylic acid In the same manner as in Example 43b), the title compound was obtained as a yellow powder (0.89 g, 64%) from 4-azido-N-(sec-butyl)benzamide (0.91 g) obtained in Example 50a) and ethyl 3-keto-n-hexanoate (0.80 ml).
NMR (CDCl$_3$) δ: 0.84-1.03 (5H, m), 1.22-1.31 (2H, m), 1.53-1.71 (4H, m), 2.56 (2H, t, J=7.4), 2.97-3.03 (2H, m), 4.12-4.20 (1H, m), 5.91-5.94 (1H, m), 7.52-7.55 (2H, m), 7.97-8.00 (2H, m).

50c) 1-{4-[(sec-butylamino)carbonyl]phenyl}-N-cyclopropyl-5-propyl-1H-1,2,3-triazole-4-carboxamide In the same manner as in Example 43c), the title compound was obtained as a white powder (0.73 g, 74%) from 1-{4-[(sec-butylamino)carbonyl]phenyl}-5-propyl-1H-1,2,3-triazole-4-carboxylic acid (0.89 g) obtained in Example 50b) and cyclopropylamine (0.22 ml).
NMR (CDCl$_3$) δ: 0.65-0.70 (2H, m), 0.84-0.91 (5H, m), 1.00 (3H, t, J=7.4), 1.28 (3H, d, J=6.6), 1.51-1.67 (4H, m), 2.86-2.94 (1H, m), 2.99-3.04 (2H, m), 4.10-4.20 (1H, m), 5.96 (1H, d, J=8.3), 7.34 (1H, brs), 7.49-7.53 (2H, m), 7.94-7.99 (2H, m).
Elemental analysis for C$_{20}$H$_{27}$N$_5$O$_2$
Calcd. (%): C, 65.02; H, 7.37; N, 18.96.
Found (%): C, 64.96; H, 7.32; N, 19.12.

Example 51

1-{4-[(tert-butylamino)carbonyl]phenyl}-N-cyclopropyl-5-propyl-1H-1,2,3-triazole-4-carboxamide

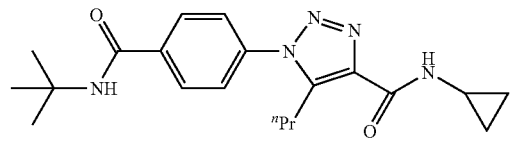

51a) 4-azido-N-(tert-butyl)benzamide

In the same manner as in Example 43a), the title compound was obtained as a pale-yellow powder (0.94 g, 86%) from 4-azidobenzoic acid (0.82 g) and 2-methylpropan-2-amine (0.63 ml).
NMR (CDCl$_3$) δ: 1.47 (9H, s), 5.88 (1H, brs), 7.02-7.07 (2H, m), 7.70-7.74 (2H, m).

51b) 1-{4-[(tert-butylamino)carbonyl]phenyl}-5-propyl-1H-1,2,3-triazole-4-carboxylic acid In the same manner as in Example 43b), the title compound was obtained as a yellow powder (1.42 g, 100%) from 4-azido-N-(tert-butyl)benzamide (0.94 g) obtained in Example 51a) and ethyl 3-keto-n-hexanoate (0.83 ml).
NMR (CDCl$_3$) δ: 0.86 (3H, t, J=7.4), 1.52 (9H, s), 1.55-1.73 (2H, m), 2.97-3.02 (2H, m), 6.04 (1H, brs), 7.52 (2H, d, J=8.5), 7.95 (2H, d, J=8.5).

51c) 1-{4-[(tert-butylamino)carbonyl]phenyl}-N-cyclopropyl-5-propyl-1H-1,2,3-triazole-4-carboxamide In the same manner as in Example 43c), the title compound was obtained as colorless plate crystals (1.17 g, 74%) from 1-{4-[(tert-butylamino)carbonyl]phenyl}-5-propyl-1H-1,2,3-triazole-4-carboxylic acid (1.42 g) obtained in Example 51b) and cyclopropylamine (0.36 ml).

NMR (CDCl$_3$) δ: 0.65-0.70 (2H, m), 0.84-0.91 (5H, m), 1.51 (9H, s), 1.53-1.61 (2H, m), 2.87-2.93 (1H, m), 2.98-3.04 (2H, m), 5.99 (1H, brs), 7.33 (1H, brs), 7.47-7.51 (2H, m), 7.90-7.95 (2H, m).

Elemental analysis for C$_{20}$H$_{27}$N$_5$O$_2$

Calcd. (%): C, 65.02; H, 7.37; N, 18.96.

Found (%): C, 64.90; H, 7.31; N, 19.04.

Example 52

N-cyclopropyl-1-{4-[(isobutylamino)carbonyl]phenyl}-5-propyl-1H-1,2,3-triazole-4-carboxamide

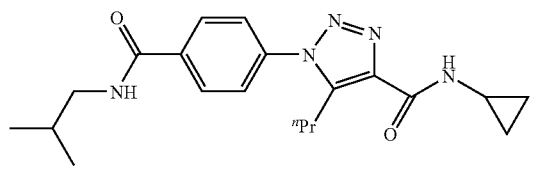

52a) 4-azido-N-isobutylbenzamide

In the same manner as in Example 43a), the title compound was obtained as a pale-yellow powder (0.85 g, 78%) from 4-azidobenzoic acid (0.82 g) and 2-methylpropan-1-amine (0.60 ml).

NMR (CDCl$_3$) δ: 0.99 (6H, d, J=6.6), 1.83-1.97 (1H, m), 3.27-3.31 (2H, m), 6.09 (1H, brs), 7.05-7.10 (2H, m), 7.75-7.79 (2H, m).

52b) 1-{4-[(isobutylamino)carbonyl]phenyl}-5-propyl-1H-1,2,3-triazole-4-carboxylic acid In the same manner as in Example 43b), the title compound was obtained as a yellow powder (1.29 g, 100%) from 4-azido-N-isobutylbenzamide (0.85 g) obtained in Example 52a) and ethyl 3-keto-n-hexanoate (0.75 ml).

NMR (CDCl$_3$) δ: 0.87 (3H, t, J=7.4), 1.02 (6H, d, J=6.9), 1.54-1.62 (2H, m), 1.93-2.12 (1H, m), 2.96-3.03 (2H, m), 3.33-3.37 (2H, m), 6.21 (1H, brs), 7.53-7.56 (2H, m), 7.98-8.01 (2H, m).

52c) N-cyclopropyl-1-{4-[(isobutylamino)carbonyl]phenyl}-5-propyl-1H-1,2,3-triazole-4-carboxamide In the same manner as in Example 43c), the title compound was obtained as colorless needle crystals (1.10 g, 76%) from 1-{4-[(isobutylamino)carbonyl]phenyl}-5-propyl-1H-1,2,3-triazole-4-carboxylic acid (1.29 g) obtained in Example 52b) and cyclopropylamine (0.32 ml).

NMR (CDCl$_3$) δ: 0.65-0.70 (2H, m), 0.82-0.91 (5H, m), 1.01 (6H, d, J=6.7), 1.52-1.64 (2H, m), 1.90-1.99 (1H, m), 2.86-2.94 (1H, m), 2.99-3.05 (2H, m), 3.32-3.36 (2H, m), 6.22 (1H, brs), 7.33 (1H, brs), 7.50-7.54 (2H, m), 7.95-7.99 (2H, m).

Elemental analysis for C$_{20}$H$_{27}$N$_5$O$_2$

Calcd. (%): C, 65.02; H, 7.37; N, 18.96.

Found (%): C, 65.02; H, 7.33; N, 19.06.

Example 53

N-cyclopropyl-1-{4-[(cyclopropylamino)carbonyl]phenyl}-5-propyl-1H-1,2,3-triazole-4-carboxamide

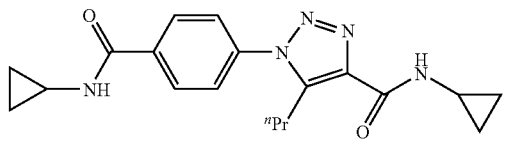

53a) 4-azido-N-cyclopropylbenzamide

In the same manner as in Example 43a), the title compound was obtained as a brown powder (1.44 g) from 4-azidobenzoic acid (1.00 g) and cyclopropylamine (0.85 ml).

53b) 1-{4-[(cyclopropylamino)carbonyl]phenyl}-5-propyl-1H-1,2,3-triazole-4-carboxylic acid In the same manner as in Example 43b), the title compound was obtained as a brown powder (1.53 g, 79%) from 4-azido-N-cyclopropylbenzamide (1.44 g) obtained in Example 53a).

NMR (CDCl$_3$) δ: 0.58-0.62 (2H, m), 0.70-0.76 (5H, m), 1.37-1.45 (2H, m), 2.87-2.96 (3H, m), 7.72 (2H, d, J=8.6), 8.06 (2H, d, J=8.6), 8.68 (1H, d, J=4.1).

53c) N-cyclopropyl-1-{4-[(cyclopropylamino)carbonyl]phenyl}-5-propyl-1H-1,2,3-triazole-4-carboxamide In the same manner as in Example 43c), the title compound was obtained as a colorless powder (0.84 g, 81%) from 1-{4-[(cyclopropylamino)carbonyl]phenyl}-5-propyl-1H-1,2,3-triazole-4-carboxylic acid (0.92 g) obtained in Example 53b).

NMR (CDCl$_3$) δ: 0.65-0.70 (4H, m), 0.84-0.96 (7H, m), 1.53-1.61 (2H, m), 2.89-2.93 (2H, m), 2.99-3.04 (2H, m), 6.30 (1H, brs), 7.35 (1H, brs), 7.51 (2H, d, J=8.6), 7.95 (2H, d, J=8.6).

Elemental analysis for C$_{19}$H$_{23}$N$_5$O$_2$

Calcd. (%): C, 64.57; H, 6.56; N, 19.82.

Found (%): C, 64.77; H, 6.58; N, 19.83.

Example 54

1-{4-[(cyclopentylamino)carbonyl]phenyl}-N-cyclopropyl-5-propyl-1H-1,2,3-triazole-4-carboxamide

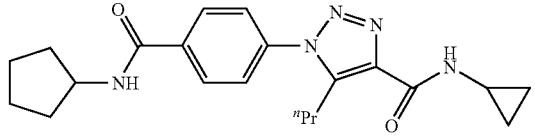

54a) 4-azido-N-cyclopentylbenzamide

In the same manner as in Example 43a), the title compound was obtained as a pale-brown powder (1.75 g) from 4-azidobenzoic acid (1.00 g) and cyclopentylamine (1.21 ml).

54b) 1-{4-[(cyclopentylamino)carbonyl]phenyl}-5-propyl-1H-1,2,3-triazole-4-carboxylic acid In the same manner as in Example 43b), the title compound was obtained as a pale-brown powder (1.84 g, 88%) from 4-azido-N-cyclopentylbenzamide (1.75 g) obtained in Example 54a).

NMR (CDCl$_3$) δ: 0.73 (3H, t, J=7.5), 1.36-1.54 (2H, m), 1.55-1.57 (4H, m), 1.71-1.73 (2H, m), 1.90-1.99 (2H, m), 2.94 (2H, t, J=7.6), 4.23-4.30 (1H, m), 7.72 (2H, d, J=8.5), 8.08 (2H, d, J=8.5), 8.53 (1H, d, J=7.1).

54c) 1-{4-[(cyclopentylamino)carbonyl]phenyl}-N-cyclopropyl-5-propyl-1H-1,2,3-triazole-4-carboxamide In the same manner as in Example 43c), the title compound was obtained as a colorless powder (0.26 g, 23%) from 1-{4-[(cyclopentylamino)carbonyl]phenyl}-5-propyl-1H-1,2,3-triazole-4-carboxylic acid (1.00 g) obtained in Example 54b).

NMR (CDCl$_3$) δ: 0.65-0.70 (2H, m), 0.84-0.91 (5H, m), 1.21-1.28 (4H, m), 1.53-1.57 (2H, m), 1.73-1.76 (2H, m), 2.13-2.17 (2H, m), 2.88-2.92 (1H, m), 3.01-3.04 (2H, m), 4.12 (1H, q, J=7.1), 6.09 (1H, brs), 7.35 (1H, brs), 7.51 (2H, d, 8.5), 7.95 (2H, d, J=8.5).

Elemental analysis for C$_{21}$H$_{27}$N$_5$O$_2$
Calcd. (%): C, 66.12; H, 7.13; N, 18.36.
Found (%): C, 66.26; H, 7.18; N, 18.15.

Example 55

N-cyclopropyl-5-propyl-1-{4-[(propylamino)carbonyl]phenyl}-1H-1,2,3-triazole-4-carboxamide

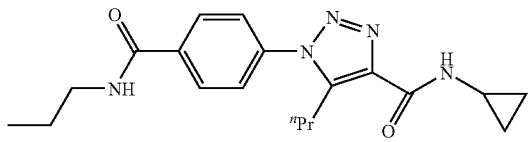

55a) 4-azido-N-propylbenzamide

4-Azidobenzoic acid (866 mg, 5.20 mmol), HOBt (710 mg, 5.20 mmol, 1.0 eq.) and n-propylamine (0.568 ml, 7.60 mmol, 1.3 eq.) were dissolved in acetonitrile (6 ml) and DMF (6 ml), WSC (1.22 g, 6.24 mmol, 1.2 eq.) was added, and the mixture was stirred at room temperature for 4 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid (2.0 g, including residual solvent).

$^1$H NMR (200 MHz, CDCl$_3$) δ: 0.99 (3H, t, J=7.4 Hz), 1.64 (2H, q, J=7.3 Hz), 3.42 (2H, brq, J=6.6 Hz), 6.08 (1H, br), 7.07 (2H, dt, J=8.8, 2.4 Hz), 7.77 (2H, dt, J=8.4, 2.2 Hz).

55b) 5-propyl-1-{4-[(propylamino)carbonyl]phenyl}-1H-1,2,3-triazole-4-carboxylic acid 4-Azido-N-propylbenzamide (2.0 g) obtained in Example 55a) and ethyl 3-oxohexanoate (1.09 ml, 6.50 mmol, 1.25 eq.) were dissolved in ethanol (20 ml), sodium ethoxide (491 mg, 6.50 mmol, 1.25 eq.) was added, and the mixture was stirred at room temperature for 30 min, and then at 60° C. for 14 hr. Water (20 ml) was added to the reaction mixture. After concentration, the mixture was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a pale-yellow powder (1.58 g, 4.99 mmol, 96.0%).

$^1$H NMR (200 MHz, CDCl$_3$-DMSO-d$_6$=19:1) δ: 0.84 (3H, t, J=7.3 Hz), 1.01 (3H, t, J=7.3 Hz), 1.64 (2H, brq, J=7.7 Hz), 1.68 (2H, q, J=7.3 Hz), 2.98 (2H, brt, J=7.7 Hz), 3.43 (2H, brq, J=6.0 Hz), 7.35 (1H, br), 7.51 (2H, d, J=8.8 Hz), 8.06 (2H, d, J=8.8 Hz).

Elemental analysis for C$_{16}$H$_{20}$N$_4$O$_3$
Calcd. (%): C, 60.75; H, 6.37; N, 17.71.
Found (%): C, 60.66; H, 6.34; N, 17.79.

55c) N-cyclopropyl-5-propyl-1-{4-[(propylamino)carbonyl]phenyl}-1H-1,2,3-triazole-4-carboxamide 5-Propyl-1-{4-[(propylamino)carbonyl]phenyl}-1H-1,2,3-triazole-4-carboxylic acid (498 mg, 1.57 mmol) obtained in Example 55b), HOBt (215 mg, 1.57 mmol, 1.0 eq.) and cyclopropylamine (0.146 ml, 2.05 mmol, 1.3 eq.) were dissolved in acetonitrile (4 ml) and DMF (4 ml), WSC (370 mg, 1.89 mmol, 1.2 eq.) was added and the mixture was stirred at room temperature for 2.5 hr. The reaction mixture was concentrated, dissolved in ethyl acetate (50 ml), and washed with 5% aqueous sodium hydrogen carbonate solution, 10% aqueous ammonium chloride solution and saturated brine. The aqueous layers were each extracted with ethyl acetate-hexane (2:1, 20 ml). The organic layers were combined, dried over anhydrous sodium sulfate, and concentrated, and diethyl ether was added. The precipitate was collected by filtration, washed with diethyl ether and dried to give the title compound as a white powder (542 mg, 1.52 mmol, 97.1%).

$^1$H NMR (200 MHz, CDCl$_3$) δ: 0.68 (2H, m), 0.87 (3H, t, J=7.1 Hz), 0.88 (2H, m), 1.02 (3H, t, J=7.5 Hz), 1.58 (2H, m), 1.67 (2H, quintet, J=7.2 Hz), 2.90 (1H, octet, J=3.7 Hz), 3.02 (2H, m), 3.47 (2H, brq, J=6.8 Hz), 6.20 (1H, brt, J=5 Hz), 7.34 (1H, brd, J=5 Hz), 7.51 (2H, dt, J=8.4, 1.8 Hz), 7.97 (2H, dt, J=8.4, 1.8 Hz).

Elemental analysis for C$_{19}$H$_{25}$N$_5$O$_2$
Calcd. (%): C, 64.20; H, 7.09; N, 19.70.
Found (%): C, 64.34; H, 6.97; N, 19.73.

Example 56

1-{4-[(butylamino)carbonyl]phenyl}-N-cyclopropyl-5-propyl-1H-1,2,3-triazole-4-carboxamide

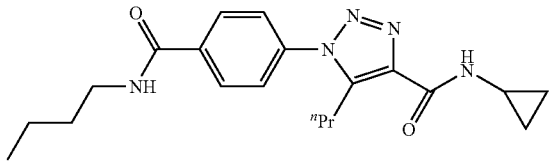

56a) 4-azido-N-butylbenzamide

4-Azidobenzoic acid (843 mg, 5.06 mmol), HOBt (691 mg, 5.06 mmol, 1.0 eq.) and n-butylamine (0.667 ml, 6.58 mmol, 1.3 eq.) were dissolved in acetonitrile (6 ml) and DMF (6 ml), WSC (1.19 g, 6.08 mmol, 1.2 eq.) was added, and the mixture was stirred at room temperature for 4 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid (2.3 g, including residual solvent).

$^1$H NMR (200 MHz, CDCl$_3$) δ: 0.96 (3H, t, J=7.1 Hz), 1.42 (2H, br sextet, J=7.9 Hz), 1.61 (2H, br quintet, J=7.4 Hz), 3.46 (2H, dt, J=6.0, 7.0 Hz), 6.05 (1H, br), 7.07 (2H, dt, J=8.4, 2.2 Hz), 7.77 (2H, dt, J=8.8, 2.2 Hz).

56b) 1-{4-[(butylamino)carbonyl]phenyl}-5-propyl-1H-1,2,3-triazole-4-carboxylic acid 4-Azido-N-butylbenzamide (2.3 g) obtained in Example 56a) and ethyl 3-oxohexanoate (1.06 ml, 6.33 mmol, 1.25 eq.) were dissolved in ethanol (20 ml), sodium ethoxide (479 mg, 6.33 mmol, 1.25 eq.) was added, and the mixture was stirred at room temperature for 30 min, and then at 60° C. for 14 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a pale-yellow powder (1.62 g, 4.91 mmol, 97.1%).

$^1$H NMR (200 MHz, CDCl$_3$-DMSO-d$_6$=19:1) δ: 0.84 (3H, t, J=7.3 Hz), 0.97 (3H, t, J=7.3 Hz), 1.44 (2H, m), 1.51 (2H, q, J=7.1 Hz), 1.61 (2H, br quintet, J=7.8 Hz), 2.98 (2H, m), 3.46 (2H, brq, J=6.4 Hz), 7.51 (2H, dt, J=8.4, 1.8 Hz), 7.54 (1H, br), 8.07 (2H, dt, J=8.6, 2.0 Hz).

Elemental analysis for C$_{17}$H$_{22}$N$_4$O$_3$
Calcd. (%): C, 61.80; H, 6.71; N, 16.96.
Found (%): C, 61.74; H, 6.70; N, 17.01.

56c) 1-{4-[(butylamino)carbonyl]phenyl}-N-cyclopropyl-5-propyl-1H-1,2,3-triazole-4-carboxamide 1-{4-[(Butylamino)carbonyl]phenyl}-5-propyl-1H-1,2,3-triazole-4-carboxylic acid (504 mg, 1.53 mmol) obtained in Example 56b), HOBt (208 mg, 1.53 mmol, 1.0 eq.) and cyclopropylamine (0.142 ml, 1.98 mmol, 1.3 eq.) were dissolved in acetonitrile (4 ml) and DMF (4 ml), WSC (358 mg, 1.83 mmol, 1.2 eq.) was added, and the mixture was stirred at room temperature for 2.5 hr. The reaction mixture was concentrated, dissolved in ethyl acetate (50 ml), and washed with 5% aqueous sodium hydrogen carbonate solution, 10% aqueous ammonium chloride solution and saturated brine. The aqueous layers were each extracted with ethyl acetate-hexane (2:1, 20 ml). The organic layers were combined, dried over anhydrous sodium sulfate, and concentrated, and diethyl ether was added. The precipitate was collected by filtration, washed with diethyl ether and dried to give the title compound as a white powder (535 mg, 1.45 mmol, 94.9%).

$^1$H NMR (200 MHz, CDCl$_3$) δ: 0.68 (2H, m), 0.86 (3H, t, J=7.4 Hz), 0.88 (2H, m), 0.98 (3H, t, J=7.2 Hz), 1.44 (2H, m), 1.49-1.70 (4H, m), 2.90 (1H, octet, J=3.6 Hz), 3.02 (2H, m), 3.51 (2H, brq, J=6.4 Hz), 6.21 (1H, brt, J=5.5 Hz), 7.34 (1H, brd, J=2 Hz), 7.51 (2H, dt, J=8.8, 2.2 Hz), 7.97 (2H, dt, J=8.8, 2.2 Hz).

Elemental analysis for C$_{20}$H$_{27}$N$_5$O$_2$
Calcd. (%): C, 65.02; H, 7.37; N, 18.96.
Found (%): C, 65.24; H, 7.28; N, 18.96.

Example 57

N-cyclopropyl-1-{4-[(pentylamino)carbonyl]phenyl}-5-propyl-1H-1,2,3-triazole-4-carboxamide

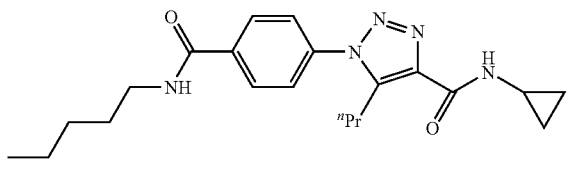

57a) 4-azido-N-pentylbenzamide

4-Azidobenzoic acid (846 mg, 5.08 mmol), HOBt (694 mg, 5.08 mmol, 1.0 eq.) and n-pentylamine (0.783 ml, 6.61 mmol, 1.3 eq.) were dissolved in acetonitrile (6 ml) and DMF (6 ml), WSC (1.19 g, 6.10 mmol, 1.2 eq.) was added, and the mixture was stirred at room temperature for 3 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid (1.5 g, including residual solvent).

$^1$H NMR (200 MHz, CDCl$_3$) δ: 0.92 (3H, brt, J=7.0 Hz), 1.31-1.42 (4H, m), 1.62 (2H, br), 3.43 (2H, dd, J=7.2, 5.8 Hz), 6.04 (1H, br), 7.07 (2H, dt, J=8.8, 2.4 Hz), 7.77 (2H, dt, J=8.8, 2.4 Hz).

57b) 1-{4-[(pentylamino)carbonyl]phenyl}-5-propyl-1H-1,2,3-triazole-4-carboxylic acid The pale-yellow solid (1.5 g) obtained in Example 57a) and ethyl 3-oxohexanoate (1.07 ml, 6.35 mmol, 1.25 eq.) were dissolved in ethanol (20 ml), sodium ethoxide (480 mg, 6.35 mmol, 1.25 eq.) was added, and the mixture was stirred at room temperature for 30 min, and then at 60° C. for 19 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a pale-yellow powder (1.71 g, 4.97 mmol, 97.7%).

$^1$H NMR (200 MHz, CDCl$_3$-DMSO-d$_6$=19:1) δ: 0.84 (3H, t, J=7.3 Hz), 0.93 (3H, t, J=7.2 Hz), 1.38 (4H, m), 1.54 (2H, brq, J=7.8 Hz), 1.64 (2H, m), 2.98 (2H, brt, J=7.9 Hz), 3.46 (2H, brq, J=6.6 Hz), 7.12 (1H, brt, J=6 Hz), 7.51 (2H, dt, J=8.4, 1.8 Hz), 8.04 (2H, dt, J=8.6, 2.1 Hz).

Elemental analysis for C$_{18}$H$_{24}$N$_4$O$_3$
Calcd. (%): C, 62.77; H, 7.02; N, 16.27.
Found (%): C, 62.63; H, 6.95; N, 16.25.

57c) N-cyclopropyl-1-{4-[(pentylamino)carbonyl]phenyl}-5-propyl-1H-1,2,3-triazole-4-carboxamide 1-{4-[(Pentylamino)carbonyl]phenyl}-5-propyl-1H-1,2,3-triazole-4-carboxylic acid (487 mg, 1.41 mmol) obtained in Example 57b), HOBt (193 mg, 1.41 mmol, 1.0 eq.) and cyclopropylamine (0.131 ml, 1.84 mmol, 1.3 eq.) were dissolved in acetonitrile-DMF (1:1, 7.5 ml), WSC (332 mg, 1.70 mmol, 1.2 eq.) was added, and the mixture was stirred at room temperature for 2 hr. The reaction mixture was concentrated, dissolved in ethyl acetate (40 ml), and washed with 5% aqueous sodium hydrogen carbonate solution, 10% aqueous ammonium chloride solution and saturated brine. The aqueous layers were each extracted with ethyl acetate-hexane (2:1, 30 ml). The organic layers were combined, dried over anhydrous sodium sulfate, and concentrated to give a white powder. This was crystallized from methanol-ethyl acetate to give the title compound as a white powder (298 mg, 0.777 mmol, 55.1%). The mother liquor was concentrated, and crystallized from diethyl ether to give the title compound as a white powder (225 mg, 0.587 mmol, 41.6%).

$^1$H NMR (200 MHz, CDCl$_3$) δ: 0.68 (2H, m), 0.87 (3H, t, J=7.3 Hz), 0.88 (2H, m), 0.93 (3H, brt, J=7.0 Hz), 1.35-1.44 (4H, m), 1.56 (2H, m), 1.65 (2H, m), 2.90 (1H, octet, J=3.7 Hz), 3.02 (2H, m), 3.50 (2H, brq, J=6.4 Hz), 6.18 (1H, brt, J=6 Hz), 7.34 (1H, brd, J=3 Hz), 7.51 (2H, dt, J=8.8, 2.0 Hz), 7.97 (2H, dt, J=8.4, 2.0 Hz).

Elemental analysis for C$_{21}$H$_{29}$N$_5$O$_2$
Calcd. (%): C, 65.77; H, 7.62; N, 18.26.
Found (%): C, 65.83; H, 7.59; N, 18.33.

Example 58

1-{4-[(benzylamino)carbonyl]phenyl}-N-cyclopropyl-5-propyl-1H-1,2,3-triazole-4-carboxamide

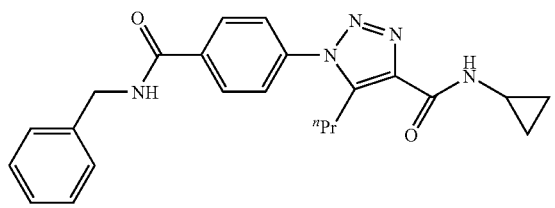

58a) 4-azido-N-benzylbenzamide

4-Azidobenzoic acid (858 mg, 5.15 mmol), HOBt (704 mg, 5.15 mmol, 1.0 eq.) and benzylamine (0.745 ml, 6.70 mmol, 1.3 eq.) were dissolved in acetonitrile (6 ml) and DMF (6 ml), WSC (1.21 g, 6.19 mmol, 1.2 eq.) was added, and the mixture was stirred at room temperature for 3 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid.

58b) 1-{4-[(benzylamino)carbonyl]phenyl}-5-propyl-1H-1,2,3-triazole-4-carboxylic acid 4-Azido-N-benzylbenzamide obtained in Example 58a) and ethyl 3-oxohexanoate (1.08 ml, 6.44 mmol, 1.25 eq.) were dissolved in ethanol (20 ml), sodium ethoxide (487 mg, 6.44 mmol, 1.25 eq.) was added, and the mixture was stirred at room temperature for 10 min, and then at 60° C. for 14 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a grayish white powder (1.71 g, 4.70 mmol, 91.3%).

$^1$H NMR (200 MHz, CDCl$_3$-DMSO-d$_6$=9:1) δ: 0.84 (3H, t, J=7.3 Hz), 1.54 (2H, brq, J=7.7 Hz), 2.98 (2H, brt, J=7.5 Hz), 4.67 (2H, d, J=5.6 Hz), 7.27-7.42 (5H, m), 7.52 (2H, d, J=8.4 Hz), 8.15 (2H, d, J=8.4 Hz), 8.25 (1H, br).

Elemental analysis for C$_{20}$H$_{20}$N$_4$O$_3$.0.2H$_2$O
Calcd. (%): C, 65.28; H, 5.59; N, 15.22.
Found (%): C, 65.30; H, 5.62; N, 14.94.

58c) 1-{4-[(benzylamino)carbonyl]phenyl}-N-cyclopropyl-5-propyl-1H-1,2,3-triazole-4-carboxamide 1-{4-[(Benzylamino)carbonyl]phenyl}-5-propyl-1H-1,2,3-triazole-4-carboxylic acid (507 mg, 1.39 mmol) obtained in Example 58b), HOBt (95 mg, 0.696 mmol, 0.5 eq.) and cyclopropylamine (0.129 ml, 1.81 mmol, 1.3 eq.) were dissolved in acetonitrile-DMF (2:1, 9.0 ml), WSC (327 mg, 1.67 mmol, 1.2 eq.) was added, and the mixture was stirred at room temperature for 2 hr. The reaction mixture was concentrated, dissolved in ethyl acetate (40 ml), and washed with 5% aqueous sodium hydrogen carbonate solution, 10% aqueous ammonium chloride solution and saturated brine. The aqueous layers were each extracted with ethyl acetate-hexane (1:1, 30 ml). The organic layers were combined, dried over anhydrous sodium sulfate, and concentrated, and diethyl ether was added. The precipitate was collected by filtration, washed with diethyl ether and dried to give the title compound as a white powder (520 mg, 1.29 mmol, 92.7%).

$^1$H NMR (200 MHz, CDCl$_3$) δ: 0.68 (2H, m), 0.86 (3H, t, J=7.3 Hz), 0.87 (2H, m), 1.57 (2H, brq, J=7.6 Hz), 2.90 (1H, octet, J=3.7 Hz), 3.01 (2H, m), 4.69 (2H, d, J=5.6 Hz), 6.52 (1H, brt, J=5.6 Hz), 7.30-7.41 (5H, m), 7.51 (2H, dt, J=8.8, 1.8 Hz), 8.00 (2H, dt, J=8.8, 1.8 Hz).

Elemental analysis for C$_{23}$H$_{25}$N$_5$O$_2$.0.2H$_2$O
Calcd. (%): C, 68.16; H, 6.27; N, 17.28.
Found (%): C, 68.15; H, 6.15; N, 17.20.

Example 59

N-cyclopropyl-1-(4-{[(2-phenylethyl)amino]carbonyl}phenyl)-5-propyl-1H-1,2,3-triazole-4-carboxamide

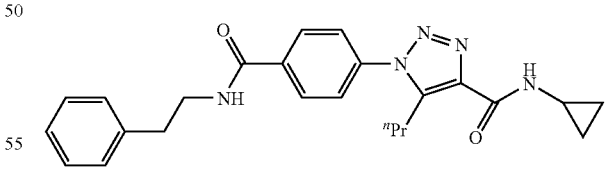

59a) 4-azido-N-(2-phenethyl)benzamide

4-Azidobenzoic acid (844 mg, 5.07 mmol), HOBt (693 mg, 5.07 mmol, 1.0 eq.) and 2-phenethylamine (0.848 ml, 6.59 mmol, 1.3 eq.) were dissolved in acetonitrile (6 ml) and DMF (6 ml), WSC (1.19 g, 6.08 mmol, 1.2 eq.) was added, and the mixture was stirred at room temperature for 3 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid.

59b) 1-(4-{[(2-phenylethyl)amino]carbonyl}phenyl)-5-propyl-1H-1,2,3-triazole-4-carboxylic acid 4-Azido-N-(2-phenethyl)benzamide obtained in Example 59a) and ethyl 3-oxohexanoate (1.07 ml, 6.34 mmol, 1.25 eq.) were dissolved in ethanol (20 ml), sodium ethoxide (479 mg, 6.34 mmol, 1.25 eq.) was added, and the mixture was stirred at room temperature for 10 min, and then at 60° C. for 13 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a grayish white powder (1.86 g, 4.92 mmol, 97.1%).

$^1$H NMR (200 MHz, CDCl$_3$-DMSO-d$_6$=19:1) δ: 0.84 (3H, t, J=7.5 Hz), 1.55 (2H, brq, J=7.5 Hz), 2.97 (2H, m), 2.98 (2H, t, J=7.0 Hz), 3.72 (2H, brq, J=6.4 Hz), 7.23-7.38 (6H, m), 7.50 (2H, dt, J=8.4, 1.8 Hz), 8.00 (2H, dt, J=8.8, 1.8 Hz).

Elemental analysis for C$_{21}$H$_{22}$N$_4$O$_3$

Calcd. (%): C, 66.65; H, 5.86; N, 14.81.

Found (%): C, 66.58; H, 5.82; N, 14.87.

59c) N-cyclopropyl-1-(4-{[(2-phenylethyl)amino]carbonyl}phenyl)-5-propyl-1H-1,2,3-triazole-4-carboxamide 1-(4-{[(2-Phenylethyl)amino]carbonyl}phenyl)-5-propyl-1H-1,2,3-triazole-4-carboxylic acid (510 mg, 1.35 mmol) obtained in Example 59b), HOBt (92 mg, 0.674 mmol, 0.5 eq.) and cyclopropylamine (0.125 ml, 1.75 mmol, 1.3 eq.) were dissolved in acetonitrile-DMF (2:1, 9.0 ml), WSC (316 mg, 1.62 mmol, 1.2 eq.) was added, and the mixture was stirred at room temperature for 2 hr. 2% Aqueous sodium carbonate solution (10 ml) was added to the reaction mixture and the mixture was stirred at room temperature for 1 hr. The precipitate was collected by filtration, washed with ice-cold water and dried to give a grayish white powder. This was crystallized from methanol-diethyl ether to give the title compound as a white powder (421 mg, 1.01 mmol, 74.7%).

$^1$H NMR (200 MHz, CDCl$_3$) δ: 0.67 (2H, m), 0.86 (3H, t, J=7.3 Hz), 0.86 (2H, m), 1.57 (2H, brq, J=7.7 Hz), 2.90 (1H, octet, J=3.5 Hz), 2.98 (2H, t, J=6.6 Hz), 3.01 (2H, m), 3.77 (2H, q, J=6.3 Hz), 6.21 (1H, brt, J=6 Hz), 7.22-7.40 (5H, m), 7.48 (2H, dt, J=8.8, 2.2 Hz), 7.88 (2H, dt, J=8.4, 2.0 Hz).

Elemental analysis for C$_{24}$H$_{27}$N$_5$O$_2$

Calcd. (%): C, 69.04; H, 6.52; N, 16.77.

Found (%): C, 68.89; H, 6.51; N, 16.70.

Example 60

N-cyclopropyl-1-(4-{[(3-phenylpropyl)amino]carbonyl}phenyl)-5-propyl-1H-1,2,3-triazole-4-carboxamide

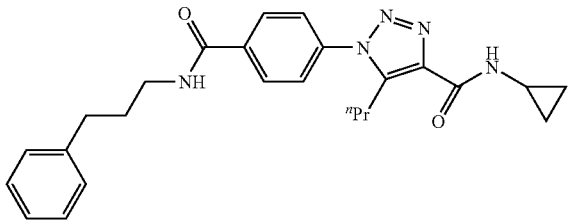

60a) 4-azido-N-(3-phenylpropyl)benzamide

4-Azidobenzoic acid (855 mg, 5.14 mmol), HOBt (701 mg, 5.14 mmol, 1.0 eq.) and 3-phenylpropylamine (0.969 ml, 6.68 mmol, 1.3 eq.) were dissolved in acetonitrile (6 ml) and DMF (6 ml), WSC (1.21 g, 6.16 mmol, 1.2 eq.) was added, and the mixture was stirred at room temperature for 3 hr. The reaction mixture was concentrated, dissolved in ethyl acetate (50 ml), washed with 5% aqueous sodium hydrogen carbonate solution and saturated brine, dried over anhydrous sodium sulfate, and concentrated at 30° C. or below to give the title compound as a pale-yellow solid.

60b) 1-(4-{[(3-phenylpropyl)amino]carbonyl}phenyl)-5-propyl-1H-1,2,3-triazole-4-carboxylic acid The pale-yellow solid of 4-azido-N-(3-phenylpropyl)benzamide obtained in Example 60a) and ethyl 3-oxohexanoate (1.08 ml, 6.43 mmol, 1.25 eq.) were dissolved in ethanol (20 ml), sodium ethoxide (486 mg, 6.43 mmol, 1.25 eq.) was added, and the mixture was stirred at room temperature for 10 min, and then at 60° C. for 13 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (1:1, 30 ml), acidified with 6N hydrochloric acid and stood still at 0° C. The precipitate was collected by filtration, washed with ice-cold water and dried to give the title compound as a grayish white powder (1.99 g, 5.07 mmol, 98.7%)

$^1$H NMR (200 MHz, CDCl$_3$-DMSO-d$_6$=19:1) δ: 0.84 (3H, t, J=7.5 Hz), 1.54 (2H, brq, J=7.5 Hz), 2.00 (2H, br quintet, J=7.4 Hz), 2.75 (2H, brt, J=7.7 Hz), 2.98 (2H, m), 3.50 (2H, brq, J=6.6 Hz), 7.14-7.34 (5H, m), 7.50 (2H, d, J=8.6 Hz), 7.70 (1H, brt, J=6 Hz), 8.04 (2H, d, J=8.8 Hz).

Elemental analysis for C$_{22}$H$_{24}$N$_4$O$_3$

Calcd. (%): C, 67.33; H, 6.16; N, 14.28.

Found (%): C, 67.04; H, 6.15; N, 14.18.

60c) N-cyclopropyl-1-(4-{[(3-phenylpropyl)amino]carbonyl}phenyl)-5-propyl-1H-1,2,3-triazole-4-carboxamide 1-(4-{[(3-Phenylpropyl)amino]carbonyl}phenyl)-5-propyl-1H-1,2,3-triazole-4-carboxylic acid (505 mg, 1.29 mmol) obtained in Example 60b), HOBt (87.8 mg, 0.643 mmol, 0.5 eq.) and cyclopropylamine (0.120 ml, 1.67 mmol, 1.3 eq.) were dissolved in acetonitrile-DMF (2:1, 9.0 ml), WSC (302 mg, 1.54 mmol, 1.2 eq.) was added, and the mixture was stirred at room temperature for 2.5 hr. The reaction mixture was concentrated, dissolved in ethyl acetate (35 ml) and washed with 2% aqueous sodium carbonate solution, 10% aqueous ammonium chloride solution and saturated brine. The aqueous layers were each extracted with ethyl acetate (25 ml). The organic layers were combined, dried over anhydrous sodium sulfate, and concentrated, and diethyl ether was added. The precipitate was collected by filtration, washed with diethyl ether and dried to give the title compound as a white powder (505 mg, 1.17 mmol, 90.7%).

$^1$H NMR (200 MHz, CDCl$_3$) δ: 0.68 (2H, m), 0.87 (3H, t, J=7.3 Hz), 0.87 (2H, m), 1.57 (2H, brq, J=7.7 Hz), 2.02 (2H, quintet, J=7.1 Hz), 2.77 (2H, t, J=7.5 Hz), 2.90 (1H, octet, J=3.5 Hz), 3.01 (2H, m), 3.56 (2H, q, J=6.4 Hz), 6.13 (1H, brt, J=6 Hz), 7.20-7.36 (6H, m), 7.47 (2H, d, J=8.4 Hz), 7.82 (2H, d, J=8.4 Hz).

Elemental analysis for $C_{25}H_{29}N_5O_2$
Calcd. (%): C, 69.58; H, 6.77; N, 16.23.
Found (%): C, 69.42; H, 6.75; N, 16.24.

Example 61

N-cyclopropyl-1-(4-{[(2-morpholin-4-ylethyl) amino]carbonyl}phenyl)-5-propyl-1H-1,2,3-triazole-4-carboxamide

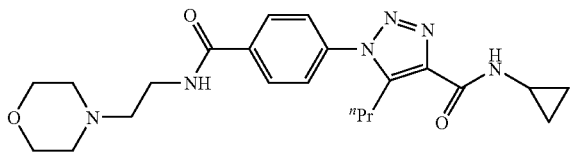

61a) 4-azido-N-(2-morpholin-4-ylethyl)benzamide

4-Azidobenzoic acid (846 mg, 5.08 mmol), HOBt (416 mg, 3.05 mmol, 0.6 eq.) and N-(2-aminoethyl)morpholine (0.716 ml, 5.34 mmol, 1.05 eq.) were dissolved in acetonitrile (9 ml) and DMF (3 ml), WSC (1.19 g, 6.10 mmol, 1.2 eq.) was added, and the mixture was stirred at room temperature for 2 hr. The reaction mixture was concentrated, dissolved in ethyl acetate (40 ml), and washed with 5% aqueous sodium carbonate solution and saturated brine. The aqueous layers were each extracted with ethyl acetate (30 ml). The organic layers were combined, dried over anhydrous sodium sulfate, and concentrated at 30° C. or below to give the title compound as a pale-yellow solid.

61b) sodium 1-(4-{[(2-morpholin-4-ylethyl)amino] carbonyl}phenyl)-5-propyl-1H-1,2,3-triazole-4-carboxylate 4-Azido-N-(2-morpholin-4-ylethyl)benzamide obtained in Example 61a) and ethyl 3-oxohexanoate (1.07 ml, 6.35 mmol, 1.25 eq.) were dissolved in ethanol (23 ml), sodium ethoxide (480 mg, 6.35 mmol, 1.25 eq.) was added, and the mixture was stirred at room temperature for 20 min, and then at 60° C. for 13 hr. The resulting solid was suspended in ethyl acetate, and the insoluble material was collected by filtration, washed with ethyl acetate and dried to give the title compound as a grayish white powder (2.44 g, 5.09 mmol, quant.).

$^1$H NMR (200 MHz, DMSO-d$_6$) δ: 0.70 (3H, t, J=7.3 Hz), 1.36 (2H, brq, J=7.7 Hz), 2.43 (4H, brt, J=4.8 Hz), 2.50 (2H, m), 3.03 (2H, brt, J=7.5 Hz), 3.44 (2H, m), 3.58 (4H, brt, J=4.5 Hz), 7.64 (2H, d, J=8.8 Hz), 8.04 (2H, d, J=8.4 Hz), 8.68 (1H, brt, J=5.4 Hz).

Elemental analysis for $C_{19}H_{24}N_5O_4Na·0.5EtOH·1.3H_2O$
Calcd. (%): C, 52.69; H, 6.54; N, 15.36.
Found (%): C, 52.80; H, 6.62; N, 15.29.

61c) N-cyclopropyl-1-(4-{[(2-morpholin-4-ylethyl) amino]carbonyl}phenyl)-5-propyl-1H-1,2,3-triazole-4-carboxamide Sodium 1-(4-{[(2-morpholin-4-ylethyl)amino] carbonyl}phenyl)-5-propyl-1H-1,2,3-triazole-4-carboxylate (642 mg, 1.34 mmol) obtained in Example 61b), HOBt (91.6 mg, 0.671 mmol, 0.5 eq.) and cyclopropylamine (0.125 ml, 1.74 mmol, 1.3 eq.) were dissolved in acetonitrile-DMF (2:1, 9.0 ml), WSC (315 mg, 1.61 mmol, 1.2 eq.) was added, and the mixture was stirred at room temperature for 12 hr. The reaction mixture was concentrated, dissolved in ethyl acetate (35 ml) and washed with 2% aqueous sodium carbonate solution and saturated brine. The aqueous layers were each extracted with ethyl acetate (25 ml). The organic layers were combined, dried over anhydrous sodium sulfate, and concentrated, and ethyl acetate and diethyl ether were added. The precipitate was collected by filtration, washed with diethyl ether and dried to give the title compound as a white powder (397 mg, 0.932 mmol, 69.6%).

$^1$H NMR (200 MHz, CDCl$_3$) δ: 0.68 (2H, m), 0.87 (3H, t, J=7.3 Hz), 0.88 (2H, m), 1.59 (2H, brq, J=7.7 Hz), 2.59 (4H, brt, J=4.4 Hz), 2.69 (2H, t, J=5.8 Hz), 2.91 (1H, octet, J=3.7 Hz), 3.03 (2H, m), 3.63 (2H, brq, J=5.7 Hz), 3.78 (4H, brt, J=4.6 Hz), 7.06 (1H, br), 7.35 (1H, brd, J=3 Hz), 7.53 (2H, d, J=8.8 Hz), 8.02 (2H, d, J=8.4 Hz).

Elemental analysis for $C_{22}H_{30}N_6O_3$
Calcd. (%): C, 61.95; H, 7.09; N, 19.70.
Found (%): C, 61.87; H, 7.06; N, 19.76.

Example 62

N-cyclopropyl-1-(4-{[(2-piperidin-1-ylethyl)amino] carbonyl}phenyl)-5-propyl-1H-1,2,3-triazole-4-carboxamide

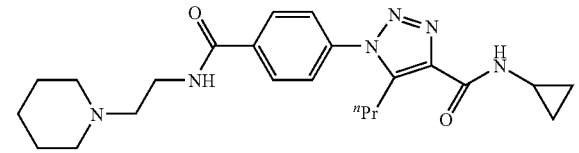

62a) 4-azido-N-(2-piperidin-1-ylethyl)benzamide

4-Azidobenzoic acid (858 mg, 5.15 mmol), HOBt (704 mg, 5.15 mmol, 1.0 eq.) and N-(2-aminoethyl)piperidine (0.788 ml, 5.41 mmol, 1.05 eq.) were dissolved in acetonitrile (6 ml) and DMF (6 ml), WSC (1.21 g, 6.19 mmol, 1.2 eq.) was added, and the mixture was stirred at room temperature for 3 hr. The reaction mixture was concentrated, dissolved in ethyl acetate (50 ml) and washed with 5% aqueous sodium carbonate solution and saturated brine. The aqueous layers were each extracted with ethyl acetate (30 ml). The organic layers were combined, dried over anhydrous sodium sulfate and concentrated at 30° C. or below to give the title compound as a pale-yellow oil.

62b) 1-(4-{[(2-piperidin-1-ylethyl)amino]carbonyl}phenyl)-5-propyl-1H-1,2,3-triazole-4-carboxylic acid 4-Azido-N-(2-piperidin-1-ylethyl)benzamide obtained in Example 62a) and ethyl 3-oxohexanoate (1.08 ml, 6.44 mmol, 1.25 eq.) were dissolved in ethanol (20 ml), sodium ethoxide (487 mg, 6.44 mmol, 1.25 eq.) was added, and the mixture was stirred at room temperature for 30 min, and then at 60° C. for 13 hr. Water (40 ml) was added to the reaction mixture, ethanol was evaporated, and the residue was washed twice with ethyl acetate-hexane (2:1, 50 ml). The aqueous layer was neutralized (pH 6-7) with 6N hydrochloric acid and concentrated. The residue was dissolved in isobutanol, THF and ethyl acetate, dried over anhydrous sodium sulfate and concentrated, and ethyl acetate and THF were added to the residue. The precipitate was collected by filtration, washed with ethyl acetate and dried to give the title compound as a pale-brown powder (purity 90%, 2.05 g, 4.78 mmol, 92.9%).

$^1$H NMR (200 MHz, DMSO-d$_6$) δ: 0.69 (3H, t, J=7.3 Hz), 1.36 (2H, brq, J=7.4 Hz), 1.43 (2H, m), 1.59 (4H, m), 2.63 (4H, m), 2.69 (2H, brt, J=6.8 Hz), 2.89 (2H, brt, J=7.4 Hz), 3.51 (2H, q, J=6.1 Hz), 7.55 (2H, d, J=8.4 Hz), 8.03 (2H, d, J=8.4 Hz), 8.82 (1H, brt, J=5.4 Hz).

62c) N-cyclopropyl-1-(4-{[(2-piperidin-1-ylethyl)amino]carbonyl}phenyl)-5-propyl-1H-1,2,3-triazole-4-carboxamide 1-(4-{[(2-Piperidin-1-ylethyl)amino]carbonyl}phenyl)-5-propyl-1H-1,2,3-triazole-4-carboxylic acid (650 mg, 1.52 mmol) obtained in Example 62b), HOBt (104 mg, 0.759 mmol, 0.5 eq.) and cyclopropylamine (0.152 ml, 2.12 mmol, 1.4 eq.) were dissolved in acetonitrile-DMF (1:1, 10 ml), WSC (386 mg, 1.97 mmol, 1.3 eq.) was added, and the mixture was stirred at room temperature for 61 hr. The reaction mixture was concentrated, dissolved in ethyl acetate (35 ml) and washed sequentially with 2% aqueous sodium carbonate solution-saturated brine (1:1, 40 ml×2, 1:4, 40 ml×1). The aqueous layers were each extracted with ethyl acetate (30 ml). The organic layers were combined and dried over anhydrous sodium sulfate and concentrated, the residue was dissolved in toluene, and the solution was subjected to column chromatography on NH silica gel (Fuji Silysia Chemical Ltd., 100-200 mesh, DM1020, 6 g). The flow-through solution and the fraction obtained by elution with ethyl acetate-hexane (1:1-2:1) were concentrated, and ethyl acetate and diethyl ether were added. The precipitate was collected by filtration, washed with diethyl ether and dried to give the title compound as a white powder (408 mg, 0.961 mmol, 63.2%).

$^1$H NMR (200 MHz, CDCl$_3$) δ: 0.68 (2H, m), 0.87 (3H, t, J=7.4 Hz), 0.87 (2H, m), 1.54 (2H, m), 1.58 (2H, brq, J=7.8 Hz), 1.68 (4H, m), 2.59 (4H, m), 2.70 (2H, t, J=5.7 Hz), 2.91 (1H, m), 3.03 (2H, m), 3.63 (2H, brq, J=5.5 Hz), 7.35 (1H, brd, J=3 Hz), 7.53 (2H, dt, J=8.8, 1.8 Hz), 8.07 (2H, dt, J=8.8, 1.8 Hz).

Elemental analysis for C$_{23}$H$_{32}$N$_6$O$_2$
Calcd. (%): C, 65.07; H, 7.60; N, 19.80.
Found (%): C, 64.98; H, 7.49; N, 19.80.

Example 63

N-cyclopropyl-1-[4-({[2-(4-methylpiperazin-1-yl)ethyl]amino}carbonyl)phenyl]-5-propyl-1H-1,2,3-triazole-4-carboxamide

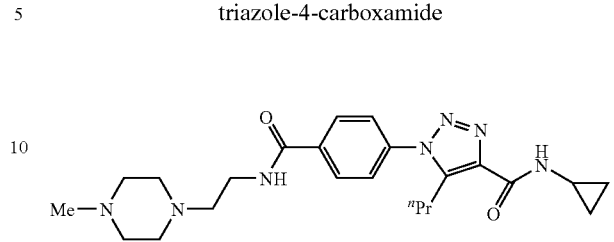

63a) 4-azido-N-(2-bromoethyl)benzamide

4-Azidobenzoic acid (1.62 g, 9.70 mmol), HOBt (662 mg, 5.15 mmol, 0.5 eq.) and 2-bromoethylamine hydrobromide (2.43 g, 11.6 mmol, 1.2 eq.) were dissolved in DMF (20 ml), WSC (2.28 g, 11.6 mmol, 1.2 eq.) was added, triethylamine (1.62 ml, 11.6 mmol, 1.2 eq.) was added, and the mixture was stirred at room temperature for 2.5 hr. The reaction mixture was diluted with ethyl acetate (70 ml) and hexane (30 ml) and washed with 2% aqueous sodium carbonate solution, saturated aqueous sodium hydrogen carbonate solution, 10% aqueous sodium chloride solution and saturated brine. The aqueous layers were each extracted with ethyl acetate-hexane (2:1, 75 ml). The organic layers were combined, dried over anhydrous sodium sulfate and concentrated at 30° C. or below to give the title compound as a pale-brown solid (2.0 g).

63b) 4-azido-N-[2-(4-methylpiperazin-1-yl)ethyl]benzamide

4-Azido-N-(2-bromoethyl)benzamide (2.0 g) obtained in Example 63a) and potassium carbonate (1.34 g, 9.70 mmol, 1.0 eq.) were suspended in acetonitrile (40 ml), N-methylpiperazine (1.63 ml, 14.6 mmol, 1.5 eq.) was added, and the mixture was stirred at room temperature for 16 hr and at 75° C. for 7 hr. The reaction mixture was concentrated, diluted with water (40 ml) and washed with ethyl acetate-hexane (2:1, 50 ml). The organic layer was extracted twice with water (20 ml). The aqueous layers were combined, concentrated, saturated with sodium chloride and extracted with ethyl acetate (40 ml and 30 ml). The organic layers were combined, dried over anhydrous sodium sulfate and concentrated at 30° C. or below to give the title compound as a pale-yellow solid (0.69 g, 2.39 mmol, 24.7%).

$^1$H NMR (200 MHz, CDCl$_3$) δ: 2.36 (3H, s), 2.59 (4H, br), 2.66 (4H, br), 2.69 (2H, t, J=5.8 Hz), 3.58 (2H, brq, J=5.7 Hz), 7.00 (1H, br), 7.09 (2H, dt, J=8.8, 2.2 Hz), 7.82 (2H, dt, J=8.6, 2.0 Hz).

63c) 1-[4-({[2-(4-methylpiperazin-1-yl)ethyl]amino}carbonyl)phenyl]-5-propyl-1H-1,2,3-triazole-4-carboxylic acid 4-Azido-N-[2-(4-methylpiperazin-1-yl)ethyl]benzamide obtained in Example 63b) and ethyl 3-oxohexanoate (0.503 ml, 2.99 mmol, 1.25 eq.) were dissolved in ethanol (15 ml), sodium ethoxide (226 mg, 2.99 mmol, 1.25 eq.) was added, and the mixture was stirred at room temperature for 30 min and at 60° C. for 10.5 hr. 1N hydrochloric acid (3.0 ml) was added to the reaction mixture, and the mixture was concentrated. The residue was diluted with acetonitrile (20 ml) and ethanol (40 ml), and the mixture was concentrated. Ethanol (15 ml), THF (20 ml) and ethyl acetate (20 ml) were added to the residue. The precipitate was collected by filtration, washed with ethyl acetate and dried to give the title compound as a pale-brown powder (purity 90%, containing sodium chloride, 1.04 g, 2.33 mmol, 98.2%).

$^1$H NMR (200 MHz, DMSO-d$_6$) δ: 0.72 (3H, t, J=7.3 Hz), 1.40 (2H, brq, J=7.5 Hz), 2.31 (3H, s), 2.56 (10H, br), 2.97 (2H, brt, J=7.3 Hz), 3.43 (2H, brq, J=6.1 Hz), 7.70 (2H, d, J=8.4 Hz), 8.09 (2H, d, J=8.6 Hz), 8.77 (1H, brt, J=5.1 Hz).

63d) N-cyclopropyl-1-[4-({[2-(4-methylpiperazin-1-yl)ethyl]amino}carbonyl)phenyl]-5-propyl-1H-1,2,3-triazole-4-carboxamide 1-[4-({[2-(4-Methylpiperazin-1-yl)ethyl]amino}carbonyl)phenyl]-5-propyl-1H-1,2,3-triazole-4-carboxylic acid (purity 90%, 687 mg, 1.54 mmol) obtained in Example 63c), HOBt (105 mg, 0.771 mmol, 0.5 eq.) and cyclopropylamine (0.143 ml, 2.00 mmol, 1.3 eq.) were dissolved in acetonitrile-DMF (1:1, 10 ml), WSC (362 mg, 1.85 mmol, 1.2 eq.) was added, and the mixture was stirred at room temperature for 20 hr. The reaction mixture was concentrated, the residue was dissolved in ethyl acetate (40 ml), and the mixture was washed sequentially with 2% aqueous sodium carbonate solution-saturated brine (1:1, 40 ml×2, 1:4, 40 ml×1). The aqueous layers were each extracted with ethyl acetate (30 ml). The organic layers were combined, dried over anhydrous sodium sulfate and concentrated, and ethyl acetate and diethyl ether were added. The precipitate was collected by filtration, washed with ethyl acetate-diethyl ether (1:1) and diethyl ether and dried to give the title compound as a white powder (418 mg, 0.951 mmol, 61.8%).

$^1$H NMR (200 MHz, CDCl$_3$) δ: 0.69 (2H, m), 0.87 (3H, t, J=7.4 Hz), 0.88 (2H, m), 1.59 (2H, brq, J=7.7 Hz), 2.33 (3H, s), 2.54 (4H, br), 2.62 (4H, br), 2.68 (2H, t, J=5.8 Hz), 2.91 (1H, m), 3.03 (2H, m), 3.61 (2H, brq, J=5.5 Hz), 7.08 (1H, brt, J=5 Hz), 7.35 (1H, brd, J=3 Hz), 7.53 (2H, d, J=8.4 Hz), 8.00 (2H, brd, J=8.4 Hz).

Elemental analysis for C$_{23}$H$_{33}$N$_7$O$_2$
Calcd. (%): C, 62.85; H, 7.57; N, 22.31.
Found (%): C, 62.67; H, 7.55; N, 22.26.

Example 64

1-[4-(aminocarbonyl)phenyl]-N-cyclopropyl-5-propyl-1H-1,2,3-triazole-4-carboxamide

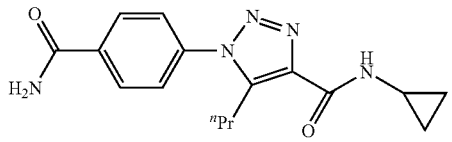

64a) 1-(4-cyanophenyl)-5-propyl-1H-1,2,3-triazole-4-carboxylic acid

In the same manner as in Example 1a), 4-azidobenzonitrile was obtained as a crude product (3.99 g) from 4-aminobenzonitrile (3.54 g), sodium nitrite (2.10 g) and sodium azide (1.95 g). Then, in the same manner as in Example 1b), the title compound was obtained as a pale-yellow powder (1.56 g, 20%) from 4-azidobenzonitrile (3.99 g) and ethyl 3-keto-n-hexanoate (5.8 ml).

NMR (CDCl$_3$) δ: 0.90 (3H, t, J=7.4), 1.54-1.64 (2H, m), 3.01-3.06 (2H, m), 7.63-7.66 (2H, m), 7.92-7.94 (2H, m).

64b) 1-(4-cyanophenyl)-N-cyclopropyl-5-propyl-1H-1,2,3-triazole-4-carboxamide In the same manner as in Example 1c), the title compound was obtained as a pale-yellow oil (0.11 g, 36%) from 1-(4-cyanophenyl)-5-propyl-1H-1,2,3-triazole-4-carboxylic acid (0.26 g) obtained in Example 64a) and cyclopropylamine (0.08 ml).

NMR (CDCl$_3$) δ: 0.65-0.70 (2H, m), 0.86-0.92 (5H, m), 1.54-1.64 (2H, m), 2.86-2.93 (1H, m), 3.03-3.08 (2h, m), 7.34 (1H, brs), 7.59-7.63 (2H, m), 7.88-7.93 (2H, m).

64c) 1-[4-(aminocarbonyl)phenyl]-N-cyclopropyl-5-propyl-1H-1,2,3-triazole-4-carboxamide To a solution of 1-(4-cyanophenyl)-N-cyclopropyl-5-propyl-1H-1,2,3-triazole-4-carboxamide (0.43 g) obtained in Example 64b) in ethanol (15 ml) was added Raney-nickel (0.09 g), and the mixture was stirred at room temperature for 14 hr under a hydrogen atmosphere. The reaction mixture was filtered through celite, and the filtrate was concentrated under reduced pressure. The residue was purified by silica gel column (ethyl acetate/hexane=1/1 to ethyl acetate) to give the title compound as a pale-yellow powder (0.11 g, 24%).

NMR (CDCl$_3$) δ: 0.65-0.71 (2H, m), 0.82-0.92 (5H, m), 1.52-1.62 (2H, m), 2.86-2.95 (1H, m), 3.01-3.06 (2H, m), 5.92 (1H, brs), 6.21 (1H, brs), 7.36 (1H, brs), 7.55 (2H, d, J=8.5), 8.03 (2H, d, J=8.5).

Elemental analysis for C$_{16}$H$_{19}$N$_5$O$_2$·0.1AcOEt·0.25H$_2$O
Calcd. (%): C, 60.30; H, 6.26; N, 21.44.
Found (%): C, 60.59; H, 6.38; N, 21.23.

Example 65

N-cyclopropyl-1-{3-methyl-4-[(methylamino)carbonyl]phenyl}-5-propyl-1H-1,2,3-triazole-4-carboxamide

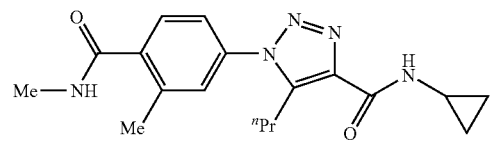

65a) 4-amino-N,2-dimethylbenzamide

In the same manner as in Example 1d), the title compound was obtained as a yellow oil (0.36 g) from 4-nitro-N,2-dimethylbenzamide (0.40 g).

65b) 4-azido-N,2-dimethylbenzamide

In the same manner as in Example 1a), the title compound was obtained as a pale-brown powder (0.27 g, 65%) from 4-amino-N,2-dimethylbenzamide (0.40 g) obtained in Example 65a).

65c) 1-{3-methyl-4-[(methylamino)carbonyl]phenyl}-5-propyl-1H-1,2,3-triazole-4-carboxylic acid In the same manner as in Example 43b), the title compound was obtained as a white powder (0.32 g, 75%) from 4-azido-N,2-dimethylbenzamide (0.27 g) obtained in Example 65b).

NMR (DMSO-$d_6$) δ: 0.74 (3H, t, J=7.2), 1.39-1.49 (2H, m), 2.41 (3H, s), 2.79 (3H, d, J=4.5), 2.92 (2H, t, J=7.7), 7.44-7.55 (3H, m), 8.38 (1H, q, J=4.5).

65d) N-cyclopropyl-1-{3-methyl-4-[(methylamino)carbonyl]phenyl}-5-propyl-1H-1,2,3-triazole-4-carboxamide In the same manner as in Example 43c), the title compound was obtained as a colorless powder (0.24 g, 67%) from 1-{3-methyl-4-[(methylamino)carbonyl]phenyl}-5-propyl-1H-1,2,3-triazole-4-carboxylic acid (0.32 g) obtained in Example 65c).

NMR (CDCl$_3$) δ: 0.64-0.70 (2H, m), 0.85-0.91 (5H, m), 1.53-1.61 (2H, m), 2.53 (3H, s), 2.86-2.92 (1H, m), 2.96-3.01 (2H, m), 3.04 (3H, d, J=4.8), 5.90 (1H, brs), 7.23-7.33 (3H, m), 7.53 (1H, d, J=8.1).

Elemental analysis for $C_{18}H_{23}N_5O_2$
Calcd. (%): C, 63.32; H, 6.79; N, 20.51.
Found (%): C, 63.30; H, 6.72; N, 20.43.

Example 66

1-{3-chloro-4-[(ethylamino)carbonyl]phenyl}-N-cyclopropyl-5-propyl-1H-1,2,3-triazole-4-carboxamide

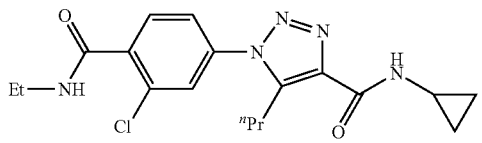

66a) 2-chloro-N-ethyl-4-nitrobenzamide

In the same manner as in Example 43a), the title compound was obtained as a colorless powder (5.74 g, 76%) from 2-chloro-4-nitrobenzoic acid (6.66 g).

NMR (CDCl$_3$) δ: 1.29 (3H, t, J=7.2), 3.49-3.58 (2H, m), 6.14 (1H, brs), 7.78 (1H, d, J=8.4), 8.15 (1H, dd, J=8.4, 2.1), 8.27 (1H, d, J=2.1).

66b) 4-amino-2-chloro-N-ethylbenzamide

2-Chloro-N-ethyl-4-nitrobenzamide (2.00 g) obtained in Example 66a), iron powder (2.43 g) and calcium chloride (0.48 g) were suspended in an aqueous solution (30 ml) of 85% ethanol, and the mixture was refluxed for 1 hr. After cooling to room temperature, the reaction mixture was diluted with ethyl acetate (100 ml), and the insoluble material was removed by filtration through celite. The filtrate was concentrated, and the residue was purified by silica gel column (ethyl acetate/hexane=1/1 to ethyl acetate) to give the title compound as a yellow powder (1.55 g, 90%).

NMR (CDCl$_3$) δ: 1.24 (3H, t, J=7.2), 3.43-3.52 (2H, m), 4.01 (2H, brs), 6.42 (1H, brs), 6.56 (1H, dd, J=8.4, 2.4), 6.63 (1H, d, J=2.4), 7.62 (1H, d, J=8.4).

66c) 4-azido-2-chloro-N-ethylbenzamide

In the same manner as in Example 1a), the title compound was obtained as a pale-brown powder (1.22 g, 70%) from 4-amino-2-chloro-N-ethylbenzamide (1.55 g) obtained in Example 66b).

66d) 1-{3-chloro-4-[(ethylamino)carbonyl]phenyl}-5-propyl-1H-1,2,3-triazole-4-carboxylic acid In the same manner as in Example 43b), the title compound was obtained as a white powder (1.67 g, 91%) from 4-azido-2-chloro-N-ethylbenzamide (1.22 g) obtained in Example 66c).

NMR (CDCl$_3$) δ: 0.75 (3H, t, J=7.4), 1.14 (3H, t, J=7.4), 1.40-1.47 (2H, m), 2.94 (2H, t, J=7.5), 3.24-3.34 (2H, m), 7.67 (2H, s), 7.89 (1H, s), 8.62 (1H, t, J=5.3).

66e) 1-{3-chloro-4-[(ethylamino)carbonyl]phenyl}-N-cyclopropyl-5-propyl-1H-1,2,3-triazole-4-carboxamide In the same manner as in Example 43c), the title compound was obtained as a colorless powder (0.42 g, 37%) from 1-{3-chloro-4-[(ethylamino)carbonyl]phenyl}-5-propyl-1H-1,2,3-triazole-4-carboxylic acid (1.00 g) obtained in Example 66d).

NMR (CDCl$_3$) δ: 0.65-0.70 (2H, m), 0.85-0.92 (5H, m), 1.30 (3H, t, J=7.2), 1.52-1.62 (2H, m), 2.86-2.92 (1H, m), 2.99-3.04 (2H, m), 3.51-3.60 (2H, m), 6.32 (1H, brs), 7.33 (1H, brs), 7.40 (1H, dd, J=7.8, 2.1), 7.54 (1H, d, J=2.1), 7.84 (1H, d, J=7.8).

Elemental analysis for $C_{18}H_{22}N_5O_2Cl$
Calcd. (%): C, 57.52; H, 5.90; N, 18.63.
Found (%): C, 57.29; H, 5.81; N, 18.38.

Example 67

N-cyclopropyl-1-{4-[(ethylamino)carbonyl]-3-fluorophenyl}-5-propyl-1H-1,2,3-triazole-4-carboxamide and N-cyclopropyl-1-{3-ethoxy-4-[(ethylamino)carbonyl]phenyl}-5-propyl-1H-1,2,3-triazole-4-carboxamide

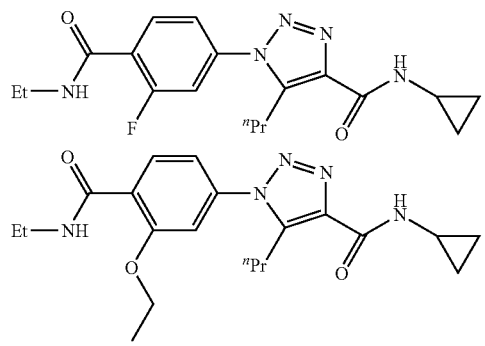

67a) N-ethyl-2-fluoro-4-nitrobenzamide

In the same manner as in Example 43a), the title compound was obtained as a colorless powder (0.85 g, 36%) from 2-fluoro-4-nitrobenzoic acid (2.00 g).

NMR (CDCl₃) δ: 1.29 (3H, t, J=7.2), 3.48-3.63 (2H, m), 6.71 (1H, brs), 8.02 (1H, dd, J=11.2, 2.2), 8.12 (1H, dd, J=8.4, 2.2), 8.30 (1H, dd, J=8.4, 7.6).

67b) 4-amino-N-ethyl-2-fluorobenzamide

In the same manner as in Example 1d), the title compound was obtained as a yellow powder (0.81 g, quant.) from N-ethyl-2-fluoro-4-nitrobenzamide (0.85 g) obtained in Example 67a).
NMR (CDCl₃) δ: 1.23 (3H, t, J=7.4), 3.43-3.53 (2H, m), 3.89 (2H, brs), 6.32 (1H, dd, J=14.4, 2.4), 6.48 (1H, dd, J=8.4, 2.4), 6.61 (1H, brs), 7.90 (1H, dd, J=9.0, 8.4).

67c) 4-azido-N-ethyl-2-fluorobenzamide

In the same manner as in Example 1a), the title compound was obtained as an orange powder (0.74 g, 89%) from 4-amino-N-ethyl-2-fluorobenzamide (0.81 g) obtained in Example 67b).

67d) 1-{4-[(ethylamino)carbonyl]-3-fluorophenyl}-5-propyl-1H-1,2,3-triazole-4-carboxylic acid and 1-{3-ethoxy-4-[(ethylamino)carbonyl]phenyl}-5-propyl-1H-1,2,3-triazole-4-carboxylic acid In the same manner as in Example 43b), a mixture of the title compounds (about 6:4 mixture) was obtained as a brown oil (1.29 g) from 4-azido-N-ethyl-2-fluorobenzamide (0.74 g) obtained in Example 67c).

67e) N-cyclopropyl-1-{3-ethoxy-4-[(ethylamino) carbonyl]phenyl}-5-propyl-1H-1,2,3-triazole-4-carboxamide and N-cyclopropyl-1-{4-[(ethylamino) carbonyl]-3-fluorophenyl}-5-propyl-1H-1,2,3-triazole-4-carboxamide In the same manner as in Example 43c), N-cyclopropyl-1-{4-[(ethylamino)carbonyl]-3-fluorophenyl}-5-propyl-1H-1,2,3-triazole-4-carboxamide (pale-yellow powder, 0.33 g, 31%) and N-cyclopropyl-1-{3-ethoxy-4-[(ethylamino)carbonyl]phenyl}-5-propyl-1H-1,2,3-triazole-4-carboxamide (white powder, 0.14 g, 9%) were obtained from a mixture (1.29 g) of 1-{4-[(ethylamino)carbonyl]-3-fluorophenyl}-5-propyl-1H-1,2,3-triazole-4-carboxylic acid and 1-{3-ethoxy-4-[(ethylamino)carbonyl]phenyl}-5-propyl-1H-1,2,3-triazole-4-carboxylic acid obtained in Example 67d).

N-cyclopropyl-1-{4-[(ethylamino)carbonyl]-3-fluorophenyl}-5-propyl-1H-1,2,3-triazole-4-carboxamide NMR (CDCl₃) δ: 0.63-0.71 (2H, m), 0.84-0.91 (5H, m), 1.30 (3H, t, J=7.4), 1.51-1.69 (2H, m), 2.84-2.95 (1H, m), 3.02-3.10 (2H, m), 3.50-3.63 (2H, m), 6.73 (1H, brs), 7.26-7.40 (3H, m), 8.33 (1H, t, J=8.4).
Elemental analysis for C₁₈H₂₂N₅O₂F
Calcd. (%): C, 60.15; H, 6.17; N, 19.41.
Found (%): C, 60.15; H, 6.11; N, 19.41.

N-cyclopropyl-1-{3-ethoxy-4-[(ethylamino)carbonyl]phenyl}-5-propyl-1H-1,2,3-triazole-4-carboxamide NMR (CDCl₃) δ: 0.65-0.70 (2H, m), 0.85-0.91 (5H, m), 1.28 (3H, t, J=7.2), 1.54-1.62 (5H, m), 2.86-2.93 (1H, m), 3.00-3.05 (2H, m), 3.49-3.58 (2H, m), 4.23 (2H, q, J=7.0), 7.04 (1H, d, J=1.8), 7.09 (1H, dd, J=8.1, 1.8), 7.33 (1H, brs), 7.91 (1H, brs), 8.40 (1H, d, J=8.1).
Elemental analysis for C₂₀H₂₇N₅O₃
Calcd. (%): C, 62.32; H, 7.06; N, 18.17.
Found (%): C, 62.07; H, 6.97; N, 18.16.

Example 68

N-cyclopropyl-1-{4-[(ethylamino)carbonyl]-3-methylphenyl}-5-propyl-1H-1,2,3-triazole-4-carboxamide

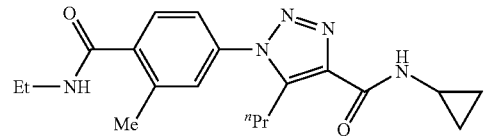

68a) N-ethyl-2-methyl-4-nitrobenzamide

In the same manner as in Example 43a), the title compound was obtained as a colorless powder (0.92 g, 40%) from 2-methyl-4-nitrobenzoic acid (2.00 g).
NMR (CDCl₃) δ: 1.27 (3H, t, J=7.3), 2.53 (3H, s), 3.44-3.58 (2H, m), 5.79 (1H, brs), 7.49 (1H, d, J=8.0), 8.02-8.09 (2H, m).

68b) 4-amino-N-ethyl-2-methylbenzamide

In the same manner as in Example 1d), the title compound was obtained as a yellow powder (0.95 g, quant.) from N-ethyl-2-methyl-4-nitrobenzamide (0.92 g) obtained in Example 68a).
NMR (CDCl₃) δ: 1.22 (3H, t, J=7.2), 2.39 (3H, s), 3.39-3.49 (2H, m), 3.73 (2H, brs), 5.73 (1H, brs), 6.44-6.50 (2H, m), 7.20 (1H, d, J=8.1).

68c) 4-azido-N-ethyl-2-methylbenzamide

In the same manner as in Example 1a), the title compound was obtained as an orange powder (0.81 g, 90%) from 4-amino-N-ethyl-2-methylbenzamide (0.95 g) obtained in Example 68b).

68d) 1-{4-[(ethylamino)carbonyl]-3-methylphenyl}-5-propyl-1H-1,2,3-triazole-4-carboxylic acid In the same manner as in Example 43b), the title compound was obtained as a white powder (1.01 g, 80%) from 4-azido-N-ethyl-2-methylbenzamide (0.81 g) obtained in Example 68c).
NMR (DMSO-d₆) δ: 0.75 (3H, t, J=7.4), 1.14 (3H, t, J=7.2), 1.40-1.47 (2H, m), 2.42 (3H, s), 2.93 (2H, t, J=7.7), 3.24-3.33 (2H, m), 7.45-7.55 (3H, m), 8.45 (1H, t, J=5.6).

68e) N-cyclopropyl-1-{4-[(ethylamino)carbonyl]-3-methylphenyl}-5-propyl-1H-1,2,3-triazole-4-carboxamide In the same manner as in Example 43c), the title compound was obtained as a colorless powder (0.43 g, 82%) from 1-{4-[(ethylamino)carbonyl]-3-methylphenyl}-5-propyl-1H-1,2,3-triazole-4-carboxylic acid (0.60 g) obtained in Example 68d).

NMR (CDCl$_3$) δ: 0.64-0.69 (2H, m), 0.84-0.90 (5H, m), 1.28 (3H, t, J=7.2), 1.53-1.60 (2H, m), 2.53 (3H, s), 2.86-2.91 (1H, m), 2.92-3.01 (2H, m), 3.47-3.57 (2H, m), 5.84 (1H, brs), 7.23-7.33 (3H, m), 7.53 (1H, d, J=8.4).

Elemental analysis for C$_{19}$H$_{25}$N$_5$O$_2$

Calcd. (%): C, 64.20; H, 7.09; N, 19.70.

Found (%): C, 63.96; H, 6.80; N, 19.64.

Example 69

N-cyclopropyl-1-{4-[(ethylamino)carbonyl]-3-methoxyphenyl}-5-propyl-1H-1,2,3-triazole-4-carboxamide

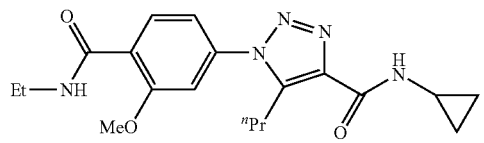

69a) 4-amino-N-ethyl-2-methoxybenzamide

In the same manner as in Example 43a), the title compound was obtained as a yellow powder (1.10 g, 54%) from 4-amino-2-methoxybenzoic acid (1.75 g).

NMR (CDCl$_3$) δ: 1.21 (3H, t, J=7.4), 2.26 (2H, s), 3.30-3.48 (2H, m), 3.88 (3H, s), 6.20 (1H, d, J=2.1), 6.32 (1H, dd, J=8.7, 2.1), 7.71 (1H, brs), 8.01 (1H, d, J=8.7).

69b) 4-azido-N-ethyl-2-methoxybenzamide

In the same manner as in Example 1a), the title compound was obtained as a yellow powder (0.87 g, 70%) from 4-amino-N-ethyl-2-methoxybenzamide (1.10 g) obtained in Example 69a).

69c) 1-{4-[(ethylamino)carbonyl]-3-methoxyphenyl}-5-propyl-1H-1,2,3-triazole-4-carboxylic acid In the same manner as in Example 43b), the title compound was obtained as a white powder (0.93 g, 71%) from 4-azido-N-ethyl-2-methoxybenzamide (0.87 g) obtained in Example 69b).

NMR (DMSO-d$_6$) δ: 0.76 (3H, t, J=7.4), 1.14 (3H, t, J=7.4), 1.41-1.49 (2H, m), 2.96 (2H, t, J=7.7), 3.27-3.42 (2H, m), 3.92 (3H, s), 7.22-7.26 (1H, m), 7.39 (1H, d, J=1.8), 7.87 (1H, d, J=8.1), 8.31 (1H, t, J=5.6).

69d) N-cyclopropyl-1-{4-[(ethylamino)carbonyl]-3-methoxyphenyl}-5-propyl-1H-1,2,3-triazole-4-carboxamide In the same manner as in Example 43c), the title compound was obtained as a colorless powder (0.29 g, 58%) from 1-{4-[(ethylamino)carbonyl]-3-methoxyphenyl}-5-propyl-1H-1,2,3-triazole-4-carboxylic acid (0.60 g) obtained in Example 69c).

NMR (CDCl$_3$) δ: 0.65-0.70 (2H, m), 0.85-0.90 (5H, m), 1.28 (3H, t, J=7.4), 1.56-1.66 (2H, m), 2.87-2.93 (1H, m), 3.01-3.06 (2H, m), 3.49-3.58 (2H, m), 4.02 (3H, s), 7.08-7.14 (2H, m), 7.33 (1H, brs), 7.73 (1H, brs), 8.40 (1H, d, J=8.4).

Elemental analysis for C$_{19}$H$_{25}$N$_5$O$_3$

Calcd. (%): C, 61.44; H, 6.78; N, 18.85.

Found (%): C, 61.47; H, 6.73; N, 18.85.

Example 70

N-cyclopropyl-1-{4-[(ethylamino)carbonyl]-2-methylphenyl}-5-propyl-1H-1,2,3-triazole-4-carboxamide

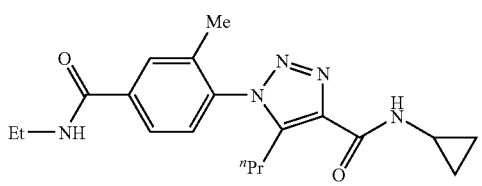

70a) N-ethyl-3-methyl-4-nitrobenzamide

In the same manner as in Example 43a), the title compound was obtained as a white powder (5.8 g, 93%) from 3-methyl-4-nitrobenzoic acid (5.4 g) and 2M ethylamine in THF solution (18 ml).

NMR (CDCl$_3$) δ: 1.28 (3H, t, J=7.2), 2.64 (3H, s), 3.52 (2H, dq, J=5.7, 7.2), 6.21 (1H, brs), 7.68 (1H, dd, J=1.5, 8.5), 7.76 (1H, d, J=1.5), 7.99 (1H, d, J=8.5).

70b) 4-amino-N-ethyl-3-methylbenzamide monohydrochloride

To a solution of N-ethyl-3-methyl-4-nitrobenzamide (5.8 g) obtained in Example 70a) in ethanol (100 ml) was added 10% Pd/C (50% wet, 0.58 g), and the mixture was stirred for 24 hr under a hydrogen atmosphere. The reaction mixture was filtered through celite, and the filtrate was evaporated under reduced pressure. The residue was purified by silica gel column (ethyl acetate/hexane=1/1 to ethyl acetate). 4N hydrochloric acid-ethyl acetate solution (14 ml) was added to a solution of the purified substance in ethyl acetate (30 ml) under ice-cooling, and the mixture was stirred for 5 min. The precipitated insoluble material was collected by filtration and washed with ethyl acetate to give the title compound as a white powder (5.3 g, 89%).

NMR (DMSO-d$_6$) δ: 1.10 (3H, t, J=7.3), 2.29 (3H, s), 3.21-3.30 (2H, m), 7.19 (1H, d, J=8.3), 7.64 (1H, dd, J=1.9, 8.3), 7.69 (1H, d, J=1.9), 8.35 (1H, brs).

70c) 4-azido-N-ethyl-3-methylbenzamide

In the same manner as in Example 1a), the title compound was obtained as a yellow solid (1.7 g, 94%) from 4-amino-N-ethyl-3-methylbenzamide monohydrochloride (1.9 g) obtained in Example 70b), 1 M aqueous sodium nitrite solution (8.9 ml) and sodium azide (0.58 g).

NMR (CDCl$_3$) δ: 1.25 (3H, t, J=7.2), 1.64 (3H, s), 3.44-3.53 (2H, m), 6.09 (1H, brs), 7.13 (1H, d, J=8.1), 7.58-7.67 (2H, m).

70d) 1-{4-[(ethylamino)carbonyl]-2-methylphenyl}-5-propyl-1H-1,2,3-triazole-4-carboxylic acid In the same manner as in Example 43b), the title compound was obtained as a red oil (0.58 g, 43%) from 4-azido-N-ethyl-3-methylbenzamide (0.85 g) obtained in Example 70c) and ethyl 3-keto-n-hexanoate (0.8 ml). The obtained crude product was used for the next reaction without further purification.

70e) N-cyclopropyl-1-{4-[(ethylamino)carbonyl]-2-methylphenyl}-5-propyl-1H-1,2,3-triazole-4-carboxamide In the same manner as in Example 43c), the title compound was obtained as a yellow amorphous solid (0.20 g, 31%) from 1-{4-[(ethylamino)carbonyl]-2-methylphenyl}-5-propyl-1H-1,2,3-triazole-4-carboxylic acid (0.58 g) obtained in Example 70d) and cyclopropylamine (0.15 ml).

NMR (CDCl$_3$) δ: 0.66-0.71 (2H, m), 0.79-0.92 (5H, m), 1.24-1.31 (3H, m), 1.42-1.54 (2H, m), 2.06 (3H, s), 2.80-2.95 (3H, m), 3.48-3.58 (2H, m), 3.52 (1H, brt, J=5.1), 7.27 (1H, d, J=8.7), 7.38 (1H, brd, J=2.6), 7.76 (1H, dd, J=1.7, 8.1), 7.85 (1H, d, J=1.7).

Elemental analysis for $C_{19}H_{25}N_5O_2 \cdot 0.25AcOEt \cdot 0.25H_2O$
Calcd. (%): C, 62.89; H, 7.26; N, 18.34.
Found (%): C, 62.59; H, 7.15; N, 18.31.

Example 71

N-cyclopropyl-1-{4-[(ethylamino)carbonyl]-2-methoxyphenyl}-5-propyl-1H-1,2,3-triazole-4-carboxamide

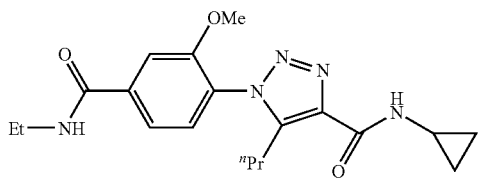

71a) N-ethyl-3-methoxy-4-nitrobenzamide

In the same manner as in Example 43a), the title compound was obtained as a yellow oil (6.7 g, 100%) from 3-methoxy-4-nitrobenzoic acid (5.9 g) and 2M ethylamine in THF solution (18 ml).

NMR (CDCl$_3$) δ: 1.27 (3H, t, J=7.2), 3.51 (2H, dq, J=5.8, 7.2), 4.00 (3H, s), 6.49 (1H, brs), 7.30 (1H, dd, J=1.5, 8.3), 7.61 (1H, d, J=1.5), 7.83 (1H, d, J=8.3).

71b) 4-amino-N-ethyl-3-methoxybenzamide monohydrochloride

In the same manner as in Example 70b), the title compound was obtained as a white powder (6.5 g, 94%) from N-ethyl-3-methoxy-4-nitrobenzamide (6.7 g) obtained in Example 71a) and 10% Pd/C (50% wet, 0.67 g).

NMR (DMSO-d$_6$) δ: 1.12 (3H, t, J=7.3), 3.23-3.32 (2H, m), 3.90 (3H, s), 7.19 (1H, d, J=8.1), 7.43 (1H, dd, J=1.9, 8.3), 7.53 (1H, d, J=1.9), 8.46 (1H, brs).

71c) 4-azido-N-ethyl-3-methoxybenzamide

In the same manner as in Example 1a), the title compound was obtained as a brown solid (2.9 g, 94%) from 4-amino-N-ethyl-3-methoxybenzamide monohydrochloride (3.1 g) obtained in Example 71b), 1 M aqueous sodium nitrite solution (13 ml) and sodium azide (0.87 g).

NMR (CDCl$_3$) δ: 1.26 (3H, t, J=7.4), 3.45-3.54 (2H, m), 3.93 (3H, s), 6.16 (1H, brs), 6.98 (1H, d, J=8.3), 7.22 (1H, dd, J=1.8, 8.1), 7.44 (1H, d, J=1.8).

71d) 1-{4-[(ethylamino)carbonyl]-2-methoxyphenyl}-5-propyl-1H-1,2,3-triazole-4-carboxylic acid In the same manner as in Example 43b), the title compound was obtained as a red oil (1.2 g, 59%) from 4-azido-N-ethyl-3-methoxybenzamide (1.4 g) obtained in Example 71c) and ethyl 3-keto-n-hexanoate (1.2 ml). The obtained crude product was used for the next reaction without further purification.

71e) N-cyclopropyl-1-{4-[(ethylamino)carbonyl]-2-methoxyphenyl}-5-propyl-1H-1,2,3-triazole-4-carboxamide In the same manner as in Example 43c), the title compound was obtained as a white powder (0.57 g, 42%) from 1-{4-[(ethylamino)carbonyl]-2-methoxyphenyl}-5-propyl-1H-1,2,3-triazole-4-carboxylic acid (1.2 g) obtained in Example 71d) and cyclopropylamine (0.31 ml).

NMR (CDCl$_3$) δ: 0.64-0.70 (2H, m), 0.79 (3H, t, J=7.4), 0.84-0.90 (2H, m), 1.28 (3H, t, J=7.4), 1.49 (2H, sextet, J=7.5), 2.85-2.93 (3H, m), 3.49-3.58 (2H, m), 3.84 (3H, s), 6.51 (1H, brt, J=5.3), 7.32-7.35 (2H, m), 7.40 (1H, dd, J=1.7, 8.1), 7.62 (1H, d, J=1.7).

Elemental analysis for $C_{19}H_{25}N_5O_3$
Calcd. (%): C, 61.44; H, 6.78; N, 18.85.
Found (%): C, 61.12; H, 6.84; N, 18.65.

Example 72

1-{2-chloro-4-[(ethylamino)carbonyl]phenyl}-N-cyclopropyl-5-propyl-1H-1,2,3-triazole-4-carboxamide

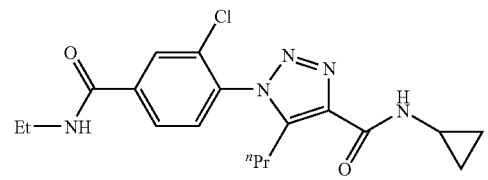

72a) 4-amino-3-chlorobenzoic acid

To a solution of methyl 4-amino-3-chlorobenzoate (3.3 g) in ethanol (53 ml) was added 8N aqueous sodium hydroxide solution (4.4 ml), and the mixture was stirred at 40° C. for 3.5 hr. The solvent was evaporated under reduced pressure, and the residue was dissolved in water. The obtained aqueous solution was washed with diethyl ether and neutralized with 1N aqueous hydrochloric acid solution. The precipitated insoluble material was collected by filtration and air-dried to give the title compound as a pale-brown powder (3.0 g, 100%).

NMR (DMSO-d$_6$) δ: 6.15 (2H, s), 6.79 (1H, d, J=8.5), 7.59 (1H, dd, J=1.9, 8.5), 7.70 (1H, d, J=1.9), 12.37 (1H, brs).

72b) 4-amino-3-chloro-N-ethylbenzamide

In the same manner as in Example 43a), the title compound was obtained as a white solid (3.5 g, 100%) from 4-amino-3-chlorobenzoic acid (3.0 g) obtained in Example 72a) and 2M ethylamine in THF solution (11 ml).

NMR (CDCl$_3$) δ: 1.23 (3H, t, J=7.4), 3.41-3.50 (2H, m), 4.38 (2H, brs), 6.07 (1H, brs), 6.74 (1H, d, J=8.3), 7.49 (1H, dd, J=2.1, 8.3), 7.71 (1H, d, J=2.1).

72c) 4-azido-3-chloro-N-ethylbenzamide

In the same manner as in Example 1a), the title compound was obtained as a brown solid (2.8 g, 69%) from 4-amino-3-chloro-N-ethylbenzamide (3.5 g) obtained in Example 72b), 1M aqueous sodium nitrite solution (21 ml) and sodium azide (1.4 g). The obtained crude product was used for the next reaction without further purification.

72d) 1-{2-chloro-4-[(ethylamino)carbonyl]phenyl}-5-propyl-1H-1,2,3-triazole-4-carboxylic acid In the same manner as in Example 43b), the title compound was obtained as a red oil (0.91 g, 44%) from 4-azido-3-chloro-N-ethylbenzamide (1.4 g) obtained in Example 72c) and ethyl 3-keto-n-hexanoate (1.2 ml). The obtained crude product was used for the next reaction without further purification.

72e) 1-{2-chloro-4-[(ethylamino)carbonyl]phenyl}-N-cyclopropyl-5-propyl-1H-1,2,3-triazole-4-carboxamide In the same manner as in Example 43c), the title compound was obtained as a brown amorphous solid (0.08 g, 8%) from 1-{2-chloro-4-[(ethylamino)carbonyl]phenyl}-5-propyl-1H-1,2,3-triazole-4-carboxylic acid (0.91 g) obtained in Example 72d) and cyclopropylamine (0.23 ml).

NMR (CDCl$_3$) δ: 0.66-0.71 (2H, m), 0.79-0.91 (5H, m), 1.21-1.32 (4H, m), 1.44-1.57 (2H, m), 2.85-2.95 (1H, m), 3.50-3.59 (2H, m), 6.42 (1H, brt, J=5.3), 7.36 (1H, brd, J=2.5), 7.47 (1H, d, J=8.1), 7.86 (1H, dd, J=1.9, 8.1), 8.04 (1H, d, J=1.9).

Elemental analysis for C$_{18}$H$_{22}$ClN$_5$O$_2$.0.5AcOEt-0.25Et$_2$O
Calcd. (%): C, 57.86; H, 6.59; N, 16.07.
Found (%): C, 58.11; H, 6.27; N, 15.80.

Example 73

1-{2-chloro-4-[(ethylamino)carbonyl]-5-methoxyphenyl}-N-cyclopropyl-5-propyl-1H-1,2,3-triazole-4-carboxamide

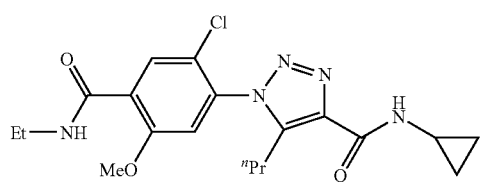

73a)
4-amino-5-chloro-N-ethyl-2-methoxybenzamide

In the same manner as in Example 43a), the title compound was obtained as a white powder (2.3 g, 100%) from 4-amino-5-chloro-2-methoxybenzoic acid (2.0 g) and 2M ethylamine in THF solution (6 ml).

NMR (CDCl$_3$) δ: 1.22 (3H, t, J=6.8), 3.39-3.52 (2H, m), 3.89 (3H, s), 4.40 (2H, brs), 6.30 (1H, s), 7.63 (1H, brs), 8.11 (1H, s).

73b) 4-azido-5-chloro-N-ethyl-2-methoxybenzamide

In the same manner as in Example 1a), the title compound was obtained as a brown solid (2.0 g, 80%) from 4-amino-5-chloro-N-ethyl-2-methoxybenzamide (2.3 g) obtained in Example 73a), 1M aqueous sodium nitrite solution (10 ml) and sodium azide (0.65 g). The obtained crude product was used for the next reaction without further purification.

73c) 1-{2-chloro-4-[(ethylamino)carbonyl]-5-methoxyphenyl}-5-propyl-1H-1,2,3-triazole-4-carboxylic acid In the same manner as in Example 43b), the title compound was obtained as a brown oil (0.46 g, 31%) from 4-azido-5-chloro-N-ethyl-2-methoxybenzamide (1.0 g) obtained in Example 73b) and ethyl 3-keto-n-hexanoate (0.77 ml). The obtained crude product was used for the next reaction without further purification.

73d) 1-{2-chloro-4-[(ethylamino)carbonyl]-5-methoxyphenyl}-N-cyclopropyl-5-propyl-1H-1,2,3-triazole-4-carboxamide In the same manner as in Example 43c), the title compound was obtained as a white powder (0.02 g, 3%) from 1-{2-chloro-4-[(ethylamino)carbonyl]-5-methoxyphenyl}-5-propyl-1H-1,2,3-triazole-4-carboxylic acid (0.46 g) obtained in Example 73c) and cyclopropylamine (0.10 ml).

NMR (CDCl$_3$) δ: 0.66-0.71 (2H, m), 0.82-0.92 (5H, m), 1.28 (3H, t, J=7.4), 1.50-1.57 (2H, m), 2.87-2.95 (3H, m), 3.49-3.58 (2H, m), 3.99 (3H, s), 7.01 (1H, s), 7.34 (1H, brs), 7.68 (1H, brs), 8.44 (1H, s).

Elemental analysis for C$_{19}$H$_{24}$ClN$_5$O$_3$.0.25H$_2$O
Calcd. (%): C, 55.61; H, 6.02; N, 17.07.
Found (%): C, 55.88; H, 5.93; N, 16.82.

Example 74

N-cyclopropyl-1-{2-ethoxy-4-[(ethylamino)carbonyl]phenyl}-5-propyl-1H-1,2,3-triazole-4-carboxamide

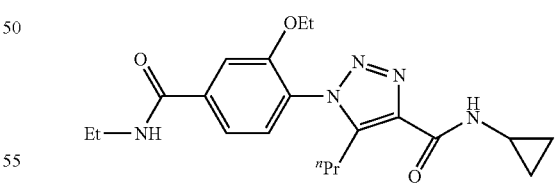

74a) N-ethyl-3-hydroxy-4-nitrobenzamide

In the same manner as in Example 43a), the title compound was obtained as a yellow solid (11 g, 100%) from 3-hydroxy-4-nitrobenzoic acid (9.2 g) and 2M ethylamine in THF solution (30 ml).

NMR (CDCl$_3$) δ: 1.25 (3H, t, J=7.2), 3.49 (2H, dq, J=5.7, 7.2), 7.07 (1H, brs), 7.38 (1H, dd, J=1.7, 8.7), 7.55 (1H, d, J=1.9), 8.11 (1H, d, J=8.7), 8.97 (1H, brs).

74b) 3-ethoxy-N-ethyl-4-nitrobenzamide

To a solution of N-ethyl-3-hydroxy-4-nitrobenzamide (2.1 g) obtained in Example 74a) in acetone (100 ml) were added potassium carbonate (1.4 g) and bromoethane (0.75 ml), and the mixture was heated under reflux overnight. After cooling to room temperature, the solvent was evaporated under reduced pressure. Water and ethyl acetate were added to the residue, and the organic layer was fractionated. The organic layer was dried over sodium sulfate, and the solvent was evaporated under reduced pressure to give the title compound as a pale-brown solid (0.72 g, 30%).

NMR (CDCl$_3$) δ: 1.27 (3H, t, J=7.2), 1.47 (3H, t, J=7.0), 3.49 (2H, dq, J=5.7, 7.2), 4.23 (2H, q, J=7.0), 6.47 (1H, s), 7.26-7.29 (1H, m), 7.58 (1H, d, J=1.5), 7.79 (1H, d, J=8.5).

74c) 4-amino-3-ethoxy-N-ethylbenzamide

In the same manner as in Example 1d), the title compound was obtained as a colorless oil (0.53 g, 84%) from 3-ethoxy-N-ethyl-4-nitrobenzamide (0.72 g) obtained in Example 74b) and 10% Pd/C (50% wet, 0.07 g).

NMR (CDCl$_3$) δ: 1.21 (3H, t, J=7.4), 1.41 (3H, t, J=7.0), 3.44 (2H, dq, J=5.7, 7.4), 4.07 (2H, q, J=7.0), 4.13 (2H, brs), 6.25 (1H, brs), 6.63 (1H, d, J=8.1), 7.14 (1H, dd, J=1.9, 8.1), 7.34 (1H, d, J=1.9).

74d) 4-azido-3-ethoxy-N-ethylbenzamide

In the same manner as in Example 1a), the title compound was obtained as a yellow oil (0.50 g, 85%) from 4-amino-3-ethoxy-N-ethylbenzamide (0.53 g) obtained in Example 74c), 1M aqueous sodium nitrite solution (2.5 ml) and sodium azide (0.17 g). The obtained crude product was used for the next reaction without further purification.

74e) 1-{2-ethoxy-4-[(ethylamino)carbonyl]phenyl}-5-propyl-1H-1,2,3-triazole-4-carboxylic acid In the same manner as in Example 43b), the title compound was obtained as a pale-brown solid (0.25 g, 73%) from 4-azido-3-ethoxy-N-ethylbenzamide (0.25 g) obtained in Example 74d) and ethyl 3-keto-n-hexanoate (0.19 ml). The obtained crude product was used for the next reaction without further purification.

74f) N-cyclopropyl-1-{2-ethoxy-4-[(ethylamino)carbonyl]phenyl}-5-propyl-1H-1,2,3-triazole-4-carboxamide In the same manner as in Example 43c), the title compound was obtained as a pale-yellow powder (0.09 g, 31%) from 1-{2-ethoxy-4-[(ethylamino)carbonyl]phenyl}-5-propyl-1H-1,2,3-triazole-4-carboxylic acid (0.25 g) obtained in Example 74e) and cyclopropylamine (0.06 ml).

NMR (CDCl$_3$) δ: 0.65-0.71 (2H, m), 0.79 (3H, t, J=7.4), 0.84-0.90 (2H, m), 1.24-1.31 (7H, m), 1.43-1.56 (2H, m), 2.82-2.92 (2H, m), 3.49-3.58 (2H, m), 4.08-4.16 (2H, m), 6.40 (1H, brt, J=5.3), 7.35-7.39 (3H, m), 7.60 (1H, d, J=1.1).

Elemental analysis for $C_{20}H_{27}N_5O_3 \cdot 0.25H_2O$
Calcd. (%): C, 61.60; H, 7.11; N, 17.96.
Found (%): C, 61.59; H, 7.18; N, 17.70.

Example 75

N-cyclopropyl-1-{4-[(ethylamino)carbonyl]-2-propoxyphenyl}-5-propyl-1H-1,2,3-triazole-4-carboxamide

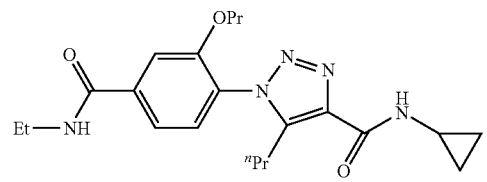

75a) N-ethyl-4-nitro-3-propoxybenzamide

In the same manner as in Example 74b), the title compound was obtained as a yellow oil (0.47 g, 19%) from N-ethyl-3-hydroxy-4-nitrobenzamide (2.1 g) obtained in Example 74a), potassium carbonate (1.4 g) and 1-bromopropane (0.91 ml).

NMR (CDCl$_3$) δ: 1.05 (3H, t, J=7.3), 1.27 (3H, t, J=7.2), 1.80-1.90 (2H, m), 3.49 (2H, dq, J=5.7, 7.3), 4.11 (2H, t, J=6.6), 6.47 (1H, brs), 7.27 (1H, dd, J=1.9, 8.5), 7.58 (1H, d, J=1.7), 7.80 (1H, d, J=8.3).

75b) 4-amino-N-ethyl-3-propoxybenzamide

In the same manner as in Example 1d), the title compound was obtained as a colorless oil (0.29 g, 70%) from N-ethyl-4-nitro-3-propoxybenzamide (0.47 g) obtained in Example 75a) and 10% Pd/C (50% wet, 0.05 g).

NMR (CDCl$_3$) δ: 1.03 (3H, t, J=7.5), 1.22 (3H, t, J=7.2), 1.82 (2H, sextet, J=7.2), 3.46 (2H, dq, J=5.7, 7.2), 3.98 (2H, t, J=6.6), 4.12 (2H, brs), 6.17 (1H, brs), 6.46 (1H, d, J=8.1), 7.13 (1H, dd, J=1.9, 8.1), 7.35 (1H, d, J=1.9).

75c) 4-azido-N-ethyl-3-propoxybenzamide

In the same manner as in Example 1a), the title compound was obtained as a yellow oil (0.33 g, 100%) from 4-amino-N-ethyl-3-propoxybenzamide (0.29 g) obtained in Example 75b), 1M aqueous sodium nitrite solution (1.3 ml) and sodium azide (0.09 g). The obtained crude product was used for the next reaction without further purification.

75d) 1-{4-[(ethylamino)carbonyl]-2-propoxyphenyl}-5-propyl-1H-1,2,3-triazole-4-carboxylic acid In the same manner as in Example 43b), the title compound was obtained as a red oil (0.11 g, 46%) from 4-azido-N-ethyl-3-propoxybenzamide (0.16 g) obtained in Example 75c) and ethyl 3-keto-n-hexanoate (0.10 ml). The obtained crude product was used for the next reaction without further purification.

75e) N-cyclopropyl-1-{4-[(ethylamino)carbonyl]-2-propoxyphenyl}-5-propyl-1H-1,2,3-triazole-4-carboxamide In the same manner as in Example 43c), the title compound was obtained as a pale-yellow amorphous solid (0.07 g, 61%) from 1-{4-[(ethylamino)carbonyl]-2-propoxyphenyl}-5-propyl-1H-1,2,3-triazole-4-carboxylic acid (0.11 g) obtained in Example 75d) and cyclopropylamine (0.03 ml).

NMR (CDCl$_3$) δ: 0.65-0.71 (2H, m), 0.78 (3H, t, J=7.4), 0.82-0.89 (5H, m), 1.29 (3H, t, J=7.4), 1.42-1.55 (2H, m), 1.59-1.71 (2H, m), 2.84-2.97 (3H, m), 3.49-3.58 (2H, m), 3.98-4.02 (2H, m), 6.32 (1H, t, J=5.3), 7.32-7.38 (3H, m), 7.60 (1H, brs).

Elemental analysis for C$_{21}$H$_{29}$N$_5$O$_3$·0.2AcOEt·0.2H$_2$O
Calcd. (%): C, 62.24; H, 7.43; N, 16.65.
Found (%): C, 62.54; H, 7.48; N, 16.86.

Example 76

1-{2-chloro-4-[(ethylamino)carbonyl]-5-methoxyphenyl}-N-cyclopropyl-5-methyl-1H-1,2,3-triazole-4-carboxamide

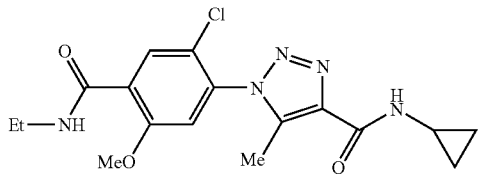

76a) 1-{2-chloro-4-[(ethylamino)carbonyl]-5-methoxyphenyl}-5-methyl-1H-1,2,3-triazole-4-carboxylic acid To a solution of 4-azido-5-chloro-N-ethyl-2-methoxybenzamide (1.0 g) obtained in Example 73b) and ethyl 3-keto-n-butanoate (0.61 ml) in ethanol (20 ml) was added 20% sodium ethoxide in ethanol solution (1.85 ml) at room temperature, and the mixture was stirred at 60° C. for 5 hr. The reaction mixture was cooled to room temperature, and the solvent was evaporated under reduced pressure. The residue was diluted with water and washed with ethyl acetate. The aqueous layer was acidified with 1N hydrochloric acid and extracted with ethyl acetate. The extract was dried over anhydrous magnesium sulfate, and the solvent was evaporated under reduced pressure to give the title compound as a pale-brown solid (0.38 g, 28%). The obtained crude product was used for the next reaction without further purification.

76b) 1-{2-chloro-4-[(ethylamino)carbonyl]-5-methoxyphenyl}-N-cyclopropyl-5-methyl-1H-1,2,3-triazole-4-carboxamide In the same manner as in Example 43c), the title compound was obtained as colorless needle crystals (0.22 g, 51%) from 1-{2-chloro-4-[(ethylamino)carbonyl]-5-methoxyphenyl}-5-methyl-1H-1,2,3-triazole-4-carboxylic acid (0.38 g) obtained in Example 76a) and cyclopropylamine (0.09 ml).

NMR (CDCl$_3$) δ: 0.66-0.71 (2H, m), 0.85-0.92 (2H, m), 1.28 (3H, t, J=7.4), 2.52 (3H, s), 2.87-2.95 (1H, m), 3.49-3.58 (2H, m), 4.01 (3H, s), 7.04 (1H, s), 7.32 (1H, brd, J=2.6), 7.70 (1H, brt, J=5.1), 8.43 (1H, s).

Elemental analysis for C$_{17}$H$_{20}$ClN$_5$O$_3$
Calcd. (%): C, 54.04; H, 5.34; N, 18.54.
Found (%): C, 54.02; H, 5.26; N, 18.50.

Example 77

N-cyclopropyl-1-{4-[(ethylamino)carbonyl]-2-methylphenyl}-5-methyl-1H-1,2,3-triazole-4-carboxamide

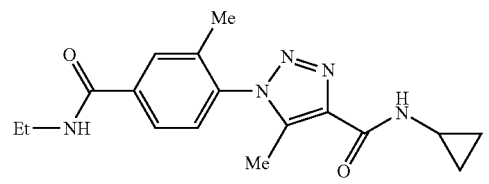

77a) 1-{4-[(ethylamino)carbonyl]-2-methylphenyl}-5-methyl-1H-1,2,3-triazole-4-carboxylic acid In the same manner as in Example 76a), the title compound was obtained as a red oil (0.43 g, 36%) from 4-azido-N-ethyl-3-methylbenzamide (0.85 g) obtained in Example 70c) and ethyl 3-keto-n-butanoate (0.64 ml). The obtained crude product was used for the next reaction without further purification.

77b) N-cyclopropyl-1-{4-[(ethylamino)carbonyl]-2-methylphenyl}-5-methyl-1H-1,2,3-triazole-4-carboxamide In the same manner as in Example 43c), the title compound was obtained as a white powder (0.23 g, 46%) from 1-{4-[(ethylamino)carbonyl]-2-methylphenyl}-5-methyl-1H-1,2,3-triazole-4-carboxylic acid (0.43 g) obtained in Example 77a) and cyclopropylamine (0.13 ml).

NMR (CDCl$_3$) δ: 0.66-0.71 (2H, m), 0.85-0.92 (2H, m), 1.28 (3H, t, J=7.2), 2.07 (3H, s), 2.43 (3H, s), 2.89-2.94 (1H, m), 3.48-3.58 (2H, m), 6.50 (1H, brt, J=5.1), 7.27 (1H, d, J=8.1), 7.36 (1H, brd, J=2.6), 7.76 (1H, dd, J=1.9, 8.1), 7.85 (1H, d, J=1.9).

Elemental analysis for C$_{17}$H$_{21}$N$_5$O$_2$
Calcd. (%): C, 62.37; H, 6.47; N, 21.39.
Found (%): C, 62.25; H, 6.43; N, 21.25.

Example 78

N-cyclopropyl-1-{4-[(ethylamino)carbonyl]-2-methoxyphenyl}-5-methyl-1H-1,2,3-triazole-4-carboxamide

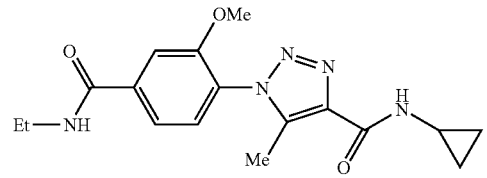

78a) 1-{4-[(ethylamino)carbonyl]-2-methoxyphenyl}-5-methyl-1H-1,2,3-triazole-4-carboxylic acid In the same manner as in Example 76a), the title compound was obtained as a red oil (0.85 g, 45%) from 4-azido-N-ethyl-3-methoxybenzamide (1.4 g) obtained in Example 71c) and ethyl 3-keto-n-butanoate (0.96 ml). The obtained crude product was used for the next reaction without further purification.

78b) N-cyclopropyl-1-{4-[(ethylamino)carbonyl]-2-methoxyphenyl}-5-methyl-1H-1,2,3-triazole-4-carboxamide In the same manner as in Example 43c), the title compound was obtained as a white powder (0.41 g, 43%) from 1-{4-[(ethylamino)carbonyl]-2-methoxyphenyl}-5-methyl-1H-1,2,3-triazole-4-carboxylic acid (0.85 g) obtained in Example 78a) and cyclopropylamine (0.24 ml).

NMR (CDCl$_3$) δ: 0.64-0.70 (2H, m), 0.84-0.90 (2H, m), 1.29 (3H, t, J=7.4), 2.44 (3H, s), 2.87-2.93 (1H, m), 3.49-3.58 (2H, m), 3.86 (3H, s), 6.44 (1H, brt, J=5.1), 7.32 (1H, brd, J=2.6), 7.38-7.39 (2H, m), 7.63 (1H, brs).

Elemental analysis for $C_{17}H_{21}N_5O_3$
Calcd. (%): C, 59.46; H, 6.16; N, 20.40.
Found (%): C, 59.29; H, 6.17; N, 20.25.

Example 79

1-{2-chloro-4-[(ethylamino)carbonyl]phenyl}-N-cyclopropyl-5-methyl-1H-1,2,3-triazole-4-carboxamide

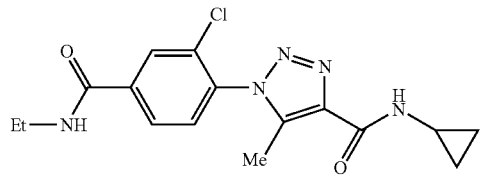

79a) 1-{2-chloro-4-[(ethylamino)carbonyl]phenyl}-5-methyl-1H-1,2,3-triazole-4-carboxylic acid In the same manner as in Example 76a), the title compound was obtained as a red oil (0.85 g, 45%) from 4-azido-3-chloro-N-ethylbenzamide (1.4 g) obtained in Example 72c) and ethyl 3-keto-n-butanoate (0.94 ml). The obtained crude product was used for the next reaction without further purification.

79b) 1-{2-chloro-4-[(ethylamino)carbonyl]phenyl}-N-cyclopropyl-5-methyl-1H-1,2,3-triazole-4-carboxamide In the same manner as in Example 43c), the title compound was obtained as a white powder (0.11 g, 12%) from 1-{2-chloro-4-[(ethylamino)carbonyl]phenyl}-5-methyl-1H-1,2,3-triazole-4-carboxylic acid (0.85 g) obtained in Example 79a) and cyclopropylamine (0.23 ml).

NMR (CDCl$_3$) δ: 0.66-0.71 (2H, m), 0.85-0.91 (2H, m), 1.24-1.31 (3H, m), 2.47 (3H, s), 2.86-2.93 (1H, m), 3.49-3.58 (2H, m), 6.67 (1H, t, J=5.3), 7.36 (1H, brd, J=2.8), 7.46 (1H, d, J=8.1), 7.88 (1H, dd, J=1.9, 8.1), 8.06 (1H, d, J=1.8).

Elemental analysis for $C_{16}H_{18}ClN_5O_2 \cdot 0.25^iPr_2O \cdot 0.3H_2O$
Calcd. (%): C, 55.50; H, 5.80; N, 18.49.
Found (%): C, 55.17; H, 5.51; N, 18.32.

Example 80

N-cyclopropyl-1-{2-ethoxy-4-[(ethylamino)carbonyl]phenyl}-5-methyl-1H-1,2,3-triazole-4-carboxamide

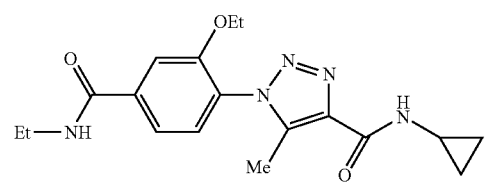

80a) 1-{2-ethoxy-4-[(ethylamino)carbonyl]phenyl}-5-methyl-1H-1,2,3-triazole-4-carboxylic acid In the same manner as in Example 76a), the title compound was obtained as a pale-brown solid (0.19 g, 60%) from 4-azido-3-ethoxy-N-ethylbenzamide (0.25 g) obtained in Example 74d) and ethyl 3-keto-n-butanoate (0.15 ml). The obtained crude product was used for the next reaction without further purification.

80b) N-cyclopropyl-1-{2-ethoxy-4-[(ethylamino)carbonyl]phenyl}-5-methyl-1H-1,2,3-triazole-4-carboxamide In the same manner as in Example 43c), the title compound was obtained as a white powder (0.13 g, 60%) from 1-{2-ethoxy-4-[(ethylamino)carbonyl]phenyl}-5-methyl-1H-1,2,3-triazole-4-carboxylic acid (0.19 g) obtained in Example 80a) and cyclopropylamine (0.05 ml).

NMR (CDCl$_3$) δ: 0.65-0.70 (2H, m), 0.84-0.91 (2H, m), 1.28 (3H, t, J=7.2), 1.29 (3H, t, J=7.0), 2.46 (3H, s), 2.89-2.93 (1H, m), 3.48-3.57 (2H, m), 4.13 (2H, q, J=7.2), 6.55 (1H, brt, J=5.3), 7.35-7.41 (3H, m), 7.61 (1H, d, J=0.8).

Elemental analysis for $C_{18}H_{23}N_5O_3$
Calcd. (%): C, 60.49; H, 6.49; N, 19.59.
Found (%): C, 60.44; H, 6.44; N, 19.52.

Example 81

N-cyclopropyl-1-{4-[(ethylamino)carbonyl]-2-propoxyphenyl}-5-methyl-1H-1,2,3-triazole-4-carboxamide

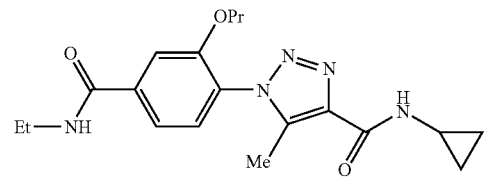

81a) 1-{4-[(ethylamino)carbonyl]-2-propoxyphenyl}-5-methyl-1H-1,2,3-triazole-4-carboxylic acid In the same manner as in Example 76a), the title compound was obtained as a red oil (0.10 g, 46%) from 4-azido-N-ethyl-3-propoxybenzamide (0.16 g) obtained in Example 75c) and ethyl 3-keto-n-butanoate (0.10 ml). The obtained crude product was used for the next reaction without further purification.

81b) N-cyclopropyl-1-{4-[(ethylamino)carbonyl]-2-propoxyphenyl}-5-methyl-1H-1,2,3-triazole-4-carboxamide In the same manner as in Example 43c), the title compound was obtained as a pale-yellow amorphous solid (0.09 g, 81%) from 1-{4-[(ethylamino)carbonyl]-2-propoxyphenyl}-5-methyl-1H-1,2,3-triazole-4-carboxylic acid (0.10 g) obtained in Example 81a) and cyclopropylamine (0.03 ml).

NMR (CDCl$_3$) δ: 0.65-0.70 (2H, m), 0.83-0.91 (5H, m), 1.28 (3H, t, J=7.4), 1.61-1.73 (2H, m), 2.46 (3H, s), 2.87-2.93 (1H, m), 3.48-3.57 (2H, m), 3.99-4.03 (2H, m), 6.51 (1H, brt, J=5.2), 7.34-7.41 (3H, m), 7.62 (1H, brs).

Elemental analysis for $C_{19}H_{25}N_5O_3 \cdot 0.25H_2O$
Calcd. (%): C, 60.70; H, 6.84; N, 18.63.
Found (%): C, 60.69; H, 7.03; N, 18.34.

Example 82

1-{4-[(ethylamino)carbonyl]phenyl}-5-propyl-N-(tetrahydrofuran-2-ylmethyl)-1H-1,2,3-triazole-4-carboxamide

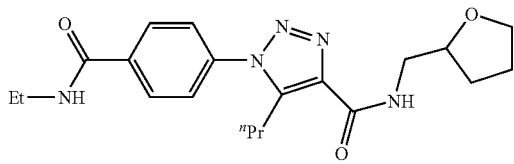

In the same manner as in Example 43c), the title compound was obtained as a colorless powder (0.36 g, 47%) from 1-{4-[(ethylamino)carbonyl]phenyl}-5-propyl-1H-1,2,3-triazole-4-carboxylic acid (0.60 g) obtained in Example 43b) and 1-(tetrahydrofuran-2-yl)methanamine (0.30 g).

NMR (CDCl$_3$) δ: 0.85 (3H, t, J=7.2), 1.29 (3H, t, J=7.4), 1.49-1.70 (3H, m), 1.88-2.08 (3H, m), 2.98-3.04 (2H, m), 3.42-3.59 (3H, m), 3.66-3.75 (1H, m), 3.77-3.82 (1H, m), 3.89-3.96 (1H, m), 4.06-4.14 (1H, m), 6.30 (1H, brs), 7.49-7.52 (2H, m), 7.56 (1H, t, J=5.9), 7.94-7.99 (2H, m).

Elemental analysis for $C_{20}H_{27}N_5O_3$
Calcd. (%): C, 63.32; H, 7.06; N, 18.17.
Found (%): C, 62.25; H, 7.07; N, 18.20.

Example 83

1-{4-[(ethylamino)carbonyl]phenyl}-N-[(5-methylpyrazin-2-yl)methyl]-5-propyl-1H-1,2,3-triazole-4-carboxamide

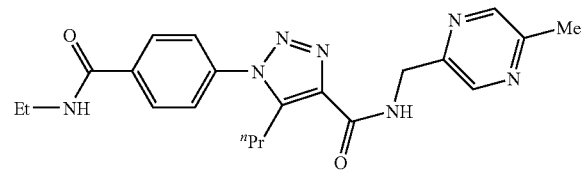

In the same manner as in Example 43c), the title compound was obtained as a colorless powder (0.59 g, 73%) from 1-{4-[(ethylamino)carbonyl]phenyl}-5-propyl-1H-1,2,3-triazole-4-carboxylic acid (0.60 g) obtained in Example 43b) and 1-(5-methylpyrazin-2-yl)methanamine (0.37 g).

NMR (CDCl$_3$) δ: 0.86 (3H, t, J=7.4), 1.30 (3H, t, J=7.2), 1.53-1.60 (2H, m), 2.57 (3H, s), 3.00-3.05 (2H, m), 3.50-3.60 (2H, m), 4.79 (2H, d, J=5.7), 6.15 (1H, brs), 7.52 (2H, d, J=8.7), 7.96 (2H, d, J=8.7), 8.05 (1H, t, J=5.7), 8.43 (1H, s), 8.55 (1H, s).

Elemental analysis for $C_{21}H_{25}N_7O_2$
Calcd. (%): C, 61.90; H, 6.18; N, 24.06.
Found (%): C, 61.92; H, 6.19; N, 24.03.

Example 84

1-{4-[(ethylamino)carbonyl]phenyl}-5-propyl-N-(pyridin-2-ylmethyl)-1H-1,2,3-triazole-4-carboxamide

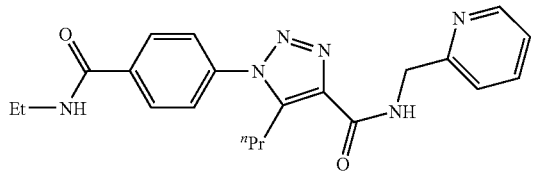

In the same manner as in Example 43c), the title compound was obtained as a colorless powder (0.40 g, 51%) from 1-{4-[(ethylamino)carbonyl]phenyl}-5-propyl-1H-1,2,3-triazole-4-carboxylic acid (0.60 g) obtained in Example 43b) and 1-(pyridin-2-yl)methanamine (0.32 g).

NMR (CDCl$_3$) δ: 0.86 (3H, t, J=7.5), 1.29 (3H, t, J=7.4), 1.50-1.61 (2H, m), 3.01-3.06 (2H, m), 3.50-3.60 (2H, m), 4.79 (2H, d, J=5.4), 6.30 (1H, brs), 7.19-7.23 (1H, m), 7.33 (1H, d, J=7.8), 7.51 (2H, d, 8.6), 7.67 (1H, dt, J=7.8, 1.8), 7.97 (2H, d, J=8.6), 8.23 (1H, t, J=5.4), 8.59 (1H, d, J=5.1).

Elemental analysis for $C_{21}H_{24}N_6O_2$
Calcd. (%): C, 64.27; H, 6.16; N, 21.41.
Found (%): C, 64.28; H, 6.19; N, 21.45.

Example 85

N-ethyl-4-[5-propyl-4-(1,3,4,9-tetrahydro-2H-β-carbolin-2-ylcarbonyl)-1H-1,2,3-triazol-1-yl]benzamide

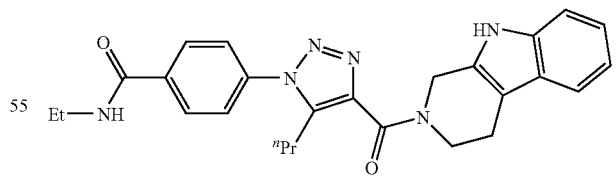

In the same manner as in Example 43c), the title compound was obtained as a colorless powder (0.44 g, 49%) from 1-{4-[(ethylamino)carbonyl]phenyl}-5-propyl-1H-1,2,3-triazole-4-carboxylic acid (0.60 g) obtained in Example 43b) and 2,3,4,9-tetrahydro-1H-β-carboline (0.51 g).

NMR (CDCl$_3$) δ: 0.74-0.84 (3H, m), 1.27 (3H, t, J=7.4), 1.43-1.55 (2H, m), 2.87-3.04 (4H, m), 3.50-3.59 (2H, m), 4.15 (1H, t, J=5.4), 4.32 (1H, t, J=5.4), 4.99 (1H, s), 5.31 (1H, s), 6.31-6.40 (1H, m), 7.08-7.18 (2H, m), 7.28-7.33 (1H, m), 7.46-7.55 (3H, m), 7.93-7.98 (2H, m), 8.28-8.30 (1H, m).

Elemental analysis for $C_{26}H_{28}N_6O_2$
Calcd. (%): C, 68.40; H, 6.18; N, 18.41.
Found (%): C, 68.25; H, 6.19; N, 18.31.

Example 86

N-(1,3-benzodioxol-5-ylmethyl)-1-{4-[(ethylamino)carbonyl]phenyl}-5-propyl-1H-1,2,3-triazole-4-carboxamide

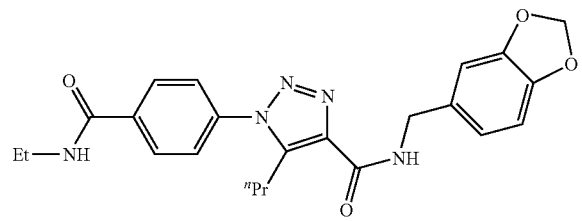

In the same manner as in Example 43c), the title compound was obtained as a colorless powder (0.61 g, 71%) from 1-{4-[(ethylamino)carbonyl]phenyl}-5-propyl-1H-1,2,3-triazole-4-carboxylic acid (0.60 g) obtained in Example 43b) and 1-(1,3-benzodioxol-5-yl)methanamine (0.45 g).

NMR (CDCl$_3$) δ: 0.86 (3H, t, J=7.4), 1.29 (3H, t, J=7.4), 1.53-1.61 (2H, m), 3.01-3.06 (2H, m), 3.50-3.59 (2H, m), 4.55 (2H, d, J=6.0), 5.94 (2H, s), 6.23 (1H, brs), 6.78-6.86 (3H, m), 7.48-7.52 (2H, m), 7.56 (1H, t, J=6.0), 7.94-7.98 (2H, m).

Elemental analysis for $C_{23}H_{25}N_5O_4$
Calcd. (%): C, 63.44; H, 5.79; N, 16.08.
Found (%): C, 63.28; H, 5.75; N, 16.06.

Example 87

1-{4-[(ethylamino)carbonyl]phenyl}-N-[2-(5-methoxy-1H-indol-3-yl)ethyl]-5-propyl-1H-1,2,3-triazole-4-carboxamide

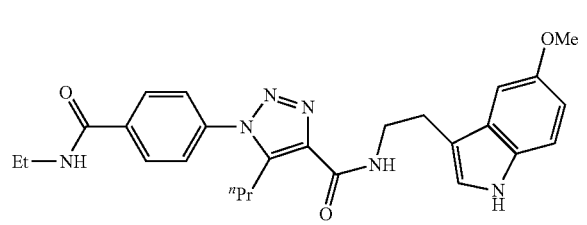

In the same manner as in Example 43c), the title compound was obtained as a colorless powder (0.50 g, 53%) from 1-{4-[(ethylamino)carbonyl]phenyl}-5-propyl-1H-1,2,3-triazole-4-carboxylic acid (0.60 g) obtained in Example 43b) and 2-(5-methoxy-1H-indol-3-yl)ethanamine (0.57 g).

NMR (CDCl$_3$) δ: 0.84 (3H, t, J=7.4), 1.29 (3H, t, J=7.2), 1.51-1.58 (2H, m), 2.99-3.10 (4H, m), 3.49-3.58 (2H, m), 3.76-3.83 (2H, m), 3.85 (3H, s), 6.29 (1H, t, J=5.4), 6.83-6.87 (1H, m), 7.06-7.08 (2H, m), 7.23-7.26 (1H, m), 7.42 (1H, t, J=6.0), 7.46-7.49 (2H, m), 7.93-7.96 (2H, m), 8.10 (1H, brs).

Elemental analysis for $C_{26}H_{30}N_6O_3$
Calcd. (%): C, 65.80; H, 6.37; N, 17.71.
Found (%): C, 65.60; H, 6.33; N, 17.57.

Example 88

1-{4-[(ethylamino)carbonyl]phenyl}-N-(3-fluorobenzyl)-5-propyl-1H-1,2,3-triazole-4-carboxamide

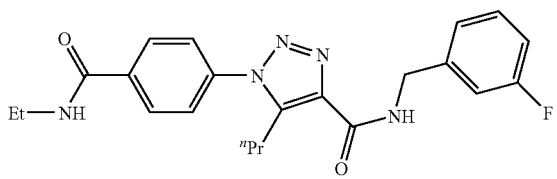

In the same manner as in Example 43c), the title compound was obtained as a colorless powder (0.43 g, 53%) from 1-{4-[(ethylamino)carbonyl]phenyl}-5-propyl-1H-1,2,3-triazole-4-carboxylic acid (0.60 g) obtained in Example 43b) and 3-fluorobenzylamine (0.37 g).

NMR (CDCl$_3$) δ: 0.86 (3H, t, J=7.4), 1.29 (3H, t, J=7.4), 1.51-1.63 (2H, m), 3.01-3.06 (2H, m), 3.50-3.59 (2H, m), 4.65 (2H, d, J=6.0), 6.25 (1H, brs), 6.94-7.00 (1H, m), 7.05-7.15 (2H, m), 7.25-7.49 (1H, m), 7.49-7.53 (2H, m), 7.67 (1H, t, J=6.0), 7.95-7.99 (2H, m).

Elemental analysis for $C_{22}H_{24}N_5O_2F$
Calcd. (%): C, 64.53; H, 5.91; N, 17.10.
Found (%): C, 64.52; H, 5.85; N, 17.13.

Example 89

1-{4-[(ethylamino)carbonyl]phenyl}-5-propyl-N-(1,2,3,4-tetrahydronaphthalen-1-yl)-1H-1,2,3-triazole-4-carboxamide

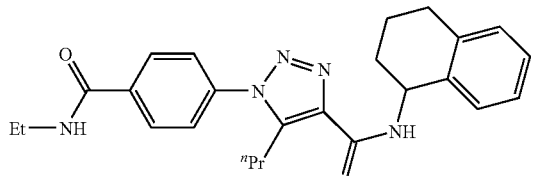

In the same manner as in Example 43c), the title compound was obtained as a colorless powder (0.70 g, 82%) from 1-{4-[(ethylamino)carbonyl]phenyl}-5-propyl-1H-1,2,3-triazole-4-carboxylic acid (0.60 g) obtained in Example 43b) and 1,2,3,4-tetrahydronaphthalen-1-amine (0.44 g).

NMR (CDCl$_3$) δ: 0.89 (3H, t, J=7.2), 1.29 (3H, t, J=7.4), 1.54-1.66 (2H, m), 1.87-2.04 (3H, m), 2.11-2.21 (1H, m), 2.77-2.92 (2H, m), 3.03-3.09 (2H, m), 3.50-3.59 (2H, m), 5.35-5.42 (1H, m), 6.25 (1H, brs), 7.11-7.22 (3H, m), 7.33-7.36 (1H, m), 7.48-7.55 (3H, m), 7.94-7.99 (2H, m).

Elemental analysis for $C_{25}H_{29}N_5O_2$
Calcd. (%): C, 69.58; H, 6.77; N, 16.23.
Found (%): C, 69.48; H, 6.74; N, 16.23.

Example 90

5-butyl-N-cyclopropyl-1-{4-[(ethylamino)carbonyl]phenyl}-1H-1,2,3-triazole-4-carboxamide

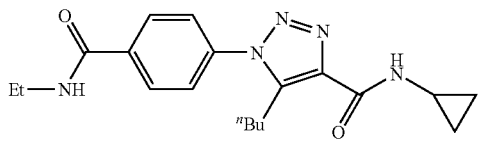

90a) 5-butyl-1-{4-[(ethylamino)carbonyl]phenyl}-1H-1,2,3-triazole-4-carboxylic acid

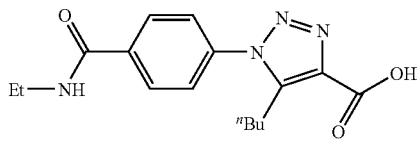

To a solution of 4-azido-N-ethylbenzamide (1.00 g) obtained in Example 43a) and methyl 3-oxoheptanoate (1.10 g) in methanol (50 ml) was added a solution of sodium methoxide in methanol (1.35 g, 28%). The reaction mixture was stirred at room temperature for 8 hr and at 70° C. for 3 hr, and 1M aqueous sodium hydroxide solution (11 ml) was added. The reaction mixture was stirred at 70° C. for 1 hr, cooled to room temperature, diluted with water, and methanol was evaporated under reduced pressure. The residual aqueous solution was acidified (pH=1) with 1M hydrochloric acid under ice-cooling, the insoluble material was collected by filtration and washed with water to give the title compound as a brown powder (1.66 g, 99%).

NMR (DMSO-$d_6$) δ: 0.72 (3H, t, J=7.4), 1.04-1.22 (5H, m), 1.33 (2H, q, J=7.0), 2.97 (2H, t, J=7.8), 3.26-3.40 (2H, m), 7.73 (2H, d, J=8.6), 8.08 (2H, d, J=8.6), 8.71 (1H, t, J=5.6).

90b) 5-butyl-N-cyclopropyl-1-{4-[(ethylamino)carbonyl]phenyl}-1H-1,2,3-triazole-4-carboxamide In the same manner as in Example 1c), the title compound was obtained as colorless plate crystals (1.53 g, 83%) from 5-butyl-1-{4-[(ethylamino)carbonyl]phenyl}-1H-1,2,3-triazole-4-carboxylic acid (1.66 g) obtained in Example 90a).

NMR (CDCl$_3$) δ: 0.65-0.70 (2H, m), 0.81 (3H, t, J=7.5), 0.85-0.91 (2H, m), 1.18-1.31 (2H, m), 1.29 (3H, t, J=7.2), 1.45-1.55 (2H, m), 2.86-2.94 (1H, m), 3.02 (2H, t, J=8.1), 3.50-3.59 (2H, m), 6.29 (1H, br), 7.35 (1H, br), 7.49 (2H, d, J=8.4), 7.95 (2H, d, J=8.4).

Elemental analysis for $C_{19}H_{25}N_5O_2$
Calcd. (%): C, 64.20; H, 7.09; N, 19.70.
Found (%): C, 64.18; H, 6.88; N, 19.58.

Example 91

5-[3-(benzyloxy)propyl]-N-cyclopropyl-1-{4-[(ethylamino)carbonyl]phenyl}-1H-1,2,3-triazole-4-carboxamide

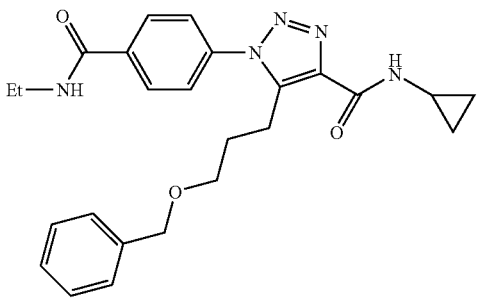

91a) methyl 6-(benzyloxy)-3-oxohexanoate

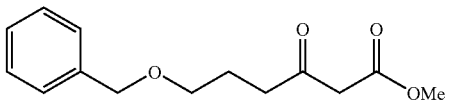

To a solution of 4-(benzyloxy)butanoic acid (25.2 g) and DMF (5 drops) in THF (200 ml) was added dropwise oxalyl chloride (25 ml) under ice-cooling. The reaction mixture was stirred at room temperature for 3 hr, and the solvent and volatile component were evaporated. A solution of the residue in dichloromethane (50 ml) was added dropwise to a solution of Meldrum's acid (15.6 g) and pyridine (18 ml) in dichloromethane (100 ml) under ice-cooling. The reaction mixture was stirred at room temperature for 11 hr, washed with 0.5M hydrochloric acid and saturated brine, dried over anhydrous sodium sulfate, and the solvent was evaporated. A solution of the residue in methanol (500 ml) was stirred with heating under reflux for 9 hr. After cooling to room temperature, the solvent was evaporated. The residue was purified by silica gel column (hexane/ethyl acetate=5/1) to give the title compound as a pale-yellow liquid (14.37 g, 55%).

NMR (CDCl$_3$) δ: 1.87-1.97 (2H, m), 2.66 (2H, t, J=7.2), 3.48 (2H, t, J=6.0), 3.72 (3H, s), 4.47 (2H, s), 4.51 (1H, s), 7.25-7.36 (5H, m).

91b) 5-[3-(benzyloxy)propyl]-1-{4-[(ethylamino)carbonyl]phenyl}-1H-1,2,3-triazole-4-carboxylic acid

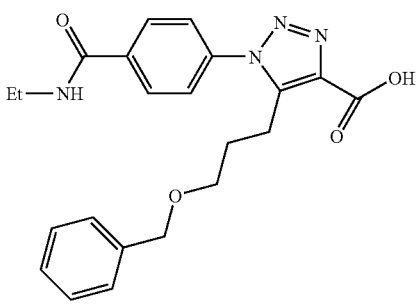

In the same manner as in Example 90a), the title compound was obtained as a brown powder (2.20 g, 99%) from methyl 6-(benzyloxy)-3-oxohexanoate (1.00 g) obtained in Example 91a).

NMR (DMSO-$d_6$) δ: 1.16 (3H, t, J=7.0), 1.73 (2H, q, J=6.6), 3.05 (3H, t, J=6.6), 3.28-3.60 (4H, m), 4.28 (2H, s), 7.12-7.34 (5H, m), 7.72 (2H, d, J=8.0), 8.07 (2H, d, J=8.0), 8.70 (1H, t, J=5.8).

91c) 5-[3-(benzyloxy)propyl]-N-cyclopropyl-1-{4-[(ethylamino)carbonyl]phenyl}-1H-1,2,3-triazole-4-carboxamide In the same manner as in Example 1c), the title compound was obtained as colorless needle crystals (1.74 g, 76%) from 5-[3-(benzyloxy)propyl]-1-{4-[(ethylamino)carbonyl]phenyl}-1H-1,2,3-triazole-4-carboxylic acid (2.10 g) obtained in Example 91b).

NMR (CDCl$_3$) δ: 0.65-0.70 (2H, m), 0.85-0.91 (2H, m), 1.28 (3H, t, J=7.2), 1.93-2.02 (2H, m), 2.86-2.92 (1H, m), 3.17 (2H, t, J=7.8), 3.47 (2H, t, J=5.7), 3.49-3.57 (2H, m), 4.36 (2H, s), 6.02 (1H, br), 7.18-7.21 (2H, m), 7.24-7.35 (4H, m), 7.52 (2H, d, J=8.4), 7.82 (2H, d, J=8.4).

Elemental analysis for $C_{25}H_{29}N_5O_3$
Calcd. (%): C, 67.09; H, 6.53; N, 15.65.
Found (%): C, 67.17; H, 6.51; N, 15.76.

Example 92

N-cyclopropyl-1-{4-[(ethylamino)carbonyl]phenyl}-5-isopropyl-1H-1,2,3-triazole-4-carboxamide

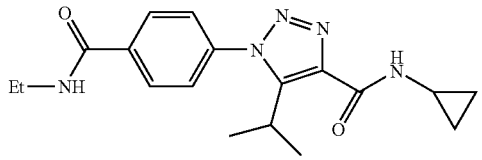

92a) 1-{4-[(ethylamino)carbonyl]phenyl}-5-isopropyl-1H-1,2,3-triazole-4-carboxylic acid 4-Azido-N-ethylbenzamide (0.94 g, 4.70 mmol) and ethyl isobutyrylacetate (1.03 g, 6.10 mmol, 1.3 eq.) were dissolved in ethanol (20 ml), sodium ethoxide (461 mg, 6.10 mmol, 1.3 eq.) was added, and the mixture was stirred at room temperature for 30 min and at 50° C. for 63 hr. Water (20 ml) was added to the reaction mixture, and ethanol was evaporated. The residue was diluted with 2% aqueous sodium carbonate solution (20 ml), and the mixture was washed with ethyl acetate-hexane (2:1, 50 ml). The aqueous layer was acidified (pH<3) with 6N hydrochloric acid and stood still at 0° C. The precipitate was collected by filtration, washed with ice-cold water and dried to give the title compound as a pale-brown powder (1.33 g, 4.39 mmol, 93.4%).

$^1$H NMR (200 MHz, CDCl$_3$-DMSO-$d_6$=9:1) δ: 1.27 (3H, t, J=7.3 Hz), 1.34 (6H, d, J=6.8 Hz), 3.36 (1H, quintet, J=7.0 Hz), 3.49 (2H, dq, J=5.6, 7.2 Hz), 7.46 (2H, dt, J=8.4, 2.1 Hz), 7.82 (1H, br), 8.09 (2H, dt, J=8.4, 2.0 Hz).

Elemental analysis for $C_{15}H_{18}N_4O_3$
Calcd. (%): C, 59.59; H, 6.00; N, 18.53.
Found (%): C, 59.33; H, 5.97; N, 18.47.

92b) N-cyclopropyl-1-{4-[(ethylamino)carbonyl]phenyl}-5-isopropyl-1H-1,2,3-triazole-4-carboxamide 1-{4-[(Ethylamino)carbonyl]phenyl}-5-isopropyl-1H-1,2,3-triazole-4-carboxylic acid (512 mg, 1.69 mmol) obtained in Example 92a), HOBt (116 mg, 0.847 mmol, 0.5 eq.) and cyclopropylamine (0.157 ml, 2.20 mmol, 1.3 eq.) were dissolved in acetonitrile-DMF (2:1, 9.0 ml), WSC (398 mg, 2.03 mmol, 1.2 eq.) was added, and the mixture was stirred at room temperature for 3 hr. The reaction mixture was concentrated, the residue was diluted with ethyl acetate-hexane (2:1, 45 ml), and the mixture was washed with 2% aqueous sodium carbonate solution, 10% aqueous ammonium chloride solution and saturated brine. The aqueous layers were each extracted with ethyl acetate-hexane (3:2, 30 ml). The organic layers were combined, dried over anhydrous sodium sulfate, and concentrated, and diethyl ether was added to the residue. The precipitate was collected by filtration, washed with diethyl ether and dried to give the title compound as a white powder (476 mg, 1.39 mmol, 91.4%).

$^1$H NMR (200 MHz, CDCl$_3$) δ: 0.68 (2H, m), 0.86 (2H, m), 1.30 (3H, t, J=7.3 Hz), 1.38 (6H, d, J=7.2 Hz), 2.91 (1H, octet, J=3.5 Hz), 3.33 (1H, quintet, J=7.0 Hz), 3.55 (2H, dq, J=5.6, 7.1 Hz), 6.22 (1H, br), 7.45 (1H, br), 7.47 (2H, dt, J=8.8, 2.2 Hz), 7.97 (2H, dt, J=9.0, 2.0 Hz).

Elemental analysis for $C_{16}H_{23}N_5O_2$
Calcd. (%): C, 63.32; H, 6.79; N, 20.51.
Found (%): C, 63.10; H, 6.78; N, 20.29.

Example 93

N-cyclopropyl-1-{4-[(ethylamino)carbonyl]phenyl}-5-isobutyl-1H-1,2,3-triazole-4-carboxamide

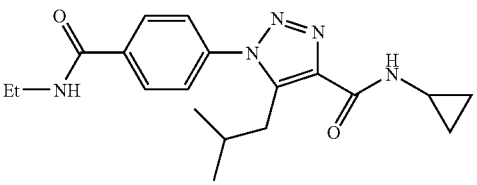

93a) ethyl 5-methyl-3-oxohexanoate

To a solution of Meldrum's acid (5.07 g, 34.5 mmol) in dichloromethane (40 ml) was added dropwise pyridine (6.41 ml, 79.3 mmol, 2.3 eq.) under ice-cooling, and a solution of isovaleryl chloride (4.03 ml, 32.7 mmol, 0.95 eq.) in dichloromethane (20 ml) was added dropwise over 1.5 hr. The reaction mixture was allowed to warm to room temperature and stirred at room temperature for 13 hr. 3N hydrochloric acid (50 ml) was added to the reaction mixture, and the mixture was blended. The aqueous layer was extracted twice with dichloromethane (40 ml). The organic layers were combined, dried over anhydrous sodium sulfate, and concentrated to give a dark purple oil.

This oil was dissolved in ethanol (100 ml), and the mixture was stirred at 80° C. for 2.5 hr under a nitrogen atmosphere. The reaction mixture was concentrated, and the residue was diluted with ethyl acetate-hexane (2:1, 100 ml) and washed with saturated aqueous sodium hydrogen carbonate solution and saturated brine. The aqueous layers were each extracted with ethyl acetate-hexane (2:1, 60 ml), and the organic layers were combined, dried over anhydrous sodium sulfate and concentrated. The residue was subjected to column chromatography (elution solvent, hexane and ethyl acetate-hexane=2:98-5:95) on silica gel (manufactured by E. Merck, Art.7734, 50 g), and the fraction obtained by elution with ethyl acetate-hexane (5:95) was concentrated to give the title compound as a yellow oil (3.80 g, 22.1 mmol, 67.5%).

$^1$H NMR (200 MHz, CDCl$_3$) δ: 0.96 (2H, d, J=6.6 Hz), 1.28 (3H, t, J=7.1 Hz), 2.16 (1H, septet, J=6.6 Hz), 2.42 (2H, d, J=7.0 Hz), 3.41 (2H, s), 4.20 (2H, q, J=7.1 Hz).

93b) 1-{4-[(ethylamino)carbonyl]phenyl}-5-isobutyl-1H-1,2,3-triazole-4-carboxylic acid Ethyl 5-methyl-3-oxohexanoate (1.20 g, 6.99 mmol, 1.4 eq.) obtained in Example 93a) and 4-azido-N-ethylbenzamide (1.00 g, 4.99 mmol) were dissolved in ethanol (20 ml), sodium ethoxide (491 mg, 6.49 mmol, 1.3 eq.) was added, and the mixture was stirred at room temperature for 30 min and at 60° C. for 18 hr. Water (20 ml) was added to the reaction mixture, and ethanol was evaporated. The residue was diluted with 2% aqueous sodium carbonate solution (25 ml), and the mixture was washed with ethyl acetate-hexane (2:1, 45 ml). The organic layer was extracted with 1% aqueous sodium carbonate solution (15 ml). The aqueous layers were combined, washed with ethyl acetate-hexane (1:1, 30 ml), acidified (pH<3) with 6N hydrochloric acid and extracted with ethyl acetate (40 ml and 30 ml). The organic layers were combined, washed with saturated brine, dried over anhydrous sodium sulfate, and concentrated, and ethyl acetate was added. The precipitate was collected by filtration, washed with ethyl acetate and diethyl ether and dried to give the title compound as a white powder (1.45 g, 4.58 mmol, 91.7%).

$^1$H NMR (200 MHz, CDCl$_3$-DMSO-d$_6$=19:1) δ: 0.73 (6H, d, J=6.4 Hz), 1.28 (3H, t, J=7.3 Hz), 1.81 (1H, quintet, J=6.8 Hz), 2.96 (2H, d, J=7.2 Hz), 3.51 (2H, dq, J=5.4, 7.2 Hz), 7.31 (1H, br), 7.50 (2H, dt, J=8.8, 1.8 Hz), 8.05 (2H, dt, J=8.8, 2.2 Hz).

Elemental analysis for C$_{16}$H$_{20}$N$_4$O$_3$
Calcd. (%): C, 60.75; H, 6.37; N, 17.71.
Found (%): C, 60.69; H, 6.37; N, 17.57.

93c) N-cyclopropyl-1-{4-[(ethylamino)carbonyl]phenyl}-5-isobutyl-1H-1,2,3-triazole-4-carboxamide 1-{4-[(Ethylamino)carbonyl]phenyl}-5-isobutyl-1H-1,2,3-triazole-4-carboxylic acid (510 mg, 1.61 mmol) obtained in Example 93b), HOBt (110 mg, 0.806 mmol, 0.5 eq.) and cyclopropylamine (0.150 ml, 2.10 mmol, 1.3 eq.) were dissolved in acetonitrile-DMF (2:1, 8.0 ml), WSC (378 mg, 1.93 mmol, 1.2 eq.) was added, and the mixture was stirred at room temperature for 2 hr. The reaction mixture was concentrated, and the residue was diluted with ethyl acetate-hexane (4:1, 50 ml) and washed with 2% aqueous sodium carbonate solution, 10% aqueous ammonium chloride solution and saturated brine. The aqueous layers were each extracted with ethyl acetate-hexane (2:1, 30 ml). The organic layers were combined, dried over anhydrous sodium sulfate, and concentrated, and ethyl acetate and diethyl ether were added to the residue. The precipitate was collected by filtration, washed with ethyl acetate-diethyl ether (1:3) and diethyl ether and dried to give the title compound as a white powder (559 mg, 1.57 mmol, 98.3%).

$^1$H NMR (200 MHz, CDCl$_3$) δ: 0.68 (2H, m), 0.74 (6H, d, J=7.0 Hz), 0.88 (2H, m), 1.30 (3H, t, J=7.4 Hz), 1.89 (1H, septet, J=6.8 Hz), 2.90 (1H, octet, J=3.7 Hz), 2.99 (2H, d, J=7.2 Hz), 3.55 (2H, dq, J=5.6, 7.3 Hz), 6.30 (1H, brt, J=5.6 Hz), 7.37 (1H, brd, J=3 Hz), 7.50 (2H, dt, J=8.4, 2.0 Hz), 7.98 (2H, dt, J=8.4, 2.0 Hz).

Elemental analysis for C$_{19}$H$_{25}$N$_5$O$_2$
Calcd. (%): C, 64.20; H, 7.09; N, 19.71.
Found (%): C, 64.10; H, 7.09; N, 19.54.

Example 94

5-[(benzyloxy)methyl]-N-cyclopropyl-1-{4-[(ethylamino)carbonyl]phenyl}-1H-1,2,3-triazole-4-carboxamide

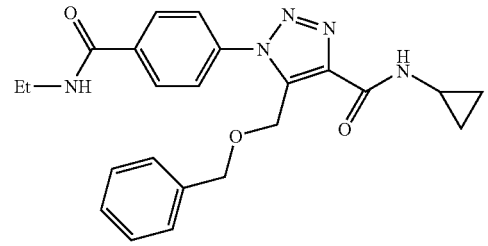

94a) methyl 4-(benzyloxy)-3-oxobutanoate

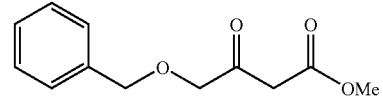

In the same manner as in Example 40b), the title compound was obtained as a pale-yellow liquid (13.2 g, 72%) from benzyloxyacetyl chloride (16.9 g).

NMR (CDCl$_3$) δ: 3.55 (2H, s), 3.71 (3H, s), 4.13 (2H, s), 4.58 (2H, s), 7.30-7.36 (5H, m).

94b) 5-[(benzyloxy)methyl]-N-cyclopropyl-1-{4-[(ethylamino)carbonyl]phenyl}-1H-1,2,3-triazole-4-carboxamide To a solution of 4-azido-N-ethylbenzamide (3.00 g) obtained in Example 43a) and methyl 4-(benzyloxy)-3-oxobutanoate (4.56 g) obtained in Example 94a) in methanol (150 ml) was added a solution of sodium methoxide in methanol (4.0 g, 28%) was added. The reaction mixture was stirred at room temperature for 8 hr and at 70° C. for 8 hr, and 1M aqueous sodium hydroxide solution (30 ml) was added. The reaction mixture was stirred at 70° C. for 1 hr, allowed to cool to room temperature and diluted with water, and methanol was evaporated under reduced pressure. The residual aqueous solution was acidified (pH=1) with 1M hydrochloric acid under ice-cooling and extracted with ethyl acetate. The extract was washed with saturated brine and dried over anhydrous magnesium sulfate, and the solvent was evaporated. To a solution of the residue, cyclopropylamine (1.5 ml), HOBt (3.3 g) and triethylamine (3.1 ml) in DMF (100 ml) was added WSC (4.2 g). The reaction mixture was stirred at room temperature for 12 hr, and the solvent and volatile component were evaporated. The residue was partitioned between ethyl acetate and water, and the organic layer was washed with saturated brine and dried over anhydrous magnesium sulfate, and the solvent was evaporated. The residue was purified by silica gel column (hexane/ethyl acetate=7/3 to hexane/ethyl acetate=1/9). The resultant product was recrystallized from ethanol to give the title compound as colorless plate crystals (4.95 g, 76%).

NMR (CDCl$_3$) δ: 0.67-0.72 (2H, m), 0.87-0.94 (2H, m), 1.29 (3H, t, J=7.2), 2.89-2.97 (1H, m), 3.54 (2H, qd, J=7.2, 1.5), 4.65 (2H, s), 4.99 (2H, s), 6.19 (1H, br), 7.23-7.85 (5H, m), 7.41 (1H, d, J=2.6), 7.78 (2H, d, J=8.7), 7.91 (2H, d, J=8.7).

Elemental analysis for C$_{23}$H$_{25}$N$_5$O$_3$
Calcd. (%): C, 65.85; H, 6.01; N, 16.70.
Found (%): C, 65.74; H, 5.82; N, 16.72.

Example 95

N-cyclopropyl-1-{4-[(ethylamino)carbonyl]phenyl}-5-(2-methylprop-1-en-1-yl)-1H-1,2,3-triazole-4-carboxamide

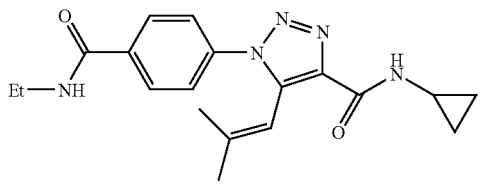

95a) ethyl 5-methyl-3-oxo-4-hexenoate

To a solution of Meldrum's acid (2.80 g, 19.0 mmol) in dichloromethane (20 ml) was added dropwise pyridine (3.54 ml, 43.8 mmol, 2.3 eq.) under ice-cooling, and a solution of 3,3-dimethylacryloyl chloride (1.97 ml, 17.1 mmol, 0.9 eq.) in dichloromethane (10 ml) was added dropwise over 2.5 hr. The reaction mixture was allowed to warm to room temperature and stirred at room temperature for 14 hr. 3N hydrochloric acid (40 ml) was added to the reaction mixture, and the mixture was blended. The aqueous layer was extracted twice with dichloromethane (30 ml). The organic layers were combined, dried over anhydrous sodium sulfate and concentrated to give a brown oil.

This oil was dissolved in ethanol (60 ml), and the mixture was stirred at 80° C. for 2.5 hr under a nitrogen atmosphere. The reaction mixture was concentrated, and the residue was diluted with ethyl acetate-hexane (1:1, 80 ml) and washed with saturated aqueous sodium hydrogen carbonate solution and saturated brine. The aqueous layers were each extracted with ethyl acetate-hexane (1:1, 80 ml), and the organic layers were combined, dried over anhydrous sodium sulfate and concentrated. The residue was subjected to column chromatography (elution solvent, hexane and ethyl acetate-hexane=5:95-10:90) on silica gel (manufactured by E. Merck, Art.7734, 15 g), and the fraction obtained by elution with ethyl acetate-hexane (5:95) was concentrated to give the title compound as a pale-brown oil (1.10 g, 6.46 mmol, 34.0%).

$^1$H NMR (200 MHz, CDCl$_3$) δ: 1.28 (3H, t, J=7.1 Hz), 1.92 (3H, d, J=1.4 Hz), 2.16 (3H, d, J=1.0 Hz), 3.44 (2H, s), 4.20 (2H, q, J=7.1 Hz), 6.12 (1H, quintet, J=1.3 Hz).

95b) 1-{4-[(ethylamino)carbonyl]phenyl}-5-(2-methylprop-1-en-1-yl)-1H-1,2,3-triazole-4-carboxylic acid Ethyl 5-methyl-3-oxo-4-hexenoate (1.10 g, 6.56 mmol, 1.1 eq.) obtained in Example 95a) and 4-azido-N-ethylbenzamide (purity 90%, 1.23 g, 5.82 mmol) were dissolved in ethanol (25 ml), sodium ethoxide (550 mg, 7.82 mmol, 1.25 eq.) was added, and the mixture was stirred at room temperature for 30 min and at 50° C. for 10.5 hr. Ethanol was evaporated from the reaction mixture, and the residue was diluted with 2% aqueous sodium carbonate solution (40 ml) and washed with ethyl acetate (40 ml). The organic layer was extracted with 2% aqueous sodium carbonate solution (15 ml). The aqueous layers were combined, washed with ethyl acetate-hexane (2:1, 50 ml), acidified (pH<3) with 6N hydrochloric acid and extracted three times with ethyl acetate (50 ml) and ethyl acetate-THF (3:1, 40 ml). The organic layers were combined, washed with saturated brine, dried over anhydrous sodium sulfate and concentrated, and ethyl acetate was added. The precipitate was collected by filtration, washed with ethyl acetate and diethyl ether and dried to give the title compound as a grayish white powder (1.43 g, 4.55 mmol, 78.2%).

$^1$H NMR (200 MHz, CDCl$_3$-DMSO-d$_6$=19:1) δ: 1.28 (3H, t, J=7.4 Hz), 1.38 (3H, d, J=1.2 Hz), 1.87 (3H, d, J=1.0 Hz), 3.51 (2H, dq, J=5.6, 7.3 Hz), 7.15 (1H, m), 7.60 (2H, dt, J=8.8, 2.2 Hz), 7.91 (2H, dt, J=8.8, 2.2 Hz).

Elemental analysis for C$_{16}$H$_{18}$N$_4$O$_3$
Calcd. (%): C, 61.13; H, 5.77; N, 17.82.
Found (%): C, 61.07; H, 5.75; N, 17.75.

95c) N-cyclopropyl-1-{4-[(ethylamino)carbonyl]phenyl}-5-(2-methylprop-1-en-1-yl)-1H-1,2,3-triazole-4-carboxamide 1-{4-[(Ethylamino)carbonyl]phenyl}-5-(2-methylprop-1-en-1-yl)-1H-1,2,3-triazole-4-carboxylic acid (490 mg, 1.56 mmol) obtained in Example 95b), HOBt (106 mg, 0.779 mmol, 0.5 eq.) and cyclopropylamine (0.145 ml, 2.03 mmol, 1.3 eq.) were dissolved in acetonitrile-DMF (2:1, 8.0 ml), WSC (366 mg, 1.87 mmol, 1.2 eq.) was added, and the mixture was stirred at room temperature for 2 hr. The reaction mixture was concentrated, and the residue was diluted with ethyl acetate-hexane (5:1, 48 ml) and washed with 2% aqueous sodium carbonate solution, 10% aqueous ammonium chloride solution and saturated brine. The aqueous layers were each extracted with ethyl acetate-hexane-THF (4:1:1, 48 ml). The organic layers were combined, dried over anhydrous sodium sulfate and concentrated, and ethyl acetate was added to the residue. The precipitate was collected by filtration, washed with ethyl acetate and diethyl ether and dried to give the title compound as a white powder (526 mg, 1.49 mmol, 95.4%).

$^1$H NMR (200 MHz, CDCl$_3$) δ: 0.67 (2H, m), 0.87 (2H, m), 1.29 (3H, t, J=7.3 Hz), 1.39 (3H, d, J=1.0 Hz), 1.88 (3H, d, J=1.4 Hz), 2.89 (1H, octet, J=3.6 Hz), 3.54 (2H, dq, J=5.4, 7.3 Hz), 6.15 (1H, quintet, J=1.2 Hz), 6.26 (1H, brt, J=5.4 Hz), 7.34 (1H, brd, J=2 Hz), 7.60 (2H, dt, J=8.8, 2.0 Hz), 7.92 (2H, dt, J=8.8, 2.0 Hz).

Elemental analysis for C$_{19}$H$_{23}$N$_5$O$_2$
Calcd. (%): C, 64.57; H, 6.56; N, 19.82.
Found (%): C, 64.55; H, 6.63; N, 19.69.

Example 96

N-cyclopropyl-5-(cyclopropylmethyl)-1-{4-[(ethylamino)carbonyl]phenyl}-1H-1,2,3-triazole-4-carboxamide

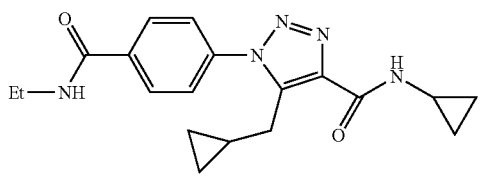

96a) ethyl 4-cyclopropyl-3-oxobutyrate

To a solution of oxalyl chloride (0.956 ml, 10.6 mmol, 1.2 eq.) in dichloromethane (5 ml) was added dropwise DMF (0.068 ml, 0.882 mmol, 0.1 eq.) under ice-cooling, a solution of cyclopropaneacetic acid (0.92 g, 8.82 mmol) in dichloromethane (5 ml) was added dropwise over 60 min. The reaction mixture was allowed to warm to room temperature and stirred at room temperature for 105 min. On the other hand, to a solution of Meldrum's acid (1.56 g, 10.6 mmol, 1.2 eq.) in dichloromethane (10 ml) was added dropwise pyridine (2.85 ml, 35.3 mmol, 4.0 eq.) under ice-cooling, and the reaction mixture obtained above was added dropwise over 1 hr. The reaction mixture was allowed to warm to room temperature, and the mixture was stirred at room temperature for 18 hr. 3N hydrochloric acid (40 ml) and dichloromethane (20 ml) were added to the reaction mixture, and the mixture was blended. The aqueous layer was extracted twice with dichloromethane (20 ml). The organic layers were combined, dried over anhydrous sodium sulfate and concentrated to give a brown oil.

This oil was dissolved in ethanol (30 ml), and the mixture was heated under reflux at 80° C. for 4 hr under a nitrogen atmosphere. The reaction mixture was concentrated, toluene (50 ml) was added, and the mixture was concentrated to give a brown oil. This oil was subjected to column chromatography (elution solvent, hexane and ethyl acetate-hexane=2:98-10:90) on silica gel (manufactured by E. Merck, Art.7734, 10 g) to give the title compound as a colorless oil (1.21 g, 7.13 mmol, 80.8%).

$^1$H NMR (200 MHz, CDCl$_3$) δ: 0.15 (2H, m), 0.60 (2H, m), 0.99 (2H, m), 1.28 (3H, t, J=7.1 Hz), 2.43 (2H, d, J=7.0 Hz), 3.50 (2H, s), 4.20 (2H, q, J=7.2 Hz).

96b) 5-(cyclopropylmethyl)-1-{4-[(ethylamino)carbonyl]phenyl}-1H-1,2,3-triazole-4-carboxylic acid Ethyl 4-cyclopropyl-3-oxobutyrate (1.20 g, 7.05 mmol, 1.2 eq.) obtained in Example 96a) and 4-azido-N-ethylbenzamide (1.20 g, 5.88 mmol) were dissolved in ethanol (25 ml), sodium ethoxide (556 mg, 7.35 mmol, 1.25 eq.) was added, and the mixture was stirred at room temperature for 30 min and at 80° C. for 2.5 hr. 2% Aqueous sodium carbonate solution (40 ml) was added to the reaction mixture, ethanol was evaporated, and the residue was diluted with water (20 ml) and washed twice with ethyl acetate-hexane (2:1, 50 ml). The organic layer was extracted with 1% aqueous sodium carbonate solution (20 ml). The aqueous layers were combined, acidified (pH<3) with 6N hydrochloric acid, and stood still at 5° C. The precipitate was collected by filtration, washed with cold water and dried to give the title compound as a pale-brown powder (1.88 g, 5.98 mmol, 101.7%).

$^1$H NMR (200 MHz, CDCl$_3$-DMSO-d$_6$=19:1) δ: 0.03 (2H, m), 0.32 (2H, m), 0.78 (2H, m), 1.28 (3H, t, J=7.1 Hz), 2.99 (2H, d, J=7.0 Hz), 3.52 (2H, dq, J=4.8, 7.4 Hz), 7.25 (1H, m), 7.55 (2H, brd, J=8.4 Hz), 8.05 (2H, d, J=8.4 Hz).

Elemental analysis for C$_{16}$H$_{18}$N$_4$O$_3$
Calcd. (%): C, 61.13; H, 5.77; N, 17.82.
Found (%): C, 61.06; H, 5.75; N, 17.65.

96c) N-cyclopropyl-5-(cyclopropylmethyl)-1-{4-[(ethylamino)carbonyl]phenyl}-1H-1,2,3-triazole-4-carboxamide 5-(Cyclopropylmethyl)-1-{4-[(ethylamino)carbonyl]phenyl}-1H-1,2,3-triazole-4-carboxylic acid (503 mg, 1.60 mmol) obtained in Example 96b), HOBt (109 mg, 0.800 mmol, 0.5 eq.) and cyclopropylamine (0.149 ml, 2.08 mmol, 1.3 eq.) were dissolved in acetonitrile-DMF (2:1, 8 ml), WSC (376 mg, 1.92 mmol, 1.2 eq.) was added, and the mixture was stirred at room temperature for 2.5 hr. The reaction mixture was concentrated, and the residue was diluted with ethyl acetate (50 ml) and washed with 2% aqueous sodium carbonate solution (×2), 10% aqueous ammonium chloride solution and saturated brine. The aqueous layers were each extracted with ethyl acetate-hexane (3:1, 40 ml). The organic layers were combined, dried over anhydrous sodium sulfate and concentrated, and diethyl ether was added to the residue. The precipitate was collected by filtration, washed with diethyl ether and dried to give the title compound as a white powder (518 mg, 1.47 mmol, 91.6%).

$^1$H NMR (200 MHz, CDCl$_3$) δ: 0.09 (2H, m), 0.33 (2H, m), 0.68 (2H, m), 0.79 (2H, m), 0.88 (2H, m), 1.30 (3H, t, J=7.4 Hz), 2.91 (1H, octet, J=3.5 Hz), 3.05 (2H, d, J=7.0 Hz), 3.55 (2H, dq, J=5.6, 7.3 Hz), 6.24 (1H, brt, J=5 Hz), 7.36 (1H, brd, J=2 Hz), 7.54 (2H, dt, J=8.4, 1.8 Hz), 7.97 (2H, dt, J=8.4, 1.8 Hz).

Elemental analysis for C$_{19}$H$_{23}$N$_5$O$_2$
Calcd. (%): C, 64.57; H, 6.56; N, 19.82.
Found (%): C, 64.34; H, 6.62; N, 19.67.

Example 97

N-cyclopropyl-1-{4-[(ethylamino)carbonyl]phenyl}-5-(3-methylbutyl)-1H-1,2,3-triazole-4-carboxamide

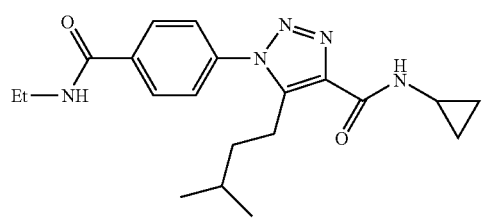

97a) ethyl 6-methyl-3-oxoheptanoate

To a solution of oxalyl chloride (1.54 ml, 17.1 mmol, 1.1 eq.) in dichloromethane (6 ml) was added dropwise DMF (0.120 ml, 1.56 mmol, 0.1 eq.) under ice-cooling, and a solution of 4-methylpentanoic acid (2.00 ml, 15.6 mmol) in dichloromethane (6 ml) was added dropwise over 70 min. The reaction mixture was allowed to warm to room temperature and stirred at room temperature for 2 hr. On the other hand, to a solution of Meldrum's acid (2.75 g, 18.7 mmol, 1.2 eq.) in dichloromethane (15 ml) was added dropwise pyridine (5.03 ml, 62.2 mmol, 4.0 eq.) under ice-cooling, and the reaction mixture obtained above was added dropwise over 1.5 hr. The reaction mixture was allowed to warm to room temperature and stirred at room temperature for 17 hr. 3N hydrochloric acid (40 ml) and dichloromethane (30 ml) were added to the reaction mixture, and the mixture was blended. The aqueous layer was extracted twice with dichloromethane (30 ml). The organic layers were combined, dried over anhydrous sodium sulfate and concentrated to give a dark purple oil.

This oil was dissolved in ethanol (50 ml), and the mixture was heated under reflux for 2 hr under a nitrogen atmosphere. To the reaction mixture was added toluene (80 ml), and the mixture was concentrated to give a brown oil, which was subjected to column chromatography (elution solvent, hexane and ethyl acetate-hexane=2:98-10:90) on silica gel (manufactured by E. Merck, Art.7734, 20 g). The fraction obtained by elution with ethyl acetate-hexane (2:98-5:95) was concentrated to give the title compound as a pale-yellow oil (2.22 g, 11.3 mmol, 72.8%).

$^1$H NMR (200 MHz, CDCl$_3$) δ: 0.89 (6H, d, J=6.2 Hz), 1.28 (3H, t, J=7.1 Hz), 1.50 (2H, m), 1.56 (2H, m), 2.54 (2H, t, J=7.5 Hz), 3.44 (2H, s), 4.20 (2H, q, J=7.1 Hz).

97b) 1-{4-[(ethylamino)carbonyl]phenyl}-5-(3-methylbutyl)-1H-1,2,3-triazole-4-carboxylic acid Ethyl 6-methyl-3-oxoheptanoate (1.08 g, 5.53 mmol, 1.25 eq.) obtained in Example 97a) and 4-azido-N-ethylbenzamide (0.842 g, 4.43 mmol) were dissolved in ethanol (25 ml), sodium ethoxide (418 mg, 5.53 mmol, 1.25 eq.) was added, and the mixture was stirred at room temperature for 30 min and at 60° C. for 17 hr. 2% Aqueous sodium carbonate solution (20 ml) was added to the reaction mixture, ethanol was evaporated, and the residue was diluted with water (20 ml) and washed with ethyl acetate-hexane (2:1, 40 ml). The organic layer was extracted with 2% aqueous sodium carbonate solution (20 ml). The aqueous layers were combined, acidified (pH<3) with 6N hydrochloric acid, and stood still at 0° C. The precipitate was collected by filtration and washed with cold water and dried to give the title compound as a grayish white powder (1.41 g, 4.27 mmol, 96.3%).

$^1$H NMR (200 MHz, CDCl$_3$-DMSO-d$_6$=19:1) δ: 0.80 (6H, d, J=6.2 Hz), 1.28 (3H, t, J=7.3 Hz), 1.35-1.50 (3H, m), 3.00 (2H, m), 3.51 (2H, dq, J=5.4, 7.2 Hz), 7.48 (1H, m), 7.50 (2H, d, J=8.4 Hz), 8.08 (2H, d, J=8.4 Hz).

Elemental analysis for C$_{17}$H$_{22}$N$_4$O$_3$
Calcd. (%): C, 61.80; H, 6.71; N, 16.96.
Found (%): C, 61.80; H, 6.72; N, 16.72.

97c) N-cyclopropyl-1-{4-[(ethylamino)carbonyl]phenyl}-5-(3-methylbutyl)-1H-1,2,3-triazole-4-carboxamide 1-{4-[(Ethylamino)carbonyl]phenyl}-5-(3-methylbutyl)-1H-1,2,3-triazole-4-carboxylic acid (462 mg, 1.40 mmol) obtained in Example 97b), HOBt (95.4 mg, 0.700 mmol, 0.5 eq.) and cyclopropylamine (0.130 ml, 1.82 mmol, 1.3 eq.) were dissolved in acetonitrile-DMF (2:1, 7.5 ml), WSC (328 mg, 1.68 mmol, 1.2 eq.) was added, and the mixture was stirred at room temperature for 2 hr. The reaction mixture was concentrated, and the residue was diluted with ethyl acetate (40 ml) and washed with 2% aqueous sodium carbonate solution (×2), 10% aqueous ammonium chloride solution and saturated brine. The aqueous layers were each extracted with ethyl acetate-hexane (2:1, 30 ml). The organic layers were combined, dried over anhydrous sodium sulfate and concentrated, and diethyl ether was added to the residue. The precipitate was collected by filtration, washed with diethyl ether and dried to give the title compound as a grayish white powder (481 mg, 1.30 mmol, 93.0%).

$^1$H NMR (200 MHz, CDCl$_3$) δ: 0.68 (2H, m), 0.82 (6H, d, J=6.2 Hz), 0.89 (2H, m), 1.30 (3H, t, J=7.1 Hz), 1.36-1.56 (3H, m), 2.91 (1H, octet, J=3.4 Hz), 3.04 (2H, m), 3.55 (2H, dq, J=5.6, 7.1 Hz), 6.21 (1H, brt, J=5 Hz), 7.34 (1H, brd, J=2 Hz), 7.52 (2H, dt, J=8.4, 2.0 Hz), 7.98 (2H, dt, J=8.4, 2.0 Hz).

Elemental analysis for C$_{20}$H$_{27}$N$_5$O$_2$
Calcd. (%): C, 65.02; H, 7.37; N, 18.96.
Found (%): C, 65.04; H, 7.31; N, 18.93.

Example 98

N-cyclopropyl-1-{4-[(ethylamino)carbonyl]phenyl}-5-(2-phenylethyl)-1H-1,2,3-triazole-4-carboxamide

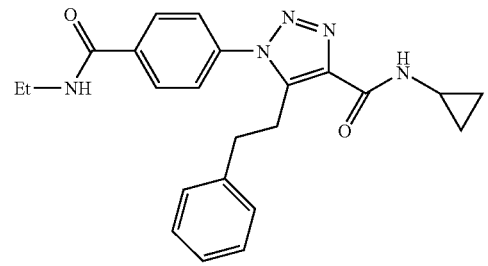

98a) ethyl 5-phenyl-3-oxovalerate

To a solution of Meldrum's acid (2.54 g, 17.3 mmol) in dichloromethane (15 ml) was added dropwise pyridine (3.21 ml, 39.7 mmol, 2.3 eq.) under ice-cooling, and a solution of 3-phenylpropionyl chloride (2.44 ml, 15.7 mmol, 0.91 eq.) in dichloromethane (10 ml) was added dropwise over 2 hr. The reaction mixture was allowed to warm to room temperature, and the mixture was stirred at room temperature for 14 hr. 3N hydrochloric acid (40 ml) and dichloromethane (30 ml) was added to the reaction mixture, and the mixture was blended. The aqueous layer was extracted twice with dichloromethane (40 ml). The organic layers were combined, dried over anhydrous sodium sulfate and concentrated to give an orange oil.

This oil was dissolved in ethanol (50 ml), and the mixture was heated under reflux for 3 hr under a nitrogen atmosphere. To the reaction mixture was added toluene (80 ml), and the mixture was concentrated to give a yellow oil, which was subjected to column chromatography (elution solvent, hexane and ethyl acetate-hexane=2:98-10:90) on silica gel (manufactured by E. Merck, Art.7734, 20 g). The fraction obtained by elution with ethyl acetate-hexane (5:95) was concentrated to give the title compound as a pale-yellow oil (2.54 g, 11.0 mmol, 70.0%).

$^1$H NMR (200 MHz, CDCl$_3$) δ: 1.26 (3H, t, J=7.2 Hz), 2.91 (4H, m), 3.42 (2H, s), 4.18 (2H, q, J=7.1 Hz).

98b) 1-{4-[(ethylamino)carbonyl]phenyl}-5-(2-phenylethyl)-1H-1,2,3-triazole-4-carboxylic acid Ethyl 5-phenyl-3-oxovalerate (1.27 g, 5.52 mmol, 1.25 eq.) obtained in Example 98a) and 4-azido-N-ethylbenzamide (0.842 g, 4.43 mmol) were dissolved in ethanol (25 ml), sodium ethoxide (417 mg, 5.52 mmol, 1.25 eq.) was added, and the mixture was stirred at room temperature for 30 min and at 80° C. for 3 hr. 2% Aqueous sodium carbonate solution (20 ml) was added to the reaction mixture, ethanol was evaporated, and the residue was diluted with water (20 ml) and washed with ethyl acetate-hexane (2:1, 40 ml). The organic layer was extracted with 2% aqueous sodium carbonate solution (20 ml). The aqueous layers were combined, acidified (pH<3) with 6N hydrochloric acid and extracted with ethyl acetate (35 ml×2). The organic layers were combined, washed with saturated brine, dried over anhydrous sodium sulfate and concentrated, and diethyl ether-ethyl acetate (2:1, about 8 ml) was added. The precipitate was collected by filtration, washed with diethyl ether and dried to give the title compound as a pale-brown powder (1.56 g, 4.27 mmol, 96.4%).

$^1$H NMR (200 MHz, CDCl$_3$-DMSO-d$_6$=19:1) δ: 1.28 (3H, t, J=7.1 Hz), 2.91 (2H, brt, J=7.5 Hz), 3.26 (2H, brt, J=7.5 Hz), 3.51 (2H, dq, J=5.6, 7.1 Hz), 6.91 (2H, m), 7.15 (2H, d, J=8.4 Hz), 7.15-7.20 (3H, m), 7.24 (1H, brt, J=6 Hz), 7.94 (2H, d, J=8.4 Hz).

Elemental analysis for C$_{20}$H$_{20}$N$_4$O$_3$
Calcd. (%): C, 65.92; H, 5.53; N, 15.38.
Found (%): C, 65.89; H, 5.56; N, 15.38.

98c) N-cyclopropyl-1-{4-[(ethylamino)carbonyl]phenyl}-5-(2-phenylethyl)-1H-1,2,3-triazole-4-carboxamide 1-{4-[(Ethylamino)carbonyl]phenyl}-5-(2-phenylethyl)-1H-1,2,3-triazole-4-carboxylic acid (501 mg, 1.37 mmol) obtained in Example 98b), HOBt (93.8 mg, 0.687 mmol, 0.5 eq.) and cyclopropylamine (0.128 ml, 1.79 mmol, 1.3 eq.) were dissolved in acetonitrile-DMF (2:1, 7.5 ml), WSC (323 mg, 1.65 mmol, 1.2 eq.) was added, and the mixture was stirred at room temperature for 1.5 hr. The reaction mixture was concentrated, and the residue was diluted with ethyl acetate (40 ml) and washed with 2% aqueous sodium carbonate solution (×2), 10% aqueous ammonium chloride solution and saturated brine. The aqueous layer was each extracted with ethyl acetate-hexane (2:1, 30 ml). The organic layers were combined, dried over anhydrous sodium sulfate and concentrated, and diethyl ether was added to the residue. The precipitate was collected by filtration, washed with diethyl ether and dried to give the title compound as a white powder (526 mg, 1.30 mmol, 95.2%).

$^1$H NMR (200 MHz, CDCl$_3$) δ: 0.71 (2H, m), 0.91 (2H, m), 1.30 (3H, t, J=7.4 Hz), 2.92 (1H, m), 2.97 (2H, brt, J=7.6 Hz), 3.29 (2H, brt, J=7.6 Hz), 3.54 (2H, dq, J=5.8, 7.4 Hz), 6.18 (1H, brt, J=6 Hz), 6.93 (2H, m), 7.13 (2H, d, J=8.0 Hz), 7.14-7.20 (3H, m), 7.37 (1H, brd, J=2 Hz), 7.85 (2H, d, J=8.4 Hz).

Elemental analysis for C$_{23}$H$_{25}$N$_5$O$_2$
Calcd. (%): C, 68.47; H, 6.25; N, 17.36.
Found (%): C, 68.44; H, 6.31; N, 17.27.

Example 99

5-benzyl-N-cyclopropyl-1-{4-[(ethylamino)carbonyl]phenyl}-1H-1,2,3-triazole-4-carboxamide

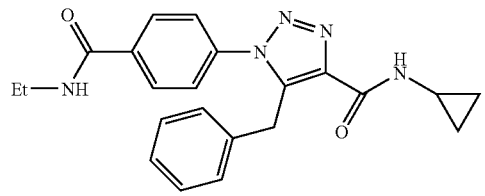

99a) 5-benzyl-1-{4-[(ethylamino)carbonyl]phenyl}-1H-1,2,3-triazole-4-carboxylic acid 4-Azido-N-ethylbenzamide (0.571 g, 3.00 mmol) and ethyl 4-phenyl-3-oxobutyrate (0.692 g, 3.60 mmol, 1.25 eq.) were dissolved in ethanol (15 ml), sodium ethoxide (284 mg, 3.60 mmol, 1.25 eq.) was added, and the mixture was stirred at room temperature for 30 min and at 80° C. for 2 hr. 2% aqueous sodium carbonate solution (20 ml) was added to the reaction mixture, and the mixture was further stirred for 30 min. Ethanol was evaporated, and the residue was diluted with 2% aqueous sodium carbonate solution (20 ml) and washed with ethyl acetate (40 ml). The organic layer was extracted with 2% aqueous sodium carbonate solution (20 ml). The aqueous layers were combined, concentrated to about 30 ml, acidified (pH<3) with 6N hydrochloric acid and extracted with ethyl acetate (35 ml×2). The organic layers were combined, washed with saturated brine, dried over anhydrous sodium sulfate and concentrated, and diethyl ether and ethyl acetate were added. The precipitate was collected by filtration, washed with diethyl ether and dried to give the title compound as a pale-brown powder (796 mg, 2.27 mmol, 75.7%).

$^1$H NMR (200 MHz, CDCl$_3$-DMSO-d$_6$=19:1) δ: 1.27 (3H, t, J=7.3 Hz), 3.50 (2H, dq, J=6.6, 7.0 Hz), 4.43 (2H, s), 6.92 (2H, m), 7.15-7.21 (4H, m), 7.32 (2H, d, J=8.4 Hz), 7.94 (2H, d, J=8.4 Hz).

Elemental analysis for C$_{19}$H$_{18}$N$_4$O$_3$.0.5EtOAc
Calcd. (%): C, 64.75; H, 5.32; N, 15.41.
Found (%): C, 64.79; H, 5.34; N, 15.40.

99b) 5-benzyl-N-cyclopropyl-1-{4-[(ethylamino)carbonyl]phenyl}-1H-1,2,3-triazole-4-carboxamide 5-Benzyl-1-{4-[(ethylamino)carbonyl]phenyl}-1H-1,2,3-triazole-4-carboxylic acid (354 mg, 1.01 mmol) obtained in Example 99a), HOBt (69.0 mg, 0.505 mmol, 0.5 eq.) and cyclopropylamine (0.094 ml, 1.31 mmol, 1.3 eq.) were dissolved in acetonitrile-DMF (2:1, 6 ml), WSC (217 mg, 1.11 mmol, 1.1 eq.) was added, and the mixture was stirred at room temperature for 3.5 hr. 1% aqueous sodium hydrogen carbonate solution (20 ml) was added to the reaction mixture, and the mixture was stirred. The precipitate was collected by filtration, washed with water and dried to give the title compound as a white powder (348 mg, 0.894 mmol, 88.5%).

$^1$H NMR (200 MHz, CDCl$_3$) δ: 0.71 (2H, m), 0.90 (2H, m), 1.29 (3H, t, J=7.1 Hz), 2.95 (1H, octet, J=3.7 Hz), 3.54 (2H, dq, J=5.8, 7.1 Hz), 4.49 (2H, s), 6.14 (1H, brt, J=5 Hz), 6.94 (2H, m), 7.14-7.19 (3H, m), 7.33 (2H, dt, J=8.8, 2.2 Hz), 7.40 (1H, brd, J=3 Hz), 7.87 (2H, dt, J=8.4, 1.8 Hz).

Elemental analysis for $C_{22}H_{23}N_5O_2$
Calcd. (%): C, 67.85; H, 5.95; N, 17.98.
Found (%): C, 67.85; H, 5.92; N, 18.12.

Example 100

N-cyclopropyl-1-{4-[(ethylamino)carbonyl]phenyl}-5-(3-phenylpropyl)-1H-1,2,3-triazole-4-carboxamide

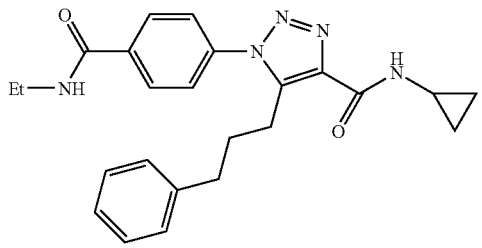

100a) ethyl 6-phenyl-3-oxohexanoate

To a solution of oxalyl chloride (1.80 ml, 19.9 mmol, 1.1 eq.) in dichloromethane (8 ml) was added dropwise DMF (0.140 ml, 1.81 mmol, 0.1 eq.) under ice-cooling, and a solution of 4-phenylbutyric acid (3.00 g, 18.1 mmol) in dichloromethane (8 ml) was added dropwise over 90 min. The reaction mixture was allowed to warm to room temperature, and the mixture was stirred at room temperature for 1.5 hr. On the other hand, to a solution of Meldrum's acid (2.93 g, 19.9 mmol, 1.1 eq.) in dichloromethane (20 ml) was added dropwise pyridine (5.85 ml, 72.4 mmol, 4.0 eq.) under ice-cooling, and the reaction mixture obtained above was added dropwise over 1.5 hr. The reaction mixture was allowed to warm to room temperature and stirred at room temperature for 18.5 hr. 3N hydrochloric acid (50 ml) was added to the reaction mixture, and the mixture was blended. The aqueous layer was extracted with dichloromethane (40 ml and 30 ml). The organic layers were combined, dried over anhydrous sodium sulfate and concentrated to give a dark purple oil.

This oil was dissolved in ethanol (70 ml), and the mixture was stirred at 80° C. for 4 hr under a nitrogen atmosphere. The reaction mixture was concentrated, and the residue was diluted with toluene (40 ml) and concentrated again to give a brown oil, which was subjected to column chromatography (elution solvent, hexane and ethyl acetate-hexane=2:98-5:95) on silica gel (manufactured by E. Merck, Art.7734, 30 g). The fraction obtained by elution with ethyl acetate-hexane (5:95) was concentrated to give the title compound as a pale-yellow oil (3.44 g, 14.7 mmol, 81.1%, 3:2 mixture with enol isomer).

$^1$H NMR (200 MHz, CDCl$_3$) δ: 1.26 (3H, t, J=7.2 Hz), 1.94 (2H, m), 2.55 (2H, t, J=7.4 Hz), 2.64 (2H, dt, J=4.0, 7.5 Hz), 3.41 (2H, s), 4.19 (2H, q, J=7.2 Hz), 7.14-7.34 (5H, m).

100b) 1-{4-[(ethylamino)carbonyl]phenyl}-5-(3-phenylpropyl)-1H-1,2,3-triazole-4-carboxylic acid Ethyl 6-phenyl-3-oxohexanoate (1.11 g, 4.73 mmol, 1.25 eq.) obtained in Example 100a) and 4-azido-N-ethylbenzamide (0.719 g, 3.78 mmol) were dissolved in ethanol (20 ml), sodium ethoxide (357 mg, 4.73 mmol, 1.25 eq.) was added, and the mixture was stirred at room temperature for 30 min and at 60° C. for 10.5 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid and stood still at 0° C. The precipitate was collected by filtration, washed with ice-cold water and dried to give the title compound as a pale-yellow powder (1.32 g, 3.50 mmol, 92.6%).

$^1$H NMR (200 MHz, CDCl$_3$-DMSO-d$_6$=19:1) δ: 1.29 (3H, t, J=7.1 Hz), 1.84 (2H, m), 2.56 (2H, t, J=7.5 Hz), 3.02 (2H, m), 3.52 (2H, dq, J=5.4, 7.1 Hz), 7.02 (2H, m), 7.15-7.27 (4H, m), 7.42 (2H, dt, J=8.4, 1.8 Hz), 7.97 (2H, dt, J=8.4, 2.2 Hz).

Elemental analysis for $C_{21}H_{22}N_4O_3$
Calcd. (%): C, 66.65; H, 5.86; N, 14.81.
Found (%): C, 66.49; H, 5.88; N, 14.57.

100c) N-cyclopropyl-1-{4-[(ethylamino)carbonyl]phenyl}-5-(3-phenylpropyl)-1H-1,2,3-triazole-4-carboxamide 1-{4-[(Ethylamino)carbonyl]phenyl}-5-(3-phenylpropyl)-1H-1,2,3-triazole-4-carboxylic acid (398 mg, 1.05 mmol) obtained in Example 100b), HOBt (71.8 mg, 0.526 mmol, 0.5 eq.) and cyclopropylamine (0.098 ml, 1.37 mmol, 1.3 eq.) were dissolved in acetonitrile-DMF (2:1, 6 ml), WSC (247 mg, 1.26 mmol, 1.2 eq.) was added, and the mixture was stirred at room temperature for 12 hr. Water (20 ml) was added to the reaction mixture, and the mixture was stirred. The precipitate was collected by filtration, washed with water and dried to give the title compound as a white powder (414 mg, 0.992 mmol, 94.4%).

$^1$H NMR (200 MHz, CDCl$_3$) δ: 0.69 (2H, m), 0.89 (2H, m), 1.31 (3H, t, J=7.3 Hz), 1.88 (2H, m), 2.60 (2H, t, J=7.3 Hz), 2.91 (1H, octet, J=3.6 Hz), 3.07 (2H, m), 3.56 (2H, dq, J=5.6, 7.3 Hz), 6.15 (1H, brt, J=5 Hz), 7.03 (2H, m), 7.15-7.23 (3H, m), 7.34 (1H, brd, J=2 Hz), 7.39 (2H, dt, J=8.8, 2.2 Hz), 7.86 (2H, dt, J=8.4, 1.8 Hz).

Elemental analysis for $C_{24}H_{27}N_5O_2$
Calcd. (%): C, 69.04; H, 6.52; N, 16.77.
Found (%): C, 68.81; H, 6.47; N, 16.79.

Example 101

N-cyclopropyl-1-{4-[(ethylamino)carbonyl]phenyl}-5-(5-phenylpentyl)-1H-1,2,3-triazole-4-carboxamide

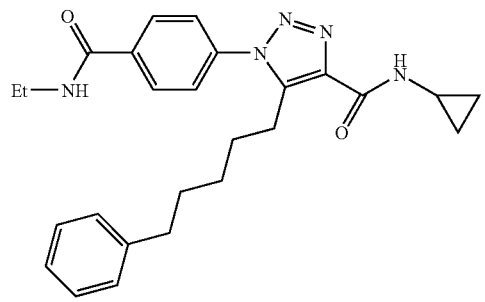

101a) ethyl 8-phenyl-3-oxooctanoate

To a solution of oxalyl chloride (1.04 ml, 11.5 mmol, 1.1 eq.) in dichloromethane (5 ml) was added dropwise DMF (0.081 ml, 1.04 mmol, 0.1 eq.) under ice-cooling, and a solution of 6-phenylhexanoic acid (2.00 g, 18.1 mmol) in dichloromethane (5 ml) was added dropwise over 30 min. The reaction mixture was allowed to warm to room temperature, and the mixture was stirred at room temperature for 3.5 hr. On the other hand, to a solution of Meldrum's acid (1.69 g, 11.5 mmol, 1.1 eq.) in dichloromethane (15 ml) was added dropwise pyridine (3.37 ml, 41.7 mmol, 4.0 eq.) under ice-cooling, and the reaction mixture obtained above was added dropwise over 1 hr. The reaction mixture was allowed to warm to room temperature, and the mixture was stirred at room temperature for 12 hr. 3N hydrochloric acid (40 ml) was added to the reaction mixture, and the mixture was blended. The aqueous layer was extracted twice with dichloromethane (30 ml). The organic layers were combined, dried over anhydrous sodium sulfate and concentrated to give a brown oil.

This oil was dissolved in ethanol (50 ml), and the solution was stirred at 80° C. for 3.5 hr under a nitrogen atmosphere. The reaction mixture was concentrated, diluted with toluene (50 ml) and concentrated again to give a brown oil, which was subjected to column chromatography (elution solvent, hexane and ethyl acetate-hexane=2:98-5:95) on silica gel (manufactured by E. Merck, Art.7734, 20 g) to give the title compound as a pale-yellow oil (2.06 g, 7.85 mmol, 75.5%, 1:1 mixture with enol isomer).

$^1$H NMR (200 MHz, CDCl$_3$) δ: 1.28 (3H, t, J=7.2 Hz), 1.37 (2H, m), 1.54-1.71 (4H, m), 2.53 (2H, t, J=7.4 Hz), 2.61 (2H, brt, J=7.2 Hz), 3.42 (2H, s), 4.19 (2H, q, J=7.1 Hz), 7.13-7.32 (5H, m).

101b) 1-{4-[(ethylamino)carbonyl]phenyl}-5-(5-phenylpentyl)-1H-1,2,3-triazole-4-carboxylic acid Ethyl 8-phenyl-3-oxooctanoate (1.01 g, 3.84 mmol, 1.23 eq.) obtained in Example 101a) and 4-azido-N-ethylbenzamide (purity 95%, 0.624 g, 3.12 mmol) were dissolved in ethanol (20 ml), sodium ethoxide (290 mg, 3.84 mmol, 1.23 eq.) was added, and the mixture was stirred at room temperature for 30 min and at 60° C. for 14 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid and stood still at 0° C. The precipitate was collected by filtration, washed with ice-cold water and dried to give the title compound as a pale-yellow powder (1.26 g, 3.10 mmol, 99.5%).

$^1$H NMR (200 MHz, CDCl$_3$-DMSO-d$_6$=19:1) δ: 1.26 (2H, m), 1.28 (3H, t, J=7.1 Hz), 1.45-1.59 (4H, m), 2.51 (2H, brt, J=7.5 Hz), 2.99 (2H, brt, J=7.7 Hz), 3.51 (2H, dq, J=5.4, 7.3 Hz), 7.10 (2H, brd, J=7.6 Hz), 7.18 (1H, m), 7.20 (1H, br), 7.25 (2H, tt, J=6.8, 1.7 Hz), 7.49 (2H, dt, J=8.4, 1.8 Hz), 8.04 (2H, dt, J=8.4, 1.8 Hz).

Elemental analysis for C$_{21}$H$_{22}$N$_4$O$_3$
Calcd. (%): C, 67.96; H, 6.45; N, 13.78.
Found (%): C, 67.85; H, 6.52; N, 13.46.

101c) N-cyclopropyl-1-{4-[(ethylamino)carbonyl]phenyl}-5-(5-phenylpentyl)-1H-1,2,3-triazole-4-carboxamide 1-{4-[(Ethylamino)carbonyl]phenyl}-5-(5-phenylpentyl)-1H-1,2,3-triazole-4-carboxylic acid (392 mg, 0.964 mmol) obtained in Example 101b), HOBt (67.3 mg, 0.482 mmol, 0.5 eq.) and cyclopropylamine (0.090 ml, 1.25 mmol, 1.3 eq.) were dissolved in acetonitrile-DMF (2:1, 6 ml), WSC (226 mg, 1.16 mmol, 1.2 eq.) was added, and the mixture was stirred at room temperature for 13.5 hr. Water (10 ml) was added to the reaction mixture, and the mixture was stirred. The precipitate was collected by filtration, washed with water and methanol-water (1:1) and dried to give the title compound as a white powder (412 mg, 0.925 mmol, 95.9%).

$^1$H NMR (200 MHz, CDCl$_3$) δ: 0.68 (2H, m), 0.89 (2H, m), 1.30 (3H, t, J=7.4 Hz), 1.28 (2H, m), 1.46-1.62 (4H, m), 2.51 (2H, t, J=7.7 Hz), 2.91 (1H, octet, J=3.5 Hz), 3.03 (2H, m), 3.55 (2H, dq, J=5.8, 7.3 Hz), 6.12 (1H, m), 7.09 (2H, brd, J=7.2 Hz), 7.16 (1H, m), 7.22 (2H, m), 7.34 (1H, brd, J=3 Hz), 7.49 (2H, dt, J=8.8, 2.2 Hz), 7.95 (2H, dt, J=8.8, 1.8 Hz).

Elemental analysis for C$_{26}$H$_{31}$N$_5$O$_2$
Calcd. (%): C, 70.09; H, 7.01; N, 15.72.
Found (%): C, 70.06; H, 6.91; N, 15.66.

Example 102

5-(cyclohexylmethyl)-N-cyclopropyl-1-{4-[(ethylamino)carbonyl]phenyl}-1H-1,2,3-triazole-4-carboxamide

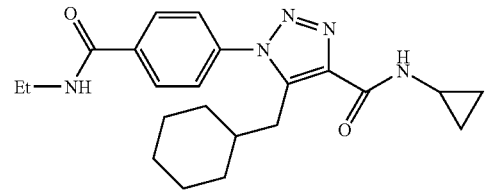

102a) ethyl 4-cyclohexyl-3-oxobutyrate

To a solution of oxalyl chloride (1.90 ml, 21.0 mmol, 1.1 eq.) in dichloromethane (6 ml) was added dropwise DMF (0.148 ml, 1.91 mmol, 0.1 eq.) under ice-cooling, and a solution of cyclohexaneacetic acid (2.77 g, 19.1 mmol) in dichloromethane (6 ml) was added dropwise over 80 min. The reaction mixture was allowed to warm to room temperature, and the mixture was stirred at room temperature for 1.5 hr. On the other hand, to a solution of Meldrum's acid (3.09 g, 21.0 mmol, 1.1 eq.) in dichloromethane (20 ml) was added dropwise pyridine (6.18 ml, 76.4 mmol, 4.0 eq.) under ice-cooling, and then the reaction mixture obtained above was added dropwise over 2 hr. The reaction mixture was allowed to warm to room temperature, and the mixture was stirred at room temperature for 12 hr. The reaction mixture was blended with 3N hydrochloric acid (50 ml). The aqueous layer was extracted twice with dichloromethane (40 ml). The organic layers were combined, dried over anhydrous sodium sulfate, and concentrated to give a dark purple oil.

This oil was dissolved in ethanol (60 ml), and the solution was stirred at 80° C. for 2.5 hr under a nitrogen atmosphere. To the reaction mixture was added toluene (60 ml) and the mixture was concentrated to give a brown oil, which was subjected to column chromatography (elution solvent, hexane and ethyl acetate-hexane=2:98-5:95) on silica gel (manufactured by E. Merck, Art.7734, 30 g). The fraction obtained by elution with ethyl acetate-hexane (2:98-5:95) was concentrated to give the title compound as a pale-yellow oil (3.10 g, 14.6 mmol, 76.5%).

$^1$H NMR (200 MHz, CDCl$_3$) δ: 0.93 (2H, brq, J=11 Hz), 1.18-1.36 (3H, br), 1.28 (3H, t, J=7.1 Hz), 1.68 (6H, brd, J=11 Hz), 2.40 (2H, d, J=6.6 Hz), 3.41 (2H, s), 4.19 (2H, q, J=7.2 Hz).

102b) 5-(cyclohexylmethyl)-1-{4-[(ethylamino)carbonyl]phenyl}-1H-1,2,3-triazole-4-carboxylic acid Ethyl 4-cyclohexyl-3-oxobutyrate (0.84 g, 3.96 mmol, 1.25 eq.) obtained in Example 102a) and 4-azido-N-ethylbenzamide (0.60 g, 3.15 mmol) were dissolved in ethanol (20 ml), sodium ethoxide (298 mg, 3.96 mmol, 1.25 eq.) was added, and the mixture was stirred at room temperature for 30 min, and then at 50° C. for 14 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid, and extracted with ethyl acetate-THF (4:1, 40 ml) and ethyl acetate (30 ml). The organic layers were combined, washed with saturated brine, dried over anhydrous sodium sulfate, and concentrated, and diethyl ether and ethyl acetate were added. The precipitate was collected by filtration, washed with diethyl ether and dried to give the title compound as a pale-yellow powder (1.04 g, 2.91 mmol, 92.4%).

$^1$H NMR (200 MHz, CDCl$_3$-DMSO-d$_6$=19:1) δ: 0.75 (2H, brq, J=11 Hz), 1.00 (2H, brq, J=8.0 Hz), 1.07 (1H, m), 1.29 (3H, t, J=7.4 Hz), 1.34-1.60 (6H, m), 2.95 (2H, d, J=7.0 Hz), 3.51 (2H, dq, J=5.4, 7.0 Hz), 7.28 (1H, brt, J=5 Hz), 7.50 (2H, d, J=8.8 Hz), 8.06 (2H, d, J=8.8 Hz).

Elemental analysis for C$_{19}$H$_{24}$N$_4$O$_3$
Calcd. (%): C, 64.03; H, 6.79; N, 15.72.
Found (%): C, 63.88; H, 6.81; N, 15.60.

102c) 5-(cyclohexylmethyl)-N-cyclopropyl-1-{4-[(ethylamino)carbonyl]phenyl}-1H-1,2,3-triazole-4-carboxamide 5-(Cyclohexylmethyl)-1-{4-[(ethylamino)carbonyl]phenyl}-1H-1,2,3-triazole-4-carboxylic acid (357 mg, 1.00 mmol) obtained in Example 102b), HOBt (68.2 mg, 0.500 mmol, 0.5 eq.) and cyclopropylamine (0.093 ml, 1.30 mmol, 1.3 eq.) were dissolved in acetonitrile-DMF (2:1, 4.5 ml), WSC (215 mg, 1.10 mmol, 1.1 eq.) was added, and the mixture was stirred at room temperature for 14 hr. Water was added to the reaction mixture, and the obtained suspension was diluted with 2% aqueous sodium hydrogen carbonate solution. The precipitate was collected by filtration, washed with water and dried to give the title compound as a white powder (363 mg, 0.918 mmol, 91.8%).

$^1$H NMR (200 MHz, CDCl$_3$) δ: 0.68 (2H, m), 0.72-0.86 (2H, m), 0.89 (2H, m), 1.03 (2H, brd, J=8.4 Hz), 1.09 (1H, m), 1.30 (3H, t, J=7.1 Hz), 1.36-1.60 (6H, m), 2.91 (1H, octet, J=3.7 Hz), 2.99 (2H, d, J=7.0 Hz), 3.56 (2H, dq, J=5.6, 7.3 Hz), 6.18 (1H, brt, J=6 Hz), 7.35 (1H, brd, J=3 Hz), 7.50 (2H, dt, J=8.6, 2.1 Hz), 7.97 (2H, dt, J=8.8, 2.0 Hz).

Elemental analysis for C$_{22}$H$_{29}$N$_5$O$_2$
Calcd. (%): C, 66.81; H, 7.39; N, 17.71.
Found (%): C, 66.75; H, 7.38; N, 17.69.

Example 103

5-(cyclopentylmethyl)-N-cyclopropyl-1-{4-[(ethylamino)carbonyl]phenyl}-1H-1,2,3-triazole-4-carboxamide

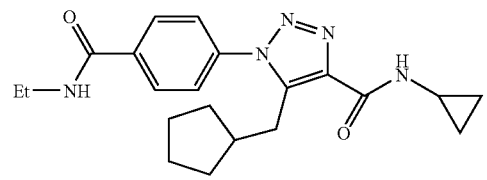

103a) ethyl 4-cyclopentyl-3-oxobutyrate

To a solution of oxalyl chloride (1.54 ml, 17.0 mmol, 1.1 eq.) in dichloromethane (5 ml) was added dropwise DMF (0.120 ml, 1.55 mmol, 0.1 eq.) under ice-cooling, then a solution of cyclopentaneacetic acid (2.04 g, 15.5 mmol) in dichloromethane (5 ml) was added dropwise over 60 min. The reaction mixture was allowed to warm to room temperature, and the mixture was stirred at room temperature for 1.5 hr. On the other hand, to a solution of Meldrum's acid (2.50 g, 17.0 mmol, 1.1 eq.) in dichloromethane (15 ml) was added dropwise pyridine (5.00 ml, 61.9 mmol, 4.0 eq.) under ice-cooling, and then the reaction mixture obtained above was added dropwise over 1.5 hr. The reaction mixture was allowed to warm to room temperature, and the mixture was stirred at room temperature for 13.5 hr. The reaction mixture was blended with 3N hydrochloric acid (50 ml). The aqueous layer was extracted twice with dichloromethane (40 ml). The organic layers were combined, dried over anhydrous sodium sulfate, and concentrated to give a dark red-purple oil.

This oil was dissolved in ethanol (50 ml), and the solution was stirred at 80° C. for 4 hr under a nitrogen atmosphere. The reaction mixture was concentrated, diluted with toluene (60 ml) and concentrated again to give a brown oil, which was subjected to column chromatography (elution solvent, hexane and ethyl acetate-hexane=2:98-5:95) on silica gel (manufactured by E. Merck, Art.7734, 25 g). The fraction obtained by elution with ethyl acetate-hexane (2:98-5:95) was concentrated to give the title compound as a pale-yellow oil (2.90 g, 13.9 mmol, 89.7%, including residual solvent).

$^1$H NMR (200 MHz, CDCl$_3$) δ: 1.10 (2H, m), 1.28 (3H, t, J=7.1 Hz), 1.48-1.70 (4H, m), 1.82 (2H, m), 2.23 (1H, m), 2.56 (2H, d, J=6.8 Hz), 3.42 (2H, s), 4.20 (2H, q, J=7.1 Hz).

103b) 5-(cyclopentylmethyl)-1-{4-[(ethylamino)carbonyl]phenyl}-1H-1,2,3-triazole-4-carboxylic acid Ethyl 4-cyclopentyl-3-oxobutyrate (0.781 g, 3.94 mmol, 1.25 eq.) obtained in Example 103a) and 4-azido-N-ethylbenzamide (0.60 g, 3.15 mmol) were dissolved in ethanol (20 ml), sodium ethoxide (298 mg, 3.94 mmol, 1.25 eq.) was added, and the mixture was stirred at room temperature for 30 min, and then at 50° C. for 12 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid, and extracted with ethyl acetate (35 ml and 30 ml). The organic layers were combined, washed with saturated brine, dried over anhydrous sodium sulfate, and concentrated, and diethyl ether and ethyl acetate were added. The precipitate was collected by filtration, washed with diethyl ether and dried to give the title compound as a pale-yellow powder (971 mg, 2.84 mmol, 90.0%).

$^1$H NMR (200 MHz, CDCl$_3$-DMSO-d$_6$=19:1) δ: 0.98 (2H, m), 1.28 (3H, t, J=7.3 Hz), 1.32-1.56 (6H, m), 1.91 (1H, m), 3.09 (2H, d, J=7.8 Hz), 3.51 (2H, dq, J=5.4, 7.1 Hz), 7.41 (1H, m), 7.51 (2H, d, J=8.4 Hz), 8.07 (2H, d, J=8.4 Hz).

Elemental analysis for C$_{18}$H$_{22}$N$_4$O$_3$
Calcd. (%): C, 63.14; H, 6.48; N, 16.36.
Found (%): C, 63.11; H, 6.46; N, 16.29.

103c) 5-(cyclopentylmethyl)-N-cyclopropyl-1-{4-[(ethylamino)carbonyl]phenyl}-1H-1,2,3-triazole-4-carboxamide 5-(Cyclopentylmethyl)-1-{4-[(ethylamino)carbonyl]phenyl}-1H-1,2,3-triazole-4-carboxylic acid (359 mg, 1.05 mmol) obtained in Example 103b), HOBt (71.6 mg, 0.524 mmol, 0.5 eq.) and cyclopropylamine (0.097 ml, 1.36 mmol, 1.3 eq.) were dissolved in acetonitrile-DMF (2:1, 4.5 ml), WSC (246 mg, 1.26 mmol, 1.2 eq.) was added, and the mixture was stirred at room temperature for 14 hr. Water (15 ml) was added to the reaction mixture and the mixture was stirred at 0° C. The precipitate was collected by filtration, washed with water and dried to give the title compound as a white powder (400 mg, 1.05 mmol, quant.).

$^1$H NMR (200 MHz, CDCl$_3$) δ: 0.68 (2H, m), 0.88 (2H, m), 0.98 (2H, m), 1.30 (3H, t, J=7.3 Hz), 1.32-1.58 (6H, m), 1.98 (1H, m), 2.91 (1H, octet, J=3.4 Hz), 3.12 (2H, d, J=7.8 Hz), 3.55 (2H, dq, J=5.6, 7.3 Hz), 6.20 (1H, brt, J=6 Hz), 7.36 (1H, brd, J=3 Hz), 7.51 (2H, dt, J=8.8, 2.2 Hz), 7.97 (2H, dt, J=8.8, 2.2 Hz).

Elemental analysis for C$_{21}$H$_{27}$N$_5$O$_2$·0.5H$_2$O
Calcd. (%): C, 64.59; H, 7.23; N, 17.94.
Found (%): C, 64.37; H, 7.25; N, 17.95.

Example 104

5-(chloromethyl)-N-cyclopropyl-1-{4-[(ethylamino)carbonyl]phenyl}-1H-1,2,3-triazole-4-carboxamide

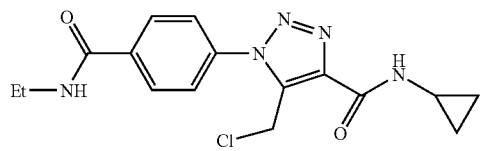

104a) ethyl 5-(chloromethyl)-1-{4-[(ethylamino)carbonyl]phenyl}-1H-1,2,3-triazole-4-carboxylate 4-Azido-N-ethylbenzamide (0.600 g, 3.15 mmol) and ethyl 4-chloro-3-oxobutyrate (0.721 g, 3.94 mmol, 1.25 eq.) were dissolved in ethanol (20 ml), sodium ethoxide (298 mg, 3.94 mmol, 1.25 eq.) was added, and the mixture was stirred at room temperature for 3 hr, and then at 60° C. for 14 hr. Water (20 ml) was added to the reaction mixture, ethanol was evaporated, and the residue was extracted with ethyl acetate-hexane (4:1, 50 ml). The organic layer was washed with 2% aqueous sodium carbonate solution and saturated brine, dried over anhydrous sodium sulfate, and concentrated to give a brown oil (1.0 g). This was subjected to column chromatography (elution solvent, ethyl acetate-hexane=1:4-3:2) on silica gel (manufactured by E. Merck, Art.7734, 10 g). The fraction obtained by elution with ethyl acetate-hexane (2:3-3:2) was concentrated, and diethyl ether was added to the residue. The precipitate was collected by filtration, washed with diethyl ether and dried to give the title compound as a pale-yellow powder (244 mg, 0.725 mmol, 23.0%).

$^1$H NMR (200 MHz, CDCl$_3$) δ: 1.30 (3H, t, J=7.3 Hz), 1.48 (3H, t, J=7.1 Hz), 3.56 (2H, dq, J=5.4, 7.3 Hz), 4.52 (2H, q, J=7.1 Hz), 4.89 (2H, s), 6.21 (1H, brt, J=5 Hz), 7.72 (2H, dt, J=8.8, 2.0 Hz), 8.02 (2H, dt, J=8.8, 2.2 Hz).

Elemental analysis for C$_{15}$H$_{17}$N$_4$O$_3$Cl·0.5Et$_2$O
Calcd. (%): C, 53.97; H, 5.45; N, 15.93.
Found (%): C, 53.96; H, 5.22; N, 15.95.

104b) 5-(chloromethyl)-1-{4-[(ethylamino)carbonyl]phenyl}-1H-1,2,3-triazole-4-carboxylic acid Ethyl 5-(chloromethyl)-1-{4-[(ethylamino)carbonyl]phenyl}-1H-1,2,3-triazole-4-carboxylate (140 mg, 0.416 mmol) obtained in 104a) was dissolved in ethanol (2.0 ml), 1N aqueous sodium hydroxide solution (2.0 ml) was added, and the mixture was stirred at room temperature for 40 min. To the reaction mixture was added 1N hydrochloric acid (2.2 ml), and the mixture was stirred for 30 min. The precipitate was collected by filtration, washed with water and dried to give the title compound as a white powder (103 mg, 0.334 mmol, 80.2%).

104c) 5-(chloromethyl)-N-cyclopropyl-1-{4-[(ethylamino)carbonyl]phenyl}-1H-1,2,3-triazole-4-carboxamide 5-(Chloromethyl)-1-{4-[(ethylamino)carbonyl]phenyl}-1H-1,2,3-triazole-4-carboxylic acid (103 mg, 0.334 mmol) obtained in Example 104b), HOBt (23 mg, 0.167 mmol, 0.5 eq.) and cyclopropylamine (0.031 ml, 0.434 mmol, 1.3 eq.) were dissolved in acetonitrile-DMF (2:1, 1.5 ml), WSC (78.4 mg, 0.401 mmol, 1.2 eq.) was added, and the mixture was stirred at room temperature for 2.5 hr. water (10 ml) was added to the reaction mixture and the mixture was extracted with ethyl acetate (30 ml). The organic layer was extracted with 2% aqueous sodium carbonate solution, washed with 10% aqueous ammonium chloride solution and saturated brine, dried over anhydrous sodium sulfate, and concentrated to give a white powder. This was subjected to column chromatography (elution solvent, ethyl acetate-hexane=2:3-3:2) on silica gel (manufactured by E. Merck, Art.7734, 10 g). The fraction obtained by elution with ethyl acetate-hexane (1:1-3:2) was concentrated, and diethyl ether was added to the residue. The precipitate was collected by filtration, washed with diethyl ether and dried to give the title compound as a white powder (76 mg, 0.219 mmol, 65.4%).

$^1$H NMR (200 MHz, CDCl$_3$) δ: 0.71 (2H, m), 0.91 (2H, m), 1.30 (3H, t, J=7.3 Hz), 2.95 (1H, octet, J=3.7 Hz), 3.56 (2H, dq, J=5.4, 7.3 Hz), 5.02 (2H, s), 6.19 (1H, brt, J=5 Hz), 7.34 (1H, m), 7.71 (2H, brd, J=8.6 Hz), 8.01 (2H, d, J=8.4 Hz).

Elemental analysis for C$_{16}$H$_{18}$N$_5$O$_2$Cl·0.1Et$_2$O
Calcd. (%): C, 55.45; H, 5.39; N, 19.72; Cl, 9.98.
Found (%): C, 55.37; H, 5.35; N, 19.77; Cl, 9.65.

Example 105

N-cyclopropyl-1-{4-[(ethylamino)carbonyl]phenyl}-5-phenyl-1H-1,2,3-triazole-4-carboxamide

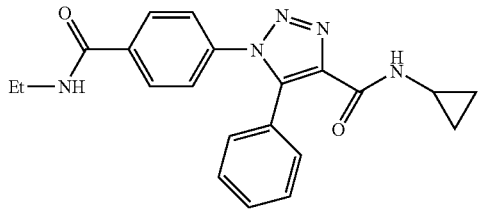

105a) 1-{4-[(ethylamino)carbonyl]phenyl}-5-phenyl-1H-1,2,3-triazole-4-carboxylic acid 4-Azido-N-ethylbenzamide (267 mg, 1.40 mmol) and ethyl benzoylacetate (0.316 ml, 1.75 mmol, 1.25 eq.) were dissolved in ethanol (8 ml), sodium ethoxide (122 mg, 1.75 mmol, 1.25 eq.) was added, and the mixture was stirred at room temperature for 30 min, and then at 60° C. for 13 hr. Water (20 ml) was added to the reaction mixture, ethanol was evaporated, and the residue was diluted with 2% aqueous sodium carbonate solution (20 ml) and washed with ethyl acetate-hexane (3:1, 40 ml). The organic layer was extracted with 2% aqueous sodium carbonate solution (20 ml). The aqueous layers were combined, acidified (pH<3) with 6N hydrochloric acid, and stood still at 0° C. The precipitate was collected by filtration, washed with water and dried to give the title compound as a pale-yellow powder (465 mg, 1.38 mmol, 98.8%).

$^1$H NMR (200 MHz, CDCl$_3$-DMSO-d$_6$=19:1) δ: 1.24 (3H, t, J=7.1 Hz), 3.46 (2H, br quintet, J=6.0 Hz), 7.26-7.41 (8H, m), 7.85 (2H, brd, J=8.4 Hz).

Elemental analysis for C$_{18}$H$_{22}$N$_4$O$_3$.0.15EtOAc.0.15hexane

Calcd. (%): C, 64.61; H, 5.37; N, 15.46.

Found (%): C, 64.60; H, 5.40; N, 15.41.

105b) N-cyclopropyl-1-{4-[(ethylamino)carbonyl]phenyl}-5-phenyl-1H-1,2,3-triazole-4-carboxamide 1-{4-[(Ethylamino)carbonyl]phenyl}-5-phenyl-1H-1,2,3-triazole-4-carboxylic acid (203 mg, 0.604 mmol) obtained in Example 105a), HOBt (41.2 mg, 0.302 mmol, 0.5 eq.) and cyclopropylamine (0.056 ml, 0.785 mmol, 1.3 eq.) were dissolved in acetonitrile-DMF (2:1, 3.0 ml), WSC (142 mg, 0.724 mmol, 1.2 eq.) was added, and the mixture was stirred at room temperature for 14 hr. Water (5 ml) was added to the reaction mixture and the mixture was stirred at 0° C. The precipitate was collected by filtration, washed with water and dried to give the title compound as a white powder (198 mg, 0.527 mmol, 87.3%).

$^1$H NMR (200 MHz, CDCl$_3$) δ: 0.67 (2H, m), 0.85 (2H, m), 1.25 (3H, t, J=7.3 Hz), 2.87 (1H, octet, J=3.6 Hz), 3.49 (2H, dq, J=5.6, 7.3 Hz), 6.12 (1H, brt, J=6 Hz), 7.31-7.43 (8H, m), 7.77 (2H, dt, J=8.4, 2.0 Hz).

Elemental analysis for C$_{21}$H$_{21}$N$_5$O$_2$

Calcd. (%): C, 67.18; H, 5.64; N, 18.65.

Found (%): C, 67.13; H, 5.66; N, 18.70.

Example 106

N-cyclopropyl-1-{4-[(ethylamino)carbonyl]phenyl}-5-[(E)-2-phenylvinyl]-1H-1,2,3-triazole-4-carboxamide

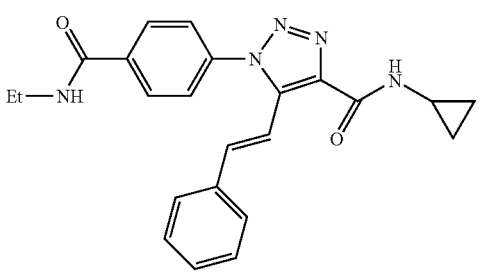

106a) ethyl cinnamoylacetate

To a solution of Meldrum's acid (2.55 g, 17.3 mmol, 1.1 eq.) in dichloromethane (15 ml) was added dropwise pyridine (3.23 ml, 39.9 mmol, 2.3 eq.) under ice-cooling, then a solution of cinnamoyl chloride (2.77 g, 15.8 mmol) in dichloromethane (10 ml) was added dropwise over 1.5 hr. The reaction mixture was allowed to warm to room temperature, and the mixture was stirred at room temperature for 16 hr. The reaction mixture was blended with 3N hydrochloric acid (40 ml). The aqueous layer was extracted twice with dichloromethane (35 ml). The organic layers were combined, dried over anhydrous sodium sulfate, and concentrated to give a dark brown oil.

This oil was dissolved in ethanol (60 ml), and the solution was stirred at 80° C. for 3 hr under a nitrogen atmosphere. The reaction mixture was diluted with toluene (80 ml) and concentrated to give a brown oil. This was subjected to column chromatography (elution solvent, hexane and ethyl acetate-hexane=2:98-5:95) on silica gel (manufactured by E. Merck, Art.7734, 25 g) to give the title compound as a colorless oil (purity 90%, 1.17 g, 4.82 mmol, 30.5%, keto-enol mixture).

106b) 1-{4-[(ethylamino)carbonyl]phenyl}-5-[(E)-2-phenylvinyl]-1H-1,2,3-triazole-4-carboxylic acid Ethyl cinnamoylacetate (1.17 g, 4.82 mmol, 1.2 eq.) obtained in Example 106a) and 4-azido-N-ethylbenzamide (0.750 g, 3.94 mmol) were dissolved in ethanol (25 ml), sodium ethoxide (373 mg, 4.93 mmol, 1.25 eq.) was added, and the mixture was stirred at room temperature for 30 min, and then at 60° C. for 10.5 hr. Water (20 ml) was added to the reaction mixture, ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, washed with ethyl acetate-hexane (2:1, 40 ml), acidified (pH<3) with 6N hydrochloric acid, and extracted with ethyl acetate (25 ml×3). The organic layers were combined, washed with saturated brine, dried over anhydrous sodium sulfate, and concentrated, and ethyl acetate was added. The precipitate was collected by filtration, washed with diethyl ether and dried to give the title compound as a pale-brown powder (627 mg, 1.73 mmol, 43.9%).

¹H NMR (200 MHz, CDCl₃-DMSO-d₆=19:1) δ: 1.28 (3H, t, J=7.1 Hz), 3.51 (2H, dq, J=5.4, 7.1 Hz), 7.21 (1H, d, J=16.6 Hz), 7.31 (1H, d, J=16.8 Hz), 7.30-7.36 (5H, m), 7.43 (1H, brt, J=6 Hz), 7.61 (2H, dt, J=8.8, 2.0 Hz), 8.08 (2H, brdt, J=8.6, 2.0 Hz).

Elemental analysis for $C_{20}H_{18}N_4O_3$
Calcd. (%): C, 66.29; H, 5.01; N, 15.46.
Found (%): C, 66.00; H, 4.84; N, 15.29.

106c) N-cyclopropyl-1-{4-[(ethylamino)carbonyl]phenyl}-5-[(E)-2-phenylvinyl]-1H-1,2,3-triazole-4-carboxamide 1-{4-[(Ethylamino)carbonyl]phenyl}-5-[(E)-2-phenylvinyl]-1H-1,2,3-triazole-4-carboxylic acid (264 mg, 0.728 mmol) obtained in Example 106b), HOBt (49.7 mg, 0.364 mmol, 0.5 eq.) and cyclopropylamine (0.068 ml, 0.947 mmol, 1.3 eq.) were dissolved in acetonitrile-DMF (3:1, 4 ml), WSC (171 mg, 0.874 mmol, 1.2 eq.) was added, and the mixture was stirred at room temperature for 13 hr. Water (10 ml) was added to the reaction mixture and the mixture was stirred. The precipitate was collected by filtration, washed with water and dried to give the title compound as a white powder (258 mg, 0.643 mmol, 88.3%).

¹H NMR (200 MHz, CDCl₃) δ: 0.71 (2H, m), 0.92 (2H, m), 1.31 (3H, t, J=7.2 Hz), 2.94 (1H, octet, J=3.4 Hz), 3.56 (2H, dq, J=5.6, 7.3 Hz), 6.17 (1H, br), 7.31 (3H, m), 7.39 (2H, m), 7.51 (1H, brd, J=3 Hz), 7.62 (2H, dt, J=8.8, 2.0 Hz), 7.73 (1H, d, J=16.6 Hz), 7.99 (2H, dt, J=8.8, 2.0 Hz).

Elemental analysis for $C_{23}H_{23}N_5O_2$
Calcd. (%): C, 68.81; H, 5.77; N, 17.44.
Found (%): C, 68.75; H, 5.76; N, 17.41.

Example 107

5-[2-(benzyloxy)ethyl]-N-cyclopropyl-1-{4-[(ethylamino)carbonyl]phenyl}-1H-1,2,3-triazole-4-carboxamide

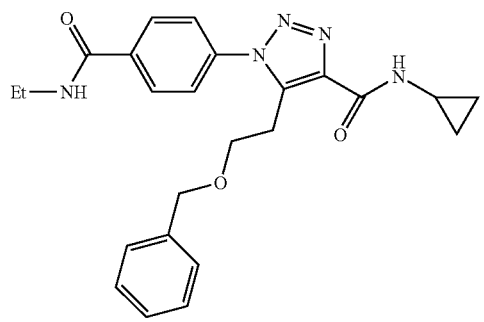

107a) ethyl 5-benzyloxy-3-oxovalerate

To a solution of oxalyl chloride (0.934 ml, 10.3 mmol, 1.1 eq.) in dichloromethane (5 ml) was added dropwise DMF (0.073 ml, 0.940 mmol, 0.1 eq.) under ice-cooling, then a solution of 3-benzyloxypropionic acid (purity 70%, 2.42 g, 9.40 mmol) in dichloromethane (5 ml) was added dropwise over 50 min. The reaction mixture was allowed to warm to room temperature, and the mixture was stirred at room temperature for 1.5 hr. On the other hand, to a solution of Meldrum's acid (1.52 g, 10.3 mmol, 1.1 eq.) in dichloromethane (10 ml) was added dropwise pyridine (3.04 ml, 37.6 mmol, 4.0 eq.) under ice-cooling, and then the reaction mixture obtained above was added dropwise over 1.5 hr. The reaction mixture was allowed to warm to room temperature, and the mixture was stirred at room temperature for 17 hr. The reaction mixture was blended with 3N hydrochloric acid (40 ml). The aqueous layer was extracted twice with dichloromethane (35 ml). The organic layers were combined, dried over anhydrous sodium sulfate, and concentrated to give a brown oil.

This oil was dissolved in ethanol (60 ml), and the solution was stirred at 80° C. for 2.5 hr under a nitrogen atmosphere. The reaction mixture was concentrated, diluted with toluene (60 ml) and concentrated again to give a brown oil, which was subjected to column chromatography (elution solvent, hexane and ethyl acetate-hexane=2:98-10:90) on silica gel (manufactured by E. Merck, Art.7734, 20 g). The fraction obtained by elution with ethyl acetate-hexane (5:95-10:90) was concentrated to give the title compound as a colorless oil (purity 85%, 1.35 g, 4.57 mmol, 48.7%, including residual solvent).

¹H NMR (200 MHz, CDCl₃) δ: 1.27 (3H, t, J=7.1 Hz), 2.83 (2H, t, J=6.0 Hz), 3.49 (2H, s), 3.76 (2H, t, J=6.3 Hz), 4.19 (2H, q, J=7.1 Hz), 4.51 (2H, s), 7.27-7.39 (5H, m).

107b) 5-[2-(benzyloxy)ethyl]-1-{4-[(ethylamino)carbonyl]phenyl}-1H-1,2,3-triazole-4-carboxylic acid Ethyl 5-benzyloxy-3-oxovalerate (purity 85%, 1.34 g, 4.55 mmol, 1.27 eq.) obtained in Example 107a) and 4-azido-N-ethylbenzamide (0.680 g, 3.58 mmol) were dissolved in ethanol (20 ml), sodium ethoxide (351 mg, 4.65 mmol, 1.3 eq.) was added, and the mixture was stirred at room temperature for 10 min, and then at 60° C. for 3 hr. 1N Aqueous sodium hydroxide solution (3.58 ml, 1.0 eq.) was added to the reaction mixture and the mixture was further stirred for 1 hr. Ethanol was evaporated from the reaction mixture, and the residue was diluted with 2% aqueous sodium carbonate solution (30 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid, and extracted with ethyl acetate (30 ml×2). The organic layers were combined, washed with saturated brine, dried over anhydrous sodium sulfate, and concentrated, and diethyl ether and ethyl acetate were added. The precipitate was collected by filtration, washed with ethyl acetate-diethyl ether and diethyl ether and dried to give the title compound as a pale-brown powder (purity 80%, 1.13 g, 2.29 mmol, 64.0%).

¹H NMR (200 MHz, CDCl₃-DMSO-d₆=19:1) δ: 1.28 (3H, t, J=7.3 Hz), 1.32-1.56 (6H, m), 1.91 (1H, m), 3.09 (2H, d, J=7.8 Hz), 3.51 (2H, dq, J=5.4, 7.1 Hz), 7.41 (1H, m), 7.51 (2H, d, J=8.4 Hz), 8.07 (2H, d, J=8.4 Hz).

107c) 5-[2-(benzyloxy)ethyl]-N-cyclopropyl-1-{4-[(ethylamino)carbonyl]phenyl}-1H-1,2,3-triazole-4-carboxamide 5-[2-(Benzyloxy)ethyl]-1-{4-[(ethylamino)carbonyl]phenyl}-1H-1,2,3-triazole-4-carboxylic acid (375 mg, 0.951 mmol) obtained in Example 107b), HOBt (64.9 mg, 0.475 mmol, 0.5 eq.) and cyclopropylamine (0.088 ml, 1.24 mmol, 1.3 eq.) were dissolved in acetonitrile-DMF (2:1, 4.5 ml), WSC (223 mg, 1.14 mmol, 1.2 eq.) was added, and the mixture was stirred at room temperature for 3 hr. The reaction mixture was diluted with ethyl acetate-hexane (4:1, 50 ml), washed twice with 2% aqueous sodium carbonate solution and with 10% aqueous sodium chloride solution and saturated brine, dried over anhydrous sodium sulfate, and concentrated. The residue was subjected to column chromatography (elution solvent, ethyl acetate-hexane=1:2-3:2) on silica gel (manufactured by E. Merck, Art.7734, 10 g). The fraction obtained by elution with ethyl acetate-hexane (1:1-3:2) was concentrated, and diethyl ether was added. The precipitate was collected by filtration, washed with diethyl ether and dried to give the title compound as a white powder (262 mg, 0.604 mmol, 79.4%).

$^1$H NMR (200 MHz, CDCl$_3$) δ: 0.67 (2H, m), 0.88 (2H, m), 1.29 (3H, t, J=7.3 Hz), 2.88 (1H, octet, J=3.5 Hz), 3.26 (2H, t, J=5.7 Hz), 3.54 (2H, dq, J=5.6, 7.3 Hz), 3.88 (2H, t, J=5.7 Hz), 4.38 (2H, s), 6.13 (1H, brt, J=6 Hz), 7.12 (2H, m), 7.28 (3H, m), 7.34 (1H, m), 7.63 (2H, dt, J=8.8, 2.0 Hz), 7.84 (2H, dt, J=8.8, 2.0 Hz).

Elemental analysis for C$_{24}$H$_{27}$N$_5$O$_3$
Calcd. (%): C, 66.49; H, 6.28; N, 16.16.
Found (%): C, 66.19; H, 6.30; N, 16.33.

Example 108

N-cyclopropyl-1-{4-[(ethylamino)carbonyl]phenyl}-5-(4-fluorobutyl)-1H-1,2,3-triazole-4-carboxamide

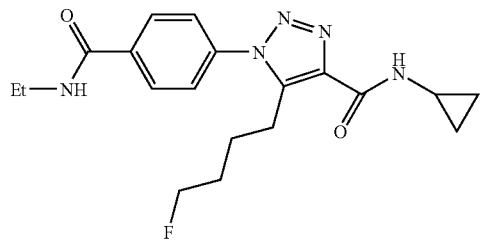

108a) ethyl 7-fluoro-3-oxoheptanoate

To a solution of oxalyl chloride (1.66 ml, 18.4 mmol, 1.2 eq.) in dichloromethane (7 ml) was added dropwise DMF (0.118 ml, 1.53 mmol, 0.1 eq.) under ice-cooling, then a solution of 5-fluorovaleric acid (4.40 g, 15.3 mmol) in dichloromethane (7 ml) was added dropwise over 100 min. The reaction mixture was allowed to warm to room temperature, and the mixture was stirred at room temperature for 1 hr. On the other hand, to a solution of Meldrum's acid (1.52 g, 10.3 mmol, 1.1 eq.) in dichloromethane (15 ml) was added dropwise pyridine (4.95 ml, 61.2 mmol, 4.0 eq.) under ice-cooling, and then the reaction mixture obtained above was added dropwise over 2 hr. The reaction mixture was allowed to warm to room temperature, and the mixture was stirred at room temperature for 17 hr. The reaction mixture was blended with 3N hydrochloric acid (40 ml). The aqueous layer was extracted twice with dichloromethane (35 ml). The organic layers were combined, dried over anhydrous sodium sulfate, and concentrated to give a purple-brown oil.

This oil was dissolved in ethanol (60 ml), and the solution was stirred at 80° C. for 2.5 hr under a nitrogen atmosphere. The reaction mixture was concentrated, diluted with toluene (100 ml) and concentrated again to give a brown oil, which was subjected to column chromatography (elution solvent, hexane and ethyl acetate-hexane=2:98-10:90) on silica gel (manufactured by E. Merck, Art.7734, 25 g). The fraction obtained by elution with ethyl acetate-hexane (5:95-10:90) was concentrated to give the title compound as a pale-yellow oil (0.924 g, 4.86 mmol, 31.8%).

$^1$H NMR (200 MHz, CDCl$_3$) δ: 1.28 (3H, t, J=7.1 Hz), 1.69 (2H, m), 1.75 (2H, m), 2.62 (2H, t, J=6.7 Hz), 3.44 (2H, s), 4.20 (2H, q, J=7.1 Hz), 4.44 (2H, dt, J=47.4, 5.7 Hz).

108b) 1-{4-[(ethylamino)carbonyl]phenyl}-5-(4-fluorobutyl)-1H-1,2,3-triazole-4-carboxylic acid Ethyl 7-fluoro-3-oxoheptanoate (0.920 g, 4.84 mmol, 1.17 eq.) obtained in Example 108a) and 4-azido-N-ethylbenzamide (0.790 g, 4.15 mmol) were dissolved in ethanol (25 ml), sodium ethoxide (366 mg, 4.84 mmol, 1.17 eq.) was added, and the mixture was stirred at room temperature for 30 min, and then at 60° C. for 11 hr. 1N Aqueous sodium hydroxide solution (4.15 ml, 1.0 eq.) was added to the reaction mixture and the mixture was further stirred for 1 hr. Water (20 ml) was added to the reaction mixture, ethanol was evaporated, and washed with ethyl acetate-hexane (1:1, 50 ml). The organic layer was extracted with 2% aqueous sodium carbonate solution (20 ml). The aqueous layers were combined, and acidified (pH<3) with 6N hydrochloric acid. The precipitate was collected by filtration, washed with water and dried to give the title compound as a pale-gray powder (1.26 g, 3.77 mmol, 90.8%).

$^1$H NMR (200 MHz, CDCl$_3$-DMSO-d$_6$=19:1) δ: 1.28 (3H, t, J=7.3 Hz), 1.59 (2H, m), 1.67 (2H, m), 3.06 (2H, brt, J=7.3 Hz), 3.52 (2H, dq, J=5.6, 7.3 Hz), 4.35 (2H, dt, J=47.8, 5.7 Hz), 7.29 (1H, m), 7.52 (2H, dt, J=8.8, 2.0 Hz), 8.07 (2H, dt, J=8.4, 2.0 Hz).

Elemental analysis for C$_{16}$H$_{19}$N$_4$O$_3$F
Calcd. (%): C, 57.48; H, 5.73; N, 16.76; F, 5.68.
Found (%): C, 57.40; H, 5.69; N, 16.80; F, 5.51.

108c) N-cyclopropyl-1-{4-[(ethylamino)carbonyl]phenyl}-5-(4-fluorobutyl)-1H-1,2,3-triazole-4-carboxamide 1-{4-[(Ethylamino)carbonyl]phenyl}-5-(4-fluorobutyl)-1H-1,2,3-triazole-4-carboxylic acid (375 mg, 1.12 mmol) obtained in Example 108b), HOBt (76.5 mg, 0.561 mmol, 0.5 eq.) and cyclopropylamine (0.104 ml, 1.46 mmol, 1.3 eq.) were dissolved in acetonitrile-DMF (2:1, 4.5 ml), WSC (263 mg, 1.35 mmol, 1.2 eq.) was added, and the mixture was stirred at room temperature for 4 hr. The reaction mixture was diluted with 2% aqueous sodium carbonate solution (5 ml) and water (10 ml), and the mixture was stirred at room temperature. The precipitate was collected by filtration, washed with water and dried to give the title compound as a white powder (369 mg, 0.988 mmol, 88.2%).

$^1$H NMR (200 MHz, CDCl$_3$) δ: 0.68 (2H, m), 0.89 (2H, m), 1.30 (3H, t, J=7.3 Hz), 1.60-1.76 (4H, m), 2.90 (1H, octet, J=3.7 Hz), 3.09 (2H, brt, J=7.7 Hz), 3.55 (2H, dq, J=5.4, 7.3 Hz), 4.37 (2H, dt, J=47.8, 5.5 Hz), 6.18 (1H, brt, J=5 Hz), 7.35 (1H, brd, J=3 Hz), 7.52 (2H, dt, J=8.8, 2.0 Hz), 7.98 (2H, dt, J=8.8, 2.0 Hz).

Elemental analysis for C$_{19}$H$_{24}$N$_5$O$_2$F
Calcd. (%): C, 61.11; H, 6.48; N, 18.75; F, 5.09.
Found (%): C, 61.04; H, 6.44; N, 18.78; F, 5.10.

Example 109

N-cyclopropyl-1-{4-[(ethylamino)carbonyl]phenyl}-5-(3-fluoropropyl)-1H-1,2,3-triazole-4-carboxamide

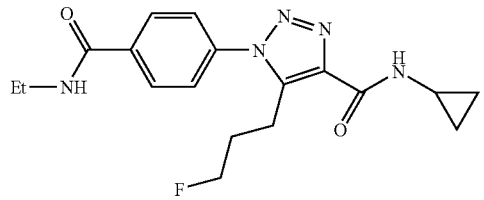

To a solution of N-cyclopropyl-1-{4-[(ethylamino)carbonyl]phenyl}-5-(3-hydroxypropyl)-1H-1,2,3-triazole-4-carboxamide (0.40 g) obtained in Example 113 in dichloromethane (4.5 ml) was added diethylaminosulfur trifluoride (0.18 ml) at −78° C. The reaction mixture was stirred for 5 hr while gradually heating to room temperature. Saturated aqueous sodium hydrogen carbonate solution was added to the reaction mixture, and the mixture was extracted with ethyl acetate. The organic layer was washed with saturated brine, and dried over anhydrous magnesium sulfate, and the solvent was evaporated. The residue was purified by silica gel column (hexane/ethyl acetate=6/4 to ethyl acetate). The resultant product was recrystallized from ethyl acetate/hexane to give the title compound as a colorless powder (0.024 g, 6%).

NMR (CDCl$_3$) δ: 0.65-0.71 (2H, m), 0.86-0.93 (2H, m), 1.30 (3H, t, J=6.9), 1.97-2.04 (1H, m), 2.06-2.15 (1H, m), 2.85-2.94 (1H, m), 3.17 (2H, t, J=7.8), 3.55 (2H, qd, J=6.9, 1.5), 4.34 (1H, t, J=5.7), 4.50 (1H, t, J=5.7), 6.18 (1H, br), 7.35 (1H, br), 7.53 (2H, d, J=8.7), 7.98 (2H, d, J=8.7).

Elemental analysis for $C_{18}H_{22}FN_5O_2$

Calcd. (%): C, 60.15; H, 6.17; N, 19.49.

Found (%): C, 60.16; H, 6.14; N, 19.39.

Example 110

N-cyclopropyl-1-{4-[(ethylamino)carbonyl]phenyl}-5-(fluoromethyl)-1H-1,2,3-triazole-4-carboxamide

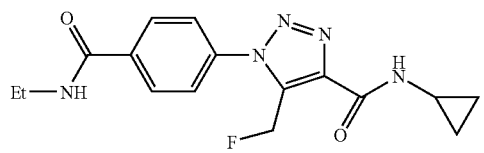

In the same manner as in Example 109, the title compound was obtained as a colorless powder (0.58 g, 29%) from N-cyclopropyl-1-{4-[(ethylamino)carbonyl]phenyl}-5-(hydroxymethyl)-1H-1,2,3-triazole-4-carboxamide (0.20 g) obtained in Example 112.

NMR (CDCl$_3$) δ: 0.68-0.73 (2H, m), 0.88-0.95 (2H, m), 1.30 (3H, t, J=7.2), 2.90-2.98 (1H, m), 3.55 (2H, qd, J=7.2, 1.8), 5.75 (1H, s), 5.90 (1H, s), 6.16 (1H, br), 7.38 (1H, br), 7.71 (2H, d, J=9.0), 7.99 (2H, d, J=9.0).

Elemental analysis for $C_{16}H_{18}FN_5O_2$

Calcd. (%): C, 58.00; H, 5.48; N, 21.14.

Found (%): C, 57.98; H, 5.48; N, 21.26.

Example 111

N-cyclopropyl-1-{4-[(ethylamino)carbonyl]phenyl}-5-(5-fluoropentyl)-1H-1,2,3-triazole-4-carboxamide

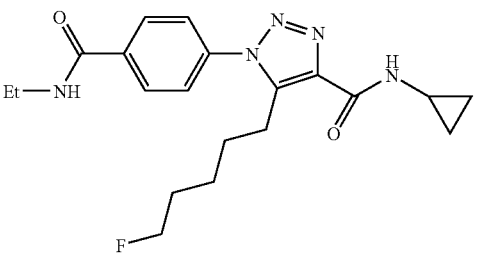

111a) ethyl 8-fluoro-3-oxooctanoate

To a solution of oxalyl chloride (5.24 ml, 58.1 mmol, 1.15 eq.) in dichloromethane (20 ml) was added dropwise DMF (0.390 ml, 5.05 mmol, 0.1 eq.) under ice-cooling, then a solution of 6-fluorohexanoic acid (purity 90%, 7.53 g, 50.5 mmol) in dichloromethane (15 ml) was added dropwise over 50 min. The reaction mixture was allowed to warm to room temperature, and the mixture was stirred at room temperature for 1 hr. On the other hand, to a solution of Meldrum's acid (8.91 g, 60.6 mmol, 1.2 eq.) in dichloromethane (40 ml) was added dropwise pyridine (16.3 ml, 0.202 mol, 4.0 eq.) under ice-cooling, and then the reaction mixture obtained above was added dropwise over 1.5 hr. The reaction mixture was allowed to warm to room temperature, and the mixture was stirred at room temperature for 11 hr. The reaction mixture was blended with 6N hydrochloric acid (60 ml). The aqueous layer was extracted twice with dichloromethane (50 ml). The organic layers were combined, dried over anhydrous sodium sulfate, and concentrated to give a dark purple oil.

This oil was dissolved in ethanol (100 ml), and the solution was stirred at 80° C. for 3 hr under a nitrogen atmosphere. The reaction mixture was concentrated, diluted with toluene and concentrated again to give a brown oil, which was subjected to column chromatography (elution solvent, hexane and ethyl acetate-hexane=2:98-10:90) on silica gel (manufactured by E. Merck, Art.7734, 50 g). The fraction obtained by elution with ethyl acetate-hexane (2:98-10:90) was concentrated to give the title compound as a pale-brown oil (purity 94%, 7.73 g, 35.5 mmol, 70.3%).

$^1$H NMR (200 MHz, CDCl$_3$) δ: 1.28 (3H, t, J=7.1 Hz), 1.43 (2H, m), 1.63 (2H, m), 1.73 (2H, m), 2.57 (2H, t, J=7.2 Hz), 3.44 (2H, s), 4.20 (2H, q, J=7.1 Hz), 4.44 (2H, dt, J=47.4, 6.0 Hz).

111b) 1-{4-[(ethylamino)carbonyl]phenyl}-5-(5-fluoropentyl)-1H-1,2,3-triazole-4-carboxylic acid Ethyl 8-fluoro-3-oxooctanoate (purity 94%, 1.19 g, 5.47 mmol, 1.3 eq.) obtained in Example 111a) and 4-azido-N-ethylbenzamide (0.800 g, 4.21 mmol) were dissolved in ethanol (25 ml), sodium ethoxide (413 mg, 5.47 mmol, 1.3 eq.) was added and the mixture was stirred at room temperature for 20 min, and then at 60° C. for 10.5 hr. The reaction mixture was concentrated, diluted with water (20 ml), and washed with ethyl acetate-hexane (1:1, 50 ml). The organic layer was extracted with 2% aqueous sodium carbonate solution (20 ml). The aqueous layers were combined, acidified (pH<3) with 6N hydrochloric acid, and extracted with ethyl acetate (35 ml×2). The organic layer was washed with saturated brine, dried over anhydrous sodium sulfate, and concentrated, and to the residue were added ethyl acetate and diethyl ether. The precipitate was collected by filtration, washed with ethyl acetate-diethyl ether and dried to give the title compound as a pale-brown powder (1.40 g, 4.02 mmol, 95.5%).

$^1$H NMR (200 MHz, CDCl$_3$-DMSO-d$_6$=19:1) δ: 1.28 (3H, t, J=7.3 Hz), 1.33 (2H, m), 1.47-1.70 (4H, m), 3.02 (2H, brt, J=7.7 Hz), 3.51 (2H, brdq, J=5.6, 7.3 Hz), 4.35 (2H, dt, J=47.4, 6.0 Hz), 7.52 (1H, m), 7.52 (2H, d, J=8.4 Hz), 8.08 (2H, d, J=8.6 Hz).

Elemental analysis for C$_{17}$H$_{21}$N$_4$O$_3$F
Calcd. (%): C, 58.61; H, 6.08; N, 16.08.
Found (%): C, 58.47; H, 6.02; N, 16.07.

111c) N-cyclopropyl-1-{4-[(ethylamino)carbonyl]phenyl}-5-(5-fluoropentyl)-1H-1,2,3-triazole-4-carboxamide 1-{4-[(Ethylamino)carbonyl]phenyl}-5-(5-fluoropentyl)-1H-1,2,3-triazole-4-carboxylic acid (353 mg, 1.01 mmol) obtained in Example 111b), HOBt (55.3 mg, 0.405 mmol, 0.4 eq.) and cyclopropylamine (0.094 ml, 1.32 mmol, 1.3 eq.) were dissolved in acetonitrile-DMF (2:1, 4.5 ml), WSC (218 mg, 1.11 mmol, 1.1 eq.) was added, and the mixture was stirred at room temperature for 12.5 hr. The reaction mixture was diluted with 2% aqueous sodium carbonate solution (20 ml), and the mixture was stirred at room temperature. The precipitate was collected by filtration, washed with water and dried to give a white powder. This was crystallized from ethyl acetate-diethyl ether, and the precipitate was collected by filtration, washed with diethyl ether and dried to give the title compound as a white powder (333 mg, 0.859 mmol, 85.1%).

$^1$H NMR (200 MHz, CDCl$_3$) δ: 0.68 (2H, m), 0.89 (2H, m), 1.30 (3H, t, J=7.3 Hz), 1.37 (2H, m), 1.48-1.75 (4H, m), 2.90 (1H, octet, J=3.6 Hz), 3.06 (2H, brt, J=7.7 Hz), 3.55 (2H, dq, J=5.6, 7.3 Hz), 4.36 (2H, dt, J=47.2, 5.8 Hz), 6.25 (1H, brt, J=6 Hz), 7.34 (1H, brd, J=3 Hz), 7.50 (2H, dt, J=8.8, 2.0 Hz), 7.98 (2H, dt, J=8.4, 1.8 Hz).

Elemental analysis for C$_{20}$H$_{26}$N$_5$O$_2$F
Calcd. (%): C, 62.00; H, 6.76; N, 18.08; F, 4.90.
Found (%): C, 61.89; H, 6.76; N, 18.05; F, 4.99.
melting point: 150.3° C.

Example 112

N-cyclopropyl-1-{4-[(ethylamino)carbonyl]phenyl}-5-(hydroxymethyl)-1H-1,2,3-triazole-4-carboxamide

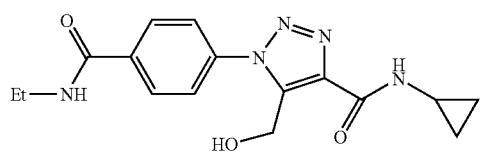

To a solution of 5-[(benzyloxy)methyl]-N-cyclopropyl-1-{4-[(ethylamino)carbonyl]phenyl}-1H-1,2,3-triazole-4-carboxamide (4.29 g) obtained in Example 94 in DMF (60 ml)-methanol (180 ml) was added palladium-carbon (1.0 g). The reaction mixture was stirred under a hydrogen atmosphere at room temperature for 5 days, and the insoluble material was filtered off. The solvent was evaporated, and the residue was purified by silica gel column (hexane/ethyl acetate=1/1 to ethyl acetate/methanol=4/1). The resultant product was recrystallized from ethyl acetate/hexane to give the title compound as a colorless powder (2.56 g, 76%).

NMR (CDCl$_3$) δ: 0.70-0.75 (2H, m), 0.90-0.97 (2H, m), 1.80 (3H, t, J=7.2), 2.91-2.99 (1H, m), 3.55 (2H, qd, J=7.2, 1.5), 4.82 (2H, d, J=6.8), 5.69 (1H, t, J=6.8), 6.20 (1H, br), 7.49-7.50 (1H, br), 7.54 (2H, d, J=8.7), 7.98 (2H, d, J=8.7).

Elemental analysis for C$_{16}$H$_{19}$N$_5$O$_3$
Calcd. (%): C, 58.35; H, 5.81; N, 21.26.
Found (%): C, 58.43; H, 5.80; N, 21.24.

Example 113

N-cyclopropyl-1-{4-[(ethylamino)carbonyl]phenyl}-5-(3-hydroxypropyl)-1H-1,2,3-triazole-4-carboxamide

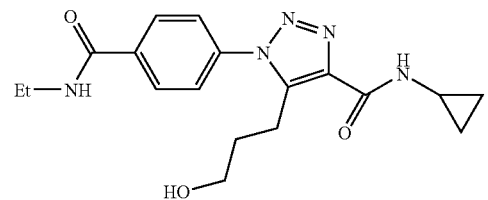

In the same manner as in Example 112, the title compound was obtained as colorless needle crystals (3.42 g, 63%) from 5-[3-(benzyloxy)propyl]-N-cyclopropyl-1-{4-[(ethylamino)carbonyl]phenyl}-1H-1,2,3-triazole-4-carboxamide (6.83 g) obtained in Example 91.

NMR (CDCl$_3$) δ: 0.66-0.72 (2H, m), 0.87-0.94 (2H, m), 1.29 (3H, t, J=7.4), 1.62-1.70 (2H, m), 2.91-2.98 (1H, m), 3.20 (2H, t, J=6.8), 3.45-3.52 (2H, m), 3.55 (2H, qd, J=7.4, 1.7), 3.72 (1H, t, J=6.6), 6.24 (1H, br), 7.44 (1H, d, J=2.8), 7.52 (2H, d, J=8.7), 7.98 (2H, d, J=8.7).

Elemental analysis for C$_{18}$H$_{23}$N$_5$O$_3$
Calcd. (%): C, 60.49; H, 6.49; N, 19.59.
Found (%): C, 60.49; H, 6.37; N, 19.60.

Example 114

N-cyclopropyl-1-{4-[(ethylamino)carbonyl]phenyl}-5-(2-hydroxyethyl)-1H-1,2,3-triazole-4-carboxamide

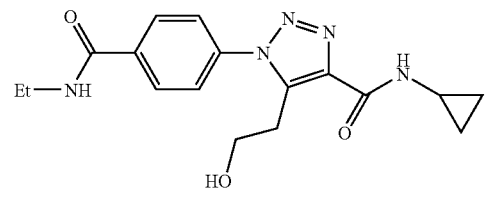

5-[2-(Benzyloxy)ethyl]-N-cyclopropyl-1-{4-[(ethylamino)carbonyl]phenyl}-1H-1,2,3-triazole-4-carboxamide (737 mg, 1.70 mmol) obtained in Example 107 was dissolved in methanol-acetic acid (25:1, 26 ml), and the mixture was stirred at room temperature for 63 hr in the presence of 10% palladium carbon (wet, purity 50%, 150 mg) under a hydrogen atmosphere. The reaction mixture was filtered to remove the catalyst, the filtrate was concentrated to dryness, and ethyl acetate-diethyl ether was added. The precipitate was collected by filtration, washed with diethyl ether and dried to give the title compound as a white powder (480 mg, 1.40 mmol, 82.2%).

$^1$H NMR (200 MHz, CDCl$_3$) δ: 0.70 (2H, m), 0.90 (2H, m), 1.29 (3H, t, J=7.3 Hz), 2.92 (1H, octet, J=3.7 Hz), 3.22 (2H, t, J=5.9 Hz), 3.54 (2H, dq, J=5.8, 7.2 Hz), 3.91 (2H, t, J=5.9 Hz), 6.23 (1H, brt, J=6 Hz), 7.44 (1H, brd, J=3 Hz), 7.57 (2H, dt, J=8.8, 2.0 Hz), 7.96 (2H, dt, J=8.4, 2.0 Hz).

Elemental analysis for C$_{17}$H$_{21}$N$_5$O$_3$·0.2H$_2$O
Calcd. (%): C, 58.84; H, 6.22; N, 20.18.
Found (%): C, 58.96; H, 6.25; N, 19.99.
melting point: 156° C.

Example 115

N-cyclopropyl-1-{4-[(ethylamino)carbonyl]phenyl}-5-vinyl-1H-1,2,3-triazole-4-carboxamide

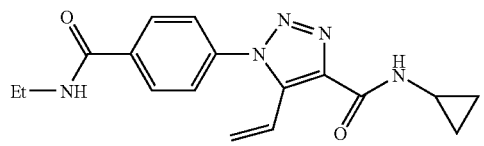

N-Cyclopropyl-1-{4-[(ethylamino)carbonyl]phenyl}-5-(2-hydroxyethyl)-1H-1,2,3-triazole-4-carboxamide (124 mg, 0.361 mmol) obtained in Example 114 was dissolved in THF (2.5 ml), tributylphosphine (102 mg, 0.469 mmol, 1.3 eq.) and ADDP (120 mg, 0.469 mmol, 1.3 eq.) were added, and the mixture was stirred at room temperature for 1.5 hr. The reaction mixture was diluted with ethyl acetate (30 ml), washed with 2% aqueous sodium carbonate solution, 10% aqueous sodium chloride solution and saturated brine, dried over anhydrous sodium sulfate, and concentrated. The residue was subjected to column chromatography (elution solvent, ethyl acetate-hexane=1:1-2:1) on silica gel (manufactured by E. Merck, Art.7734, 10 g). The fraction obtained by elution with ethyl acetate-hexane (3:2-2:1) was concentrated, and diethyl ether was added. The precipitate was collected by filtration, washed with diethyl ether and dried to give the title compound as a white powder (101 mg, 0.310 mmol, 86.0%).

$^1$H NMR (200 MHz, CDCl$_3$) δ: 0.69 (2H, m), 0.90 (2H, m), 1.29 (3H, t, J=7.1 Hz), 2.92 (1H, octet, J=3.5 Hz), 3.55 (2H, dq, J=5.4, 7.3 Hz), 5.70 (1H, dd, J=12.0, 1.0 Hz), 6.13 (1H, dd, J=17.8, 1.0 Hz), 6.25 (1H, brt, J=6 Hz), 6.90 (1H, dd, J=18.0, 1.2 Hz), 7.44 (1H, br), 7.55 (2H, dt, J=8.4, 2.0 Hz), 7.97 (2H, dt, J=8.4, 2.0 Hz).

Elemental analysis for C$_{17}$H$_{19}$N$_5$O$_2$
Calcd. (%): C, 62.75; H, 5.89; N, 21.52.
Found (%): C, 62.54; H, 5.84; N, 21.39.
melting point: 162° C.

Example 116

5-[(4-bromophenoxy)methyl]-N-cyclopropyl-1-{4-[(ethylamino)carbonyl]phenyl}-1H-1,2,3-triazole-4-carboxamide

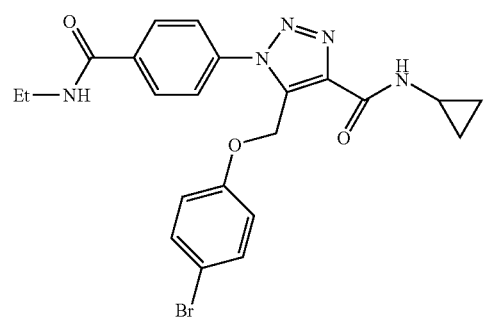

To a suspension of N-cyclopropyl-1-{4-[(ethylamino)carbonyl]phenyl}-5-(hydroxymethyl)-1H-1,2,3-triazole-4-carboxamide (0.10 g) obtained in Example 112 in THF (3 ml)—toluene (3 ml) were added 4-bromophenol (0.053 g), tributylphosphine (0.15 ml) and ADDP (0.15 g). The reaction mixture was stirred at room temperature for 15 min, the insoluble material was filtered off, and the solvent was evaporated. The residue was purified by silica gel column (hexane/ethyl acetate=1/2 to ethyl acetate). The resultant product was recrystallized from ethyl acetate/hexane to give the title compound as a colorless powder (0.14 g, 95%).

NMR (CDCl$_3$) δ: 0.67-0.72 (2H, m), 0.86-0.91 (2H, m), 1.28 (3H, t, J=7.4), 2.88-2.96 (1H, m), 3.54 (2H, qd, J=7.4, 1.7), 5.51 (2H, s), 6.18 (1H, t, J=5.8), 6.79 (2H, d, J=8.9), 7.36 (2H, d, J=8.9), 7.41 (1H, br), 7.68 (2H, d, J=8.5), 7.94 (2H, d, J=8.5).

Elemental analysis for C$_{22}$H$_{22}$BrN$_5$O$_3$
Calcd. (%): C, 54.56; H, 4.58; N, 14.46.
Found (%): C, 54.65; H, 4.59; N, 14.45.

Example 117

N-cyclopropyl-1-{4-[(ethylamino)carbonyl]phenyl}-5-{[4-(trifluoromethyl)phenoxy]methyl}-1H-1,2,3-triazole-4-carboxamide

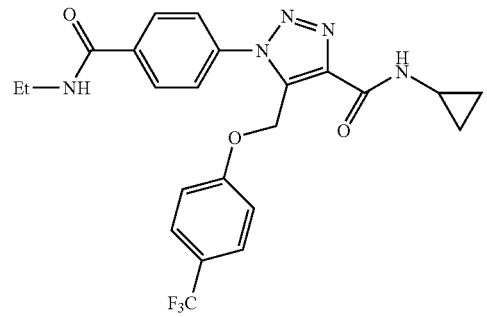

In the same manner as in Example 116, the title compound was obtained as colorless needle crystals (0.11 g, 76%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.68-0.75 (2H, m), 0.86-0.92 (2H, m), 1.28 (3H, t, J=7.5), 2.90-2.96 (1H, m), 3.53 (2H, qd, J=7.5, 1.7), 5.59 (2H, s), 6.19 (1H, br), 6.99 (2H, d, J=8.7), 7.43 (1H, br), 7.53 (2H, d, J=8.7), 7.68 (2H, d, J=8.5), 7.95 (2H, d, J=8.5).

Elemental analysis for C$_{23}$H$_{22}$F$_3$N$_5$O$_3$
Calcd. (%): C, 58.35; H, 4.68; N, 14.79.
Found (%): C, 58.39; H, 4.89; N, 14.65.

Example 118

5-{[(6-chloropyridin-2-yl)oxy]methyl}-N-cyclopropyl-1-{4-[(ethylamino)carbonyl]phenyl}-1H-1,2,3-triazole-4-carboxamide

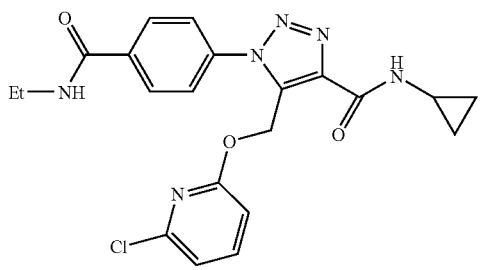

In the same manner as in Example 116, the title compound was obtained as a colorless powder (0.13 g, 97%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.67-0.72 (2H, m), 0.85-0.92 (2H, m), 1.27 (3H, t, J=7.2), 2.88-2.96 (1H, m), 3.51 (2H, qd, J=7.2, 1.5), 5.75 (2H, s), 6.20 (1H, br), 6.59 (1H, d, J=7.9), 6.93 (1H, d, J=7.9), 7.88 (1H, br), 7.51 (1H, t, J=7.9), 7.64 (2H, d, J=8.5), 7.89 (2H, d, J=8.5).

Elemental analysis for C$_{21}$H$_{21}$ClN$_6$O$_3$
Calcd. (%): C, 57.21; H, 4.80; N, 19.06.
Found (%): C, 57.24; H, 4.76; N, 19.36.

Example 119

N-cyclopropyl-1-{4-[(ethylamino)carbonyl]phenyl}-5-{[4-(1H-imidazol-1-yl)phenoxy]methyl}-1H-1,2,3-triazole-4-carboxamide

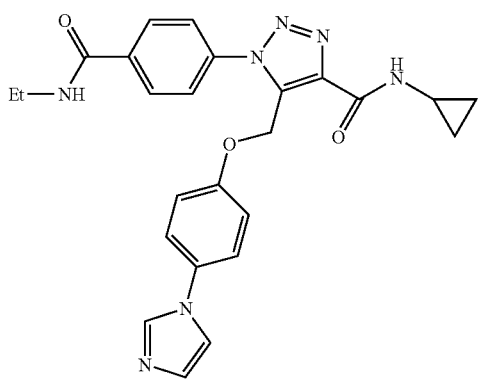

In the same manner as in Example 116, the title compound was obtained as a colorless powder (0.11 g, 78%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.68-0.73 (2H, m), 0.86-0.95 (2H, m), 1.28 (3H, t, J=7.4), 2.89-2.96 (1H, m), 3.53 (2H, qd, J=7.4, 1.7), 5.58 (2H, s), 6.28 (1H, br), 7.02 (2H, d, J=9.0), 7.18-7.20 (2H, m), 7.28 (2H, d, J=9.0), 7.45 (1H, d, J=3.0), 7.71 (2H, d, J=8.7), 7.75 (1H, br), 7.97 (2H, d, J=8.7).

Elemental analysis for C$_{25}$H$_{25}$N$_7$O$_3$
Calcd. (%): C, 63.68; H, 5.34; N, 20.79.
Found (%): C, 63.89; H, 5.12; N, 20.76.

Example 120

N-cyclopropyl-1-{4-[(ethylamino)carbonyl]phenyl}-5-{[(6-methylpyridin-3-yl)oxy]methyl}-1H-1,2,3-triazole-4-carboxamide

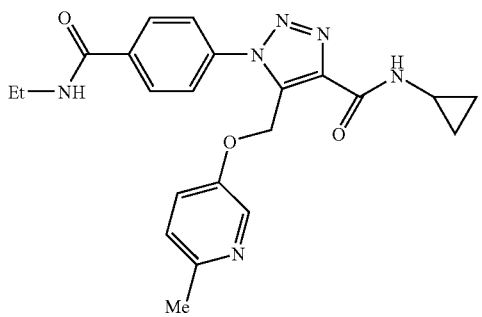

In the same manner as in Example 116, the title compound was obtained as colorless needle crystals (0.13 g, 99%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.67-0.73 (2H, m), 0.86-0.94 (2H, m), 1.28 (3H, t, J=7.2), 2.48 (3H, s), 2.88-2.97 (1H, m), 3.53 (2H, qd, J=7.2, 1.5), 5.55 (2H, s), 6.28 (1H, br), 7.06 (1H, d, J=8.5), 7.22 (1H, dd, J=8.5, 3.0), 7.42 (1H, d, J=2.4), 7.68 (2H, d, J=8.7), 7.95 (2H, d, J=8.7), 8.09 (1H, d, J=3.0).

Elemental analysis for C$_{22}$H$_{24}$N$_6$O$_3$
Calcd. (%): C, 62.84; H, 5.75; N, 19.99.
Found (%): C, 62.76; H, 5.81; N, 20.13.

Example 121

N-cyclopropyl-1-{4-[(ethylamino)carbonyl]phenyl}-5-[(3-morpholin-4-ylphenoxy)methyl]-1H-1,2,3-triazole-4-carboxamide

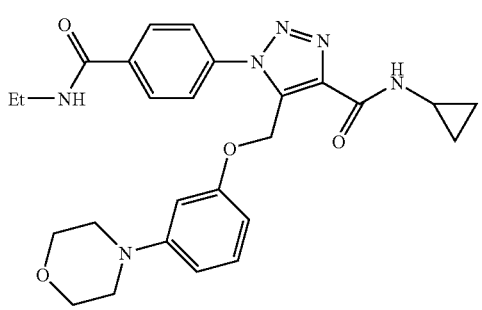

In the same manner as in Example 116, the title compound was obtained as colorless needle crystals (0.14 g, 94%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.67-0.72 (2H, m), 0.86-0.93 (2H, m), 1.28 (3H, t, J=7.2), 2.88-2.96 (1H, m), 3.12 (4H, t, J=4.7), 3.53 (2H, qd, J=7.2, 1.5), 3.84 (4H, t, J=4.7), 5.54 (2H, s), 6.19 (1H, br), 6.39 (1H, dd, J=7.9, 2.1), 6.44 (1H, t, J=2.1), 6.53 (1H, dd, J=7.9, 2.1), 7.13 (1H, t, J=8.1), 7.41 (1H, d, J=3.2), 7.69 (2H, d, J=8.7), 7.93 (2H, d, J=8.7).

Elemental analysis for C$_{26}$H$_{30}$N$_6$O$_4$
Calcd. (%): C, 63.66; H, 6.16; N, 17.13.
Found (%): C, 63.61; H, 5.89; N, 17.10.

Example 122

N-cyclopropyl-1-{4-[(ethylamino)carbonyl]phenyl}-5-[(4-methoxyphenoxy)methyl]-1H-1,2,3-triazole-4-carboxamide

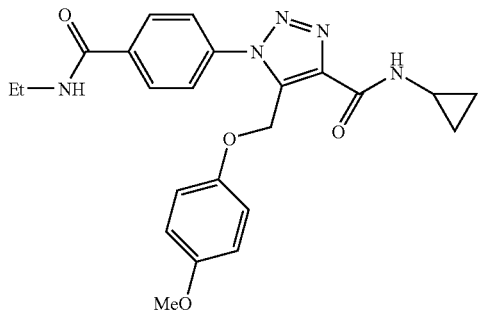

In the same manner as in Example 116, the title compound was obtained as colorless needle crystals (0.11 g, 82%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.67-0.72 (2H, m), 0.86-0.96 (2H, m), 1.28 (3H, t, J=7.0), 2.88-2.97 (1H, m), 3.53 (2H, qd, J=7.0, 1.5), 3.76 (3H, s), 5.47 (2H, s), 6.25 (1H, br), 6.82 (4H, AB, J=7.7), 7.41 (1H, d, J=2.6), 7.73 (2H, d, J=8.5), 7.94 (2H, d, J=8.5).

Elemental analysis for C$_{23}$H$_{25}$N$_5$O$_4$
Calcd. (%): C, 63.44; H, 5.79; N, 16.08.
Found (%): C, 63.42; H, 5.99; N, 15.89.

Example 123

N-cyclopropyl-1-{4-[(ethylamino)carbonyl]phenyl}-5-[(4-fluorophenoxy)methyl]-1H-1,2,3-triazole-4-carboxamide

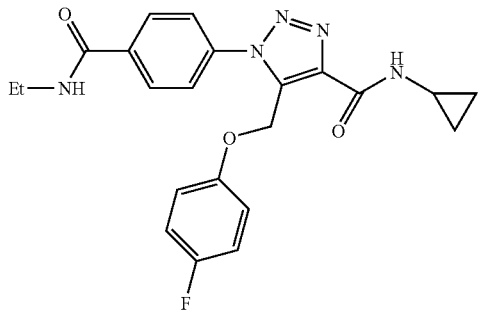

In the same manner as in Example 116, the title compound was obtained as colorless needle crystals (0.12 g, 97%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.67-0.72 (2H, m), 0.86-0.94 (2H, m), 1.28 (3H, t, J=7.2), 2.88-2.97 (1H, m), 3.53 (2H, qd, J=7.2, 1.7), 5.49 (2H, s), 6.21 (1H, br), 6.83-6.88 (2H, m), 6.92-6.98 (2H, m), 7.41 (1H, br), 7.71 (2H, d, J=8.5), 7.94 (2H, d, J=8.5).

Elemental analysis for C$_{22}$H$_{22}$FN$_5$O$_3$
Calcd. (%): C, 62.40; H, 5.24; N, 16.54.
Found (%): C, 62.15; H, 5.27; N, 16.57.

Example 124

5-[(1,3-benzothiazol-2-yloxy)methyl]-N-cyclopropyl-1-{4-[(ethylamino)carbonyl]phenyl}-1H-1,2,3-triazole-4-carboxamide

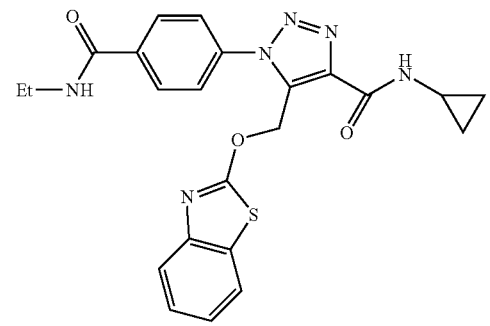

In the same manner as in Example 116, the title compound was obtained as a colorless powder (0.11 g, 78%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.73-0.79 (2H, m), 0.93-0.99 (2H, m), 1.30 (3H, t, J=7.4), 2.97-3.05 (1H, m), 3.53 (2H, qd, J=7.4, 1.5), 5.86 (2H, s), 6.21 (1H, br), 6.93 (1H, d, J=7.5), 7.07 (2H, d, J=8.5), 7.11-7.80 (2H, m), 7.88 (1H, d, J=7.5), 7.47 (1H, br), 7.76 (2H, d, J=8.5).

Elemental analysis for C$_{23}$H$_{22}$N$_6$O$_3$S
Calcd. (%): C, 59.73; H, 4.79; N, 18.17.
Found (%): C, 59.79; H, 4.83; N, 18.00.

Example 125

N-cyclopropyl-1-{4-[(ethylamino)carbonyl]phenyl}-5-{[(1-oxo-2,3-dihydro-1H-inden-5-yl)oxy]methyl}-1H-1,2,3-triazole-4-carboxamide

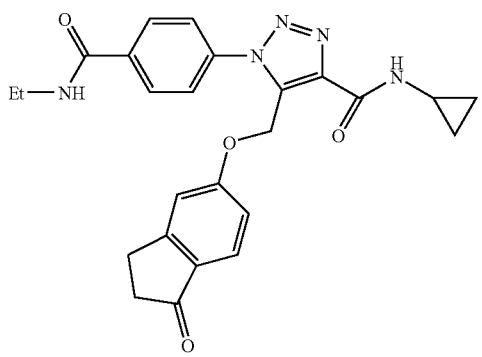

In the same manner as in Example 116, the title compound was obtained as pale-yellow needle crystals (0.10 g, 72%) from N-cyclopropyl-1-{4-[(ethylamino)carbonyl]phenyl}-5-(hydroxymethyl)-1H-1,2,3-triazole-4-carboxamide (0.10 g) obtained in Example 112.

NMR (CDCl$_3$) δ: 0.68-0.73 (2H, m), 0.86-0.94 (2H, m), 1.28 (3H, t, J=7.2), 2.67 (2H, t, J=6.0), 2.89-2.97 (1H, m), 3.07 (2H, t, J=6.0), 3.52 (2H, qd, J=7.2, 1.5), 5.61 (2H, s), 6.18 (1H, br), 6.85 (1H, dd, J=8.5, 2.3), 6.99 (1H, d, J=2.3), 7.43 (1H, d, J=3.0), 7.66 (1H, d, J=8.5), 7.68 (2H, d, J=8.5), 7.95 (2H, d, J=8.5).

Elemental analysis for C$_{25}$H$_{25}$N$_5$O$_4$
Calcd. (%): C, 65.35; H, 5.48; N, 15.24.
Found (%): C, 65.39; H, 5.41; N, 14.99.

Example 126

5-[(benzylamino)methyl]-N-cyclopropyl-1-{4-[(ethylamino)carbonyl]phenyl}-1H-1,2,3-triazole-4-carboxamide

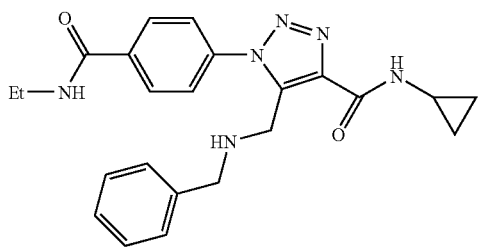

126a) (4-[(cyclopropylamino)carbonyl]-1-{4-[(ethylamino)carbonyl]phenyl}-1H-1,2,3-triazol-5-yl)methyl methanesulfonate N-Cyclopropyl-1-{4-[(ethylamino)carbonyl]phenyl}-5-(hydroxymethyl)-1H-1,2,3-triazole-4-carboxamide (1.12 g, 3.39 mmol) obtained in Example 112 and mesyl chloride (0.293 ml, 3.73 mmol, 1.1 eq.) were dissolved in THF (22 ml), and a solution of triethylamine (0.615 ml, 4.41 mmol, 1.3 eq.) in THF (2 ml) was added dropwise over 10 min with stirring at 0° C. The reaction mixture was stirred at 0° C. for 50 min. The reaction mixture was diluted with ethyl acetate (50 ml) and washed with 10% brine and saturated brine. The aqueous layers were each extracted with ethyl acetate (50 ml). The organic layers were combined, dried over anhydrous sodium sulfate and concentrated. Diethyl ether was added and the precipitate was collected by filtration, washed with diethyl ether and dried to give the title compound as a white powder (1.31 g, 3.21 mmol, 94.6%).

$^1$H NMR (200 MHz, CDCl$_3$) δ: 0.71 (2H, m), 0.92 (2H, m), 1.30 (3H, t, J=7.4 Hz), 2.92 (1H, octet, J=3.7 Hz), 3.24 (3H, s), 3.55 (2H, dq, J=5.6, 7.3 Hz), 5.57 (2H, s), 6.20 (1H, m), 7.41 (1H, brd, J=3 Hz), 7.68 (2H, dt, J=8.8, 2.0 Hz), 8.01 (2H, dt, J=8.8, 2.0 Hz).

126b) 5-[(benzylamino)methyl]-N-cyclopropyl-1-{4-[(ethylamino)carbonyl]phenyl}-1H-1,2,3-triazole-4-carboxamide (4-[(Cyclopropylamino)carbonyl]-1-{4-[(ethylamino)carbonyl]phenyl}-1H-1,2,3-triazol-5-yl)methyl methanesulfonate (225 mg, 0.552 mmol) obtained in Example 126a), potassium carbonate (76.3 mg, 0.552 mmol, 1.0 eq.) and benzylamine (0.123 ml, 1.10 mmol, 2.0 eq.) were suspended in acetonitrile (7.5 ml), sodium iodide (16.6 mg, 0.110 mmol, 0.2 eq.) was added, and the mixture was stirred at room temperature for 12 hr. The reaction mixture was diluted with ethyl acetate (30 ml), washed with saturated aqueous sodium hydrogen carbonate solution and saturated brine, dried over anhydrous sodium sulfate and concentrated. Diethyl ether was added and the precipitate was collected by filtration, washed with diethyl ether and dried to give the title compound as a white powder (208 mg, 0.497 mmol, 90.0%).

$^1$H NMR (200 MHz, CDCl$_3$) δ: 0.70 (2H, m), 0.91 (2H, m), 1.30 (3H, t, J=7.4 Hz), 2.92 (1H, octet, J=3.6 Hz), 3.47 (2H, dq, J=5.6, 7.3 Hz), 3.85 (2H, s), 3.99 (2H, s), 6.15 (1H, brt, J=5 Hz), 7.26-7.35 (5H, m), 7.39 (1H, brd, J=3 Hz), 7.67 (2H, d, J=8.4 Hz), 7.84 (2H, d, J=8.8 Hz).

Elemental analysis for C$_{23}$H$_{26}$N$_6$O$_2$.0.2H$_2$O
Calcd. (%): C, 65.45; H, 6.30; N, 19.91.
Found (%): C, 65.43; H, 6.24; N, 19.97.
melting point: 153° C.

Example 127

N-cyclopropyl-1-{4-[(ethylamino)carbonyl]phenyl}-5-(pyrrolidin-1-ylmethyl)-1H-1,2,3-triazole-4-carboxamide

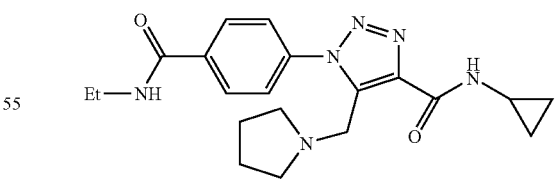

(4-[(Cyclopropylamino)carbonyl]-1-{4-[(ethylamino)carbonyl]phenyl}-1H-1,2,3-triazol-5-yl)methyl methanesulfonate (204 mg, 0.501 mmol) obtained in Example 126a), potassium carbonate (69.2 mg, 0.501 mmol, 1.0 eq.) and pyrrolidine (0.084 ml, 1.00 mmol, 2.0 eq.) were suspended in acetonitrile (4.0 ml), and the mixture was stirred at room temperature for 110 min. The reaction mixture was diluted with ethyl acetate (30 ml), washed twice with 2% aqueous sodium carbonate solution and with saturated brine, dried over anhydrous sodium sulfate, and concentrated to give a colorless oil. The oil was crystallized from ethyl acetate and diethyl ether, and the precipitate was collected by filtration, washed with diethyl ether and dried to give the title compound as a white powder (160 mg, 0.418 mmol, 83.5%).

$^1$H NMR (200 MHz, CDCl$_3$) δ: 0.67 (2H, m), 0.89 (2H, m), 1.29 (3H, t, J=7.3 Hz), 1.77 (4H, m), 2.66 (4H, m), 2.92 (1H, octet, J=3.5 Hz), 3.54 (2H, dq, J=5.4, 7.4 Hz), 4.06 (2H, brs), 6.26 (1H, brt, J=5 Hz), 7.63 (1H, brd, J=3 Hz), 7.95 (4H, s).

Elemental analysis for C$_{20}$H$_{26}$N$_6$O$_2$
Calcd. (%): C, 62.81; H, 6.85; N, 21.97.
Found (%): C, 62.62; H, 6.75; N, 21.88.
melting point: 164° C.

Example 128

N-cyclopropyl-1-{4-[(ethylamino)carbonyl]phenyl}-5-(morpholin-4-ylmethyl)-1H-1,2,3-triazole-4-carboxamide

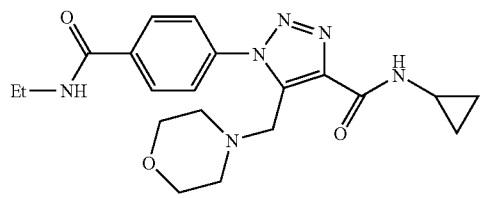

(4-[(Cyclopropylamino)carbonyl]-1-{4-[(ethylamino)carbonyl]phenyl}-1H-1,2,3-triazol-5-yl)methyl methanesulfonate (195 mg, 0.479 mmol) obtained in Example 126a), potassium carbonate (66.1 mg, 0.479 mmol, 1.0 eq.) and morpholine (0.085 ml, 0.957 mmol, 2.0 eq.) were suspended in acetonitrile (4.0 ml), and the mixture was stirred at room temperature for 15 hr. The reaction mixture was diluted with ethyl acetate (30 ml) and washed with 2% aqueous sodium carbonate solution, saturated aqueous sodium hydrogen carbonate solution and saturated brine. The aqueous layers were each extracted with ethyl acetate (15 ml). The organic layers were combined, dried over anhydrous sodium sulfate and concentrated. Diethyl ether was added and the precipitate was collected by filtration and crystallized from ethyl acetate. The precipitate was collected by filtration and crystallized from ethanol again to give the title compound as a white powder (142 mg, 0.356 mmol, 74.4%).

$^1$H NMR (200 MHz, CDCl$_3$) δ: 0.68 (2H, m), 0.90 (2H, m), 1.30 (3H, t, J=7.1 Hz), 2.55 (4H, br), 2.91 (1H, octet, J=3.7 Hz), 3.55 (2H, dq, J=6.0, 7.1 Hz), 3.63 (4H, br), 3.92 (2H, brs), 6.25 (1H, brt, J=5 Hz), 7.45 (1H, brd, J=3 Hz), 7.96 (4H, s).

Elemental analysis for C$_{20}$H$_{26}$N$_6$O$_3$.0.1H$_2$O.0.1EtOH
Calcd. (%): C, 59.92; H, 6.67; N, 20.76.
Found (%): C, 59.75; H, 6.59; N, 20.76.
melting point: 234° C. (decomposition)

Example 129

N-cyclopropyl-1-{4-[(ethylamino)carbonyl]phenyl}-5-[(methylthio)methyl]-1H-1,2,3-triazole-4-carboxamide

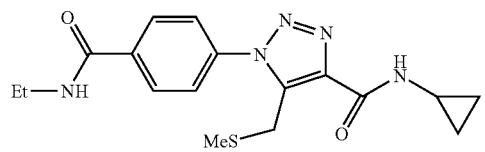

(4-[(Cyclopropylamino)carbonyl]-1-{4-[(ethylamino)carbonyl]phenyl}-1H-1,2,3-triazol-5-yl)methyl methanesulfonate (196 mg, 0.481 mmol) obtained in Example 126a), potassium carbonate (33.2 mg, 0.241 mmol, 0.5 eq.) and 15% aqueous sodium thiomethoxide solution (0.449 ml, 0.962 mmol, 2.0 eq.) were dissolved in ethanol (3.5 ml), and the mixture was stirred at room temperature for 2 hr. The reaction mixture was diluted with ethyl acetate (30 ml), washed twice with 2% aqueous sodium carbonate solution and with saturated brine, dried over anhydrous sodium sulfate and concentrated. Diethyl ether was added and the precipitate was collected by filtration, washed with diethyl ether and dried to give the title compound as a white powder (160 mg, 0.445 mmol, 92.5%).

$^1$H NMR (200 MHz, CDCl$_3$) δ: 0.68 (2H, m), 0.90 (2H, m), 1.30 (3H, t, J=7.3 Hz), 2.14 (3H, s), 2.91 (1H, octet, J=3.5 Hz), 3.55 (2H, dq, J=5.8, 7.1 Hz), 4.15 (2H, s), 6.17 (1H, brt, J=6 Hz), 7.36 (1H, br), 7.70 (2H, dt, J=8.4, 2.0 Hz), 7.97 (2H, d, J=8.8 Hz).

Elemental analysis for C$_{17}$H$_{21}$N$_5$O$_2$S
Calcd. (%): C, 56.80; H, 5.89; N, 19.48; S, 8.92.
Found (%): C, 56.68; H, 5.82; N, 19.21; S, 8.80.
melting point: 192° C.

Example 130

N-cyclopropyl-1-{4-[(ethylamino)carbonyl]phenyl}-5-[(phenylthio)methyl]-1H-1,2,3-triazole-4-carboxamide

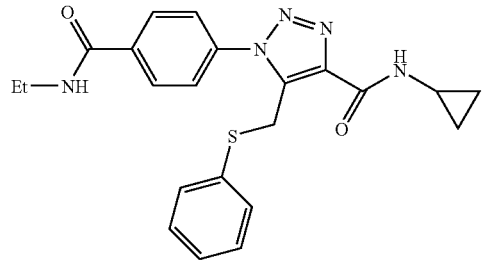

(4-[(Cyclopropylamino)carbonyl]-1-{4-[(ethylamino)carbonyl]phenyl}-1H-1,2,3-triazol-5-yl)methyl methanesulfonate (310 mg, 0.761 mmol) obtained in Example 126a), potassium carbonate (52.6 mg, 0.380 mmol, 0.5 eq.) and sodium thiophenoxide (168 mg, 1.14 mmol, 1.5 eq.) were dissolved in ethanol (6.0 ml), and the mixture was stirred at room temperature for 2 hr. The reaction mixture was diluted with ethyl acetate (30 ml) and hexane (2 ml), washed twice with 2% aqueous sodium carbonate solution and with saturated brine, dried over anhydrous sodium sulfate and concentrated. Diethyl ether was added and the precipitate was collected by filtration, washed with diethyl ether and dried to give the title compound as a white powder (290 mg, 0.688 mmol, 90.4%).

$^1$H NMR (200 MHz, CDCl$_3$) δ: 0.64 (2H, m), 0.87 (2H, m), 1.30 (3H, t, J=7.3 Hz), 2.85 (1H, octet, J=3.7 Hz), 3.55 (2H, dq, J=5.6, 7.3 Hz), 4.57 (2H, s), 6.17 (1H, brt, J=5 Hz), 7.17-7.29 (6H, m), 7.54 (2H, dt, J=8.4, 2.0 Hz), 7.91 (2H, dt, J=8.4, 2.0 Hz).

Elemental analysis for C$_{22}$H$_{23}$N$_5$O$_2$S
Calcd. (%): C, 62.69; H, 5.50; N, 16.61; S, 7.61.
Found (%): C, 62.56; H, 5.42; N, 16.55; S, 7.64.

Example 131

N-cyclopropyl-1-{2-ethoxy-4-[(ethylamino)carbonyl]phenyl}-1H-1,2,3-triazole-4-carboxamide

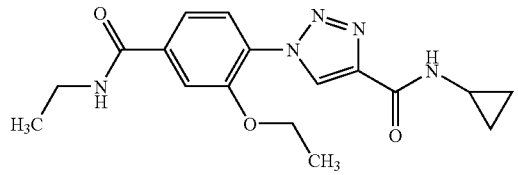

131a) N-ethyl-3-hydroxy-4-nitrobenzamide

To a solution of 3-hydroxy-4-nitrobenzoic acid (9.16 g) in DMF (100 ml) were successively added 2M ethylamine in THF solution (30 ml), triethylamine (8.3 ml), HOBt (9.19 g) and WSC (11.5 g), and the reaction mixture was stirred at room temperature overnight. The solvent was evaporated under reduced pressure, ethyl acetate and 1N hydrochloric acid were added to the residue and the insoluble material was filtered off. The filtrate was extracted with ethyl acetate, the organic layer was dried over anhydrous sodium sulfate, and the solvent was evaporated under reduced pressure to give the title compound as a yellow solid (10.6 g, 100%).

NMR (CDCl$_3$) δ: 1.25 (3H, t, J=7.2), 3.49 (2H, dq, J=5.7, 7.2), 7.07 (1H, brs), 7.38 (1H, dd, J=1.7, 8.7), 7.55 (1H, d, J=1.9), 8.11 (1H, d, J=8.7), 8.97 (1H, brs).

131b) 3-ethoxy-N-ethyl-4-nitrobenzamide

To a solution of N-ethyl-3-hydroxy-4-nitrobenzamide (2.10 g) obtained in Example 131a) in acetone (100 ml) were added ethyl bromide (0.75 ml) and potassium carbonate (1.38 g), and the reaction mixture was heated under reflux overnight. The reaction mixture was allowed to cool to room temperature and the solvent was evaporated under reduced pressure. Ethyl acetate and water were added to the residue. The organic layer was dried over anhydrous sodium sulfate, and the solvent was evaporated under reduced pressure to give the title compound as a pale-brown solid (0.72 g, 30%).

NMR (CDCl$_3$) δ: 1.27 (3H, t, J=7.2), 1.47 (3H, t, J=7.0), 3.49 (2H, dq, J=5.7, 7.2), 4.23 (2H, q, J=7.0), 6.47 (1H, s), 7.26-7.29 (1H, m), 7.58 (1H, d, J=1.5), 7.79 (1H, d, J=8.5).

131c) 4-amino-3-ethoxy-N-ethylbenzamide

To a solution of 3-ethoxy-N-ethyl-4-nitrobenzamide (0.72 g) obtained in Example 131b) in ethanol (15 ml) was added 10% Pd/C (50% wet) (0.07 g), and the mixture was stirred at room temperature overnight under a hydrogen atmosphere. The reaction mixture was filtered through celite, and the filtrate was evaporated under reduced pressure. The residue was purified by silica gel column (ethyl acetate/hexane=1/1 to ethyl acetate) to give the title compound as a colorless oil (0.53 g, 84%).

NMR (CDCl$_3$) δ: 1.21 (3H, t, J=7.4), 1.41 (3H, t, J=7.0), 3.44 (2H, dq, J=5.7, 7.4), 4.07 (2H, q, J=7.0), 4.13 (2H, brs), 6.25 (1H, brs), 6.63 (1H, d, J=8.1), 7.14 (1H, dd, J=1.9, 8.1), 7.34 (1H, d, J=1.9).

131d) 4-azido-3-ethoxy-N-ethylbenzamide

To a solution of 4-amino-3-ethoxy-N-ethylbenzamide (0.53 g) obtained in Example 131c) in 0.2N hydrochloric acid (12.5 ml) was added 1M aqueous sodium nitrite solution (2.5 ml) under ice-cooling, and the mixture was stirred for 2 hr. To the obtained reaction mixture was added an aqueous solution (5 ml) of sodium azide (0.17 g) under ice-cooling, and the mixture was stirred for 30 min. The reaction mixture was extracted with ethyl acetate. The organic layer was dried over anhydrous sodium sulfate, and the solvent was evaporated under reduced pressure to give the title compound as a yellow oil (0.50 g, 85%).

NMR (CDCl$_3$) δ: 1.27 (3H, t, J=7.2), 1.50 (3H, t, J=7.2), 3.52 (2H, dq, J=5.7, 7.2), 4.24 (2H, q, J=7.0), 6.11 (1H, t, J=5.7), 7.25 (1H, dd, J=1.9, 8.1), 7.50 (1H, d, J=1.3), 7.63 (1H, d, J=8.3).

131e) ethyl 1-{2-ethoxy-4-[(ethylamino)carbonyl]phenyl}-1H-1,2,3-triazole-4-carboxylate To a solution of 4-azido-3-ethoxy-N-ethylbenzamide (0.70 g) obtained in Example 131d) in toluene (30 ml) was added ethyl propiolate (0.61 ml), and the mixture was heated under reflux overnight under a nitrogen atmosphere. The reaction mixture was allowed to cool to room temperature, and the solvent was evaporated under reduced pressure. The residue was purified by silica gel column (ethyl acetate/hexane=1/1 to ethyl acetate) to give the title compound as a white powder (0.59 g, 60%).

NMR (CDCl$_3$) δ: 1.29 (3H, t, J=7.4), 1.45 (3H, t, J=7.2), 1.46 (3H, t, J=7.0), 3.49-3.58 (2H, m), 4.26 (2H, q, J=7.0), 4.48 (2H, q, J=7.0), 6.23 (1H, t, J=4.3), 7.36 (1H, dd, J=1.7, 8.3), 7.67 (1H, d, J=1.7), 7.96 (1H, d, J=8.3), 8.78 (1H, s).

131f) 1-{2-ethoxy-4-[(ethylamino)carbonyl]phenyl}-1H-1,2,3-triazole-4-carboxylic acid To a solution of ethyl 1-{2-ethoxy-4-[(ethylamino)carbonyl]phenyl}-1H-1,2,3-triazole-4-carboxylate (0.51 g) obtained in Example 131e) in ethanol (8 ml) was added 8N aqueous sodium hydroxide solution (0.39 ml), and the mixture was stirred at room temperature for 5 hr. Water was added to the reaction mixture, and ethanol was evaporated under reduced pressure. Water was added to the obtained aqueous solution and the mixture was washed with ethyl acetate. 1N Hydrochloric acid was added to acidify the aqueous solution. The deposited precipitate was collected by filtration, washed with water and air-dried to give the title compound as a white powder (0.36 g, 76%).

NMR (CDCl$_3$) δ: 1.30 (3H, t, J=7.2), 1.48 (3H, t, J=7.2), 3.50-3.57 (2H, m), 4.28 (2H, q, J=7.2), 6.17 (1H, brs), 7.36 (1H, dd, J=1.1, 7.9), 7.69 (1H, d, J=1.1), 7.99 (1H, d, J=258.1), 8.87 (1H, s).

131g) N-cyclopropyl-1-{2-ethoxy-4-[(ethylamino)carbonyl]phenyl}-1H-1,2,3-triazole-4-carboxamide To a solution of 1-{2-ethoxy-4-[(ethylamino)carbonyl]phenyl}-1H-1,2,3-triazole-4-carboxylic acid (0.36 g) obtained in Example 131f) in DMF (3 ml) were successively added cyclopropylamine (0.10 ml), triethylamine (0.20 ml), HOBt (0.22 g) and WSC (0.27 g), and the reaction mixture was stirred at room temperature overnight. To the reaction mixture were added saturated aqueous sodium hydrogen carbonate solution and ethyl acetate, and the organic layer was separated. The solvent was evaporated under reduced pressure, and the residue was recrystallized from ethanol-water to give the title compound as a white powder (0.31 g, 76%).

NMR (CDCl$_3$) δ: 0.67-0.72 (2H, m), 0.86-0.93 (2H, m), 1.29 (3H, t, J=7.2), 1.45 (3H, t, J=7.0), 2.90-2.99 (1H, m), 3.49-3.58 (2H, m), 4.25 (2H, q, J=7.0), 6.21 (1H, t, J=4.9), 7.28 (1H, brs), 7.35 (1H, dd, J=1.3, 8.3), 7.65 (1H, d, J=0.9), 7.89 (1H, d, J=8.1), 8.72 (1H, s).

Example 132

N-cyclopropyl-1-(1-oxo-1,2,3,4-tetrahydroisoquinolin-6-yl)-5-propyl-1H-1,2,3-triazole-4-carboxamide

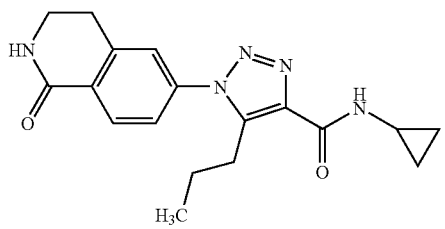

132a) methyl 2-(cyanomethyl)-4-nitrobenzoate

To a suspension of sodium cyanide (6.3 g) in DMSO (200 ml) was added trifluoroacetic acid (6.6 ml) under water-cooling, methyl 2-(bromomethyl)-4-nitrobenzoate (J. Med. Chem., 42, 3510-3519 (1999)) (11.8 g) synthesized separately was added, and the mixture was stirred for 1 hr. Water was added to the reaction mixture, and the mixture was extracted with ethyl acetate. The organic layer was dried over anhydrous sodium sulfate. The solvent was evaporated under reduced pressure, and the residue was purified by silica gel column (ethyl acetate/hexane=1/10 to 1/3) to give a crude product of the title compound as a pale-yellow powder (2.52 g, 27%). The obtained crude product was used for the next reaction without further purification.

132b) 6-azido-3,4-dihydroisoquinolin-1(2H)-one

To a solution of methyl 2-(cyanomethyl)-4-nitrobenzoate (0.95 g) obtained in Example 132a) in ethanol (95 ml) was added platinum(IV) oxide (0.10 g), and the mixture was stirred at room temperature for 6 days under a hydrogen atmosphere. The reaction mixture was filtered through celite, and the filtrate was evaporated under reduced pressure. The residue was dissolved in 0.3N hydrochloric acid and, under ice-cooling, 1M aqueous sodium nitrite solution (4.3 ml) was added and the mixture was stirred for 30 min. An aqueous solution (4 ml) of sodium azide (0.28 g) was added to the obtained reaction mixture, and the mixture was stirred under ice-cooling for 1 hr. The reaction mixture was extracted with ethyl acetate, the organic layer was dried over anhydrous sodium sulfate, and the solvent was evaporated under reduced pressure to give the title compound as a pale-yellow powder (0.24 g, 30%).

NMR (CDCl$_3$) δ: 2.99 (2H, t, J=6.6), 3.57 (2H, dt, J=2.6, 6.6), 6.43 (1H, brs), 6.85 (1H, d, J=2.1), 7.01 (1H, dd, J=2.1, 8.5), 8.06 (1H, d, J=8.3).

132c) 1-(1-oxo-1,2,3,4-tetrahydroisoquinolin-6-yl)-5-propyl-1H-1,2,3-triazole-4-carboxylic acid To a solution of 6-azido-3,4-dihydroisoquinolin-1(2H)-one (0.24 g) obtained in Example 132b) and ethyl 3-keto-n-hexanoate (0.25 ml) in ethanol (7 ml) was added 28% sodium ethoxide in ethanol solution (0.60 ml) at room temperature, and the mixture was stirred for 3 hr. The solvent was evaporated under reduced pressure, and water was added to the obtained residue. The mixture was washed with ethyl acetate, 1N hydrochloric acid was added to acidify the aqueous solution, and the mixture was extracted with ethyl acetate. The organic layer was dried over anhydrous magnesium sulfate, and the solvent was evaporated under reduced pressure to give the title compound as a yellow solid (0.22 g, 57%).

NMR (DMSO-d$_6$) δ: 0.74 (3H, t, J=7.4), 1.43 (2H, sextet, J=7.4), 2.93-2.98 (2H, m), 3.03 (2H, t, J=6.6), 3.45 (2H, dt, J=2.6, 6.6), 7.57 (1H, dd, J=2.1, 8.1), 7.61 (1H, d, J=1.5), 8.07 (1H, d, J=8.3), 8.18 (1H, t, J=2.6), 13.16 (1H, brs).

132d) N-cyclopropyl-1-(1-oxo-1,2,3,4-tetrahydroisoquinolin-6-yl)-5-propyl-1H-1,2,3-triazole-4-carboxamide In the same manner as in Example 131g), the title compound was obtained as a pale-yellow powder (0.14 g, 55%) from 1-(1-oxo-1,2,3,4-tetrahydroisoquinolin-6-yl)-5-propyl-1H-1,2,3-triazole-4-carboxylic acid (0.22 g) obtained in Example 132c).

NMR (CDCl$_3$) δ: 0.65-0.71 (2H, m), 0.86-0.91 (5H, m), 1.54-1.65 (2H, m), 2.88-2.94 (1H, m), 3.02-3.07 (2H, m), 3.12 (2H, t, J=6.6), 3.66 (2H, dt, J=2.8, 6.6), 6.34 (1H, brs), 7.36-7.42 (3H, m), 8.28 (1H, d, J=8.1).

Example 133

N-cyclopropyl-1-{4-[(ethylamino)carbonyl]-2-(3-phenylpropoxy)phenyl}-1H-1,2,3-triazole-4-carboxamide

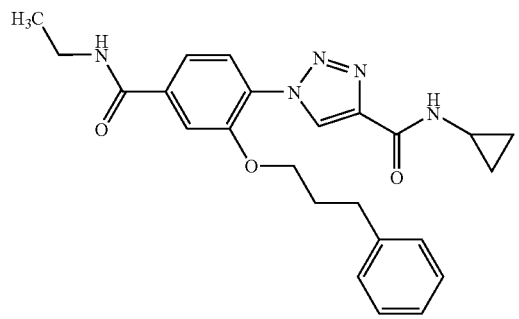

133a) 4-amino-N-ethyl-3-hydroxybenzamide

In the same manner as in Example 131c), the title compound was obtained as a yellow solid (4.73 g, 86%) from N-ethyl-3-hydroxy-4-nitrobenzamide (6.42 g) obtained in Example 131a).

NMR (DMSO-d$_6$) δ: 1.07 (3H, t, J=7.2), 3.16-3.25 (2H, m), 4.98 (2H, brs), 6.54 (1H, d, J=8.1), 7.11 (1H, dd, J=1.9, 8.1), 7.18 (1H, d, J=1.9), 7.94 (1H, t, J=5.3), 9.15 (1H, s).

133b) 4-azido-N-ethyl-3-hydroxybenzamide

In the same manner as in Example 131d), the title compound was obtained as a yellow powder (4.09 g, 75%) from 4-amino-N-ethyl-3-hydroxybenzamide (4.73 g) obtained in Example 133a).

NMR (CDCl$_3$) δ: 1.25 (3H, t, J=7.4), 3.44-3.53 (2H, m), 6.16 (1H, brs), 7.04 (1H, d, J=8.1), 7.23-7.28 (2H, m), 7.56 (1H, d, J=1.9).

133c) ethyl 1-{4-[(ethylamino)carbonyl]-2-hydroxyphenyl}-1H-1,2,3-triazole-4-carboxylate To a solution of 4-azido-N-ethyl-3-hydroxybenzamide (2.71 g) obtained in Example 133b) in toluene (65 ml) was added ethyl propiolate (2.0 ml), and the mixture was heated under reflux overnight under a nitrogen atmosphere. The reaction mixture was allowed to cool to room temperature, and the solvent was evaporated under reduced pressure. The residue was washed with dichloromethane to give the title compound as a brown solid (2.70 g, 68%).

NMR (DMSO-d$_6$) δ: 1.13 (3H, t, J=7.2), 1.34 (3H, t, J=7.2), 3.25-3.36 (2H, m), 4.36 (2H, q, J=7.2), 7.46 (1H, dd, J=1.7, 8.3), 7.59 (1H, d, J=1.7), 7.75 (1H, d, J=8.3), 8.59 (1H, t, J=5.5), 9.09 (1H, s), 11.01 (1H, s).

133d) ethyl 1-{4-[(ethylamino)carbonyl]-2-(3-phenylpropoxy)phenyl}-1H-1,2,3-triazole-4-carboxylate To a solution of ethyl 1-{4-[(ethylamino)carbonyl]-2-hydroxyphenyl}-1H-1,2,3-triazole-4-carboxylate (0.30 g) obtained in Example 133c) in DMF (10 ml) were added (3-bromopropyl)benzene (0.18 ml) and potassium carbonate (0.14 g), and the mixture was stirred overnight at 75° C. The reaction mixture was allowed to cool to room temperature, water was added, and the mixture was extracted with ethyl acetate. The organic layer was dried over anhydrous magnesium sulfate, and the solvent was evaporated under reduced pressure. The residue was purified by silica gel column (ethyl acetate/hexane=1/1 to ethyl acetate) and recrystallized from ethyl acetate-hexane to give the title compound as a pale-yellow powder (0.25 g, 57%).

NMR (CDCl$_3$) δ: 1.29 (3H, t, J=7.3), 1.43 (3H, t, J=7.2), 2.10-2.20 (2H, m), 2.71-2.76 (2H, m), 3.48-3.58 (2H, m), 4.19 (2H, t, J=6.2), 4.48 (2H, q, J=7.2), 6.15 (1H, brs), 7.14-7.22 (3H, m), 7.26-7.31 (2H, m), 7.36 (1H, dd, J=1.7, 8.3), 7.63 (1H, d, J=1.7), 7.96 (1H, d, J=8.3), 8.77 (1H, s).

133e) 1-{4-[(ethylamino)carbonyl]-2-(3-phenylpropoxy)phenyl}-1H-1,2,3-triazole-4-carboxylic acid To a solution of ethyl 1-{4-[(ethylamino)carbonyl]-2-(3-phenylpropoxy)phenyl}-1H-1,2,3-triazole-4-carboxylate (0.22 g) obtained in Example 133d) in ethanol (6 ml) was added 1N aqueous sodium hydroxide solution (1.0 ml), and the mixture was stirred overnight at room temperature. The solvent was evaporated under reduced pressure, and the residue was diluted with water. The obtained aqueous solution was washed with ethyl acetate, acidified with 1N hydrochloric acid, and the mixture was extracted with ethyl acetate. The organic layer was dried over anhydrous magnesium sulfate, and the solvent was evaporated under reduced pressure to give the title compound as a pale-yellow oil (0.21 g, 100%).

NMR (CDCl$_3$) δ: 1.28 (3H, t, J=7.4), 2.09-2.18 (2H, m), 2.72 (2H, t, J=7.4), 3.49-3.58 (2H, m), 4.19 (2H, t, J=6.4), 6.51 (1H, t, J=5.5), 7.13-7.19 (3H, m), 7.23-7.28 (2H, m), 7.41 (1H, dd, J=1.5, 8.3), 7.66 (1H, d, J=1.5), 7.95 (1H, d, J=8.3), 8.83 (1H, s), 9.82 (1H, brs).

133f) N-cyclopropyl-1-{4-[(ethylamino)carbonyl]-2-(3-phenylpropoxy)phenyl}-1H-1,2,3-triazole-4-carboxamide In the same manner as in Example 131g), the title compound was obtained as a white powder (0.14 g, 62%) from 1-{4-[(ethylamino)carbonyl]-2-(3-phenylpropoxy)phenyl}-1H-1,2,3-triazole-4-carboxylic acid (0.21 g) obtained in Example 133e).

NMR (CDCl$_3$) δ: 0.67-0.72 (2H, m), 0.86-0.93 (2H, m), 1.28 (3H, t, J=7.4), 2.10-2.19 (2H, m), 2.71 (2H, t, J=6.4), 2.88-2.98 (1H, m), 3.48-3.57 (2H, m), 4.16 (2H, t, J=6.4), 6.14 (1H, brs), 7.13-7.20 (3H, m), 7.25-7.30 (3H, m), 7.35 (1H, dd, J=1.5, 8.3), 7.60 (1H, d, J=1.5), 7.87 (1H, d, J=8.1), 8.70 (1H, s).

Example 134

N-cyclopropyl-1-{4-[(ethylamino)carbonyl]-2-(3-phenylpropoxy)phenyl}-5-methyl-1H-1,2,3-triazole-4-carboxamide

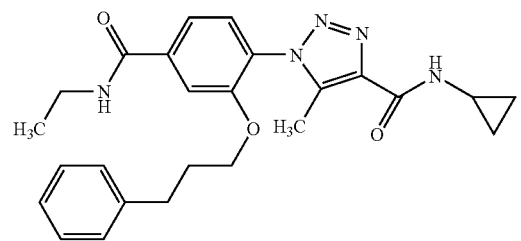

134a) 1-{4-[(ethylamino)carbonyl]-2-hydroxyphenyl}-5-methyl-1H-1,2,3-triazole-4-carboxylic acid To a solution of 4-azido-N-ethyl-3-hydroxybenzamide (0.41 g) obtained in Example 133b) and methyl 3-oxobutanoate (0.27 ml) in ethanol (10 ml) was added 28% sodium ethoxide in ethanol solution (1.0 ml) at room temperature, and the mixture was stirred overnight and at 60° C. for 9 hr. After allowing to cool to room temperature, 1N aqueous sodium hydroxide solution (4.0 ml) was added to the reaction mixture and the mixture was stirred at room temperature overnight. The solvent was evaporated under reduced pressure, and the obtained residue was diluted with water. The obtained aqueous solution was washed with ethyl acetate, acidified with 1N hydrochloric acid, and the mixture was extracted with ethyl acetate. The organic layer was dried over anhydrous sodium sulfate, and the solvent was evaporated under reduced pressure to give a crude product of the title compound as a brown solid (0.32 g, 55%). The obtained crude product was used for the next reaction without further purification.

134b) N-cyclopropyl-1-{4-[(ethylamino)carbonyl]-2-hydroxyphenyl}-5-methyl-1H-1,2,3-triazole-4-carboxamide In the same manner as in Example 131g), a crude product of the title compound was obtained as a brown solid (0.16 g, 44%) from 1-{4-[(ethylamino)carbonyl]-2-hydroxyphenyl}-5-methyl-1H-1,2,3-triazole-4-carboxylic acid obtained in Example 134a). The obtained crude product was used for the next reaction without further purification.

134c) N-cyclopropyl-1-{4-[(ethylamino)carbonyl]-2-(3-phenylpropoxy)phenyl}-5-methyl-1H-1,2,3-triazole-4-carboxamide In the same manner as in Example 133d), the title compound was obtained as a white powder (0.08 g, 38%) from N-cyclopropyl-1-{4-[(ethylamino)carbonyl]-2-hydroxyphenyl}-5-methyl-1H-1,2,3-triazole-4-carboxamide (0.16 g) obtained in Example 134b).

NMR (CDCl$_3$) δ: 0.65-0.70 (2H, m), 0.84-0.91 (2H, m), 1.27 (3H, t, J=7.4), 1.92-2.02 (2H, m), 2.48 (3H, s), 2.55 (2H, t, J=7.2), 2.87-2.93 (1H, m), 3.47-3.56 (2H, m), 4.04 (2H, t, J=6.4), 6.32 (1H, brs), 7.05-7.08 (2H, m), 7.14-7.27 (3H, m), 7.33-7.41 (3H, m), 7.56 (1H, brs).

Example 135

N-cyclopropyl-5-ethyl-1-{4-[(ethylamino)carbonyl]-2-(3-phenylpropoxy)phenyl}-1H-1,2,3-triazole-4-carboxamide

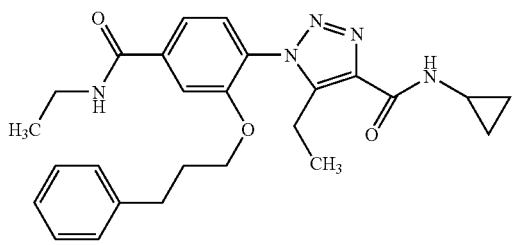

In the same manner as in Example 134, the title compound was obtained as a white powder (0.10 g, yield in 3 steps 11%) from 4-azido-N-ethyl-3-hydroxybenzamide (0.41 g) obtained in Example 133b) and methyl 3-oxopentanoate (0.30 ml).

NMR (CDCl$_3$) δ: 0.65-0.71 (2H, m), 0.84-0.91 (2H, m), 1.08 (3H, t, J=7.5), 1.28 (3H, t, J=7.2), 1.91-2.00 (2H, m), 2.52-2.57 (2H, m), 2.87-2.96 (3H, m), 3.48-3.57 (2H, m), 4.01-4.05 (2H, m), 6.18 (1H, t, J=5.0), 7.05-7.08 (2H, m), 7.14-7.28 (3H, m), 7.34-7.40 (3H, m), 7.55 (1H, brs).

Example 136

N-cyclopropyl-1-{4-[(ethylamino)carbonyl]-2-(3-phenylpropoxy)phenyl}-5-propyl-1H-1,2,3-triazole-4-carboxamide

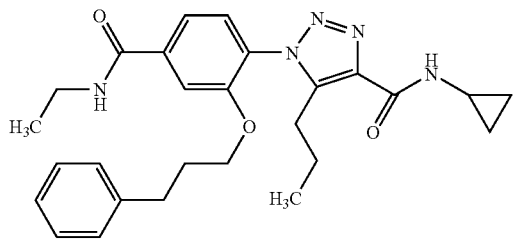

In the same manner as in Example 133d), the title compound was obtained as a pale-yellow oil (0.10 g, 88%) from N-cyclopropyl-1-{4-[(ethylamino)carbonyl]-2-hydroxyphenyl}-5-propyl-1H-1,2,3-triazole-4-carboxamide (0.08 g) obtained in Example 315.

NMR (CDCl$_3$) δ: 0.65-0.70 (2H, m), 0.80 (3H, t, J=7.4), 0.84-0.90 (2H, m), 1.28 (3H, t, J=7.2), 1.44-1.57 (2H, m), 1.90-1.99 (2H, m), 2.54 (2H, t, J=7.2), 2.86-2.95 (3H, m), 3.48-3.57 (2H, m), 4.02 (2H, t, J=6.2), 6.30 (1H, t, J=5.3), 7.05-7.08 (2H, m), 7.14-7.28 (3H, m), 7.34-7.40 (3H, m), 7.55 (1H, brs).

Example 137

1-{2-(benzyloxy)-4-[(ethylamino)carbonyl]phenyl}-N-cyclopropyl-5-(5-fluoropentyl)-1H-1,2,3-triazole-4-carboxamide

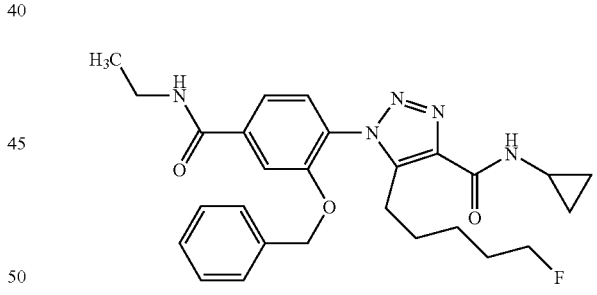

137a) 4-azido-3-(benzyloxy)-N-ethylbenzamide

To a solution of 4-azido-N-ethyl-3-hydroxybenzamide (3.44 g) obtained in Example 133b) in DMF (50 ml) were added benzyl bromide (2.4 ml) and potassium carbonate (2.76 g), and the reaction mixture was stirred at 55° C. for 3.5 hr. The reaction mixture was allowed to cool to room temperature, water was added and the resulting precipitate was collected by filtration and washed with water to give the title compound as a brown powder (4.81 g, 97%).

NMR (CDCl$_3$) δ: 1.25 (3H, t, J=7.2), 3.48 (2H, dq, J=5.7, 7.4), 5.18 (2H, s), 6.05 (1H, brs), 6.99 (1H, d, J=8.1), 7.22 (1H, dd, J=1.9, 8.1), 7.31-7.47 (5H, m), 7.53 (1H, d, J=1.9).

137b) 1-{2-(benzyloxy)-4-[(ethylamino)carbonyl]phenyl}-5-(5-fluoropentyl)-1H-1,2,3-triazole-4-carboxylic acid In the same manner as in Example 134a), a crude product of the title compound was obtained as a brown amorphous substance (0.49 g, 72%) from 4-azido-3-(benzyloxy)-N-ethylbenzamide (0.44 g) obtained in Example 137a) and ethyl 8-fluoro-3-oxooctanoate (0.35 ml). The obtained crude product was used for the next reaction without further purification.

137c) 1-{2-(benzyloxy)-4-[(ethylamino)carbonyl]phenyl}-N-cyclopropyl-5-(5-fluoropentyl)-1H-1,2,3-triazole-4-carboxamide To a solution of 1-{2-(benzyloxy)-4-[(ethylamino)carbonyl]phenyl}-5-(5-fluoropentyl)-1H-1,2,3-triazole-4-carboxylic acid (0.49 g) obtained in Example 137b) in acetonitrile (5 ml) were successively added cyclopropylamine (0.09 ml), triethylamine (0.18 ml), HOBt (0.20 g) and WSC (0.25 g), and the reaction mixture was stirred at room temperature for 3.5 hr, and then at 60° C. for 1 hr. After allowing the reaction mixture to cool, the solvent was evaporated under reduced pressure. A saturated aqueous sodium hydrogen carbonate solution and ethyl acetate were added to the residue, and the organic layer was separated. The organic layer was dried over anhydrous sodium sulfate, and the solvent was evaporated under reduced pressure. The residue was purified by silica gel column (ethyl acetate/hexane=1/1 to ethyl acetate) to give the title compound as a colorless amorphous substance (0.31 g, 59%).

NMR (CDCl$_3$) δ: 0.65-0.70 (2H, m), 0.84-0.91 (2H, m), 1.23-1.30 (6H, m), 1.44-1.61 (4H, m), 2.85-2.94 (2H, m), 3.52 (2H, dq, J=5.7, 7.2), 4.28 (2H, td, J=6.0, 47.3), 5.14 (2H, s), 6.24 (1H, t, J=5.3), 7.18-7.21 (2H, m), 7.28-7.41 (6H, m), 7.70 (1H, d, J=1.1).

Example 138

N-cyclopropyl-1-[4-[(ethylamino)carbonyl]-2-(3-phenylpropoxy)phenyl]-5-(5-fluoropentyl)-1H-1,2,3-triazole-4-carboxamide

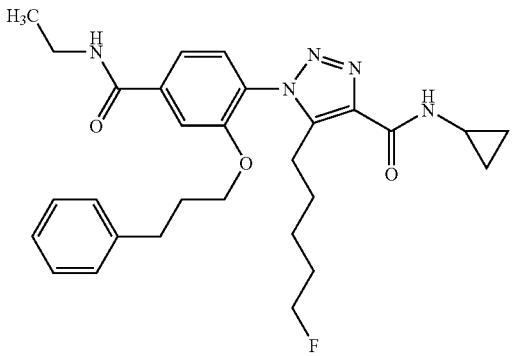

In the same manner as in Example 131c) and then Example 133d), the title compound was obtained as a colorless oil (0.26 g, yield in 2 steps 82%) from 1-{2-(benzyloxy)-4-[(ethylamino)carbonyl]phenyl}-N-cyclopropyl-5-(5-fluoropentyl)-1H-1,2,3-triazole-4-carboxamide (0.30 g) obtained in Example 137c).

NMR (CDCl$_3$) δ: 0.65-0.70 (2H, m), 0.84-0.91 (2H, m), 1.25-1.34 (6H, m), 1.48-1.65 (4H, m), 1.90-1.99 (2H, m), 2.51-2.57 (2H, m), 2.86-2.95 (2H, m), 3.52 (2H, dq, J=5.7, 7.4), 4.03 (2H, t, J=6.0), 4.32 (2H, td, J=6.0, 47.3), 6.30 (1H, t, J=5.5), 7.05-7.08 (2H, m), 7.14-7.27 (3H, m), 7.34-7.40 (3H, m), 7.55 (1H, s).

Example 139

N-cyclopropyl-1-{4-[(ethylamino)carbonyl]-2-hydroxyphenyl}-1H-1,2,3-triazole-4-carboxamide

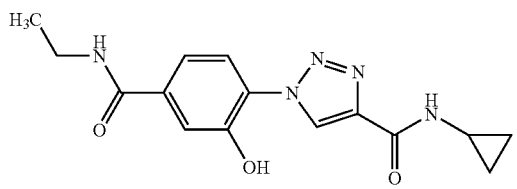

The product obtained in the same manner as in Example 133e) from ethyl 1-{4-[(ethylamino)carbonyl]-2-hydroxyphenyl}-1H-1,2,3-triazole-4-carboxylate (2.37 g) obtained in Example 133c) was dissolved in DMF (18 ml), cyclopropylamine (0.51 ml), triethylamine (1.01 ml), HOBt (1.12 g) and WSC (1.40 g) were successively added, and the mixture was stirred at room temperature overnight. Water was added to the reaction mixture, and the mixture was acidified with 1N hydrochloric acid. The precipitated crystals were collected by filtration and washed with water to give the title compound as a pale-brown powder (1.41 g, yield in 2 steps 59%).

NMR (DMSO-d$_6$) δ: 0.63-0.73 (4H, m), 1.13 (3H, t, J=7.4), 2.84-2.90 (1H, m), 3.27-3.31 (2H, m), 7.45 (1H, dd, J=1.9, 8.5), 8.58 (1H, t, J=5.7), 8.68 (1H, d, J=4.3), 8.89 (1H, s), 10.98 (1H, s).

Example 140

1-{2-(benzyloxy)-4-[(ethylamino)carbonyl]phenyl}-N-cyclopropyl-5-methyl-1H-1,2,3-triazole-4-carboxamide

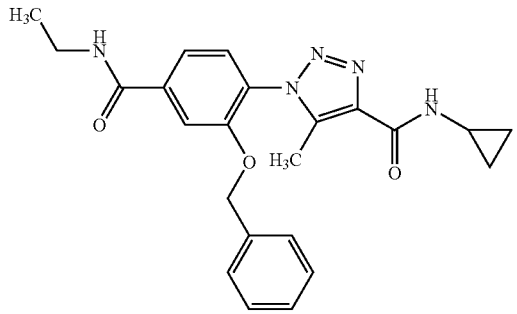

140a) 1-{2-(benzyloxy)-4-[(ethylamino)carbonyl]phenyl}-5-methyl-1H-1,2,3-triazole-4-carboxylic acid In the same manner as in Example 134a), the title compound was obtained as a pale-yellow solid (3.95 g, 70%) from 4-azido-3-(benzyloxy)-N-ethylbenzamide (4.38 g) obtained in Example 137a).

NMR (DMSO-d$_6$) δ: 1.16 (3H, t, J=7.2), 2.31 (3H, s), 3.29-3.38 (2H, m), 5.26 (2H, s), 7.25-7.38 (5H, m), 7.61 (1H, d, J=8.1), 7.65 (1H, dd, J=1.3, 8.1), 7.85 (1H, d, J=1.1), 8.71 (1H, t, J=5.5), 13.01 (1H, brs).

140b) 1-{2-(benzyloxy)-4-[(ethylamino)carbonyl]phenyl}-N-cyclopropyl-5-methyl-1H-1,2,3-triazole-4-carboxamide To a solution of 1-{2-(benzyloxy)-4-[(ethylamino)carbonyl]phenyl}-5-methyl-1H-1,2,3-triazole-4-carboxylic acid (3.95 g) obtained in Example 140a) in DMF (30 ml) were successively added cyclopropylamine (0.86 ml), triethylamine (1.73 ml), HOBt (1.91 g) and WSC (2.40 g), and the reaction mixture was stirred at room temperature overnight. Water was added to the reaction mixture, and the mixture was extracted with ethyl acetate. The organic layer was dried over anhydrous sodium sulfate, and the solvent was evaporated under reduced pressure. The residue was purified by silica gel column (ethyl acetate/hexane=1/1 to ethyl acetate) to give the title compound as a pale-yellow amorphous substance (3.30 g, 76%).

NMR (CDCl$_3$) δ: 0.64-0.69 (2H, m), 0.84-0.90 (2H, m), 1.28 (3H, t, J=7.4), 2.44 (3H, s), 2.85-2.94 (1H, m), 3.52 (2H, dq, J=5.7, 7.2), 5.15 (2H, s), 6.29 (1H, brs), 7.19-7.24 (2H, m), 7.29-7.39 (6H, m), 7.71 (1H, s).

Example 141

N-cyclopropyl-1-{4-[(ethylamino)carbonyl]-2-hydroxyphenyl}-5-methyl-1H-1,2,3-triazole-4-carboxamide

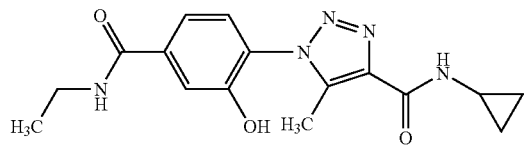

In the same manner as in Example 131c), the title compound was obtained as a pale-green powder (1.85 g, 73%) from 1-{2-(benzyloxy)-4-[(ethylamino)carbonyl]phenyl}-N-cyclopropyl-5-methyl-1H-1,2,3-triazole-4-carboxamide (3.21 g) obtained in Example 140b).

NMR (DMSO-d$_6$) δ: 0.63-0.71 (4H, m), 1.13 (3H, t, J=7.2), 2.36 (3H, s), 2.83-2.90 (1H, m), 3.25-3.32 (2H, m), 7.39-7.46 (2H, m), 7.52 (1H, s), 8.56-8.59 (2H, m), 10.88 (1H, s).

Example 142

1-{4-[(ethylamino)carbonyl]-2-(3-phenylpropoxy)phenyl}-1H-1,2,3-triazole-4-carboxamide

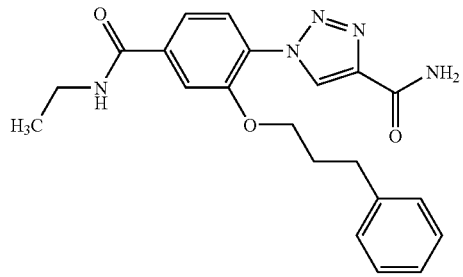

To a solution of 1-{4-[(ethylamino)carbonyl]-2-(3-phenylpropoxy)phenyl}-1H-1,2,3-triazole-4-carboxylic acid (0.14 g) obtained in Example 133e) in DMF (4 ml) were successively added HOBt-NH$_3$ (0.07 g), triethylamine (0.06 ml) and WSC (0.08 g), and the reaction mixture was stirred at room temperature overnight. Water was added to the reaction mixture and the deposited precipitate was collected by filtration, washed with water, and recrystallized from ethanol-water to give the title compound as a white powder (0.13 g, 89%).

NMR (DMSO-d$_6$) δ: 1.15 (3H, t, J=7.2), 1.97-2.04 (2H, m), 2.60-2.65 (2H, m), 3.28-3.37 (2H, m), 4.14-4.18 (2H, m), 7.14-7.18 (3H, m), 7.24-7.29 (2H, m), 7.61-7.64 (2H, m), 7.69 (1H, d, J=1.3), 7.80 (1H, d, J=8.3), 8.04 (1H, brs), 8.67 (1H, t, J=5.3), 8.94 (1H, s).

Example 143

1-{4-[(ethylamino)carbonyl]-2-(3-phenylpropoxy)phenyl}-N-(2-methoxyethyl)-1H-1,2,3-triazole-4-carboxamide

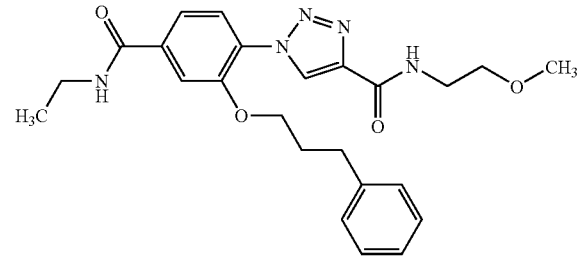

To a solution of 1-{4-[(ethylamino)carbonyl]-2-(3-phenylpropoxy)phenyl}-1H-1,2,3-triazole-4-carboxylic acid (0.14 g) obtained in Example 133e) in DMF (4 ml) were successively added 2-methoxyethylamine (0.04 ml), triethylamine (0.06 ml), HOBt (0.07 g) and WSC (0.08 g), and the mixture was stirred at room temperature overnight. Water was added to the reaction mixture and the deposited precipitate was collected by filtration, washed with water, and recrystallized from ethanol-water to give the title compound as a white powder (0.14 g, 86%).

NMR (CDCl$_3$) δ: 1.28 (3H, t, J=7.2), 2.10-2.19 (2H, m), 2.71 (2H, t, J=7.3), 3.41 (3H, s), 3.48-3.61 (4H, m), 3.67-3.73 (2H, m), 4.16 (2H, t, J=6.4), 6.15 (1H, t, J=4.9), 7.13-7.20 (3H, m), 7.25-7.29 (2H, m), 7.36 (1H, dd, J=1.7, 8.3), 7.52 (1H, t, J=5.5), 7.60 (1H, d, J=1.5), 7.89 (1H, d, J=8.1), 8.70 (1H, s).

Example 144

N-cyclopropyl-1-{4-[(ethylamino)carbonyl]-2-[(5-fluoropentyl)oxy]phenyl}-1H-1,2,3-triazole-4-carboxamide

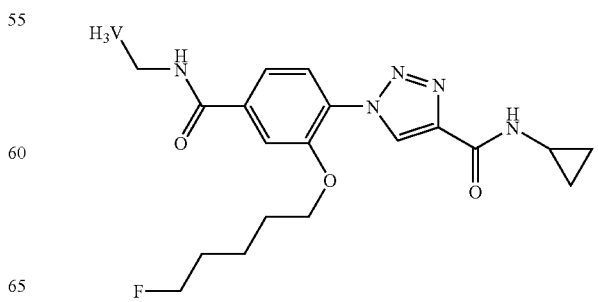

To a solution of N-cyclopropyl-1-{4-[(ethylamino)carbonyl]-2-hydroxyphenyl}-1H-1,2,3-triazole-4-carboxamide (0.16 g) obtained in Example 139 in DMF (5 ml) were added 1-bromo-5-fluoropentane (0.11 g) and potassium carbonate (0.07 g), and the mixture was stirred at 50° C. overnight. The reaction mixture was allowed to cool to room temperature, and water was added to the reaction mixture. The deposited precipitate was collected by filtration, washed with water, and recrystallized from ethanol-water to give the title compound as a pale-brown powder (0.12 g, 60%).

NMR (CDCl$_3$) δ: 0.68-0.72 (2H, m), 0.86-0.93 (2H, m), 1.29 (3H, t, J=7.2), 1.52-1.90 (7H, m), 2.93-2.96 (2H, m), 3.51-3.58 (2H, m), 4.19 (2H, t, J=6.6), 4.45 (2H, td, J=6.0, 47.3), 6.15 (1H, brs), 7.36 (1H, dd, J=1.7, 8.3), 7.65 (1H, d, J=1.7), 7.88 (1H, d, J=8.3), 8.68 (1H, s).

Example 145

N-cyclopropyl-1-{4-[(ethylamino)carbonyl]-2-[(5-fluoropentyl)oxy]phenyl}-5-methyl-1H-1,2,3-triazole-4-carboxamide

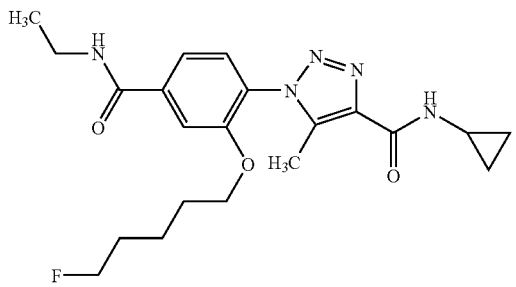

To a solution of N-cyclopropyl-1-{4-[(ethylamino)carbonyl]-2-hydroxyphenyl}-5-methyl-1H-1,2,3-triazole-4-carboxamide (0.17 g) obtained in Example 141 in DMF (5 ml) were added 1-bromo-5-fluoropentane (0.11 g) and potassium carbonate (0.07 g), and the mixture was stirred at 50° C. overnight. The reaction mixture was allowed to cool to room temperature, water was added to the reaction mixture, and the mixture was extracted with ethyl acetate-hexane (2:1). The organic layer was dried over anhydrous magnesium sulfate, and the solvent was evaporated under reduced pressure. The residue was purified by silica gel column (ethyl acetate) to give the title compound as a pale-yellow amorphous substance (0.16 g, 77%).

NMR (CDCl$_3$) δ: 0.65-0.70 (2H, m), 0.85-0.91 (2H, m), 1.29 (3H, t, J=7.2), 1.35-1.43 (2H, m), 1.57-1.76 (4H, m), 2.46 (3H, s), 2.87-2.95 (1H, m), 3.49-3.59 (2H, m), 4.07 (2H, t, J=6.6), 4.38 (2H, td, J=6.0, 47.3), 6.19 (1H, brs), 7.31-7.41 (3H, m), 7.61 (1H, d, J=1.3).

Example 146

N-cyclopropyl-1-{4-[(ethylamino)carbonyl]-2-(pent-4-yn-1-yloxy)phenyl}-1H-1,2,3-triazole-4-carboxamide

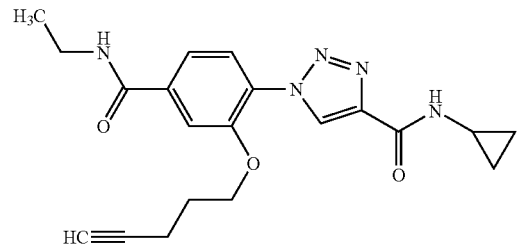

In the same manner as in Example 144, the title compound was obtained as a white powder (0.11 g, 57%) from N-cyclopropyl-1-{4-[(ethylamino)carbonyl]-2-hydroxyphenyl}-1H-1,2,3-triazole-4-carboxamide (0.16 g) obtained in Example 139 and 5-chloropent-1-yne (0.06 ml).

NMR (CDCl$_3$) δ: 0.67-0.73 (2H, m), 0.86-0.93 (2H, m), 1.29 (3H, t, J=7.2), 1.98-2.06 (3H, m), 2.31-2.36 (2H, m), 2.91-2.97 (1H, m), 3.49-3.58 (2H, m), 4.31 (2H, t, J=6.2), 6.21 (1H, t, J=4.9), 7.27 (1H, brs), 7.38 (1H, dd, J=1.7, 8.1), 7.69 (1H, d, J=1.5), 7.86 (1H, d, J=8.1), 8.67 (1H, s).

Example 147

N-cyclopropyl-1-{4-[(ethylamino)carbonyl]-2-(pent-4-yn-1-yloxy)phenyl}-5-methyl-1H-1,2,3-triazole-4-carboxamide

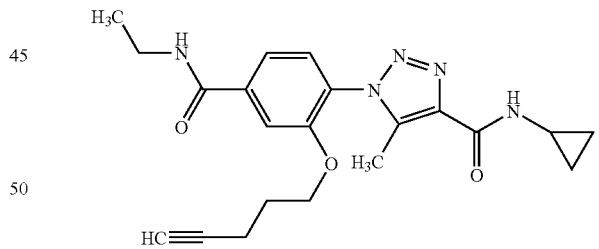

In the same manner as in Example 145, the title compound was obtained as a white solid (0.13 g, 66%) from N-cyclopropyl-1-{4-[(ethylamino)carbonyl]-2-hydroxyphenyl}-5-methyl-1H-1,2,3-triazole-4-carboxamide (0.17 g) obtained in Example 141 and 5-chloropent-1-yne (0.06 ml).

NMR (CDCl$_3$) δ: 0.65-0.71 (2H, m), 0.85-0.91 (2H, m), 1.29 (3H, t, J=7.2), 1.69 (1H, s), 1.82-1.91 (2H, m), 1.94 (1H, t, J=2.6), 2.18 (2H, dt, J=2.6, 6.6), 2.46 (3H, s), 3.49-3.58 (2H, m), 4.19 (2H, t, J=6.2), 6.31 (1H, t, J=5.3), 7.32 (1H, d, J=2.8), 7.38-7.39 (1H, m), 7.65-7.66 (1H, m), 8.01-8.02 (1H, m).

Example 148

N-cyclopropyl-1-{2-[2-(2-ethoxyethoxy)ethoxy]-4-[(ethylamino)carbonyl]phenyl}-1H-1,2,3-triazole-4-carboxamide

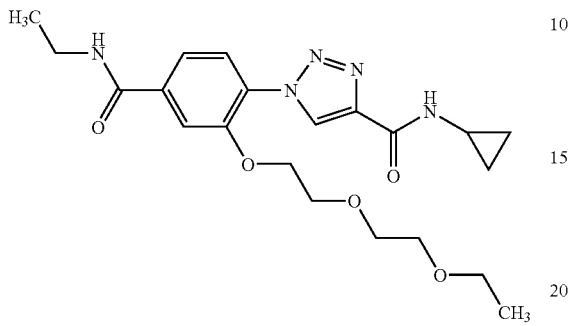

In the same manner as in Example 144, the title compound was obtained as a white powder (0.12 g, 56%) from N-cyclopropyl-1-{4-[(ethylamino)carbonyl]-2-hydroxyphenyl}-1H-1,2,3-triazole-4-carboxamide (0.16 g) obtained in Example 139 and 1-bromo-2-(2-ethoxyethoxy)ethane (0.09 ml).

NMR (CDCl$_3$) δ: 0.66-0.72 (2H, m), 0.86-0.92 (2H, m), 1.16 (2H, t, J=7.2), 1.29 (3H, t, J=7.4), 1.59-1.60 (2H, m), 2.89-2.98 (1H, m), 3.48-3.56 (4H, m), 3.66-3.75 (4H, m), 3.86-3.89 (2H, m), 4.34-4.37 (2H, m), 6.25 (1H, brs), 7.40 (1H, dd, J=1.9, 8.3), 7.67 (1H, d, J=1.7), 7.94 (1H, d, J=8.3), 8.93 (1H, s).

Example 149

1-{2-(2-butoxyethoxy)-4-[(ethylamino)carbonyl]phenyl}-N-cyclopropyl-1H-1,2,3-triazole-4-carboxamide

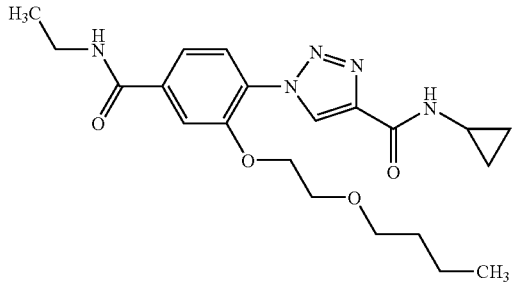

In the same manner as in Example 144, the title compound was obtained as a white powder (0.17 g, 82%) from N-cyclopropyl-1-{4-[(ethylamino)carbonyl]-2-hydroxyphenyl}-1H-1,2,3-triazole-4-carboxamide (0.16 g) obtained in Example 139 and 1-(2-chloroethoxy)butane (0.09 ml).

NMR (CDCl$_3$) δ: 0.66-0.71 (2H, m), 0.86-0.92 (5H, m), 1.26-1.40 (5H, m), 1.53-1.63 (2H, m), 2.91-2.97 (1H, m), 3.49-3.58 (4H, m), 3.77-3.80 (2H, m), 4.32-4.35 (2H, m), 6.15 (1H, brs), 7.25 (1H, brs), 7.38 (1H, dd, J=1.7, 8.3), 7.68 (1H, d, J=1.7), 7.94 (1H, d, J=8.3), 8.87 (1H, s).

Example 150

1-{2-(2-chloroethoxy)-4-[(ethylamino)carbonyl]phenyl}-N-cyclopropyl-1H-1,2,3-triazole-4-carboxamide

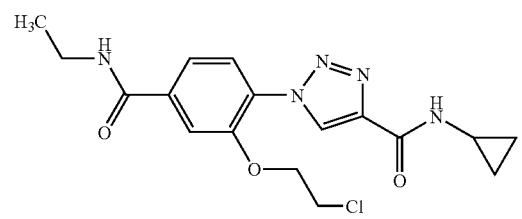

In the same manner as in Example 144, the title compound was obtained as a white powder (0.07 g, 38%) from N-cyclopropyl-1-{4-[(ethylamino)carbonyl]-2-hydroxyphenyl}-1H-1,2,3-triazole-4-carboxamide (0.16 g) obtained in Example 139 and 1-bromo-2-chloroethane (0.05 ml).

NMR (CDCl$_3$) δ: 0.67-0.72 (2H, m), 0.86-0.93 (2H, m), 1.29 (3H, t, J=7.4), 2.91-2.97 (1H, m), 3.49-3.59 (2H, m), 3.82-3.86 (2H, m), 4.45 (2H, t, J=5.5), 6.17 (1H, brs), 7.24 (1H, brs), 7.40 (1H, dd, J=1.5, 8.3), 7.67 (1H, d, J=1.5), 7.94 (1H, d, J=8.3), 8.83 (1H, s).

Example 151

1-{2-(2-chloroethoxy)-4-[(ethylamino)carbonyl]phenyl}-N-cyclopropyl-5-methyl-1H-1,2,3-triazole-4-carboxamide

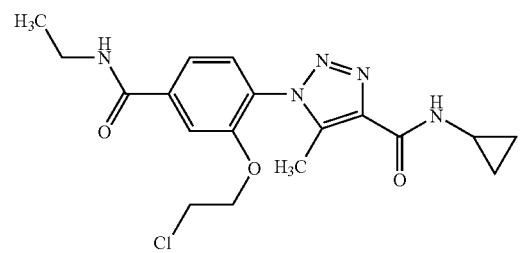

In the same manner as in Example 145, a product was obtained from N-cyclopropyl-1-{4-[(ethylamino)carbonyl]-2-hydroxyphenyl}-5-methyl-1H-1,2,3-triazole-4-carboxamide (0.17 g) obtained in Example 141 and 1-bromo-2-chloroethane (0.05 ml), and the title compound was obtained as a white powder (0.06 g, 31%) by recrystallization from ethyl acetate-hexane.

NMR (CDCl$_3$) δ: 0.65-0.71 (2H, m), 0.85-0.91 (2H, m), 1.30 (3H, t, J=7.4), 2.50 (3H, s), 2.88-2.94 (1H, m), 3.50-3.59 (2H, m), 3.67 (2H, t, J=5.5), 4.32 (2H, t, J=5.7), 6.17 (1H, brs), 7.31 (1H, brs), 7.38-7.44 (2H, m), 7.64 (1H, s).

Example 152

N-cyclopropyl-1-{2-[2-(3,4-dichlorophenoxy)ethoxy]-4-[(ethylamino)carbonyl]phenyl}-5-methyl-1H-1,2,3-triazole-4-carboxamide

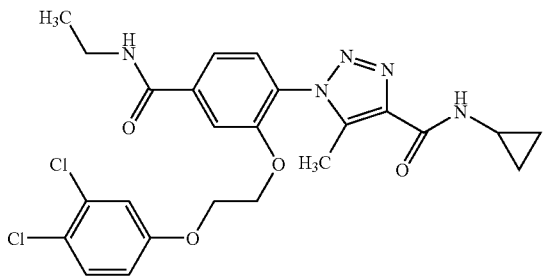

In the same manner as in Example 151, the title compound was obtained as a white powder (0.10 g, 38%) from 1-{2-(2-chloroethoxy)-4-[(ethylamino)carbonyl]phenyl}-N-cyclopropyl-5-methyl-1H-1,2,3-triazole-4-carboxamide (0.20 g) obtained in Example 151 and 3,4-dichlorophenol (0.16 g).

NMR (CDCl$_3$) δ: 0.65-0.71 (2H, m), 0.84-0.91 (2H, m), 1.30 (3H, t, J=7.4), 2.48 (3H, s), 2.85-2.96 (1H, m), 3.50-3.60 (2H, m), 4.14-4.17 (2H, m), 4.40-4.43 (2H, m), 6.17 (1H, brs), 6.69 (1H, dd, J=2.8, 8.9), 6.92 (1H, d, J=2.8), 7.27 (1H, brs), 7.30 (1H, d, J=8.9), 7.38-7.44 (2H, m), 7.72 (1H, d, J=1.1).

Example 153

N-cyclopropyl-1-{5-[(ethylamino)carbonyl]-2-(3-phenylpropoxy)phenyl}-1H-1,2,3-triazole-4-carboxamide

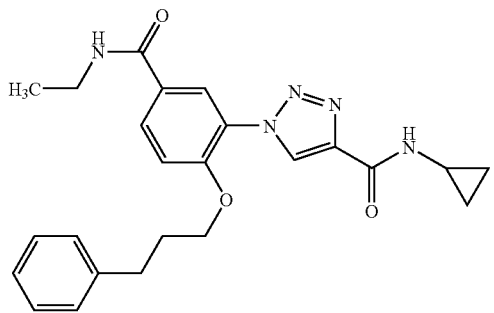

153a) N-ethyl-4-hydroxy-3-nitrobenzamide

In the same manner as in Example 131a), the title compound was obtained as a yellow powder (6.31 g, 100%) from 4-hydroxy-3-nitrobenzoic acid (5.49 g).

NMR (CDCl$_3$) δ: 1.27 (3H, t, J=7.4), 3.51 (2H, dq, J=5.7, 7.3), 6.31 (1H, brs), 7.21 (1H, d, J=8.9), 8.06 (1H, dd, J=2.3, 8.9), 8.51 (1H, d, J=2.3).

153b) 3-amino-N-ethyl-4-hydroxybenzamide

In the same manner as in Example 131c), a crude product of the title compound was obtained as a white powder (5.41 g, 100%) from N-ethyl-4-hydroxy-3-nitrobenzamide (6.31 g) obtained in Example 153a). The obtained crude product was used for the next reaction without further purification.

153c) 3-azido-N-ethyl-4-hydroxybenzamide

In the same manner as in Example 131d), the title compound was obtained as a red solid (4.63 g, 75%) from 3-amino-N-ethyl-4-hydroxybenzamide (5.41 g) obtained in Example 153b).

NMR (DMSO-d$_6$) δ: 1.10 (3H, t, J=7.2), 3.21-3.30 (2H, m), 6.91 (1H, d, J=8.5), 7.49 (1H, d, J=2.0), 7.55 (1H, dd, J=2.0, 8.5), 8.33 (1H, t, J=5.5), 10.65 (1H, brs).

153d) 1-{5-[(ethylamino)carbonyl]-2-hydroxyphenyl}-1H-1,2,3-triazole-4-carboxylic acid In the same manner as in Example 133c), a crude product of the title compound was obtained as a brown powder (0.83 g, 100%) from 3-azido-N-ethyl-4-hydroxybenzamide (0.62 g) obtained in Example 153c) and propiolic acid (0.58 ml). The obtained crude product was used for the next reaction without further purification.

153e) N-cyclopropyl-1-{5-[(ethylamino)carbonyl]-2-hydroxyphenyl}-1H-1,2,3-triazole-4-carboxamide In the same manner as in Example 131g), the title compound was obtained as a pale-yellow powder (0.54 g, 57%) from 1-{5-[(ethylamino)carbonyl]-2-hydroxyphenyl}-1H-1,2,3-triazole-4-carboxylic acid (0.83 g) obtained in Example 153d).

NMR (DMSO-d$_6$) δ: 0.62-0.71 (4H, m), 1.11 (3H, t, J=7.2), 3.23-3.32 (2H, m), 7.20 (1H, d, J=8.7), 7.90 (1H, dd, J=2.3, 8.7), 7.95 (1H, brs), 8.15 (1H, d, J=2.1), 8.49 (1H, t, J=5.5), 8.70 (1H, d, J=4.7), 8.87 (1H, s), 11.38 (1H, s).

153f) N-cyclopropyl-1-{5-[(ethylamino)carbonyl]-2-(3-phenylpropoxy)phenyl}-1H-1,2,3-triazole-4-carboxamide In the same manner as in Example 133d), the title compound was obtained as a white powder (0.14 g, 47%) from N-cyclopropyl-1-{5-[(ethylamino)carbonyl]-2-hydroxyphenyl}-1H-1,2,3-triazole-4-carboxamide (0.22 g) obtained in Example 153e).

NMR (CDCl$_3$) δ: 0.68-0.73 (2H, m), 0.87-0.93 (2H, m), 1.26 (3H, t, J=7.2), 2.08-2.18 (2H, m), 2.70 (2H, t, J=7.2), 2.92-2.99 (2H, m), 3.46-3.55 (2H, m), 4.12 (2H, t, J=6.6), 6.14 (1H, brs), 7.06-7.21 (4H, m), 7.25-7.30 (3H, m), 7.95 (1H, dd, J=2.3, 8.9), 8.14 (1H, d, J=2.1), 8.63 (1H, s).

Example 154

1-{5-[(ethylamino)carbonyl]-2-(3-phenylpropoxy)phenyl}-1H-1,2,3-triazole-4-carboxamide

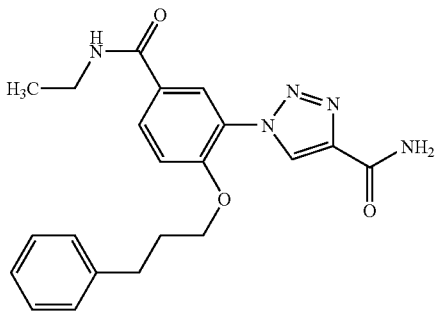

154a) ethyl 1-{5-[(ethylamino)carbonyl]-2-hydroxyphenyl}-1H-1,2,3-triazole-4-carboxylate In the same manner as in Example 133c), a crude product of the title compound was obtained as a brown powder (0.56 g, 61%) from 3-azido-N-ethyl-4-hydroxybenzamide (0.62 g) obtained in Example 153c). The obtained crude product was used for the next reaction without further purification.

154b) ethyl 1-{5-[(ethylamino)carbonyl]-2-(3-phenylpropoxy)phenyl}-1H-1,2,3-triazole-4-carboxylate In the same manner as in Example 133d), the title compound was obtained as a pale-yellow powder (0.47 g, 62%) from ethyl 1-{5-[(ethylamino)carbonyl]-2-hydroxyphenyl}-1H-1,2,3-triazole-4-carboxylate (0.61 g) obtained in Example 154a).

NMR (CDCl$_3$) δ: 1.25 (3H, t, J=7.2), 1.41 (3H, t, J=7.2), 2.08-2.17 (2H, m), 2.69-2.74 (2H, m), 3.50 (2H, dq, J=5.7, 7.2), 4.14 (2H, t, J=6.2), 4.45 (2H, q, J=7.2), 6.56 (1H, t, J=5.3), 7.09 (1H, d, J=8.7), 7.12-7.30 (5H, m), 7.99 (1H, dd, J=2.3, 8.7), 8.22 (1H, d, J=2.3), 8.63 (1H, s).

154c) 1-{5-[(ethylamino)carbonyl]-2-(3-phenylpropoxy)phenyl}-1H-1,2,3-triazole-4-carboxylic acid In the same manner as in Example 133e), the title compound was obtained as a pale-yellow powder (0.42 g, 97%) from ethyl 1-{5-[(ethylamino)carbonyl]-2-(3-phenylpropoxy)phenyl}-1H-1,2,3-triazole-4-carboxylate (0.47 g) obtained in Example 154b).

NMR (DMSO-d$_6$) δ: 1.13 (3H, t, J=7.2), 1.91-2.01 (2H, m), 2.59-2.64 (2H, m), 3.25-3.32 (2H, m), 4.15 (2H, t, J=6.0), 7.14-7.19 (3H, m), 7.24-7.29 (2H, m), 7.40 (1H, d, J=8.9), 8.05 (1H, dd, J=2.1, 8.9), 8.21 (1H, d, J=2.3), 8.56 (1H, t, J=5.5), 9.09 (1H, s), 13.30 (1H, s).

154d) 1-{5-[(ethylamino)carbonyl]-2-(3-phenylpropoxy)phenyl}-1H-1,2,3-triazole-4-carboxamide In the same manner as in Example 142, the title compound was obtained as a pale-yellow powder (0.14 g, 70%) from 1-{5-[(ethylamino)carbonyl]-2-(3-phenylpropoxy)phenyl}-1H-1,2,3-triazole-4-carboxylic acid (0.20 g) obtained in Example 154c).

NMR (CDCl$_3$) δ: 1.27 (3H, t, J=7.2), 2.09-2.18 (2H, m), 2.71 (2H, t, J=7.2), 3.51 (2H, dq, J=5.7, 7.4), 4.14 (2H, t, J=6.4), 5.68 (1H, brs), 6.16 (1H, brs), 7.08-7.22 (4H, m), 7.25-7.31 (2H, m), 7.96 (1H, dd, J=2.3, 8.7), 8.17 (1H, d, J=2.3), 8.69 (1H, s).

In the same manner as in Example 152, the compounds of Example 155 to Example 165 were synthesized.

Example 155

1-{2-[2-(3-chlorophenoxy)ethoxy]-4-[(ethylamino)carbonyl]phenyl}-N-cyclopropyl-5-methyl-1H-1,2,3-triazole-4-carboxamide NMR (CDCl$_3$) δ: 0.63-0.68 (2H, m), 0.83-0.89 (2H, m), 1.30 (3H, t, J=7.2), 2.48 (3H, s), 2.86-2.93 (1H, m), 3.50-3.59 (2H, m), 4.16-4.19 (2H, m), 4.40-4.43 (2H, m), 6.18 (1H, brs), 6.72 (1H, ddd, J=0.9, 2.4, 8.3), 6.82 (1H, t, J=2.3), 6.94 (1H, ddd, J=0.9, 1.9, 7.9), 7.18 (1H, t, J=8.1), 7.28 (1H, brs), 7.38-7.44 (2H, m), 7.71 (1H, brs).

Example 156

1-{2-[2-(4-bromophenoxy)ethoxy]-4-[(ethylamino)carbonyl]phenyl}-N-cyclopropyl-5-methyl-1H-1,2,3-triazole-4-carboxamide NMR (CDCl$_3$) δ: 0.63-0.69 (2H, m), 0.84-0.90 (2H, m), 1.30 (3H, t, J=7.2), 2.49 (3H, s), 2.85-2.94 (1H, m), 3.50-3.59 (2H, m), 4.14-4.17 (2H, m), 4.39-4.42 (2H, m), 6.18 (1H, brs), 6.88-6.73 (2H, m), 7.27 (1H, brs), 7.32-7.37 (2H, m), 7.40-7.44 (2H, m), 7.71 (1H, d, J=0.9).

Example 157

1,1'-[ethane-1,2-diylbis(oxy{4-[(ethylamino)carbonyl]-2,1-phenylene})]bis(N-cyclopropyl-5-methyl-1H-1,2,3-triazole-4-carboxamide)

NMR (CDCl$_3$) δ: 0.62-0.73 (4H, m), 0.80-0.93 (4H, m), 1.30 (6H, t, J=7.3), 2.34 (6H, s), 2.81-2.94 (2H, m), 3.45-3.61 (4H, m), 4.22 (4H, s), 6.69 (2H, t, J=6.0), 7.30-7.53 (8H, m).

Example 158

1-(2-{2-[(6-chloropyridin-3-yl)oxy]ethoxy}-4-[(ethylamino)carbonyl]phenyl)-N-cyclopropyl-5-methyl-1H-1,2,3-triazole-4-carboxamide NMR (DMSO-d$_6$) δ: 0.62-0.67 (4H, m), 1.17 (3H, t, J=7.2), 2.36 (3H, s), 2.82-2.88 (1H, m), 3.30-3.39 (2H, m), 4.31-4.34 (2H, m), 4.48-4.50 (2H, m), 7.38 (2H, d, J=1.9), 7.57 (1H, d, J=8.1), 7.64 (1H, dd, J=1.5, 8.1), 7.79 (1H, d, J=1.5), 8.05 (1H, t, J=1.9), 8.54 (1H, d, J=4.5), 8.69 (1H, t, J=5.5).

Example 159

1-{2-[2-(5-chloro-2-oxopyridin-1(2H)-yl)ethoxy]-4-[(ethylamino)carbonyl]phenyl}-N-cyclopropyl-1H-1,2,3-triazole-4-carboxamide NMR (DMSO-d$_6$) δ: 0.60-0.75 (5H, m), 1.16 (3H, t, J=7.2), 2.85-2.93 (1H, m), 3.27-3.33 (3H, m), 4.30-4.34 (2H, m), 4.43-4.46 (2H, m), 6.39 (1H, d, J=9.8), 7.42 (1H, dd, J=3.0, 9.8), 7.59-7.64 (2H, m), 8.66-8.67 (2H, m), 8.91 (1H, s).

Example 160

1-{2-{2-[(5-chloropyridin-2-yl)oxy]ethoxy}-4-[(ethylamino)carbonyl]phenyl}-N-cyclopropyl-1H-1,2,3-triazole-4-carboxamide NMR (DMSO-$d_6$) δ: 0.61-0.73 (4H, m), 1.16 (3H, t, J=7.2), 2.84-2.90 (1H, m), 3.34-3.37 (2H, m), 4.54-4.60 (4H, m), 6.94 (1H, d, J=9.2), 7.65 (1H, dd, J=1.5, 8.3), 7.79-7.84 (3H, m), 8.19-8.20 (1H, m), 8.67 (1H, t, J=4.7), 8.91 (1H, s).

Example 161

1-{2-{2-[(6-chloropyridin-3-yl)oxy]ethoxy}-4-[(ethylamino)carbonyl]phenyl}-N-cyclopropyl-1H-1,2,3-triazole-4-carboxamide NMR (DMSO-$d_6$) δ: 0.61-0.72 (4H, m), 1.16 (3H, t, J=7.2), 2.83-2.89 (1H, m), 3.29-3.38 (2H, m), 4.42-4.44 (2H, m), 4.56-4.58 (2H, m), 7.40 (1H, d, J=8.5), 7.52 (1H, dd, J=3.2, 8.7), 7.65 (1H, dd, J=1.5, 8.3), 7.82-7.84 (2H, m), 8.16 (1H, d, J=2.8), 8.64-8.69 (2H, m), 8.93 (1H, s).

Example 162

1-{2-[2-(5-chloro-2-oxopyridin-1(2H)-yl)ethoxy]-4-[(ethylamino)carbonyl]phenyl}-N-cyclopropyl-5-methyl-1H-1,2,3-triazole-4-carboxamide NMR (DMSO-$d_6$) δ: 0.63-0.69 (4H, m), 1.16 (3H, t, J=7.2), 2.25 (3H, s), 2.83-2.89 (1H, m), 3.28-3.37 (2H, m), 4.19 (2H, t, J=5.3), 4.39 (2H, t, J=5.3), 6.35-6.39 (1H, m), 7.39-7.43 (2H, m), 7.51 (1H, d, J=8.1), 7.62 (1H, dd, J=1.5, 8.1), 7.72 (1H, d, J=1.5), 8.50 (1H, d, J=4.5), 8.68 (1H, t, J=5.7).

Example 163

1,1'-[but-2-yn-1,4-diylbis(oxy{4-[(ethylamino)carbonyl]-2,1-phenylene})]bis(N-cyclopropyl-1H-1,2,3-triazole-4-carboxamide)

NMR (DMSO-$d_6$) δ: 0.65-0.73 (8H, m), 1.09 (6H, t, J=7.2), 2.85-2.91 (2H, m), 3.21-3.25 (4H, m), 5.09-5.12 (4H, m), 7.59 (2H, dd, J=1.3, 8.3), 7.68-7.72 (4H, m), 8.51 (2H, t, J=5.3), 8.69-8.70 (2H, m), 8.83 (2H, s).

Example 164

N-cyclopropyl-1-{4-[(ethylamino)carbonyl]-2-[2-(2-phenoxyethoxy)ethoxy]phenyl}-5-methyl-1H-1,2,3-triazole-4-carboxamide NMR (CDCl$_3$) δ: 0.64-0.68 (2H, m), 0.83-0.90 (2H, m), 1.27 (3H, t, J=7.4), 2.50 (3H, s), 2.86-2.92 (1H, m), 3.50 (2H, dq, J=5.7, 7.2), 3.71-3.74 (2H, m), 3.77-3.80 (2H, m), 4.03-4.06 (2H, m), 4.24-4.27 (2H, m), 6.18 (1H, t, J=5.7), 6.86-6.97 (3H, m), 7.23-7.30 (3H, m), 7.37-7.43 (2H, m), 7.65 (1H, brs).

Example 165

N-cyclopropyl-1-{4-[(ethylamino)carbonyl]-2-[2-(ethylthio)ethoxy]phenyl}-1H-1,2,3-triazole-4-carboxamide NMR (CDCl$_3$) δ: 0.66-0.72 (2H, m), 0.86-0.93 (2H, m), 1.12-1.26 (2H, m), 1.26 (3H, t, J=7.4), 1.29 (3H, t, J=7.2), 2.58 (2H, q, J=7.4), 2.90-2.97 (2H, m), 3.54 (2H, dq, J=5.7, 7.2), 4.31-4.35 (2H, m), 6.18 (1H, brs), 7.38 (1H, dd, J=1.7, 8.3), 7.66 (1H, d, J=1.7), 7.90 (1H, d, J=8.1), 8.83 (1H, s).

In the same manner as in Examples 134a)-c) or Example 139 and Example 144, the compounds of Example 166 to Example 195 were synthesized.

Example 166

1-{2-(benzyloxy)-4-[(ethylamino)carbonyl]phenyl}-N-cyclopropyl-1H-1,2,3-triazole-4-carboxamide NMR (DMSO-$d_6$) δ: 0.62-0.72 (4H, m), 1.16 (3H, t, J=7.2), 2.83-2.89 (1H, m), 3.26-3.31 (2H, m), 5.31 (2H, s), 7.32-7.41 (5H, m), 7.64 (1H, dd, J=1.5, 8.3), 7.89 (1H, d, J=8.3), 7.84 (1H, d, J=1.5), 8.67-8.71 (2H, m), 8.91 (1H, s).

Example 167

N-cyclopropyl-1-{5-[(ethylamino)carbonyl]-2-(3-phenylpropoxy)phenyl}-5-methyl-1H-1,2,3-triazole-4-carboxamide NMR (CDCl$_3$) δ: 0.64-0.72 (2H, m), 0.82-0.93 (2H, m), 1.21-1.30 (3H, m), 1.91-2.03 (2H, m), 2.48 (3H, s), 2.56 (2H, t, J=7.4), 2.89-2.95 (1H, m), 3.49 (2H, dq, J=5.7, 7.2), 4.02 (2H, t, J=6.5), 6.16-6.26 (1H, m), 7.01-7.10 (3H, m), 7.14-7.30 (2H, m), 7.33 (1H, d, J=2.8), 7.77 (1H, d, J=2.3), 7.97 (1H, d, J=2.3), 7.99-8.03 (1H, m)

Example 168

1-{2-[2-(4-chlorophenoxy)ethoxy]-5-[(ethylamino)carbonyl]phenyl}-N-cyclopropyl-5-methyl-1H-1,2,3-triazole-4-carboxamide NMR (CDCl$_3$) δ: 0.62-0.69 (2H, m), 0.83-0.90 (2H, m), 1.25 (3H, t, J=7.2), 2.46 (3H, s), 2.84-2.93 (1H, m), 3.45-3.54 (2H, m), 4.14-4.17 (2H, m), 4.37-4.40 (2H, m), 6.27 (1H, brs), 6.71-6.76 (2H, m), 7.18-7.23 (3H, m), 7.28 (1H, brs), 7.78 (1H, d, J=2.1), 8.05 (1H, dd, J=2.3, 8.9).

Example 169

1-{5-[(ethylamino)carbonyl]-2-(3-phenylpropoxy)phenyl}-5-methyl-1H-1,2,3-triazole-4-carboxamide NMR (CDCl$_3$) δ: 1.25 (3H, t, J=7.4), 1.95-2.04 (2H, m), 2.49 (3H, s), 2.57 (2H, t, J=7.4), 3.50 (2H, dq, J=5.7, 7.2), 4.03 (2H, t, J=6.4), 5.51 (1H, brs), 6.06 (1H, brs), 7.05-7.29 (7H, m), 7.77 (1H, d, J=2.3), 7.99 (1H, dd, J=2.3, 8.7).

Example 170

1-{2-[2-(4-chlorophenoxy)ethoxy]-5-[(ethylamino)carbonyl]phenyl}-5-methyl-1H-1,2,3-triazole-4-carboxamide NMR (CDCl$_3$) δ: 1.26 (3H, t, J=7.2), 2.48 (3H, s), 3.50 (2H, dq, J=5.7, 7.2), 4.16-4.19 (2H, m), 4.39-4.42 (2H, m), 5.50 (1H, brs), 6.13 (1H, t, J=5.3), 6.72-6.77 (2H, m), 7.08 (1H, brs), 7.19-7.24 (2H, m), 7.78 (1H, d, J=2.3), 8.02 (1H, brs), 8.05 (1H, dd, J=2.3, 8.7).

Example 171

N-cyclopropyl-1-{4-[(ethylamino)carbonyl]-2-(pyridin-2-ylmethoxy)phenyl}-1H-1,2,3-triazole-4-carboxamide NMR (DMSO-d$_6$) δ: 0.60-0.74 (4H, m), 1.15 (3H, t, J=7.3), 2.79-2.96 (1H, m), 3.25-3.39 (2H, m), 5.42 (2H, s), 7.31-7.45 (2H, m), 7.66 (1H, dd, J=8.3, 1.7), 7.76-7.87 (3H, m), 8.55-8.62 (2H, m), 8.64-8.73 (2H, m), 9.10 (1H, s)

Example 172

1-{4-[(ethylamino)carbonyl]-2-(pent-4-en-1-yloxy)phenyl}-1H-1,2,3-triazole-4-carboxamide NMR (CDCl$_3$) δ: 1.29 (3H, t, J=7.4), 1.88-1.97 (2H, m), 2.13-2.21 (2H, m), 3.49-3.59 (2H, m), 4.19 (2H, t, J=6.6), 4.99-5.06 (2H, m), 5.60 (1H, brs), 5.73-5.82 (1H, m), 6.15 (1H, brs), 7.09 (1H, brs), 7.36 (1H, dd, J=1.5, 8.3), 7.66 (1H, d, J=1.3), 7.91 (1H, d, J=8.3), 8.73 (1H, s).

Example 173

1-{4-[(ethylamino)carbonyl]-2-[(5-fluoropentyl)oxy]phenyl}-1H-1,2,3-triazole-4-carboxamide NMR (DMSO-d$_6$) δ: 1.16 (3H, t, J=7.2), 1.38-1.46 (2H, m), 1.56-1.77 (4H, m), 3.28-3.37 (2H, m), 4.18 (2H, t, J=6.4), 4.41 (2H, td, J=6.0, 47.5), 7.59 (1H, brs), 7.62 (1H, dd, J=1.7, 8.1), 7.72 (1H, d, J=1.5), 7.78 (1H, d, J=8.1), 8.00 (1H, brs), 8.67 (1H, t, J=5.5), 8.85 (1H, s).

Example 174

1-{2-[(2,6-difluorobenzyl)oxy]-4-[(ethylamino)carbonyl]phenyl}-1H-1,2,3-triazole-4-carboxamide NMR (CDCl$_3$) δ: 1.31 (3H, t, J=7.2), 3.51-3.60 (2H, m), 5.35 (2H, s), 5.51 (1H, brs), 6.14 (1H, brs), 6.93-7.03 (3H, m), 7.32-7.38 (1H, m), 7.44 (1H, dd, J=1.7, 8.1), 7.85 (1H, d, J=1.3), 7.93 (1H, d, J=8.3), 8.66 (1H, s).

Example 175

1-{2-[(3-bromobenzyl)oxy]-4-[(ethylamino)carbonyl]phenyl}-1H-1,2,3-triazole-4-carboxamide NMR (DMSO-d$_6$) δ: 1.16 (3H, t, J=7.2), 3.28-3.37 (2H, m), 5.32 (2H, s), 7.33 (1H, t, J=7.7), 7.38-7.41 (1H, m), 7.50-7.58 (3H, m), 7.65 (1H, dd, J=1.5, 8.3), 7.79-7.82 (2H, m), 7.99 (1H, brs), 8.68 (1H, t, J=5.5), 8.95 (1H, s).

Example 176

1-(4-[(ethylamino)carbonyl]-2-{[3-(trifluoromethyl)benzyl]oxy}phenyl)-1H-1,2,3-triazole-4-carboxamide NMR (DMSO-d$_6$) δ: 1.16 (3H, t, J=7.2), 3.29-3.38 (2H, m), 5.42 (2H, s), 7.56-7.71 (6H, m), 7.81 (1H, d, J=8.3), 7.84 (1H, d, J=1.5), 7.96 (1H, brs), 8.69 (1H, t, J=5.5), 8.96 (1H, s).

Example 177

1-(2-(pent-4-en-1-yloxy)-4-{[(2,2,2-trifluoroethyl)amino]carbonyl}phenyl)-1H-1,2,3-triazole-4-carboxamide NMR (DMSO-d$_6$) δ: 1.75-1.84 (2H, m), 2.06-2.13 (2H, m), 4.09-4.21 (4H, m), 4.93-5.03 (2H, m), 5.73-5.87 (1H, m), 7.60 (1H, brs), 7.68 (1H, dd, J=1.5, 8.3), 7.76 (1H, d, J=1.5), 7.84 (1H, d, J=8.1), 8.02 (1H, brs), 8.89 (1H, s), 9.30 (1H, t, J=6.2).

Example 178

1-(2-[(5-fluoropentyl)oxy]-4-{[(2,2,2-trifluoroethyl)amino]carbonyl}phenyl)-1H-1,2,3-triazole-4-carboxamide NMR (DMSO-d$_6$) δ: 1.36-1.46 (2H, m), 1.56-1.77 (4H, m), 4.12-4.22 (4H, m), 4.33 (1H, t, J=6.0), 4.49 (1H, t, J=6.0), 7.59 (1H, brs), 7.68 (1H, dd, J=1.7, 8.3), 7.78 (1H, d, J=1.5), 7.84 (1H, d, J=8.3), 8.01 (1H, brs), 8.87 (1H, s), 9.29 (1H, t, J=6.0).

Example 179

1-(2-[(2,6-difluorobenzyl)oxy]-4-{[(2,2,2-trifluoroethyl)amino]carbonyl}phenyl)-1H-1,2,3-triazole-4-carboxamide NMR (DMSO-d$_6$) δ: 4.12-4.24 (2H, m), 5.38 (2H, s), 7.12-7.20 (2H, m), 7.46-7.56 (2H, m), 7.73 (1H, dd, J=1.3, 8.3), 7.85 (1H, d, J=8.3), 7.97 (1H, brs), 8.02 (1H, d, J=1.3), 8.67 (1H, s), 9.33 (1H, t, J=6.0).

Example 180

1-(2-[(3-bromobenzyl)oxy]-4-{[(2,2,2-trifluoroethyl)amino]carbonyl}phenyl)-1H-1,2,3-triazole-4-carboxamide NMR (DMSO-d$_6$) δ: 4.10-4.22 (2H, m), 5.34 (2H, s), 7.33 (1H, t, J=7.7), 7.39-7.42 (1H, m), 7.51-7.59 (3H, m), 7.72 (1H, dd, J=1.3, 8.1), 7.85-7.87 (2H, m), 7.99 (1H, brs), 8.96 (1H, s), 9.31 (1H, t, J=5.7).

Example 181

1-(4-{[(2,2,2-trifluoroethyl)amino]carbonyl}-2-{[3-(trifluoromethyl)benzyl]oxy}phenyl)-1H-1,2,3-triazole-4-carboxamide NMR (DMSO-d$_6$) δ: 4.10-4.22 (2H, m), 5.44 (2H, s), 7.57-7.75 (6H, m), 7.85-7.90 (2H, m), 7.97 (1H, brs), 8.97 (1H, s), 9.30-9.34 (1H, m).

Example 182

1-{2-[(6-chlorohexyl)oxy]-4-[(ethylamino)carbonyl]phenyl}-N-cyclopropyl-1H-1,2,3-triazole-4-carboxamide NMR (DMSO-d$_6$) δ: 0.62-0.73 (4H, m), 1.15 (3H, t, J=7.2), 1.32-1.41 (4H, m), 1.64-1.75 (4H, m), 2.85-2.91 (1H, m), 3.28-3.37 (2H, m), 3.60 (2H, t, J=6.6), 4.16 (2H, t, J=6.2), 7.61 (1H, dd, J=1.7, 8.1), 7.71 (1H, d, J=1.5), 7.77 (1H, d, J=8.1), 8.65-8.68 (2H, m), 8.85 (1H, s).

Example 183

N-cyclopropyl-1-{4-[(ethylamino)carbonyl]-2-[(6-hydroxyhexyl)oxy]phenyl}-1H-1,2,3-triazole-4-carboxamide NMR (DMSO-d$_6$) δ: 0.63-0.73 (4H, m), 1.15 (3H, t, J=7.2), 1.28-1.41 (6H, m), 1.65-1.71 (2H, m), 2.85-2.91 (1H, m), 3.28-3.39 (4H, m), 4.16 (2H, t, J=6.6), 4.32 (1H, t, J=5.1), 7.61 (1H, dd, J=1.5, 8.3), 7.71 (1H, d, J=1.5), 7.77 (1H, d, J=8.1), 8.65-8.69 (2H, m), 8.84 (1H, s).

Example 184

1-(2-(4,4,4-trifluorobutoxy)-4-{[(2,2,2-trifluoroethyl)amino]carbonyl}phenyl)-1H-1,2,3-triazole-4-carboxamide NMR (DMSO-d$_6$) δ: 1.91-1.98 (2H, m), 2.28-2.37 (2H, m), 4.10-4.18 (2H, m), 4.22-4.27 (2H, m), 7.59 (1H, brs), 7.70 (1H, dd, J=1.5, 8.3), 7.77 (1H, d, J=1.3), 7.84 (1H, d, J=8.3), 8.01 (1H, brs), 8.94 (1H, s), 9.31 (1H, t, J=6.2).

Example 185

1-{2-[2-(4-chlorophenoxy)ethoxy]-4-[(ethylamino)carbonyl]phenyl}-5-methyl-1H-1,2,3-triazole-4-carboxamide NMR (CDCl$_3$) δ: 1.30 (3H, t, J=7.2), 3.50-3.60 (2H, m), 4.16-4.19 (2H, m), 4.40-4.43 (2H, m), 5.47 (1H, brs), 6.17 (1H, brs), 6.72-6.78 (2H, m), 7.07 (1H, brs), 7.18-7.24 (2H, m), 7.40 (1H, dd, J=1.7, 8.1), 7.44 (1H, d, J=8.1), 7.72 (1H, d, J=1.3).

Example 186

1-(2-[2-(4-chlorophenoxy)ethoxy]-4-{[(2,2,2-trifluoroethyl)amino]carbonyl}phenyl)-5-methyl-1H-1,2,3-triazole-4-carboxamide NMR (DMSO-d$_6$) δ: 2.38 (3H, s), 4.11-4.25 (4H, m), 4.48-4.51 (2H, m), 6.87-6.92 (2H, m), 7.26-7.31 (2H, m), 7.47 (1H, brs), 7.63 (1H, d, J=8.3), 7.71 (1H, dd, J=1.7, 8.1), 7.86 (1H, d, J=1.5), 7.88 (1H, brs), 9.33 (1H, t, J=6.2).

Example 187

1-{2-(3-chloropropoxy)-4-[(ethylamino)carbonyl]phenyl}-N-cyclopropyl-1H-1,2,3-triazole-4-carboxamide NMR (DMSO-d$_6$) δ: 0.62-0.70 (4H, m), 1.16 (3H, t, J=7.2), 2.14-2.24 (2H, m), 2.85-2.91 (1H, m), 3.29-3.38 (2H, m), 3.67-3.71 (2H, m), 4.26-4.31 (2H, m), 7.62-7.65 (1H, m), 7.74-7.77 (2H, m), 8.68-8.70 (2H, m), 8.90 (1H, s).

Example 188

1-{2-[(4-chlorobut-2-yn-1-yl)oxy]-4-[(ethylamino)carbonyl]phenyl}-N-cyclopropyl-1H-1,2,3-triazole-4-carboxamide NMR (CDCl$_3$) δ: 0.67-0.72 (2H, m), 0.87-0.93 (2H, m), 1.29 (3H, t, J=7.2), 2.90-2.99 (1H, m), 3.49-3.58 (2H, m), 4.15 (2H, s), 4.93 (2H, s), 6.22 (1H, t, J=5.7), 7.28 (1H, brs), 7.48 (1H, dd, J=1.5, 8.3), 7.72 (1H, d, J=1.5), 7.92 (1H, d, J=8.3), 8.70 (1H, s).

Example 189

1-{2-(4-chlorobutoxy)-4-[(ethylamino)carbonyl]phenyl}-N-cyclopropyl-1H-1,2,3-triazole-4-carboxamide NMR (CDCl$_3$) δ: 0.67-0.72 (2H, m), 0.86-0.93 (2H, m), 1.29 (3H, t, J=7.2), 1.83-1.91 (2H, m), 1.95-2.04 (2H, m), 2.91-2.97 (1H, m), 3.49-3.58 (4H, m), 4.21 (2H, t, J=6.2), 6.20 (1H, brs), 7.28 (1H, brs), 7.37 (1H, dd, J=1.7, 8.3), 7.66 (1H, d, J=1.7), 7.86 (1H, d, J=8.3), 8.64 (1H, s).

Example 190

N-cyclopropyl-1-{4-[(ethylamino)carbonyl]-2-(2-fluoroethoxy)phenyl}-1H-1,2,3-triazole-4-carboxamide NMR (DMSO-d$_6$) δ: 0.61-0.75 (4H, m), 1.16 (3H, t, J=7.3), 2.80-2.93 (1H, m), 3.25-3.40 (2H, m), 4.35-4.56 (2H, m), 4.61-4.86 (2H, m), 7.65 (1H, dd, J=8.2, 1.6), 7.75 (1H, d, J=1.5), 7.81 (1H, d, J=8.1), 8.63-8.75 (2H, m), 8.87 (1H, s).

Example 191

N-cyclopropyl-1-{4-[(ethylamino)carbonyl]-3-(3-phenylpropoxy)phenyl}-1H-1,2,3-triazole-4-carboxamide NMR (DMSO-d$_6$) δ: 0.64-0.71 (4H, m), 1.15 (3H, t, J=7.2), 2.10-2.15 (2H, m), 2.73-2.81 (2H, m), 2.89-2.92 (1H, m), 3.33-3.41 (2H, m), 4.23 (2H, t, J=6.2), 7.17-7.33 (5H, m), 7.63-7.67 (2H, m), 7.86 (1H, d, J=8.3), 8.17 (1H, t, J=5.7), 8.73 (1H, d, J=4.7), 9.42 (1H, s).

Example 192

N-cyclopropyl-1-{4-[(ethylamino)carbonyl]-3-(pent-4-en-1-yloxy)phenyl}-1H-1,2,3-triazole-4-carboxamide NMR (DMSO-d$_6$) δ: 0.67-0.71 (4H, m), 1.14 (3H, t, J=7.2), 1.87-1.96 (2H, m), 2.19-2.30 (2H, m), 2.87-2.93 (1H, m), 3.26-3.33 (2H, m), 4.24 (2H, t, J=6.2), 4.99-5.11 (2H, m), 5.83-5.94 (1H, m), 7.63-7.68 (2H, m), 7.86 (1H, d, J=8.3), 8.12 (1H, t, J=5.3), 8.73 (1H, d, J=4.5), 9.44 (1H, s).

Example 193

N-cyclopropyl-1-{4-[(ethylamino)carbonyl]-2-[2-(tetrahydro-2H-pyran-2-yloxy)ethoxy]phenyl}-1H-1,2,3-triazole-4-carboxamide NMR (DMSO-$d_6$) δ: 0.60-0.73 (4H, m), 1.16 (3H, t, J=7.4), 1.38-1.63 (5H, m), 2.82-2.90 (1H, m), 3.31-3.42 (4H, m), 3.57-3.72 (2H, m), 3.87-3.93 (1H, m), 4.33-4.38 (2H, m), 4.56-4.58 (1H, m), 7.63 (1H, dd, J=1.5, 8.3), 7.76 (1H, d, J=1.5), 7.82 (1H, d, J=8.3), 8.65-8.68 (2H, m), 8.90 (1H, s).

Example 194

N-cyclopropyl-1-{4-[(ethylamino)carbonyl]-2-(4-fluorobutoxy)phenyl}-1H-1,2,3-triazole-4-carboxamide NMR (CDCl$_3$) δ: 0.67-0.72 (2H, m), 0.86-0.93 (2H, m), 1.29 (3H, t, J=7.2), 1.71-1.88 (2H, m), 1.92-2.01 (2H, m), 2.90-2.99 (1H, m), 3.54 (2H, dq, J=5.7, 7.2), 4.23 (2H, t, J=6.6), 4.48 (2H, td, J=5.7, 47.1), 6.22 (1H, t, J=5.3), 7.29 (1H, brs), 7.37 (1H, dd, J=1.7, 8.3), 7.66 (1H, d, J=1.7), 7.86 (1H, d, J=8.3), 8.66 (1H, s).

Example 195

1-{2-[2-(cyclohexyloxy)ethoxy]-4-[(ethylamino)carbonyl]phenyl}-N-cyclopropyl-1H-1,2,3-triazole-4-carboxamide NMR (DMSO-$d_6$) δ: 0.61-0.73 (4H, m), 1.11-1.18 (8H, m), 1.45-1.87 (5H, m), 2.83-2.90 (1H, m), 3.20-3.37 (3H, m), 3.71-3.74 (2H, m), 4.28-4.31 (2H, m), 7.62 (1H, dd, J=1.5, 8.3), 7.74 (1H, d, J=1.5), 7.83 (1H, d, J=8.3), 8.64-8.68 (2H, m), 8.91 (1H, s).

In the same manner as in Example 133 or Examples 134a)-b), the compounds of Example 196 to Example 293 were synthesized.

Example 196

1-{3-(benzyloxy)-4-[(ethylamino)carbonyl]phenyl}-N-cyclopropyl-1H-1,2,3-triazole-4-carboxamide NMR (CDCl$_3$) δ: 0.65-0.75 (2H, m), 0.87-0.95 (2H, m), 1.01 (3H, t, J=7.3), 2.88-2.99 (1H, m), 3.40 (2H, dq, J=7.3, 5.3), 5.27 (2H, s), 7.23-7.26 (1H, m), 7.38 (1H, dd, J=8.5, 2.1), 7.42-7.55 (5H, m), 7.63 (1H, d, J=1.9), 7.78 (1H, brs), 8.43 (1H, d, J=8.5), 8.56 (1H, s).

Example 197

1-{4-[(ethylamino)carbonyl]phenyl}-5-[2-(methylthio)ethyl]-1H-1,2,3-triazole-4-carboxamide NMR (CDCl$_3$) δ: 1.30 (3H, t, J=7.4), 1.94 (3H, s), 2.76 (2H, t, J=7.0), 3.33 (2H, t, J=7.0), 3.56 (2H, dq, J=5.7, 7.2), 5.57 (1H, brs), 6.19 (1H, brs), 7.16 (1H, brs), 7.55-7.61 (2H, m), 7.97-8.00 (2H, m).

Example 198

N-cyclopropyl-1-{4-[(ethylamino)carbonyl]phenyl}-5-[2-(methylthio)ethyl]-1H-1,2,3-triazole-4-carboxamide NMR (CDCl$_3$) δ: 0.64-0.73 (2H, m), 0.85-0.93 (2H, m), 1.30 (3H, t, J=7.3), 1.95 (3H, s), 2.78 (2H, t, J=7.3), 2.85-2.97 (1H, m), 3.32 (2H, t, J=7.3), 3.49-3.61 (2H, m), 6.16 (1H, brs), 7.31-7.40 (1H, m), 7.51-7.60 (2H, m), 7.93-8.02 (2H, m).

Example 199

1-{4-[(ethylamino)carbonyl]phenyl}-N-(2-methoxyethyl)-5-[2-(methylthio)ethyl]-1H-1,2,3-triazole-4-carboxamide NMR (CDCl$_3$) δ: 1.30 (3H, t, J=7.3), 1.94 (3H, s), 2.76 (2H, t, J=7.3), 3.32 (2H, t, J=7.3), 3.41 (3H, s), 3.47-3.72 (6H, m), 6.18 (1H, brs), 7.46-7.65 (3H, m), 7.93-8.03 (2H, m).

Example 200

1-{4-[(ethylamino)carbonyl]phenyl}-N-(3-fluorobenzyl)-5-[2-(methylthio)ethyl]-1H-1,2,3-triazole-4-carboxamide NMR (CDCl$_3$) δ: 1.30 (3H, t, J=7.3), 1.94 (3H, s), 2.77 (2H, t, J=7.3), 3.35 (2H, t, J=7.3), 3.48-3.61 (2H, m), 4.67 (2H, d, J=6.2), 6.20 (1H, brs), 6.99 (1H, dt, J=8.5, 2.1), 7.04-7.18 (2H, m), 7.27-7.38 (1H, m), 7.49-7.60 (2H, m), 7.68 (1H, t, J=6.1), 7.91-8.05 (2H, m).

Example 201

5-[2-(methylthio)ethyl]-1-(4-{[(2,2,2-trifluoroethyl)amino]carbonyl}phenyl)-1H-1,2,3-triazole-4-carboxamide NMR (CDCl$_3$) δ: 1.94 (3H, s), 2.78 (2H, t, J=7.3), 3.34 (2H, t, J=7.3), 4.19 (2H, dq, J=9.0, 6.4), 5.55 (1H, brs), 6.46 (1H, brs), 7.16 (1H, brs), 7.53-7.70 (2H, m), 7.97-8.13 (2H, m).

Example 202

N-cyclopropyl-5-[2-(methylthio)ethyl]-1-(4-{[(2,2,2-trifluoroethyl)amino]carbonyl}phenyl)-1H-1,2,3-triazole-4-carboxamide NMR (CDCl$_3$) δ: 0.64-0.74 (2H, m), 0.83-0.94 (2H, m), 1.95 (3H, s), 2.79 (2H, t, J=7.3), 2.84-2.97 (1H, m), 3.33 (2H, t, J=7.3), 4.18 (2H, dq, J=9.0, 6.4), 6.62 (1H, t, J=6.3), 7.37 (1H, d, J=2.8), 7.56-7.64 (2H, m), 7.98-8.08 (2H, m).

Example 203

N-(2-methoxyethyl)-5-[2-(methylthio)ethyl]-1-(4-{[(2,2,2-trifluoroethyl)amino]carbonyl}phenyl)-1H-1,2,3-triazole-4-carboxamide NMR (CDCl$_3$) δ: 1.94 (3H, s), 2.77 (2H, t, J=7.3), 3.33 (2H, t, J=7.3), 3.41 (3H, s), 3.53-3.72 (4H, m), 4.18 (2H, dq, J=8.9, 6.5), 6.56 (1H, t, J=6.3), 7.55-7.64 (3H, m), 7.99-8.08 (2H, m).

Example 204

N-(3-fluorobenzyl)-5-[2-(methylthio)ethyl]-1-(4-{[(2,2,2-trifluoroethyl)amino]carbonyl}phenyl)-1H-1,2,3-triazole-4-carboxamide NMR (CDCl$_3$) δ: 1.94 (3H, s), 2.79 (2H, t, J=7.2), 3.36 (2H, t, J=7.3), 4.18 (2H, dq, J=8.9, 6.6), 4.67 (2H, d, J=6.2), 6.50 (1H, t, J=6.4), 6.94-7.03 (1H, m), 7.05-7.12 (1H, m), 7.12-7.18 (1H, m), 7.28-7.38 (1H, m), 7.58-7.72 (3H, m), 7.99-8.07 (2H, m).

Example 205

N-cyclopropyl-1-(2-[2-(2-fluoroethoxy)ethoxy]-4-{[(2,2,2-trifluoroethyl)amino]carbonyl}phenyl)-1H-1,2,3-triazole-4-carboxamide NMR (CDCl$_3$) δ: 0.62-0.73 (2H, m), 0.83-0.98 (2H, m), 2.87-2.99 (1H, m), 3.77-3.96 (4H, m), 4.16 (2H, dq, J=9.0, 6.6), 4.32-4.44 (2H, m), 4.56-4.80 (2H, m), 6.53 (1H, d, J=6.6), 7.21-7.30 (1H, m), 7.48 (1H, dd, J=8.3, 1.7), 7.72 (1H, d, J=1.7), 8.02 (1H, d, J=8.3), 8.99 (1H, s).

Example 206

1-(2-[2-(2-fluoroethoxy)ethoxy]-4-{[(2,2,2-trifluoroethyl)amino]carbonyl}phenyl)-N-(2-methoxyethyl)-1H-1,2,3-triazole-4-carboxamide NMR (CDCl$_3$) δ: 3.41 (3H, s), 3.54-3.96 (8H, m), 4.16 (2H, qd, J 9.0, 6.6), 4.32-4.42 (2H, m), 4.55-4.79 (2H, m), 6.61 (1H, t, J=6.4), 7.42-7.56 (2H, m), 7.72 (1H, d, J=1.7), 8.01 (1H, d, J=8.3), 8.95 (1H, s).

Example 207

N-(3-fluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide NMR (CDCl$_3$) δ: 3.75-3.95 (3H, m), 4.15 (2H, qd, J=9.0, 6.6), 4.34-4.41 (2H, m), 4.55-4.77 (2H, m), 4.68 (2H, d, J=6.2), 6.64 (1H, d, J=6.2), 6.94-7.18 (3H, m), 7.28-7.36 (2H, m), 7.49 (1H, dd, J=8.3, 1.7), 7.59 (1H, t, J=6.1), 7.72 (1H, d, J=1.7), 8.00 (1H, d, J=8.3), 8.99 (1H, s).

Example 208

5-[(benzyloxy)methyl]-N-(2-methoxyethyl)-1-(4-{[(2,2,2-trifluoroethyl)amino]carbonyl}phenyl)-1H-1,2,3-triazole-4-carboxamide NMR (CDCl$_3$) δ: 3.41 (3H, s), 3.55-3.73 (4H, m), 4.17 (2H, dq, J=9.0, 6.5), 4.63 (2H, s), 4.99 (2H, s), 6.50 (1H, t, J=6.3), 7.19-7.36 (5H, m), 7.64 (1H, t, J=5.5), 7.78-7.85 (2H, m), 7.89-7.97 (2H, m).

Example 209

5-[(benzyloxy)methyl]-1-{4-[(ethylamino)carbonyl]phenyl}-N-(2-methoxyethyl)-1H-1,2,3-triazole-4-carboxamide NMR (CDCl$_3$) δ: 1.29 (3H, t, J=7.3), 3.41 (3H, s), 3.50-3.72 (6H, m), 4.63 (2H, s), 4.99 (2H, s), 6.11-6.23 (1H, m), 7.22-7.35 (5H, m), 7.64 (1H, t, J=5.5), 7.73-7.81 (2H, m), 7.88-7.94 (2H, m).

Example 210

5-[(benzyloxy)methyl]-1-{4-[(ethylamino)carbonyl]phenyl}-N-(2-hydroxyethyl)-1H-1,2,3-triazole-4-carboxamide NMR (CDCl$_3$) δ: 1.30 (3H, t, J=7.3), 2.01 (1H, brs), 3.48-3.60 (2H, m), 3.63-3.72 (2H, m), 3.87 (2H, t, J=5.0), 4.63 (2H, s), 4.96 (2H, s), 6.14-6.25 (1H, m), 7.19-7.37 (5H, m), 7.69-7.81 (3H, m), 7.85-7.93 (2H, m).

Example 211

5-[(benzyloxy)methyl]-N-(2-hydroxyethyl)-1-(4-{[(2,2,2-trifluoroethyl)amino]carbonyl}phenyl)-1H-1,2,3-triazole-4-carboxamide NMR (CDCl$_3$) δ: 1.66 (1H, brs), 3.63-3.72 (2H, m), 3.88 (2H, t, J=5.0), 4.18 (2H, dq, J=9.0, 6.4), 4.63 (2H, s), 4.98 (2H, s), 6.50 (1H, t, J=6.3), 7.20-7.37 (5H, m), 7.67-7.76 (1H, m), 7.78-7.85 (2H, m), 7.89-7.97 (2H, m).

Example 212

N-cyclopropyl-1-{4-[(ethylamino)carbonyl]phenyl}-1H-1,2,3-triazole-4-carboxamide NMR (DMSO-d$_6$) δ: 0.63-0.74 (4H, m), 1.15 (3H, t, J=7.2), 2.85-2.94 (1H, m), 3.27-3.37 (2H, m), 8.03-8.12 (4H, m), 8.65 (1H, t, J=5.5), 8.74 (1H, d, J=4.5), 9.36 (1H, s).

Example 213

1-{4-[(ethylamino)carbonyl]phenyl}-N-(3-fluorophenyl)-1H-1,2,3-triazole-4-carboxamide NMR (DMSO-d$_6$) δ: 1.16 (3H, t, J=7.2), 3.26-3.39 (2H, m), 6.96 (1H, td, J=8.5, 2.4), 7.35-7.47 (1H, m), 7.68-7.75 (1H, m), 7.83 (1H, dt, J=11.7, 2.1), 8.04-8.18 (4H, m), 8.67 (1H, t, J=5.5), 9.57 (1H, s), 10.86 (1H, s).

Example 214

1-{4-[(ethylamino)carbonyl]phenyl}-N-(3-fluorobenzyl)-1H-1,2,3-triazole-4-carboxamide NMR (DMSO-d$_6$) δ: 1.15 (3H, t, J=7.2), 3.23-3.39 (2H, m), 4.51 (2H, d, J=6.4), 6.99-7.24 (3H, m), 7.27-7.46 (1H, m), 8.00-8.15 (4H, m), 8.65 (1H, t, J=5.5), 9.35 (1H, t, J=6.3), 9.41 (1H, s).

Example 215 benzyl [2-({[5-(5-fluoropentyl)-1-(4-{[(2,2,2-trifluoroethyl)amino]carbonyl}phenyl)-1H-1,2,3-triazol-4-yl]carbonyl}amino)ethyl]carbamate NMR (CDCl$_3$) δ: 1.30-1.40 (2H, m), 1.51-1.69 (4H, m), 3.02-3.07 (2H, m), 3.44-3.49 (2H, m), 3.60-3.66 (2H, m), 4.18 (2H, dq, J=6.4, 8.9), 4.34 (2H, td, J=5.8, 47.3), 5.11 (2H, s), 5.29 (1H, brs), 6.57 (1H, t, J=6.4), 7.30-7.36 (5H, m), 7.54-7.61 (3H, m), 8.00-8.05 (2H, m).

Example 216 benzyl {2-[({1-{4-[(ethylamino)carbonyl]phenyl}-5-[(methylthio)methyl]-1H-1,2,3-triazol-4-yl}carbonyl)amino]ethyl}carbamate NMR (CDCl$_3$) δ: 1.29 (3H, t, J=7.2), 2.07 (3H, s), 3.43-3.50 (2H, m), 3.54 (2H, dq, J=5.7, 7.2), 3.59-3.66 (2H, m), 4.11 (2H, s), 5.10 (2H, s), 5.36 (1H, t, J=4.9), 6.27 (1H, t, J=5.3), 7.28-7.35 (5H, m), 7.65-7.71 (3H, m), 7.95-7.98 (2H, m).

Example 217

N-[(1,5-dimethyl-1H-pyrazol-3-yl)methyl]-5-(5-fluoropentyl)-1-(4-{[(2,2,2-trifluoroethyl)amino]carbonyl}phenyl)-1H-1,2,3-triazole-4-carboxamide NMR (CDCl$_3$) δ: 1.31-1.41 (2H, m), 1.53-1.66 (4H, m), 2.25 (3H, s), 3.05-3.10 (2H, m), 3.75 (3H, s), 4.17 (2H, dq, J=6.6, 9.0), 4.36 (2H, td, J=6.0, 47.3), 4.59 (2H, d, J=5.7), 6.02 (1H, s), 6.68 (1H, t, J=6.4), 7.53-7.56 (2H, m), 7.64 (1H, t, J=5.5), 8.00-8.05 (2H, m).

Example 218

N-[(1,5-dimethyl-1H-pyrazol-3-yl)methyl]-1-{4-[(ethylamino)carbonyl]phenyl}-5-[(methylthio)methyl]-1H-1,2,3-triazole-4-carboxamide NMR (CDCl$_3$) δ: 1.29 (3H, t, J=7.2), 2.12 (3H, s), 2.25 (3H, s), 3.55 (2H, dq, J=5.7, 7.2), 3.75 (3H, s), 4.17 (2H, s), 4.59 (2H, d, J=5.5), 6.01 (1H, s), 6.19 (1H, t, J=5.5), 7.64-7.71 (3H, m), 7.95-7.99 (2H, m).

Example 219 tert-butyl [2-({[5-(5-fluoropentyl)-1-(4-{[(2,2,2-trifluoroethyl)amino]carbonyl}phenyl)-1H-1,2,3-triazol-4-yl]carbonyl}amino)ethyl]carbamate NMR (CDCl$_3$) δ: 1.34-1.42 (2H, m), 1.44 (9H, s), 1.53-1.71 (4H, m), 3.03-3.09 (2H, m), 3.36-3.42 (2H, m), 3.56-3.62 (2H, m), 4.18 (2H, dq, J=6.4, 8.9), 4.36 (2H, td, J=6.0, 47.3), 4.96 (1H, brs), 6.64 (1H, t, J=6.2), 7.55-7.61 (3H, m), 8.02-8.05 (2H, m).

Example 220 tert-butyl {2-[({1-{4-[(ethylamino)carbonyl]phenyl}-5-[(methylthio)methyl]-1H-1,2,3-triazol-4-yl}carbonyl)amino]ethyl}carbamate NMR (CDCl$_3$) δ: 1.30 (3H, t, J=7.2), 1.44 (9H, s), 2.12 (3H, s), 3.36-3.42 (2H, m), 3.50-3.63 (4H, m), 4.14 (2H, s), 4.97 (1H, brs), 6.20 (1H, t, J=5.3), 7.62 (1H, brs), 7.68-7.73 (2H, m), 7.95-8.00 (2H, m).

Example 221 methyl N-{[5-(5-fluoropentyl)-1-(4-{[(2,2,2-trifluoroethyl)amino]carbonyl}phenyl)-1H-1,2,3-triazol-4-yl]carbonyl}phenylalaninate NMR (CDCl$_3$) δ: 1.28-1.38 (2H, m), 1.49-1.68 (3H, m), 3.00-3.05 (2H, m), 3.20 (1H, dd, J=6.8, 13.8), 3.28 (1H, dd, J=5.8, 13.9), 3.75 (3H, s), 4.17 (2H, dq, J=6.4, 9.0), 4.35 (2H, td, J=6.0, 47.3), 5.03-5.10 (1H, m), 6.61 (1H, t, J=6.4), 7.20-7.34 (6H, m), 7.52-7.55 (2H, m), 7.65 (1H, d, J=8.3), 7.99-8.03 (2H, m).

Example 222 methyl N-({1-{4-[(ethylamino)carbonyl]phenyl}-5-[(methylthio)methyl]-1H-1,2,3-triazol-4-yl}carbonyl)phenylalaninate NMR (CDCl$_3$) δ: 1.29 (3H, t, J=7.2), 2.03 (3H, s), 3.18 (1H, dd, J=7.2, 13.8), 3.29 (1H, dd, J=5.7, 13.9), 3.55 (2H, dq, J=5.5, 7.2), 3.75 (3H, s), 4.05 (1H, d, J=13.9), 4.14 (1H, d, J=13.9), 5.07 (1H, ddd, J=5.7, 7.0, 12.6), 6.19 (1H, t, J=5.5), 7.19-7.34 (6H, m), 7.66-7.71 (3H, m), 7.94-7.99 (2H, m).

Example 223

N-[2-(2,4-dioxo-1,3-thiazolidin-3-yl)ethyl]-5-(5-fluoropentyl)-1-(4-{[(2,2,2-trifluoroethyl)amino]carbonyl}phenyl)-1H-1,2,3-triazole-4-carboxamide NMR (CDCl$_3$) δ: 1.34-1.41 (2H, m), 1.53-1.66 (4H, m), 3.02-3.08 (2H, m), 3.69-3.75 (2H, m), 3.92-3.96 (2H, m), 3.97 (2H, s), 4.19 (2H, dq, J=6.4, 8.9), 4.37 (2H, td, J=5.8, 47.3), 6.47 (1H, t, J=6.2), 7.50 (1H, t, J=6.2), 7.55-7.60 (2H, m), 8.00-8.05 (2H, m).

Example 224

1-{4-[(ethylamino)carbonyl]phenyl}-N-(3-fluorophenyl)-5-[(methylthio)methyl]-1H-1,2,3-triazole-4-carboxamide NMR (CDCl$_3$) δ: 1.30 (3H, t, J=7.4), 2.15 (3H, s), 3.56 (2H, dq, J=5.7, 7.2), 4.18 (2H, s), 6.20 (1H, brs), 6.84-6.90 (1H, m), 7.30-7.37 (2H, m), 7.69 (1H, brs), 7.72-7.76 (2H, m), 7.97-8.02 (2H, m), 9.15 (1H, s).

Example 225

5-(5-fluoropentyl)-N-(prop-2-yn-1-yl)-1-(4-{[(2,2,2-trifluoroethyl)amino]carbonyl}phenyl)-1H-1,2,3-triazole-4-carboxamide NMR (CDCl$_3$) δ: 1.29-1.44 (2H, m), 1.50-1.73 (4H, m), 2.29 (1H, t, J=2.4), 3.01-3.13 (2H, m), 4.11-4.24 (2H, m), 4.25-4.48 (4H, m), 6.60 (1H, t, J=6.2), 7.47 (1H, t, J=5.5), 7.56 (2H, d, J=8.5), 8.03 (2H, d, J=8.5).

Example 226

1-{4-[(ethylamino)carbonyl]phenyl}-5-[(methylthio)methyl]-N-(prop-2-yn-1-yl)-1H-1,2,3-triazole-4-carboxamide NMR (CDCl$_3$) δ: 1.30 (3H, t, J=7.3), 2.12 (3H, s), 2.29 (1H, t, J=2.4), 3.49-3.61 (2H, m), 4.14 (2H, s), 4.27 (2H, dd, J=5.5, 2.4), 6.20 (1H, brs), 7.49 (1H, t, J=5.5), 7.67-7.74 (2H, m), 7.95-8.02 (2H, m).

Example 227

N-(3,4-dimethoxybenzyl)-1-{4-[(ethylamino)carbonyl]phenyl}-5-[(methylthio)methyl]-1H-1,2,3-triazole-4-carboxamide NMR (CDCl$_3$) δ: 1.29 (3H, t, J=7.3), 2.13 (3H, s), 3.49-3.61 (2H, m), 3.88 (3H, s), 3.89 (3H, s), 4.17 (2H, s), 4.59 (2H, d, J=6.0), 6.17 (1H, brs), 6.81-6.96 (3H, m), 7.59 (1H, t, J=5.7), 7.66-7.75 (2H, m), 7.93-8.02 (2H, m).

Example 228

Nα-{[5-(5-fluoropentyl)-1-(4-{[(2,2,2-trifluoroethyl)amino]carbonyl}phenyl)-1H-1,2,3-triazol-4-yl]carbonyl}phenylalaninamide NMR (DMSO-d$_6$) δ: 1.07-1.21 (2H, m), 1.28-1.57 (4H, m), 2.90-3.23 (4H, m), 4.05-4.19 (2H, m), 4.28 (2H, dt, J=47.5, 6.2), 4.65-4.76 (1H, m), 7.13-7.30 (6H, m), 7.62 (1H, s), 7.76 (2H, d, J=8.5), 8.12 (2H, d, J=8.7), 8.27 (1H, d, J=8.5), 9.34 (1H, t, J=6.2).

Example 229

Nα-({1-{4-[(ethylamino)carbonyl]phenyl}-5-[(methylthio)methyl]-1H-1,2,3-triazol-4-yl}carbonyl)phenylalaninamide NMR (DMSO-d$_6$) δ: 1.15 (3H, t, J=7.3), 1.76 (3H, s), 2.99-3.21 (2H, m), 3.26-3.38 (2H, m), 4.12 (1H, d, J=14.5), 4.20 (1H, d, J=14.5), 4.66-4.77 (1H, m), 7.11-7.32 (6H, m), 7.63 (1H, s), 7.77 (2H, d, J=8.7), 8.05 (2H, d, J=8.7), 8.38 (1H, d, J=8.5), 8.69 (1H, t, J=5.6).

Example 230

N-(3-{[(5-chloro-2-thienyl)carbonyl]amino}propyl)-5-(5-fluoropentyl)-1-(4-{[(2,2,2-trifluoroethyl)amino]carbonyl}phenyl)-1H-1,2,3-triazole-4-carboxamide NMR (CDCl$_3$) δ: 1.31-1.45 (2H, m), 1.51-1.72 (4H, m), 1.79-1.91 (2H, m), 3.04-3.13 (2H, m), 3.43-3.53 (2H, m), 3.57-3.67 (2H, m), 4.18 (2H, qd, J=9.0, 6.4), 4.36 (2H, dt, J=47.3, 5.9), 6.66 (1H, t, J=6.2), 6.91 (1H, d, J=4.0), 7.44 (1H, d, J=4.0), 7.52-7.62 (4H, m), 8.01-8.08 (2H, m).

Example 231

N-(3-{[(5-chloro-2-thienyl)carbonyl]amino}propyl)-5-(5-fluoropentyl)-N-methyl-1-(4-{[(2,2,2-trifluoroethyl)amino]carbonyl}phenyl)-1H-1,2,3-triazole-4-carboxamide NMR (CDCl$_3$) δ: 1.22-2.14 (6H, m), 2.88 (3H, s), 2.92-3.03 (2H, m), 3.35-3.64 (3H, m), 3.72-3.90 (2H, m), 4.10-4.30 (3H, m), 4.35-4.47 (1H, m), 6.85 (1H, dd, J=21.7, 4.0), 6.99 (1H, brs), 7.43-7.69 (3H, m), 7.91-8.24 (4H, m).

Example 232

5-chloro-N-(1-{[5-(5-fluoropentyl)-1-(4-{[(2,2,2-trifluoroethyl)amino]carbonyl}phenyl)-1H-1,2,3-triazol-4-yl]carbonyl}piperidin-4-yl)thiophene-2-carboxamide NMR (CDCl$_3$) δ: 1.26-1.73 (9H, m), 2.01-2.21 (2H, m), 2.89-3.04 (3H, m), 3.32 (1H, t, J=12.3), 4.17 (2H, qd, J=8.9, 6.5), 4.38 (2H, dt, J=47.3, 5.7), 4.68-4.80 (2H, m), 6.11 (1H, d, J=7.9), 6.82-6.86 (1H, m), 6.88 (1H, d, J=4.0), 7.27 (1H, d, J=4.3), 7.55 (2H, d, J=8.5), 8.02 (2H, d, J=8.5).

Example 233

5-chloro-N-(1-{[5-(5-fluoropentyl)-1-(4-{[(2,2,2-trifluoroethyl)amino]carbonyl}phenyl)-1H-1,2,3-triazol-4-yl]carbonyl}piperidin-3-yl)thiophene-2-carboxamide NMR (CDCl$_3$) δ: 1.21-1.95 (9H, m), 2.52 (1H, d, J=10.2), 2.74-3.11 (3H, m), 3.48 (1H, d, J=13.8), 4.05-4.31 (5H, m), 4.42 (1H, t, J=5.7), 4.54 (1H, d, J=12.4), 6.86 (1H, d, J=4.0), 7.03 (1H, t, J=6.3), 7.50-7.65 (3H, m), 8.07 (2H, d, J=8.5), 8.52 (1H, brs).

Example 234

N-cyclopropyl-Nα-{[5-(5-fluoropentyl)-1-(4-{[(2,2,2-trifluoroethyl)amino]carbonyl}phenyl)-1H-1,2,3-triazol-4-yl]carbonyl}phenylalaninamide NMR (CDCl$_3$) δ: 0.24-0.40 (2H, m), 0.62-0.76 (2H, m), 1.29-1.41 (2H, m), 1.48-1.73 (4H, m), 2.56-2.68 (1H, m), 2.99-3.09 (2H, m), 3.09-3.30 (2H, m), 4.18 (2H, qd, J=9.0, 6.4), 4.35 (2H, dt, J=47.3, 5.9), 4.63-4.78 (1H, m), 5.81 (1H, d, J=2.4), 6.58 (1H, t, J=5.7), 7.19-7.37 (5H, m), 7.56 (2H, d, J=8.5), 7.75 (1H, d, J=8.3), 8.03 (2H, d, J=8.5).

Example 235

N-(3-fluorobenzyl)-Nα-{[5-(5-fluoropentyl)-1-(4-{[(2,2,2-trifluoroethyl)amino]carbonyl}phenyl)-1H-1,2,3-triazol-4-yl]carbonyl}phenylalaninamide NMR (CDCl$_3$) δ: 1.27-1.41 (2H, m), 1.45-1.68 (5H, m), 2.96-3.07 (2H, m), 3.21-3.29 (2H, m), 4.08-4.46 (6H, m), 4.78-4.90 (1H, m), 6.25 (1H, t, J=5.9), 6.57 (1H, t, J=6.3), 6.76-6.84 (1H, m), 6.84-6.97 (2H, m), 7.15-7.34 (5H, m), 7.50-7.58 (2H, m), 7.75 (1H, d, J=8.1), 7.98-8.06 (2H, m).

Example 236

N-cyclopropyl-Nα-({1-{4-[(ethylamino)carbonyl]phenyl}-5-[(methylthio)methyl]-1H-1,2,3-triazol-4-yl}carbonyl)phenylalaninamide NMR (CDCl$_3$) δ: 0.23-0.41 (2H, m), 0.63-0.78 (2H, m), 1.30 (3H, t, J=7.3), 2.04 (3H, s), 2.57-2.68 (1H, m), 3.10-3.28 (2H, m), 3.49-3.61 (2H, m), 4.02-4.16 (2H, m), 4.66-4.77 (1H, m), 5.81 (1H, brs), 6.12-6.21 (1H, m), 7.21-7.36 (5H, m), 7.66-7.73 (2H, m), 7.78 (1H, d, J=8.1), 7.93-8.01 (2H, m).

Example 237

Nα-({1-{4-[(ethylamino)carbonyl]phenyl}-5-[(methylthio)methyl]-1H-1,2,3-triazol-4-yl}carbonyl)-N-(3-fluorobenzyl)phenylalaninamide NMR (CDCl₃) δ: 1.29 (3H, t, J=7.3), 2.01 (3H, s), 3.25 (2H, d, J=7.2), 3.48-3.60 (2H, m), 4.01-4.14 (2H, m), 4.29-4.46 (2H, m), 4.84 (1H, q, J=7.2), 6.12-6.28 (2H, m), 6.76-6.84 (1H, m), 6.86-6.99 (2H, m), 7.18-7.36 (6H, m), 7.64-7.72 (2H, m), 7.78 (1H, d, J=8.1), 7.92-8.01 (2H, m).

Example 238 methyl N-{[5-(5-fluoropentyl)-1-(4-{[(2,2,2-trifluoroethyl)amino]carbonyl}phenyl)-1H-1,2,3-triazol-4-yl]carbonyl}-D-phenylalaninate NMR (CDCl₃) δ: 1.29-1.41 (2H, m), 1.46-1.70 (4H, m), 2.97-3.08 (2H, m), 3.14-3.32 (2H, m), 3.75 (3H, s), 4.18 (2H, qd, J=8.9, 6.5), 4.35 (2H, dt, J=47.3, 5.9), 5.01-5.11 (1H, m), 6.53 (1H, t, J=6.4), 7.17-7.36 (5H, m), 7.49-7.59 (2H, m), 7.65 (1H, d, J=8.5), 7.97-8.06 (2H, m).

Example 239 methyl N-{[5-(5-fluoropentyl)-1-(4-{[(2,2,2-trifluoroethyl)amino]carbonyl}phenyl)-1H-1,2,3-triazol-4-yl]carbonyl}-L-phenylalaninate NMR (CDCl₃) δ: 1.25-1.42 (2H, m), 1.46-1.70 (4H, m), 2.97-3.08 (2H, m), 3.14-3.35 (2H, m), 3.75 (3H, s), 4.17 (2H, qd, J=8.9, 6.8), 4.35 (2H, dt, J=47.3, 5.9), 5.00-5.13 (1H, m), 6.89 (1H, brs), 7.17-7.35 (5H, m), 7.55 (2H, d, J=8.5), 7.66 (1H, d, J=8.3), 8.05 (2H, d, J=8.3).

Example 240 methyl N-{[5-(5-fluoropentyl)-1-(4-{[(2,2,2-trifluoroethyl)amino]carbonyl}phenyl)-1H-1,2,3-triazol-4-yl]carbonyl}glycinate NMR (CDCl₃) δ: 1.27-1.42 (2H, m), 1.45-1.76 (4H, m), 2.99-3.12 (2H, m), 3.80 (3H, s), 4.18 (2H, qd, J=9.0, 6.4), 4.24-4.49 (4H, m), 6.70 (1H, t, J=6.3), 7.56 (2H, d, J=8.5), 7.72 (1H, t, J=5.7), 8.03 (2H, d, J=8.7).

Example 241 methyl N-({1-{4-[(ethylamino)carbonyl]phenyl}-5-[(methylthio)methyl]-1H-1,2,3-triazol-4-yl}carbonyl)glycinate NMR (CDCl₃) δ: 1.29 (3H, t, J=7.3), 2.10 (3H, s), 3.54 (2H, dq, J=7.2, 5.7), 3.80 (3H, s), 4.13 (2H, s), 4.26 (2H, d, J=5.8), 6.21-6.33 (1H, m), 7.65-7.80 (3H, m), 7.91-8.03 (2H, m).

Example 242

5-(5-fluoropentyl)-N-(trans-4-hydroxycyclohexyl)-1-(4-{[(2,2,2-trifluoroethyl)amino]carbonyl}phenyl)-1H-1,2,3-triazole-4-carboxamide NMR (CDCl₃) δ: 1.33-1.71 (11H, m), 2.04-2.14 (4H, m), 3.04-3.09 (2H, m), 3.68-3.74 (1H, m), 3.93-4.01 (1H, m), 4.18 (2H, dq, J=6.6, 8.9), 4.37 (2H, td, J=6.0, 47.3), 6.51 (1H, t, J=6.0), 7.13 (1H, d, J=8.1), 7.54-7.58 (2H, m), 8.01-8.04 (2H, m).

Example 243

1-{4-[(ethylamino)carbonyl]phenyl}-N-(trans-4-hydroxycyclohexyl)-5-[(methylthio)methyl]-1H-1,2,3-triazole-4-carboxamide NMR (CDCl₃) δ: 1.29 (3H, t, J=7.2), 1.37-1.53 (4H, m), 1.59-1.60 (1H, m), 2.04-2.14 (7H, m), 3.54 (2H, dq, J=5.7, 7.2), 3.65-3.73 (1H, m), 3.91-4.01 (1H, m), 4.14 (2H, s), 6.23 (1H, t, J=5.3), 7.15 (1H, d, J=8.3), 7.67-7.72 (2H, m), 7.95-8.00 (2H, m).

Example 244 methyl N-[(1-{4-[(ethylamino)carbonyl]-2-[(6-fluorohexyl)oxy]phenyl}-1H-1,2,3-triazol-4-yl)carbonyl]phenylalaninate NMR (CDCl₃) δ: 1.29 (3H, t, J=7.2), 1.42-1.46 (4H, m), 1.60 (3H, s), 1.79-1.86 (2H, m), 3.25 (2H, dd, J=6.4, 13.8), 3.53 (2H, dq, J=5.7, 7.2), 3.75 (3H, s), 4.17 (2H, t, J=6.6), 4.38 (2H, td, J=6.0, 47.5), 5.10 (1H, td, J=6.2, 8.3), 6.18 (1H, t, J=5.3), 7.20-7.37 (5H, m), 7.59 (1H, d, J=8.1), 7.65 (1H, d, J=1.5), 7.90 (1H, d, J=8.3), 8.67 (1H, s).

Example 245

1-{4-[(ethylamino)carbonyl]-2-[(6-fluorohexyl)oxy]phenyl}-N-[(1R)-1-(hydroxymethyl)-2-methylpropyl]-1H-1,2,3-triazole-4-carboxamide NMR (CDCl₃) δ: 1.03-1.08 (6H, m), 1.29 (3H, t, J=7.3), 1.38-1.90 (9H, m), 1.98-2.13 (1H, m), 3.47-3.61 (2H, m), 3.73-3.91 (2H, m), 3.91-4.04 (1H, m), 4.17 (2H, t, J=6.6), 4.43 (2H, dt, J=47.3, 6.0), 6.20 (1H, brs), 7.32-7.39 (2H, m), 7.65 (1H, d, J=1.7), 7.87 (1H, d, J=8.1), 8.68 (1H, s).

Example 246

N-[(1R)-1-benzyl-2-hydroxyethyl]-5-(5-fluoropentyl)-1-(4-{[(2,2,2-trifluoroethyl)amino]carbonyl}phenyl)-1H-1,2,3-triazole-4-carboxamide NMR (CDCl₃) δ: 1.30-1.41 (2H, m), 1.46-1.73 (5H, m), 2.97-3.10 (4H, m), 3.71 (1H, dd, J=10.9, 5.3), 3.82 (1H, dd, J=11.1, 3.6), 4.18 (2H, qd, J=8.9, 6.5), 4.25-4.48 (3H, m), 6.49 (1H, t, J=6.3), 7.18-7.36 (5H, m), 7.50 (1H, d, J=7.9), 7.55 (2H, d, J=8.5), 8.02 (2H, d, J=8.5).

Example 247

N-[(1S)-1-benzyl-2-hydroxyethyl]-5-(5-fluoropentyl)-1-(4-{[(2,2,2-trifluoroethyl)amino]carbonyl}phenyl)-1H-1,2,3-triazole-4-carboxamide NMR (CDCl₃) δ: 1.29-1.43 (2H, m), 1.48-1.73 (5H, m), 2.96-3.10 (4H, m), 3.71 (1H, dd, J=10.9, 5.3), 3.82 (1H, dd, J=11.1, 3.4), 4.10-4.24 (2H, m), 4.25-4.49 (3H, m), 6.52 (1H, brs), 7.20-7.37 (5H, m), 7.51 (1H, d, J=7.7), 7.55 (2H, d, J=8.3), 8.02 (2H, d, J=8.5).

Example 248

5-(5-fluoropentyl)-N-[(1R)-1-(hydroxymethyl)-3-methylbutyl]-1-(4-{[(2,2,2-trifluoroethyl)amino]carbonyl}phenyl)-1H-1,2,3-triazole-4-carboxamide NMR (CDCl$_3$) δ: 0.95-1.00 (6H, m), 1.26-1.84 (11H, m), 2.98-3.14 (2H, m), 3.66 (1H, dd, J=10.9, 6.2), 3.80 (1H, dd, J=11.1, 3.4), 4.18 (2H, qd, J=8.9, 6.5), 4.36 (2H, dt, J=47.3, 5.9), 6.54 (1H, brs), 7.30 (1H, d, J=8.3), 7.52-7.62 (2H, m), 7.96-8.09 (2H, m).

Example 249

5-(5-fluoropentyl)-N-[(1S)-1-(hydroxymethyl)-3-methylbutyl]-1-(4-{[(2,2,2-trifluoroethyl)amino]carbonyl}phenyl)-1H-1,2,3-triazole-4-carboxamide NMR (CDCl$_3$) δ: 0.95-1.03 (6H, m), 1.24-1.86 (10H, m), 3.02-3.11 (2H, m), 3.66 (1H, dd, J=11.1, 6.2), 3.80 (1H, dd, J=11.1, 3.6), 4.09-4.49 (5H, m), 6.55 (1H, t, J=6.3), 7.30 (1H, d, J=8.3), 7.51-7.60 (2H, m), 7.96-8.07 (2H, m).

Example 250

1-{4-[(ethylamino)carbonyl]phenyl}-5-[(3-fluorophenoxy)methyl]-N-(prop-2-yn-1-yl)-1H-1,2,3-triazole-4-carboxamide NMR (CDCl$_3$) δ: 1.28 (3H, t, J=7.2), 2.30 (1H, t, J=2.7), 3.53 (2H, dq, J=5.7, 7.2), 4.29 (2H, dd, J=2.3, 5.7), 5.49 (2H, s), 6.15 (1H, brs), 6.61 (1H, td, J=2.3, 10.6), 6.67-6.73 (2H, m), 7.21 (1H, dt, J=6.8, 8.3), 7.52 (1H, t, J=5.3), 7.67-7.70 (2H, m), 7.92-7.95 (2H, m).

Example 251

N-(1,1-dimethylprop-2-yn-1-yl)-1-{4-[(ethylamino)carbonyl]phenyl}-5-[(3-fluorophenoxy)methyl]-1H-1,2,3-triazole-4-carboxamide NMR (CDCl$_3$) δ: 1.28 (3H, t, J=7.2), 1.79 (6H, s), 3.53 (2H, dq, J=5.7, 7.2), 5.52 (2H, s), 6.16 (1H, t, J=4.9), 6.59-6.71 (4H, m), 7.19 (1H, dt, J=6.8, 8.3), 7.43 (1H, s), 7.65-7.68 (2H, m), 7.92-7.94 (2H, m).

Example 252

1-{4-[(ethylamino)carbonyl]phenyl}-N-(1-ethynylcyclohexyl)-5-[(3-fluorophenoxy)methyl]-1H-1,2,3-triazole-4-carboxamide NMR (CDCl$_3$) δ: 1.28 (3H, t, J=7.2), 1.33-1.37 (1H, m), 1.60-1.81 (5H, m), 1.89-1.98 (2H, m), 2.27-2.31 (2H, m), 2.49 (1H, s), 3.49-3.58 (2H, m), 5.53 (2H, s), 6.12 (1H, brs), 6.60-6.71 (3H, m), 7.15-7.22 (1H, m), 7.37 (1H, s), 7.66-7.71 (2H, m), 7.92-7.94 (2H, m).

Example 253

N-(4-chlorobut-2-yn-1-yl)-1-{4-[(ethylamino)carbonyl]phenyl}-5-[(3-fluorophenoxy)methyl]-1H-1,2,3-triazole-4-carboxamide NMR (CDCl$_3$) δ: 1.28 (3H, t, J=7.2), 3.46-3.60 (2H, m), 4.13-4.19 (2H, m), 4.28-4.39 (2H, m), 5.49 (2H, s), 6.14 (1H, brs), 6.56-6.75 (3H, m), 7.15-7.25 (1H, m), 7.47-7.57 (1H, m), 7.65-7.73 (2H, m), 7.90-7.97 (2H, m).

Example 254

N-(2,2-difluoroethyl)-1-{4-[(ethylamino)carbonyl]phenyl}-5-[(3-fluorophenoxy)methyl]-1H-1,2,3-triazole-4-carboxamide NMR (CDCl$_3$) δ: 1.28 (3H, t, J=7.4), 3.54 (2H, qd, J=7.2, 5.7), 3.80-3.95 (2H, tdd, J=14.8, 6.8, 4.2), 5.48 (2H, s), 5.96 (1H, tt, J=56.0, 4.2), 6.12 (1H, brs), 6.56-6.76 (3H, m), 7.14-7.25 (1H, m), 7.57 (1H, t, J=6.2), 7.69 (2H, d, J=8.7), 7.94 (2H, d, J=8.7).

Example 255

1-{4-[(ethylamino)carbonyl]phenyl}-5-[(3-fluorophenoxy)methyl]-N-[2-hydroxy-1-(hydroxymethyl)ethyl]-1H-1,2,3-triazole-4-carboxamide NMR (DMSO-d$_6$) δ: 1.13 (3H, t, J=7.3), 3.21-3.37 (2H, m), 3.47-3.66 (4H, m), 3.94-4.09 (1H, m), 4.80 (2H, t, J=5.6), 5.54 (2H, s), 6.65-6.89 (3H, m), 7.22-7.37 (1H, m), 7.69-7.82 (2H, m), 7.97-8.09 (2H, m), 8.19 (1H, d, J=8.5), 8.66 (1H, t, J=5.5).

Example 256

N-[(2R)-2,3-dihydroxypropyl]-1-{4-[(ethylamino)carbonyl]phenyl}-5-[(3-fluorophenoxy)methyl]-1H-1,2,3-triazole-4-carboxamide NMR (DMSO-d$_6$) δ: 1.13 (3H, t, J=7.2), 3.18-3.55 (6H, m), 3.61-3.72 (1H, m), 4.63 (1H, t, J=5.7), 4.90 (1H, d, J=4.9), 5.54 (2H, s), 6.63-6.92 (3H, m), 7.21-7.36 (1H, m), 7.76 (2H, d, J=8.7), 8.04 (2H, d, J=8.7), 8.58 (1H, t, J=5.8), 8.66 (1H, t, J=5.6).

Example 257

N-[(2S)-2,3-dihydroxypropyl]-1-{4-[(ethylamino)carbonyl]phenyl}-5-[(3-fluorophenoxy)methyl]-1H-1,2,3-triazole-4-carboxamide NMR (DMSO-d$_6$) δ: 1.14 (3H, t, J=7.2), 3.16-3.55 (4H, m), 3.57-3.74 (1H, m), 3.87 (2H, s), 4.63 (1H, t, J=5.7), 4.90 (1H, d, J=5.1), 5.54 (2H, s), 6.69-6.89 (3H, m), 7.21-7.37 (1H, m), 7.68-7.81 (2H, m), 7.99-8.08 (2H, m), 8.58 (1H, t, J=5.8), 8.66 (1H, t, J=5.5).

Example 258

1-{4-[(ethylamino)carbonyl]phenyl}-5-[(3-fluorophenoxy)methyl]-N-(4-hydroxybut-2-yn-1-yl)-1H-1,2,3-triazole-4-carboxamide NMR (CDCl$_3$) δ: 1.28 (3H, t, J=7.3), 2.58 (1H, brs), 3.48-3.60 (2H, m), 4.28-4.53 (4H, m), 5.40 (2H, s), 6.19 (1H, brs), 6.54-6.78 (3H, m), 7.16-7.25 (2H, m), 7.64-7.75 (2H, m), 7.88-7.99 (2H, m).

Example 259

5-[(3-fluorophenoxy)methyl]-N-[2-hydroxy-1-(hydroxymethyl)ethyl]-1-(4-{[(2,2,2-trifluoroethyl)amino]carbonyl}phenyl)-1H-1,2,3-triazole-4-carboxamide NMR (DMSO-d$_6$) δ: 3.50-3.63 (4H, m), 3.97-4.20 (3H, m), 4.80 (2H, t, J=5.5), 5.56 (2H, s), 6.69-6.87 (3H, m), 7.22-7.36 (1H, m), 7.76-7.86 (2H, m), 8.05-8.14 (2H, m), 8.20 (1H, d, J=8.7), 9.31 (1H, t, J=6.3).

Example 260

N-[(2R)-2,3-dihydroxypropyl]-5-[(3-fluorophenoxy)methyl]-1-(4-{[(2,2,2-trifluoroethyl)amino]carbonyl}phenyl)-1H-1,2,3-triazole-4-carboxamide NMR (DMSO-d$_6$) δ: 3.17-3.54 (4H, m), 3.58-3.74 (1H, m), 4.03-4.20 (2H, m), 4.63 (1H, t, J=5.7), 4.90 (1H, d, J=5.1), 5.57 (2H, s), 6.68-6.88 (3H, m), 7.22-7.38 (1H, m), 7.76-7.91 (2H, m), 7.99-8.16 (2H, m), 8.59 (1H, t, J=5.9), 9.31 (1H, t, J=6.3).

Example 261

N-[(2S)-2,3-dihydroxypropyl]-5-[(3-fluorophenoxy)methyl]-1-(4-{[(2,2,2-trifluoroethyl)amino]carbonyl}phenyl)-1H-1,2,3-triazole-4-carboxamide NMR (DMSO-d$_6$) δ: 3.57-3.78 (2H, m), 3.98-4.21 (4H, m), 4.31-4.41 (1H, m), 5.47 (2H, s), 6.68-6.89 (4H, m), 7.21-7.38 (1H, m), 7.71-7.86 (2H, m), 8.04-8.16 (3H, m), 8.98 (1H, brs), 9.30 (1H, t, J=6.2).

Example 262

5-[(3-fluorophenoxy)methyl]-N-(4-hydroxybut-2-yn-1-yl)-1-(4-{[(2,2,2-trifluoroethyl)amino]carbonyl}phenyl)-1H-1,2,3-triazole-4-carboxamide NMR (DMSO-d$_6$) δ: 3.16-3.74 (3H, m), 4.00-4.23 (2H, m), 4.64 (1H, brs), 4.82-4.98 (1H, m), 5.57 (2H, s), 6.67-6.87 (3H, m), 7.18-7.35 (1H, m), 7.73-7.87 (2H, m), 8.03-8.17 (2H, m), 8.59 (1H, t, J=5.9), 9.31 (1H, t, J=6.4).

Example 263

N-[(2-ethoxypyridin-4-yl)methyl]-1-{4-[(ethylamino)carbonyl]phenyl}-5-[(3-fluorophenoxy)methyl]-1H-1,2,3-triazole-4-carboxamide NMR (CDCl$_3$) δ: 1.29 (3H, t, J=7.3), 1.38 (3H, t, J=7.1), 3.47-3.60 (2H, m), 4.35 (2H, q, J=7.2), 4.64 (2H, d, J=6.4), 5.51 (2H, s), 6.12 (1H, brs), 6.58-6.65 (1H, m), 6.66-6.74 (3H, m), 6.85 (1H, dd, J=5.3, 1.3), 7.14-7.25 (1H, m), 7.64-7.78 (3H, m), 7.89-7.98 (2H, m), 8.11 (1H, d, J=5.5).

Example 264

1-{4-[(ethylamino)carbonyl]phenyl}-5-[(3-fluorophenoxy)methyl]-N-[6-(4-fluorophenoxy)pyridin-3-yl]-1H-1,2,3-triazole-4-carboxamide NMR (CDCl$_3$) δ: 1.29 (3H, t, J=7.3), 3.48-3.62 (2H, m), 5.52 (2H, s), 6.13 (1H, brs), 6.59-6.76 (3H, m), 6.97 (1H, d, J=8.7), 7.05-7.14 (4H, m), 7.17-7.25 (1H, m), 7.68-7.75 (2H, m), 7.96 (2H, d, J=8.5), 8.26 (1H, dd, J=8.9, 2.8), 8.36 (1H, d, J=2.6), 9.06 (1H, s).

Example 265

1-{4-[(ethylamino)carbonyl]phenyl}-N-[6-(4-fluorophenoxy)pyridin-3-yl]-5-[(methylthio)methyl]-1H-1,2,3-triazole-4-carboxamide NMR (CDCl$_3$) δ: 1.30 (3H, t, J=7.3), 2.14 (3H, s), 3.50-3.62 (2H, m), 4.17 (2H, s), 6.20 (1H, t, J=5.4), 6.96 (1H, d, J=8.9), 7.01-7.17 (4H, m), 7.67-7.77 (2H, m), 7.94-8.05 (2H, m), 8.25 (1H, dd, J=8.9, 2.8), 8.36 (1H, d, J=2.6), 9.05 (1H, s).

Example 266

5-[(3-fluorophenoxy)methyl]-N-(trans-4-hydroxycyclohexyl)-1-(4-{[(2,2,2-trifluoroethyl)amino]carbonyl}phenyl)-1H-1,2,3-triazole-4-carboxamide NMR (CDCl$_3$) δ: 1.35-1.54 (7H, m), 2.00-2.20 (2H, m), 3.69 (1H, brs), 3.97 (1H, brs), 4.16 (2H, qd, J=8.9, 6.5), 5.52 (2H, s), 6.40 (1H, t, J=6.3), 6.57-6.77 (3H, m), 7.13-7.25 (2H, m), 7.69-7.78 (2H, m), 7.93-8.04 (2H, m).

Example 267

5-[(3-fluorophenoxy)methyl]-1-(4-{[(2,2,2-trifluoroethyl)amino]carbonyl}phenyl)-N-(2-{[(trifluoromethyl)sulfonyl]amino}ethyl)-1H-1,2,3-triazole-4-carboxamide NMR (DMSO-d$_6$) δ: 3.31-3.41 (2H, m), 3.43-3.53 (2H, m), 4.08-4.22 (2H, m), 5.58 (2H, s), 6.68-6.87 (3H, m), 7.20-7.36 (1H, m), 7.74-7.86 (2H, m), 7.96 (1H, s), 8.06-8.17 (2H, m), 8.93-9.09 (1H, m), 9.31 (1H, t, J=6.2).

Example 268

5-[(3-fluorophenoxy)methyl]-N-(tetrahydro-2H-pyran-4-yl)-1-(4-{[(2,2,2-trifluoroethyl)amino]carbonyl}phenyl)-1H-1,2,3-triazole-4-carboxamide NMR (CDCl$_3$) δ: 1.59-1.76 (2H, m), 1.97-2.07 (2H, m), 3.54 (2H, td, J=11.7, 2.1), 3.97-4.07 (2H, m), 4.09-4.31 (3H, m), 5.52 (2H, s), 6.39 (1H, t, J=6.3), 6.58-6.78 (3H, m), 7.14-7.25 (2H, m), 7.69-7.79 (2H, m), 7.93-8.03 (2H, m).

Example 269

5-[(3-fluorophenoxy)methyl]-N-[2-(morpholin-4-yl)ethyl]-1-(4-{[(2,2,2-trifluoroethyl)amino]carbonyl}phenyl)-1H-1,2,3-triazole-4-carboxamide NMR (CDCl$_3$) δ: 2.52-2.72 (6H, m), 3.57-3.68 (2H, m), 3.74-3.83 (4H, m), 4.17 (2H, qd, J=9.0, 6.4), 5.53 (2H, s), 6.41 (1H, brs), 6.57-6.77 (3H, m), 7.14-7.25 (1H, m), 7.67-7.85 (3H, m), 7.93-8.04 (2H, m).

Example 270

1-{4-[(ethylamino)carbonyl]phenyl}-5-[(3-fluorophenoxy)methyl]-N-(2-methoxyethyl)-1H-1,2,3-triazole-4-carboxamide NMR (CDCl$_3$) δ: 1.28 (3H, t, J=7.3), 3.41 (3H, s), 3.45-3.63 (4H, m), 3.63-3.75 (2H, m), 5.51 (2H, s), 6.14 (1H, brs), 6.58-6.77 (3H, m), 7.12-7.25 (1H, m), 7.53-7.75 (3H, m), 7.89-7.97 (2H, m).

Example 271

5-[(3-fluorophenoxy)methyl]-N-(2-methoxyethyl)-1-(4-{[(2,2,2-trifluoroethyl)amino]carbonyl}phenyl)-1H-1,2,3-triazole-4-carboxamide NMR (CDCl$_3$) δ: 3.41 (3H, s), 3.54-3.73 (4H, m), 4.16 (2H, qd, J=8.9, 6.5), 5.52 (2H, s), 6.45 (1H, t, J=6.2), 6.57-6.79 (3H, m), 7.13-7.26 (1H, m), 7.57-7.68 (1H, m), 7.69-7.79 (2H, m), 7.94-8.02 (2H, m).

Example 272

N-(2-ethoxyethyl)-5-[(3-fluorophenoxy)methyl]-1-(4-{[(2,2,2-trifluoroethyl)amino]carbonyl}phenyl)-1H-1,2,3-triazole-4-carboxamide NMR (CDCl$_3$) δ: 1.24 (3H, t, J=7.1), 3.56 (2H, q, J=7.1), 3.60-3.74 (4H, m), 4.16 (2H, qd, J=9.0, 6.4), 5.52 (2H, s), 6.45 (1H, t, J=6.3), 6.56-6.75 (3H, m), 7.14-7.25 (1H, m), 7.67 (1H, t, J=5.2), 7.70-7.78 (2H, m), 7.93-8.02 (2H, m).

Example 273

1-(4-{[(2,2,2-trifluoroethyl)amino]carbonyl}phenyl)-5-{[3-(trifluoromethoxy)phenoxy]methyl}-1H-1,2,3-triazole-4-carboxamide NMR (CDCl$_3$) δ: 4.17 (2H, qd, J=8.9, 6.4), 5.56 (2H, s), 5.66 (1H, brs), 6.41 (1H, t, J=6.4), 6.72 (1H, brs), 6.83-6.88 (2H, m), 7.20-7.31 (2H, m), 7.71-7.76 (2H, m), 7.97-8.02 (2H, m).

Example 274

N-(2-methoxyethyl)-1-(4-{[(2,2,2-trifluoroethyl)amino]carbonyl}phenyl)-5-{[3-(trifluoromethoxy)phenoxy]methyl}-1H-1,2,3-triazole-4-carboxamide NMR (CDCl$_3$) δ: 3.41 (3H, s), 3.57-3.61 (2H, m), 4.17 (2H, qd, J=8.9, 6.4), 5.56 (2H, s), 6.39 (1H, t, J=6.4), 6.74 (1H, brs), 6.83-6.87 (2H, m), 7.25-7.30 (1H, m), 7.65 (1H, brs), 7.71-7.76 (2H, m), 7.96-8.01 (2H, m).

Example 275

N-(2-hydroxyethyl)-1-(4-{[(2,2,2-trifluoroethyl)amino]carbonyl}phenyl)-5-{[3-(trifluoromethoxy)phenoxy]methyl}-1H-1,2,3-triazole-4-carboxamide NMR (DMSO-d$_6$) δ: 2.86 (2H, t, J=5.7), 3.59 (2H, t, J=5.7), 4.12 (2H, qd, J=9.4, 6.4), 5.31 (1H, s), 5.72 (2H, s), 6.89-6.93 (2H, m), 7.00 (1H, dd, J=1.9, 8.5), 7.35 (1H, t, J=8.3), 7.74-7.77 (2H, m), 7.93 (1H, brs), 8.05-8.07 (2H, m), 9.29 (1H, t, J=6.4).

Example 276

N-[2-hydroxy-1-(hydroxymethyl)ethyl]-1-(4-{[(2,2,2-trifluoroethyl)amino]carbonyl}phenyl)-5-{[3-(trifluoromethoxy)phenoxy]methyl}-1H-1,2,3-triazole-4-carboxamide NMR (CDCl$_3$) δ: 3.50-3.60 (4H, m), 3.98-4.15 (3H, m), 4.81 (2H, t, J=5.7), 5.61 (2H, s), 6.88-6.96 (3H, m), 7.38 (1H, t, J=8.3), 7.80-7.82 (2H, m), 8.07-8.12 (2H, m), 8.21 (1H, d, J=8.7), 9.31 (1H, t, J=6.2).

Example 277

1-{4-[(ethylamino)carbonyl]phenyl}-5-{[3-(trifluoromethoxy)phenoxy]methyl}-1H-1,2,3-triazole-4-carboxamide NMR (DMSO-d$_6$) δ: 1.13 (3H, t, J=7.2), 3.26-3.33 (2H, m), 5.60 (2H, s), 6.91-6.96 (3H, m), 7.35-7.41 (1H, m), 7.75-7.77 (2H, m), 7.81 (1H, brs), 8.03-8.05 (2H, m), 8.24 (1H, brs), 8.67 (1H, t, J=5.3).

Example 278

1-{4-[(ethylamino)carbonyl]phenyl}-N-(2-methoxyethyl)-5-{[3-(trifluoromethoxy)phenoxy]methyl}-1H-1,2,3-triazole-4-carboxamide NMR (CDCl$_3$) δ: 1.28 (3H, t, J=7.2), 3.41 (3H, s), 3.49-3.60 (4H, m), 3.66-3.71 (2H, m), 5.54 (2H, s), 6.11 (1H, brs), 6.75 (1H, brs), 6.85 (1H, dd, J=2.3, 8.3), 7.24-7.30 (2H, m), 7.61-7.69 (3H, m), 7.92-7.95 (2H, m).

Example 279

1-{4-[(ethylamino)carbonyl]phenyl}-N-(2-hydroxyethyl)-5-{[3-(trifluoromethoxy)phenoxy]methyl}-1H-1,2,3-triazole-4-carboxamide NMR (DMSO-d$_6$) δ: 1.13 (3H, t, J=7.2), 3.26-3.41 (4H, m), 3.51-3.57 (2H, m), 4.79 (1H, t, J=5.3), 5.59 (2H, s), 6.91-6.97 (3H, m), 7.39 (1H, t, J=8.3), 7.75-7.78 (2H, m), 8.03-8.06 (2H, m), 8.67 (1H, t, J=5.3), 8.74 (1H, t, J=6.1).

Example 280

1-{4-[(ethylamino)carbonyl]phenyl}-N-[2-hydroxy-1-(hydroxymethyl)ethyl]-5-{[3-(trifluoromethoxy)phenoxy]methyl}-1H-1,2,3-triazole-4-carboxamide NMR (DMSO-d$_6$) δ: 1.13 (3H, t, J=7.2), 3.26-3.35 (2H, m), 3.50-3.62 (4H, m), 3.97-4.04 (1H, m), 4.80 (1H, t, J=5.3), 5.59 (2H, s), 6.90-6.97 (3H, m), 7.39 (1H, t, J=8.0), 7.71-7.81 (2H, m), 8.01-8.08 (2H, m), 8.20 (1H, d, J=8.3), 8.67 (1H, t, J=5.7).

Example 281

N-cyclopropyl-1-(4-{[(2,2-difluoroethyl)amino]carbonyl}phenyl)-5-[(3-fluorophenoxy)methyl]-1H-1,2,3-triazole-4-carboxamide NMR (CDCl$_3$) δ: 0.66-0.74 (2H, m), 0.86-0.95 (2H, m), 2.87-2.97 (1H, m), 3.88 (2H, tdd, J=14.9, 6.2, 3.9), 5.53 (2H, s), 6.00 (1H, tt, J=55.9, 4.1), 6.41 (1H, brs), 6.59-6.79 (3H, m), 7.15-7.26 (1H, m), 7.36-7.44 (1H, m), 7.66-7.78 (2H, m), 7.91-8.04 (2H, m).

Example 282

1-(4-{[(2,2-difluoroethyl)amino]carbonyl}phenyl)-5-[(3-fluorophenoxy)methyl]-N-(2-methoxyethyl)-1H-1,2,3-triazole-4-carboxamide NMR (CDCl$_3$) δ: 3.41 (3H, s), 3.55-3.62 (2H, m), 3.64-3.73 (2H, m), 3.88 (2H, tdd, J=14.7, 6.2, 4.0), 5.52 (2H, s), 6.00 (1H, tt, J=55.9, 4.0), 6.41 (1H, brs), 6.56-6.77 (3H, m), 7.14-7.26 (1H, m), 7.64 (1H, brs), 7.69-7.79 (2H, m), 7.93-8.01 (2H, m).

Example 283

1-(4-{[(2,2-difluoroethyl)amino]carbonyl}phenyl)-5-[(3-fluorophenoxy)methyl]-N-(2-hydroxyethyl)-1H-1,2,3-triazole-4-carboxamide NMR (DMSO-d$_6$) δ: 3.40 (2H, t, J=5.9), 3.49-3.58 (2H, m), 3.61-3.80 (2H, m), 4.78 (1H, t, J=5.6), 5.56 (2H, s), 6.14 (1H, tt, J=55.9, 4.0), 6.65-6.90 (3H, m), 7.21-7.34 (1H, m), 7.80 (2H, d, J=8.7), 8.08 (2H, d, J=8.7), 8.73 (1H, t, J=5.7), 9.06 (1H, t, J=5.8).

Example 284

1-(4-{[(2,2-difluoroethyl)amino]carbonyl}phenyl)-5-[(3-fluorophenoxy)methyl]-N-methyl-1H-1,2,3-triazole-4-carboxamide NMR (CDCl$_3$) δ: 3.06 (3H, d, J=4.9), 3.88 (2H, tdd, J=14.9, 6.2, 4.0), 5.53 (2H, s), 6.00 (1H, tt, J=55.9, 4.0), 6.42 (1H, brs), 6.57-6.78 (3H, m), 7.13-7.25 (1H, m), 7.33 (1H, brs), 7.66-7.80 (2H, m), 7.90-8.01 (2H, m).

Example 285

5-[(3-fluorophenoxy)methyl]-N-methyl-1-(4-{[(2,2,2-trifluoroethyl)amino]carbonyl}phenyl)-1H-1,2,3-triazole-4-carboxamide NMR (CDCl$_3$) δ: 3.06 (3H, d, J=4.9), 4.16 (2H, qd, J=9.0, 6.6), 5.53 (2H, s), 6.45 (1H, brs), 6.56-6.75 (3H, m), 7.14-7.25 (1H, m), 7.34 (1H, brs), 7.70-7.81 (2H, m), 7.93-8.03 (2H, m).

Example 286

1-{4-[(ethylamino)carbonyl]phenyl}-5-[(3-fluorophenoxy)methyl]-N-methyl-1H-1,2,3-triazole-4-carboxamide NMR (CDCl$_3$) δ: 1.28 (3H, t, J=7.3), 3.06 (3H, d, J=5.1), 3.53 (2H, qd, J=7.2, 5.7), 5.52 (2H, s), 6.12 (1H, brs), 6.56-6.76 (3H, m), 7.16-7.25 (1H, m), 7.31 (1H, brs), 7.63-7.75 (2H, m), 7.84-8.00 (2H, m).

Example 287

5-{[(3-fluorophenyl)thio]methyl}-N-methyl-1-(4-{[(2,2,2-trifluoroethyl)amino]carbonyl}phenyl)-1H-1,2,3-triazole-4-carboxamide NMR (CDCl$_3$) δ: 3.02 (3H, d, J=5.1), 4.19 (2H, qd, J=8.9, 6.5), 4.63 (2H, s), 6.43 (1H, brs), 6.83-6.98 (2H, m), 7.00-7.06 (1H, m), 7.11-7.22 (2H, m), 7.45-7.66 (2H, m), 7.89-8.05 (2H, m).

Example 288

5-{[(3-fluorophenyl)thio]methyl}-N-(2-hydroxyethyl)-1-(4-{[(2,2,2-trifluoroethyl)amino]carbonyl}phenyl)-1H-1,2,3-triazole-4-carboxamide NMR (DMSO-d$_6$) δ: 3.33-3.40 (2H, m), 3.47-3.56 (2H, m), 4.15 (2H, qd, J=9.6, 6.5), 4.78 (1H, t, J=5.6), 4.84 (2H, s), 6.91-7.10 (3H, m), 7.16-7.30 (1H, m), 7.76 (2H, d, J=8.7), 8.09 (2H, d, J=8.7), 8.57 (1H, t, J=5.7), 9.33 (1H, t, J=6.3).

Example 289

1-{4-[(ethylamino)carbonyl]phenyl}-5-{[(3-fluorophenyl)thio]methyl}-N-methyl-1H-1,2,3-triazole-4-carboxamide NMR (CDCl$_3$) δ: 1.30 (3H, t, J=7.3), 3.02 (3H, d, J=5.1), 3.47-3.66 (2H, m), 4.61 (2H, s), 6.16 (1H, brs), 6.86-7.00 (2H, m), 6.99-7.07 (1H, m), 7.11-7.23 (2H, m), 7.49-7.60 (2H, m), 7.86-8.00 (2H, m).

Example 290

1-{4-[(ethylamino)carbonyl]phenyl}-5-{[(3-fluorophenyl)thio]methyl}-N-(2-hydroxyethyl)-1H-1,2,3-triazole-4-carboxamide NMR (DMSO-d$_6$) δ: 1.16 (3H, t, J=7.2), 3.26-3.40 (4H, m), 3.45-3.59 (2H, m), 4.78 (1H, t, J=5.6), 4.82 (2H, s), 6.91-7.10 (3H, m), 7.14-7.31 (1H, m), 7.71 (2H, d, J=8.5), 8.04 (2H, d, J=8.5), 8.56 (1H, t, J=5.7), 8.69 (1H, t, J=5.6).

Example 291

1-(2-[(6-fluorohexyl)oxy]-4-{[(2,2,2-trifluoroethyl)amino]carbonyl}phenyl)-N-(2-methoxyethyl)-1H-1,2,3-triazole-4-carboxamide NMR (CDCl$_3$) δ: 1.44-1.47 (4H, m), 1.64-1.85 (4H, m), 3.41 (3H, s), 3.57-3.61 (2H, m), 3.67-3.72 (2H, m), 4.11-4.22 (4H, m), 4.43 (2H, td, J=6.0, 47.3), 6.52 (1H, t, J=5.7), 7.42 (1H, dd, J=1.3, 8.3), 7.53 (1H, t, J=5.3), 7.67 (1H, d, J=1.3), 7.95 (1H, d, J=8.3), 8.68 (1H, s).

Example 292

1-(2-[(6-fluorohexyl)oxy]-4-{[(2,2,2-trifluoroethyl)amino]carbonyl}phenyl)-N-(2-hydroxyethyl)-1H-1,2,3-triazole-4-carboxamide NMR (DMSO-d$_6$) δ: 1.34-1.37 (4H, m), 1.55-1.74 (4H, m), 3.36-3.39 (2H, m), 3.50-3.56 (2H, m), 4.10-4.21 (4H, m), 4.40 (2H, td, J=6.0, 47.3), 4.78 (1H, t, J=5.5), 7.68 (1H, dd, J=1.5, 8.1), 7.77 (1H, d, J=1.5), 7.83 (1H, d, J=8.3), 8.52 (1H, t, J=5.7), 8.89 (1H, s), 9.30 (1H, t, J=6.4).

Example 293

1-(2-[2-(2-fluoroethoxy)ethoxy]-4-{[(2,2,2-trifluoroethyl)amino]carbonyl}phenyl)-N-(2-hydroxyethyl)-1H-1,2,3-triazole-4-carboxamide NMR (DMSO-d$_6$) δ: 3.38 (2H, t, J=6.0), 3.53 (2H, q, J=5.9), 3.61-3.76 (2H, m), 3.78-3.84 (2H, m), 4.08-4.23 (2H, m), 4.35-4.41 (2H, m), 4.44-4.67 (2H, m), 4.78 (1H, t, J=5.7), 7.70 (1H, dd, J=8.3, 1.7), 7.82 (1H, d, J=1.7), 7.92 (1H, d, J=8.3), 8.52 (1H, t, J=5.7), 8.99 (1H, s), 9.29 (1H, d, J=6.0).

Example 294

N-{[5-(5-fluoropentyl)-1-(4-{[(2,2,2-trifluoroethyl)amino]carbonyl}phenyl)-1H-1,2,3-triazol-4-yl]carbonyl}phenylalanine In the same manner as in Example 133e), the title compound was obtained as a white powder (0.40 g, 97%) from methyl N-{[5-(5-fluoropentyl)-1-(4-{[(2,2,2-trifluoroethyl)amino]carbonyl}phenyl)-1H-1,2,3-triazol-4-yl]carbonyl}phenylalaninate (0.43 g) obtained in Example 221.

NMR (DMSO-$d_6$) δ: 1.04 (2H, d, J=6.0), 1.19 (2H, q, J=7.1), 1.31-1.60 (4H, m), 3.02 (1H, t, J=7.2), 3.14-3.28 (2H, m), 4.06-4.46 (5H, m), 7.04-7.24 (5H, m), 7.75 (2H, d, J=8.3), 8.07-8.23 (3H, m), 9.39 (1H, t, J=6.4).

Example 295

N-({1-{4-[(ethylamino)carbonyl]phenyl}-5-[(methylthio)methyl]-1H-1,2,3-triazol-4-yl}carbonyl)phenylalanine In the same manner as in Example 133e), the title compound was obtained as a white powder (0.34 g, 97%) from methyl N-({1-{4-[(ethylamino)carbonyl]phenyl}-5-[(methylthio)methyl]-1H-1,2,3-triazol-4-yl}carbonyl)phenylalaninate (0.36 g) obtained in Example 222.

NMR (CDCl$_3$) δ: 1.29 (3H, t, J=7.3), 2.02 (3H, s), 2.39 (1H, brs), 3.17-3.41 (2H, m), 3.47-3.59 (2H, m), 3.98-4.16 (2H, m), 5.00-5.10 (1H, m), 6.18-6.26 (1H, m), 7.20-7.37 (5H, m), 7.64-7.73 (3H, m), 7.92-7.99 (2H, m).

Example 296

N-(2-aminoethyl)-5-(5-fluoropentyl)-1-(4-{[(2,2,2-trifluoroethyl)amino]carbonyl}phenyl)-1H-1,2,3-triazole-4-carboxamide monohydrochloride To a solution of tert-butyl [2-({[5-(5-fluoropentyl)-1-(4-{[(2,2,2-trifluoroethyl)amino]carbonyl}phenyl)-1H-1,2,3-triazol-4-yl]carbonyl}amino)ethyl]carbamate (0.86 g) obtained in Example 219 in ethyl acetate (10 ml) was added 4N hydrochloric acid/ethyl acetate solution (10 ml), and the mixture was stirred at room temperature overnight. The solvent was evaporated under reduced pressure, diisopropyl ether was added to the obtained residue, and the resultant precipitate was collected by filtration to give the title compound as a white powder (0.76 g, 99%).

LCMS (m/z); 445.33.

In the same manner as in Example 296, the compound of Example 297 was synthesized.

Example 297

N-(2-aminoethyl)-1-{4-[(ethylamino)carbonyl]phenyl}-5-[(methylthio)methyl]-1H-1,2,3-triazole-4-carboxamide monohydrochloride LCMS (m/z); 363.27.

Example 298

5-(5-fluoropentyl)-N-[2-({[(3-fluorophenyl)amino]carbonyl}amino)ethyl]-1-(4-{[(2,2,2-trifluoroethyl)amino]carbonyl}phenyl)-1H-1,2,3-triazole-4-carboxamide To a suspension of N-(2-aminoethyl)-5-(5-fluoropentyl)-1-(4-{[(2,2,2-trifluoroethyl)amino]carbonyl}phenyl)-1H-1,2,3-triazole-4-carboxamide monohydrochloride (0.12 g) obtained in Example 296 in dichloromethane (5.0 ml) were added triethylamine (0.07 ml) and 1-fluoro-3-isocyanatobenzene (0.06 ml), and the mixture was stirred at room temperature overnight. Water was added to the reaction mixture, and the resultant precipitate was collected by filtration, washed with water and recrystallized from ethanol-water to give the title compound as a white powder (0.14 g, 98%).

NMR (DMSO-$d_6$) δ: 1.12-1.26 (2H, m), 1.36-1.60 (4H, m), 2.97-3.08 (2H, m), 3.25-3.47 (4H, m), 4.07-4.19 (2H, m), 4.30 (2H, dt, J=47.5, 6.0), 6.40 (1H, t, J=5.5), 6.65-6.72 (1H, m), 7.01-7.06 (1H, m), 7.18-7.27 (1H, m), 7.45 (1H, dt, J=12.2, 2.3), 7.76 (2H, d, J=8.7), 8.14 (2H, d, J=8.7), 8.69 (1H, t, J=5.5), 8.89 (1H, s), 9.36 (1H, t, J=6.3).

In the same manner as in Example 298, the compounds of Example 299 to Example 304 were synthesized.

Example 299

N-[2-({[(3-fluorobenzyl)amino]carbonyl}amino)ethyl]-5-(5-fluoropentyl)-1-(4-{[(2,2,2-trifluoroethyl)amino]carbonyl}phenyl)-1H-1,2,3-triazole-4-carboxamide NMR (DMSO-$d_6$) δ: 1.11-1.28 (2H, m), 1.34-1.62 (4H, m), 2.97-3.09 (2H, m), 3.18-3.41 (4H, m), 4.04-4.45 (6H, m), 6.17 (1H, t, J=5.6), 6.52 (1H, t, J=6.0), 6.96-7.14 (3H, m), 7.27-7.40 (1H, m), 7.76 (2H, d, J=8.7), 8.14 (2H, d, J=8.5), 8.65 (1H, t, J=5.6), 9.35 (1H, t, J=6.3).

Example 300

N-(2-{[(ethylamino)carbonyl]amino}ethyl)-5-(5-fluoropentyl)-1-(4-{[(2,2,2-trifluoroethyl)amino]carbonyl}phenyl)-1H-1,2,3-triazole-4-carboxamide NMR (DMSO-$d_6$) δ: 0.98 (3H, t, J=7.2), 1.14-1.26 (2H, m), 1.36-1.60 (4H, m), 2.94-3.08 (4H, m), 3.13-3.36 (4H, m), 4.15 (2H, qd, J=9.7, 6.6), 4.32 (2H, dt, J=47.5, 6.0), 5.89 (1H, t, J=5.7), 5.96 (1H, t, J=5.6), 7.76 (2H, d, J=8.7), 8.14 (2H, d, J=8.5), 8.63 (1H, t, J=5.5), 9.34 (1H, t, J=6.3).

Example 301

N-[2-({[(2-chloroethyl)amino]carbonyl}amino)ethyl]-5-(5-fluoropentyl)-1-(4-{[(2,2,2-trifluoroethyl)amino]carbonyl}phenyl)-1H-1,2,3-triazole-4-carboxamide NMR (DMSO-$d_6$) δ: 1.12-1.28 (2H, m), 1.36-1.61 (4H, m), 2.96-3.09 (2H, m), 3.14-3.26 (2H, m), 3.25-3.37 (4H, m), 3.54-3.59 (2H, m), 4.15 (2H, qd, J=9.7, 6.4), 4.32 (2H, dt, J=47.5, 6.1), 6.16-6.28 (2H, m), 7.72-7.81 (2H, m), 8.02-8.23 (2H, m), 8.62 (1H, t, J=5.6), 9.34 (1H, t, J=6.2).

Example 302

N-{2-[(aminocarbonyl)amino]ethyl}-5-(5-fluoropentyl)-1-(4-{[(2,2,2-trifluoroethyl)amino]carbonyl}phenyl)-1H-1,2,3-triazole-4-carboxamide NMR (DMSO-d$_6$) δ: 1.11-1.28 (2H, m), 1.32-1.64 (4H, m), 2.95-3.60 (6H, m), 4.08-4.43 (4H, m), 6.12 (1H, brs), 7.65 (1H, brs), 7.70-7.80 (2H, m), 7.87 (1H, brs), 8.09-8.18 (2H, m), 8.64 (1H, t, J=4.5), 9.36 (1H, t, J=6.2).

Example 303

2-({[5-(5-fluoropentyl)-1-(4-{[(2,2,2-trifluoroethyl)amino]carbonyl}phenyl)-1H-1,2,3-triazol-4-yl]carbonyl}amino)ethyl (3-fluorophenyl)carbamate NMR (CDCl$_3$) δ: 1.34-1.41 (2H, m), 1.52-1.68 (2H, m), 3.04-3.09 (2H, m), 3.77-3.82 (2H, m), 4.18 (2H, td, J=6.0, 47.3), 4.38 (2H, t, J=5.1), 6.52 (1H, t, J=6.4), 6.77 (1H, dt, J=2.5, 8.5), 7.00-7.06 (2H, m), 7.21-7.34 (4H, m), 7.57 (1H, d, J=8.3), 7.60 (1H, d, J=6.2), 8.03 (2H, d, J=8.5).

Example 304

2-({[5-(5-fluoropentyl)-1-(4-{[(2,2,2-trifluoroethyl)amino]carbonyl}phenyl)-1H-1,2,3-triazol-4-yl]carbonyl}amino)ethyl (3-fluorobenzyl)carbamate NMR (CDCl$_3$) δ: 1.34-1.42 (2H, m), 1.53-1.71 (2H, m), 3.04-3.10 (2H, m), 3.72-3.77 (2H, m), 4.19 (2H, dq, J=6.4, 9.0), 4.36 (2H, td, J=6.0, 47.3), 4.32 (2H, t, J=5.1), 4.38 (2H, d, J=6.0), 5.17 (1H, brs), 6.48 (1H, t, J=6.0), 6.91-7.09 (3H, m), 7.28-7.33 (3H, m), 7.56-7.61 (3H, m), 8.01-8.05 (2H, m).

Example 305

N-cyclopropyl-1-{4-[(ethylamino)carbonyl]-2-(vinyloxy)phenyl}-1H-1,2,3-triazole-4-carboxamide To a suspension of sodium hydride (0.06 g, purity 60%) in DMF (5 ml) was added 1-{2-(2-chloroethoxy)-4-[(ethylamino)carbonyl]phenyl}-N-cyclopropyl-1H-1,2,3-triazole-4-carboxamide (0.19 g) obtained in Example 150, and the mixture was stirred at 0° C. for 30 min and at room temperature overnight. Water was added to the reaction mixture, and the mixture was extracted with ethyl acetate. The organic layer was dried over anhydrous sodium sulfate, and the solvent was evaporated under reduced pressure. The residue was purified by silica gel column (ethyl acetate/hexane=1/1 to ethyl acetate) and recrystallized from ethanol-water to give the title compound as a pale-yellow powder (0.02 g, 13%).

NMR (DMSO-d$_6$) δ: 0.60-0.76 (4H, m), 1.14 (3H, d, J=7.2), 2.82-2.93 (1H, m), 3.24-3.44 (2H, m), 4.67 (1H, dd, J=6.0, 2.1), 4.83 (1H, dd, J=13.5, 2.0), 6.92 (1H, dd, J=13.6, 6.0), 7.75-7.82 (2H, m), 7.85 (1H, d, J=8.7), 8.69-8.77 (2H, m), 8.91 (1H, s).

Example 306

5-(5-fluoropentyl)-N-[2-(2-oxoimidazolidin-1-yl)ethyl]-1-(4-{[(2,2,2-trifluoroethyl)amino]carbonyl}phenyl)-1H-1,2,3-triazole-4-carboxamide To a solution of N-[2-({[(2-chloroethyl)amino]carbonyl}amino)ethyl]-5-(5-fluoropentyl)-1-(4-{[(2,2,2-trifluoroethyl)amino]carbonyl}phenyl)-1H-1,2,3-triazole-4-carboxamide (0.06 g) obtained in Example 301 in THF (5.5 ml) was added potassium tert-butoxide (0.03 g), and the mixture was stirred at room temperature overnight. The reaction mixture was neutralized with 1N hydrochloric acid, and the solvent was evaporated under reduced pressure. Water was added to the obtained residue, and the mixture was extracted with ethyl acetate. The organic layer was dried over anhydrous sodium sulfate, and the solvent was evaporated under reduced pressure. The residue was purified by preparative HPLC (acetonitrile-water) and recrystallized from acetonitrile-water to give the title compound as a white powder (0.01 g, 14%).

NMR (DMSO-d$_6$) δ: 1.10-1.28 (2H, m), 1.33-1.63 (4H, m), 2.97-3.09 (2H, m), 3.15-3.29 (4H, m), 3.35-3.49 (4H, m), 4.06-4.19 (2H, m), 4.31 (2H, dt, J=47.4, 6.1), 6.28 (1H, s), 7.77 (2H, d, J=8.5), 8.13 (2H, d, J=8.3), 8.65 (1H, t, J=5.7), 9.34 (1H, t, J=6.2).

Example 307

N-cyclopropyl-1-{4-[(ethylamino)carbonyl]-2-[(6-fluorohexyl)oxy]phenyl}-1H-1,2,3-triazole-4-carboxamide To a suspension of N-cyclopropyl-1-{4-[(ethylamino)carbonyl]-2-[(6-hydroxyhexyl)oxy]phenyl}-1H-1,2,3-triazole-4-carboxamide (0.14 g) obtained in Example 183 in dichloromethane (10 ml) was added DAST (0.10 ml) at −78° C. The reaction mixture was slowly allowed to warm to room temperature and stirred overnight. Saturated aqueous sodium hydrogen carbonate solution was added to the reaction mixture, and the organic layer was separated. The organic layer was dried over anhydrous sodium sulfate, and the solvent was evaporated under reduced pressure. The residue was purified by silica gel column (ethyl acetate) and recrystallized from ethyl acetate-diisopropyl ether to give the title compound as a white powder (0.02 g, 15%).

NMR (CDCl$_3$) δ: 0.67-0.72 (2H, m), 0.86-0.93 (2H, m), 1.29 (3H, t, J=7.2), 1.42-1.47 (4H, m), 1.63-1.86 (4H, m), 2.90-2.98 (1H, m), 3.49-3.58 (2H, m), 4.17 (2H, t, J=6.6), 4.44 (2H, td, J=6.0, 47.5), 6.17 (1H, t, J=4.9), 7.27 (1H, brs), 7.35 (1H, dd, J=1.7, 8.3), 7.65 (1H, d, J=1.7), 7.87 (1H, d, J=8.3), 8.68 (1H, s).

Example 308

N-cyclopropyl-1-{4-[(ethylamino)carbonyl]-2-[2-(2-fluoroethoxy)ethoxy]phenyl}-1H-1,2,3-triazole-4-carboxamide 308a) N-cyclopropyl-1-{2-[2-(2-bromoethoxy)ethoxy]-4-[(ethylamino)carbonyl]phenyl}-1H-1,2,3-triazole-4-carboxamide In the same manner as in Example 133d), the title compound was obtained as a white powder (0.60 g, 64%) from N-cyclopropyl-1-{4-[(ethylamino)carbonyl]-2-hydroxyphenyl}-1H-1,2,3-triazole-4-carboxamide (0.63 g) obtained in Example 139 and 1-bromo-2-(2-bromoethoxy)ethane (0.28 ml).

NMR (CDCl$_3$) δ: 0.66-0.72 (2H, m), 0.86-0.93 (2H, m), 1.29 (3H, t, J=7.2), 2.89-2.98 (1H, m), 3.46-3.60 (4H, m), 3.82-3.91 (4H, m), 4.35-4.38 (2H, m), 6.20 (1H, t, J=5.7), 7.28 (1H, brs), 7.40 (1H, dd, J=1.7, 8.3), 7.68 (1H, d, J=1.7), 7.95 (1H, d, J=8.3), 8.93 (1H, s).

308b) N-cyclopropyl-1-{4-[(ethylamino)carbonyl]-2-[2-(2-fluoroethoxy)ethoxy]phenyl}-1H-1,2,3-triazole-4-carboxamide To a solution of N-cyclopropyl-1-{2-[2-(2-bromoethoxy)ethoxy]-4-[(ethylamino)carbonyl]phenyl}-1H-1,2,3-triazole-4-carboxamide (0.23 g) obtained in Example 308a) in acetonitrile (10 ml) was added tetrabutylammonium fluoride monohydrate (0.39 g), and the mixture was stirred at 80° C. overnight. The reaction mixture was allowed to cool to room temperature, and the solvent, was evaporated under reduced pressure. The residue was purified by preparative HPLC (acetonitrile-water) and recrystallized from acetonitrile-water to give the title compound as a white powder (0.04 g, 21%).

NMR (CDCl$_3$) δ: 0.66-0.71 (2H, m), 0.86-0.92 (2H, m), 1.29 (3H, t, J=7.2), 2.89-2.97 (1H, m), 3.53 (2H, dq, J=5.7, 7.2), 3.79-3.82 (1H, m), 3.89-3.93 (3H, m), 4.35-4.38 (2H, m), 4.59-4.62 (1H, m), 4.75-4.78 (1H, m), 6.20 (1H, t, J=5.2), 7.29 (1H, brs), 7.40 (1H, dd, J=1.7, 8.3), 7.68 (1H, d, J=1.7), 7.97 (1H, d, J=8.3), 8.98 (1H, s).

In the same manner as in Example 308, the compound of Example 309 was synthesized.

Example 309

N-cyclopropyl-1-{4-[(ethylamino)carbonyl]-2-[2-(2-fluoroethoxy)ethoxy]phenyl}-5-methyl-1H-1,2,3-triazole-4-carboxamide NMR (CDCl$_3$) δ: 0.66-0.70 (2H, m), 0.84-0.91 (2H, m), 1.28 (3H, t, J=7.2), 2.48 (3H, s), 2.86-2.95 (1H, m), 3.48-3.58 (3H, m), 3.65-3.68 (1H, m), 3.72-3.75 (2H, m), 4.21-4.24 (2H, m), 4.39-4.58 (2H, m), 6.38 (1H, t, J=6.4), 7.32 (1H, d, J=2.8), 7.39-7.46 (2H, m), 7.65 (1H, d, J=1.3).

Example 310

1-{4-[(ethylamino)carbonyl]phenyl}-N-(4-fluorobut-2-yn-1-yl)-5-[(3-fluorophenoxy)methyl]-1H-1,2,3-triazole-4-carboxamide In the same manner as in Example 308b), the title compound was obtained as a white powder (0.03 g, 34%) from N-(4-chlorobut-2-yn-1-yl)-1-{4-[(ethylamino)carbonyl]phenyl}-5-[(3-fluorophenoxy)methyl]-1H-1,2,3-triazole-4-carboxamide (0.10 g) obtained in Example 253.

NMR (CDCl$_3$) δ: 1.29 (3H, t, J=7.3), 3.49-3.59 (2H, m), 5.39 (1H, d, J=11.7), 5.50 (2H, s), 5.89 (1H, d, J=17.5), 6.13 (1H, brs), 6.53-6.62 (1H, m), 6.62-6.77 (3H, m), 7.13 (1H, s), 7.17-7.26 (2H, m), 7.71-7.80 (2H, m), 7.89-8.00 (2H, m).

Example 311

5-{[benzyl(methyl)amino]methyl}-N-cyclopropyl-1-{4-[(ethylamino)carbonyl]phenyl}-1H-1,2,3-triazole-4-carboxamide

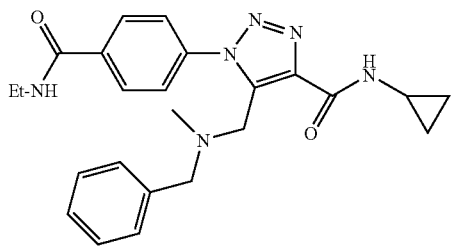

In the same manner as in Example 126, the title compound was obtained as a white powder (123 mg, 57%).

$^1$H NMR (300 MHz, CDCl$_3$) δ: 0.65-0.70 (2H, m), 0.86-0.92 (2H, m), 1.31 (3H, t, J=7.1 Hz), 2.16 (3H, s), 2.88-2.94 (1H, m), 3.51-3.60 (4H, m), 4.02 (2H, s), 6.20 (1H, brs), 7.07-7.10 (2H, m), 7.21-7.28 (3H, m), 7.47 (1H, brs), 7.90-7.96 (4H, m).

Example 312

1-{2-(benzyloxy)-4-[(ethylamino)carbonyl]phenyl}-N-cyclopropyl-5-propyl-1H-1,2,3-triazole-4-carboxamide

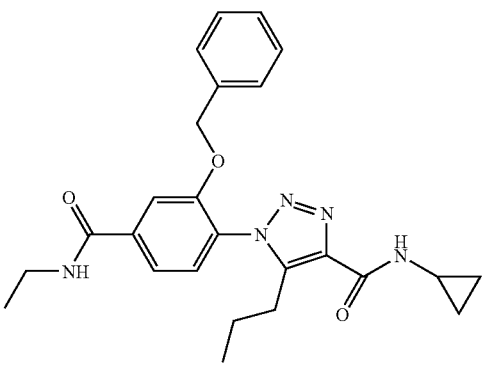

312a) N-ethyl-3-hydroxy-4-nitrobenzamide

3-Hydroxy-4-nitrobenzoic acid (6.06 g, 32.1 mmol), HOBt (0.876 g, 6.42 mmol, 0.2 eq.) and ethylamine hydrochloride (3.03 g, 35.3 mmol, 1.1 eq.) were suspended in DMF (80 ml), triethylamine (5.82 ml, 41.7 mmol, 1.3 eq.) was added, WSC (6.91 g, 35.3 mmol, 1.1 eq.) was added, and the mixture was stirred at room temperature for 14.5 hr. The reaction mixture was suspended in ethyl acetate-hexane (4:1, 250 ml) and washed sequentially with 8% acidic solution of ammonium chloride in water (×2), 10% aqueous ammonium chloride solution and saturated brine. The aqueous layers were each extracted with ethyl acetate-hexane (4:1, 150 ml). The organic layers were combined, dried over anhydrous sodium sulfate, and concentrated, and the residue was diluted with diethyl ether. The precipitate was collected by filtration, washed with diethyl ether and dried to give the title compound as a yellow powder (5.14 g, 24.5 mmol, 76.2%).

NMR (200 MHz, CDCl$_3$) δ: 1.28 (3H, t, J=7.3 Hz), 3.52 (2H, dq, J=5.6, 7.3 Hz), 6.11 (1H, br), 7.36 (1H, dd, J=8.8, 2.0 Hz), 7.51 (1H, d, J=1.8 Hz), 8.18 (1H, d, J=8.8 Hz), 10.57 (1H, s).

312b) N-ethyl-3-benzyloxy-4-nitrobenzamide

N-Ethyl-3-hydroxy-4-nitrobenzamide (5.23 g, 24.9 mmol) obtained in Example 312a) was dissolved in anhydrous DMF (100 ml), potassium carbonate (4.47 g, 32.3 mmol, 1.3 eq.) was added at room temperature, benzyl bromide (3.17 ml, 26.1 mmol, 1.05 eq.) was added dropwise, and the mixture was stirred at room temperature for 15 hr. The reaction mixture was diluted with 5% aqueous sodium hydrogen carbonate solution (200 ml) and extracted with ethyl acetate-hexane (3:1, 200 ml and 150 ml). The organic layer was washed sequentially with 5% aqueous sodium hydrogen carbonate solution and saturated brine, dried over anhydrous sodium sulfate and concentrated, and diethyl ether was added to the residue. The precipitate was collected by filtration, washed with diethyl ether and dried to give the title compound as a yellow powder (5.42 g, 18.1 mmol, 72.5%).

NMR (200 MHz, CDCl$_3$) δ: 1.27 (3H, t, J=7.1 Hz), 3.51 (2H, dq, J=5.8, 7.2 Hz), 5.29 (2H, s), 6.10 (1H, br), 7.27 (1H, dd, J=8.4, 1.4 Hz), 7.33-7.50 (5H, m), 7.67 (1H, d, J=1.8 Hz), 7.87 (1H, d, J=8.0 Hz).

312c) N-ethyl-4-amino-3-benzyloxybenzamide

N-Ethyl-3-benzyloxy-4-nitrobenzamide (5.40 g, 18.0 mmol) obtained in Example 312b) was dissolved in ethyl acetate (60 ml) and methanol (40 ml), anhydrous tin(II) chloride (17.6 g, 89.9 mmol, 5.0 eq.) was added, and the mixture was stirred at room temperature for 21 hr. The reaction mixture was concentrated, and methanol was evaporated. The residue was diluted with ethyl acetate (200 ml) and mixed with 1.44N sodium hydroxide (150 ml). The obtained suspension was filtered through celite (diameter 60 mm) and washed with ethyl acetate (100 ml). The filtrate and washing were combined, washed sequentially with saturated aqueous sodium hydrogen carbonate solution and saturated brine, dried over anhydrous sodium sulfate and concentrated. The residue was subjected to column chromatography (elution solvent, ethyl acetate-hexane=1:1-2:1) on silica gel (manufactured by E. Merck, Art.7734, 50 g). The fraction obtained by elution with ethyl acetate-hexane (3:2) was concentrated, and diethyl ether was added. The precipitate was collected by filtration, washed with diethyl ether and dried to give the title compound as a white powder (4.27 g, 15.8 mmol, 87.8%).

NMR (200 MHz, CDCl$_3$-DMSO-d$_6$=19:1) δ: 1.23 (3H, t, J=7.1 Hz), 3.45 (2H, dq, J=5.4, 7.2 Hz), 5.14 (2H, s), 6.57 (1H, m), 6.84 (1H, d, J=8.0 Hz), 7.23 (1H, dd, J=8.0, 2.0 Hz), 7.34-7.47 (5H, m), 7.49 (1H, d, J=2.0 Hz).

Elemental analysis for C$_{16}$H$_{18}$N$_2$O$_2$
Calcd.: C, 71.09; H, 6.71; N, 10.36.
Found: C, 70.98; H, 6.76; N, 10.30.

312d) N-ethyl-4-azido-3-benzyloxybenzamide

N-Ethyl-4-amino-3-benzyloxybenzamide (900 mg, 3.33 mmol) obtained in Example 312c) was dissolved in water (9 ml) and acetic acid (6 ml), 1N hydrochloric acid (3.33 ml, 1.0 eq.) was added. An aqueous solution (3 ml) of sodium nitrite (234 mg, 3.33 mmol, 1.0 eq.) was added at 0° C., and the mixture was stirred for 20 min. An aqueous solution (3 ml) of sodium azide (221 mg, 3.33 mmol, 1.0 eq.) was further added, and the mixture was stirred at 0° C. for 1.5 hr. The reaction mixture was diluted with ethyl acetate-hexane (3:1, 50 ml), washed sequentially with water, 0.1N hydrochloric acid, saturated aqueous sodium hydrogen carbonate solution and saturated brine, dried over anhydrous sodium sulfate and concentrated, and diethyl ether was added to the residue. The precipitate was collected by filtration, washed with diethyl ether and dried to give the title compound as a yellow powder (782 mg, 2.64 mmol, 79.2%).

NMR (200 MHz, CDCl$_3$) δ: 1.25 (3H, t, J=7.1 Hz), 3.49 (2H, dq, J=5.6, 7.3 Hz), 5.19 (2H, s), 6.01 (1H, m), 7.00 (1H, d, J=8.4 Hz), 7.22 (1H, dd, J=8.2, 2.0 Hz), 7.33-7.50 (5H, m), 7.53 (1H, d, J=1.8 Hz).

312e) 1-{2-(benzyloxy)-4-[(ethylamino)carbonyl]phenyl}-5-propyl-1H-1,2,3-triazole-4-carboxylic acid N-Ethyl-4-azido-3-benzyloxybenzamide (1.03 g, 3.33 mmol) obtained in the same manner as in Example 312d) and ethyl 3-oxohexanoate (0.672 ml, 4.00 mmol, 1.2 eq.) were dissolved in ethanol (25 ml), sodium ethoxide (302 mg, 4.00 mmol, 1.2 eq.) was added, and the mixture was stirred at room temperature for 15 min and at 60° C. for 11 hr. Ethyl 3-oxohexanoate (0.112 ml, 0.666 mmol, 0.2 eq.) was added, and the mixture was stirred for 5 hr. Then, 1N sodium hydroxide (3.33 ml, 1.0 eq.) was added, and the mixture was stirred for 4 hr. The reaction mixture was diluted with water (20 ml), ethanol was evaporated, and the residue was diluted with 2% aqueous sodium carbonate solution (20 ml) and washed with ethyl acetate-hexane (2:1, 50 ml). The organic layer was extracted with 2% aqueous sodium carbonate solution (20 ml). The aqueous layers were combined, acidified (pH<3) with 6N hydrochloric acid and extracted with ethyl acetate (35 ml×2). The organic layer was washed with saturated brine, dried over anhydrous sodium sulfate, and concentrated to dryness to give the title compound as a pale-brown solid (purity about 90%, 1.05 g, 2.3 mmol, 70%). This solid (purity about 90%, 1.05 g, 2.32 mmol), HOBt (159 mg, 1.16 mmol, 0.5 eq.) and cyclopropylamine (0.232 ml, 3.25 mmol, 1.4 eq.) was dissolved in acetonitrile (16 ml), WSC (568 mg, 2.91 mmol, 1.25 eq.) was added, and the mixture was stirred at room temperature for 5 hr. The reaction mixture was concentrated, diluted with ethyl acetate (50 ml) and washed sequentially with 2% aqueous sodium carbonate solution, 10% aqueous ammonium chloride solution and saturated brine, dried over anhydrous sodium sulfate and concentrated. The residue was subjected to column chromatography (elution solvent, ethyl acetate-hexane=1:4-3:2) on silica gel (manufactured by E. Merck, Art.7734, 10 g), and the fraction obtained by elution with ethyl acetate-hexane (1:1-3:2) was concentrated. The residue was again subjected to column chromatography (elution solvent, ethyl acetate-hexane=1:2-1:1) on silica gel (20 g), and the object fraction was concentrated to dryness to give the title compound as yellow foamy powder (724 mg, 1.62 mmol, 69.7%).

NMR (200 MHz, CDCl$_3$) δ: 0.68 (2H, m), 0.78 (3H, t, J=7.4 Hz), 0.87 (2H, m), 1.29 (3H, t, J=7.4 Hz), 1.48 (2H, brq, J=7.5 Hz), 2.90 (1H, octet, J=3.5 Hz), 3.53 (2H, dq, J=6.0, 7.2 Hz), 5.15 (2H, s), 6.14 (1H, brt, J=6 Hz), 7.21 (2H, m), 7.26-7.34 (4H, m), 7.37 (2H, d, J=0.8 Hz), 7.69 (1H, brs).

Elemental analysis for C$_{25}$H$_{29}$N$_5$O$_3$
Calcd.: C, 67.09; H, 6.53; N, 15.65.
Found: C, 66.88; H, 6.73; N, 15.34.

Example 313

N-cyclopropyl-1-{4-[(ethylamino)carbonyl]phenyl}-5-[(phenylsulfinyl)methyl]-1H-1,2,3-triazole-4-carboxamide

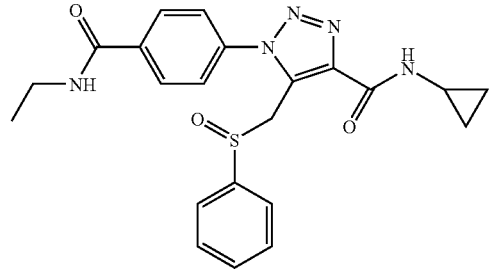

N-Cyclopropyl-1-{4-[(ethylamino)carbonyl]phenyl}-5-[(phenylthio)methyl]-1H-1,2,3-triazole-4-carboxamide (145 mg, 0.344 mmol) obtained in Example 130 was dissolved in THF (3.0 ml), m-chloroperbenzoic acid (purity 65%, 110 mg, 0.412 mmol, 1.2 eq.) was added with stirring at 0° C., and the mixture was stirred for additional 1.5 hr. The reaction mixture was diluted with ethyl acetate (20 ml), washed with 5% aqueous sodium sulfite solution, 2% aqueous sodium hydrogen carbonate solution and saturated brine, dried over anhydrous sodium sulfate and concentrated. The residue was subjected to column chromatography (elution solvent, ethyl acetate-hexane=1:1-5:1) on silica gel (manufactured by E. Merck, Art.7734, 10 g). The fraction obtained by elution with ethyl acetate-hexane (5:1) was concentrated, and diethyl ether was added. The precipitate was collected by filtration, washed with diethyl ether and dried to give the title compound as a white powder (38 mg, 0.087 mmol, 25.3%).

NMR (200 MHz, CDCl$_3$) δ: 0.71 (2H, m), 0.92 (2H, m), 1.30 (3H, t, J=7.2 Hz), 2.91 (1H, octet, J=3.7 Hz), 3.55 (2H, dq, J=5.4, 7.3 Hz), 4.20 (1H, d, J=12.8 Hz), 4.69 (1H, d, J=13.2 Hz), 6.18 (1H, m), 7.34 (1H, brd, J=3 Hz), 7.52 (3H, m), 7.70 (2H, m), 7.81 (2H, d, J=8.8 Hz), 7.95 (2H, d, J=8.4 Hz).

Elemental analysis for $C_{22}H_{23}N_5O_3S \cdot 0.2H_2O \cdot 0.1Et_2O$
Calcd.: C, 59.98; H, 5.48; N, 15.61.
Found: C, 59.72; H, 5.49; N, 15.63.

Example 314

N-cyclopropyl-1-{4-[(ethylamino)carbonyl]phenyl}-5-[(phenylsulfonyl)methyl]-1H-1,2,3-triazole-4-carboxamide

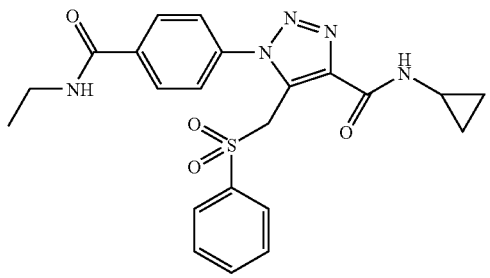

N-Cyclopropyl-1-{4-[(ethylamino)carbonyl]phenyl}-5-[(phenylsulfinyl)methyl]-1H-1,2,3-triazole-4-carboxamide (107 mg, 0.24 mmol) obtained in Example 313 was dissolved in THF (2.0 ml), m-chloroperbenzoic acid (purity 65%, 64 mg, 0.24 mmol, 1.0 eq.) was added with stirring at 0° C., and the mixture was stirred for 1 hr and at room temperature for 2 hr. The reaction mixture was diluted with ethyl acetate (25 ml), washed with 5% aqueous sodium sulfite solution, 2% aqueous sodium carbonate solution and saturated brine, dried over anhydrous sodium sulfate and concentrated. Diethyl ether was added to the residue, and the precipitate was collected by filtration, washed with diethyl ether and dried to give the title compound as a white powder (111 mg, 0.24 mmol, quant.).

NMR (200 MHz, CDCl$_3$) δ: 0.53 (2H, m), 0.80 (2H, m), 1.31 (3H, t, J=7.2 Hz), 2.64 (1H, octet, J=3.6 Hz), 3.56 (2H, dq, J=5.6, 7.1 Hz), 5.04 (2H, s), 6.23 (1H, brt, J=6 Hz), 7.07 (1H, brd, J=3 Hz), 7.63-7.74 (5H, m), 7.91 (2H, brt, J=7.3 Hz), 8.00 (2H, d, J=8.8 Hz).

Elemental analysis for $C_{22}H_{23}N_5O_3S$
Calcd.: C, 58.26; H, 5.11; N, 15.44.
Found: C, 58.24; H, 5.15; N, 15.24.
melting point: 169-172° C.

Example 315

N-cyclopropyl-1-{4-[(ethylamino)carbonyl]-2-hydroxyphenyl}-5-propyl-1H-1,2,3-triazole-4-carboxamide

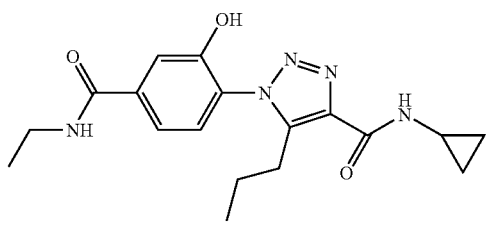

1-{2-(Benzyloxy)-4-[(ethylamino)carbonyl]phenyl}-N-cyclopropyl-5-propyl-1H-1,2,3-triazole-4-carboxamide compound (582 mg, 1.30 mmol) obtained in Example 312 was dissolved in methanol (20 ml), and the mixture was stirred at room temperature for 4 hr in the presence of 10% palladium carbon (wet, purity 50%, 116 mg) under a hydrogen atmosphere. The reaction mixture was filtrated to removed the catalyst, and the filtrate was concentrated to dryness to give a yellow oil. This was subjected to column chromatography (elution solvent, ethyl acetate-hexane=1:2-7:3) on silica gel (manufactured by E. Merck, Art.7734, 10 g), and the object fraction was concentrated and diluted with ethyl acetate-diethyl ether. The precipitate was collected by filtration, washed with diethyl ether and dried to give the title compound as a white powder (409 mg, 1.14 mmol, 88.0%).

NMR (200 MHz, CDCl$_3$) δ: 0.68 (2H, m), 0.81 (3H, t, J=7.2 Hz), 0.88 (2H, m), 1.22 (3H, t, J=7.5 Hz), 1.54 (2H, brq, J=7.7 Hz), 2.90 (1H, m), 2.93 (2H, m), 3.45 (2H, dq, J=5.7, 7.2 Hz), 6.89 (1H, br), 7.20 (1H, d, J=8.1 Hz), 7.22 (1H, dd, J=8.4, 1.2 Hz), 7.34 (1H, d, J=3.3 Hz), 7.66 (1H, brs), 9.27 (1H, br).

Elemental analysis for $C_{18}H_{23}N_5O_3$
Calcd.: C, 60.49; H, 6.49; N, 19.59.
Found: C, 60.37; H, 6.40; N, 19.60.
melting point: 203° C.

Example 316

1-{2-(benzyloxy)-4-[(ethylamino)carbonyl]phenyl}-5-[(benzyloxy)methyl]-N-cyclopropyl-1H-1,2,3-triazole-4-carboxamide

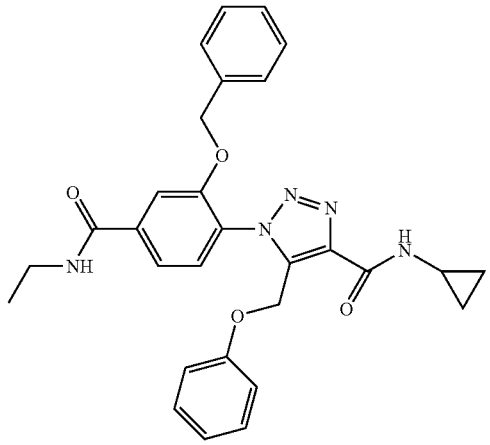

N-Ethyl-4-amino-3-benzyloxybenzamide (1.52 g, 5.62 mmol) obtained in Example 312c) was dissolved in water (20 ml) and acetic acid (10 ml), 1N hydrochloric acid (5.62 ml, 1.0 eq.) was added. An aqueous solution (5 ml) of sodium nitrite (394 mg, 5.62 mmol, 1.0 eq.) was added at 0° C., and the mixture was stirred for 30 min. An aqueous solution (5 ml) of sodium azide (373 mg, 5.62 mmol, 1.0 eq.) was further added, and the mixture was stirred at 0° C. for 1.5 hr. The reaction mixture was diluted with ethyl acetate-hexane (3:1, 80 ml), washed sequentially with water, 0.1N hydrochloric acid, saturated aqueous sodium hydrogen carbonate solution and saturated brine, dried over anhydrous sodium sulfate and concentrated to dryness to give N-ethyl-4-azido-3-benzyloxybenzamide as a yellow powder (1.64 g). This powder (1.64 g) and ethyl 4-benzyloxy-3-oxobutyrate (1.35 g, 5.71 mmol) were dissolved in ethanol (40 ml), sodium ethoxide (454 mg, 6.00 mmol) was added, and the mixture was stirred at room temperature for 30 min and at 60° C. for 14 hr. 1N sodium hydroxide (5.71 ml) was added to the reaction mixture, and the mixture was stirred for 2 hr. The reaction mixture was diluted with water (30 ml), ethanol was evaporated, and the residue was diluted with water (40 ml) and washed with ethyl acetate-hexane (2:1, 90 ml). The organic layer was extracted with 1% aqueous sodium carbonate solution (50 ml). The aqueous layers were combined, acidified (pH<3) with 6N hydrochloric acid and extracted with ethyl acetate (90 ml and 50 ml). The organic layer was washed with saturated brine, dried over anhydrous sodium sulfate, and concentrated to dryness to give a pale-brown solid (purity about 90%, 2.10 g, 3.9 mmol, 69%).

$^1$H NMR (200 MHz, CDCl$_3$) δ: 1.30 (3H, t, J=7.4 Hz), 3.54 (2H, dq, J=5.6, 7.1 Hz), 4.34 (2H, s), 4.82 (2H, brs), 5.03 (2H, s), 6.26 (1H, brt, J=5.9 Hz), 6.96 (2H, m), 7.12 (2H, m), 7.20-7.30 (6H, m), 7.36 (1H, dd, J=7.6, 1.2 Hz), 7.45 (1H, d, J=8.0 Hz), 7.66 (1H, d, J=1.0 Hz).

This solid (purity about 90%, 2.10 g, 3.9 mmol), HOBt (265 mg, 1.94 mmol, 0.5 eq.) and cyclopropylamine (0.389 ml, 5.44 mmol, 1.4 eq.) were dissolved in acetonitrile-DMF (4:1, 30 ml), WSC (988 mg, 5.05 mmol, 1.3 eq.) was added, and the mixture was stirred at room temperature for 1.5 hr. The reaction mixture was concentrated, diluted with ethyl acetate-hexane (4:1, 70 ml) and washed sequentially with 2% aqueous sodium carbonate solution (×2), 10% aqueous ammonium chloride solution and saturated brine. The aqueous layers were each extracted with ethyl acetate-hexane (3:1, 80 ml). The organic layers were combined, dried over anhydrous sodium sulfate and concentrated, and the residue was diluted with ethyl acetate (about 10 ml). The precipitate was collected by filtration, washed with diethyl ether and dried to give the title compound as a white powder (1.80 g, 3.43 mmol, 88.5%).

$^1$H NMR (200 MHz, CDCl$_3$) δ: 0.68 (2H, m), 0.88 (2H, m), 1.29 (3H, t, J=7.2 Hz), 2.91 (1H, octet, J=3.5 Hz), 3.53 (2H, dq, J=5.4, 7.3 Hz), 4.37 (2H, s), 4.94 (2H, brs), 5.02 (2H, s), 6.11 (1H, brt, J=4.6 Hz), 6.94 (2H, m), 7.13 (2H, m), 7.18-7.24 (3H, m), 7.25-7.30 (3H, m), 7.33 (1H, dd, J=8.0, 1.8 Hz), 7.36 (1H, brd, J=3.0 Hz), 7.42 (1H, d, J=8.0 Hz), 7.61 (1H, d, J=1.4 Hz).

Elemental analysis for C$_{30}$H$_{31}$N$_5$O$_4$
Calcd.: C, 68.55; H, 5.94; N, 13.32.
Found: C, 68.46; H, 5.99; N, 13.25.
melting point: 132° C.

Example 317

N-cyclopropyl-1-{4-[(ethylamino)carbonyl]-2-hydroxyphenyl}-5-(hydroxymethyl)-1H-1,2,3-triazole-4-carboxamide

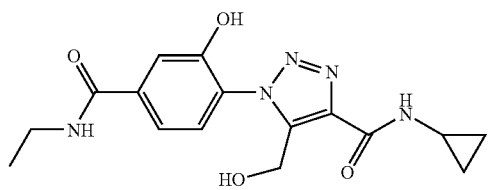

1-{2-(Benzyloxy)-4-[(ethylamino)carbonyl]phenyl}-5-[(benzyloxy)methyl]-N-cyclopropyl-1H-1,2,3-triazole-4-carboxamide (1.50 g, 2.85 mmol) obtained in Example 316 was dissolved in methanol-acetic acid (9:1, 50 ml), and the mixture was stirred at room temperature for 68 hr in the presence of 10% palladium carbon (wet, purity 50%, 300 mg) under a hydrogen atmosphere. The reaction mixture was filtrated to remove the catalyst, the filtrate was concentrated, diluted with toluene (100 ml) and concentrated, and ethyl acetate was added to the residue. The precipitate was collected by filtration, washed with diethyl ether and dried to give the title compound as a white powder (1.00 g, quant.). This powder (0.700 g) was crystallized from ethyl acetate, washed with ethyl acetate and diethyl ether and dried to give the title compound as a white powder (637 mg, 1.84 mmol, 64.7%).

$^1$H NMR (200 MHz, CDCl$_3$-DMSO-d$_6$=19:1) δ: 0.74 (2H, m), 0.91 (2H, m), 1.25 (3H, t, J=7.3 Hz), 2.94 (1H, octet, J=3.7 Hz), 3.47 (2H, dq, J=5.6, 7.3 Hz), 4.69 (2H, s), 7.21 (1H, br), 7.40 (2H, d, J=1.0 Hz), 7.60 (1H, brt, J=1.0 Hz), 7.77 (1H, brd, J=3.2 Hz).

Elemental analysis for C$_{16}$H$_{19}$N$_5$O$_4$.0.2EtOAc
Calcd.: C, 55.59; H, 5.72; N, 19.29.
Found: C, 55.61; H, 5.87; N, 19.06.
melting point: 185° C.

Example 318

5-[(benzyloxy)methyl]-N-cyclopropyl-1-{4-[(ethylamino)carbonyl]-2-hydroxyphenyl}-1H-1,2,3-triazole-4-carboxamide

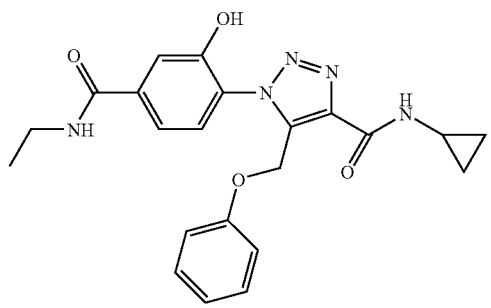

1-{2-(Benzyloxy)-4-[(ethylamino)carbonyl]phenyl}-5-[(benzyloxy)methyl]-N-cyclopropyl-1H-1,2,3-triazole-4-carboxamide (205 mg, 0.390 mmol) obtained in Example 316 was dissolved in methanol (7.0 ml), and the mixture was stirred at room temperature for 4 hr in the presence of 10% palladium carbon (wet, purity 50%, 41 mg) under a hydrogen atmosphere. The reaction mixture was filtrated to remove the catalyst, and the filtrate was concentrated to dryness to give a colorless oil. This was subjected to column chromatography (elution solvent, ethyl acetate-hexane=1:1-4:1) on silica gel (manufactured by E. Merck, Art.7734, 10 g), and the fraction obtained by elution with ethyl acetate-hexane (2:1-4:1) was concentrated and diluted with ethyl acetate-diethyl ether. The precipitate was collected by filtration, washed with diethyl ether and dried to give the title compound as a white powder (131 mg, 0.301 mmol, 77.1%).

NMR (200 MHz, CDCl$_3$) δ: 0.69 (2H, m), 0.90 (2H, m), 1.23 (3H, t, J=7.2 Hz), 2.91 (1H, octet, J=3.4 Hz), 3.45 (2H, dq, J=6.0, 7.1 Hz), 4.50 (2H, s), 4.99 (2H, s), 6.64 (1H, m), 7.08 (2H, m), 7.18-7.26 (4H, m), 7.38 (2H, m), 7.60 (1H, brd, J=0.8 Hz), 9.14 (1H, br).

Elemental analysis for $C_{23}H_{244}N_5O_4$

Calcd.: C, 63.44; H, 5.79; N, 16.08.

Found: C, 63.43; H, 5.86; N, 15.91.

melting point: 146° C.

Example 319

N$^3$-cyclopropyl-N$^7$-ethyl-4H-[1,2,3]triazolo[5,1-c][1,4]benzoxazine-3,7-dicarboxamide

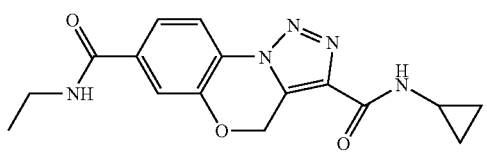

N-Cyclopropyl-1-{4-[(ethylamino)carbonyl]-2-hydroxyphenyl}-5-(hydroxymethyl)-1H-1,2,3-triazole-4-carboxamide (300 mg, 0.868 mmol) obtained in Example 317 was dissolved in THF (6.0 ml), tributylphosphine (0.300 ml, 1.13 mmol, 1.3 eq.) and ADDP (290 mg, 1.13 mmol, 1.3 eq.) were added, and the mixture was stirred at room temperature for 7 hr. The reaction mixture was diluted with ethyl acetate (10 ml), and the precipitate was collected by filtration, washed with ethyl acetate and suspended in water. The insoluble component was collected by filtration, washed with water and methanol and dried to give the title compound as a white powder (228 mg, 0.697 mmol, 80.2%).

NMR (200 MHz, DMSO-d$_6$) δ: 0.66 (2H, brs), 0.69 (2H, brd, J=2.6 Hz), 1.13 (3H, t, J=7.1 Hz), 2.87 (1H, m), 3.29 (2H, dq, J=5.6, 7.2 Hz), 5.75 (2H, s), 7.66 (1H, brs), 7.69 (1H, dd, J=8.0, 2.0 Hz), 8.08 (2H, d, J=8.0 Hz), 8.61 (1H, brt, J=5.5 Hz), 8.88 (1H, brd, J=4.4 Hz).

Elemental analysis for $C_{16}H_{17}N_5O_3$

Calcd.: C, 58.71; H, 5.23; N, 21.39.

Found: C, 58.64; H, 5.28; N, 21.26.

Example 320

N-cyclopropyl-1-{4-[(cyclopropylamino)carbonyl]-2-ethoxyphenyl}-1H-1,2,3-triazole-4-carboxamide

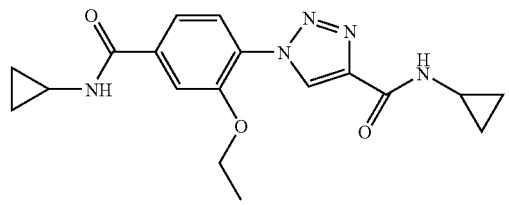

320a) methyl 4-amino-3-ethoxybenzoate

To a mixed solution of methyl 3-ethoxy-4-nitrobenzoate (6.05 g) in methanol (100 ml) and THF (100 ml) was added 10% Pd/C (50% wet, 0.60 g), and the mixture was stirred under a hydrogen atmosphere overnight. The reaction mixture was filtered through celite, and the filtrate was evaporated under reduced pressure to give a crude product (5.21 g) of the title compound. The obtained crude product was used for the next reaction without further purification.

NMR (CDCl$_3$) δ: 1.45 (3H, t, J=7.0), 3.86 (3H, s), 4.13 (2H, q, J=7.0), 6.78 (1H, d, J=8.4), 7.45-7.46 (1H, m), 7.52-7.57 (1H, m).

320b) methyl 4-azido-3-ethoxybenzoate

In the same manner as in Example 1a), the title compound was obtained as a brown powder (1.65 g, 73%) from methyl 4-amino-3-ethoxybenzoate (2.0 g) obtained in Example 320a).

NMR (CDCl$_3$) δ: 1.48 (3H, t, J=6.9), 3.90 (3H, s), 4.15 (2H, q, J=6.9), 6.97 (1H, dd, J=0.6, 8.1), 7.52-7.53 (1H, m), 7.58-7.61 (1H, m).

320c) ethyl 1-[2-ethoxy-4-(methoxycarbonyl)phenyl]-1H-1,2,3-triazole-4-carboxylate A solution of methyl 4-azido-3-ethoxybenzoate (1.0 g) obtained in Example 320b) and ethyl propiolate (0.92 ml) in toluene (10 ml) was stirred at 100° C. overnight. After the reaction solution was allowed to cool to room temperature, the resultant precipitate was collected by filtration to give the title compound as a white solid (0.76 g).

NMR (CDCl$_3$) δ: 1.43-1.50 (6H, m), 3.97 (3H, s), 4.26 (2H, q, J=6.9), 4.49 (2H, q, J=7.2), 7.77-7.81 (2H, m), 8.01 (1H, d, J=8.7), 8.80 (1H, m).

320d) 1-[2-ethoxy-4-(carboxy)phenyl]-1H-1,2,3-triazole-4-carboxylic acid

To a solution of ethyl 1-[2-ethoxy-4-(methoxycarbonyl) phenyl]-1H-1,2,3-triazole-4-carboxylate (0.92 g) obtained in Example 320c) in ethanol (10 ml) were added 8N aqueous sodium hydroxide solution (0.72 ml) and water (2 ml), and the reaction mixture was stirred at 100° C. for 1 hr. After ethanol was evaporated under reduced pressure, 1N hydrochloric acid was added to the obtained aqueous solution, and the resultant precipitant was collected by filtration to give the title compound as a white powder (0.87 g).

NMR (CDCl₃) δ: 1.33 (3H, t, J=6.9), 4.24 (2H, q, J=6.9), 7.70-7.75 (2H, m), 7.84 (1H, d, J=8.1), 9.04 (1H, s).

320e) N-cyclopropyl-1-{4-[(cyclopropylamino)carbonyl]-2-ethoxyphenyl}-1H-1,2,3-triazole-4-carboxamide In the same manner as in Example 43c), the title compound was obtained as a white powder (0.48 g, 71%) from 1-[2-ethoxy-4-(carboxy)phenyl]-1H-1,2,3-triazole-4-carboxylic acid (0.53 g) obtained in Example 320d) and cyclopropylamine (0.53 ml).
NMR (CDCl₃) δ: 0.64-0.72 (4H, m), 0.86-0.94 (5H, m), 1.44 (3H, t, J=7.2), 2.89-2.99 (2H, m), 4.20-4.27 (2H, m), 6.43 (1H, brs), 7.26-7.33 (2H, m), 7.64 (2H, d, J=1.8), 7.86 (1H, d, J=8.1), 8.71 (1H, s).

Example 321

N-cyclopropyl-1-{4-[(ethylamino)carbonyl]phenyl}-5-[(E)-2-(1,3-thiazol-2-yl)vinyl]-1H-1,2,3-triazole-4-carboxamide

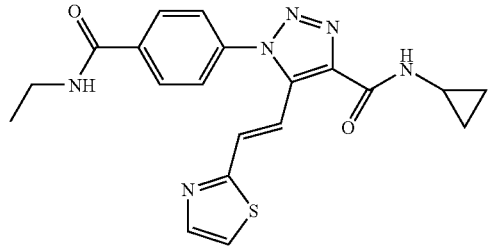

321a) 5-(bromomethyl)-N-cyclopropyl-1-{4-[(ethylamino)carbonyl]phenyl}-1H-1,2,3-triazole-4-carboxamide To a suspension of N-cyclopropyl-1-{4-[(ethylamino)carbonyl]phenyl}-5-(hydroxymethyl)-1H-1,2,3-triazole-4-carboxamide (500 mg) obtained in Example 112 and carbon tetrabromide (630 mg) in dichloromethane (5 ml) was added in small portions triphenylphosphine (598 mg) at 0° C., and the reaction mixture was stirred at 0° C. for 30 min. The reaction mixture was concentrated under reduced pressure, and the obtained residue was purified by silica gel column (ethyl acetate/hexane=4/1 to ethyl acetate) to give the title compound as a white solid (890 mg).
NMR (CDCl₃) δ: 0.67-0.73 (2H, m), 0.87-0.93 (2H, m), 1.21-1.32 (3H, m), 2.91-2.97 (1H, m), 3.48-3.57 (2H, m), 4.83 (2H, s), 7.01 (1H, brs), 7.36 (2H, m), 7.52-7.58 (2H, m), 8.05-8.09 (2H, m).

321b) N-cyclopropyl-5-(diethylphosphonomethyl)-1-{4-[(ethylamino)carbonyl]phenyl}-1H-1,2,3-triazole-4-carboxamide 5-(Bromomethyl)-N-cyclopropyl-1-{4-[(ethylamino)carbonyl]phenyl}-1H-1,2,3-triazole-4-carboxamide (890 mg) obtained in Example 321a) was dissolved in triethyl phosphite (2 ml), and the mixture was stirred at 120° C. for 3 days. An excess amount of triethyl phosphite was evaporated under reduced pressure, and the obtained residue was purified by silica gel column (ethyl acetate to ethyl acetate/methanol=4/1) to give the title compound as a colorless oil (640 mg).
NMR (CDCl₃) δ: 0.67-0.73 (2H, m), 0.86-0.93 (2H, m), 1.10-1.41 (9H, m), 2.88-2.94 (1H, m), 3.50-3.59 (2H, m), 3.81 (2H, d, J=22.2), 3.95-4.24 (4H, m), 6.26 (1H, brs), 7.32 (1H, brs), 7.69 (2H, d, J=8.7), 7.97 (2H, d, J=8.7).

321c) N-cyclopropyl-1-{4-[(ethylamino)carbonyl]phenyl}-5-[(E)-2-(1,3-thiazol-2-yl)vinyl]-1H-1,2,3-triazole-4-carboxamide To a suspension of N-cyclopropyl-5-(diethylphosphonomethyl)-1-{4-[(ethylamino)carbonyl]phenyl}-1H-1,2,3-triazole-4-carboxamide (340 mg) obtained in Example 321b) in THF (5 ml) was added sodium hydride (50% oil dispersion, 55 mg) at 0° C., and the mixture was stirred at room temperature for 30 min. A solution of 2-formylthiazole (86 mg) in THF (1 ml) was added to the obtained reaction mixture, and the mixture was stirred at room temperature for 2 hr. The resultant precipitate was collected by filtration to give the title compound as a white solid (149 mg).
NMR (CDCl₃) δ: 0.71-0.73 (4H, m), 1.16 (3H, t, J=7.2), 2.90-2.96 (1H, m), 3.28-3.42 (2H, m), 7.46 (1H, d, J=16.5), 7.76-7.86 (4H, m), 7.89 (1H, d, J=3.3), 8.11 (2H, J=8.4), 8.75 (1H, t, J=5.3), 8.91 (1H, d, J=4.5).

Example 322

N-cyclopropyl-1-{4-[(ethylamino)carbonyl]phenyl}-5-[(E)-2-(1H-imidazol-2-yl)vinyl]-1H-1,2,3-triazole-4-carboxamide

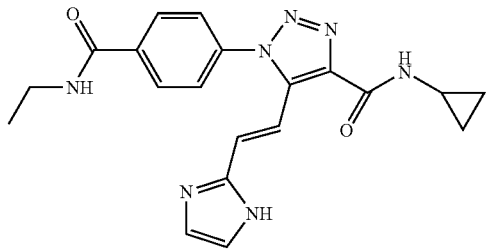

322a) N-cyclopropyl-1-{4-[(ethylamino)carbonyl]phenyl}-5-[(E)-2-(1-trityl-1H-imidazol-2-yl)vinyl]-1H-1,2,3-triazole-4-carboxamide To a suspension of N-cyclopropyl-5-(diethylphosphonomethyl)-1-{4-[(ethylamino)carbonyl]phenyl}-1H-1,2,3-triazole-4-carboxamide (500 mg) obtained in Example 321b) in THF (20 ml) was added sodium hydride (50% oil dispersion, 80 mg) at 0° C., and the mixture was stirred at room temperature for 1 hr. A solution of 1-trityl-1H-imidazole-2-carbaldehyde (367 mg) in THF (5 ml) was added to the obtained reaction mixture, and the mixture was stirred at room temperature overnight. Water was added to the reaction mixture, and the mixture was extracted with ethyl acetate. The extract was dried over magnesium sulfate and concentrated under reduced pressure to give a crude product of the title compound as a pale-yellow solid (670 mg).
NMR (CDCl₃) δ: 0.57-0.63 (2H, m), 0.79-0.88 (2H, m), 1.34 (3H, t, J=7.1), 2.80-3.52 (1H, m), 3.52-3.61 (2H, m), 6.17 (1H, brs), 6.35 (1H, d, J=16.1), 6.72 (1H, s), 6.90-7.01 (7H, m), 7.12-7.34 (8H, m), 7.56-7.59 (2H, m), 7.85 (1H, d, J=16.1).

322b) N-cyclopropyl-1-{4-[(ethylamino)carbonyl]phenyl}-5-[(E)-2-(1H-imidazol-2-yl)vinyl]-1H-1,2,3-triazole-4-carboxamide N-Cyclopropyl-1-{4-[(ethylamino)carbonyl]phenyl}-5-[(E)-2-(1-trityl-1H-imidazol-2-yl)vinyl]-1H-1,2,3-triazole-4-carboxamide (670 mg) obtained in Example 322a) was dissolved in trifluoroacetic acid (5 ml), and the mixture was stirred at room temperature for 30 min. The reaction mixture was concentrated under reduced pressure, and the obtained residue was dissolved in chloroform. This chloroform solution was washed with saturated aqueous sodium hydrogen carbonate solution and saturated aqueous sodium chloride solution, dried over anhydrous magnesium sulfate and concentrated under reduced pressure. The obtained residue was purified by basic silica gel column (ethyl acetate to ethyl acetate/methanol=4/1) to give the title compound as a white powder (220 mg).

NMR (CDCl$_3$) δ: 0.70-0.72 (2H, m), 0.80-0.91 (2H, m), 1.33 (3H, t, J=7.4), 2.86-2.93 (1H, m), 3.48-3.57 (2H, m), 7.05-7.11 (3H, m), 7.28-7.33 (2H, m), 7.55-7.60 (2H, m), 7.69-7.72 (2H, m), 8.18 (2H, d, J=16.2), 11.72 (1H, brs).

Example 323

N-cyclopropyl-1-{4-[(ethylamino)carbonyl]phenyl}-5-[(E)-2-(2-methyl-1,3-oxazol-4-yl)vinyl]-1H-1,2,3-triazole-4-carboxamide

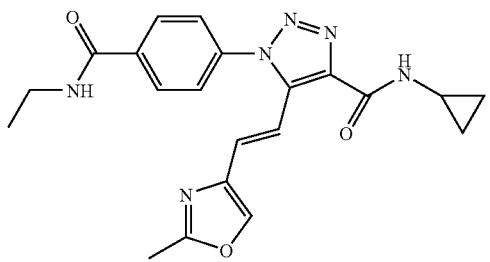

To a suspension of N-cyclopropyl-5-(diethylphosphonomethyl)-1-{4-[(ethylamino)carbonyl]phenyl}-1H-1,2,3-triazole-4-carboxamide (500 mg) obtained in Example 321b) in THF (20 ml) was added sodium hydride (50% oil dispersion, 80 mg) at 0° C., and the mixture was stirred at room temperature for 1 hr. A solution of 2-methyl-1,3-oxazole-4-carbaldehyde (148 mg) in THF (5 ml) was added to the obtained reaction mixture, and the mixture was stirred at room temperature overnight. Water was added to the reaction mixture, and the mixture was extracted with ethyl acetate. The extract was dried over magnesium sulfate and concentrated under reduced pressure, and the obtained residue was purified by silica gel column (ethyl acetate to ethyl acetate/methanol=4/1) to give the title compound as a white powder (380 mg).

NMR (CDCl$_3$) δ: 0.64-0.75 (4H, m), 1.64 (3H, t, J=7.2), 2.38 (3H, s), 2.86-2.94 (1H, m), 3.28-3.42 (2H, m), 7.08 (1H, d, J=15.9), 7.71-7.76 (3H, m), 8.10 (2H, d, J=8.4), 8.19 (1H, s), 8.75 (1H, t, J=5.6), 8.79 (1H, d, J=4.5).

Example 324

N-cyclopropyl-1-{4-[(ethylamino)carbonyl]phenyl}-5-[(E)-2-(1H-1,2,4-triazol-3-yl)vinyl]-1H-1,2,3-triazole-4-carboxamide

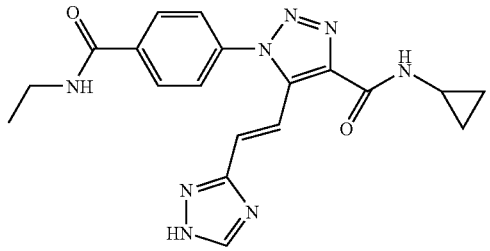

In the same manner as in Example 322, the title compound was obtained as a white solid.

NMR (CDCl$_3$) δ: 0.67-0.73 (4H, m), 1.64 (3H, t, J=7.2), 2.90-2.96 (1H, m), 3.30-3.38 (2H, m), 7.45 (1H, d, J=16.5), 7.67 (1H, d, J=16.5), 7.75 (1H, d, J=8.6), 8.10 (2H, d, J=8.6), 8.34 (1H, s), 8.75 (1H, t, J=5.3), 8.83 (1H, d, J=4.5).

Example 325

N-cyclopropyl-1-{4-[(ethylamino)carbonyl]phenyl}-5-[(E)-2-(1H-pyrazol-4-yl)vinyl]-1H-1,2,3-triazole-4-carboxamide trifluoroacetate

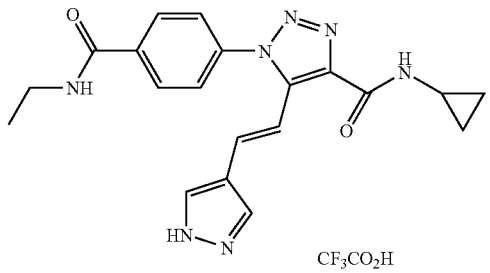

325a) N-cyclopropyl-1-{4-[(ethylamino)carbonyl]phenyl}-5-[(E)-2-(1-trityl-1H-pyrazol-4-yl)vinyl]-1H-1,2,3-triazole-4-carboxamide In the same manner as in Example 322a), the title compound was obtained as a white solid.

NMR (CDCl$_3$) δ: 0.65-0.70 (2H, m), 0.85-0.92 (2H, m), 1.30 (3H, t, J=7.2), 2.85-2.91 (1H, m), 3.50-3.59 (2H, m), 6.19 (1H, brs), 6.67 (1H, d, J=16.2), 7.09-7.16 (5H, m), 7.26-7.35 (8H, m), 7.50-7.60 (3H, m), 7.74 (1H, s), 7.91-7.99 (2H, m).

325b) N-cyclopropyl-1-{4-[(ethylamino)carbonyl]phenyl}-5-[(E)-2-(1H-pyrazol-4-yl)vinyl]-1H-1,2,3-triazole-4-carboxamide N-Cyclopropyl-1-{4-[(ethylamino)carbonyl]phenyl}-5-[(E)-2-(1-trityl-1H-pyrazol-4-yl)vinyl]-1H-1,2,3-triazole-4-carboxamide (910 mg) obtained in Example 325a) was dissolved in trifluoroacetic acid (5 ml), and the mixture was stirred at room temperature for 30 min. The reaction mixture was concentrated under reduced pressure, and the obtained residue was triturated with water to give the title compound as a white powder (470 mg).

NMR (CDCl$_3$) δ: 0.65-0.71 (4H, m), 1.16 (3H, t, J=7.2), 2.87-2.93 (1H, m), 3.22-3.45 (2H, m), 6.84 (1H, d, J=16.5), 7.54 (1H, d, J=16.5), 7.69-7.72 (2H, m), 7.83 (1H, brs), 8.07-8.10 (2H, m), 8.71-8.74 (2H, m).

Example 326

N-cyclopropyl-1-{4-[(ethylamino)carbonyl]phenyl}-5-[(E)-2-(1-methyl-1H-imidazol-2-yl)vinyl]-1H-1,2,3-triazole-4-carboxamide

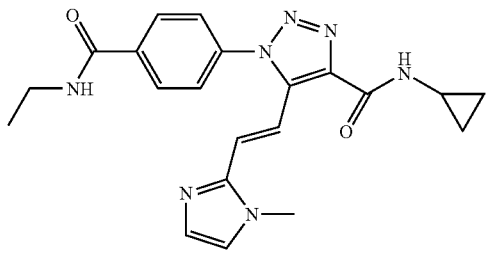

N-Cyclopropyl-1-{4-[(ethylamino)carbonyl]phenyl}-5-[(E)-2-(1H-imidazol-2-yl)vinyl]-1H-1,2,3-triazole-4-carboxamide (150 mg) obtained in Example 322 was dissolved in acetone (3 ml) and DMF (3 ml), methyl iodide (72 µl) and potassium carbonate (300 mg) were added, and the mixture was stirred at room temperature for 3 days. After an insoluble material was removed by filtration, the reaction mixture was concentrated under reduced pressure, and the obtained residue was dissolved in chloroform. The obtained chloroform solution was washed with water, dried over anhydrous magnesium sulfate and concentrated under reduced pressure. The obtained residue was recrystallized from ethyl acetate-methanol (10:1) to give the title compound as a white powder (20 mg).

NMR (CDCl$_3$) δ: 0.68-0.76 (4H, m), 1.61 (3H, t, J=7.2), 2.91-2.97 (1H, m), 3.28-3.47 (2H, m), 3.60 (3H, s), 6.96 (1H, s), 7.19 (1H, d, J=15.8), 7.24 (1H, s), 7.72-7.76 (2H, m), 8.04 (1H, d, J=15.8), 8.08-8.11 (2H, m), 8.74 (1H, d, J=5.4), 8.82 (1H, d, J=4.5).

Example 327

N-cyclopropyl-1-{4-[(ethylamino)carbonyl]phenyl}-5-[(E)-2-(1-methyl-1H-1,2,4-triazol-3-yl)vinyl]-1H-1,2,3-triazole-4-carboxamide and N-cyclopropyl-1-{4-[(ethylamino)carbonyl]phenyl}-5-[(E)-2-(1-methyl-1H-1,2,4-triazol-5-yl)vinyl]-1H-1,2,3-triazole-4-carboxamide

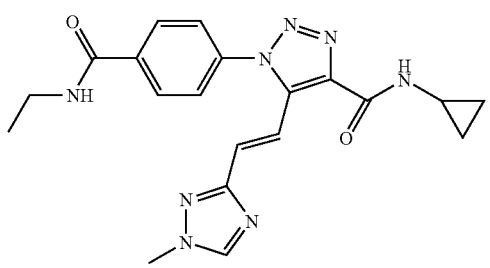

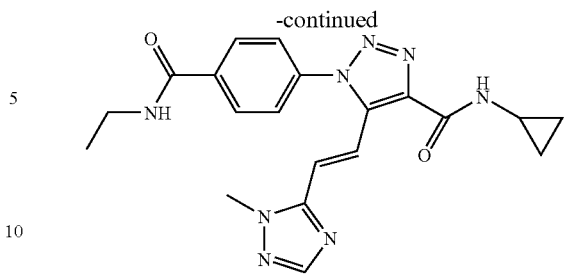

The crude product obtained by the similar reaction as in Example 326 was purified by silica gel column (ethyl acetate to ethyl acetate/methanol=4/1) to give N-cyclopropyl-1-{4-[(ethylamino)carbonyl]phenyl}-5-[(E)-2-(1-methyl-1H-1,2,4-triazol-3-yl)vinyl]-1H-1,2,3-triazole-4-carboxamide as a first eluted fraction, N-cyclopropyl-1-{4-[(ethylamino)carbonyl]phenyl}-5-[(E)-2-(1-methyl-1H-1,2,4-triazol-5-yl)vinyl]-1H-1,2,3-triazole-4-carboxamide as a second eluted fraction, which were each white powders.

First Eluted Fraction

NMR (CDCl$_3$) δ: 0.67-0.76 (4H, m), 1.17 (3H, t, J=7.2), 2.90-2.96 (1H, m), 3.29-3.49 (2H, m), 3.84 (3H, s), 7.46 (2H, s), 7.73-7.76 (2H, m), 8.09-8.12 (2H, m), 8.45 (1H, s), 8.76 (1H, t, J=5.6), 8.83 (1H, d, J=4.8).

Second Eluted Fraction

NMR (CDCl$_3$) δ: 0.68-0.76 (4H, m), 1.16 (3H, t, J=7.2), 2.94-2.96 (1H, m), 3.26-3.45 (2H, m), 3.82 (3H, s), 7.39 (1H, d, J=15.9), 7.75 (1H, d, J=8.4), 7.92 (1H, s), 8.07-8.10 (3H, m), 8.72 (1H, t, J=5.5), 8.89 (1H, d, J=4.6).

Example 328

N-cyclopropyl-1-{4-[(ethylamino)carbonyl]phenyl}-5-[(E)-2-(1-methyl-1H-pyrazol-4-yl)vinyl]-1H-1,2,3-triazole-4-carboxamide

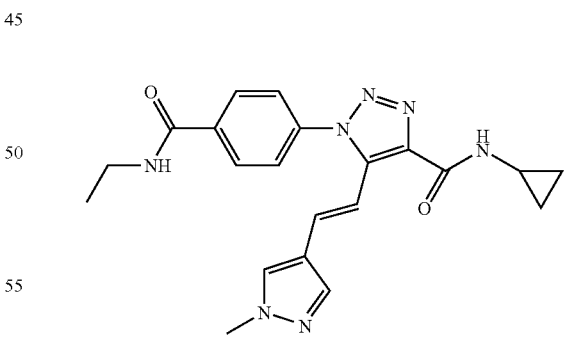

In the same manner as in Example 326, the title compound was obtained as a white powder.

NMR (CDCl$_3$) δ: 0.68-0.72 (4H, m), 1.16 (3H, t, J=7.2), 2.87-2.91 (1H, m), 3.30-3.40 (2H, m), 3.79 (3H, s), 6.80 (1H, d, J=16.4), 7.51 (1H, d, J=16.4), 7.62 (1H, s), 7.70 (1H, d, J=8.4), 7.92 (1H, s), 8.09 (2H, d, J=8.4), 8.70-8.72 (2H, m).

Example 329

N-cyclopropyl-1-{4-[(ethylamino)carbonyl]phenyl}-5-[2-(1,3-thiazol-2-yl)ethyl]-1H-1,2,3-triazole-4-carboxamide

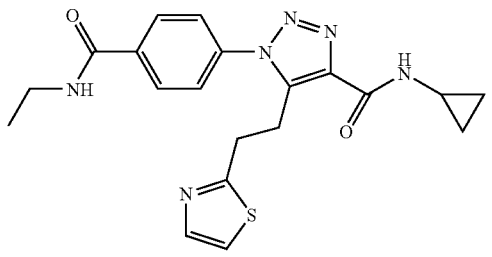

To a solution of N-cyclopropyl-1-{4-[(ethylamino)carbonyl]phenyl}-5-[(E)-2-(1,3-thiazol-2-yl)vinyl]-1H-1,2,3-triazole-4-carboxamide (130 mg) obtained in Example 321 in DMF (10 ml) was added 10% Pd/C (50% wet, 15 mg), and the mixture was stirred for 3 days under a hydrogen atmosphere. After the reaction mixture was filtered through celite, the filtrate was evaporated under reduced pressure. The residue was purified by silica gel column (ethyl acetate to ethyl acetate/methanol=4/1) to give the title compound as a white powder (100 mg).

NMR (CDCl$_3$) δ: 0.66-0.74 (2H, m), 0.82-0.95 (2H, m), 1.29 (3H, t, J=7.4), 2.89-2.97 (1H, m), 3.48-3.61 (6H, m), 6.17 (1H, brs), 7.14 (1H, d, J=3.2), 7.30-7.36 (2H, m), 7.37 (1H, brs), 7.55 (1H, d, J=3.2), 7.89-7.94 (2H, m).

In the same manner as in Example 329, the compounds of Example 330 to Example 334 were synthesized.

Example 330

N-cyclopropyl-1-{4-[(ethylamino)carbonyl]phenyl}-5-[2-(1H-imidazol-2-yl)ethyl]-1H-1,2,3-triazole-4-carboxamide

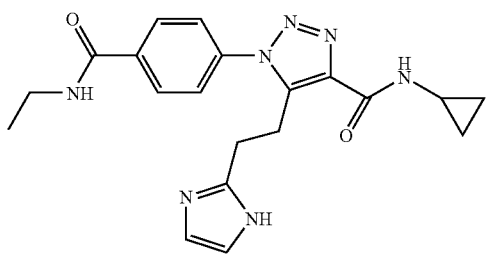

NMR (CDCl$_3$) δ: 0.66-0.69 (4H, m), 1.17 (3H, t, J=7.2), 2.82-2.87 (1H, m), 3.16-3.21 (2H, m), 3.29-3.42 (4H, m), 7.46 (2H, s), 7.59 (2H, d, J=8.7), 8.08 (2H, d, J=8.7), 8.78-8.79 (2H, m).

Example 331

N-cyclopropyl-1-{4-[(ethylamino)carbonyl]phenyl}-5-[2-(1-methyl-1H-imidazol-2-yl)ethyl]-1H-1,2,3-triazole-4-carboxamide

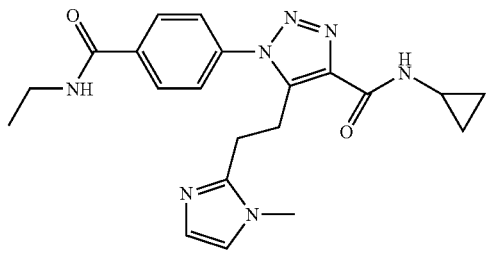

NMR (CDCl$_3$) δ: 0.67-0.70 (4H, m), 1.16 (3H, t, J=7.2), 2.84-2.90 (1H, m), 3.02-3.07 (2H, m), 3.27-3.31 (2H, m), 3.51 (3H, s), 7.04 (1H, s), 7.22 (1H, s), 7.62 (1H, d, J=8.4), 8.07 (1H, d, J=8.4), 8.74 (1H, brs), 8.79 (1H, d, J=4.5).

Example 332

N-cyclopropyl-1-{4-[(ethylamino)carbonyl]phenyl}-5-[2-(2-methyl-1,3-oxazol-4-yl)ethyl]-1H-1,2,3-triazole-4-carboxamide

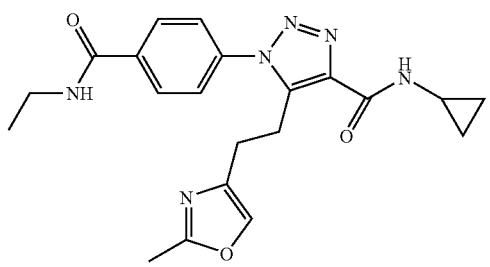

NMR (CDCl$_3$) δ: 0.68-0.73 (4H, m), 1.15 (3H, t, J=7.2), 2.21 (3H, s), 2.62 (2H, t, J=7.2), 2.88-2.92 (1H, m), 3.25 (2H, t, J=7.2), 3.31-3.45 (2H, m), 7.48 (1H, s), 7.56 (2H, d, J=8.4), 8.04 (2H, d, J=8.4), 8.68-8.73 (2H, m).

Example 333

N-cyclopropyl-1-{4-[(ethylamino)carbonyl]phenyl}-5-[2-(1H-1,2,4-triazol-3-yl)ethyl]-1H-1,2,3-triazole-4-carboxamide

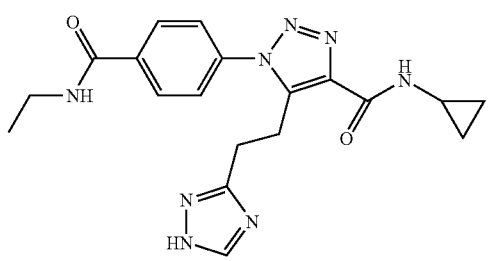

NMR (CDCl$_3$) δ: 0.68-0.70 (4H, m), 1.15 (3H, t, J=7.2), 2.89-2.97 (3H, m), 3.28-3.37 (4H, m), 7.57 (1H, d, J=8.4), 8.02-8.05 (3H, m), 8.68-8.72 (2H, m).

Example 334

N-cyclopropyl-1-{4-[(ethylamino)carbonyl]phenyl}-5-[2-(1-methyl-1H-1,2,4-triazol-3-yl)ethyl]-1H-1,2,3-triazole-4-carboxamide

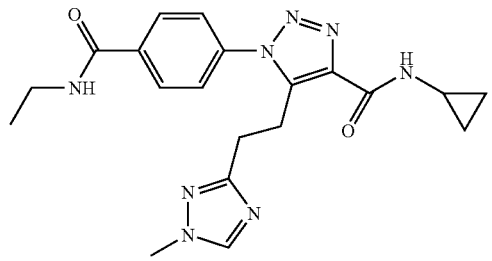

NMR (CDCl$_3$) δ: 0.68-0.69 (2H, m), 0.82-0.85 (2H, m), 1.26 (3H, t, J=7.2), 2.84-2.90 (1H, m), 3.06-3.08 (2H, m), 3.30-3.32 (2H, m), 3.42-3.49 (2H, m), 3.84 (3H, s), 7.53 (1H, d, J=7.2), 8.03 (1H, d, J=7.2), 8.68 (1H, s).

Example 335

N$^3$-cyclopropyl-N$^9$-ethyl-5,6-dihydro-4H-[1,2,3]triazolo[5,1-e][1,6]benzoxazocine-3,9-dicarboxamide

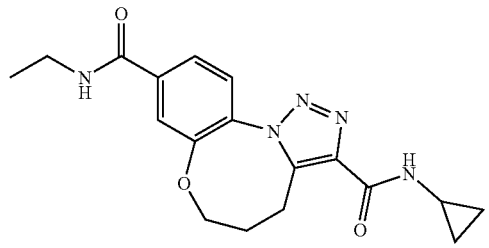

335a) 1-{(2-(benzyloxy)-4-[(ethylamino)carbonyl]phenyl}-5-[3-(benzyloxy)propyl]-N-cyclopropyl-1H-1,2,3-triazole-4-carboxylic acid In the same manner as in Example 1b), the title compound was obtained as a brown oil (LC/MS ESI(pos) 515 [M+H]$^+$). The obtained crude product was used for the next reaction without further purification.

335b) 1-{2-(benzyloxy)-4-[(ethylamino)carbonyl]phenyl}-5-[3-(benzyloxy)propyl]-N-cyclopropyl-1H-1,2,3-triazole-4-carboxamide In the same manner as in Example 1c), the title compound was obtained as an orange oil.
NMR (CDCl$_3$) δ: 0.66-0.70 (2H, m), 0.84-0.90 (2H, m), 1.26 (3H, t, J=7.2), 1.79 (2H, m), 2.86-2.92 (1H, m), 2.99 (2H, brs), 3.37 (3H, t, J=6.0), 3.45-3.55 (2H, m), 4.29 (2H, s), 5.11 (2H, 2), 6.07 (1H, d, J=5.3), 7.12-7.45 (13H, m), 7.65 (1H, s).

335c) N-cyclopropyl-1-{4-[(ethylamino)carbonyl]-2-hydroxyphenyl}-5-(3-hydroxypropyl)-1H-1,2,3-triazole-4-carboxamide To a solution of 1-{2-(benzyloxy)-4-[(ethylamino)carbonyl]phenyl}-5-[3-(benzyloxy)propyl]-N-cyclopropyl-1H-1,2,3-triazole-4-carboxamide (1.17 g) obtained in Example 335b) in ethanol (50 ml) was added 10% Pd(OH)$_2$/C (120 mg), and the mixture was stirred under 5 atm at 80° C. for 2 hr. The reaction mixture was filtered through celite, and the filtrate was evaporated under reduced pressure. The obtained residue was purified by silica gel column (ethyl acetate to ethyl acetate/methanol=5/1) to give the title compound as a white powder (520 mg).
NMR (CDCl$_3$) δ: 0.65-0.69 (4H, m), 1.13 (3H, t, J=7.3), 1.47-1.56 (2H, m), 2.79-2.88 (3H, m), 3.20-3.35 (4H, m), 4.43 (1H, brs), 7.38-7.52 (3H, m), 8.58-8.63 (2H, m).

335d) N$^3$-cyclopropyl-N$^9$-ethyl-5,6-dihydro-4H-[1,2,3]triazolo[5,1-e][1,6]benzoxazocine-3,9-dicarboxamide N-Cyclopropyl-1-{4-[(ethylamino)carbonyl]-2-hydroxyphenyl}-5-(3-hydroxypropyl)-1H-1,2,3-triazole-4-carboxamide (260 mg) obtained in Example 335c) and tributylphosphine (4.1 ml) were dissolved in THF (50 ml), ADDP (4.16 g) was added under an argon atmosphere, and the mixture was stirred overnight. The reaction mixture was concentrated under reduced pressure, and the obtained residue was dissolved in ethyl acetate. This ethyl acetate solution was washed with 1N hydrochloric acid, dried over anhydrous magnesium sulfate and concentrated under reduced pressure. The obtained residue was purified by silica gel column (ethyl acetate to ethyl acetate/methanol=5/1) and further triturated with ether to give the title compound as a white powder (30 mg).
NMR (CDCl$_3$) δ: 0.66-0.71 (2H, m), 0.85-0.92 (2H, m), 1.29 (3H, t, J=7.4), 2.04-2.12 (2H, m), 2.88-2.93 (1H, m), 3.15-3.19 (2H, m), 3.47-3.58 (2H, m), 4.29 (2H, t, J=5.3), 6.22 (1H, brs), 7.34 (1H, brs), 7.62-7.72 (3H, m).

Example 336

N-cyclopropyl-1-{4-[(ethylamino)carbonyl]phenyl}-5-(2-thienyl)-1H-1,2,3-triazole-4-carboxamide

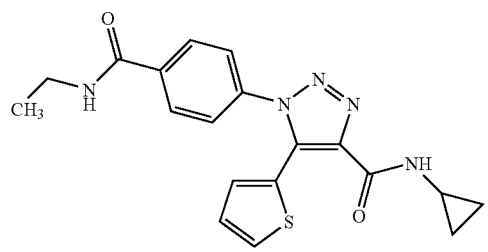

336a) 1-{4-[(ethylamino)carbonyl]phenyl}-5-(2-thienyl)-1H-1,2,3-triazole-4-carboxylic acid Ethyl 3-oxo-3-(2-thienyl)propanoate (500 mg, 2.50 mmol) and 4-azido-N-ethylbenzamide (500 mg, 2.50 mmol, 1.0 eq.) obtained in Example 43a) were dissolved in ethanol (20 ml), a solution of sodium ethoxide in ethanol (20%, 1.3 g, 3.82 mmol, 1.5 eq.) was added, and the mixture was stirred at room temperature for 30 min and at 60° C. for 7 hr. Water (20 ml) was added to the reaction mixture, ethanol was evaporated, and the residue was diluted with 2% aqueous sodium carbonate solution (20 ml) and washed with ethyl acetate-hexane (2:1). The organic layer was extracted with 2% aqueous sodium carbonate solution. The aqueous layers were combined, acidified (pH<3) with 6N hydrochloric acid and stood still at 0° C. The precipitate was collected by filtration, washed with ice-cold water and dried to give the title compound as a pale-yellow powder (764 mg, 89%).

NMR (DMSO-$d_6$) δ: 1.12 (3H, t, J=7.2), 3.29 (2H, q, J=7.2), 7.09 (1H, dd, J=3.9, 5.1), 7.32 (1H, d, J=3.9), 7.55 (2H, d, J=8.1), 7.77 (1H, d, J=5.1), 7.94 (2H, d, J=8.1), 8.64 (1H, t, J=5.5).

336b) N-cyclopropyl-1-{4-[(ethylamino)carbonyl]phenyl}-5-(2-thienyl)-1H-1,2,3-triazole-4-carboxamide To a solution of 1-{4-[(ethylamino)carbonyl]phenyl}-5-(2-thienyl)-1H-1,2,3-triazole-4-carboxylic acid (764 mg) obtained in Example 336a) in DMF (5 ml) were sequentially added cyclopropylamine (0.23 ml), triethylamine (0.46 ml), HOBt (170 mg) and WSC (640 mg), and the reaction mixture was stirred at room temperature overnight. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure. The residue was purified by silica gel column (ethyl acetate/hexane=4/6 to ethyl acetate) and recrystallized from ethyl acetate to give the title compound as a colorless powder (543 mg, 64%).

NMR (CDCl$_3$) δ: 0.65-0.71 (2H, m), 0.84-0.90 (2H, m), 1.27 (3H, t, J=7.5), 2.86-2.93 (1H, m), 3.52 (2H, qd, J=7.5), 6.16 (1H, brs), 7.02 (1H, dd, J=4.5, 3.3), 7.38 (1H, dd, J=3.3, 1.2), 7.42 (2H, d, J=8.4), 7.46 (1H, dd, J=4.5, 1.2), 7.85 (2H, d, J=8.4).

Example 337

N-cyclopropyl-1-{4-[(ethylamino)carbonyl]phenyl}-5-(3,3,3-trifluoropropyl)-1H-1,2,3-triazole-4-carboxamide

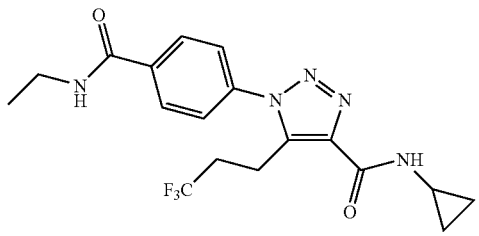

337a) methyl 6,6,6-trifluoro-3-oxohexanoate

In the same manner as in Example 91a), the title compound was obtained as a pale-yellow liquid (4.35 g, 23%) from 4,4,4-trifluorobutanoic acid (17 g, 120 mmol).

NMR (CDCl$_3$) δ: 1.29 (3H, t, J=6.9), 2.37-2.52 (2H, m), 2.86 (2H, t, J=8.1), 3.49 (2H, s), 4.22 (2H, q, J=6.9).

337b) 1-{4-[(ethylamino)carbonyl]phenyl}-5-(3,3,3-trifluoropropyl)-1H-1,2,3-triazole-4-carboxylic acid In the same manner as in Example 90a), the title compound was obtained as a brown powder (775 mg, 90%) from methyl 6,6,6-trifluoro-3-oxohexanoate (515 mg) obtained in Example 337a).

NMR (DMSO-$d_6$) δ: 1.15 (3H, t, J=6.9), 2.54-2.60 (2H, m), 3.17 (2H, t, J=9.0), 3.28-3.35 (2H, m), 7.74 (2H, d, J=7.2), 8.09 (2H, d, J=7.2), 8.73 (1H, t, J=1.9).

337c) N-cyclopropyl-1-{4-[(ethylamino)carbonyl]phenyl}-5-(3,3,3-trifluoropropyl)-1H-1,2,3-triazole-4-carboxamide In the same manner as in Example 336b), the title compound was obtained as a colorless powder (273 mg, 35%) from 1-{4-[(ethylamino)carbonyl]phenyl}-5-(3,3,3-trifluoropropyl)-1H-1,2,3-triazole-4-carboxylic acid (775 mg) obtained in Example 337b).

NMR (CDCl$_3$) δ: 0.67-0.72 (2H, m), 0.87-0.94 (2H, m), 1.30 (3H, t, J=7.2), 2.51-2.67 (2H, m), 2.86-2.94 (1H, m), 3.25 (2H, t, J=7.8), 3.55 (2H, qd, J=7.2, 1.2), 6.19 (1H, brs), 7.36 (1H, brs), 7.48 (2H, d, J=9.0), 7.99 (2H, d, J=9.0).

Example 338

N-cyclopropyl-1-{4-[(ethylamino)carbonyl]phenyl}-5-[(1E)-2-phenylprop-1-en-1-yl]-1H-1,2,3-triazole-4-carboxamide

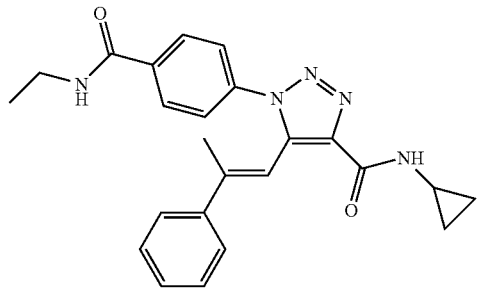

To a suspension of N-cyclopropyl-5-(diethylphosphonomethyl)-1-{4-[(ethylamino)carbonyl]phenyl}-1H-1,2,3-triazole-4-carboxamide (450 mg, 1.00 mmol) obtained in Example 321b) in THF (5 ml) was added sodium hydride (50% oil dispersion, 75 mg) at 0° C., and the mixture was stirred at room temperature for 1 hr. A solution of acetophenone (117 μl) in THF (5 ml) was added to the obtained reaction mixture, and the mixture was stirred at room temperature for 3 hr. The reaction mixture was stirred at 60° C. for 15 hr and cooled to 0° C. Water was added to the reaction mixture, and the mixture was extracted with ethyl acetate. The organic layer was dried over anhydrous magnesium sulfate, and the solvent was evaporated under reduced pressure. The residue was purified by silica gel column (ethyl acetate/hexane=1/4 to ethyl acetate) and recrystallized from ethyl acetate-hexane to give the title compound as a colorless powder (150 mg, 36%).

NMR (CDCl$_3$) δ: 0.66-0.71 (2H, m), 0.85-0.92 (2H, m), 1.23 (3H, t, J=7.2), 1.76 (3H, s), 2.87-2.94 (1H, m), 3.53 (2H, q, J=7.2), 6.14 (1H, brs), 6.78 (1H, s), 7.33-7.37 (4H, m), 7.45-7.48 (2H, m), 7.67 (2H, d, J=8.7), 7.91 (2H, d, J=8.7).

Example 339

N-cyclopropyl-1-{4-[(ethylamino)carbonyl]phenyl}-5-[(1Z)-2-phenylprop-1-en-1-yl]-1H-1,2,3-triazole-4-carboxamide

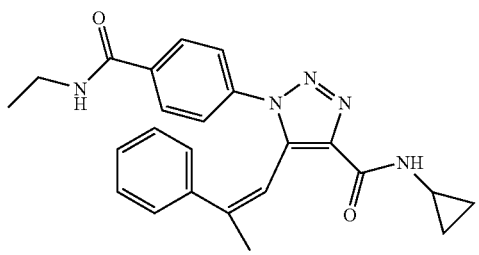

The second fraction obtained by silica gel column chromatography in Example 338 was recrystallized from ethyl acetate-hexane to give the title compound as a colorless powder (44.5 mg, 11%).

NMR (CDCl$_3$) δ: 0.68-0.73 (2H, m), 0.87-0.93 (2H, m), 1.29 (3H, t, J=7.2), 2.16 (3H, s), 2.90-2.96 (1H, m), 3.53 (2H, q, J=7.2), 6.04 (1H, brs), 6.48 (2H, d, J=7.2), 6.78 (1H, s), 6.90-6.99 (4H, m), 7.06 (1H, t, J=7.5), 7.28 (1H, brs), 7.61 (2H, d, J=8.4).

Example 340

N-cyclopropyl-1-{4-[(ethylamino)carbonyl]phenyl}-5-(2-ethylbut-1-en-1-yl)-1H-1,2,3-triazole-4-carboxamide

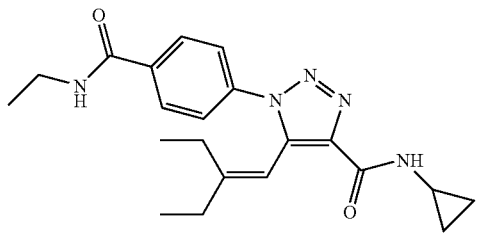

In the same manner as in Example 338, the title compound was obtained as a colorless powder (11.9 mg, 4.7%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b) and 3-pentanone (71 μl, 0.67 mmol).

NMR (CDCl$_3$) δ: 0.63-0.68 (2H, m), 0.82-0.93 (5H, m), 1.25-1.32 (6H, m), 1.46-1.50 (2H, m), 1.95-2.02 (2H, m), 2.89-2.93 (1H, m), 3.54 (2H, q, J=7.2), 6.13-6.18 (2H, m), 7.32-7.38 (1H, m), 7.42-7.61 (2H, m), 7.90-7.94 (2H, m).

Example 341

N-cyclopropyl-1-{4-[(ethylamino)carbonyl]phenyl}-5-(2-methylbut-1-en-1-yl)-1H-1,2,3-triazole-4-carboxamide

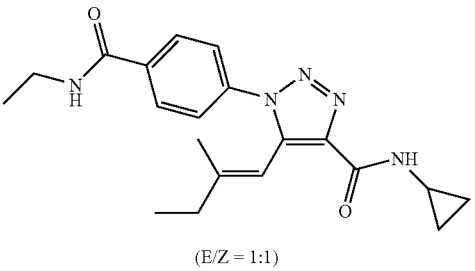

(E/Z = 1:1)

In the same manner as in Example 338, the title compound was obtained as a colorless powder (100 mg, 41%) from N-cyclopropyl-5-(diethylphosphonomethyl)-1-{4-[(ethylamino)carbonyl]phenyl}-1H-1,2,3-triazole-4-carboxamide (300 mg, 0.67 mmol) and 2-butanone (60 μl, 0.67 mmol) obtained in Example 321b).

NMR (CDCl$_3$) δ: 0.65-0.70 (2H, m), 0.86-0.90 (3.5H, m), 1.07 (1.5H, t, J=7.5), 1.29 (3H, t, J=6.6), 1.38 (1.5H, s), 1.45-1.48 (1H, m), 1.57 (1.5H, s), 2.18 (1H, q, J=6.9), 2.87-2.93 (1H, m), 3.54 (2H, q, J=6.6), 6.15-6.17 (2H, m), 7.34 (1H, brs), 7.53 (1H, d, J=8.7), 7.61 (1H, d, J=8.7), 7.89-7.94 (2H, m).

Example 342

5-[3-(benzyloxy)propyl]-N-cyclopropyl-1-{4-[(cyclopropylamino)carbonyl]phenyl}-1H-1,2,3-triazole-4-carboxamide

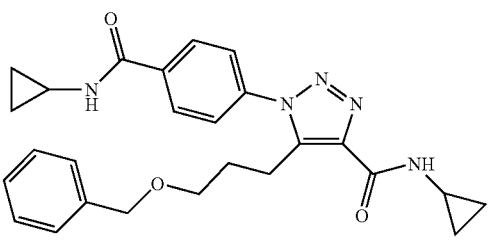

342a) 4-azido-N-cyclopropylbenzamide

In the same manner as in Example 43a), the title compound was obtained as a pale-yellow liquid (680 mg, 38%) from 4-azidobenzoic acid (1.50 g, 9.19 mmol).

NMR (CDCl$_3$) δ: 0.59-0.65 (2H, m), 0.85-0.91 (2H, m), 2.87-2.91 (1H, m), 6.19 (1H, brs), 7.05 (2H, d, J=8.4), 7.74 (2H, d, J=8.4).

342b) 5-[3-(benzyloxy)propyl]-1-{4-[(cyclopropylamino)carbonyl]phenyl}-1H-1,2,3-triazole-4-carboxylic acid In the same manner as in Example 90a), the title compound was obtained as a brown powder (1.31 g, 99%) from methyl 6-(benzyloxy)-3-oxohexanoate (1.30 g, 5.19 mmol) obtained in Example 91a) and 4-azido-N-cyclopropylbenzamide (680 mg, 3.36 mmol) obtained in Example 342a). The obtained product was directly used for Example 342c).

342c) 5-[3-(benzyloxy)propyl]-N-cyclopropyl-1-{4-[(cyclopropylamino)carbonyl]phenyl}-1H-1,2,3-triazole-4-carboxamide In the same manner as in Example 1c), the title compound was obtained as colorless needle crystals (454 mg, 76%) from 5-[3-(benzyloxy)propyl]-1-{4-[(cyclopropylamino)carbonyl]phenyl}-1H-1,2,3-triazole-4-carboxylic acid (1.30 g, 3.09 mmol) obtained in Example 342b).

NMR (CDCl₃) δ: 0.64-0.71 (4H, m), 0.86-0.95 (4H, m), 1.96-2.14 (2H, m), 2.86-2.97 (2H, m), 3.17 (2H, t, J=8.1), 4.34-4.42 (3H, m), 4.49 (1H, t, J=5.7), 6.30 (1H, brs), 7.35 (1H, brs), 7.43-7.81 (7H, m), 7.95 (2H, d, J=8.7).

Example 343

5-[3-(benzyloxy)propyl]-N-cyclopropyl-1-(4-{[(2-fluoroethyl)amino]carbonyl}phenyl)-1H-1,2,3-triazole-4-carboxamide

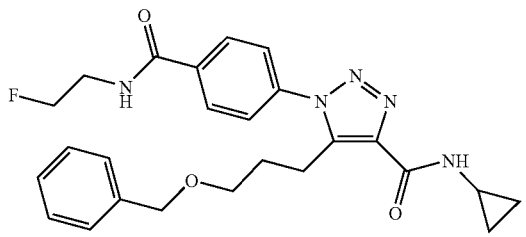

343a) 4-azido-N-(2-fluoroethyl)benzamide

In the same manner as in Example 43a), the title compound was obtained as a pale-yellow liquid (1.37 g, 72%) from 4-azidobenzoic acid (1.50 g, 9.19 mmol).

NMR (CDCl₃) δ: 0.59-0.65 (2H, m), 0.85-0.91 (2H, m), 2.87-2.91 (1H, m), 6.19 (1H, brs), 7.05 (2H, d, J=8.4), 7.74 (2H, d, J=8.4).

343b) 5-[3-(benzyloxy)propyl]-1-(4-{[(2-fluoroethyl)amino]carbonyl}phenyl)-1H-1,2,3-triazole-4-carboxylic acid In the same manner as in Example 90a), the title compound was obtained as a brown powder (1.95 g, 71%) from methyl 6-(benzyloxy)-3-oxohexanoate (2.50 g, 6.48 mmol) obtained in Example 91a) and 4-azido-N-(2-fluoroethyl)benzamide (1.35 g, 6.48 mmol) obtained in Example 343a). The obtained product was directly used for Example 343c).

343c) 5-[3-(benzyloxy)propyl]-N-cyclopropyl-1-(4-{[(2-fluoroethyl)amino]carbonyl}phenyl)-1H-1,2,3-triazole-4-carboxamide In the same manner as in Example 1c), the title compound was obtained as a pale-yellow powder (686 mg, 33%) from 5-[3-(benzyloxy)propyl]-1-(4-{[(2-fluoroethyl)amino]carbonyl}phenyl)-1H-1,2,3-triazole-4-carboxylic acid (1.89 g, 4.43 mmol) obtained in Example 343b).

NMR (CDCl₃) δ: 0.65-0.70 (2H, m), 0.85-0.91 (2H, m), 1.91-1.98 (2H, m), 2.85-2.93 (1H, m), 3.12-3.17 (2H, m), 3.45 (2H, t, J=6.0), 3.61-3.66 (2H, m), 3.83-3.85 (2H, m), 4.35 (2H, s), 6.84 (1H, brs), 7.18-7.20 (2H, m), 7.24-7.34 (3H, m), 7.40 (1H, d, J=3.0), 7.49 (2H, d, J=8.4), 7.87 (2H, d, J=8.4).

Example 344

5-[3-(benzyloxy)propyl]-N-cyclopropyl-1-{4-[(methoxyamino)carbonyl]phenyl}-1H-1,2,3-triazole-4-carboxamide

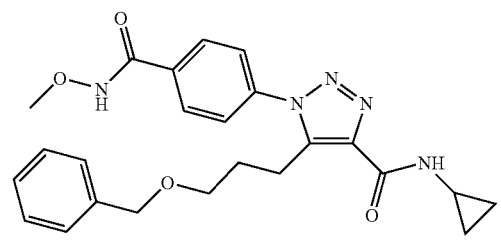

344a) 4-azido-N-methoxybenzamide

In the same manner as in Example 43a), the title compound was obtained as a pale-yellow solid (1.29 g, 73%) from 4-azidobenzoic acid (1.50 g, 9.19 mmol).

NMR (CDCl₃) δ: 3.85 (3H, s), 7.03 (2H, d, J=8.4), 7.77 (2H, d, J=8.4).

344b) 5-[3-(benzyloxy)propyl]-1-{4-[(methoxyamino)carbonyl]phenyl}-1H-1,2,3-triazole-4-carboxylic acid In the same manner as in Example 90a), the title compound was obtained as a pale-yellow powder (2.09 g, 79%) from methyl 6-(benzyloxy)-3-oxohexanoate (2.50 g, 6.48 mmol) obtained in Example 91a) and 4-azido-N-methoxybenzamide (1.25 g, 6.50 mmol) obtained in Example 344a). The obtained product was directly used for Example 344c).

344c) 5-[3-(benzyloxy)propyl]-N-cyclopropyl-1-{4-[(methoxyamino)carbonyl]phenyl}-1H-1,2,3-triazole-4-carboxamide In the same manner as in Example 1c), the title compound was obtained as a brown powder (396 mg, 18%) from 5-[3-(benzyloxy)propyl]-1-{4-[(methoxyamino)carbonyl]phenyl}-1H-1,2,3-triazole-4-carboxylic acid (2.00 g, 4.87 mmol) obtained in Example 344b).

NMR (CDCl₃) δ: 0.65-0.70 (2H, m), 0.86-0.91 (2H, m), 1.96-2.02 (2H, m), 2.86-2.92 (1H, m), 3.19 (2H, t, J=7.8), 3.46-3.50 (2H, m), 3.91 (3H, s), 4.36 (2H, s), 7.21-7.24 (2H, m), 7.31-7.36 (3H, m), 7.56 (2H, d, J=8.4), 7.75 (2H, d, J=8.4), 7.75 (2H, d, J=8.4).

Example 345

5-[3-(benzyloxy)propyl]-N-cyclopropyl-1-(4-{[(2,2,2-trifluoroethyl)amino]carbonyl}phenyl)-1H-1,2,3-triazole-4-carboxamide

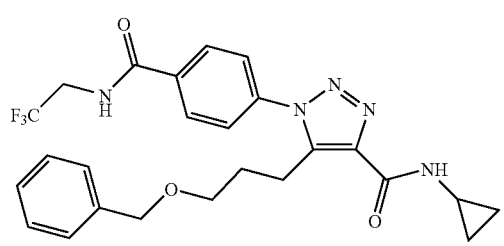

345a) 4-azido-N-(2,2,2-trifluoroethyl)benzamide

In the same manner as in Example 43a), the title compound was obtained as pale-yellow crystals (2.06 g, 92%) from 4-azidobenzoic acid (1.50 g, 9.19 mmol).

NMR (CDCl$_3$) δ: 4.07-4.18 (2H, m), 6.38 (1H, brs), 7.10 (2H, d, J=9.0), 7.81 (2H, d, J=9.0).

345b) 5-[3-(benzyloxy)propyl]-1-(4-{[(2,2,2-trifluoroethyl)amino]carbonyl}phenyl)-1H-1,2,3-triazole-4-carboxylic acid In the same manner as in Example 90a), the title compound was obtained as a colorless powder (3.80 g, 98%) from methyl 6-(benzyloxy)-3-oxohexanoate (3.17 g, 12.6 mmol) obtained in Example 91a) and 4-azido-N-(2,2,2-trifluoroethyl)benzamide (2.06 g, 8.44 mmol) obtained in Example 345a). The obtained product was directly used for Example 345c).

345c) 5-[3-(benzyloxy)propyl]-N-cyclopropyl-1-(4-{[(2,2,2-trifluoroethyl)amino]carbonyl}phenyl)-1H-1,2,3-triazole-4-carboxamide In the same manner as in Example 1c), the title compound was obtained as a pale-yellow powder (3.86 g, 94%) from 5-[3-(benzyloxy)propyl]-1-(4-{[(2,2,2-trifluoroethyl)amino]carbonyl}phenyl)-1H-1,2,3-triazole-4-carboxylic acid (3.80 g, 8.22 mmol) obtained in Example 345b).

NMR (CDCl$_3$) δ: 0.65-0.70 (2H, m), 0.85-0.91 (2H, m), 1.95-2.04 (2H, m), 2.86-2.92 (1H, m), 3.19 (2H, t, J=7.8), 3.48 (2H, t, J=5.4), 4.08-4.19 (2H, m), 4.36 (2H, s), 6.54 (1H, t, J=6.3), 7.20-7.23 (2H, m), 7.28-7.37 (4H, m), 7.57 (2H, d, J=8.4), 7.84 (2H, d, J=8.4).

Example 346

5-(cyclohexylidenemethyl)-N-cyclopropyl-1-{4-[(ethylamino)carbonyl]phenyl}-1H-1,2,3-triazole-4-carboxamide

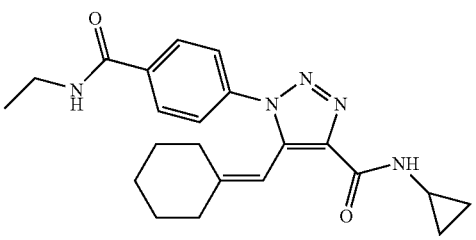

In the same manner as in Example 338, the title compound was obtained as a colorless powder (205 mg, 78%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b).

NMR (CDCl$_3$) δ: 0.65-0.70 (2H, m), 0.85-0.91 (2H, m), 1.30 (3H, t, J=7.2), 1.43-1.57 (4H, m), 1.79-1.85 (4H, m), 2.87-2.95 (1H, m), 3.55 (2H, qd, J=7.2, 1.8), 3.74 (2H, brs), 4.98 (1H, s), 6.18 (1H, brs), 7.34 (1H, brs), 7.54 (2H, d, J=8.7), 7.94 (2H, d, J=8.7).

Example 347

5-(cyclopentylidenemethyl)-N-cyclopropyl-1-{4-[(ethylamino)carbonyl]phenyl}-1H-1,2,3-triazole-4-carboxamide

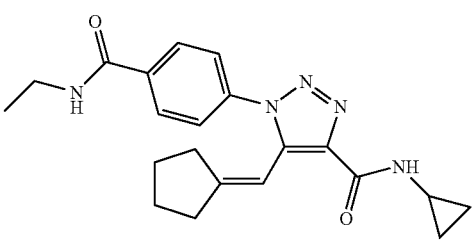

In the same manner as in Example 338, the title compound was obtained as a colorless powder (143 mg, 57%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b).

NMR (CDCl$_3$) δ: 0.65-0.70 (2H, m), 0.84-0.91 (2H, m), 1.29 (3H, t, J=7.5), 1.77-1.87 (2H, m), 2.18-2.23 (4H, m), 2.87-2.95 (1H, m), 3.54 (2H, qd, J=7.5, 1.5), 3.85 (2H, brs), 5.00-5.02 (1H, m), 6.21 (1H, brs), 7.33 (1H, d, J=1.5), 7.54 (2H, d, J=9.0), 7.94 (2H, d, J=9.0).

Example 348

5-(cyclobutylidenemethyl)-N-cyclopropyl-1-{4-[(ethylamino)carbonyl]phenyl}-1H-1,2,3-triazole-4-carboxamide

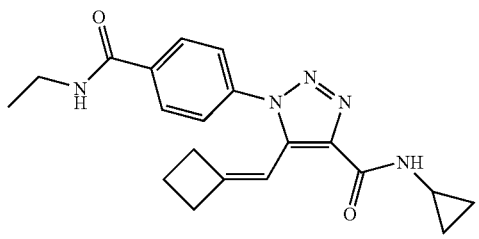

In the same manner as in Example 338, the title compound was obtained as a colorless powder (126 mg, 52%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b).

NMR (CDCl$_3$) δ: 0.65-0.70 (2H, m), 0.85-0.91 (2H, m), 1.30 (3H, t, J=6.9), 1.76-1.86 (2H, m), 1.97-2.02 (2H, m), 2.74-2.86 (2H, m), 2.86-2.94 (1H, m), 3.55 (2H, qd, J=6.9, 1.8), 6.20 (1H, brs), 6.46-6.49 (1H, m), 7.32 (1H, brs), 7.61 (2H, d, J=8.7), 7.94 (2H, d, J=8.7).

Example 349

N-cyclopropyl-1-{4-[(ethylamino)carbonyl]phenyl}-5-methyl-1H-1,2,3-triazole-4-carboxamide

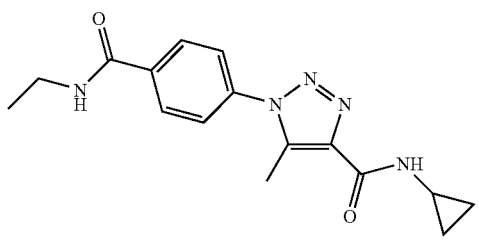

In the same manner as in Example 338, the title compound was obtained as a colorless powder (8.1 mg, 3.0%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b) and 2-acetylthiophene (72 µl, 0.67 mmol).

NMR (CDCl$_3$) δ: 0.65-0.71 (2H, m), 0.85-0.91 (2H, m), 1.27 (3H, t, J=7.2), 2.67 (3H, s), 2.88-2.92 (1H, m), 3.51 (2H, q, J=7.2), 6.13 (1H, s), 7.32 (1H, d, J=3.0), 7.55 (2H, d, J=8.4), 7.97 (2H, d, J=8.4).

Example 350

N-cyclopropyl-1-{4-[(ethylamino)carbonyl]phenyl}-5-[(1E)-2-(1,3-thiazol-2-yl)prop-1-en-1-yl]-1H-1,2,3-triazole-4-carboxamide

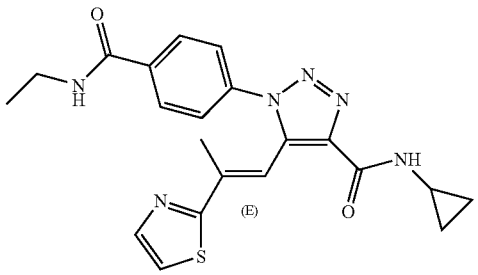

In the same manner as in Example 338, the title compound was obtained as a colorless powder (52.6 mg, 19%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b).

NMR (CDCl$_3$) δ: 0.65-0.71 (2H, m), 0.85-0.91 (2H, m), 1.27 (3H, t, J=7.2), 1.93 (3H, s), 2.88-2.92 (1H, m), 3.51 (2H, q, J=7.2), 6.10 (1H, s), 7.33 (1H, d, J=3.0), 7.37 (1H, brs), 7.39 (1H, brs), 7.65 (2H, d, J=8.4), 7.81 (1H, d, J=3.0), 7.90 (2H, d, J=8.4).

Example 351

N-cyclopropyl-1-{4-[(cyclopropylamino)carbonyl]phenyl}-5-(3-fluoropropyl)-1H-1,2,3-triazole-4-carboxamide

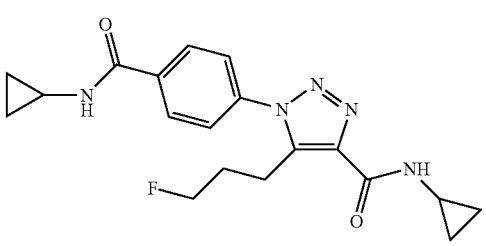

351a) N-cyclopropyl-1-{4-[(cyclopropylamino)carbonyl]phenyl}-5-(3-hydroxypropyl)-1H-1,2,3-triazole-4-carboxamide In the same manner as in Example 114, the title compound was obtained as a pale-yellow solid (238 mg, 98%) from 5-[3-(benzyloxy)propyl]-N-cyclopropyl-1-{4-[(cyclopropylamino)carbonyl]phenyl}-1H-1,2,3-triazole-4-carboxamide (307 mg, 0.67 mmol) obtained in Example 342.

NMR (CDCl$_3$) δ: 0.64-0.72 (4H, m), 0.87-0.95 (4H, m), 1.62-1.70 (2H, m), 2.89-2.98 (2H, m), 3.18 (2H, t, J=6.9), 3.48 (2H, t, J=5.7), 6.46 (1H, brs), 7.50 (2H, d, J=8.7), 7.54 (1H, brs), 7.95 (2H, d, J=8.7).

351b) N-cyclopropyl-1-{4-[(cyclopropylamino)carbonyl]phenyl}-5-(3-fluoropropyl)-1H-1,2,3-triazole-4-carboxamide To a solution of N-cyclopropyl-1-{4-[(cyclopropylamino)carbonyl]phenyl}-5-(3-hydroxypropyl)-1H-1,2,3-triazole-4-carboxamide (240 mg, 0.65 mmol) obtained in Example 351a) and triethylamine (140 μl, 1.00 mmol) in dichloromethane (10 ml) was added methanesulfonyl chloride (60 μl, 0.78 mmol), and the mixture was stirred at room temperature for 6 hr. The reaction mixture was washed with saturated brine, dried over anhydrous magnesium sulfate, and the solvent was evaporated under reduced pressure. The residue was dissolved in acetonitrile (10 ml), tetrabutylammonium fluoride monohydrate (425 mg, 1.63 mmol) was added, and the mixture was stirred at 80° C. for 16 hr. After the reaction mixture was allowed to cool to room temperature, the solvent was evaporated under reduced pressure. The residue was purified by silica gel column (ethyl acetate/hexane=1/1 to ethyl acetate) and recrystallized from ethyl acetate-hexane to give the title compound as a colorless powder (90 mg, 37%).

NMR (CDCl$_3$) δ: 0.64-0.71 (4H, m), 0.86-0.95 (4H, m), 1.96-2.14 (2H, m), 2.86-2.97 (2H, m), 3.17 (2H, t, J=8.1), 4.34 (1H, t, J=5.7), 4.49 (1H, t, J=5.7), 6.30 (1H, brs), 7.35 (1H, brs), 7.52 (2H, d, J=8.7), 7.95 (2H, d, J=8.7).

Example 352

N-cyclopropyl-1-(4-{[(2-fluoroethyl)amino]carbonyl}phenyl)-5-(3-fluoropropyl)-1H-1,2,3-triazole-4-carboxamide

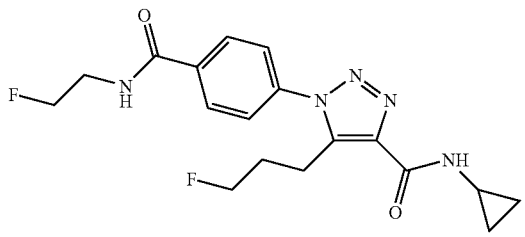

352a) N-cyclopropyl-1-(4-{[(2-fluoroethyl)amino]carbonyl}phenyl)-5-(3-hydroxypropyl)-1H-1,2,3-triazole-4-carboxamide In the same manner as in Example 114, the title compound was obtained as a colorless solid (465 mg, 98%) from 5-[3-(benzyloxy)propyl]-N-cyclopropyl-1-(4-{[(2-fluoroethyl)amino]carbonyl}phenyl)-1H-1,2,3-triazole-4-carboxamide (589 mg, 1.27 mmol) obtained in Example 343.

NMR (CDCl$_3$) δ: 0.67-0.72 (2H, m), 0.87-0.94 (2H, m), 1.63-1.69 (2H, m), 2.36 (1H, s), 2.90-2.96 (1H, m), 3.18 (2H, t, J=6.6), 3.48 (2H, t, J=5.4), 3.65-3.70 (2H, m), 3.88 (2H, t, J=5.4), 6.89 (1H, brs), 7.48-7.53 (3H, m), 8.00 (2H, d, J=8.4).

352b) N-cyclopropyl-1-(4-{[(2-fluoroethyl)amino]carbonyl}phenyl)-5-(3-fluoropropyl)-1H-1,2,3-triazole-4-carboxamide In the same manner as in Example 351b), the title compound was obtained as a colorless powder (95 mg, 20%) from N-cyclopropyl-1-(4-{[(2-fluoroethyl)amino]carbonyl}phenyl)-5-(3-hydroxypropyl)-1H-1,2,3-triazole-4-carboxamide (470 mg, 1.25 mmol) obtained in Example 352a).

NMR (CDCl$_3$) δ: 0.67-0.71 (2H, m), 0.86-0.92 (2H, m), 1.96-2.14 (2H, m), 2.85-2.94 (1H, m), 3.17 (2H, t, J=7.8), 4.12 (2H, t, J=9.3), 4.33 (1H, t, J=5.4), 4.47-4.53 (3H, m), 7.36 (1H, brs), 7.50 (2H, d, J=8.7), 8.16 (2H, d, J=8.7).

Example 353

N-cyclopropyl-5-(3-fluoropropyl)-1-{4-[(methoxyamino)carbonyl]phenyl}-1H-1,2,3-triazole-4-carboxamide

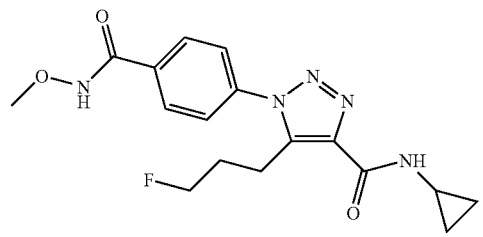

353a) N-cyclopropyl-5-(3-hydroxypropyl)-1-{4-[(methoxyamino)carbonyl]phenyl}-1H-1,2,3-triazole-4-carboxamide In the same manner as in Example 114, the title compound was obtained as a colorless solid (262 mg, 99%) from 5-[3-(benzyloxy)propyl]-N-cyclopropyl-1-{4-[(methoxyamino)carbonyl]phenyl}-1H-1,2,3-triazole-4-carboxamide (331 mg, 0.74 mmol) obtained in Example 344.

NMR (CDCl$_3$) δ: 0.64-0.72 (2H, m), 0.87-0.95 (2H, m), 1.61-1.70 (2H, m), 2.10 (3H, s), 2.90-2.96 (1H, m), 3.19 (2H, t, J=6.6), 3.48 (2H, t, J=5.4), 6.44 (1H, brs), 7.49-7.54 (3H, m), 7.95 (2H, d, J=8.4).

353b) N-cyclopropyl-5-(3-fluoropropyl)-1-{4-[(methoxyamino)carbonyl]phenyl}-1H-1,2,3-triazole-4-carboxamide In the same manner as in Example 351b), the title compound was obtained as a colorless powder (10 mg, 4.0%) from N-cyclopropyl-5-(3-hydroxypropyl)-1-{4-[(methoxyamino)carbonyl]phenyl}-1H-1,2,3-triazole-4-carboxamide (260 mg, 0.73 mmol) obtained in Example 353a).

NMR (CDCl$_3$) δ: 0.64-0.71 (2H, m), 0.86-0.95 (2H, m), 1.96-2.14 (2H, m), 2.85-2.90 (1H, m), 3.17 (2H, t, J=7.8), 3.75 (3H, s), 4.34 (1H, t, J=5.7), 4.49 (1H, t, J=5.7), 6.32 (1H, brs), 7.35 (1H, brs), 7.52 (2H, d, J=8.7), 7.95 (2H, d, J=8.7).

Example 354

5-(3-chloropropyl)-N-cyclopropyl-1-(4-{[(2,2,2-trifluoroethyl)amino]carbonyl}phenyl)-1H-1,2,3-triazole-4-carboxamide

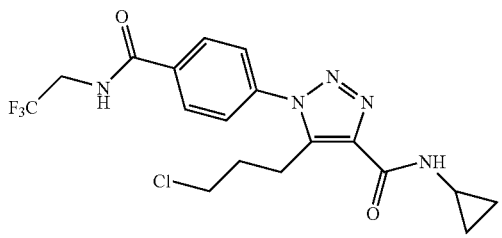

In the same manner as in Example 351, the title compound was obtained as a colorless powder (214 mg, 43%) from 5-[3-(benzyloxy)propyl]-N-cyclopropyl-1-(4-{[(2,2,2-trifluoroethyl)amino]carbonyl}phenyl)-1H-1,2,3-triazole-4-carboxamide (3.03 g, 6.04 mmol) obtained in Example 345.

NMR (CDCl$_3$) δ: 0.66-0.71 (2H, m), 0.86-0.93 (2H, m), 2.10-2.19 (2H, m), 2.85-2.93 (1H, m), 3.21 (2H, t, J=8.1), 3.54 (2H, t, J=6.3), 4.11-4.24 (2H, m), 6.49 (1H, t, J=6.0), 7.35 (1H, brs), 7.59 (2H, d, J=8.1), 8.03 (2H, d, J=8.1).

In the same manner as in Example 46, the compounds of Examples 355 to 359 were synthesized.

Example 355

5-[3-(benzyloxy)propyl]-1-(4-{[(2,2,2-trifluoroethyl)amino]carbonyl}phenyl)-1H-1,2,3-triazole-4-carboxamide

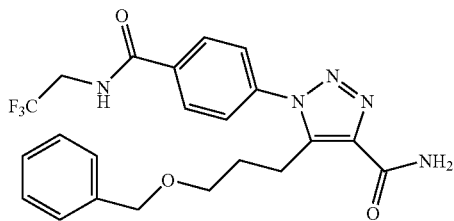

NMR (CDCl$_3$) δ: 1.95-2.05 (2H, m), 3.21 (2H, t, J=7.4), 3.48 (2H, t, J=5.4), 4.06-4.23 (2H, m), 4.37 (2H, s), 5.12 (1H, brs), 6.24 (1H, brs), 7.14 (1H, brs), 7.21-7.34 (5H, m), 7.60 (2H, d, J=8.4), 7.83 (2H, d, J=8.4).

Example 356

5-(5-fluoropentyl)-1-(4-{[(2,2,2-trifluoroethyl)amino]carbonyl}phenyl)-1H-1,2,3-triazole-4-carboxamide

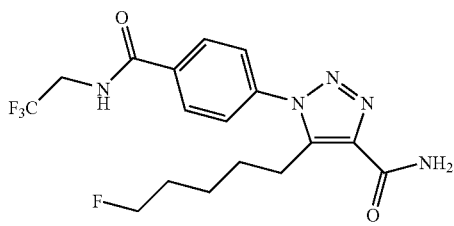

NMR (CDCl$_3$) δ: 1.34-1.42 (2H, m), 1.50-1.61 (4H, m), 3.08 (2H, t, J=7.5), 4.09-4.24 (2H, m), 4.29 (1H, t, J=5.7), 4.44 (1H, t, J=5.7), 5.50 (1H, brs), 6.43 (1H, brs), 7.13 (1H, brs), 7.58 (2H, d, J=9.0), 8.03 (2H, d, J=9.0).

Example 357

N-cyclopropyl-5-(5-fluoropentyl)-1-(4-{[(2,2,2-trifluoroethyl)amino]carbonyl}phenyl)-1H-1,2,3-triazole-4-carboxamide

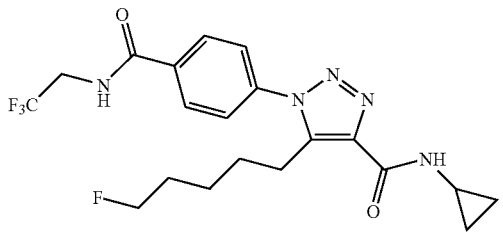

NMR (CDCl$_3$) δ: 0.65-0.70 (2H, m), 0.86-0.92 (2H, m), 1.34-1.43 (2H, m), 1.54-1.70 (4H, m), 2.87-2.93 (1H, m), 3.07 (2H, t, J=7.8), 4.13-4.24 (2H, m), 4.29 (1H, t, J=5.7), 4.44 (1H, t, J=5.7), 6.48 (1H, t, J=6.3), 7.34 (1H, brs), 7.56 (2H, d, J=8.4), 8.02 (2H, d, J=8.4).

Example 358

5-(5-fluoropentyl)-N-(2-hydroxyethyl)-1-(4-{[(2,2,2-trifluoroethyl)amino]carbonyl}phenyl)-1H-1,2,3-triazole-4-carboxamide

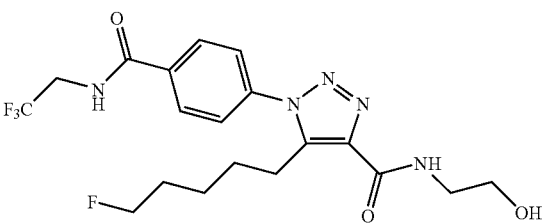

NMR (CDCl$_3$) δ: 1.32-1.42 (2H, m), 1.54-1.71 (4H, m), 2.69 (1H, brs), 3.07 (2H, t, J=8.1), 3.66 (2H, q, J=4.7), 3.86 (2H, t, J=5.1), 4.13-4.24 (2H, m), 4.29 (1H, t, J=5.8), 4.44 (1H, t, J=5.8), 6.53 (1H, t, J=6.4), 7.57 (2H, d, J=8.5), 7.67 (1H, t, J=5.5), 8.03 (2H, d, J=8.5).

Example 359

5-(5-fluoropentyl)-N-(2-methoxyethyl)-1-(4-{[(2,2,2-trifluoroethyl)amino]carbonyl}phenyl)-1H-1,2,3-triazole-4-carboxamide

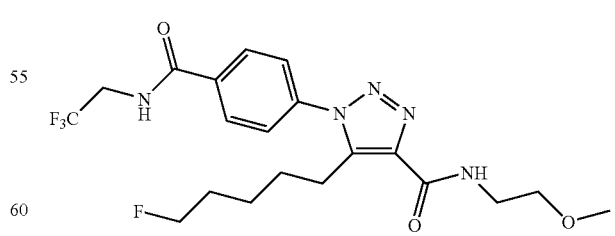

NMR (CDCl$_3$) δ: 1.31-1.42 (2H, m), 1.53-1.68 (4H, m), 3.07 (2H, t, J=8.1), 3.41 (3H, s), 3.58 (2H, t, J=4.7), 3.67 (2H, q, J=5.5), 4.13-4.24 (2H, m), 4.28 (1H, t, J=6.0), 4.44 (1H, t, J=6.0), 6.55 (1H, t, J=6.0), 7.55-7.60 (3H, m), 8.03 (2H, d, J=8.5).

Example 360

3-[4-(aminocarbonyl)-1-(4-{[(2,2,2-trifluoroethyl)amino]carbonyl}phenyl)-1H-1,2,3-triazol-5-yl]propyl acetate

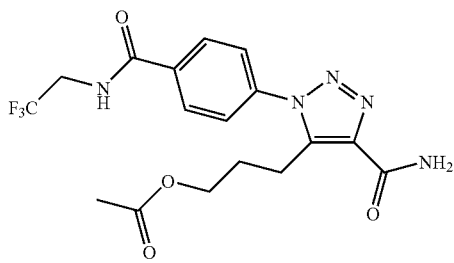

In the same manner as in Example 351, the title compound was obtained as a colorless powder (128 mg, 30%) from 5-[3-(benzyloxy)propyl]-1-(4-{[(2,2,2-trifluoroethyl)amino]carbonyl}phenyl)-1H-1,2,3-triazole-4-carboxamide (541 mg, 1.17 mmol) obtained in Example 355.

NMR (CDCl$_3$) δ: 1.70-1.76 (2H, m), 2.00 (3H, s), 3.09 (2H, t, J=7.8), 3.82 (2H, t, J=5.7), 4.09-4.21 (2H, m), 7.55 (1H, brs), 7.77 (2H, d, J=8.4), 7.98 (1H, brs), 8.13 (2H, d, J=8.4), 9.35 (1H, t, J=6.6).

In the same manner as in Example 133, the compounds of Examples 361 to 369 were synthesized.

Example 361

1-{4-[(ethylamino)carbonyl]-2-(3-phenylpropoxy)phenyl}-N-(2,2,2-trifluoroethyl)-1H-1,2,3-triazole-4-carboxamide

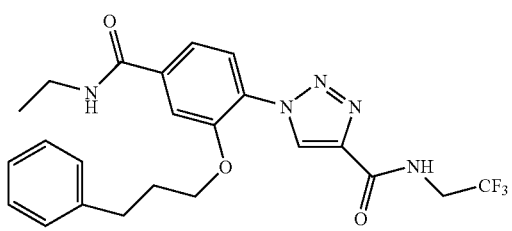

NMR (CDCl$_3$) δ: 1.29 (3H, t, J=7.2), 2.15 (2H, q, J=7.2), 2.71 (2H, t, J=7.2), 3.53 (2H, qd, J=7.2, 1.8), 4.10-4.21 (4H, m), 6.15 (1H, brs), 7.13-7.29 (5H, m), 7.36 (1H, dd, J=8.4, 1.8), 7.51 (1H, t, J=1.8), 7.61 (1H, d, J=1.8), 7.90 (1H, d, J=8.1), 8.76 (1H, s).

Example 362

1-{4-[(ethylamino)carbonyl]-2-(3-phenylpropoxy)phenyl}-N-(2-fluoroethyl)-1H-1,2,3-triazole-4-carboxamide

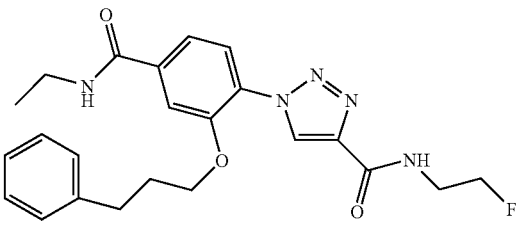

NMR (CDCl$_3$) δ: 1.29 (3H, t, J=7.5), 2.15 (2H, q, J=7.5), 2.71 (2H, t, J=7.5), 3.53 (2H, q, J=7.5), 3.78 (1H, q, J=5.4), 3.87 (1H, q, J=5.4), 4.17 (2H, t, J=7.5), 4.55 (1H, t, J=5.4), 4.71 (1H, t, J=5.4), 6.13 (1H, brs), 7.13-7.29 (5H, m), 7.36 (1H, dd, J=8.4, 1.8), 7.54 (1H, brs), 7.60 (1H, d, J=1.8), 7.90 (1H, d, J=8.4), 8.72 (1H, s).

Example 363

1-{4-[(ethylamino)carbonyl]-2-(3-phenylpropoxy)phenyl}-N-methyl-1H-1,2,3-triazole-4-carboxamide

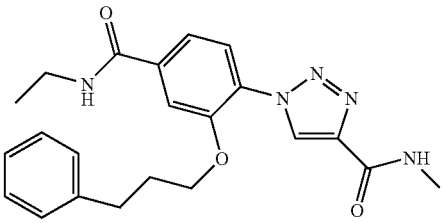

NMR (CDCl$_3$) δ: 1.28 (3H, t, J=7.5), 2.10-2.19 (2H, m), 2.71 (2H, t, J=7.5), 3.06 (3H, d, J=5.1), 3.48-3.57 (2H, m), 4.16 (2H, t, J=6.3), 6.15 (1H, brs), 7.13-7.30 (5H, m), 7.36 (1H, dd, J=8.1, 1.5), 7.60 (1H, d, J=1.8), 7.89 (2H, d, J=8.4), 8.70 (1H, s).

Example 364

N-cyclopropyl-1-(2-(3-phenylpropoxy)-4-{[(2,2,2-trifluoroethyl)amino]carbonyl}phenyl)-1H-1,2,3-triazole-4-carboxamide

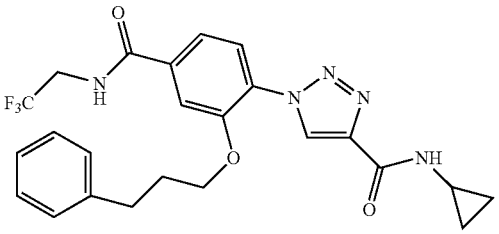

NMR (CDCl$_3$) δ: 0.68-0.73 (2H, m), 0.87-0.93 (2H, m), 2.10-2.19 (2H, m), 2.71 (2H, t, J=7.5), 2.91-2.98 (1H, m), 4.09-4.20 (4H, m), 6.70 (1H, t, J=6.3), 7.13-7.31 (5H, m), 7.44 (1H, dd, J=8.4, 1.2), 7.61 (1H, s), 7.91 (1H, dd, J=8.4, 1.2), 8.69 (1H, s).

Example 365

1-(2-(3-phenylpropoxy)-4-{[(2,2,2-trifluoroethyl)amino]carbonyl}phenyl)-1H-1,2,3-triazole-4-carboxamide

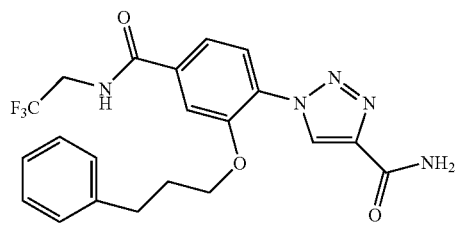

NMR (CDCl$_3$) δ: 1.98-2.02 (2H, m), 2.64 (2H, t, J=8.4), 4.09-4.20 (4H, m), 7.16-7.19 (3H, m), 7.23-7.28 (2H, m), 7.63 (1H, brs), 7.69 (1H, d, J=8.7), 7.75 (1H, s), 7.86 (1H, d, J=8.7), 8.05 (1H, brs), 8.96 (1H, s), 9.30 (1H, t, J=6.3).

Example 366

N-(2-hydroxyethyl)-1-(2-(3-phenylpropoxy)-4-{[(2,2,2-trifluoroethyl)amino]carbonyl}phenyl)-1H-1,2,3-triazole-4-carboxamide

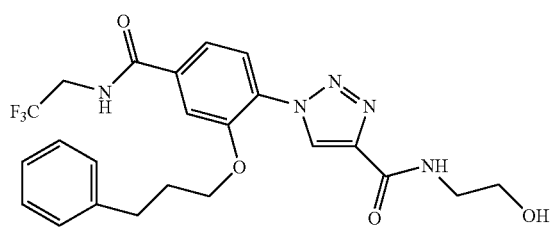

NMR (DMSO-d$_6$) δ: 1.93-2.03 (2H, m), 2.63 (2H, t, J=7.8), 3.34-3.41 (2H, m), 3.51-3.57 (2H, m), 4.09-4.20 (3H, m), 4.79 (1H, t, J=5.7), 7.15-7.18 (3H, m), 7.24-7.29 (2H, m), 7.67-7.70 (1H, m), 7.75 (1H, brs), 7.85 (1H, d, J=7.2), 8.55 (1H, t, J=6.0), 8.97 (1H, s), 9.29 (1H, t, J=6.3).

Example 367

N-(2-hydroxyethyl)-1-(2-(pent-4-en-1-yloxy)-4-{[(2,2,2-trifluoroethyl)amino]carbonyl}phenyl)-1H-1,2,3-triazole-4-carboxamide

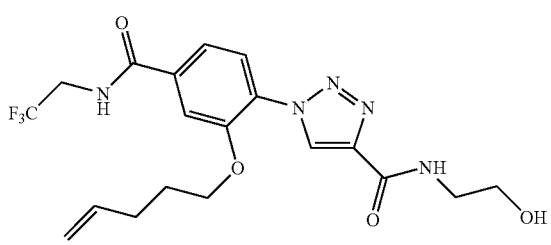

NMR (DMSO-d$_6$) δ: 1.75-1.84 (2H, m), 2.06-2.13 (2H, m), 3.34-3.40 (2H, m), 3.50-3.56 (2H, m), 4.10-4.21 (2H, m), 4.78 (1H, t, J=5.5), 4.94-5.04 (2H, m), 5.73-5.87 (1H, m), 7.68 (1H, dd, J=8.3, 1.7), 7.77 (1H, d, J=1.7), 7.84 (1H, d, J=8.3), 8.52 (1H, t, J=5.8), 8.91 (1H, s), 9.30 (1H, t, J=6.2).

Example 368

N-(2-methoxyethyl)-1-(2-(pent-4-en-1-yloxy)-4-{[(2,2,2-trifluoroethyl)amino]carbonyl}phenyl)-1H-1,2,3-triazole-4-carboxamide

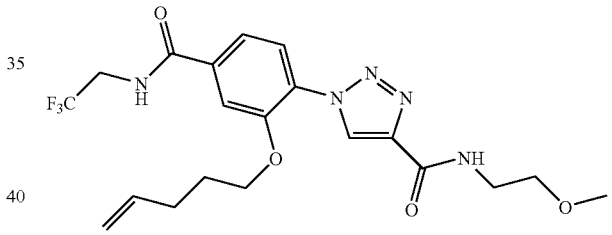

NMR (DMSO-d$_6$) δ: 1.75-1.84 (2H, m), 2.06-2.13 (2H, m), 3.28 (3H, s), 3.45-3.50 (4H, m), 4.10-4.21 (4H, m), 4.94-5.04 (2H, m), 5.73-5.87 (1H, m), 7.69 (1H, dd, J=8.3, 1.7), 7.77 (1H, d, J=1.7), 7.84 (1H, d, J=8.3), 8.59 (1H, t, J=5.1), 8.91 (1H, s), 9.30 (1H, t, J=6.4).

Example 369

N-cyclopropyl-1-(2-(pent-4-en-1-yloxy)-4-{[(2,2,2-trifluoroethyl)amino]carbonyl}phenyl)-1H-1,2,3-triazole-4-carboxamide

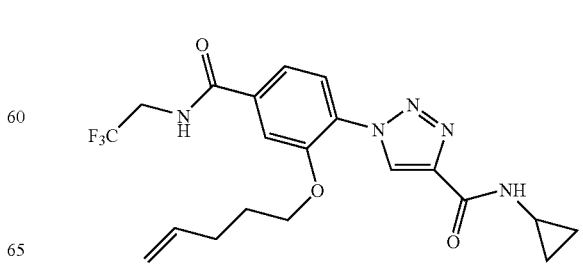

NMR (DMSO-d$_6$) δ: 0.64-0.71 (4H, m), 1.75-1.84 (2H, m), 2.06-2.13 (2H, m), 2.84-2.93 (1H, m), 4.11-4.21 (4H, m), 4.94-5.04 (2H, m), 5.74-5.87 (1H, m), 7.68 (1H, dd, J=8.3, 1.5), 7.77 (1H, d, J=1.5), 7.83 (1H, d, J=8.3), 8.71 (1H, d, J=4.5), 8.89 (1H, s), 9.30 (1H, brs).

In the same manner as in Example 134, the compounds of Example 370 and Example 371 were synthesized.

Example 370

1-{2-(benzyloxy)-4-[(ethylamino)carbonyl]phenyl}-5-(trifluoromethyl)-1H-1,2,3-triazole-4-carboxamide

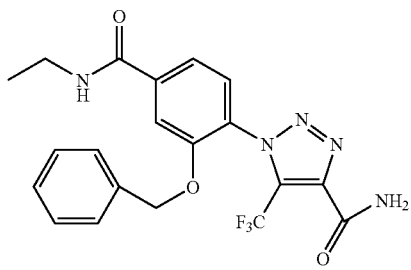

NMR (CDCl$_3$) δ: 1.28 (3H, t, J=6.9), 3.52 (2H, qd, J=6.9, 1.5), 5.17 (2H, s), 5.71 (1H, brs), 6.11 (1H, brs), 7.15 (1H, brs), 7.21-7.33 (5H, m), 7.37 (1H, dd, J=8.1, 1.8), 7.46 (1H, d, J=8.1), 7.66 (1H, d, J=1.8).

Example 371

1-{4-[(ethylamino)carbonyl]-2-(3-phenylpropoxy)phenyl}-5-(trifluoromethyl)-1H-1,2,3-triazole-4-carboxamide

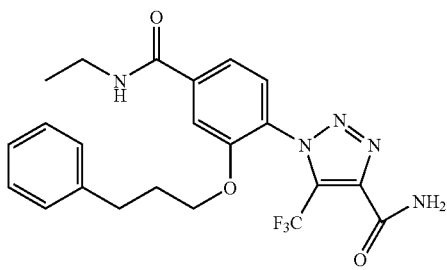

NMR (CDCl$_3$) δ: 1.15 (3H, t, J=6.9), 1.82-1.90 (2H, m), 2.46 (2H, t, J=8.1), 3.27-3.37 (2H, m), 4.04-4.13 (2H, m), 7.05-7.08 (2H, m), 7.17 (1H, d, J=7.2), 7.22-7.27 (3H, m), 7.62 (1H, d, J=8.4), 7.65-7.66 (2H, m), 7.79 (1H, d, J=8.4), 7.95 (1H, brs), 8.37 (1H, brs), 8.69 (1H, t, J=5.7).

Example 372

N-cyclopropyl-1-{4-[(ethylamino)carbonyl]phenyl}-5-(tetrahydro-4H-pyran-4-ylidenemethyl)-1H-1,2,3-triazole-4-carboxamide

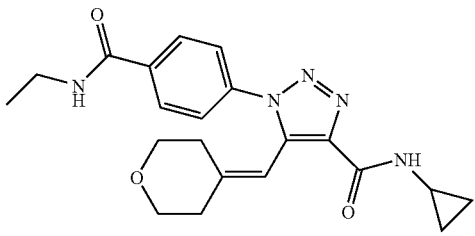

In the same manner as in Example 338, the title compound was obtained as a colorless powder (78.6 mg, 73%) from N-cyclopropyl-5-(diethylphosphonomethyl)-1-{4-[(ethylamino)carbonyl]phenyl}-1H-1,2,3-triazole-4-carboxamide (123 mg, 0.27 mmol) obtained in Example 321b).

NMR (CDCl$_3$) δ: 0.66-0.71 (2H, m), 0.86-0.92 (2H, m), 1.30 (3H, t, J=7.5), 1.99 (2H, brs), 2.87-2.95 (1H, m), 3.54 (2H, qd, J=7.5, 1.5), 3.71 (2H, t, J=5.7), 3.81 (2H, brs), 3.97-3.99 (2H, m), 5.04 (1H, brs), 6.19 (1H, brs), 7.35 (1H, brs), 7.54 (2H, d, J=7.8), 7.95 (2H, d, J=7.8).

In the same manner as in Example 94, the compounds of Example 373 and Example 374 were synthesized.

Example 373

5-[(benzyloxy)methyl]-1-(4-{[(2,2,2-trifluoroethyl)amino]carbonyl}phenyl)-1H-1,2,3-triazole-4-carboxamide

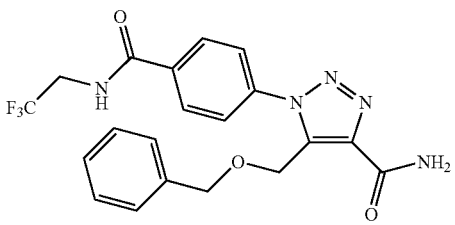

NMR (CDCl$_3$) δ: 4.11-4.23 (2H, m), 4.63 (2H, s), 5.00 (2H, s), 5.60 (1H, brs), 6.38 (1H, brs), 7.19-7.33 (6H, m), 7.84 (2H, d, J=8.4), 7.95 (2H, d, J=8.4).

Example 374

5-[(benzyloxy)methyl]-N-cyclopropyl-1-(4-{[(2,2,2-trifluoroethyl)amino]carbonyl}phenyl)-1H-1,2,3-triazole-4-carboxamide

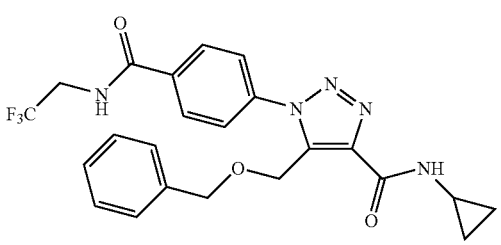

NMR (CDCl$_3$) δ: 0.67-0.72 (4H, m), 2.86-2.96 (1H, m), 4.10-4.22 (2H, m), 4.45 (s, 2H), 4.99 (s, 2H), 7.08 (1H, d,

J=2.1), 7.10 (1H, d, J=3.9), 7.25 (2H, d, J=2.4), 7.26 (1H, d, J=1.2), 7.84 (2H, d, J=8.4), 8.11 (2H, d, J=8.4), 8.81 (1H, d, J=4.8), 9.32 (1H, t, J=6.0).

In the same manner as in Example 111, the compounds of Example 375 and Example 376 were synthesized.

Example 375

5-(4-fluorobutyl)-1-(4-{[(2,2,2-trifluoroethyl)amino]carbonyl}phenyl)-1H-1,2,3-triazole-4-carboxamide

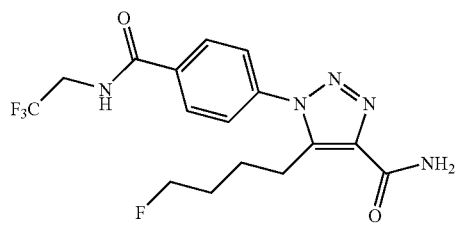

NMR (CDCl$_3$) δ: 1.45-1.53 (4H, m), 3.06 (2H, t, J=6.9), 4.09-4.19 (2H, m), 4.23 (1H, t, J=5.4), 4.39 (1H, t, J=5.4), 7.54 (1H, brs), 7.78 (2H, d, J=8.7), 7.98 (1H, brs), 8.13 (2H, d, J=8.7), 9.35 (1H, t, J=6.3).

Example 376

N-cyclopropyl-5-(4-fluorobutyl)-1-(4-{[(2,2,2-trifluoroethyl)amino]carbonyl}phenyl)-1H-1,2,3-triazole-4-carboxamide

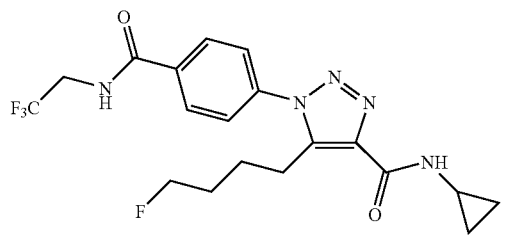

NMR (CDCl$_3$) δ: 0.65-0.70 (2H, m), 0.85-0.92 (2H, m), 1.60-1.72 (4H, m), 2.85-2.94 (1H, m), 3.09 (2H, t, J=7.16), 4.11-4.23 (2H, m), 4.30 (1H, t, J=5.5), 4.45 (1H, t, J=5.5), 6.89 (1H, t, J=6.4), 7.38 (1H, d, J=2.8), 7.55 (2H, d, J=8.7), 8.04 (2H, d, J=8.7).

In the same manner as in Example 134, the compounds of Example 377 and Example 378 were synthesized.

Example 377

N-cyclopropyl-5-methyl-1-(2-(3-phenylpropoxy)-4-{[(2,2,2-trifluoroethyl)amino]carbonyl}phenyl)-1H-1,2,3-triazole-4-carboxamide

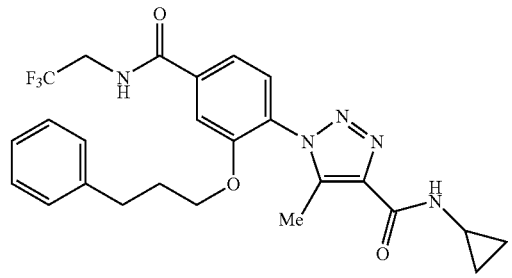

NMR (CDCl$_3$) δ: 0.65-0.70 (2H, m), 0.84-0.91 (2H, m), 1.93-2.03 (2H, m), 2.48 (3H, s), 2.56 (2H, t, J=7.2), 2.86-2.95 (1H, m), 4.04 (2H, t, J=6.3), 4.09-4.21 (2H, m), 6.67 (1H, t, J=6.3), 7.06 (2H, d, J=7.2), 7.15-7.28 (3H, m), 7.34 (1H, d, J=2.4), 7.43 (2H, s), 7.57 (1H, s).

Example 378

5-methyl-1-(2-(3-phenylpropoxy)-4-{[(2,2,2-trifluoroethyl)amino]carbonyl}phenyl)-1H-1,2,3-triazole-4-carboxamide

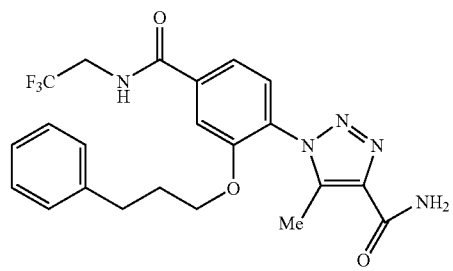

NMR (CDCl$_3$) δ: 1.95-2.04 (2H, m), 2.48 (3H, s), 2.57 (2H, t, J=7.8), 4.06 (2H, t, J=6.3), 4.10-4.21 (2H, m), 5.60 (1H, brs), 6.60 (1H, t, J=6.3), 7.05-7.09 (2H, m), 7.14-7.28 (4H, m), 7.41-7.45 (2H, m), 7.57 (1H, s).

Example 379

N-cyclopropyl-1-(2-iodo-4-{[(2,2,2-trifluoroethyl)amino]carbonyl}phenyl)-1H-1,2,3-triazole-4-carboxamide

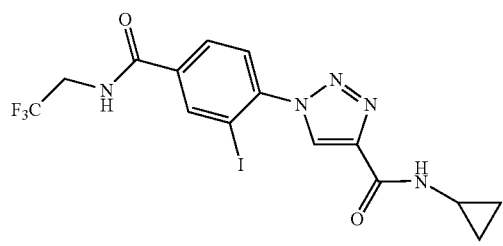

379a) 4-azido-3-iodobenzoic acid

To a solution of methyl 4-amino-3-iodobenzoate (10.0 g, 36.1 mmol) in THF (200 ml), 1M hydrochloric acid (75 ml)

and water (300 ml) was added sodium nitrite (2.5 g, 36.1 mmol) under ice-cooling, and the mixture was stirred for 30 min. Sodium azide (2.5 g, 36.1 mmol) was added to the reaction mixture, and the mixture was stirred at room temperature for 6 hr and extracted with ethyl acetate. The organic layer was washed with saturated brine and dried over magnesium sulfate, and the solvent was evaporated under reduced pressure. The residue was dissolved in methanol (370 ml), 8M aqueous sodium hydroxide solution (20 ml) and water (30 ml), and the reaction mixture was stirred at room temperature for 18 hr. Methanol was evaporated under reduced pressure, and the obtained residual aqueous solution was acidified (pH<3) with 6M hydrochloric acid and stood still at 0° C. The precipitate was collected by filtration, washed with water and dried to give the title compound as a pale-yellow powder (9.05 g, 95%).

NMR (DMSO-$d_6$) δ: 7.44 (1H, d, J=12.0), 8.00 (1H, d, J=12.0), 8.29 (1H, s).

379b) 4-azido-3-iodo-N-(2,2,2-trifluoroethyl)benzamide

To a solution of 4-azido-3-iodobenzoic acid (5.00 g, 17.3 mmol) obtained in Example 379a) in DMF (80 ml) were added sequentially 2,2,2-trifluoroethylamine (2.5 g), triethylamine (3.6 ml), HOBt (1.3 g) and WSC (5.0 g), and the reaction mixture was stirred at room temperature overnight. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure. The residue was purified by silica gel column (ethyl acetate/hexane=1/20 to 1/1) to give the title compound as a pale-yellow solid (2.93 g, 46%).

NMR (CDCl$_3$) δ: 4.06-4.17 (2H, m), 6.47 (1H, brs), 7.18 (1H, d, J=8.3), 7.83 (1H, dd, J=8.3, 1.9), 8.21 (1H, d, J=1.9).

379c) ethyl 1-(2-iodo-4-{[(2,2,2-trifluoroethyl)amino]carbonyl}phenyl)-1H-1,2,3-triazole-4-carboxylate To a solution of 4-azido-3-iodo-N-(2,2,2-trifluoroethyl)benzamide (2.93 g, 7.92 mmol) obtained in Example 379b) in toluene (80 ml) was added ethyl propiolate (2.33 g, 23.7 mmol), the reaction mixture was stirred with heating under reflux for 18 hr. After cooling to room temperature, the precipitate was collected by filtration, washed with hexane and dried to give the title compound as a pale-yellow powder (2.80 g, 76%).

NMR (CDCl$_3$) δ: 1.45 (3H, t, J=7.2), 4.13-4.24 (2H, m), 4.48 (2H, q, J=7.2), 7.03 (1H, t, J=6.0), 7.54 (1H, d, J=8.1), 7.99 (1H, d, J=8.1), 8.45 (1H, s), 8.47 (1H, s).

379d) 1-(2-iodo-4-{[(2,2,2-trifluoroethyl)amino]carbonyl}phenyl)-1H-1,2,3-triazole-4-carboxylic acid A solution of ethyl 1-(2-iodo-4-{[(2,2,2-trifluoroethyl)amino]carbonyl}phenyl)-1H-1,2,3-triazole-4-carboxylate (3.39 g, 7.24 mmol) obtained in Example 379c) in ethanol (100 ml), 8M aqueous sodium hydroxide solution (7 ml) and water (15 ml) was stirred at room temperature for 18 hr. Ethanol was evaporated under reduced pressure, and the obtained residual aqueous solution was acidified (pH<3) with 6M hydrochloric acid and stood still at 0° C. The precipitate was collected by filtration and washed with water and dried to give the title compound as a pale-yellow powder (2.59 g, 81%).

NMR (DMSO-$d_6$) δ: 4.06-4.21 (2H, m), 7.76 (1H, d, J=7.8), 8.09 (1H, dd, J=7.8, 1.8), 8.55 (1H, d, J=1.8), 9.17 (1H, s), 9.41 (1H, t, J=6.3).

379e) N-cyclopropyl-1-(2-iodo-4-{[(2,2,2-trifluoroethyl)amino]carbonyl}phenyl)-1H-1,2,3-triazole-4-carboxamide To a solution of 1-(2-iodo-4-{[(2,2,2-trifluoroethyl)amino]carbonyl}phenyl)-1H-1,2,3-triazole-4-carboxylic acid (2.08 g, 4.73 mmol) obtained in Example 379d) in DMF (20 ml) were sequentially added cyclopropylamine (500 mg), triethylamine (1.0 ml), HOBt (360 mg) and WSC (1.4 g), and the reaction mixture was stirred at room temperature overnight. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure. The residue was purified by silica gel column (ethyl acetate/hexane=1/20 to 1/1) to give the title compound as a colorless powder (1.66 g, 73%).

NMR (DMSO-$d_6$) δ: 0.67-0.72 (4H, m), 2.88-2.90 (1H, m), 4.02-4.21 (2H, m), 7.73 (1H, d, J=8.4), 8.08 (1H, dd, J=8.4, 1.9), 8.54 (1H, d, J=1.9), 8.77 (1H, d, J=8.4), 8.98 (1H, s), 9.41 (1H, t, J=6.8).

In the same manner as in Example 379, the compounds of Examples 380 to 382 were synthesized.

Example 380

1-(2-iodo-4-{[(2,2,2-trifluoroethyl)amino]carbonyl}phenyl)-1H-1,2,3-triazole-4-carboxamide

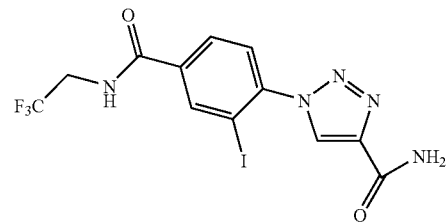

NMR (DMSO-$d_6$) δ: 4.09-4.18 (2H, m), 7.65 (1H, brs), 7.75 (1H, d, J=8.4), 8.07-8.12 (2H, m), 8.55 (1H, d, J=1.8), 8.97 (1H, s), 9.42 (1H, t, J=6.6).

Example 381

1-{4-[(ethylamino)carbonyl]-2-iodophenyl}-1H-1,2,3-triazole-4-carboxamide

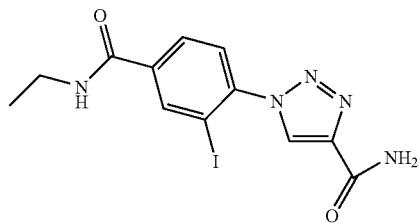

NMR (DMSO-$d_6$) δ: 1.15 (3H, t, J=7.1), 3.28-3.34 (2H, m), 7.63 (1H, brs), 7.70 (1H, d, J=8.4), 8.03 (1H, d, J=8.4), 8.49 (1H, brs), 8.75 (1H, t, J=5.1), 8.95 (1H, s).

Example 382

N-cyclopropyl-1-{4-[(ethylamino)carbonyl]-2-iodophenyl}-1H-1,2,3-triazole-4-carboxamide

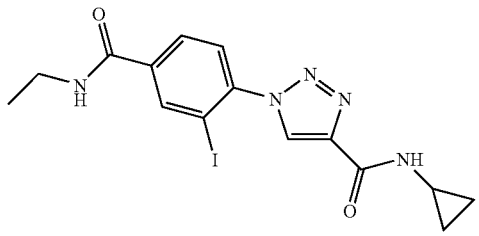

NMR (CDCl₃) δ: 0.69-0.74 (2H, m), 0.88-0.94 (2H, m), 1.29 (3H, t, J=7.2), 2.91-2.98 (1H, m), 3.53 (2H, qd, J=7.2, 1.8), 6.27 (1H, brs), 7.34 (1H, brs), 7.48 (1H, d, J=8.1), 7.90 (1H, dd, J=8.1, 1.8), 8.40 (1H, d, J=1.8), 8.41 (1H, s).

Example 383

N-cyclopropyl-1-{4-[(ethylamino)carbonyl]-2-(4-phenylbut-1-yn-1-yl)phenyl}-1H-1,2,3-triazole-4-carboxamide

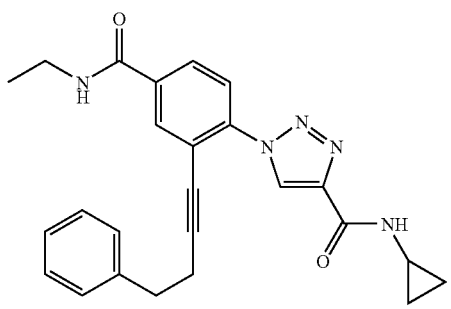

To a solution of N-cyclopropyl-1-{4-[(ethylamino)carbonyl]-2-iodophenyl}-1H-1,2,3-triazole-4-carboxamide (300 mg, 0.71 mmol) obtained in Example 382 in DMF (7.0 ml) were successively added potassium carbonate (200 mg), copper(I) iodide (15 mg), bis(triphenylphosphine)palladium(II) dichloride (25 mg) and but-3-yn-1-ylbenzene (110 mg), and the reaction mixture was stirred at room temperature overnight. Excess reagents and byproducts derived from the reagents were removed from the reaction mixture by adsorption onto silica gel column (ethyl acetate), and the eluate was evaporated under reduced pressure. The residue was purified by silica gel column (ethyl acetate/hexane=1/4 to ethyl acetate) to give the title compound as a colorless powder (163 mg, 54%).

NMR (DMSO-d₆) δ: 0.64-0.71 (4H, m), 1.14 (3H, t, J=7.2), 2.64-2.77 (4H, m), 2.85-2.94 (1H, m), 3.32 (2H, qd, J=7.2, 1.7), 7.15-7.28 (5H, m), 7.79 (1H, d, J=8.3), 7.99 (1H, dd, J=8.3, 1.9), 8.07 (1H, d, J=1.9), 8.71-8.76 (2H, m), 9.04 (1H, s).

In the same manner as in Example 383, the compounds of Examples 384 to 390 were synthesized.

Example 384

N-cyclopropyl-1-(2-(4-phenylbut-1-yn-1-yl)-4-{[(2,2,2-trifluoroethyl)amino]carbonyl}phenyl)-1H-1,2,3-triazole-4-carboxamide

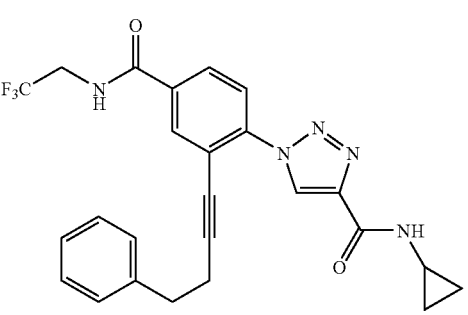

NMR (DMSO-d₆) δ: 0.64-0.71 (4H, m), 2.65-2.78 (4H, m), 2.85-2.94 (1H, m), 4.07-4.19 (2H, m), 7.15-7.28 (5H, m), 7.84 (1H, d, J=8.3), 8.04 (1H, dd, J=8.3, 2.1), 8.12 (1H, d, J=2.1), 8.75 (1H, d, J=4.5), 9.06 (1H, s), 9.37 (1H, t, J=6.0).

Example 385

N-cyclopropyl-1-(2-(4-hydroxybut-1-yn-1-yl)-4-{[(2,2,2-trifluoroethyl)amino]carbonyl}phenyl)-1H-1,2,3-triazole-4-carboxamide

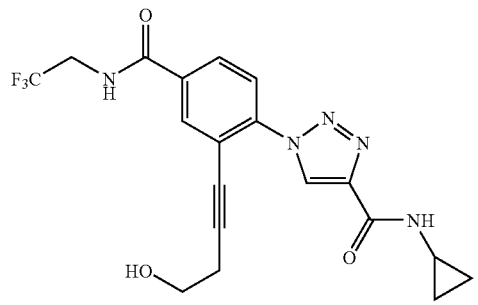

NMR (DMSO-d₆) δ: 0.64-0.72 (4H, m), 2.49-2.53 (2H, m), 2.86-2.93 (1H, m), 3.51 (2H, q, J=5.8), 4.08-4.20 (2H, m), 4.95 (1H, t, J=5.7), 7.87 (1H, d, J=8.3), 8.06 (1H, dd, J=8.3, 2.1), 8.19 (1H, d, J=2.1), 8.73 (1H, d, J=4.5), 9.12 (1H, s), 9.39 (1H, t, J=6.4).

Example 386

N-cyclopropyl-1-(2-(3-hydroxyprop-1-yn-1-yl)-4-{[(2,2,2-trifluoroethyl)amino]carbonyl}phenyl)-1H-1,2,3-triazole-4-carboxamide

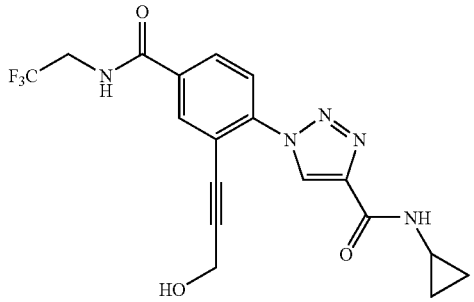

NMR (DMSO-d$_6$) δ: 0.63-0.74 (4H, m), 2.85-2.92 (1H, m), 4.09-4.20 (2H, m), 4.24 (2H, d, J=5.8), 5.40 (1H, t, J=5.8), 7.87 (1H, d, J=8.3), 8.09 (1H, dd, J=8.3, 1.5), 8.23 (1H, d, J=1.5), 8.73 (1H, d, J=4.7), 9.06 (1H, s), 9.42 (1H, t, J=6.2).

Example 387

N-cyclopropyl-1-(2-(5-hydroxypent-1-yn-1-yl)-4-{[(2,2,2-trifluoroethyl)amino]carbonyl}phenyl)-1H-1,2,3-triazole-4-carboxamide

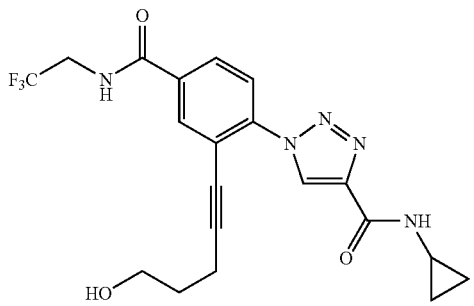

NMR (DMSO-d$_6$) δ: 0.66-0.71 (4H, m), 1.58 (2H, t, J=6.6), 2.41 (2H, t, J=6.6), 2.87-2.89 (1H, m), 3.33-3.42 (2H, m), 4.10-4.18 (2H, m), 4.49 (1H, t, J=5.1), 7.84 (1H, d, J=8.4), 8.05 (1H, dd, J=8.4, 1.5), 8.16 (1H, d, J=1.5), 8.72 (1H, d, J=4.2), 9.06 (1H, s), 9.38 (1H, t, J=6.3).

Example 388

N-cyclopropyl-1-(2-(pyridin-2-ylethynyl)-4-{[(2,2,2-trifluoroethyl)amino]carbonyl}phenyl)-1H-1,2,3-triazole-4-carboxamide

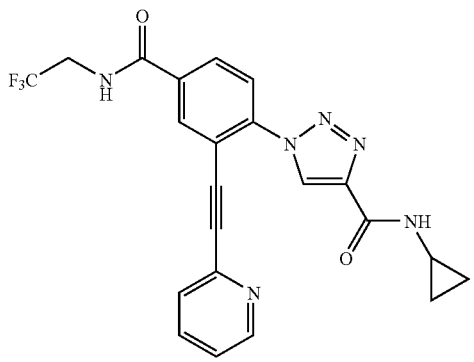

NMR (DMSO-d$_6$) δ: 0.67-0.74 (4H, m), 2.87-2.92 (1H, m), 4.11-4.21 (2H, m), 7.43-7.51 (2H, m), 7.87 (1H, t, J=7.8), 7.97 (1H, d, J=8.4), 8.18 (1H, d, J=9.3), 8.42 (1H, brs), 8.61 (1H, d, J=4.2), 8.77 (1H, d, J=4.5), 9.24 (1H, s), 9.46 (1H, t, J=6.3).

Example 389

N-cyclopropyl-1-{4-[(ethylamino)carbonyl]-2-(5-hydroxypent-1-yn-1-yl)phenyl}-1H-1,2,3-triazole-4-carboxamide

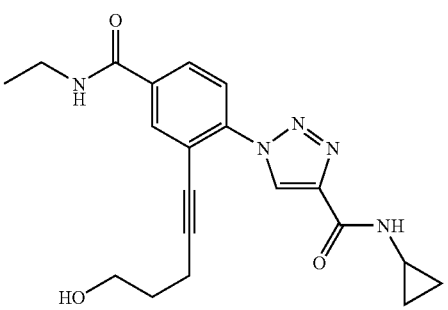

NMR (DMSO-d$_6$) δ: 0.62-0.75 (4H, m), 1.15 (3H, t, J=7.2), 1.53-1.62 (2H, m), 2.41 (2H, t, J=7.0), 2.86-2.94 (1H, m), 3.27-3.50 (4H, m), 4.54 (1H, t, J=5.1), 7.80 (1H, d, J=8.3), 8.00 (1H, dd, J=8.3, 1.9), 8.11 (1H, d, J=1.9), 8.72-8.77 (2H, m), 9.04 (1H, s).

Example 390

N-cyclopropyl-1-{4-[(ethylamino)carbonyl]-2-(pyridin-2-ylethynyl)phenyl}-1H-1,2,3-triazole-4-carboxamide

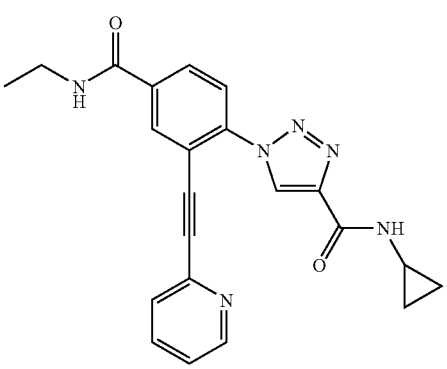

NMR (DMSO-d$_6$) δ: 0.66-0.71 (4H, m), 1.17 (3H, t, J=6.9), 2.88-2.90 (1H, m), 3.35-3.48 (2H, m), 7.42-7.49 (2H, m), 7.85 (1H, d, J=7.2), 7.92 (1H, d, J=8.7), 8.13 (1H, d, J=8.7), 8.35 (1H, brs), 8.59-8.62 (1H, m), 8.76-8.82 (2H, m), 9.22 (1H, s).

Example 391

N-cyclopropyl-1-(2-(4-phenylbutyl)-4-{[(2,2,2-trifluoroethyl)amino]carbonyl}phenyl)-1H-1,2,3-triazole-4-carboxamide

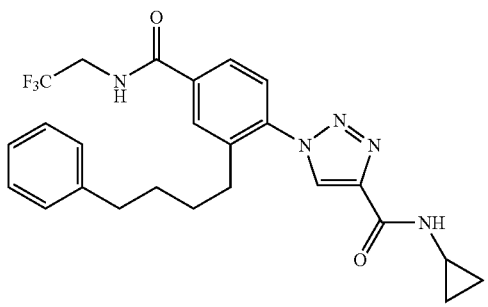

To a solution of N-cyclopropyl-1-(2-(4-phenylbut-1-yn-1-yl)-4-{[(2,2,2-trifluoroethyl)amino]carbonyl}phenyl)-1H-1,2,3-triazole-4-carboxamide (42.8 mg) obtained in Example 384 in acetic acid (7.0 ml)—ethanol (5.0 ml) was added palladium-carbon (20 mg). The reaction mixture was stirred under a hydrogen atmosphere at room temperature for 2 days, and the insoluble material was filtered off. The solvent was evaporated, and the residue was purified by silica gel column (hexane/ethyl acetate=4/1 to 2/3). The resultant product was recrystallized from ethyl acetate/hexane to give the title compound as a colorless powder (4.3 mg, 10%).

NMR (CDCl$_3$) δ: 0.68-0.72 (2H, m), 0.90-0.93 (2H, m), 1.51-1.59 (4H, m), 2.51-2.57 (4H, m), 2.94-2.97 (1H, m), 4.12-4.19 (2H, m), 6.41 (1H, t, J=6.3), 7.10 (1H, d, J=7.0), 7.18 (1H, d, J=7.0), 7.23-7.28 (4H, m), 7.38 (1H, d, J=8.1), 7.75 (1H, dd, J=8.4, 1.5), 7.83 (1H, d, J=1.5), 8.23 (1H, s).

In the same manner as in Example 391, the compounds of Examples 392 to 397 were synthesized.

Example 392

N-cyclopropyl-1-(2-(4-hydroxybutyl)-4-{[(2,2,2-trifluoroethyl)amino]carbonyl}phenyl)-1H-1,2,3-triazole-4-carboxamide

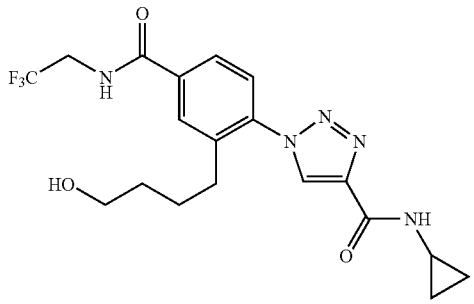

NMR (DMSO-d$_6$) δ: 0.64-0.72 (4H, m), 1.25-1.34 (2H, m), 1.40-1.50 (2H, m), 2.84-2.93 (1H, m), 3.26-3.42 (4H, m), 4.08-4.20 (2H, m), 4.36 (1H, t, J=5.1), 7.60 (1H, d, J=8.1), 7.91 (1H, dd, J=8.1, 2.1), 8.02 (1H, d, J=2.1), 8.73 (1H, d, J=4.5), 8.96 (1H, s), 9.31 (1H, t, J=6.2).

Example 393

N-cyclopropyl-1-(2-(3-hydroxypropyl)-4-{[(2,2,2-trifluoroethyl)amino]carbonyl}phenyl)-1H-1,2,3-triazole-4-carboxamide

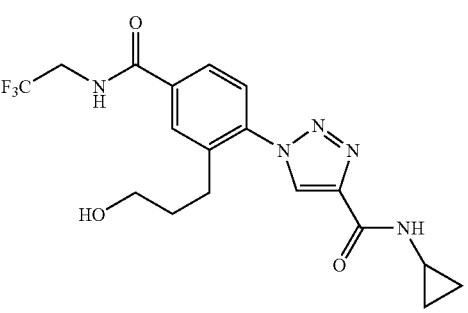

NMR (DMSO-d$_6$) δ: 0.64-0.73 (4H, m), 1.52-1.62 (2H, m), 2.84-2.93 (1H, m), 3.27-3.49 (4H, m), 4.08-4.20 (2H, m), 4.49 (1H, t, J=4.9), 7.60 (1H, d, J=8.3), 7.91 (1H, dd, J=8.3, 1.9), 8.02 (1H, d, J=1.9), 8.72 (1H, d, J=4.3), 8.96 (1H, s), 9.31 (1H, t, J=6.2).

Example 394

N-cyclopropyl-1-(2-(5-hydroxypentyl)-4-{[(2,2,2-trifluoroethyl)amino]carbonyl}phenyl)-1H-1,2,3-triazole-4-carboxamide

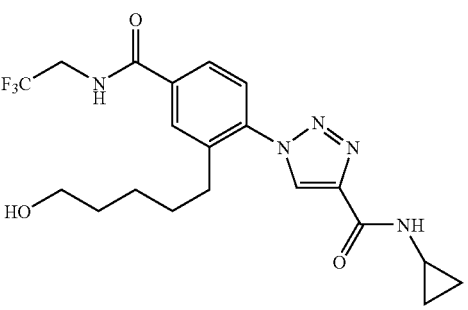

NMR (DMSO-d$_6$) δ: 0.64-0.72 (4H, m), 1.14-1.23 (2H, m), 1.27-1.46 (4H, m), 2.84-2.93 (1H, m), 3.28-3.36 (4H, m), 4.08-4.20 (2H, m), 4.32 (1H, t, J=5.3), 7.60 (1H, d, J=8.1), 7.91 (1H, dd, J=8.1, 1.7), 8.01 (1H, d, J=1.7), 8.73 (1H, d, J=4.5), 8.97 (1H, s), 9.29 (1H, t, J=6.2).

Example 395

N-cyclopropyl-1-{4-[(ethylamino)carbonyl]-2-(4-phenylbutyl)phenyl}-1H-1,2,3-triazole-4-carboxamide

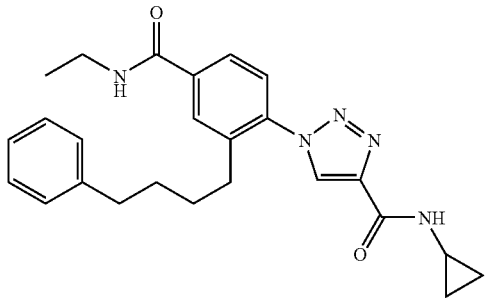

NMR (CDCl$_3$) δ: 0.68-0.74 (2H, m), 0.86-0.94 (2H, m), 1.29 (3H, t, J=7.2), 1.50-1.58 (4H, m), 2.52-2.58 (4H, m), 2.91-3.00 (1H, m), 3.53 (2H, qd, J=7.2, 1.5), 6.17 (1H, t, J=5.3), 7.09-7.35 (7H, m), 7.70 (1H, dd, J=8.3, 2.1), 7.81 (1H, d, J=2.1), 8.24 (1H, s).

Example 396

N-cyclopropyl-1-{4-[(ethylamino)carbonyl]-2-(5-hydroxypentyl)phenyl}-1H-1,2,3-triazole-4-carboxamide

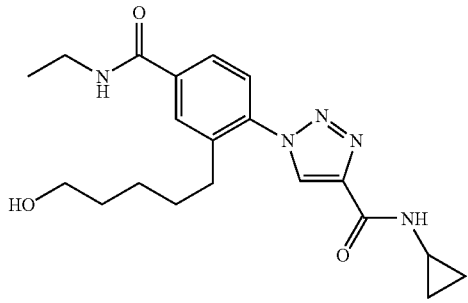

NMR (DMSO-d$_6$) δ: 0.63-0.74 (4H, m), 1.14-1.22 (2H, m), 1.15 (3H, t, J=7.2), 1.27-1.45 (4H, m), 2.46-2.51 (2H, m), 2.84-2.93 (1H, m), 3.29-3.36 (4H, m), 4.35 (1H, brs), 7.54 (1H, d, J=8.3), 7.86 (1H, dd, J=8.3, 1.7), 7.96 (1H, d, J=1.7), 8.70 (1H, t, J=5.5), 8.76 (1H, d, J=4.5), 8.97 (1H, s).

Example 397

N-cyclopropyl-1-{4-[(ethylamino)carbonyl]-2-[2-(pyridin-2-yl)ethyl]phenyl}-1H-1,2,3-triazole-4-carboxamide

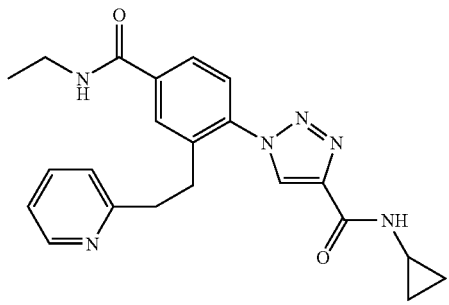

NMR (DMSO-d$_6$) δ: 0.66-0.72 (4H, m), 1.15 (3H, t, J=7.2), 2.84-2.95 (5H, m), 3.21-3.37 (2H, m), 7.11 (1H, d, J=7.7), 7.17 (1H, dd, J=7.2, 5.5), 7.56 (1H, d, J=8.3), 7.64 (1H, td, J=7.7, 1.7), 7.86 (1H, dd, J=8.5, 1.7), 8.01 (1H, d, J=1.7), 8.42 (1H, d, J=4.7), 8.65 (1H, t, J=5.8), 8.72 (1H, d, J=4.3), 8.90 (1H, s).

In the same manner as in Example 112, the compound of Example 398 was synthesized.

Example 398

5-(3-hydroxypropyl)-1-(4-{[(2,2,2-trifluoroethyl)amino]carbonyl}phenyl)-1H-1,2,3-triazole-4-carboxamide

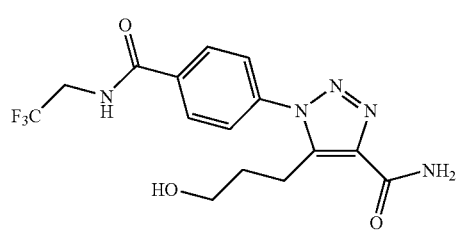

NMR (DMSO-d$_6$) δ: 1.52-1.58 (2H, m), 3.02 (2H, t, J=7.5), 3.23-3.29 (2H, m), 4.08-4.20 (2H, m), 4.45 (1H, t, J=5.1), 7.54 (1H, brs), 7.77 (2H, d, J=8.1), 7.97 (1H, brs), 8.12 (2H, d, J=8.1), 9.34 (1H, t, J=6.0).

Example 399

N-cyclopropyl-5-[(1E)-prop-1-en-1-yl]-1-(4-{[(2,2,2-trifluoroethyl)amino]carbonyl}phenyl)-1H-1,2,3-triazole-4-carboxamide

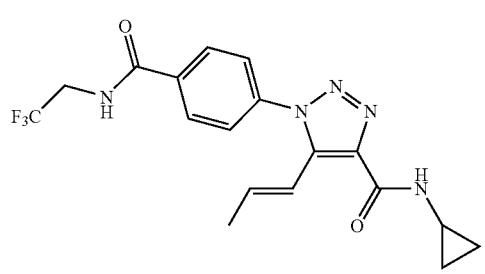

399a) 5-(3-bromopropyl)-N-cyclopropyl-1-(4-{[(2,2,2-trifluoroethyl)amino]carbonyl}phenyl)-1H-1,2,3-triazole-4-carboxamide To a solution of 5-(3-hydroxypropyl)-1-(4-{[(2,2,2-trifluoroethyl)amino]carbonyl}phenyl)-1H-1,2,3-triazole-4-carboxamide (381 mg, 0.93 mmol) obtained in Example 398 and triphenylphosphine (365 mg) in dichloromethane (12 ml) was added tetrabromomethane (460 mg), and the mixture was stirred at room temperature for 15 hr. The reaction mixture was concentrated under reduced pressure, and the obtained residue was purified by silica gel column (hexane/ethyl acetate=20/1 to 2/5) to give the title compound as a colorless solid (219 mg, 50%).

NMR (CDCl$_3$) δ: 0.64-0.72 (2H, m), 0.85-0.95 (2H, m), 2.14-2.28 (2H, m), 2.84-2.94 (1H, m), 3.17-3.25 (2H, m), 3.39 (2H, t, J=6.2), 4.08-4.25 (2H, m), 6.79 (1H, t, J=6.0), 7.35 (1H, brs), 7.56 (2H, d, J=8.4), 8.06 (2H, d, J=8.4).

399b) N-cyclopropyl-5-[(1E)-prop-1-en-1-yl]-1-(4-{[(2,2,2-trifluoroethyl)amino]carbonyl}phenyl)-1H-1,2,3-triazole-4-carboxamide 5-(3-Bromopropyl)-N-cyclopropyl-1-(4-{[(2,2,2-trifluoroethyl)amino]carbonyl}phenyl)-1H-1,2,3-triazole-4-carboxamide (212 mg, 0.45 mmol) obtained in Example 399a) was dissolved in acetonitrile (5.0 ml), tetrabutylammonium fluoride monohydrate (140 mg, 0.54 mmol) was added, and the mixture was stirred at 80° C. for 16 hr. The reaction mixture was allowed to cool to room temperature and the solvent was evaporated under reduced pressure. The residue was purified by silica gel column (ethyl acetate/hexane=1/9 to 7/3) and recrystallized from ethyl acetate-hexane to give the title compound as a colorless powder (27.7 mg, 16%).

NMR (CDCl₃) δ: 0.65-0.71 (2H, m), 0.85-0.92 (2H, m), 1.26-2.28 (1H, m), 1.85 (3H, dd, J=6.6, 1.8), 2.86-2.93 (1H, m), 4.18 (2H, qd, J=9.0, 2.4), 6.49 (1H, dq, J=16.2, 1.5), 6.63 (1H, t, J=6.6), 6.80 (1H, dq, J=16.2, 6.6), 7.43 (1H, brs), 7.58 (2H, d, J=8.7), 8.00 (2H, d, J=8.7).

Example 400

N-cyclopropyl-1-[4-[(ethylamino)carbonyl]-2-(5-fluoropentyl)phenyl]-1H-1,2,3-triazole-4-carboxamide

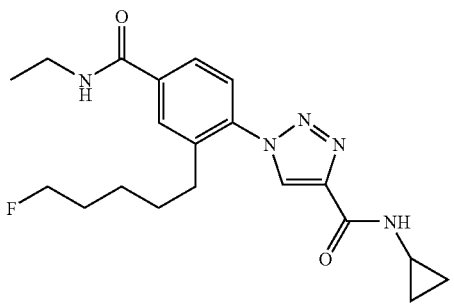

To a suspension of N-cyclopropyl-1-(2-(5-hydroxypentyl)-4-{[(2,2,2-trifluoroethyl)amino]carbonyl}phenyl)-1H-1,2,3-triazole-4-carboxamide (50.0 mg, 0.13 mmol) obtained in Example 394 in acetonitrile (3.0 ml) was added 2,2-difluoro-1,3-dimethylimidazolidine (20 µl, 0.16 mmol) and the mixture was stirred at 60° C. for 1 hr. The solvent was evaporated under reduced pressure, and the residue was purified by silica gel column (ethyl acetate/hexane=1/4 to ethyl acetate) and recrystallized from ethyl acetate-hexane to give the title compound as a colorless powder (26.8 mg, 53%).

NMR (CDCl₃) δ: 0.67-0.75 (2H, m), 0.87-0.96 (2H, m), 1.29 (3H, t, J=7.2), 1.26-1.42 (2H, m), 1.48-1.73 (4H, m), 2.56 (2H, t, J=8.2), 2.90-3.00 (1H, m), 3.54 (2H, qd, J=7.2, 1.6), 4.28 (1H, t, J=5.8), 4.51 (1H, t, J=5.8), 6.17 (1H, brs), 7.29-7.37 (2H, m), 7.71 (1H, dd, J=8.0, 1.8), 7.85 (1H, d, J=1.8), 8.26 (1H, s).

Example 401

N-cyclopropyl-1-{4-[(ethylamino)carbonyl]phenyl}-5-{(E)-2-[4-(methylsulfonyl)phenyl]vinyl}-1H-1,2,3-triazole-4-carboxamide

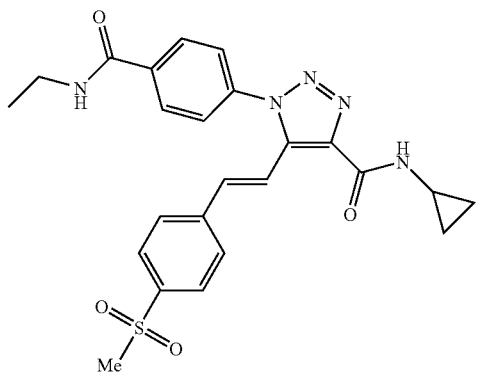

In the same manner as in Example 338, the title compound was obtained as a colorless powder (48.5 mg, 15%) from N-cyclopropyl-5-(diethylphosphonomethyl)-1-{4-[(ethylamino)carbonyl]phenyl}-1H-1,2,3-triazole-4-carboxamide (300 mg, 0.67 mmol) obtained in Example 321b).

NMR (DMSO-d₆) δ: 0.67-0.74 (4H, m), 1.15 (3H, t, J=7.2), 2.88-2.97 (1H, m), 3.21 (3H, s), 3.33 (2H, qd, J=7.2, 1.5), 7.35 (1H, d, J=16.6), 7.56 (1H, d, J=16.6), 7.70 (1H, d, J=8.5), 7.76 (1H, d, J=8.5), 7.91 (1H, d, J=8.5), 8.11 (1H, d, J=8.5), 8.80 (1H, t, J=5.5), 8.87 (1H, d, J=4.7).

Example 402

N-cyclopropyl-1-{4-[(ethylamino)carbonyl]phenyl}-5-{2-[4-(methylsulfonyl)phenyl]ethyl}-1H-1,2,3-triazole-4-carboxamide

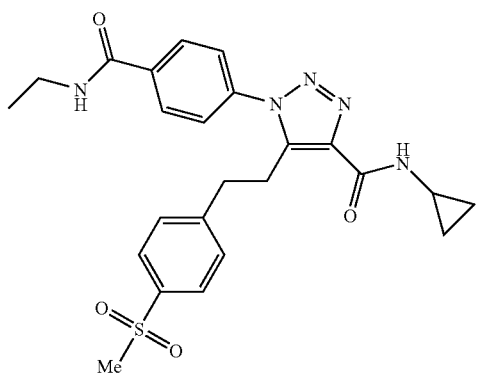

To a solution of N-cyclopropyl-1-{4-[(ethylamino)carbonyl]phenyl}-5-{(E)-2-[4-(methylsulfonyl)phenyl]vinyl}-1H-1,2,3-triazole-4-carboxamide (230 mg, 0.48 mmol) obtained in Example 401 in acetic acid (12 ml) and ethanol (4.0 ml) was added palladium-carbon (25 mg). The reaction mixture was stirred under a hydrogen atmosphere at room temperature for 5 days, and the insoluble material was filtered off. The solvent was evaporated, and the residue was purified by silica gel column (ethyl acetate/methanol=20/1 to 10/1).

The resultant product was recrystallized from ethyl acetate/hexane to give the title compound as a colorless powder (150 mg, 65%).

NMR (DMSO-d$_6$) δ: 0.67-0.72 (4H, m), 1.16 (3H, t, J=7.2), 2.88-2.95 (3H, m), 3.18 (3H, s), 3.27-3.38 (4H, m), 7.22 (2H, d, J=8.3), 7.52 (2H, d, J=8.7), 7.74 (2H, d, J=8.3), 8.02 (2H, d, J=8.7), 8.66-8.71 (2H, m).

Example 403

N-cyclopropyl-1-(2-[(6-fluorohexyl)oxy]-4-{[(2-methoxyethyl)amino]carbonyl}phenyl)-1H-1,2,3-triazole-4-carboxamide

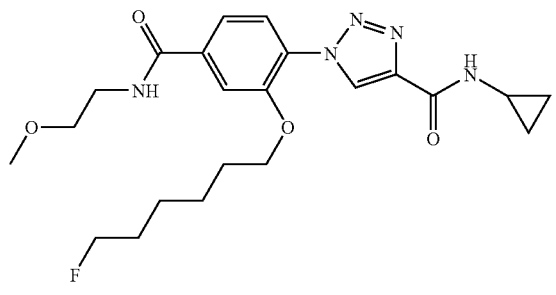

403a) 4-{4-[(cyclopropylamino)carbonyl]-1H-1,2,3-triazol-1-yl}-3-[(6-fluorohexyl)oxy]benzoic acid In the same manner as in Example 133, the title compound was obtained as a white powder (0.13 g, 44%).

NMR (CDCl$_3$) δ: 0.70-0.75 (2H, m), 0.88-0.94 (2H, m), 1.44-1.51 (4H, m), 1.63-1.88 (4H, m), 2.95-3.01 (1H, m), 4.19 (2H, t, J=6.6), 4.44 (2H, td, J=6.0, 47.3), 7.44 (1H, d, J=3.4), 7.83 (1H, d, J=1.5), 7.88 (1H, dd, J=1.5, 8.3), 7.98 (1H, d, J=8.3), 8.79 (1H, s).

403b) N-cyclopropyl-1-(2-[(6-fluorohexyl)oxy]-4-{[(2-methoxyethyl)amino]carbonyl}phenyl)-1H-1,2,3-triazole-4-carboxamide In the same manner as in Example 143, the title compound was obtained as a brown powder (0.03 g, 42%) from 4-{4-[(cyclopropylamino)carbonyl]-1H-1,2,3-triazol-1-yl}-3-[(6-fluorohexyl)oxy]benzoic acid (0.07 g) obtained in Example 403a).

NMR (CDCl$_3$) δ: 0.67-0.72 (2H, m), 0.86-0.93 (2H, m), 1.40-1.47 (4H, m), 1.61-1.86 (7H, m), 2.91-2.99 (1H, m), 3.58-3.61 (2H, m), 3.64-3.71 (2H, m), 4.17 (2H, t, J=6.6), 4.43 (2H, td, J=6.0, 47.5), 6.70 (1H, t, J=5.3), 7.31 (1H, d, J=2.6), 7.41 (1H, dd, J=1.7, 8.3), 7.66 (1H, d, J=1.5), 7.88 (1H, d, J=8.1), 8.69 (1H, s).

Example 404

N-cyclopropyl-5-[(3-fluorophenoxy)methyl]-1-{4-[(3,3,3-trifluoropropanoyl)amino]phenyl}-1H-1,2,3-triazole-4-carboxamide

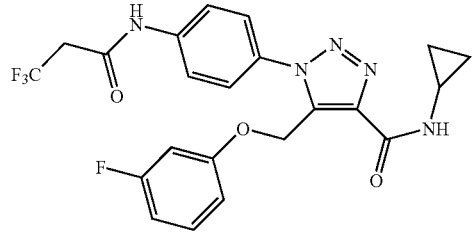

In the same manner as in Example 19, the title compound was synthesized.

NMR (CDCl$_3$) δ: 0.62-0.74 (2H, m), 0.81-0.98 (2H, m), 2.83-2.99 (1H, m), 3.29 (2H, q, J=10.2), 5.47 (2H, s), 6.55-6.75 (3H, m), 7.12-7.26 (1H, m), 7.41 (1H, brs), 7.47-7.62 (2H, m), 7.64-7.78 (3H, m).

In the same manner as in Example 404, the compounds of Example 405 to Example 408 were synthesized.

Example 405

N-cyclopropyl-1-{2-(3-phenylpropoxy)-4-[(3,3,3-trifluoropropanoyl)amino]phenyl}-1H-1,2,3-triazole-4-carboxamide

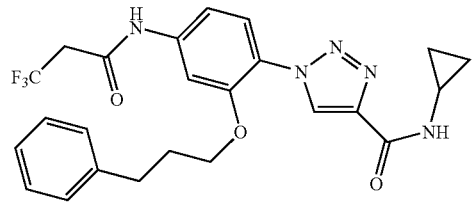

NMR (CDCl$_3$) δ: 0.61-0.74 (2H, m), 0.81-0.97 (2H, m), 1.96-2.12 (2H, m), 2.58-2.69 (2H, m), 2.84-3.00 (1H, m), 3.31 (2H, q, J=10.2), 4.04 (2H, t, J=6.4), 6.97 (1H, dd, J=8.7, 2.1), 7.06-7.29 (5H, m), 7.34 (1H, d, J=3.0), 7.54-7.68 (1H, m), 7.71 (1H, d, J=1.9), 8.24 (1H, s), 8.54 (1H, s).

Example 406

N-(2-hydroxyethyl)-5-propyl-1-{4-[(3,3,3-trifluoropropanoyl)amino]phenyl}-1H-1,2,3-triazole-4-carboxamide

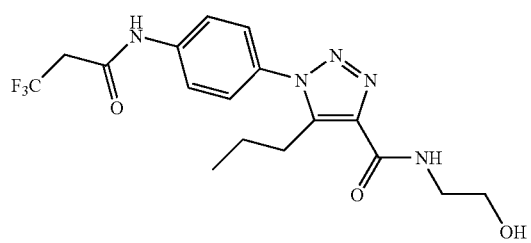

NMR (DMSO-d$_6$) δ: 0.72 (3H, t, J=7.3), 1.31-1.57 (2H, m), 2.83-3.01 (2H, m), 3.31-3.42 (2H, m), 3.44-3.75 (4H, m), 4.76 (1H, t, J=5.5), 7.56 (2H, d, J=8.7), 7.82 (2H, d, J=8.7), 8.23-8.53 (1H, m), 10.66 (1H, s).

Example 407

N-(3-hydroxypropyl)-5-propyl-1-{4-[(3,3,3-trifluoropropanoyl)amino]phenyl}-1H-1,2,3-triazole-4-carboxamide

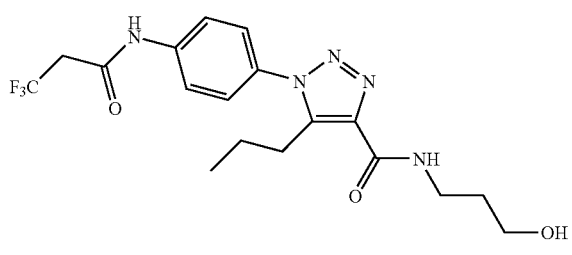

NMR (DMSO-$d_6$) δ: 0.72 (3H, t, J=7.3), 1.34-1.48 (2H, m), 1.61-1.73 (2H, m), 2.91 (2H, d, J=8.1), 3.28-3.39 (3H, m), 3.42-3.52 (2H, m), 3.59 (2H, q, J=11.1), 4.52 (1H, t, J=4.9), 7.56 (2H, d, J=8.7), 7.82 (2H, d, J=8.7), 8.56 (1H, t, J=5.8).

Example 408

5-propyl-1-{4-[(3,3,3-trifluoropropanoyl)amino]phenyl}-1H-1,2,3-triazole-4-carboxamide

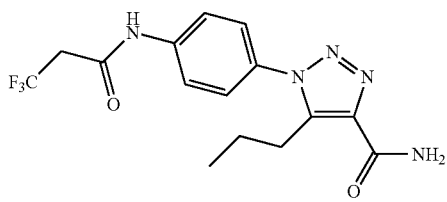

NMR (DMSO-$d_6$) δ: 0.72 (3H, t, J=7.3), 1.32-1.51 (2H, m), 2.85-3.01 (2H, m), 3.59 (2H, q, J=11.1), 7.48 (1H, brs), 7.57 (2H, d, J=8.9), 7.82 (2H, d, J=8.7), 7.91 (1H, brs), 10.66 (1H, s).

Example 409

1-{4-[(ethylamino)carbonyl]phenyl}-N-(2-fluoroethyl)-5-propyl-1H-1,2,3-triazole-4-carboxamide

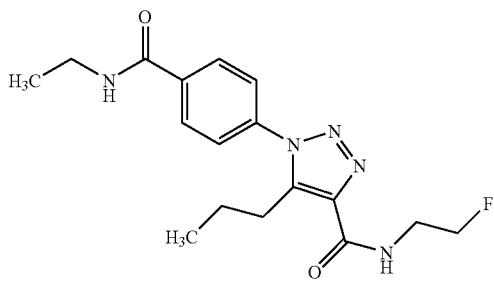

In the same manner as in Example 43, the title compound was obtained.

NMR (CDCl$_3$) δ: 0.86 (3H, t, J=7.2), 1.29 (3H, t, J=7.2), 1.50-1.63 (2H, m), 2.99-3.05 (2H, m), 3.51-3.60 (2H, m), 3.73 (1H, m), 3.84 (1H, m), 4.54 (1H, t, J=5.4), 4.69 (1H, t, J=5.4), 6.21 (1H, brs), 7.52 (2H, t, J=8.6), 7.60 (1H, brs), 7.97 (2H, d, J=8.6).

Example 410

N-(2-ethoxyethyl)-1-{4-[(ethylamino)carbonyl]phenyl}-5-propyl-1H-1,2,3-triazole-4-carboxamide

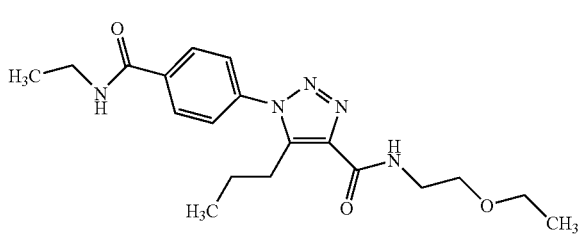

In the same manner as in Example 43, the title compound was obtained.

NMR (CDCl$_3$) δ: 0.86 (3H, t, J=7.2), 1.24 (3H, t, J=7.2), 1.30 (3H, t, J=7.2), 1.50-1.60 (2H, m), 3.01-3.51 (2H, m), 3.52-3.70 (8H, m), 6.19 (1H, brs), 7.51 (2H, t, J=8.4), 7.60 (1H, brs), 7.98 (2H, d, J=8.4).

Example 411

N-(cyclopropylmethyl)-1-{4-[(ethylamino)carbonyl]phenyl}-5-propyl-1H-1,2,3-triazole-4-carboxamide

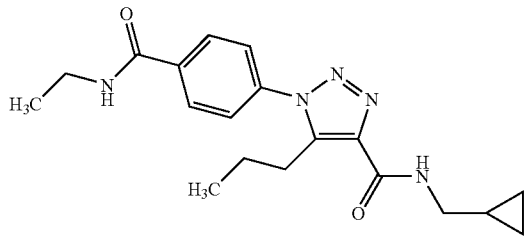

In the same manner as in Example 43, the title compound was obtained.

NMR (CDCl$_3$) δ: 0.27-0.32 (2H, m), 0.55-0.61 (2H, m), 0.86 (3H, t, J=7.2), 1.12 (1H, m), 1.30 (3H, t, J=7.4), 1.52-1.60 (2H, m), 3.00-3.05 (2H, m), 3.31-3.36 (2H, m), 3.49-3.60 (2H, m), 6.19 (1H, brs), 7.38 (1H, brs), 7.52 (2H, t, J=8.4), 7.97 (2H, d, J=8.4).

Example 412

(4-[(cyclopropylamino)carbonyl]-1-{4-[(ethylamino)carbonyl]phenyl}-1H-1,2,3-triazol-5-yl)methyl (4-fluorophenyl)carbamate

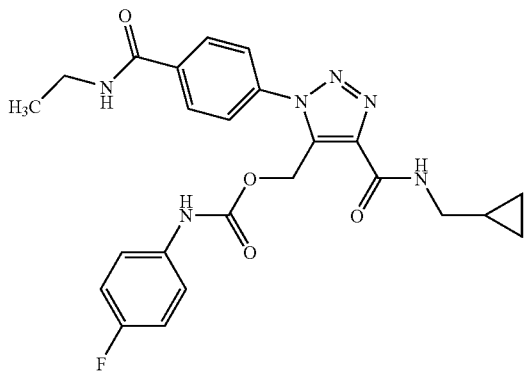

To a solution of N-cyclopropyl-1-{4-[(ethylamino)carbonyl]phenyl}-5-(hydroxymethyl)-1H-1,2,3-triazole-4-carboxamide (200 mg) obtained in Example 112 in pyridine (5 ml) was added 1-fluoro-4-isocyanatobenzene (125 mg) and the mixture was heated at 60° C. for 18 hr. The solvent was evaporated under reduced pressure and the obtained residue was recrystallized from ethyl acetate/hexane to give the title compound as a colorless powder (101 mg).

NMR (CD$_3$OD) δ: 0.69-0.73 (2H, m), 0.81-0.85 (2H, m), 1.23 (3H, t, J=7.2), 2.88 (1H, m), 3.48 (2H, q, J=7.2), 5.60 (2H, s), 6.97 (2H, t, J=9.0), 7.29 (1H, m), 7.71 (2H, d, J=8.6), 8.02 (2H, d, J=8.6).

Example 413

(4-[(cyclopropylamino)carbonyl]-1-{4-[(ethylamino)carbonyl]phenyl}-1H-1,2,3-triazol-5-yl)methyl propylcarbamate

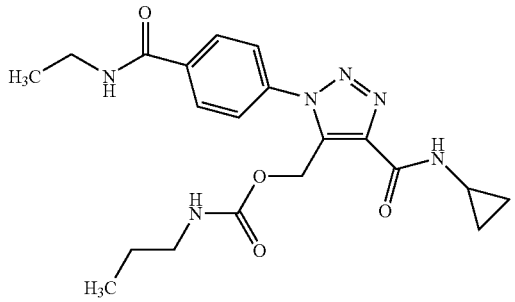

In the same manner as in Example 412, the title compound was obtained.

NMR (CDCl$_3$) δ: 0.66-0.71 (2H, m), 0.86-0.92 (5H, m), 1.29 (3H, t, J=7.2), 1.42-1.49 (2H, m), 2.92 (1H, m), 3.03-3.09 (2H, m), 3.49-3.58 (2H, m), 4.69 (1H, brs), 5.51 (2H, s), 6.24 (1H, brs), 7.36 (1H, brs), 7.58 (2H, d, J=8.5), 7.94 (2H, d, J=8.5).

Example 414

N-cyclopropyl-1-{4-[(ethylamino)carbonyl]phenyl}-5-[(3-fluorophenoxy)methyl]-1H-1,2,3-triazole-4-carboxamide

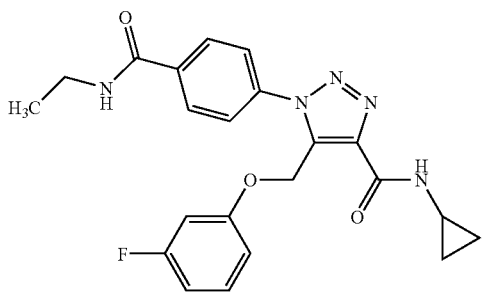

To a solution of N-cyclopropyl-1-{4-[(ethylamino)carbonyl]phenyl}-5-(hydroxymethyl)-1H-1,2,3-triazole-4-carboxamide (200 mg) obtained in Example 112 in THF (4 ml) were added 3-fluorophenol (68 mg), tributylphosphine (182 μM) and ADDP (184 mg), and the mixture was stirred at room temperature for 6 hr. Water was added to the reaction mixture, and the mixture was extracted with ethyl acetate and washed with saturated brine. The organic layer was dried over anhydrous sodium sulfate, and the solvent was evaporated under reduced pressure. The residue was purified by silica gel column (ethyl acetate/hexane=1/1 to 2/1) and recrystallized from ethyl acetate/hexane to give the title compound as a colorless powder (180 mg).

NMR (CDCl$_3$) δ: 0.67-0.73 (2H, m), 0.88-0.93 (2H, m), 1.28 (3H, t, J=7.2), 2.92 (1H, m), 3.48-3.57 (2H, m), 5.51 (2H, s), 6.17 (1H, brs), 6.59-6.72 (3H, m), 7.18 (1H, m), 7.39 (1H, brs), 7.69 (2H, d, J=8.6), 7.94 (2H, d, J=8.6).

Example 415

N-cyclopropyl-1-{4-[(ethylamino)carbonyl]phenyl}-5-[(2-fluorophenoxy)methyl]-1H-1,2,3-triazole-4-carboxamide

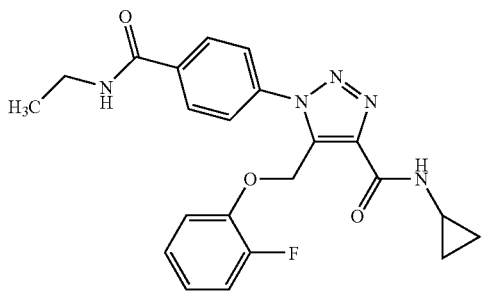

In the same manner as in Example 414, the title compound was obtained.

NMR (CDCl₃) δ: 0.66-0.70 (2H, m), 0.87-0.92 (2H, m), 1.29 (3H, t, J=7.5), 2.92 (1H, m), 3.49-3.58 (2H, m), 5.54 (2H, s), 6.92-7.08 (3H, m), 7.21 (1H, m), 7.40 (1H, brs), 7.76 (2H, d, J=8.6), 7.95 (2H, d, J=8.6).

Example 416

5-(4-fluorobutyl)-N-[2-(methylsulfonyl)ethyl]-1-(4-{[(2,2,2-trifluoroethyl)amino]carbonyl}phenyl)-1H-1,2,3-triazole-4-carboxamide

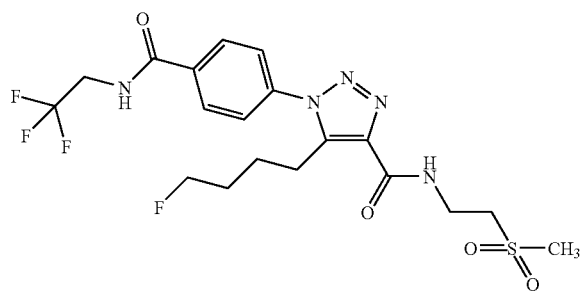

In the same manner as in Example 111, the title compound was obtained.

NMR (DMSO-d₆) δ: 1.41-1.59 (6H, m), 3.05 (3H, s), 3.40 (2H, t, J=7.2), 3.70-3.76 (2H, m), 4.08-4.19 (2H, m), 4.23 (1H, t, J=4.0), 4.39 (1H, d, J=4.8), 7.77 (2H, d, J=8.4), 8.12 (2H, d, J=8.4), 8.85 (1H, t, J=6.3), 9.35 (1H, brs).

Example 417

N-cyclopropyl-1-{4-[(ethylamino)carbonyl]phenyl}-5-(phenoxymethyl)-1H-1,2,3-triazole-4-carboxamide

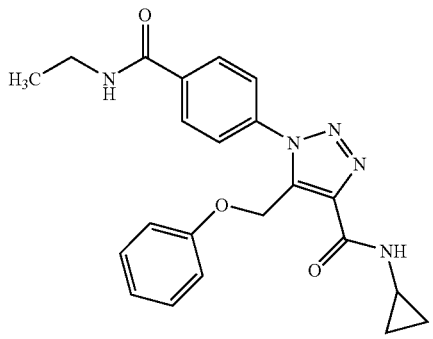

In the same manner as in Example 414, the title compound was obtained.

NMR (CDCl₃) δ: 0.67-0.72 (2H, m), 0.87-0.92 (2H, m), 1.29 (3H, t, J=7.6), 2.92 (1H, m), 3.48-3.57 (2H, m), 5.53 (2H, s), 6.17 (1H, brs), 6.87-7.02 (3H, m), 7.23-7.28 (2H, m), 7.40 (1H, brs), 7.72 (2H, d, J=8.4), 7.94 (2H, d, J=8.4).

Example 418

N-cyclopropyl-1-{4-[(ethylamino)carbonyl]phenyl}-5-[2-(6-methylpyridin-2-yl)vinyl]-1H-1,2,3-triazole-4-carboxamide

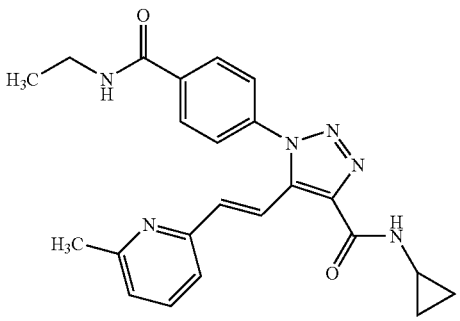

In the same manner as in Example 321, the title compound was obtained.

NMR (DMSO-d₆) δ: 0.68-0.73 (4H, m), 1.16 (3H, t, J=7.5), 2.49 (3H, s), 2.94 (1H, m), 3.25-3.34 (2H, m), 7.14-7.20 (2H, m), 7.44 (2H, d, J=16.5), 7.62-7.76 (2H, m), 7.75 (2H, d, J=7.4), 8.08 (2H, d, J=7.4), 8.75 (1H, t, J=5.6), 8.01 (1H, d, J=4.8).

Example 419

N-cyclopropyl-1-{4-[(ethylamino)carbonyl]phenyl}-5-[2-(3-fluorophenyl)vinyl]-1H-1,2,3-triazole-4-carboxamide

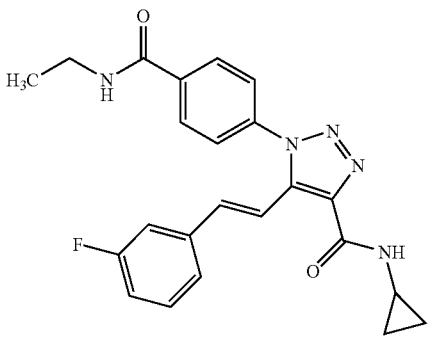

In the same manner as in Example 321, the title compound was obtained.

NMR (DMSO-d₆) δ: 0.69-0.72 (4H, m), 1.15 (3H, t, J=7.4), 2.91 (1H, m), 3.37 (2H, m), 7.18-7.53 (6H, m), 7.74 (2H, d, J=8.4), 8.08 (2H, d, J=8.4), 8.73 (1H, brt, J=5.6), 8.80 (1H, brd, J=4.4).

Example 420

N-cyclopropyl-1-{4-[(ethylamino)carbonyl]phenyl}-5-[2-(3-fluorophenyl)ethyl]-1H-1,2,3-triazole-4-carboxamide

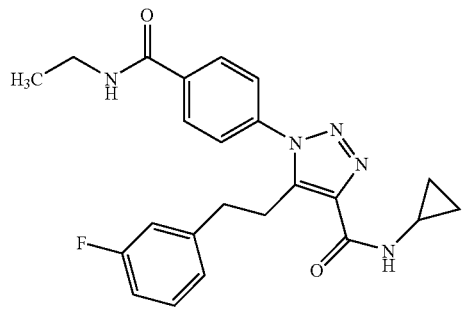

To a mixed solution of N-cyclopropyl-1-{4-[(ethylamino)carbonyl]phenyl}-5-[2-(3-fluorophenyl)vinyl]-1H-1,2,3-triazole-4-carboxamide (140 mg) obtained in Example 419 in ethanol/acetic acid (1/3, 8 ml) was added Pd/C (80 mg), and the mixture was stirred under a hydrogen stream for 15 hr. The catalyst was removed by filtration through celite, and the filtrate was evaporated under reduced pressure. The residue was purified by silica gel column (ethyl acetate) and recrystallized from ethyl acetate/hexane to give the title compound as a colorless powder (110 mg).

NMR (CDCl$_3$) δ: 0.68-0.73 (2H, m), 0.88-0.95 (2H, m), 1.28 (3H, t, J=7.6), 2.90-2.98 (3H, m), 3.31 (2H, t, J=7.2), 3.50-3.60 (2H, m), 6.16 (1H, brs), 6.62 (1H, m), 6.71 (1H, d, J=5.2), 6.84 (1H, m), 7.11 (1H, m), 7.27 (2H, d, J=8.6), 7.37 (1H, brs), 7.88 (2H, d, J=8.6).

Example 421

N-cyclopropyl-5-[(2,3-difluorophenoxy)methyl]-1-{4-[(ethylamino)carbonyl]phenyl}-1H-1,2,3-triazole-4-carboxamide

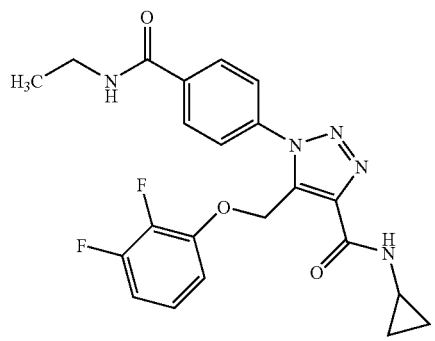

In the same manner as in Example 414, the title compound was obtained.

NMR (CDCl$_3$) δ: 0.65-0.73 (2H, m), 0.86-0.96 (2H, m), 1.29 (3H, t, J=7.4), 2.91 (1H, m), 3.47-3.61 (2H, m), 5.56 (2H, s), 6.17 (1H, brs), 6.81 (1H, m), 6.97-7.03 (2H, m), 7.40 (1H, brs), 7.77 (2H, d, J=8.6), 7.97 (2H, d, J=8.8).

Example 422

N-cyclopropyl-1-{4-[(ethylamino)carbonyl]phenyl}-5-{[3-(trifluoromethyl)phenoxy]methyl}-1H-1,2,3-triazole-4-carboxamide

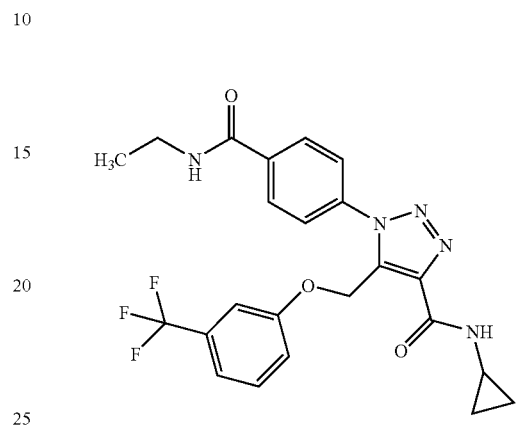

In the same manner as in Example 414, the title compound was obtained.

NMR (CDCl$_3$) δ: 0.67-0.70 (2H, m), 0.87-0.92 (2H, m), 1.30 (3H, t, J=7.2), 2.93 (1H, m), 3.53 (2H, m), 5.58 (2H, s), 6.13 (1H, brs), 7.09-7.11 (2H, m), 7.23 (1H, m), 7.38-7.41 (2H, m), 7.69 (2H, d, J=8.6), 7.95 (2H, d, J=8.8).

Example 423

N-cyclopropyl-1-{4-[(ethylamino)carbonyl]phenyl}-5-[3-(2-fluorophenoxy)propyl]-1H-1,2,3-triazole-4-carboxamide

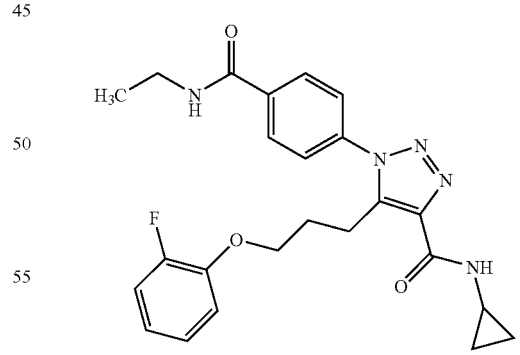

In the same manner as in Example 414, the title compound was obtained.

NMR (CDCl$_3$) δ: 0.62-0.69 (2H, m), 0.84-0.91 (2H, m), 1.31 (3H, t, J=7.4), 2.07-2.20 (2H, m), 2.89 (1H, m), 3.26 (2H, brt, J=7.8), 3.48-3.61 (2H, m), 3.86 (2H, t, J=7.4), 6.11 (1H, m), 6.77-7.06 (4H, m), 7.33 (1H, brs), 7.48 (2H, d, J=8.8), 7.88 (2H, d, J=8.8).

Example 424

N-cyclopropyl-1-{4-[(ethylamino)carbonyl]phenyl}-5-[3-(3-fluorophenoxy)propyl]-1H-1,2,3-triazole-4-carboxamide

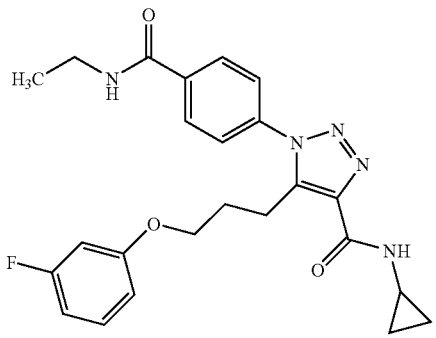

In the same manner as in Example 414, the title compound was obtained.

NMR (CDCl$_3$) δ: 0.62-0.70 (2H, m), 0.84-0.91 (2H, m), 1.30 (3H, t, J=7.4), 2.07-2.20 (2H, m), 2.89 (1H, m), 3.26 (2H, brt, J=7.8), 3.48-3.61 (2H, m), 3.86 (2H, t, J=7.4), 6.11 (1H, m), 6.33 (1H, m), 6.45 (1H, m), 6.66 (1H, m), 7.13 (1H, m), 7.33 (1H, brs), 7.48 (2H, d, J=8.8), 7.88 (2H, d, J=8.8).

Example 425

N-cyclopropyl-1-{4-[(ethylamino)carbonyl]phenyl}-5-[2-(6-methylpyridin-2-yl)ethyl]-1H-1,2,3-triazole-4-carboxamide

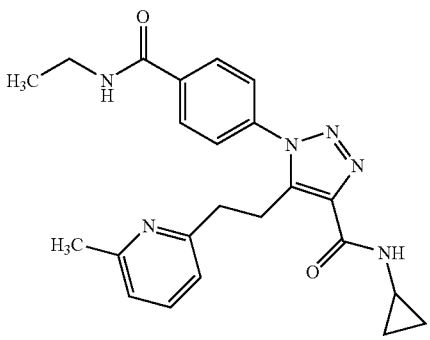

In the same manner as in Example 420, the title compound was obtained using N-cyclopropyl-1-{4-[(ethylamino)carbonyl]phenyl}-5-[2-(6-methylpyridin-2-yl)vinyl]-1H-1,2,3-triazole-4-carboxamide obtained in Example 418.

NMR (CDCl$_3$) δ: 0.61-0.69 (2H, m), 0.81-0.91 (2H, m), 1.24 (3H, t, J=7.0), 2.30 (3H, s), 2.88 (1H, m), 3.08 (2H, brt, J=7.2), 3.39-3.57 (4H, m), 6.12 (1H, m), 6.75 (1H, d, J=8.0), 6.85 (1H, d, J=8.0), 7.26-7.37 (4H, m), 7.82 (2H, d, J=8.8).

Example 426

1-{4-[(ethylamino)carbonyl]phenyl}-5-[(3-fluorophenoxy)methyl]-1H-1,2,3-triazole-4-carboxamide

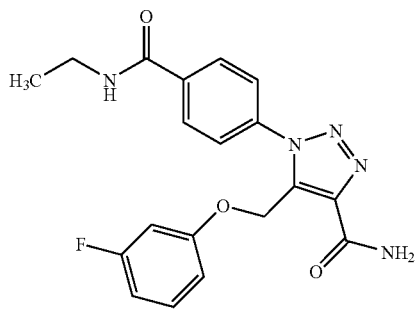

In the same manner as in Example 131g), the title compound was obtained.

NMR (DMSO-d$_6$) δ: 1.14 (3H, t, J=7.1), 3.24-3.38 (2H, m), 5.55 (2H, s), 6.70-6.83 (3H, m), 7.27 (1H, m), 7.75 (2H, d, J=8.8), 7.79 (1H, brs), 8.04 (2H, d, J=8.8), 8.23 (1H, brs), 8.66 (1H, brt, J=5.4).

Example 427

N-cyclopropyl-5-[(3-fluorophenoxy)methyl]-1-(4-{[(2,2,2-trifluoroethyl)amino]carbonyl}phenyl)-1H-1,2,3-triazole-4-carboxamide

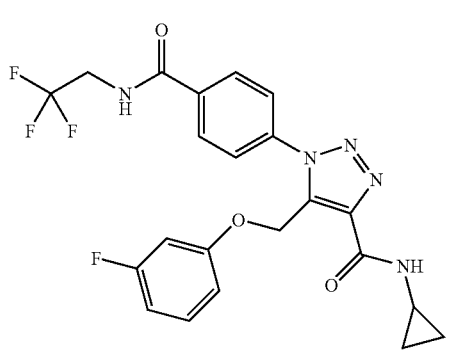

In the same manner as in Example 414, the title compound was obtained.

NMR (CDCl$_3$) δ: 0.67-0.73 (2H, m), 0.88-0.94 (2H, m), 2.93 (1H, m), 4.11-4.22 (2H, m), 5.53 (2H, s), 6.46 (1H, brs), 6.60-6.72 (3H, m), 7.23 (1H, m), 7.41 (1H, brs), 7.75 (2H, d, J=8.6), 7.97 (2H, d, J=8.8).

Example 428

5-[(3-fluorophenoxy)methyl]-1-(4-{[(2,2,2-trifluoro-ethyl)amino]carbonyl}phenyl)-1H-1,2,3-triazole-4-carboxamide

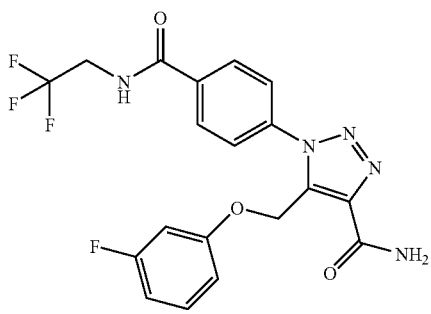

In the same manner as in Example 131g), the title compound was obtained.

NMR (DMSO-d$_6$) δ: 4.01-4.15 (2H, m), 5.57 (2H, s), 6.70-6.84 (3H, m), 7.26 (1H, m), 7.79 (1H, brs), 7.80 (2H, d, J=8.4), 8.08 (2H, d, J=8.4), 8.24 (1H, brs), 9.31 (1H, brs).

Example 429

1-{4-[(ethylamino)carbonyl]phenyl}-N-(3-fluorobenzyl)-5-[(3-fluorophenoxy)methyl]-1H-1,2,3-triazole-4-carboxamide

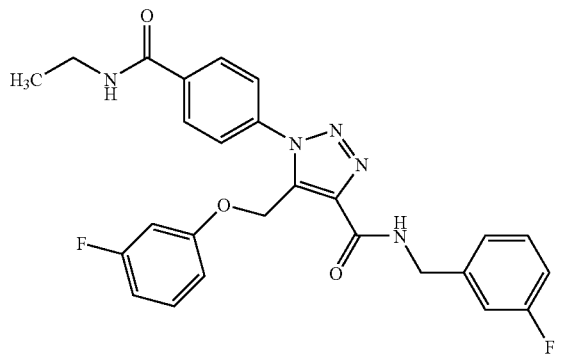

In the same manner as in Example 414, the title compound was obtained.

NMR (CDCl$_3$) δ: 1.28 (3H, t, J=7.2), 3.46-3.60 (2H, m), 4.67 (2H, d, J=5.8), 5.52 (2H, s), 6.17 (1H, brs), 6.17-6.75 (3H, m), 6.96-7.38 (5H, m), 7.72 (2H, d, J=8.8), 7.74 (1H, brt, J=5.0), 7.93 (2H, d, J=8.8).

Example 430

1-{4-[(ethylamino)carbonyl]phenyl}-5-[(2-fluorophenoxy)methyl]-1H-1,2,3-triazole-4-carboxamide

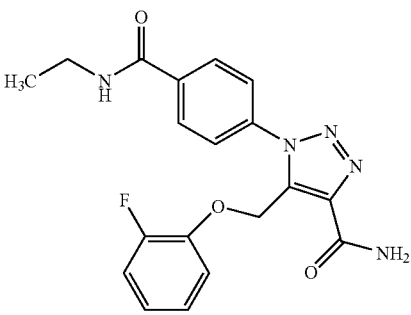

In the same manner as in Example 131g), the title compound was obtained.

NMR (CDCl$_3$) δ: 1.14 (3H, t, J=7.2), 3.24-3.38 (2H, m), 5.61 (2H, s), 6.95-7.25 (4H, m), 7.76-7.80 (3H, m), 8.04 (2H, d, J=8.6), 8.22 (1H, brs), 8.66 (1H, t, J=5.2).

Example 431

1-{4-[(ethylamino)carbonyl]phenyl}-5-[(2-fluorophenoxy)methyl]-N-(2-hydroxyethyl)-1H-1,2,3-triazole-4-carboxamide

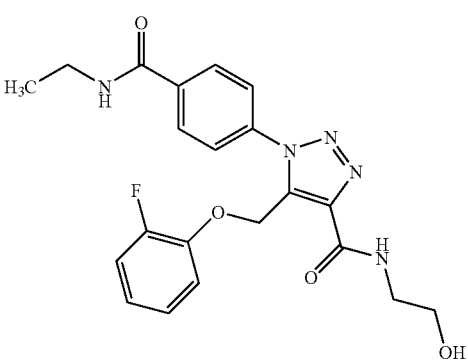

In the same manner as in Example 131g), the title compound was obtained.

NMR (CDCl$_3$) δ: 1.29 (3H, t, J=7.2), 2.66 (1H, t, J=5.6), 3.47-3.57 (2H, m), 3.62-3.70 (2H, m), 3.82-3.90 (2H, m), 5.52 (2H, s), 6.21 (1H, brs), 6.94-7.22 (4H, m), 7.74 (1H, brs), 7.78 (2H, d, J=8.8), 7.96 (2H, d, J=8.8).

Example 432

N-cyclopropyl-5-[(2-fluorophenoxy)methyl]-1-(4-{[(2,2,2-trifluoroethyl)amino]carbonyl}phenyl)-1H-1,2,3-triazole-4-carboxamide

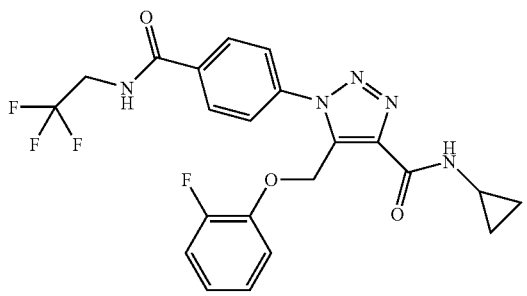

In the same manner as in Example 414, the title compound was obtained.

NMR (CDCl$_3$) δ: 0.66-0.71 (2H, m), 0.87-0.93 (2H, m), 2.91 (1H, m), 4.10-4.21 (2H, m), 5.55 (2H, s), 6.60 (1H, brt, J=6.3), 6.94-7.09 (2H, m), 7.21 (1H, m), 7.40 (1H, brs), 7.85 (2H, d, J=8.4), 8.00 (2H, d, J=8.8).

Example 433

5-[(2-fluorophenoxy)methyl]-1-(4-{[(2,2,2-trifluoroethyl)amino]carbonyl}phenyl)-1H-1,2,3-triazole-4-carboxamide

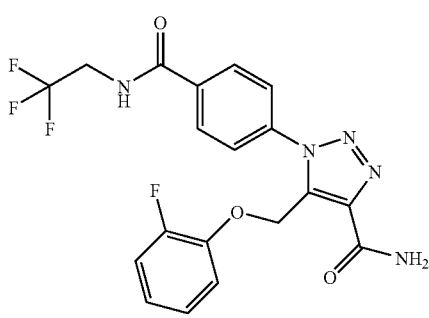

In the same manner as in Example 131g), the title compound was obtained.

NMR (CDCl$_3$) δ: 4.11-4.22 (2H, m), 5.56 (2H, s), 5.65 (1H, brs), 6.46 (1H, brt, J=5.7), 6.95-7.21 (5H, m), 7.88 (2H, d, J=8.8), 8.08 (2H, d, J=8.8).

Example 434

N-cyclopropyl-1-{4-[(ethylamino)carbonyl]phenyl}-5-{[3-(trifluoromethoxy)phenoxy]methyl}-1H-1,2,3-triazole-4-carboxamide

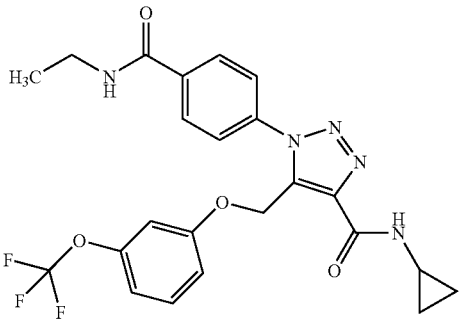

In the same manner as in Example 414, the title compound was obtained.

NMR (CDCl$_3$) δ: 0.67-0.73 (2H, m), 0.88-0.94 (2H, m), 1.28 (3H, t, J=7.0), 2.92 (1H, m), 3.49-3.58 (2H, m), 5.55 (2H, s), 6.13 (1H, brs), 6.74 (1H, brs), 6.84-6.88 (2H, m), 7.24-7.30 (2H, m), 7.41 (1H, brs), 7.67 (2H, d, J=8.8), 7.94 (2H, d, J=8.8).

Example 435

5-[(4-chloro-3-fluorophenoxy)methyl]-N-cyclopropyl-1-{4-[(ethylamino)carbonyl]phenyl}-1H-1,2,3-triazole-4-carboxamide

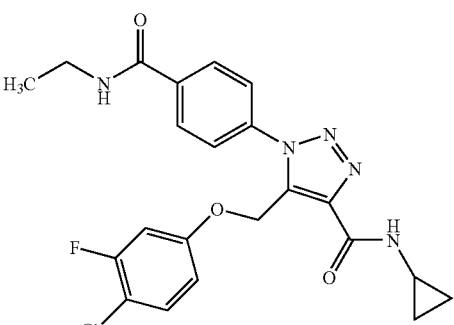

In the same manner as in Example 414, the title compound was obtained.

NMR (CDCl$_3$) δ: 0.67-0.73 (2H, m), 0.88-0.93 (2H, m), 1.28 (3H, t, J=7.0), 2.91 (1H, m), 3.49-3.58 (2H, m), 5.51 (2H, s), 6.14 (1H, brs), 6.66-6.77 (2H, m), 7.26 (1H, m), 7.40 (1H, brs), 7.68 (2H, d, J=8.6), 7.96 (2H, d, J=8.6).

Example 436

5-[(4-chloro-2-fluorophenoxy)methyl]-N-cyclopropyl-1-{4-[(ethylamino)carbonyl]phenyl}-1H-1,2,3-triazole-4-carboxamide

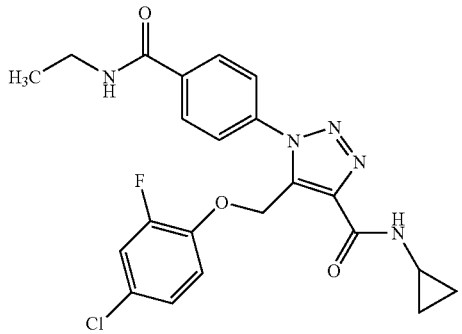

In the same manner as in Example 414, the title compound was obtained.

NMR (CDCl₃) δ: 0.66-0.72 (2H, m), 0.88-0.94 (2H, m), 1.29 (3H, t, J=7.2), 2.91 (1H, m), 3.50-3.59 (2H, m), 5.53 (2H, s), 6.14 (1H, brs), 7.03-7.10 (2H, m), 7.19 (1H, t, J=9.0), 7.39 (1H, brs), 7.79 (2H, d, J=8.8), 7.97 (2H, d, J=8.8).

Example 437

N-cyclopropyl-1-{4-[(ethylamino)carbonyl]phenyl}-5-({[1-methyl-3-(trifluoromethyl)-1H-pyrazol-5-yl]oxy}methyl)-1H-1,2,3-triazole-4-carboxamide

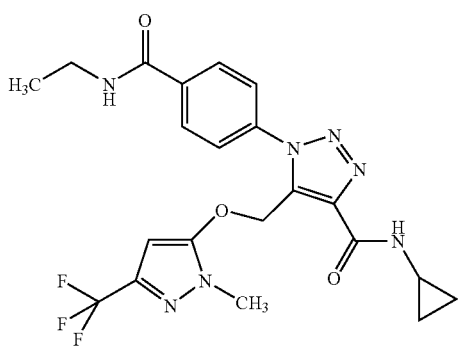

In the same manner as in Example 414, the title compound was obtained.

NMR (CDCl₃) δ: 0.67-0.73 (2H, m), 0.89-0.96 (2H, m), 1.27 (3H, t, J=7.2), 2.94 (1H, m), 3.48 (3H, s), 3.50-3.59 (2H, m), 5.6.4 (2H, s), 5.95 (1H, s), 6.14 (1H, brs), 7.40 (1H, brs), 7.66 (2H, d, J=8.4), 7.97 (2H, d, J=8.4).

Example 438

N-cyclopropyl-1-{4-[(ethylamino)carbonyl]phenyl}-5-{[2-fluoro-3-(trifluoromethyl)phenoxy]methyl}-1H-1,2,3-triazole-4-carboxamide

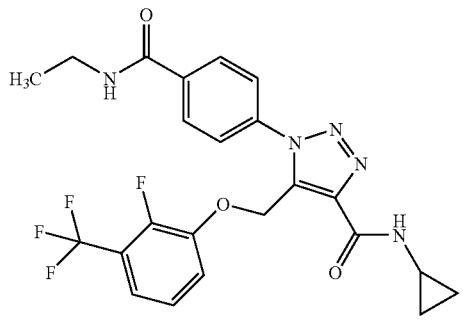

In the same manner as in Example 414, the title compound was obtained.

NMR (CDCl₃) δ: 0.67-0.72 (2H, m), 0.88-0.95 (2H, m), 1.29 (3H, t, J=7.2), 2.92 (1H, m), 3.50-3.59 (2H, m), 5.60 (2H, s), 6.14 (1H, brs), 7.15-7.25 (2H, m), 7.48 (1H, brs), 7.54 (1H, m), 7.78 (2H, d, J=8.8), 7.96 (2H, d, J=8.8).

Example 439

5-{[2-chloro-3-(trifluoromethyl)phenoxy]methyl}-N-cyclopropyl-1-{4-[(ethylamino)carbonyl]phenyl}-1H-1,2,3-triazole-4-carboxamide

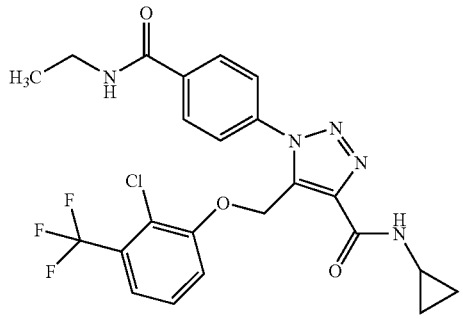

In the same manner as in Example 414, the title compound was obtained.

NMR (CDCl₃) δ: 0.68-0.73 (2H, m), 0.86-0.93 (2H, m), 1.29 (3H, t, J=7.0), 2.92 (1H, m), 3.50-3.57 (2H, m), 5.64 (2H, s), 6.12 (1H, brs), 7.31-7.38 (2H, m), 7.44 (1H, brs), 7.55 (1H, m), 7.82 (2H, d, J=8.8), 7.95 (2H, d, J=8.8).

Example 440

5-[(4-chlorophenoxy)methyl]-N-cyclopropyl-1-{4-[(ethylamino)carbonyl]phenyl}-1H-1,2,3-triazole-4-carboxamide

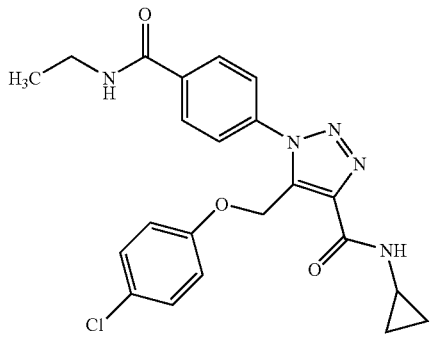

In the same manner as in Example 414, the title compound was obtained.

NMR (CDCl$_3$) δ: 0.67-0.72 (2H, m), 0.88-0.94 (2H, m), 1.29 (3H, t, J=7.2), 2.93 (1H, m), 3.49-3.58 (2H, m), 5.51 (2H, s), 6.13 (1H, brs), 6.83 (2H, d, J=8.4), 7.22 (2H, d, J=8.4), 7.40 (1H, brs), 7.71 (2H, d, J=8.8), 7.94 (2H, d, J=8.8).

Example 441

5-[(3-chlorophenoxy)methyl]-N-cyclopropyl-1-{4-[(ethylamino)carbonyl]phenyl}-1H-1,2,3-triazole-4-carboxamide

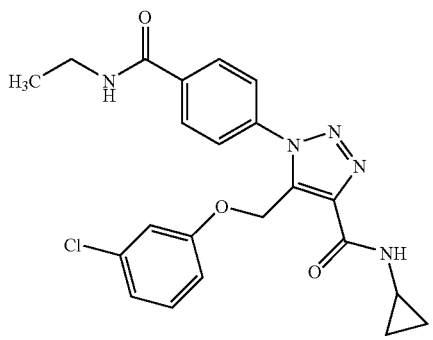

In the same manner as in Example 414, the title compound was obtained.

NMR (CDCl$_3$) δ: 0.67-0.73 (2H, m), 0.87-0.94 (2H, m), 1.28 (3H, t, J=7.2), 2.93 (1H, m), 3.49-3.58 (2H, m), 5.52 (2H, s), 6.13 (1H, brs), 6.81 (1H, m), 6.90 (1H, m), 6.96 (1H, m), 7.19 (1H, t, J=5.1), 7.40 (1H, brs), 7.70 (2H, d, J=8.8), 7.94 (2H, d, J=8.8).

Example 442

5-[(2-chlorophenoxy)methyl]-N-cyclopropyl-1-{4-[(ethylamino)carbonyl]phenyl}-1H-1,2,3-triazole-4-carboxamide

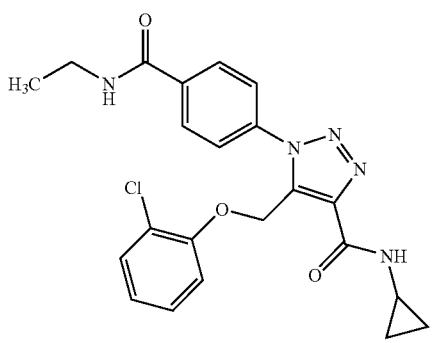

In the same manner as in Example 414, the title compound was obtained.

NMR (CDCl$_3$) δ: 0.69-0.72 (2H, m), 0.88-0.92 (2H, m), 1.29 (3H, t, J=7.0), 2.92 (1H, m), 3.49-3.58 (2H, m), 5.59 (2H, s), 6.15 (1H, brs), 6.94 (1H, m), 7.19-7.27 (2H, m), 7.32 (1H, dd, J=1.5, 7.2), 7.41 (1H, brs), 7.86 (2H, d, J=8.6), 7.94 (2H, d, J=8.6).

Example 443

5-[(2-chloro-5-fluorophenoxy)methyl]-N-cyclopropyl-1-{4-[(ethylamino)carbonyl]phenyl}-1H-1,2,3-triazole-4-carboxamide

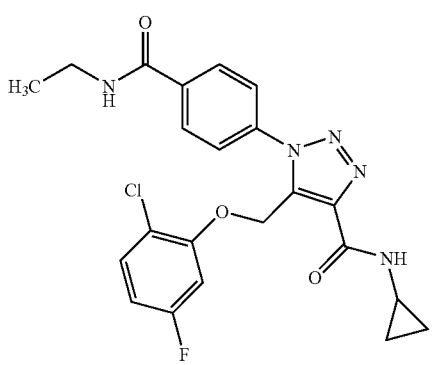

In the same manner as in Example 414, the title compound was obtained.

NMR (CDCl$_3$) δ: 0.70-0.71 (2H, m), 0.88-0.95 (2H, m), 1.29 (3H, t, J=7.0), 2.93 (1H, m), 3.49-3.58 (2H, m), 5.57 (2H, s), 6.13 (1H, brs), 6.67 (1H, m), 7.05 (1H, dd, J=2.7, 10.2), 7.26 (1H, m), 7.43 (1H, brs), 7.83 (2H, d, J=8.4), 7.95 (2H, d, J=8.4).

Example 444

N-cyclopropyl-5-[(2,6-difluorophenoxy)methyl]-1-{4-[(ethylamino)carbonyl]phenyl}-1H-1,2,3-triazole-4-carboxamide

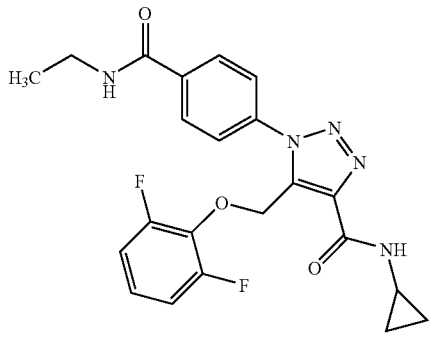

In the same manner as in Example 414, the title compound was obtained.

NMR (CDCl$_3$) δ: 0.57-0.62 (2H, m), 0.81-0.87 (2H, m), 1.28 (3H, t, J=7.4), 2.81 (1H, m), 3.51-3.60 (2H, m), 5.58 (2H, s), 6.17 (1H, brs), 6.84-6.91 (2H, m), 7.02 (1H, m), 7.26 (1H, brs), 7.89 (2H, d, J=8.6), 7.99 (2H, d, J=8.6).

Example 445

N-cyclopropyl-5-[(2,6-dichlorophenoxy)methyl]-1-{4-[(ethylamino)carbonyl]phenyl}-1H-1,2,3-triazole-4-carboxamide

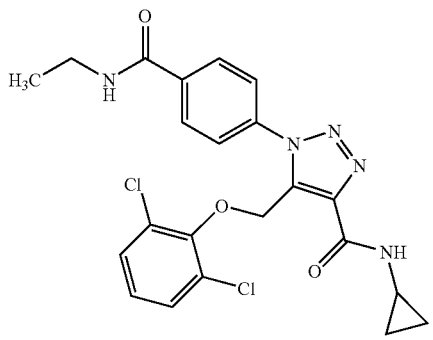

In the same manner as in Example 414, the title compound was obtained.

NMR (CDCl$_3$) δ: 0.52-0.57 (2H, m), 0.77-0.83 (2H, m), 1.30 (3H, t, J=7.2), 2.73 (1H, m), 3.51-3.60 (2H, m), 5.62 (2H, s), 6.22 (1H, brs), 7.01 (1H, t, J=7.5), 7.21 (1H, brs), 7.27 (2H, d, J=7.5), 7.94 (2H, d, J=8.7), 7.98 (2H, d, J=8.7).

Example 446

N-cyclopropyl-1-{4-[(ethylamino)carbonyl]phenyl}-5-[2-(2-fluorophenyl)vinyl]-1H-1,2,3-triazole-4-carboxamide

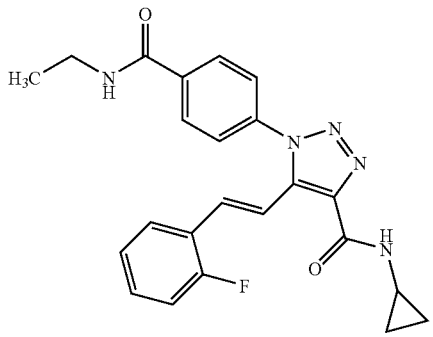

In the same manner as in Example 321, the title compound was obtained.

NMR (DMSO-d$_6$) δ: 0.69-0.72 (4H, m), 1.16 (3H, t, J=7.2), 2.92 (1H, m), 3.28-3.34 (2H, m), 7.19-7.21 (2H, m), 7.28 (1H, d, J=16.5), 7.40 (1H, m), 7.59 (1H, t, J=7.2), 7.70 (1H, d, J=16.5), 7.75 (2H, d, J=8.4), 8.10 (2H, d, J=8.4), 8.72 (1H, t, J=5.7), 8.83 (1H, d, J=4.5).

Example 447

5-(4-fluorobutyl)-N-(2-oxotetrahydrofuran-3-yl)-1-(4-{[(2,2,2-trifluoroethyl)amino]carbonyl}phenyl)-1H-1,2,3-triazole-4-carboxamide

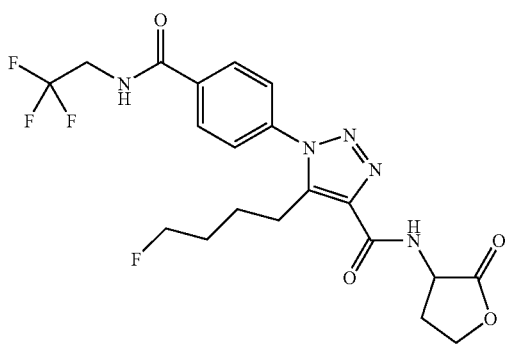

In the same manner as in Example 43, the title compound was obtained.

NMR (DMSO-d$_6$) δ: 1.46-1.52 (4H, m), 2.43-2.50 (2H, m), 3.02-3.05 (2H, m), 4.09-4.40 (6H, m), 4.85 (1H, m), 7.79 (2H, d, J=8.8), 8.13 (2H, d, J=8.8), 9.19 (1H, brd, J=7.8), 9.36 (1H, t, J=6.3).

Example 448

N-cyclopropyl-1-{4-[(ethylamino)carbonyl]phenyl}-5-[(3,4,5-trifluorophenoxy)methyl]-1H-1,2,3-triazole-4-carboxamide

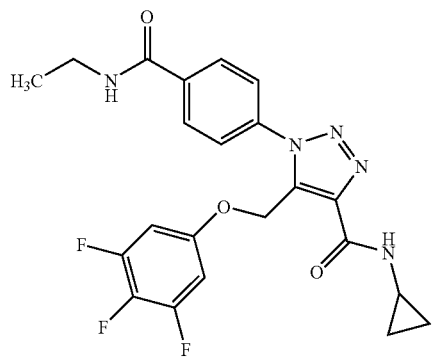

In the same manner as in Example 414, the title compound was obtained.

NMR (CDCl$_3$) δ: 0.68-0.73 (2H, m), 0.88-0.95 (2H, m), 1.27 (3H, t, J=7.4), 2.92 (1H, m), 3.50-3.59 (2H, m), 5.47 (2H, s), 6.14 (1H, brs), 6.56-6.63 (2H, m), 7.42 (1H, brs), 7.65 (2H, d, J=8.6), 7.96 (2H, d, J=8.6).

Example 449

1-{4-[(ethylamino)carbonyl]phenyl}-N-(2-oxotetrahydrofuran-3-yl)-5-propyl-1H-1,2,3-triazole-4-carboxamide

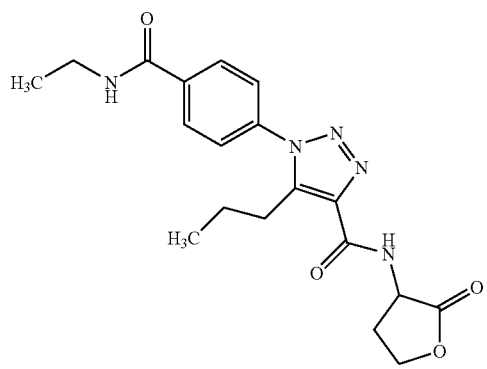

In the same manner as in Example 43, the title compound was obtained.

NMR (DMSO-d$_6$) δ: 0.73 (3H, t, J=7.5), 1.16 (3H, t, J=7.2), 1.37-1.45 (2H, m), 2.41-2.52 (2H, m), 2.98 (2H, t, J=7.2), 3.29-3.38 (2H, m), 4.27 (1H, m), 4.41 (1H, m), 4.82 (1H, dd, J=7.5, 18.2), 7.73 (2H, d, J=8.8), 8.08 (2H, d, J=8.8), 8.71 (1H, brt, J=5.4), 9.17 (1H, d, J=5.1).

Example 450

N-cyclopropyl-1-{4-[(ethylamino)carbonyl]phenyl}-5-[(2,3,6-trifluorophenoxy)methyl]-1H-1,2,3-triazole-4-carboxamide

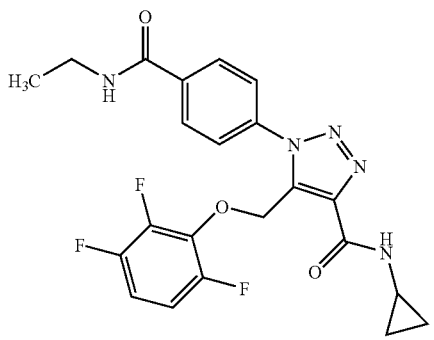

In the same manner as in Example 414, the title compound was obtained.

NMR (CDCl$_3$) δ: 0.58-0.64 (2H, m), 0.81-0.86 (2H, m), 1.29 (3H, t, J=7.6), 2.81 (1H, m), 3.50-3.59 (2H, m), 5.60 (2H, s), 6.27 (1H, brs), 6.79-6.90 (2H, m), 7.29 (1H, brs), 7.83 (2H, d, J=8.4), 8.00 (2H, d, J=8.4).

Example 451

N-cyclopropyl-1-{4-[(ethylamino)carbonyl]phenyl}-5-[2-(2-fluorophenyl)ethyl]-1H-1,2,3-triazole-4-carboxamide

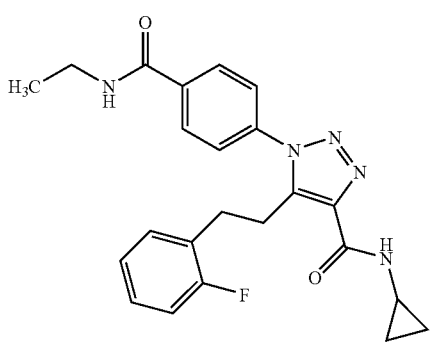

In the same manner as in Example 420, the title compound was obtained.

NMR (CDCl$_3$) δ: 0.67-0.72 (2H, m), 0.87-0.94 (2H, m), 1.30 (3H, t, J=7.4), 2.92 (1H, m), 3.03 (2H, t, J=7.8), 3.31 (2H, t, J=9.0), 3.51-3.60 (2H, m), 6.18 (1H, brs), 6.86 (1H, m), 6.94-7.07 (2H, m), 7.15 (1H, m), 7.25 (2H, d, J=8.4), 7.35 (1H, brs), 7.89 (2H, d, J=8.4).

Example 452

N-cyclopropyl-1-{4-[(ethylamino)carbonyl]phenyl}-5-[2-(4-fluorophenyl)vinyl]-1H-1,2,3-triazole-4-carboxamide

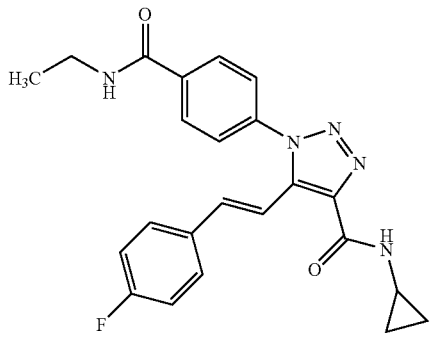

In the same manner as in Example 321, the title compound was obtained.

NMR (CDCl$_3$) δ: 0.68-0.73 (2H, m), 0.88-0.95 (2H, m), 1.33 (3H, t, J=7.4), 2.93 (1H, m), 3.51-3.58 (2H, m), 6.20 (1H, brs), 6.98 (2H, m), 7.05 (1H, d, J=16.5), 7.38 (2H, m), 7.50 (1H, brs), 7.59 (2H, d, J=8.8), 7.73 (1H, d, J=16.5), 7.98 (2H, d, J=8.8).

Example 453

N-cyclopropyl-1-{4-[(ethylamino)carbonyl]phenyl}-5-[2-(4-fluorophenyl)ethyl]-1H-1,2,3-triazole-4-carboxamide

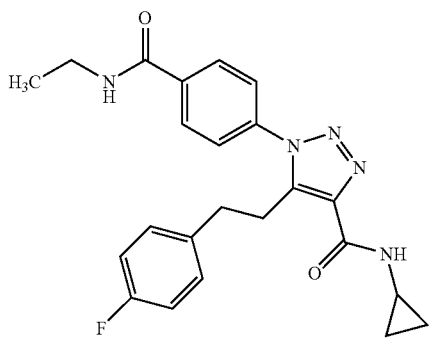

In the same manner as in Example 420, the title compound was obtained.

NMR (CDCl$_3$) δ: 0.67-0.73 (2H, m), 0.87-0.94 (2H, m), 1.29 (3H, t, J=7.4), 2.90-2.96 (3H, m), 3.28 (2H, t, J=7.8), 3.49-3.58 (2H, m), 6.44 (1H, brs), 6.75-6.90 (4H, m), 7.18 (2H, d, J=8.8), 7.37 (1H, brs), 7.88 (2H, d, J=8.8).

Example 454

N-cyclopropyl-1-{4-[(ethylamino)carbonyl]phenyl}-5-[(2,4,5-trifluorophenoxy)methyl]-1H-1,2,3-triazole-4-carboxamide

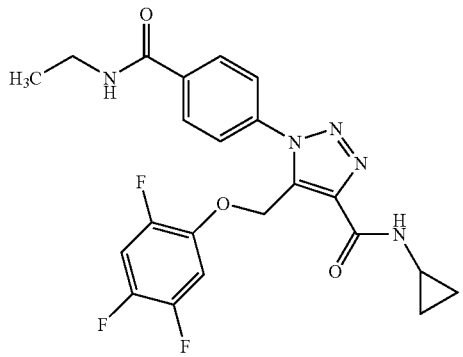

In the same manner as in Example 414, the title compound was obtained.

NMR (CDCl$_3$) δ: 0.66-0.72 (2H, m), 0.88-0.94 (2H, m), 1.29 (3H, t, J=7.2), 2.91 (1H, m), 3.49-3.58 (2H, m), 5.49 (2H, s), 6.21 (1H, brs), 6.93 (1H, m), 7.17 (1H, m), 7.40 (1H, brs), 7.78 (2H, d, J=8.8), 7.98 (2H, d, J=8.6).

Example 455

N-cyclopropyl-5-[(2,4-dichlorophenoxy)methyl]-1-{4-[(ethylamino)carbonyl]phenyl}-1H-1,2,3-triazole-4-carboxamide

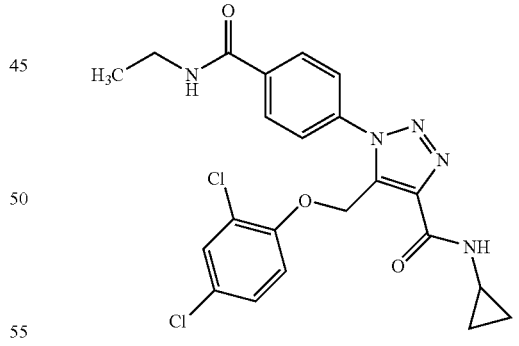

In the same manner as in Example 414, the title compound was obtained.

NMR (CDCl$_3$) δ: 0.67-0.72 (2H, m), 0.88-0.95 (2H, m), 1.29 (3H, t, J=7.2), 2.91 (1H, m), 3.49-3.58 (2H, m), 5.57 (2H, s), 6.17 (1H, brs), 7.19 (1H, dd, J=2.4, 8.7), 7.25 (1H, d, J=8.7), 7.33 (1H, d, J=2.4), 7.42 (1H, brs), 7.82 (2H, d, J=8.6), 7.96 (2H, d, J=8.6).

Example 456

N-cyclopropyl-5-[(3,4-dichlorophenoxy)methyl]-1-{4-[(ethylamino)carbonyl]phenyl}-1H-1,2,3-triazole-4-carboxamide

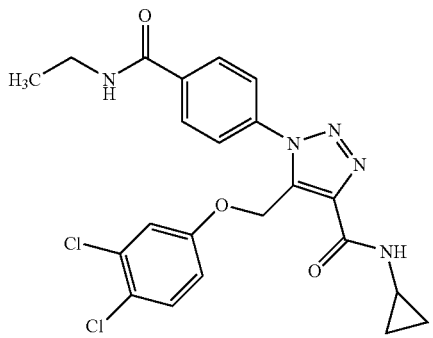

In the same manner as in Example 414, the title compound was obtained.

NMR (CDCl$_3$) δ: 0.68-0.72 (2H, m), 0.88-0.94 (2H, m), 1.28 (3H, t, J=7.4), 2.91 (1H, m), 3.49-3.58 (2H, m), 5.51 (2H, s), 6.19 (1H, brs), 6.79 (1H, dd, J=3.0, 8.7), 7.02 (1H, d, J=3.0), 7.31 (1H, d, J=8.7), 7.40 (1H, brs), 7.65 (2H, d, J=8.4), 7.96 (2H, d, J=8.4).

Example 457

5-[(2-chloro-4-fluorophenoxy)methyl]-N-cyclopropyl-1-{4-[(ethylamino)carbonyl]phenyl}-1H-1,2,3-triazole-4-carboxamide

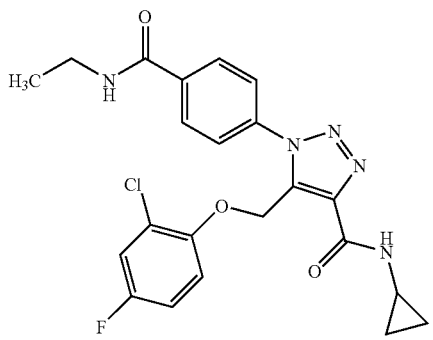

In the same manner as in Example 414, the title compound was obtained.

NMR (CDCl$_3$) δ: 0.67-0.72 (2H, m), 0.88-0.93 (2H, m), 1.29 (3H, t, J=7.4), 2.90 (1H, m), 3.49-3.58 (2H, m), 5.53 (2H, s), 6.19 (1H, brs), 6.92 (1H, m), 7.08 (1H, dd, J=3.0, 8.8), 7.26 (1H, m), 7.41 (1H, brs), 7.83 (2H, d, J=8.4), 7.95 (2H, d, J=8.4).

Example 458

5-[(3-chloro-4-fluorophenoxy)methyl]-N-cyclopropyl-1-{4-[(ethylamino)carbonyl]phenyl}-1H-1,2,3-triazole-4-carboxamide

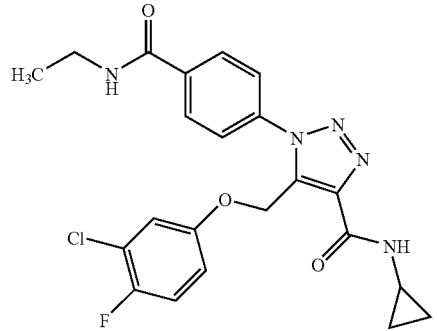

In the same manner as in Example 414, the title compound was obtained.

NMR (CDCl$_3$) δ: 0.67-0.73 (2H, m), 0.88-0.94 (2H, m), 1.29 (3H, t, J=7.6), 2.92 (1H, m), 3.49-3.58 (2H, m), 5.48 (2H, s), 6.13 (1H, brs), 6.79 (1H, m), 7.21 (1H, dd, J=3.0, 6.0), 7.02 (1H, t, J=6.0), 7.40 (1H, brs), 7.66 (2H, d, J=8.4), 7.94 (2H, d, J=8.4).

Example 459

N-cyclopropyl-5-[(3,4-difluorophenoxy)methyl]-1-{4-[(ethylamino)carbonyl]phenyl}-1H-1,2,3-triazole-4-carboxamide

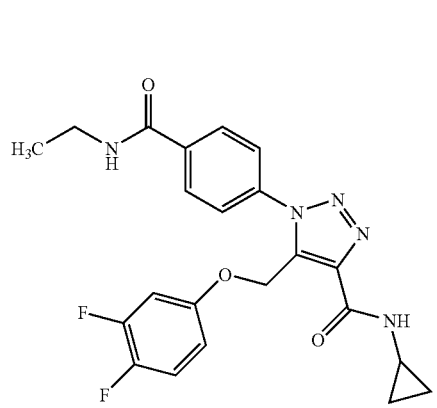

In the same manner as in Example 414, the title compound was obtained.

NMR (CDCl$_3$) δ: 0.67-0.72 (2H, m), 0.88-0.94 (2H, m), 1.28 (3H, t, J=7.6), 2.91 (1H, m), 3.49-3.58 (2H, m), 5.48 (2H, s), 6.17 (1H, brs), 6.63 (1H, m), 6.75 (1H, m), 7.03 (1H, dd, J=9.0, 18.3), 7.40 (1H, brs), 7.66 (2H, d, J=8.6), 7.94 (2H, d, J=8.6).

Example 460

N-cyclopropyl-5-[(2,4-difluorophenoxy)methyl]-1-{4-[(ethylamino)carbonyl]phenyl}-1H-1,2,3-triazole-4-carboxamide

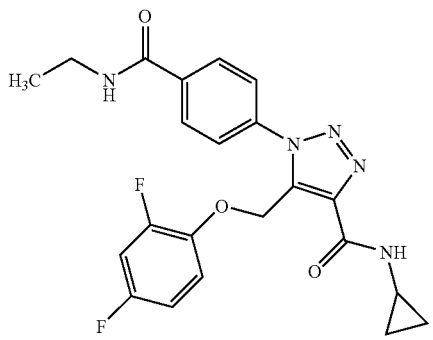

In the same manner as in Example 414, the title compound was obtained.

NMR (CDCl$_3$) δ: 0.66-0.71 (2H, m), 0.87-0.94 (2H, m), 1.29 (3H, t, J=7.6), 2.91 (1H, m), 3.50-3.59 (2H, m), 5.50 (2H, s), 6.18 (1H, brs), 6.76-6.87 (2H, m), 7.21 (1H, m), 7.39 (1H, brs), 7.82 (2H, d, J=8.4), 7.96 (2H, d, J=8.4).

Example 461

N-cyclopropyl-1-{4-[(ethylamino)carbonyl]phenyl}-5-[(3-methylphenoxy)methyl]-1H-1,2,3-triazole-4-carboxamide

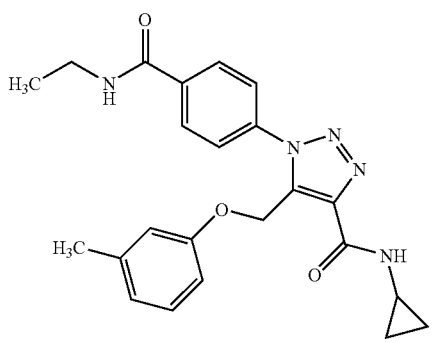

In the same manner as in Example 414, the title compound was obtained.

NMR (CDCl$_3$) δ: 0.66-0.72 (2H, m), 0.86-0.93 (2H, m), 1.27 (3H, t, J=7.4), 2.29 (3H, s), 2.92 (1H, m), 3.48-3.57 (2H, m), 5.49 (2H, s), 6.13 (1H, brs), 6.68-6.80 (3H, m), 7.13 (1H, t, J=4.5), 7.38 (1H, brs), 7.70 (2H, d, J=8.8), 7.90 (2H, d, J=8.8).

Example 462

N-(2-ethoxyethyl)-1-{4-[(ethylamino)carbonyl]phenyl}-5-[(3-fluorophenoxy)methyl]-1H-1,2,3-triazole-4-carboxamide

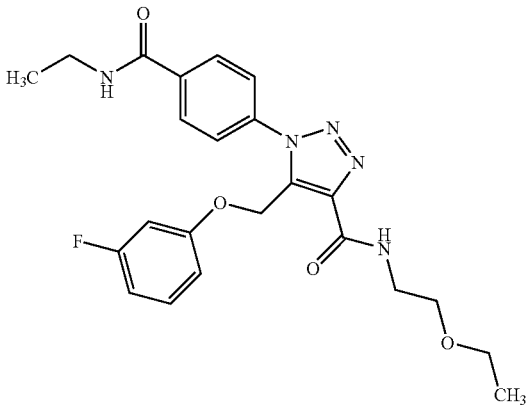

In the same manner as in Example 43, the title compound was obtained.

NMR (CDCl$_3$) δ: 1.22-1.30 (6H, m), 3.48-3.71 (8H, m), 5.50 (2H, s), 6.15 (1H, brs), 6.51-6.72 (3H, m), 7.19 (1H, m), 7.65 (1H, brs), 7.67 (2H, d, J=8.4), 7.93 (2H, d, J=8.8).

Example 463

1-{4-[(ethylamino)carbonyl]phenyl}-5-[(3-fluorophenoxy)methyl]-N-(2-oxotetrahydrofuran-3-yl)-1H-1,2,3-triazole-4-carboxamide

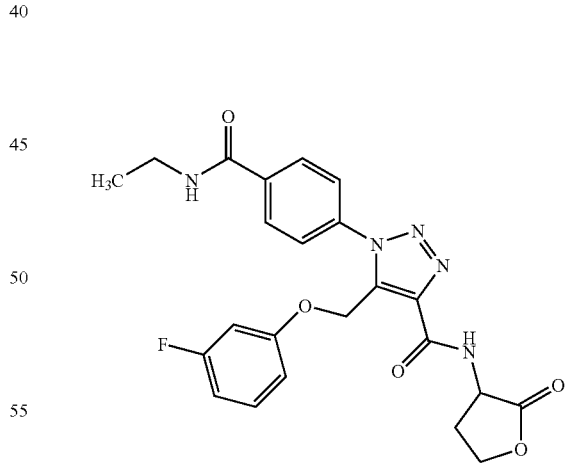

In the same manner as in Example 43, the title compound was obtained.

NMR (CDCl$_3$) δ: 1.28 (3H, t, J=7.6), 2.45 (1H, m), 2.86 (1H, m), 3.53 (2H, m), 4.34 (1H, m), 4.55 (1H, t, J=9.6), 4.78 (1H, m), 5.46 (2H, s), 6.14 (1H, brs), 6.60-6.73 (3H, m), 7.17 (1H, m), 7.65 (2H, d, J=8.8), 7.77 (1H, d, J=6.9), 7.93 (2H, d, J=8.8).

Example 464

1-{4-[(ethylamino)carbonyl]phenyl}-5-[(3-fluorophenoxy)methyl]-N-[3-(1H-1,2,4-triazol-1-yl)propyl]-1H-1,2,3-triazole-4-carboxamide

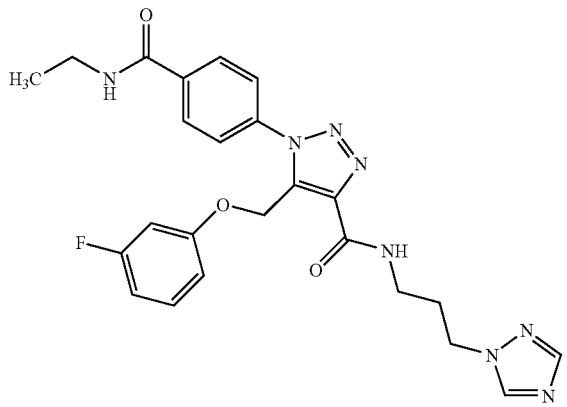

In the same manner as in Example 43, the title compound was obtained.

NMR (CDCl$_3$) δ: 1.28 (3H, t, J=7.6), 2.20-2.29 (2H, m), 3.49-3.58 (4H, m), 4.31 (2H, t, J=6.9), 5.50 (2H, s), 6.19 (1H, brs), 6.66-6.73 (3H, m), 7.18 (1H, m), 7.61 (1H, t, J=6.6), 7.68 (2H, d, J=8.8), 7.93 (2H, d, J=8.8), 7.97 (1H, s), 8.17 (1H, s).

Example 465

N-ethoxy-5-(4-fluorobutyl)-1-(4-{[(2,2,2-trifluoroethyl)amino]carbonyl}phenyl)-1H-1,2,3-triazole-4-carboxamide

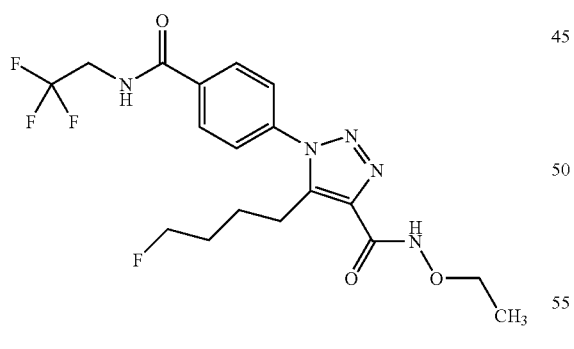

In the same manner as in Example 43, the title compound was obtained.

NMR (CDCl$_3$) δ: 1.37 (3H, t, J=7.2), 1.60-1.73 (4H, m), 3.10 (1H, t, J=8.1), 4.09-4.23 (4H, m), 4.28 (1H, t, J=5.4), 4.46 (1H, m), 6.51 (1H, t, J=6.0), 7.56 (2H, d, J=8.6), 8.03 (2H, d, J=8.6), 9.60 (1H, s).

Example 466

5-(4-fluorobutyl)-N-(2-oxotetrahydro-3-thienyl)-1-(4-{[(2,2,2-trifluoroethyl)amino]carbonyl}phenyl)-1H-1,2,3-triazole-4-carboxamide

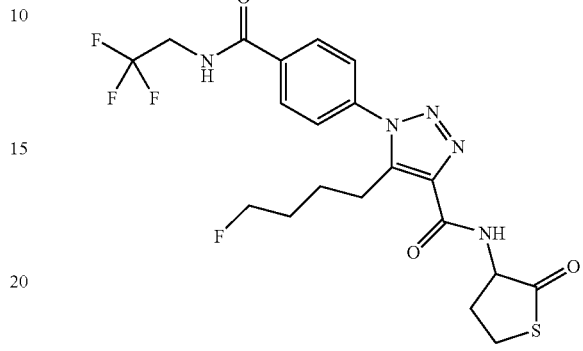

In the same manner as in Example 43, the title compound was obtained.

NMR (DMSO-d$_6$) δ: 1.46-1.54 (4H, m), 2.41-2.50 (2H, m), 3.01-3.05 (2H, m), 3.35-3.46 (2H, m), 4.10-4.20 (2H, m), 4.23 (1H, t, J=5.4), 4.39 (1H, t, J=6.0), 4.85 (1H, m), 7.77 (2H, d, J=8.6), 8.13 (2H, d, J=8.6), 9.01 (1H, d, J=9.0), 9.35 (1H, brs).

Example 467

5-(4-fluorobutyl)-N-[3-(1H-1,2,4-triazol-1-yl)propyl]1-(4-{[(2,2,2-trifluoroethyl)amino]carbonyl}phenyl)-1H-1,2,3-triazole-4-carboxamide

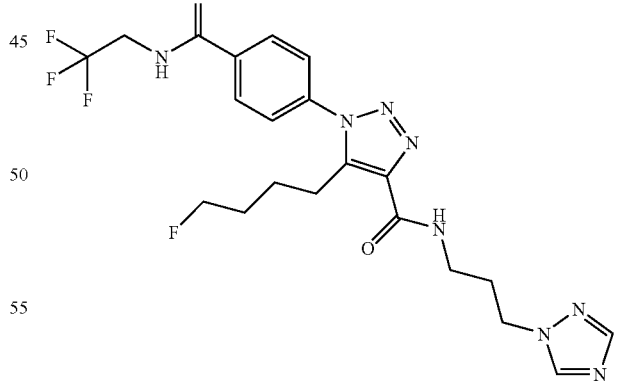

In the same manner as in Example 43, the title compound was obtained.

NMR (CDCl$_3$) δ: 1.62-1.71 (4H, m), 2.20-2.28 (2H, m), 3.11 (2H, t, J=7.2), 3.49-3.55 (2H, m), 4.15-4.24 (2H, m), 4.28-4.48 (4H, m), 6.60 (1H, t, J=6.6), 7.50 (1H, t, J=6.6), 7.55 (2H, d, J=8.6), 7.96 (1H, s), 8.02 (2H, d, J=8.6), 8.18 (1H, s).

Example 468

N-[(1,5-dimethyl-1H-pyrazol-3-yl)methyl]-1-{4-[(ethylamino)carbonyl]phenyl}-5-[(3-fluorophenoxy)methyl]-1H-1,2,3-triazole-4-carboxamide

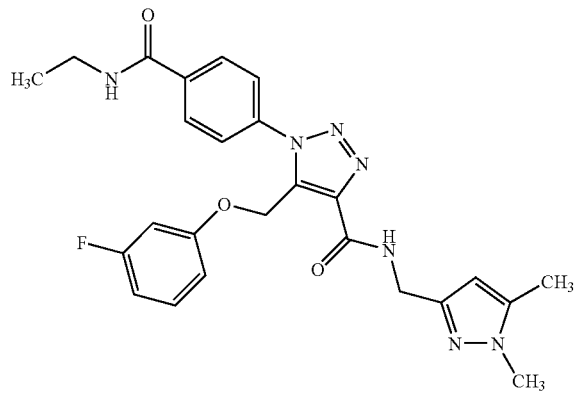

In the same manner as in Example 43, the title compound was obtained.

NMR (CDCl$_3$) δ: 1.28 (3H, t, J=7.6), 2.25 (3H, s), 3.48-3.58 (2H, m), 3.76 (3H, s), 4.60 (2H, d, J=5.4), 5.53 (2H, s), 6.02 (1H, s), 6.17 (1H, brs), 6.60-6.72 (3H, m), 7.20 (1H, m), 7.70 (2H, d, J=8.6), 7.90 (1H, brs), 7.94 (2H, d, J=8.6).

Example 469

1-{4-[(ethylamino)carbonyl]phenyl}-5-[(3-fluorophenoxy)methyl]-N-(tetrahydro-2H-pyran-4-yl)-1H-1,2,3-triazole-4-carboxamide

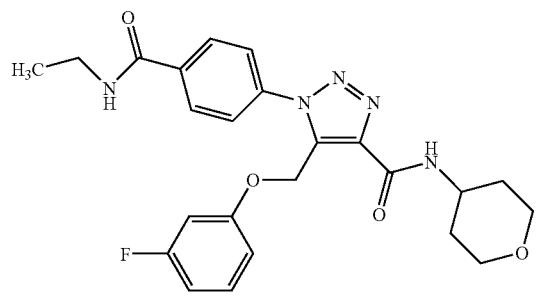

In the same manner as in Example 43, the title compound was obtained.

NMR (CDCl$_3$) δ: 1.28 (3H, t, J=7.4), 1.68-1.74 (2H, m), 1.99-2.04 (2H, m), 3.48-3.58 (4H, m), 4.00-4.04 (2H, m), 4.22 (1H, m), 5.49 (1H, s), 6.61 (1H, brs), 6.61-6.73 (3H, m), 7.21 (1H, m), 7.26 (1H, brs), 7.67 (2H, d, J=8.6), 7.94 (2H, d, J=8.6).

Example 470

1-{4-[(ethylamino)carbonyl]phenyl}-5-[(3-fluorophenoxy)methyl]-N-[2-(morpholin-4-yl)ethyl]-1H-1,2,3-triazole-4-carboxamide

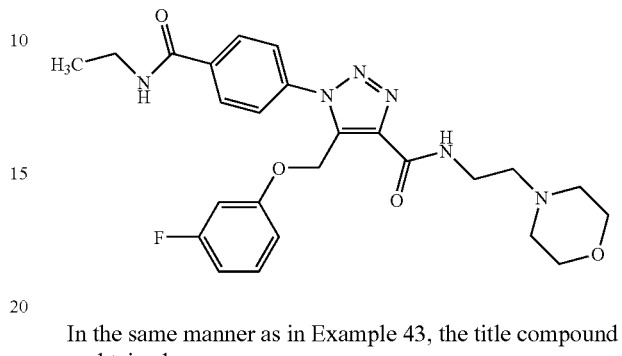

In the same manner as in Example 43, the title compound was obtained.

NMR (CDCl$_3$) δ: 1.28 (3H, t, J=7.6), 2.51-2.63 (4H, m), 2.63 (2H, t, J=6.0), 3.49-3.61 (4H, m), 3.74-3.77 (4H, m), 5.51 (2H, s), 6.18 (1H, brs), 6.61-6.73 (3H, m), 7.19 (1H, m), 7.66 (2H, d, J=8.8), 7.76 (1H, brt, J=5.4), 7.95 (2H, d, J=8.6).

Example 471

1-{4-[(ethylamino)carbonyl]phenyl}-5-[(3-fluorophenoxy)methyl]-N-(3-oxo-1,3-dihydro-2-benzofuran-5-yl)-1H-1,2,3-triazole-4-carboxamide

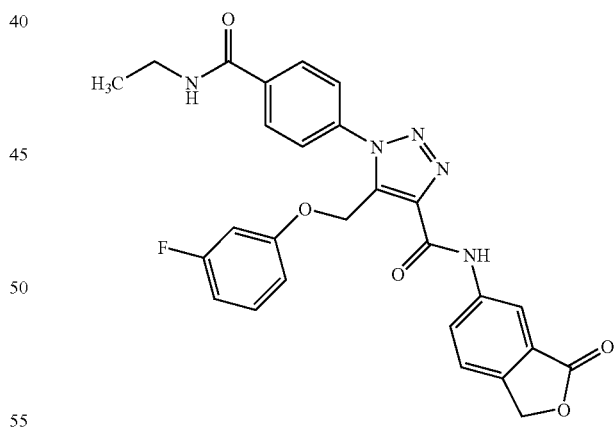

In the same manner as in Example 43, the title compound was obtained.

NMR (CDCl$_3$) δ: 1.29 (3H, t, J=7.6), 3.50-3.59 (2H, m), 5.33 (2H, s), 5.53 (2H, s), 6.02 (1H, brs), 6.63 (1H, m), 6.69-6.76 (2H, m), 7.22 (1H, m), 7.51 (1H, d, J=8.4), 7.72 (2H, d, J=8.8), 7.96 (2H, d, J=8.8), 8.05 (1H, dd, J=2.1, 8.4), 8.28 (1H, d, J=1.2), 9.31 (1H, s).

Example 472

1-{4-[(ethylamino)carbonyl]phenyl}-5-[(3-fluorophenoxy)methyl]-N-[2-(methylsulfonyl)ethyl]-1H-1,2,3-triazole-4-carboxamide

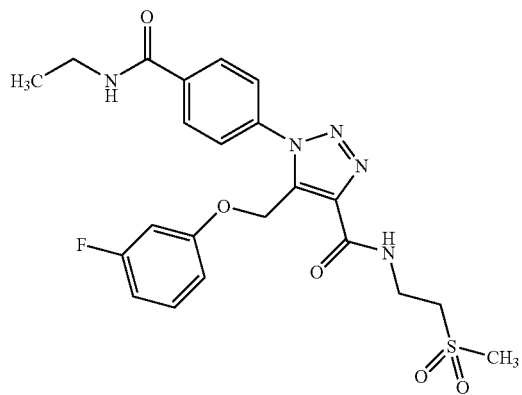

In the same manner as in Example 43, the title compound was obtained.

NMR (DMSO-d$_6$) δ: 1.13 (3H, t, J=7.6), 3.05 (3H, s), 3.23-3.33 (2H, m), 3.42 (2H, t, J=6.9), 3.71-3.78 (2H, m), 5.53 (2H, s), 6.72-6.82 (3H, m), 7.28 (1H, m), 7.75 (2H, d, J=8.8), 8.03 (2H, d, J=8.8), 8.66 (1H, t, J=4.8), 9.08 (1H, t, J=2.7).

Example 473

1-{4-[(ethylamino)carbonyl]phenyl}-5-[(3-fluorophenoxy)methyl]-N-(2-{[(trifluoromethyl)sulfonyl]amino}ethyl)-1H-1,2,3-triazole-4-carboxamide

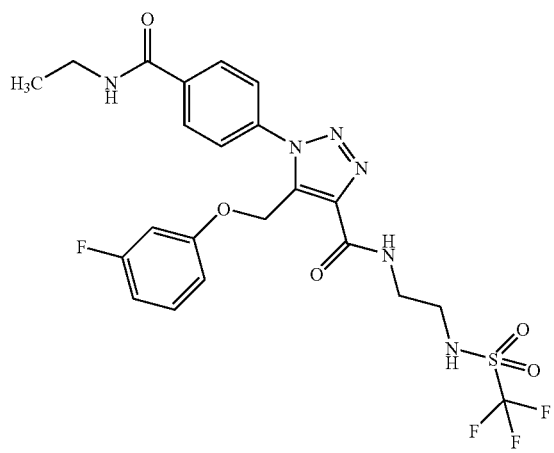

In the same manner as in Example 43, the title compound was obtained.

NMR (CDCl$_3$) δ: 1.28 (3H, t, J=7.6), 3.49-3.59 (4H, m), 3.69-3.75 (2H, m), 5.44 (2H, s), 6.15 (1H, brs), 6.56-6.73 (3H, m), 7.22 (1H, m), 7.66 (2H, d, J=8.8), 7.82 (1H, brs), 7.92 (2H, d, J=8.8).

Example 474

1-{4-[(ethylamino)carbonyl]phenyl}-5-[(3-fluorophenoxy)methyl]-N-[2-(2-hydroxyethoxy)ethyl]-1H-1,2,3-triazole-4-carboxamide

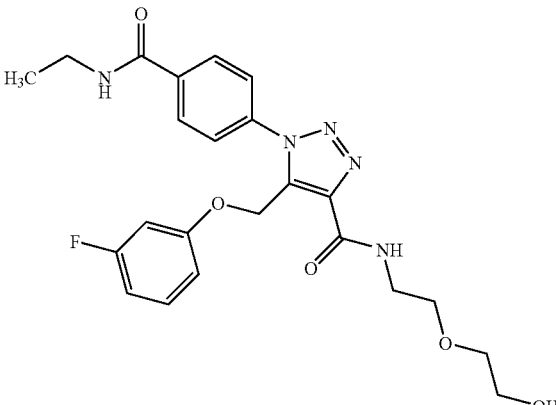

In the same manner as in Example 43, the title compound was obtained.

NMR (CDCl$_3$) δ: 1.25 (3H, t, J=7.4), 1.98 (1H, t, J=5.5), 3.35-3.87 (8H, m), 4.44 (2H, m), 5.50 (2H, s), 6.30 (1H, brs), 6.70-6.71 (2H, m), 6.86 (2H, m), 7.37 (1H, brs), 7.69 (2H, d, J=8.2), 7.92 (2H, d, J=8.2).

Example 475

5-[(3-tert-butylphenoxy)methyl]-N-cyclopropyl-1-{4-[(ethylamino)carbonyl]phenyl}-1H-1,2,3-triazole-4-carboxamide

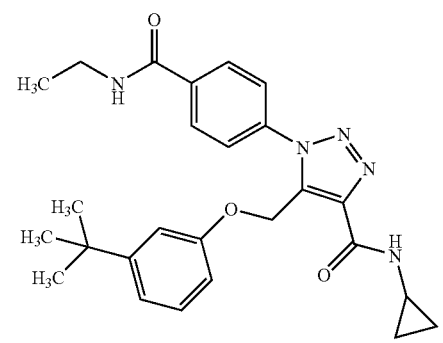

In the same manner as in Example 414, the title compound was obtained.

NMR (CDCl$_3$) δ: 0.67-0.72 (2H, m), 0.87-0.91 (2H, m), 1.27 (3H, t, J=7.4), 1.27 (9H, s), 2.92 (1H, m), 3.48-3.57 (2H, m), 5.54 (2H, s), 6.15 (1H, brs), 6.68 (1H, m), 6.86 (1H, m), 6.99 (1H, d, J=7.5), 7.20 (1H, t, J=8.4), 7.39 (1H, brs), 7.69 (2H, d, J=8.8), 7.92 (2H, d, J=8.8).

Example 476

N-(3,5-di-tert-butyl-4-hydroxybenzyl)-1-{4-[(ethylamino)carbonyl]phenyl}-5-[(3-fluorophenoxy)methyl]-1H-1,2,3-triazole-4-carboxamide

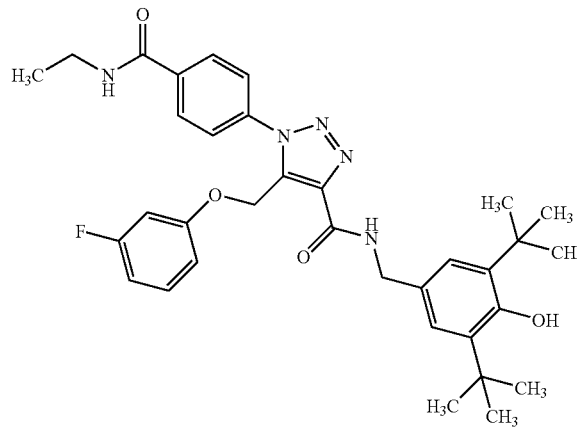

In the same manner as in Example 43, the title compound was obtained.

NMR (CDCl$_3$) δ: 1.64 (3H, t, J=6.0), 1.52 (18H, s), 1.68-1.88 (10H, m), 3.51-3.54 (2H, m), 4.41 (2H, t, J=8.4), 4.61-4.63 (2H, d, J=6.4), 5.41 (1H, s), 6.18 (1H, brs), 7.31 (2H, s), 7.38-7.42 (2H, m), 7.66 (1H, s), 7.88 (2H, d, J=8.4), 8.71 (1H, s).

Example 477

N-(3,5-di-tert-butyl-4-hydroxybenzyl)-1-{4-[(ethylamino)carbonyl]phenyl}-5-propyl-1H-1,2,3-triazole-4-carboxamide

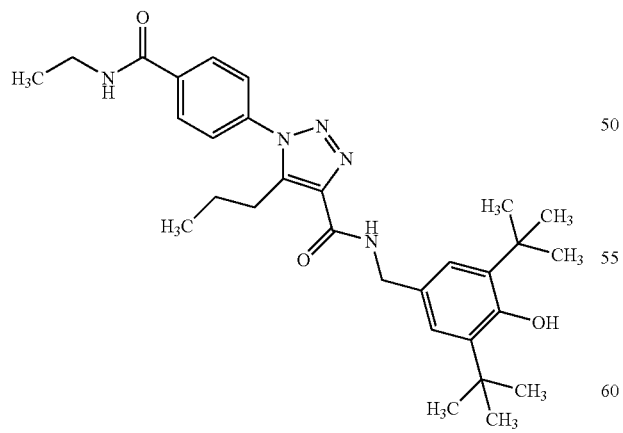

In the same manner as in Example 43, the title compound was obtained.

NMR (CDCl$_3$) δ: 1.28 (3H, t, J=6.4), 1.44 (18H, s), 3.51-3.55 (2H, m), 4.56 (2H, d, J=5.7), 5.22 (1H, s), 5.54 (2H, s), 6.12 (1H, brs), 6.61-6.72 (3H, m), 7.17 (2H, s), 7.21 (1H, m), 7.51 (1H, s), 7.68 (2H, d, J=8.6), 7.91 (2H, d, J=8.6).

Example 478

N-(3,5-di-tert-butyl-4-hydroxybenzyl)-1-{4-[(ethylamino)carbonyl]-2-[(6-fluorohexyl)oxy]phenyl}-1H-1,2,3-triazole-4-carboxamide

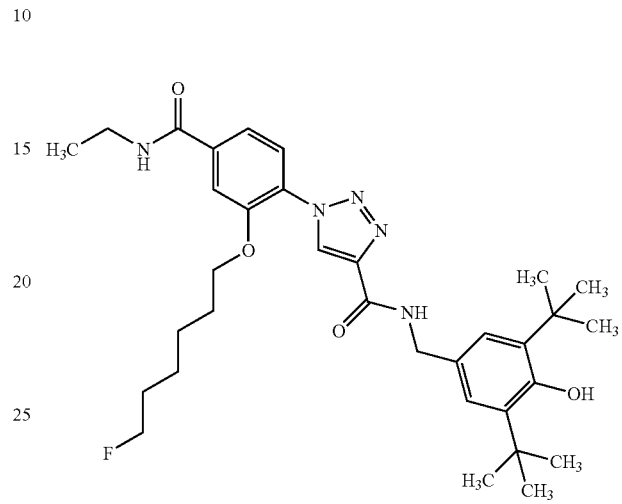

In the same manner as in Example 43, the title compound was obtained.

NMR (CDCl$_3$) δ: 0.87 (3H, t, J=6.0), 1.30 (3H, t, J=9.0), 1.45 (18H, s), 1.55-1.62 (2H, m), 3.06 (2H, t, J=9.0), 3.50-2.59 (2H, m), 4.55 (2H, d, J=6.0), 5.20 (2H, s), 6.18 (1H, brs), 7.17 (2H, s), 7.46 (1H, brs), 7.52 (2H, d, J=8.4), 7.97 (2H, d, J=8.4).

Example 479

5-[(2-tert-butylphenoxy)methyl]-N-cyclopropyl-1-{4-[(ethylamino)carbonyl]phenyl}-1H-1,2,3-triazole-4-carboxamide

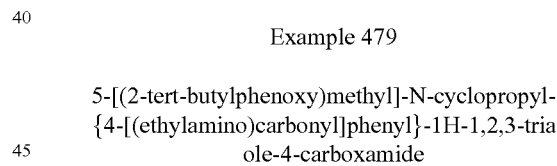
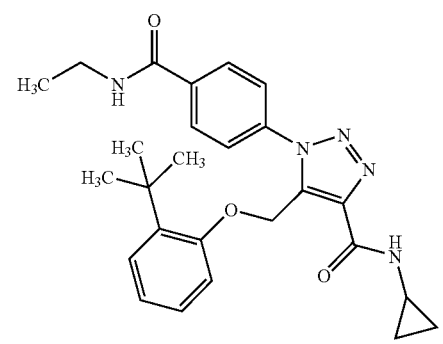

In the same manner as in Example 414, the title compound was obtained.

NMR (CDCl$_3$) δ: 0.67-0.70 (2H, m), 0.85-0.91 (2H, m), 1.16 (9H, s), 1.26 (3H, t, J=7.2), 2.89 (1H, m), 3.47-3.56 (2H, m), 5.56 (2H, s), 6.07 (1H, brs), 6.89-6.98 (2H, m), 7.13-7.24 (2H, m), 7.36 (1H, brs), 7.75 (2H, d, J=8.6), 7.93 (2H, d, J=8.6).

Example 480

N-cyclopropyl-5-[(3,5-difluorophenoxy)methyl]-1-{4-[(ethylamino)carbonyl]phenyl}-1H-1,2,3-triazole-4-carboxamide

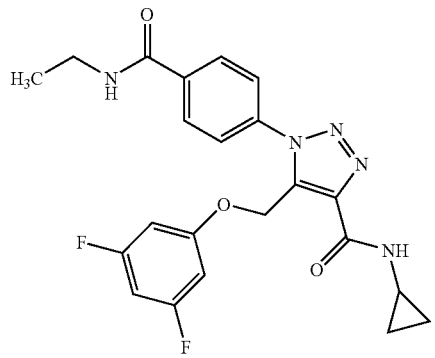

In the same manner as in Example 414, the title compound was obtained.

NMR (CDCl₃) δ: 0.62-0.73 (2H, m), 0.88-0.94 (2H, m), 1.28 (3H, t, J=7.5), 2.91 (1H, m), 3.49-3.58 (2H, m), 5.49 (2H, s), 6.15 (1H, brs), 6.44-6.47 (3H, m), 7.39 (1H, brs), 7.65 (2H, d, J=8.8), 7.94 (2H, d, J=8.8).

Example 481

N-cyclopropyl-5-[(3,5-dichlorophenoxy)methyl]-1-{4-[(ethylamino)carbonyl]phenyl}-1H-1,2,3-triazole-4-carboxamide

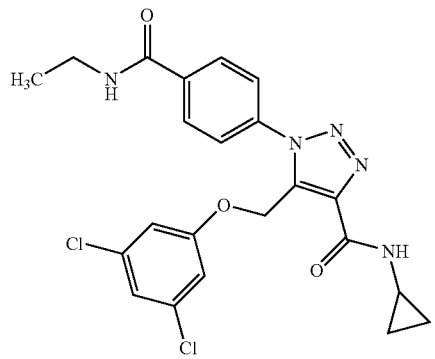

In the same manner as in Example 414, the title compound was obtained.

NMR (CDCl₃) δ: 0.68-0.72 (2H, m), 0.88-0.94 (2H, m), 1.29 (3H, t, J=7.2), 2.93 (1H, m), 3.49-3.58 (2H, m), 5.50 (2H, s), 6.13 (1H, brs), 6.82 (2H, s), 6.99 (1H, s), 7.39 (1H, brs), 7.66 (2H, d, J=8.4), 7.95 (2H, d, J=8.4).

Example 482

N-cyclopropyl-5-[(3,5-dimethylphenoxy)methyl]-1-{4-[(ethylamino)carbonyl]phenyl}-1H-1,2,3-triazole-4-carboxamide

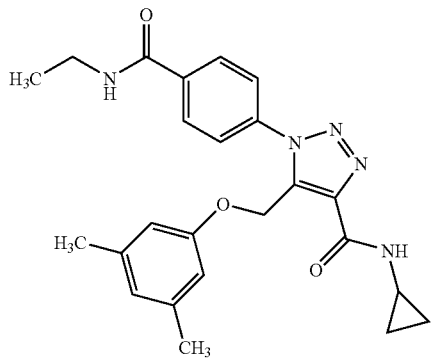

In the same manner as in Example 414, the title compound was obtained.

NMR (CDCl₃) δ: 0.66-0.72 (2H, m), 0.86-0.91 (2H, m), 1.28 (3H, t, J=7.2), 2.93 (1H, m), 3.48-3.55 (2H, m), 5.47 (2H, s), 6.09 (1H, brs), 6.52 (2H, s), 6.62 (1H, s), 7.37 (1H, brs), 7.72 (2H, d, J=8.4), 7.91 (2H, d, J=8.4).

Example 483

5-{[3,5-bis(trifluoromethyl)phenoxy]methyl}-N-cyclopropyl-1-{4-[(ethylamino)carbonyl]phenyl}-1H-1,2,3-triazole-4-carboxamide

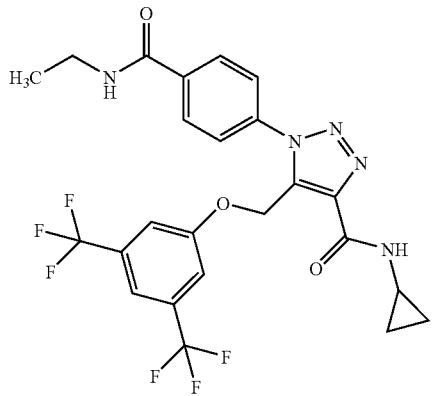

In the same manner as in Example 414, the title compound was obtained.

NMR (CDCl₃) δ: 0.67-0.72 (2H, m), 0.86-0.90 (2H, m), 1.26 (3H, t, J=7.4), 2.93 (1H, m), 3.49-3.57 (2H, m), 5.41 (2H, s), 6.12 (1H, brs), 6.34 (2H, s), 6.52 (1H, s), 7.44 (1H, brs), 7.71 (2H, d, J=8.2), 7.78 (2H, d, J=8.2).

Example 484

N-cyclopropyl-1-{4-[(ethylamino)carbonyl]phenyl}-5-[(3-ethylphenoxy)methyl]-1H-1,2,3-triazole-4-carboxamide

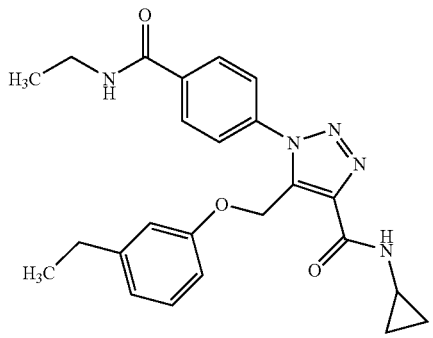

In the same manner as in Example 414, the title compound was obtained.

NMR (CDCl$_3$) δ: 0.66-0.72 (2H, m), 0.86-0.93 (2H, m), 1.17 (3H, t, J=7.4), 1.27 (3H, t, J=7.2), 2.58 (2H, q, J=7.4), 2.92 (1H, m), 3.51 (2H, q, J=7.6), 5.51 (2H, s), 6.15 (1H, brs), 6.68-6.72 (2H, m), 6.81 (1H, d, J=7.5), 7.18 (1H, t, J=8.2), 7.39 (1H, brs), 7.70 (2H, d, J=8.4), 7.91 (2H, d, J=8.4).

Example 485

5-[(3-cyanophenoxy)methyl]-N-cyclopropyl-1-{4-[(ethylamino)carbonyl]phenyl}-1H-1,2,3-triazole-4-carboxamide

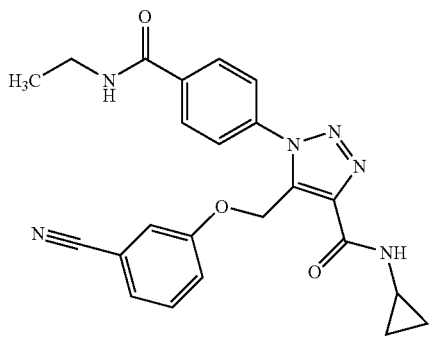

In the same manner as in Example 414, the title compound was obtained.

NMR (CDCl$_3$) δ: 0.68-0.73 (2H, m), 0.88-0.95 (2H, m), 1.29 (3H, t, J=7.4), 2.92 (1H, m), 3.49-3.59 (2H, m), 5.56 (2H, s), 6.16 (1H, brs), 7.16-7.38 (4H, m), 7.41 (1H, brs), 7.66 (2H, d, J=8.8), 7.95 (2H, d, J=8.8).

Example 486

N-cyclopropyl-5-[(3-ethoxyphenoxy)methyl]-1-{4-[(ethylamino)carbonyl]phenyl}-1H-1,2,3-triazole-4-carboxamide

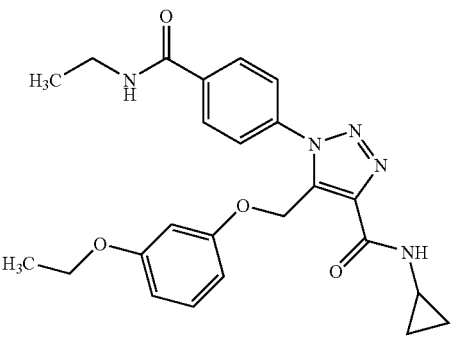

In the same manner as in Example 414, the title compound was obtained.

NMR (CDCl$_3$) δ: 0.67-0.72 (2H, m), 0.87-0.93 (2H, m), 1.28 (3H, t, J=7.4), 1.34 (3H, t, J=6.9), 2.92 (1H, m), 3.49-3.57 (2H, m), 3.96 (2H, q, J=6.9), 5.51 (2H, s), 6.12 (1H, brs), 6.43-6.53 (3H, m), 7.13 (1H, t, J=8.4), 7.39 (1H, brs), 7.69 (2H, d, J=8.4), 7.92 (2H, d, J=8.4).

Example 487

N-cyclopropyl-1-{4-[(ethylamino)carbonyl]phenyl}-5-[(3-ethynylphenoxy)methyl]-1H-1,2,3-triazole-4-carboxamide

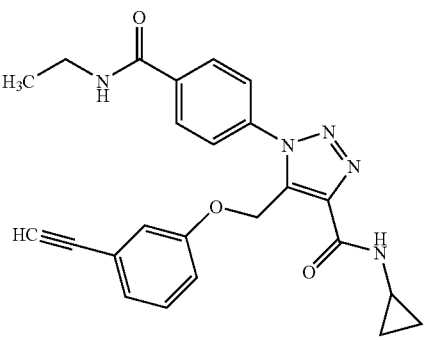

In the same manner as in Example 414, the title compound was obtained.

NMR (CDCl$_3$) δ: 0.67-0.73 (2H, m), 0.87-0.93 (2H, m), 1.28 (3H, t, J=7.4), 2.92 (1H, m), 3.06 (1H, s), 3.48-3.57 (2H, m), 5.52 (2H, s), 6.14 (1H, brs), 6.91 (1H, m), 6.99 (1H, m), 7.13 (1H, m), 7.20 (1H, m), 7.39 (1H, brs), 7.71 (2H, d, J=8.6), 7.94 (2H, d, J=8.6).

Example 488

N-cyclopropyl-1-{4-[(ethylamino)carbonyl]phenyl}-
5-{[3-(1-methyl-1H-pyrazol-5-yl)phenoxy]methyl}-
1H-1,2,3-triazole-4-carboxamide

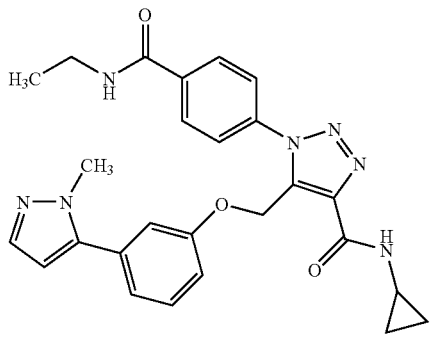

In the same manner as in Example 414, the title compound was obtained.

NMR (CDCl$_3$) δ: 0.65-0.73 (2H, m), 0.90-0.93 (2H, m), 1.25 (3H, t, J=7.4), 2.88 (1H, m), 3.46-3.56 (2H, m), 3.86 (3H, s), 5.56 (2H, s), 6.26 (1H, s), 6.41 (1H, brs), 6.93-7.03 (3H, m), 7.37-7.52 (3H, m), 7.67 (2H, d, J=8.6), 7.95 (2H, d, J=8.6).

Example 489

5-[(3-acetylphenoxy)methyl]-N-cyclopropyl-1-{4-[(ethylamino)carbonyl]phenyl}-1H-1,2,3-triazole-4-carboxamide

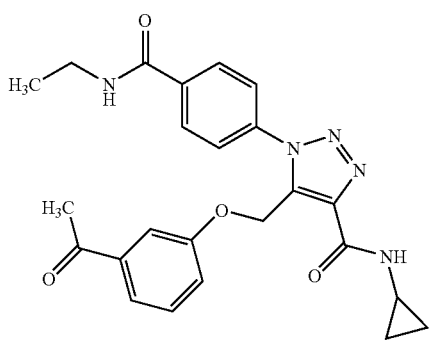

In the same manner as in Example 414, the title compound was obtained.

NMR (CDCl$_3$) δ: 0.67-0.73 (2H, m), 0.87-0.93 (2H, m), 1.28 (3H, t, J=7.4), 2.57 (3H, s), 2.93 (1H, m), 3.48-3.57 (2H, m), 5.58 (2H, s), 6.27 (1H, brs), 7.10 (1H, m), 7.25-7.41 (3H, m), 7.56 (1H, m), 7.67 (2H, d, J=8.4), 7.93 (2H, d, J=8.4).

Example 490

N-cyclopropyl-1-{4-[(ethylamino)carbonyl]phenyl}-
5-{[3-(N-hydroxyethaneimidoyl)phenoxy]methyl}-
1H-1,2,3-triazole-4-carboxamide

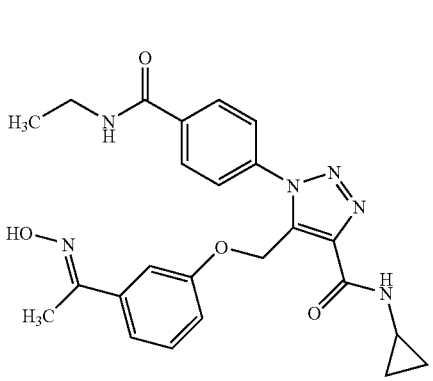

To a solution of 5-[(3-acetylphenoxy)methyl]-N-cyclopropyl-1-{4-[(ethylamino)carbonyl]phenyl}-1H-1,2,3-triazole-4-carboxamide (100 mg) obtained in Example 489 in ethanol (4 ml) were added hydroxylamine hydrochloride (78 mg) and sodium acetate (92 mg), and the mixture was heated under reflux for 4 hr. Water was added to the reaction solution, and the mixture was extracted with ethyl acetate. The organic layer was dried over anhydrous sodium sulfate, and the solvent was evaporated under reduced pressure. The residue was recrystallized from ethyl acetate/hexane to give the title compound as a colorless powder (88 mg).

NMR (CDCl$_3$) δ: 0.66-0.72 (2H, m), 0.85-0.92 (2H, m), 1.28 (3H, t, J=7.6), 2.21 (3H, s), 2.90 (1H, m), 3.48-3.55 (2H, m), 5.53 (2H, s), 6.27 (1H, brs), 6.89 (1H, m), 7.03 (1H, m), 7.16-7.25 (2H, m), 7.42 (1H, m), 7.65 (2H, d, J=8.4), 7.92 (2H, d, J=8.4), 8.20 (1H, brs).

Example 491

N-[2-(acetylamino)ethyl]-1-{4-[(ethylamino)carbonyl]phenyl}-5-[(3-fluorophenoxy)methyl]-1H-1,2,3-triazole-4-carboxamide

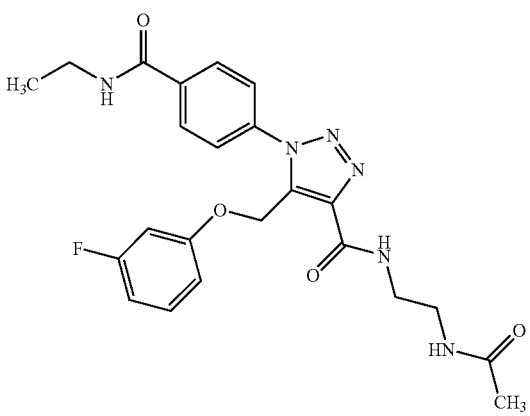

In the same manner as in Example 43, the title compound was obtained.

NMR (DMSO-d$_6$) δ: 1.13 (3H, t, J=7.4), 1.80 (3H, s), 3.22-3.39 (6H, m), 5.54 (2H, s), 6.71-6.82 (3H, m), 7.27 (1H, m), 7.75 (2H, d, J=8.4), 7.97 (1H, t, J=5.1), 8.03 (2H, d, J=8.4), 8.66 (1H, t, J=5.3), 8.90 (1H, t, J=5.4).

Example 492

1-{4-[(ethylamino)carbonyl]phenyl}-5-[(3-fluorophenoxy)methyl]-N-(3-oxoisoxazolidin-4-yl)-1H-1,2,3-triazole-4-carboxamide

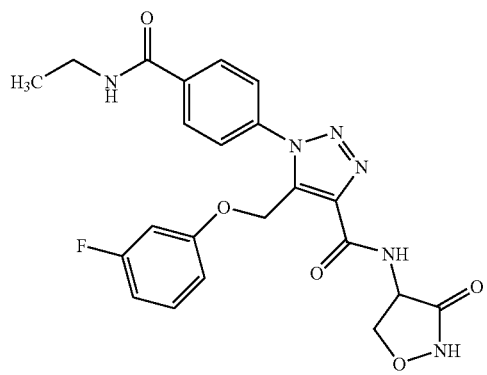

In the same manner as in Example 43, the title compound was obtained.

NMR (DMSO-d$_6$) δ: 1.13 (3H, t, J=7.6), 3.26-3.32 (2H, m), 4.23 (1H, m), 4.56 (1H, t, J=8.1), 5.05 (1H, m), 5.51 (2H, m), 6.72-6.82 (3H, m), 7.28 (1H, m), 7.75 (2H, d, J=8.6), 8.03 (2H, d, J=8.6), 8.66 (1H, t, J=5.4), 9.31 (1H, t, J=6.2).

Example 493

N-(2-anilinoethyl)-1-{4-[(ethylamino)carbonyl]phenyl}-5-[(3-fluorophenoxy)methyl]-1H-1,2,3-triazole-4-carboxamide

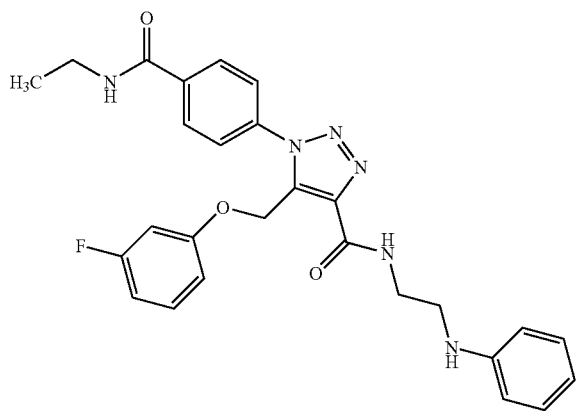

In the same manner as in Example 43, the title compound was obtained.

NMR (CDCl$_3$) δ: 1.28 (3H, t, J=7.3), 3.41-3.50 (2H, m), 3.52-3.57 (2H, m), 3.72-3.78 (2H, m), 4.06 (1H, brs), 5.50 (1H, s), 6.14 (1H, brs), 6.60-6.74 (6H, m), 7.15-7.22 (3H, m), 7.62 (1H, t, J=5.7), 7.63 (2H, d, J=8.6), 7.92 (2H, d, J=8.6).

Example 494

N-[3-(azepan-1-yl)propyl]-1-{4-[(ethylamino)carbonyl]phenyl}-5-[(3-fluorophenoxy)methyl]-1H-1,2,3-triazole-4-carboxamide

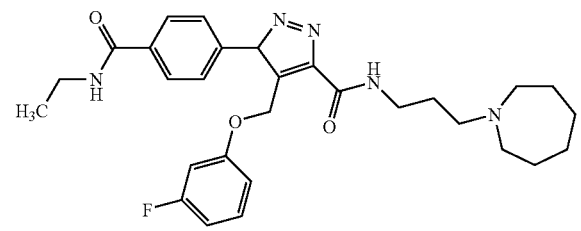

In the same manner as in Example 43, the title compound was obtained.

NMR (CDCl$_3$) δ: 1.28 (3H, t, J=7.6), 1.65-1.82 (10H, m), 2.26-2.68 (2H, m), 3.48-3.61 (4H, m), 5.52 (2H, s), 6.18 (1H, brs), 6.59-6.71 (3H, m), 7.20 (1H, m), 7.67 (2H, d, J=8.4), 7.92 (2H, d, J=8.4), 8.80 (1H, brt, J=5.4).

Example 495

1-{4-[(ethylamino)carbonyl]phenyl}-5-[(3-fluorophenoxy)methyl]-N-{2-[(methylsulfonyl)amino]ethyl}-1H-1,2,3-triazole-4-carboxamide

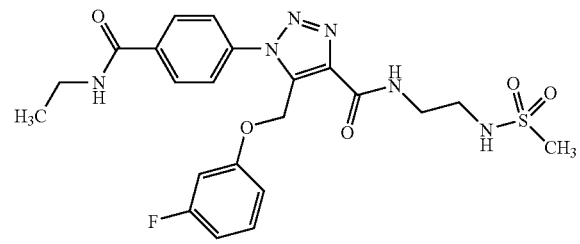

In the same manner as in Example 43, the title compound was obtained.

NMR (DMSO-d$_6$) δ: 1.13 (3H, t, J=7.4), 3.26-3.35 (2H, m), 3.64-3.70 (2H, m), 4.24 (2H, t, J=6.3), 4.50 (2H, d, J=5.4), 5.32 (1H, d, J=5.4), 5.52 (2H, s), 6.71-6.82 (4H, m), 7.11 (1H, s), 7.28 (1H, m), 7.75 (2H, d, J=8.4), 8.03 (2H, d, J=8.4), 8.66 (1H, t, J=5.4), 9.04 (1H, t, J=6.0).

Example 496

1-{4-[(ethylamino)carbonyl]phenyl}-5-[(3-fluorophenoxy)methyl]-N-{2-[2-(hydroxymethyl)-1H-imidazol-1-yl]ethyl}-1H-1,2,3-triazole-4-carboxamide

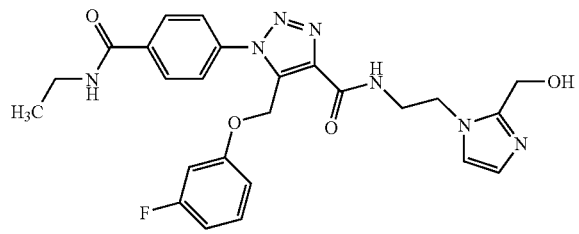

In the same manner as in Example 43, the title compound was obtained.

NMR (DMSO-$d_6$) δ: 1.13 (3H, t, J=7.2), 3.26-3.35 (2H, m), 3.64-3.70 (2H, m), 4.24 (2H, t, J=6.3), 4.50 (2H, d, J=5.4), 5.32 (1H, d, J=5.4), 5.52 (2H, s), 6.71-6.82 (4H, m), 7.11 (1H, s), 7.28 (1H, m), 7.75 (2H, d, J=8.4), 8.03 (2H, d, J=8.4), 8.66 (1H, t, J=5.4), 9.04 (1H, t, J=6.0).

Example 497

5-[(3-fluorophenoxy)methyl]-N-{2-[2-(hydroxymethyl)-1H-imidazol-1-yl]ethyl}-1-(4-{[(2,2,2-trifluoroethyl)amino]carbonyl}phenyl)-1H-1,2,3-triazole-4-carboxamide

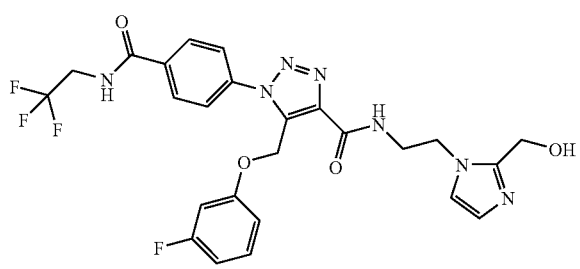

In the same manner as in Example 43, the title compound was obtained.

NMR (DMSO-$d_6$) δ: 3.66-3.67 (2H, m), 4.11-4.14 (2H, m), 4.24 (2H, t, J=6.3), 4.50 (2H, d, J=5.4), 5.30 (1H, t, J=3.0), 5.53 (2H, s), 6.71-6.81 (4H, m), 7.11 (1H, s), 7.27 (1H, m), 7.80 (2H, d, J=8.4), 8.08 (2H, d, J=8.4), 9.04 (1H, brt, J=6.0), 9.31 (1H, brs).

Example 498

1-{4-[(ethylamino)carbonyl]phenyl}-5-[(3-fluorophenoxy)methyl]-N-(2-hydroxyethyl)-1H-1,2,3-triazole-4-carboxamide

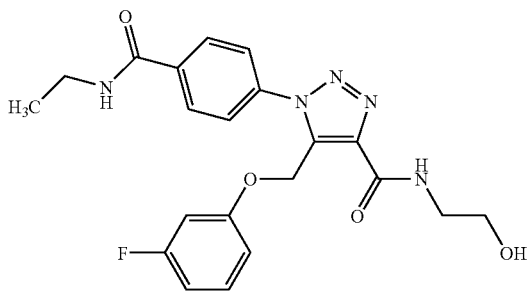

In the same manner as in Example 43, the title compound was obtained.

NMR (DMSO-$d_6$) δ: 1.13 (3H, t, J=7.0), 3.26-3.42 (4H, m), 3.51-3.57 (2H, m), 4.78 (1H, t, J=5.1), 5.54 (2H, s), 6.71-6.83 (3H, m), 7.27 (1H, m), 7.75 (2H, d, J=8.8), 8.03 (2H, d, J=8.8), 8.66 (1H, brt, J=5.4), 8.72 (1H, brt, J=5.7).

Example 499

5-[(3-fluorophenoxy)methyl]-N-(2-hydroxyethyl)-1-(4-{[(2,2,2-trifluoroethyl)amino]carbonyl}phenyl)-1H-1,2,3-triazole-4-carboxamide

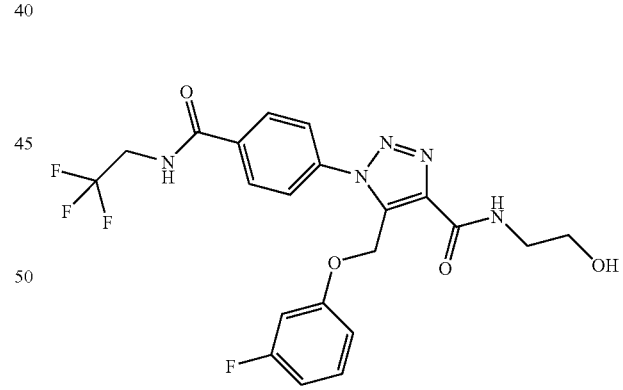

In the same manner as in Example 43, the title compound was obtained.

NMR (DMSO-$d_6$) δ: 3.33-3.40 (2H, m), 3.52-3.55 (2H, m), 4.08-4.18 (2H, m), 4.79 (1H, t, J=5.7), 5.57 (2H, s), 6.72-6.85 (3H, m), 7.27 (1H, m), 7.80 (2H, d, J=8.8), 8.10 (2H, d, J=8.8), 8.72 (1H, brt, J=5.8), 9.31 (1H, brs).

Example 500

N-[3-(azepan-1-yl)propyl]-5-[(3-fluorophenoxy)methyl]-1-(4-{[(2,2,2-trifluoroethyl)amino]carbonyl}phenyl)-1H-1,2,3-triazole-4-carboxamide

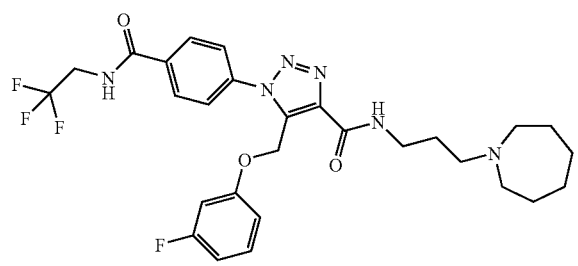

In the same manner as in Example 43, the title compound was obtained.

NMR (DMSO-$d_6$) δ: 1.56-1.73 (10H, m), 2.47-2.58 (6H, m), 3.34-3.39 (2H, m), 4.08-4.18 (2H, m), 5.57 (2H, s), 6.72-6.85 (3H, m), 7.28 (1H, m), 7.81 (2H, d, J=8.6), 8.11 (2H, d, J=8.6), 9.06 (1H, brt, J=5.4), 9.32 (1H, brs).

Example 501

1-{4-[(ethylamino)carbonyl]phenyl}-5-[(3-fluorophenoxy)methyl]-N-(2,2,6,6-tetramethylpiperidin-4-yl)-1H-1,2,3-triazole-4-carboxamide

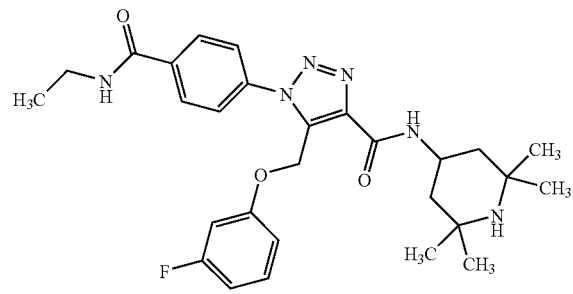

In the same manner as in Example 43, the title compound was obtained.

NMR (DMSO-$d_6$) δ: 1.04 (6H, s), 1.13 (3H, t, J=7.2), 1.17 (6H, s), 3.26-3.38 (2H, m), 4.32 (1H, m), 5.52 (2H, s), 6.72-6.83 (3H, m), 7.30 (1H, m), 7.75 (2H, d, J=8.8), 8.02 (2H, d, J=8.8), 8.61-8.67 (2H, m).

Example 502

5-[(3-fluorophenoxy)methyl]-N-(3-hydroxypropyl)-1-(4-{[(2,2,2-trifluoroethyl)amino]carbonyl}phenyl)-1H-1,2,3-triazole-4-carboxamide

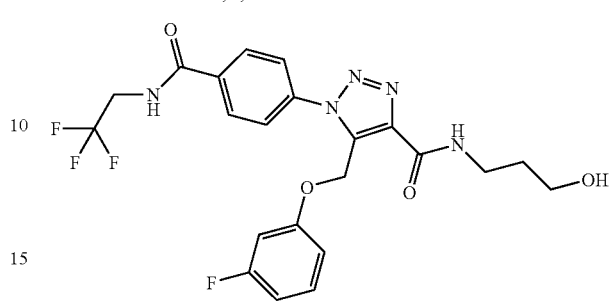

In the same manner as in Example 43, the title compound was obtained.

NMR (CDCl$_3$) δ: 1.64-1.86 (4H, m), 1.88 (1H, t, J=5.4), 3.50-3.56 (2H, m), 3.69-3.75 (2H, m), 4.09-4.20 (2H, m), 5.50 (2H, s), 6.58-6.71 (4H, m), 7.22 (1H, m), 7.55 (1H, t, J=5.7), 7.72 (2H, d, J=8.4), 7.96 (2H, d, J=8.4).

Example 503

5-[(3-fluorophenoxy)methyl]-N-(4-hydroxybutyl)-1-(4-{[(2,2,2-trifluoroethyl)amino]carbonyl}phenyl)-1H-1,2,3-triazole-4-carboxamide

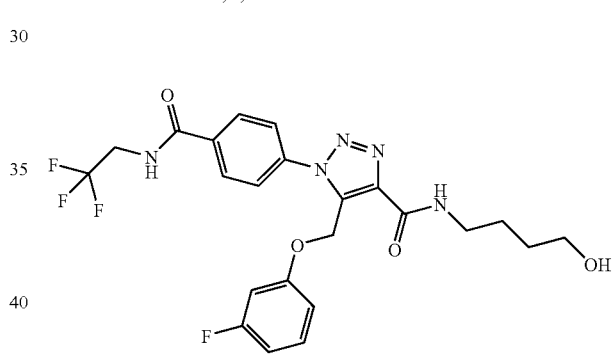

In the same manner as in Example 43, the title compound was obtained.

NMR (CDCl$_3$) δ: 1.81-1.89 (2H, m), 2.90 (1H, t, J=6.3), 3.64-3.76 (4H, m), 4.11-4.22 (2H, m), 5.53 (2H, s), 6.42 (1H, brt, J=6.3), 6.59-6.74 (3H, m), 7.21 (1H, m), 7.64 (1H, brs), 7.76 (2H, d, J=8.8), 8.00 (2H, d, J=8.8).

Example 504

5-[(3-fluorophenoxy)methyl]-N-[2-(2-hydroxyethoxy)ethyl]-1-(4-{[(2,2,2-trifluoroethyl)amino]carbonyl}phenyl)-1H-1,2,3-triazole-4-carboxamide

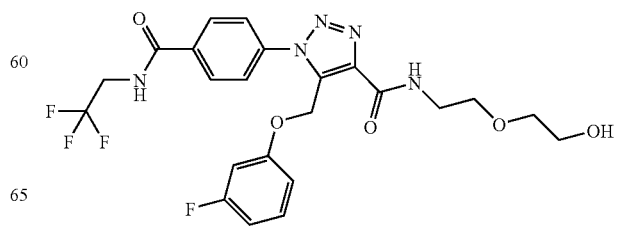

In the same manner as in Example 43, the title compound was obtained.

NMR (DMSO-d$_6$) δ: 3.44-3.59 (8H, m), 4.07-4.17 (2H, m), 4.62 (1H, t, J=5.1), 5.56 (2H, s), 6.71-6.83 (3H, m), 7.27 (1H, m), 7.81 (H, d, J=8.4), 8.10 (2H, d, J=8.4), 8.83 (1H, brt, J=5.7), 9.31 (1H, brs).

Example 505

5-[(3-fluorophenoxy)methyl]-N-(2-hydroxy-1,1-dimethylethyl)-1-(4-{[(2,2,2-trifluoroethyl)amino]carbonyl}phenyl)-1H-1,2,3-triazole-4-carboxamide

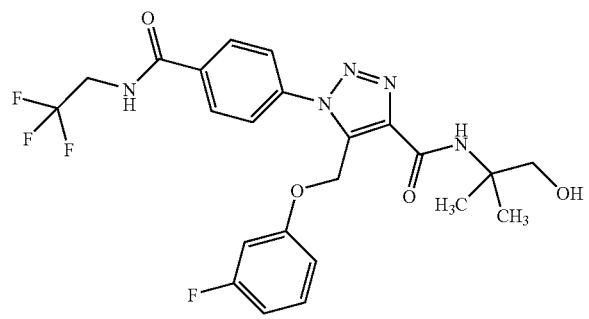

In the same manner as in Example 43, the title compound was obtained.

NMR (CDCl$_3$) δ: 3.73 (2H, d, J=6.3), 4.10-4.21 (2H, m), 4.54 (1H, t, J=6.3), 5.48 (2H, s), 6.59-6.74 (4H, m), 7.22 (1H, m), 7.42 (1H, brs), 7.71 (2H, d, J=8.8), 7.99 (2H, d, J=8.8).

Example 506

5-[(3-fluorophenoxy)methyl]-N-(2-hydroxyethyl)-N-methyl-1-(4-{[(2,2,2-trifluoroethyl)amino]carbonyl}phenyl)-1H-1,2,3-triazole-4-carboxamide

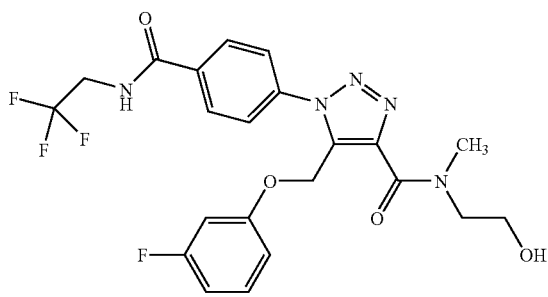

In the same manner as in Example 43, the title compound was obtained.

NMR (DMSO-d$_6$) δ: 3.17 (2.1H, s), 3.47 (0.9H, s), 3.74-3.82 (2H, m), 3.90-3.94 (2H, m), 4.08-4.13 (2H, m), 4.60 (1H, brs), 5.32 (2H, s), 6.54-6.72 (3H, m), 7.03 (0.2H, brt, J=5.4), 7.23 (1H, m), 7.37 (0.8H, brt, J=5.4), 7.69 (2H, d, J=8.4), 8.00 (2H, d, J=8.4).

Example 507

1-{4-[(ethylamino)carbonyl]phenyl}-5-[(3-fluorophenoxy)methyl]-N-(2-hydroxy-1,1-dimethylethyl)-1H-1,2,3-triazole-4-carboxamide

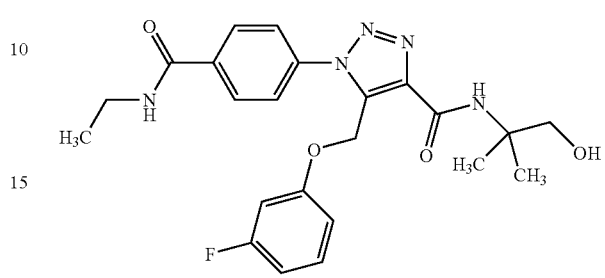

In the same manner as in Example 43, the title compound was obtained.

NMR (DMSO-d$_6$) δ: 1.15 (3H, t, J=4.8), 1.38 (6H, s), 3.26-3.33 (2H, m), 3.47 (2H, d, J=5.4), 5.19 (1H, brt, J=5.4), 5.52 (2H, s), 6.72-6.86 (3H, m), 7.28 (1H, m), 7.76 (2H, d, J=8.8), 7.77 (1H, s), 8.05 (2H, d, J=8.8), 8.67 (1H, brt, J=5.4).

Example 508

2-[({1-{4-[(ethylamino)carbonyl]phenyl}-5-[(3-fluorophenoxy)methyl]-1H-1,2,3-triazol-4-yl}carbonyl)amino]ethyl acetate

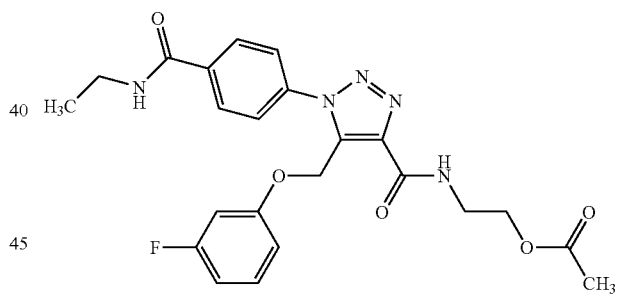

To a solution of 1-{4-[(ethylamino)carbonyl]phenyl}-5-[(3-fluorophenoxy)methyl]-N-(2-hydroxyethyl)-1H-1,2,3-triazole-4-carboxamide (500 mg) obtained in Example 498 in methylene chloride (10 ml) were added pyridine (0.2 ml) and acetic anhydride (0.17 ml), and the mixture was stirred at room temperature for 10 hr. 1N Hydrochloric acid was added to the reaction mixture, and the mixture was extracted with ethyl acetate and washed with saturated brine. The organic layer was dried over anhydrous sodium sulfate, and the solvent was evaporated under reduced pressure. The residue was purified by silica gel column (ethyl acetate/hexane=1/2 to 1/1) and recrystallized from ethyl acetate/hexane to give the title compound as a colorless powder (480 mg).

NMR (DMSO-d$_6$) δ: 1.14 (3H, t, J=7.2), 2.00 (3H, s), 3.28-3.35 (2H, m), 3.52-3.57 (2H, m), 4.16 (2H, t, J=5.7), 5.54 (2H, s), 6.71-6.82 (3H, m), 7.29 (1H, m), 7.75 (2H, d, J=8.8), 8.03 (2H, d, J=8.8), 8.66 (1H, brt, J=5.4), 9.02 (1H, brt, J=6.0).

Example 509

4-{2-[({1-{4-[(ethylamino)carbonyl]phenyl}-5-[(3-fluorophenoxy)methyl]-1H-1,2,3-triazol-4-yl}carbonyl)amino]ethoxy}-4-oxobutanoic acid

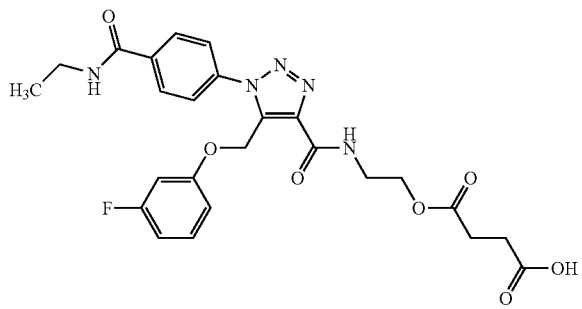

To a solution of 1-{4-[(ethylamino)carbonyl]phenyl}-5-[(3-fluorophenoxy)methyl]-N-(2-hydroxyethyl)-1H-1,2,3-triazole-4-carboxamide (500 mg) obtained in Example 498 in pyridine (10 ml) was added dihydrofuran-2,5-dione (234 mg), and the mixture was heated at 80° C. for 14 hr. The reaction solution was concentrated under reduced pressure, and the residue was recrystallized from ethyl acetate/hexane to give the title compound as a colorless powder (402 mg).

NMR (DMSO-$d_6$) δ: 1.13 (3H, t, J=7.2), 2.43-2.52 (2H, m), 3.26-3.35 (4H, m), 3.51-3.57 (2H, m), 4.17 (2H, t, J=6.0), 5.53 (2H, s), 6.71-6.82 (3H, m), 7.29 (1H, m), 7.75 (2H, d, J=8.8), 8.03 (2H, d, J=8.8), 8.66 (1H, brt, J=5.4), 9.02 (1H, brt, J=6.0).

Example 510

2-[({1-{4-[(ethylamino)carbonyl]phenyl}-5-[(3-fluorophenoxy)methyl]-1H-1,2,3-triazol-4-yl}carbonyl)amino]ethyl N,N-dimethylglycinate

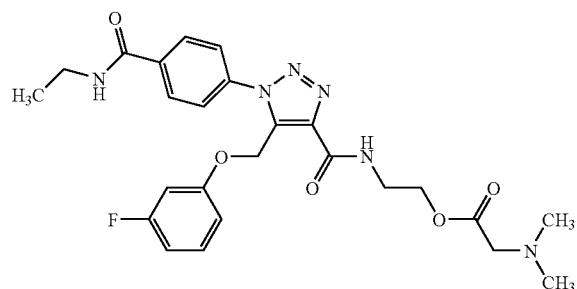

To a solution of 1-{4-[(ethylamino)carbonyl]phenyl}-5-[(3-fluorophenoxy)methyl]-N-(2-hydroxyethyl)-1H-1,2,3-triazole-4-carboxamide (500 mg) obtained in Example 498 in pyridine (10 ml) were added dimethylglycine (181 mg) and WSC (336 mg), and the mixture was stirred at room temperature for 16 hr. Water was added to the reaction mixture, and the mixture was extracted with chloroform and washed with saturated brine. The organic layer was dried over anhydrous sodium sulfate, and the solvent was evaporated under reduced pressure. The residue was purified by basic silica gel column (ethyl acetate/hexane=1/1 to 2/1) and recrystallized from ethyl acetate to give the title compound as a colorless powder (432 mg).

NMR (CDCl$_3$) δ: 1.28 (3H, t, J=7.2), 2.36 (6H, s), 3.23 (2H, s), 3.49-3.55 (2H, m), 3.76-3.82 (2H, m), 4.35 (2H, t, J=5.1), 5.49 (2H, s), 6.17 (1H, brt, J=4.8), 6.60-6.74 (3H, m), 7.20 (1H, m), 7.63 (1H, brt, J=6.0), 7.69 (2H, d, J=8.7), 7.96 (2H, d, J=8.7).

Example 511

5-[(3-fluorophenoxy)methyl]-N-(2-hydroxy-2-methylpropyl)-1-(4-{[(2,2,2-trifluoroethyl)amino]carbonyl}phenyl)-1H-1,2,3-triazole-4-carboxamide

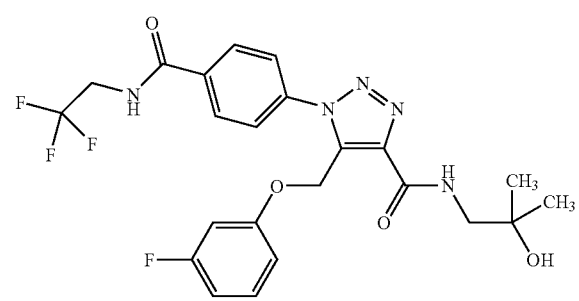

In the same manner as in Example 43, the title compound was obtained.

NMR (CDCl$_3$) δ: 1.32 (6H, s), 3.51 (2H, d, J=6.3), 4.11-4.22 (2H, m), 5.52 (2H, s), 6.50 (1H, brt, J=6.6), 6.60-6.73 (3H, m), 7.19 (1H, m), 7.72-7.73 (3H, m), 7.96-8.01 (2H, m).

Example 512

1-{4-[(ethylamino)carbonyl]phenyl}-5-[(3-fluorophenoxy)methyl]-N-(2-hydroxy-2-methylpropyl)-1H-1,2,3-triazole-4-carboxamide

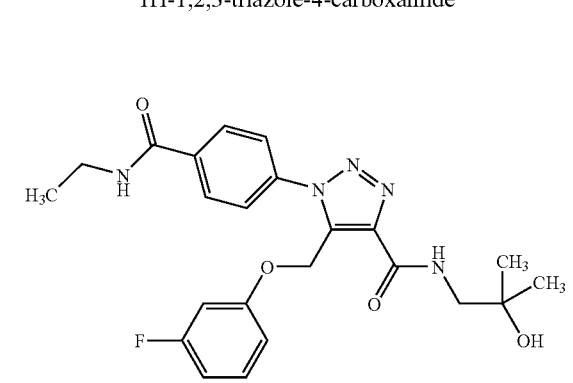

In the same manner as in Example 43, the title compound was obtained.

NMR (CDCl$_3$) δ: 1.26 (3H, t, J=7.1), 1.32 (6H, s), 3.49-3.58 (4H, m), 5.50 (2H, s), 6.18 (1H, brt, J=6.6), 6.59-6.72 (3H, m), 7.19 (1H, m), 7.66 (2H, d, J=8.6), 7.76 (1H, brt, J=5.0), 7.92 (2H, d, J=8.6).

Example 513

1-{4-[(ethylamino)carbonyl]phenyl}-5-[(3-fluorophenoxy)methyl]-N-(3-hydroxypropyl)-1H-1,2,3-triazole-4-carboxamide

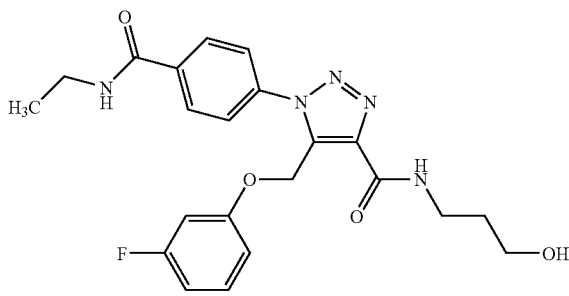

In the same manner as in Example 43, the title compound was obtained.

NMR (CDCl$_3$) δ: 1.28 (3H, t, J=7.2), 1.80-1.88 (2H, m), 2.98 (1H, t, J=6.3), 3.49-3.55 (2H, m), 3.64-3.76 (4H, m), 5.51 (2H, s), 6.18 (1H, brs), 6.58-6.73 (3H, m), 7.20 (1H, m), 7.63 (1H, m), 7.70 (2H, d, J=8.5), 7.95 (2H, d, J=8.5).

Example 514

2-[({1-{4-[(ethylamino)carbonyl]phenyl}-5-[(3-fluorophenoxy)methyl]-1H-1,2,3-triazol-4-yl}carbonyl)amino]ethyl ethyl carbonate

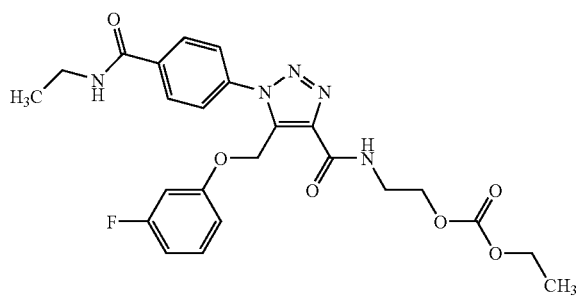

To a solution of 1-{4-[(ethylamino)carbonyl]phenyl}-5-[(3-fluorophenoxy)methyl]-N-(2-hydroxyethyl)-1H-1,2,3-triazole-4-carboxamide (600 mg) obtained in Example 498 in THF (15 ml) were added ethyl chlorocarbonate (0.15 ml) and pyridine (0.17 ml), and the mixture was stirred under ice-cooling for 4 hr. Water was added to the reaction mixture, and the mixture was extracted with ethyl acetate and washed with saturated brine. The organic layer was dried over anhydrous sodium sulfate, and the solvent was evaporated under reduced pressure. The residue was purified by silica gel column (ethyl acetate/hexane=3/1 to ethyl acetate) and recrystallized from ethyl acetate to give the title compound as a colorless powder (520 mg).

NMR (CDCl$_3$) δ: 1.27 (3H, t, J=7.2), 1.33 (3H, t, J=7.0), 3.48-3.53 (2H, m), 3.77-3.82 (2H, m), 4.22 (2H, q, J=7.0), 4.34 (2H, t, J=5.1), 5.48 (2H, s), 6.12 (1H, brs), 6.58-6.72 (3H, m), 7.20 (1H, m), 7.63 (1H, brt, J=5.0), 7.67 (2H, d, J=8.7), 7.92 (2H, d, J=8.7).

Example 515

1-{4-[(ethylamino)carbonyl]phenyl}-N-(2-hydroxyethyl)-5-[(3-methylphenoxy)methyl]-1H-1,2,3-triazole-4-carboxamide

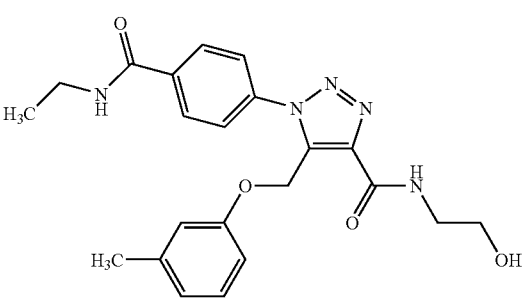

515a) ethyl 1-{4-[(ethylamino)carbonyl]phenyl}-5-[(3-methylphenoxy)methyl]-1H-1,2,3-triazole-4-carboxylate In the same manner as in Example 414, the title compound was obtained as a colorless powder (1.1 g).

NMR (CDCl$_3$) δ: 1.28 (3H, t, J=7.2), 1.42 (3H, t, J=7.6), 2.31 (3H, s), 3.46-3.57 (2H, m), 4.47 (2H, q, J=7.6), 5.35 (2H, s), 6.18 (1H, brs), 6.65-6.69 (2H, m), 6.82 (1H, d, J=7.5), 7.16 (1H, m), 7.67 (2H, d, J=8.4), 7.92 (2H, d, J=8.4).

515b) 1-{4-[(ethylamino)carbonyl]phenyl}-N-(2-hydroxyethyl)-5-[(3-methylphenoxy)methyl]-1H-1,2,3-triazole-4-carboxamide A mixture of ethyl 1-{4-[(ethylamino)carbonyl]phenyl}-5-[(3-methylphenoxy)methyl]-1H-1,2,3-triazole-4-carboxylate (720 mg) obtained in Example 515a) and ethanolamine (2.5 ml) was heated at 50° C. for 14 hr. Water was added to the reaction mixture, and the mixture was extracted with chloroform, and washed with saturated brine. The organic layer was dried over anhydrous sodium sulfate, and the solvent was evaporated under reduced pressure. The residue was purified by silica gel column (ethyl acetate to ethyl acetate/methanol=95/5) and recrystallized from ethyl acetate to give the title compound as a colorless powder (680 mg).

NMR (CDCl$_3$) δ: 1.27 (3H, t, J=7.2), 2.29 (3H, s), 2.80 (1H, t, J=5.1), 3.47-3.56 (2H, m), 3.63-3.69 (2H, m), 3.83-3.88 (2H, m), 5.45 (2H, s), 6.23 (1H, brs), 6.65-6.69 (2H, m), 6.78 (1H, d, J=8.1), 7.13 (1H, t, J=7.2), 7.67 (2H, d, J=8.7), 7.77 (1H, m), 7.91 (2H, d, J=8.7).

Example 516

5-[(3-chlorophenoxy)methyl]-1-{4-[(ethylamino)carbonyl]phenyl}-N-(2-hydroxyethyl)-1H-1,2,3-triazole-4-carboxamide

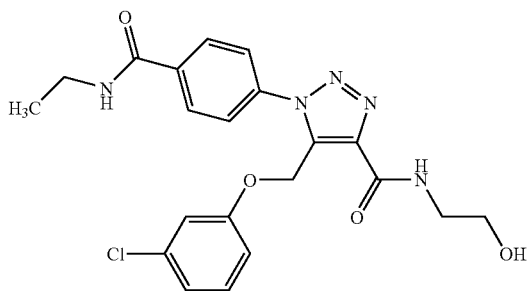

In the same manner as in Example 515, the title compound was obtained.

NMR (DMSO-$d_6$) δ: 1.14 (3H, t, J=7.2), 3.27-3.40 (4H, m), 3.52-3.58 (2H, m), 4.80 (1H, t, J=5.4), 5.56 (2H, s), 6.85 (1H, m), 7.02-7.04 (2H, m), 7.29 (1H, t, J=8.4), 7.76 (2H, d, J=8.7), 8.06 (2H, d, J=8.7), 8.68 (1H, t, J=5.1), 8.74 (1H, t, J=5.4).

Example 517

5-[(3-tert-butylphenoxy)methyl]-1-{4-[(ethylamino)carbonyl]phenyl}-N-(2-hydroxyethyl)-1H-1,2,3-triazole-4-carboxamide

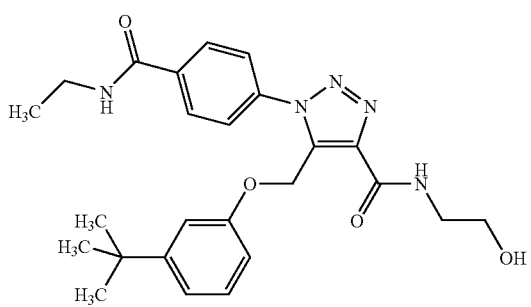

In the same manner as in Example 515, the title compound was obtained.

NMR (DMSO-$d_6$) δ: 1.13 (3H, t, J=6.9), 1.19 (9H, s), 3.28-3.41 (4H, m), 3.51-3.57 (2H, m), 4.80 (1H, t, J=5.4), 5.59 (2H, s), 6.62 (1H, m), 6.75 (1H, m), 6.94 (1H, d, J=8.1), 7.15 (1H, t, J=8.4), 7.75 (2H, d, J=8.7), 8.04 (2H, d, J=8.7), 8.65-8.73 (2H, m).

Example 518

5-[(biphenyl-3-yloxy)methyl]-1-{4-[(ethylamino)carbonyl]phenyl}-N-(2-hydroxyethyl)-1H-1,2,3-triazole-4-carboxamide

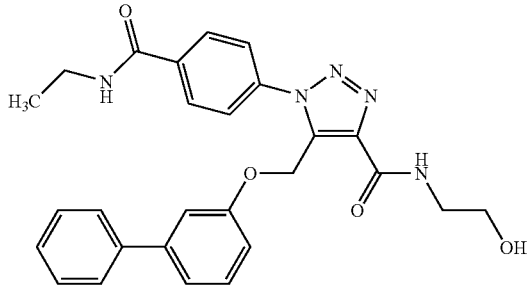

In the same manner as in Example 515, the title compound was obtained.

NMR (CDCl$_3$) δ: 1.26 (3H, t, J=7.1), 2.57 (1H, t, J=5.0), 3.48-3.56 (2H, m), 3.64-3.69 (2H, m), 3.83-3.87 (2H, m), 5.58 (2H, s), 6.14 (1H, brt, J=5.2), 6.85 (1H, m), 6.88 (1H, m), 7.10-7.55 (7H, m), 7.72 (2H, d, J=8.7), 7.91 (1H, brt, J=5.1), 7.93 (2H, d, J=8.7).

Example 519

1-{4-[(ethylamino)carbonyl]phenyl}-N-(2-hydroxyethyl)-5-[(3-phenoxyphenoxy)methyl]-1H-1,2,3-triazole-4-carboxamide

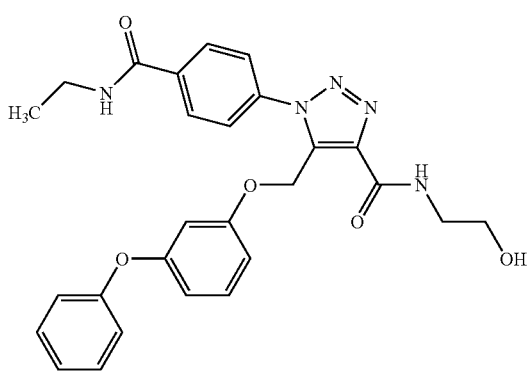

In the same manner as in Example 515, the title compound was obtained.

NMR (CDCl$_3$) δ: 1.28 (3H, t, J=7.2), 2.57 (1H, t, J=5.1), 3.48-3.53 (2H, m), 3.58-3.67 (2H, m), 3.82-3.86 (2H, m), 5.45 (2H, s), 6.15 (1H, brt, J=5.2), 6.51 (1H, m), 6.59-6.64 (2H, m), 6.97-7.33 (6H, m), 7.65 (2H, d, J=8.7), 7.87 (1H, brt, J=5.1), 7.90 (2H, d, J=8.7).

Example 520

5-[(biphenyl-3-yloxy)methyl]-N-cyclopropyl-1-{4-[(ethylamino)carbonyl]phenyl}-1H-1,2,3-triazole-4-carboxamide

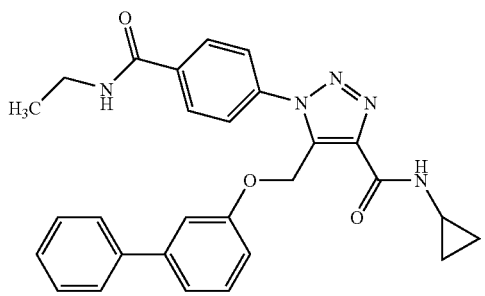

In the same manner as in Example 414, the title compound was obtained.

NMR (CDCl₃) δ: 0.66-0.71 (2H, m), 0.86-0.93 (2H, m), 1.26 (3H, t, J=7.1), 2.91 (1H, m), 3.46-3.56 (2H, m), 5.60 (2H, s), 6.09 (1H, brs), 6.87 (1H, m), 7.08 (1H, m), 7.09-7.55 (8H, m), 7.70 (2H, d, J=8.7), 7.91 (2H, d, J=8.7).

Example 521

5-[(3-anilinophenoxy)methyl]-1-{4-[(ethylamino)carbonyl]phenyl}-N-(2-hydroxyethyl)-1H-1,2,3-triazole-4-carboxamide

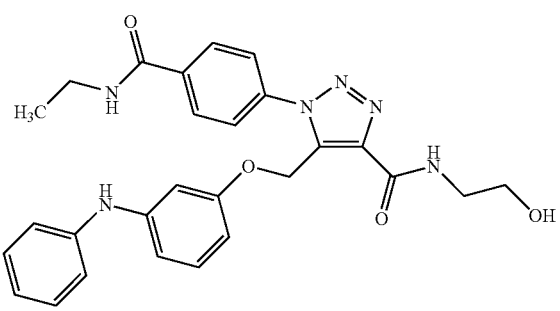

In the same manner as in Example 515, the title compound was obtained.

NMR (DMSO-d₆) δ: 1.13 (3H, t, J=7.2), 3.26-3.40 (4H, m), 3.50-3.56 (2H, m), 4.80 (1H, t, J=5.1), 5.52 (2H, s), 6.32 (1H, m), 6.44 (1H, s), 6.62 (1H, d, J=8.4), 6.82 (1H, t, J=5.2), 7.00-7.24 (5H, m), 7.76 (2H, d, J=8.7), 8.03 (2H, d, J=8.7), 8.17 (1H, s), 8.66-8.73 (2H, m).

Example 522

N-cyclopropyl-1-{4-[(ethylamino)carbonyl]phenyl}-5-{3-[4-(trifluoromethoxy)phenoxy]propyl}-1H-1,2,3-triazole-4-carboxamide

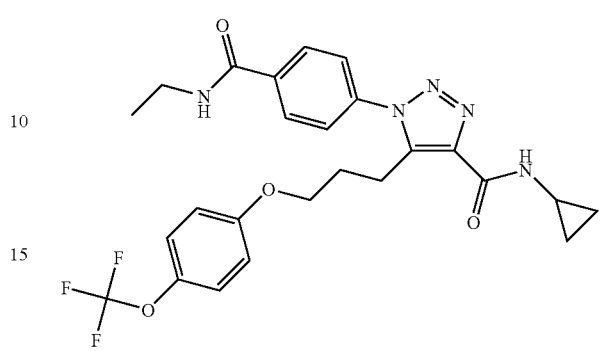

To a solution of 4-(trifluoromethoxy)phenol (52 mg) in toluene (0.5 ml) was added a solution of tributylphosphine (51 mg) in toluene (0.5 ml) under stirring, a solution of N-cyclopropyl-1-{4-[(ethylamino)carbonyl]phenyl}-5-(3-hydroxypropyl)-1H-1,2,3-triazole-4-carboxamide (29 mg) in toluene (0.5 ml) and a solution of 1,1'-[(E)-diazene-1,2-diyl-dicarbonyl]dipiperidine in toluene (0.5 ml) were successively added, and the mixture was stirred at room temperature for 64 hr. The reaction mixture was filtered through a filter tube (Biospin column, Bio-Rad), and washed with 1 ml of ethyl acetate. The filtrates were combined, 1 ml of ethyl acetate and 1 ml of saturated aqueous sodium hydrogen carbonate solution were added, and the mixture was vigorously stirred at room temperature for 30 min. The organic layer was recovered using Presep™ Dehydration (Wako Pure Chemical Industries, Ltd.) and concentrated to dryness. The residue was dissolved in DMSO (0.7 ml) and purified by preparative HPLC (Gilson, Inc., high-throughput purification system, column: YMC CombiPrep ODS-A S-5 μm, 50×20 mm, solvent: solution A; 0.1% formic acid aqueous solution, solution B; 0.1% formic acid acetonitrile solution, gradient cycle: 0 min (solution A/solution B=95/5), 1.00 min (solution A/solution B=95/5), 5.20 min (solution A/solution B=5/95), 6.40 min (solution A/solution B=5/95), 6.50 min (solution A/solution B=95/5), 6.60 min (solution A/solution B=95/5), flow rate: 25 ml/min, detection method: UV 220 nm) to give the title compound (27 mg) (LC/MS purity 100%, ESI+:518 [M+H]⁺).

Example 523

N-cyclopropyl-1-{4-[(ethylamino)carbonyl]phenyl}-5-{3-[(2-oxo-1,3-benzoxathiol-5-yl)oxy]propyl}-1H-1,2,3-triazole-4-carboxamide

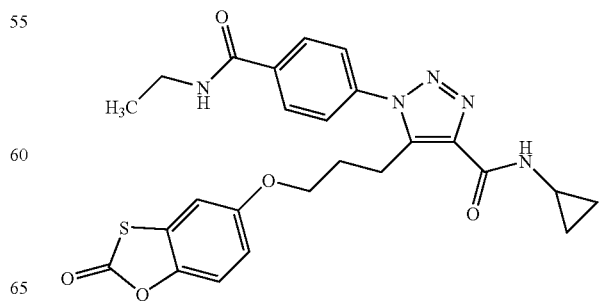

In the same manner as in Example 522, the title compound (25 mg, LC/MS purity 100%, ESI+:508 [M+H]+) was obtained.

Example 524

N-cyclopropyl-5-(3-{3-[1-(dimethylamino)ethyl]phenoxy}propyl)-1-{4-[(ethylamino)carbonyl]phenyl}-1H-1,2,3-triazole-4-carboxamide

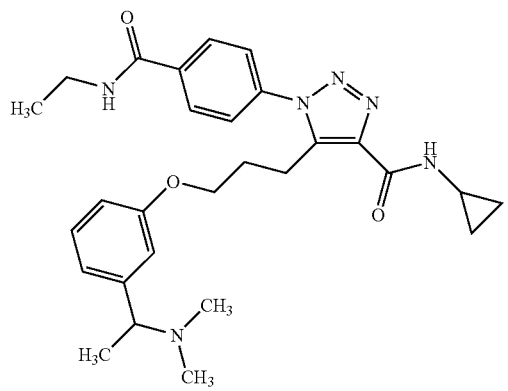

In the same manner as in Example 522, the title compound was obtained as a formate (32 mg, LC/MS purity 100%, ESI+:505 [M+H]+).

Example 525

N-cyclopropyl-1-{4-[(ethylamino)carbonyl]phenyl}-5-(3-{[6-methyl-2-(methylthio)pyrimidin-4-yl]oxy}propyl)-1H-1,2,3-triazole-4-carboxamide

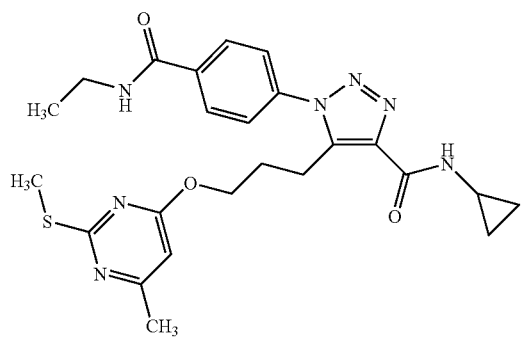

In the same manner as in Example 522, the title compound (52 mg, LC/MS purity 100%, ESI+:496 [M+H]+) was obtained.

Example 526

N-cyclopropyl-5-(3-{[2-(dimethylamino)-6-methylpyrimidin-4-yl]oxy}propyl)-1-{4-[(ethylamino)carbonyl]phenyl}-1H-1,2,3-triazole-4-carboxamide

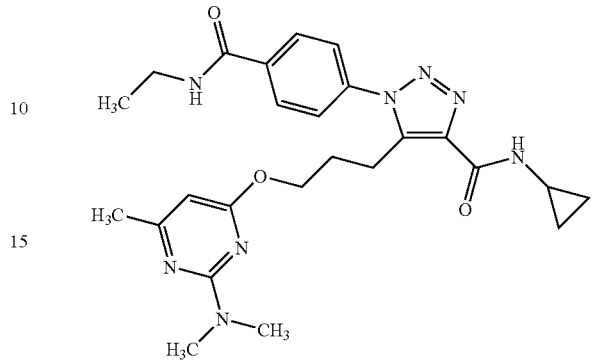

In the same manner as in Example 522, the title compound (23 mg, LC/MS purity 100%, ESI+:493 [M+H]+) was obtained.

Example 527

N-cyclopropyl-1-{4-[(ethylamino)carbonyl]phenyl}-5-[3-(1H-pyrazolo[4,3-d]pyrimidine-7-yloxy)propyl]-1H-1,2,3-triazole-4-carboxamide

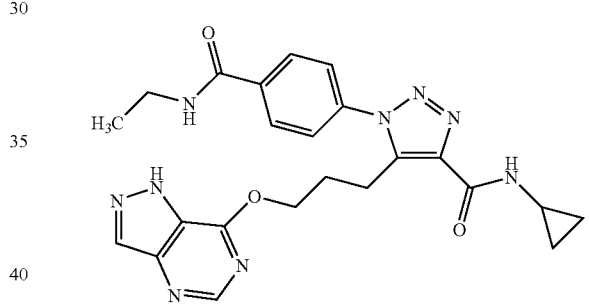

In the same manner as in Example 522, the title compound (4.7 mg, LC/MS purity 100%, ESI+:476 [M+H]+) was obtained.

Example 528 methyl 3-{4-[3-(4-[(cyclopropylamino)carbonyl]-1-{4-[(ethylamino)carbonyl]phenyl}-1H-1,2,3-triazol-5-yl)propoxy]phenyl}-3-oxopropanate

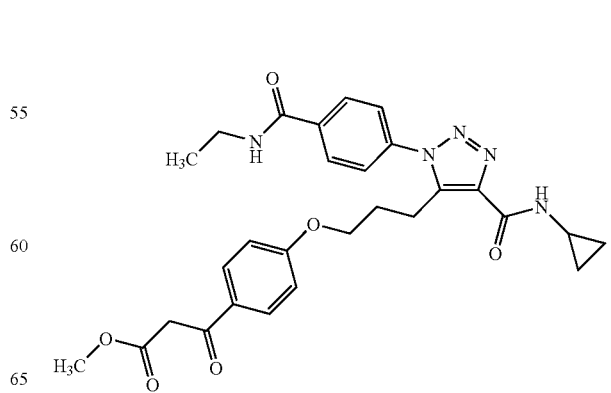

In the same manner as in Example 522, the title compound (34 mg, LC/MS purity 100%, ESI+:534 [M+H]+) was obtained.

Example 529

N-cyclopropyl-5-{3-[4-(2,5-dioxoimidazolidin-4-yl)phenoxy]propyl}-1-{4-[(ethylamino)carbonyl]phenyl}-1H-1,2,3-triazole-4-carboxamide

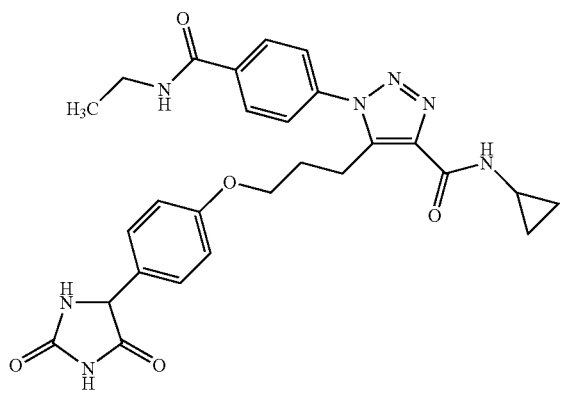

In the same manner as in Example 522, the title compound (5.1 mg, LC/MS purity 95%, ESI+:532 [M+H]+) was obtained.

Example 530

N-cyclopropyl-1-{4-[(ethylamino)carbonyl]phenyl}-5-[3-(3,4,5-trimethoxyphenoxy)propyl]-1H-1,2,3-triazole-4-carboxamide

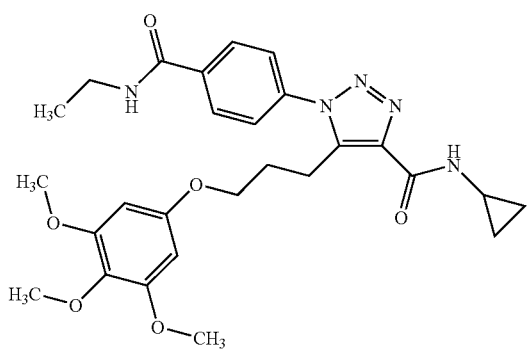

In the same manner as in Example 522, the title compound (66 mg, LC/MS purity 100%, ESI+:524 [M+H]+) was obtained.

Example 531 methyl 3-{4-[3-(4-[(cyclopropylamino)carbonyl]-1-{4-[(ethylamino)carbonyl]phenyl}-1H-1,2,3-triazol-5-yl)propoxy]phenyl}propionate

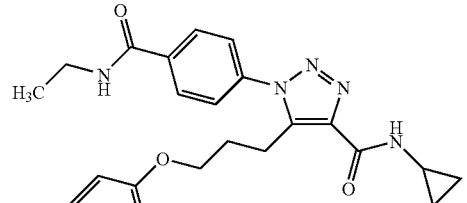

In the same manner as in Example 522, the title compound (26 mg, LC/MS purity 100%, ESI+:520 [M+H]+) was obtained.

Example 532

N-cyclopropyl-1-{4-[(ethylamino)carbonyl]phenyl}-5-{3-[3-fluoro-5-(trifluoromethyl)phenoxy]propyl}-1H-1,2,3-triazole-4-carboxamide

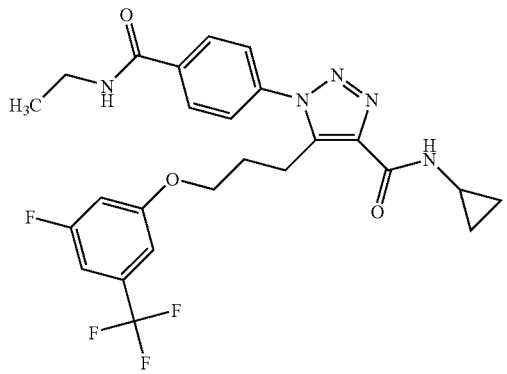

In the same manner as in Example 522, the title compound (26 mg, LC/MS purity 100%, ESI+:520 [M+H]+) was obtained.

Example 533

N-cyclopropyl-1-{4-[(ethylamino)carbonyl]phenyl}-5-{3-[(2-oxo-1,3-benzoxathiol-6-yl)oxy]propyl}-1H-1,2,3-triazole-4-carboxamide

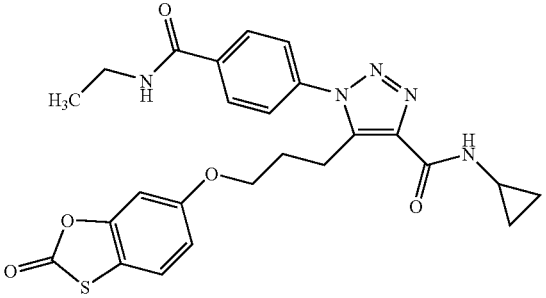

In the same manner as in Example 522, the title compound (32 mg, LC/MS purity 100%, ESI+:508 [M+H]+) was obtained.

Example 534 methyl 4-[3-(4-[(cyclopropylamino)carbonyl]-1-{4-[(ethylamino)carbonyl]phenyl}-1H-1,2,3-triazol-5-yl)propoxy]phenylacetate

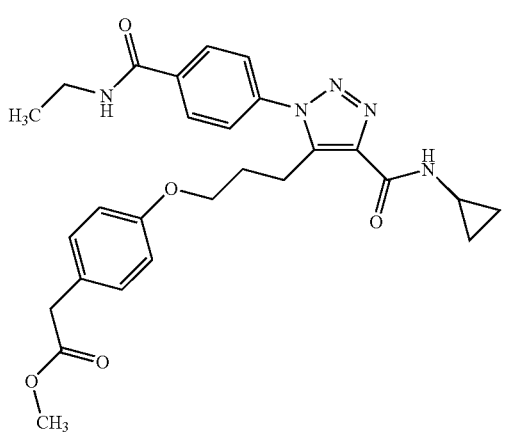

In the same manner as in Example 522, the title compound (60 mg, LC/MS purity 100%, ESI+:506 [M+H]$^+$) was obtained.

Example 535

N-cyclopropyl-1-{4-[(ethylamino)carbonyl]phenyl}-5-{3-[4-(3-oxobutyl)phenoxy]propyl}-1H-1,2,3-triazole-4-carboxamide

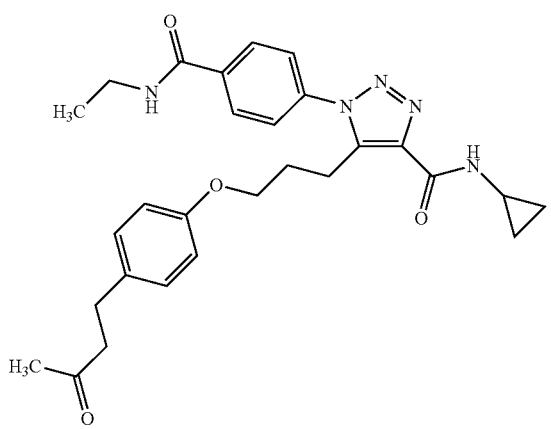

In the same manner as in Example 522, the title compound (57 mg, LC/MS purity 100%, ESI+:504 [M+H]$^+$) was obtained.

Example 536

N-cyclopropyl-1-{4-[(ethylamino)carbonyl]phenyl}-5-{3-[(2-oxo-1,2,3,4-tetrahydroquinolin-6-yl)oxy]propyl}-1H-1,2,3-triazole-4-carboxamide

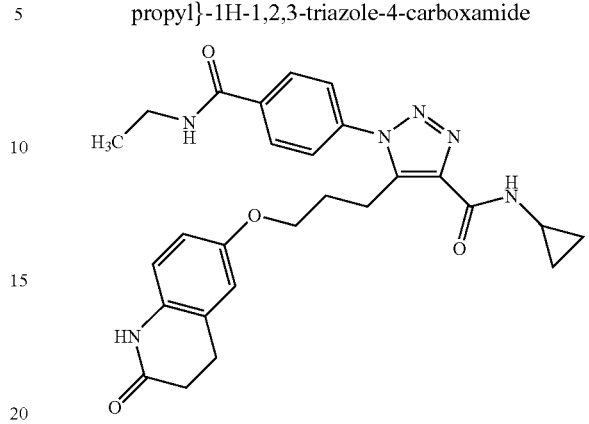

In the same manner as in Example 522, the title compound (17 mg, LC/MS purity 93%, ESI+:503 [M+H]$^+$) was obtained.

Example 537

N-cyclopropyl-1-{4-[(ethylamino)carbonyl]phenyl}-5-{3-[(2-oxo-2H-chromen-7-yl)oxy]propyl}-1H-1,2,3-triazole-4-carboxamide

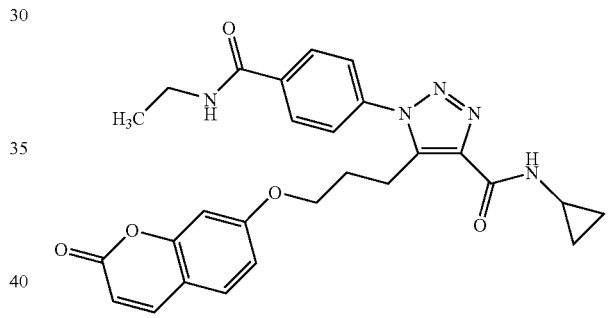

In the same manner as in Example 522, the title compound (67 mg, LC/MS purity 95%, ESI+:502 [M+H]$^+$) was obtained.

Example 538

N-cyclopropyl-1-{4-[(ethylamino)carbonyl]phenyl}-5-{3-[4-(trifluoromethyl)phenoxy]propyl}-1H-1,2,3-triazole-4-carboxamide

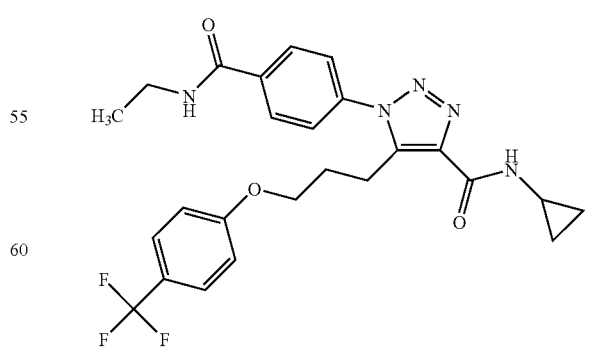

In the same manner as in Example 522, the title compound (28 mg, LC/MS purity 95%, ESI+:502 [M+H]$^+$) was obtained.

Example 539

N-cyclopropyl-1-{4-[(ethylamino)carbonyl]phenyl}-5-{3-[4-(1H-imidazol-1-yl)phenoxy]propyl}-1H-1,2,3-triazole-4-carboxamide

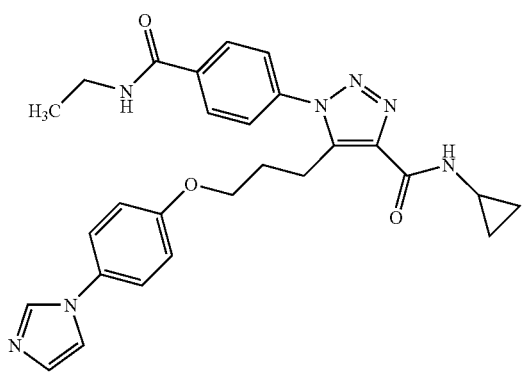

In the same manner as in Example 522, the title compound was obtained as a formate (23 mg, LC/MS purity 100%, ESI+:500 [M+H]+).

Example 540

N-cyclopropyl-5-[3-(3,5-dimethoxyphenoxy)propyl]-1-{4-[(ethylamino)carbonyl]phenyl}-1H-1,2,3-triazole-4-carboxamide

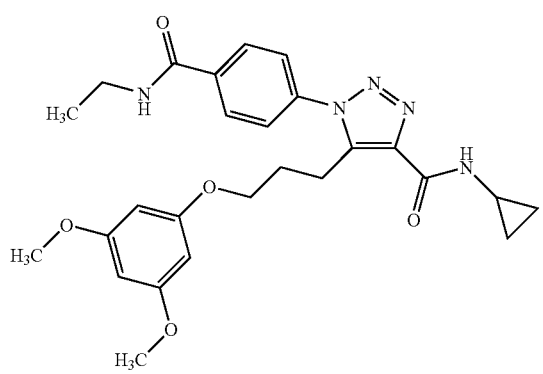

In the same manner as in Example 522, the title compound (39 mg, LC/MS purity 100%, ESI+:494 [M+H]+) was obtained.

Example 541

N-cyclopropyl-5-[3-(3,4-dimethoxyphenoxy)propyl]-1-{4-[(ethylamino)carbonyl]phenyl}-1H-1,2,3-triazole-4-carboxamide

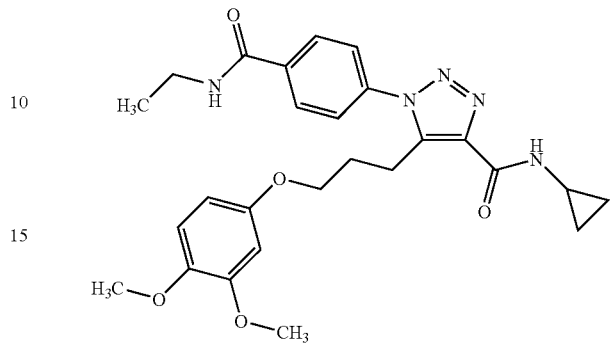

In the same manner as in Example 522, the title compound (60 mg, LC/MS purity 100%, ESI+:494 [M+H]+) was obtained.

Example 542

5-[3-(4-acetyl-3-fluorophenoxy)propyl]-N-cyclopropyl-1-{4-[(ethylamino)carbonyl]phenyl}-1H-1,2,3-triazole-4-carboxamide

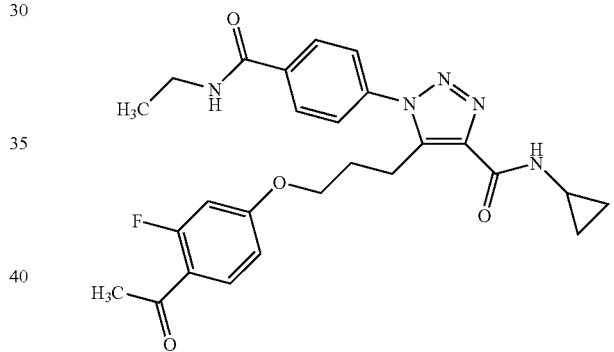

In the same manner as in Example 522, the title compound (57 mg, LC/MS purity 100%, ESI+:494 [M+H]+) was obtained.

Example 543

N-cyclopropyl-1-{4-[(ethylamino)carbonyl]phenyl}-5-{3-[(6-methyl-5-nitropyridin-2-yl)oxy]propyl}-1H-1,2,3-triazole-4-carboxamide

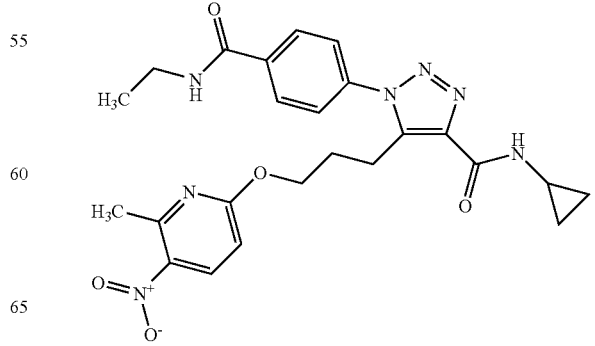

Example 544

N-cyclopropyl-1-{4-[(ethylamino)carbonyl]phenyl}-5-{3-[(4-methyl-5-nitropyridin-2-yl)oxy]propyl}-1H-1,2,3-triazole-4-carboxamide

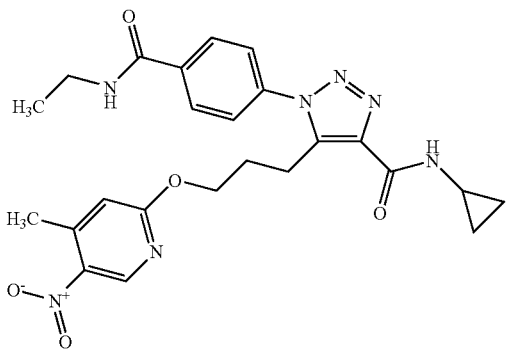

In the same manner as in Example 522, the title compound (2.3 mg, LC/MS purity 96%, ESI+:494 [M+H]$^+$) was obtained.

Example 545

5-{3-[4-(aminocarbonothioyl)phenoxy]propyl}-N-cyclopropyl-1-{4-[(ethylamino)carbonyl]phenyl}-1H-1,2,3-triazole-4-carboxamide

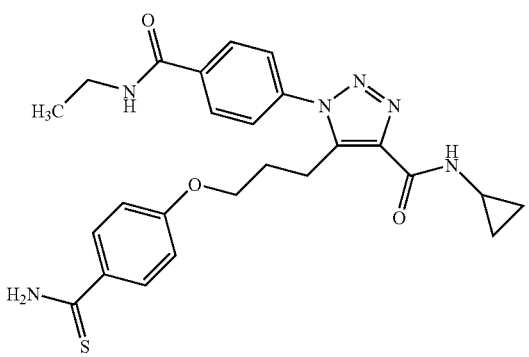

In the same manner as in Example 522, the title compound (8.2 mg, LC/MS purity 100%, ESI+:493 [M+H]$^+$) was obtained.

Example 546 methyl 5-[3-(4-[(cyclopropylamino)carbonyl]-1-{4-[(ethylamino)carbonyl]phenyl}-1H-1,2,3-triazol-5-yl)propoxy]nicotinate

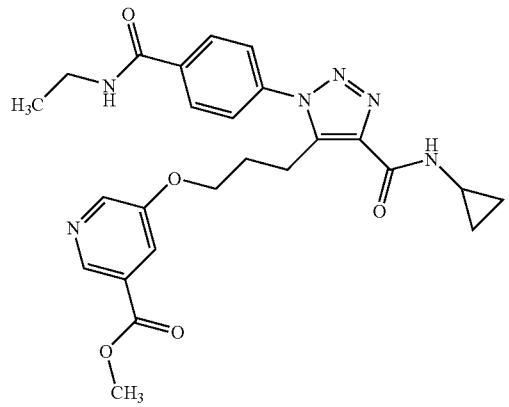

In the same manner as in Example 522, the title compound (34 mg, LC/MS purity 82%, ESI+:493 [M+H]$^+$) was obtained.

Example 547

5-(3-{3-[(aminocarbonyl)amino]phenoxy}propyl)-N-cyclopropyl-1-{4-[(ethylamino)carbonyl]phenyl}-1H-1,2,3-triazole-4-carboxamide

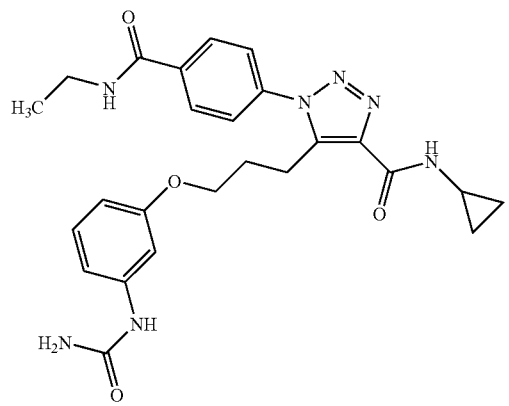

In the same manner as in Example 522, the title compound (3.6 mg, LC/MS purity 94%, ESI+:492 [M+H]$^+$) was obtained.

In the same manner as in Example 522, the title compound (19 mg, LC/MS purity 100%, ESI+:494 [M+H]$^+$) was obtained.

Example 548 methyl 4-[3-(4-[(cyclopropylamino)carbonyl]-1-{4-[(ethylamino)carbonyl]phenyl}-1H-1,2,3-triazol-5-yl)propoxy]benzoate

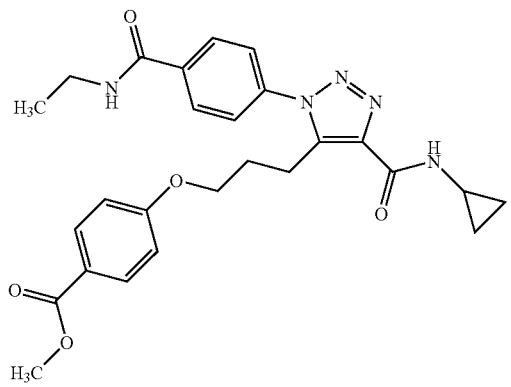

In the same manner as in Example 522, the title compound (55 mg, LC/MS purity 100%, ESI+:492 [M+H]+) was obtained.

Example 549

N-cyclopropyl-5-(3-{2-[(dimethylamino)methyl]phenoxy}propyl)-1-{4-[(ethylamino)carbonyl]phenyl}-1H-1,2,3-triazole-4-carboxamide

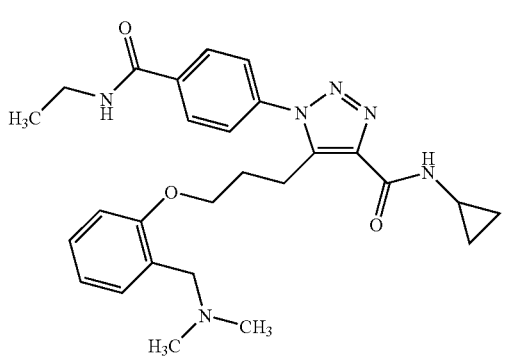

In the same manner as in Example 522, the title compound was obtained as a formate (8.6 mg, LC/MS purity 100%, ESI+:491 [M+H]+).

Example 550

5-{3-[4-(acetylamino)phenoxy]propyl}-N-cyclopropyl-1-{4-[(ethylamino)carbonyl]phenyl}-1H-1,2,3-triazole-4-carboxamide

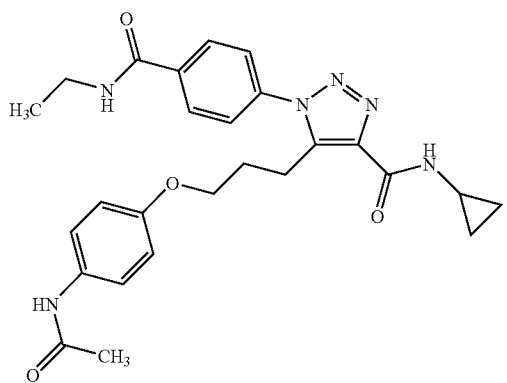

In the same manner as in Example 522, the title compound (24 mg, LC/MS purity 93%, ESI+:491 [M+H]+) was obtained.

Example 551

N-cyclopropyl-1-{4-[(ethylamino)carbonyl]phenyl}-5-{3-[(1-oxo-2,3-dihydro-1H-inden-5-yl)oxy]propyl}-1H-1,2,3-triazole-4-carboxamide

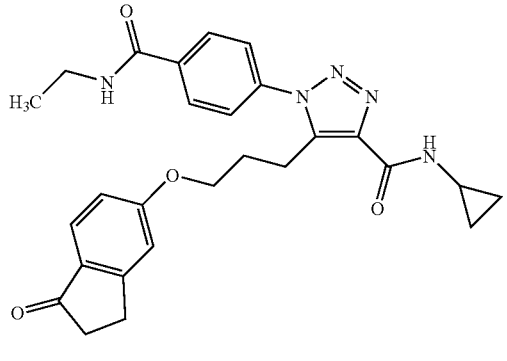

In the same manner as in Example 522, the title compound (29 mg, LC/MS purity 100%, ESI+:488 [M+H]+) was obtained.

Example 552

5-{3-[4-(2-cyanoethyl)phenoxy]propyl}-N-cyclopropyl-1-{4-[(ethylamino)carbonyl]phenyl}-1H-1,2,3-triazole-4-carboxamide

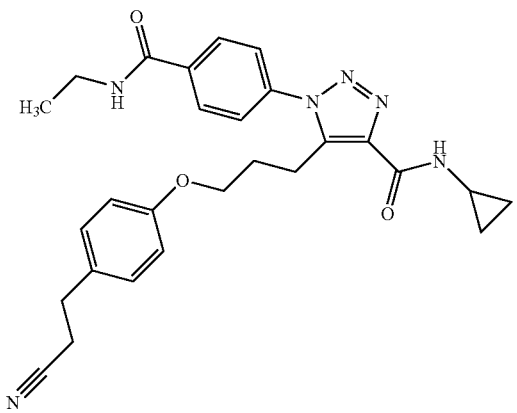

In the same manner as in Example 522, the title compound (62 mg, LC/MS purity 100%, ESI+:487 [M+H]$^+$) was obtained.

Example 553

N-cyclopropyl-1-{4-[(ethylamino)carbonyl]phenyl}-5-[3-(quinolin-6-yloxy)propyl]-1H-1,2,3-triazole-4-carboxamide

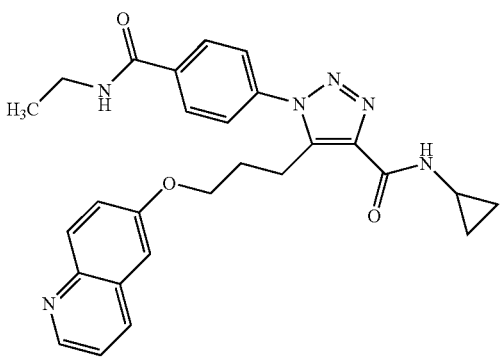

In the same manner as in Example 522, the title compound (12 mg, LC/MS purity 100%, ESI+:485 [M+H]$^+$) was obtained.

Example 554

N-cyclopropyl-1-{4-[(ethylamino)carbonyl]phenyl}-5-{3-[4-(methylthio)phenoxy]propyl}-1H-1,2,3-triazole-4-carboxamide

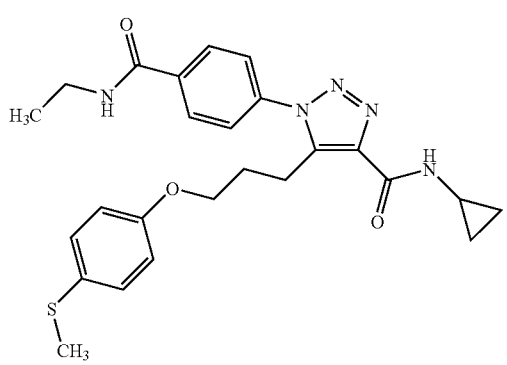

In the same manner as in Example 522, the title compound (27 mg, LC/MS purity 100%, ESI+:480 [M+H]$^+$) was obtained.

Example 555

5-[3-(1,3-benzodioxol-5-yloxy)propyl]-N-cyclopropyl-1-{4-[(ethylamino)carbonyl]phenyl}-1H-1,2,3-triazole-4-carboxamide

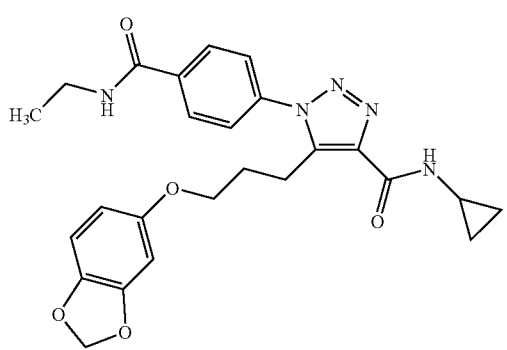

In the same manner as in Example 522, the title compound (55 mg, LC/MS purity 100%, ESI+:478 [M+H]$^+$) was obtained.

Example 556

5-{3-[4-(aminocarbonyl)phenoxy]propyl}-N-cyclopropyl-1-{4-[(ethylamino)carbonyl]phenyl}-1H-1,2,3-triazole-4-carboxamide

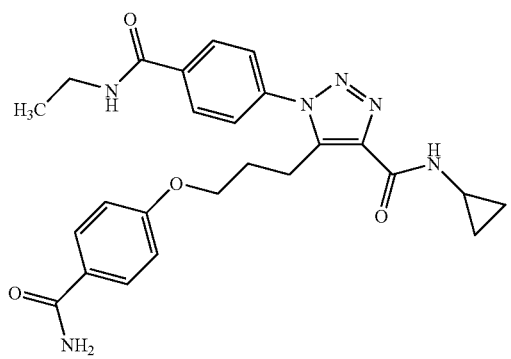

In the same manner as in Example 522, the title compound (8.5 mg, LC/MS purity 100%, ESI+:477 [M+H]$^+$) was obtained.

Example 557

5-[3-(4-acetylphenoxy)propyl]-N-cyclopropyl-1-{4-[(ethylamino)carbonyl]phenyl}-1H-1,2,3-triazole-4-carboxamide

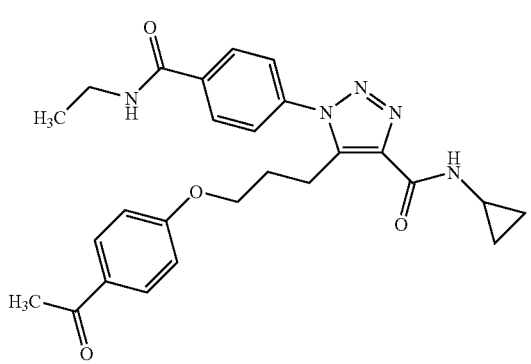

In the same manner as in Example 522, the title compound (57 mg, LC/MS purity 100%, ESI+:476 [M+H]$^+$) was obtained.

Example 558

N-cyclopropyl-1-{4-[(ethylamino)carbonyl]phenyl}-5-[3-(1H-indol-5-yloxy)propyl]-1H-1,2,3-triazole-4-carboxamide

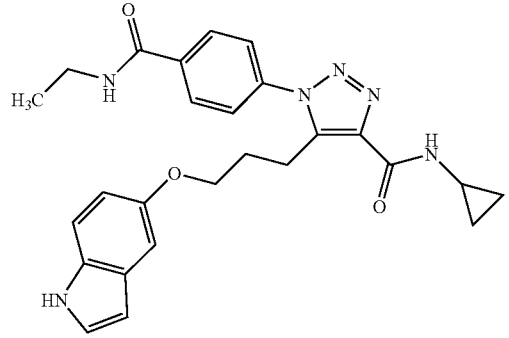

In the same manner as in Example 522, the title compound (67 mg, LC/MS purity 100%, ESI+:473 [M+H]$^+$) was obtained.

Example 559

5-{3-[4-(cyanomethyl)phenoxy]propyl}-N-cyclopropyl-1-{4-[(ethylamino)carbonyl]phenyl}-1H-1,2,3-triazole-4-carboxamide

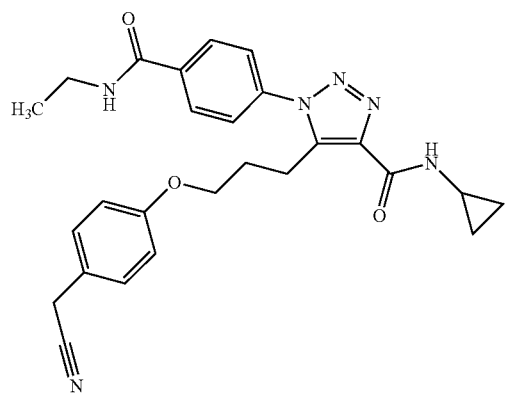

In the same manner as in Example 522, the title compound (66 mg, LC/MS purity 100%, ESI+:473 [M+H]$^+$) was obtained.

Example 560

N-cyclopropyl-5-[3-(3,4-difluorophenoxy)propyl]-1-{4-[(ethylamino)carbonyl]phenyl}-1H-1,2,3-triazole-4-carboxamide

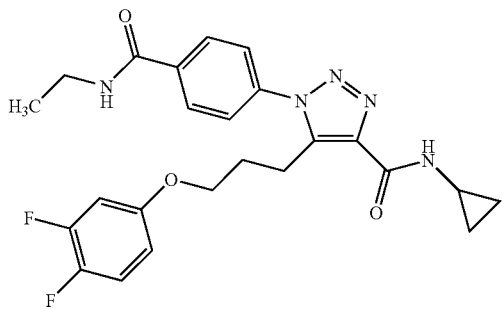

In the same manner as in Example 522, the title compound (30 mg, LC/MS purity 100%, ESI+:470 [M+H]+) was obtained.

Example 561

5-{3-[(5-chloropyridin-2-yl)oxy]propyl}-N-cyclopropyl-1-{4-[(ethylamino)carbonyl]phenyl}-1H-1,2,3-triazole-4-carboxamide

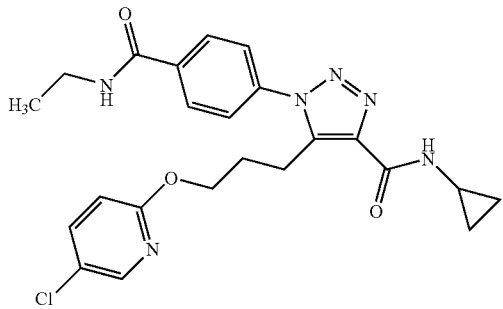

In the same manner as in Example 522, the title compound (23 mg, LC/MS purity 100%, ESI+:469 [M+H]+) was obtained.

Example 562

N-cyclopropyl-1-{4-[(ethylamino)carbonyl]phenyl}-5-[3-(4-methoxyphenoxy)propyl]-1H-1,2,3-triazole-4-carboxamide

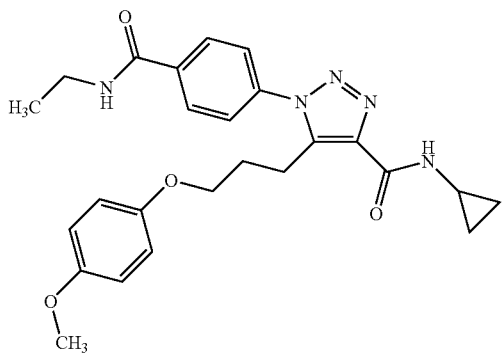

In the same manner as in Example 522, the title compound (9.7 mg, LC/MS purity 100%, ESI+:464 [M+H]+) was obtained.

Example 563

5-[3-(4-cyanophenoxy)propyl]-N-cyclopropyl-1-{4-[(ethylamino)carbonyl]phenyl}-1H-1,2,3-triazole-4-carboxamide

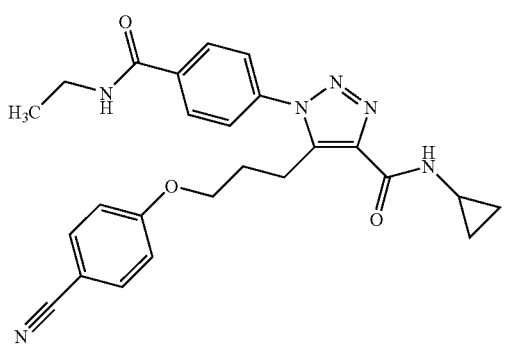

In the same manner as in Example 522, the title compound (76 mg, LC/MS purity 100%, ESI+:459 [M+H]+) was obtained.

Example 564

N-cyclopropyl-1-{4-[(ethylamino)carbonyl]phenyl}-5-[3-(4-fluorophenoxy)propyl]-1H-1,2,3-triazole-4-carboxamide

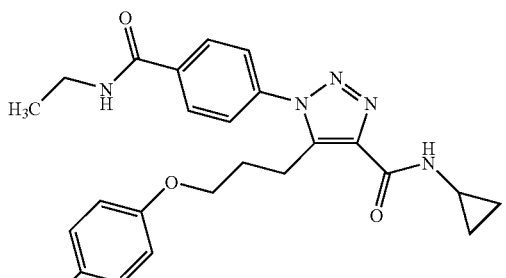

In the same manner as in Example 522, the title compound (28 mg, LC/MS purity 100%, ESI+:452 [M+H]+) was obtained.

Example 565

N-cyclopropyl-1-{4-[(ethylamino)carbonyl]phenyl}-5-{3-[(6-methylpyridin-2-yl)oxy]propyl}-1H-1,2,3-triazole-4-carboxamide

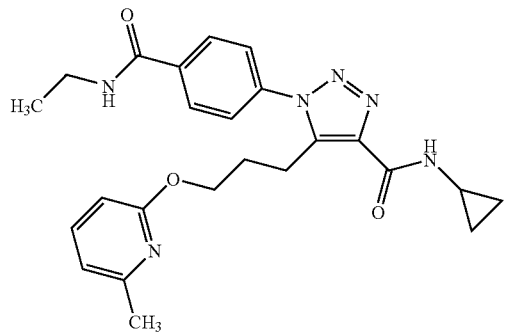

In the same manner as in Example 522, the title compound (19 mg, LC/MS purity 100%, ESI+:449 [M+H]$^+$) was obtained.

Example 566

N-cyclopropyl-1-{4-[(ethylamino)carbonyl]phenyl}-5-[3-(pyridin-2-yloxy)propyl]-1H-1,2,3-triazole-4-carboxamide

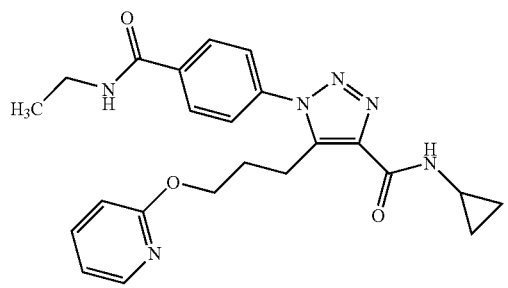

In the same manner as in Example 522, the title compound (18 mg, LC/MS purity 100%, ESI+:435 [M+H]$^+$) was obtained.

Example 567

1-[4-[(ethylamino)carbonyl]-2-(1-phenylethoxy)phenyl]-N-cyclopropyl-1H-1,2,3-triazole-4-carboxamide

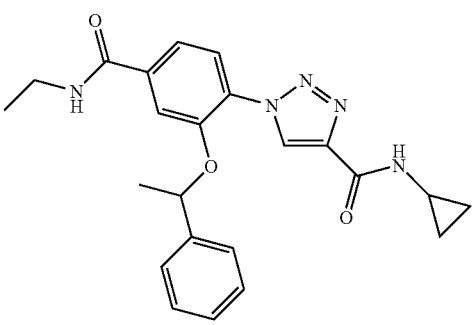

A solution (500 µl; 70 µmol) of 1-{4-[(ethylamino)carbonyl]-2-hydroxyphenyl}-N-cyclopropyl-1H-1,2,3-triazole-4-carboxamide (0.14M) in DMF, and a solution (500 µl; 105 µmol) of (1-bromoethyl)benzene (0.21M) in DMF, and a powder of potassium carbonate (30 mg) were mixed at room temperature, and the mixture was stirred for 16 hr. Water (2 ml) was added to the reaction mixture, and the mixture was extracted with dichloromethane (3 ml). The solvent was evaporated under reduced pressure, and the residue was dissolved in DMSO (1 ml) and purified by preparative HPLC (Gilson, Inc., high-throughput purification system, column: YMC CombiPrep ODS-A S-5 µm, 50×20 mm, solvent: solution A; 0.1% formic acid aqueous solution, solution B; 0.1% formic acid acetonitrile solution, gradient cycle: 0 min (solution A/solution B=95/5), 1.00 min (solution A/solution B=95/5), 5.20 min (solution A/solution B=5/95), 6.40 min (solution A/solution B=5/95), 6.50 min (solution A/solution B=95/5), 6.60 min (solution A/solution B=95/5), flow rate: 25 ml/min, detection method: UV 220 nm) to give the title compound (9.8 mg) (LC/MS purity 100%, ESI+:420 [M+H]$^+$).

The compounds described in Table 1 (Examples 568 to 676) were obtained in the same manner.

TABLE 1
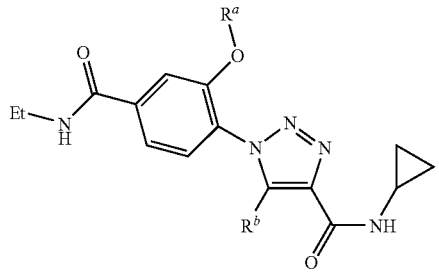
| Example No. | 568 | 569 | 570 | 571 | 572 |
|---|---|---|---|---|---|
| R$^a$ | 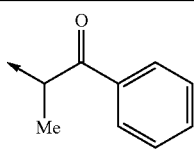 | 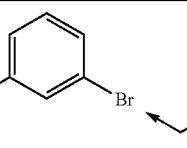 | 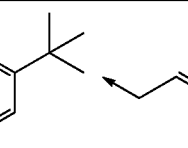 | 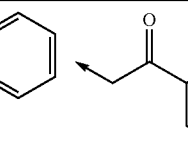 |  |
| R$^b$ | H | H | H | H | H |
| [M + H]$^+$ | 448 | 484 | 462 | 432 | 434 |
| Example No. | 573 | 574 | 575 | 576 | |
|---|---|---|---|---|---|
| R$^a$ | 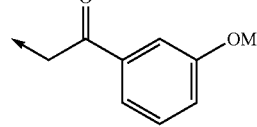 | 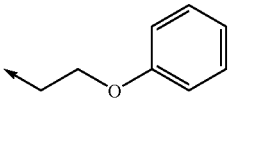 | 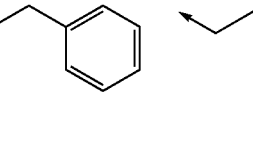 | 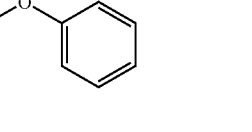 | |
| R$^b$ | H | H | H | H | |
| [M + H]$^+$ | 464 | 436 | 420 | 450 | |
| Example No. | 577 | 578 | 579 | 580 | 581 |
|---|---|---|---|---|---|
| R$^a$ | 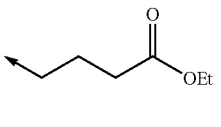 | 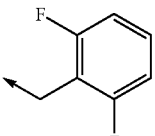 | 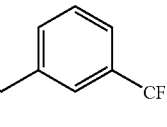 | 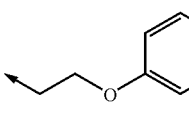 | 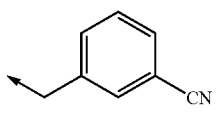 |
| R$^b$ | H | H | H | H | H |
| [M + H]$^+$ | 430 | 384 | 442 | 474 | 470 |
| Example No. | 582 | 583 | 584 | 585 | 586 |
|---|---|---|---|---|---|
| R$^a$ | 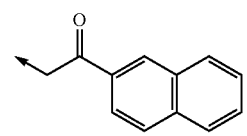 | 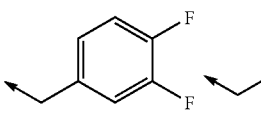 | 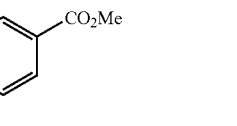 | 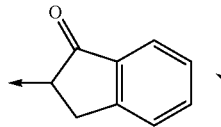 | 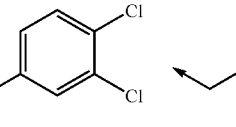 |
| R$^b$ | H | H | H | H | H |
| [M + H]$^+$ | 431 | 383 | 484 | 442 | 464 |
| Example No. | 587 | 588 | 589 | 590 | 591 |
|---|---|---|---|---|---|
| R$^a$ | 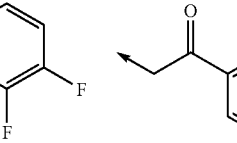 | 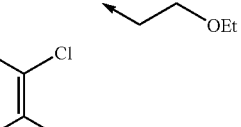 |  | | |

TABLE 1-continued
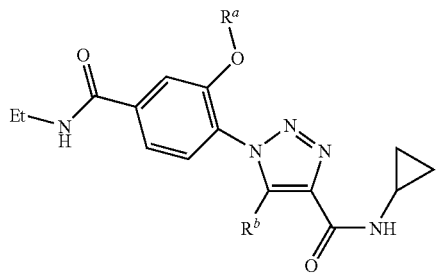
| R<sup>b</sup> [M + H]<sup>+</sup> | H 446 | H 474 | H 442 | H 502 | H 388 |
|---|---|---|---|---|---|
| Example No. | 592 | 593 | 594 | 595 | |
|---|---|---|---|---|---|
| R<sup>a</sup> | 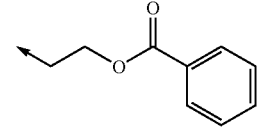 | 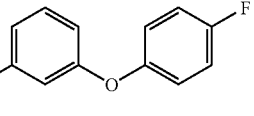 | 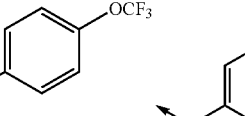 | 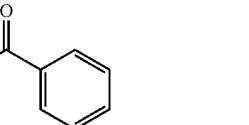 | |
| R<sup>b</sup> [M + H]<sup>+</sup> | H 464 | H 516 | H 490 | H 510 | |
| Example No. | 596 | 597 | 598 | 599 | 600 |
|---|---|---|---|---|---|
| R<sup>a</sup> | 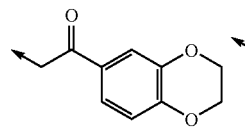 | 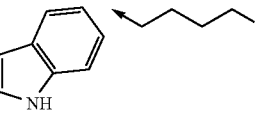 | 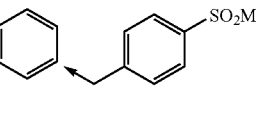 | 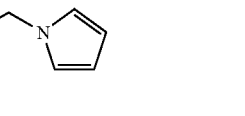 | 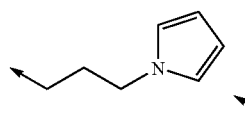 |
| R<sup>b</sup> [M + H]<sup>+</sup> | H 492 | H 459 | H 478 | H 484 | H 409 |
| Example No. | 601 | 602 | 603 | 604 | 605 |
|---|---|---|---|---|---|
| R<sup>a</sup> | 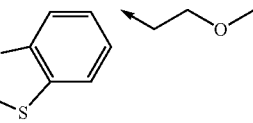 | 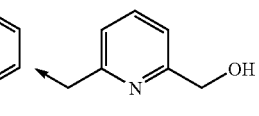 | 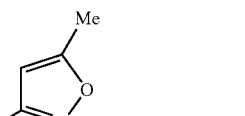 | 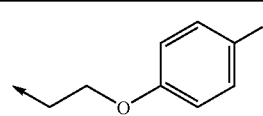 | 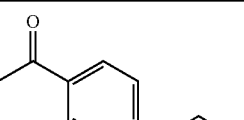 |
| R<sup>b</sup> [M + H]<sup>+</sup> | H 423 | H 463 | H 450 | H 437 | H 411 |
| Example No. | 606 | 607 | 608 | 609 | |
|---|---|---|---|---|---|
| R<sup>a</sup> | 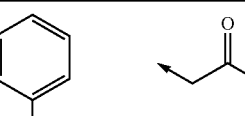 |  | | | |
| R<sup>b</sup> [M + H]<sup>+</sup> | H 454 | H 510 | H 496 | H 516 | |

TABLE 1-continued

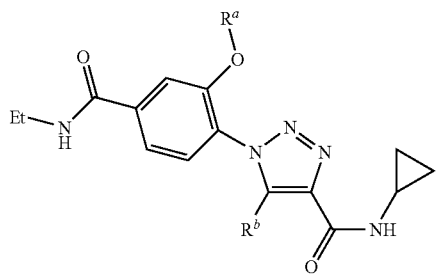

| Example No. | 610 | 611 | 612 | 613 |
|---|---|---|---|---|
| $R^a$ | (2-phenylacetamidoethyl) | (4-methoxycarbonyl-2-bromobenzyl) | (2-styryloxazol-5-yl-methyl) | (5-methyl-2-phenylthiazol-4-yl-carbonylmethyl) |
| $R^b$ | H | H | H | H |
| $[M+H]^+$ | 553 | 542 | 499 | 531 |

| Example No. | 614 | 615 | 616 | 617 |
|---|---|---|---|---|
| $R^a$ | (4-(1,3-dioxoisoindolin-2-yl)butyl) | (4-methoxycarbonylphenacyl) | (3-ethoxycarbonylimidazo[1,2-a]pyridin-2-ylmethyl) | (2-(4-methoxyphenoxy)ethyl) |
| $R^b$ | H | H | H | H |
| $[M+H]^+$ | 503 | 492 | 518 | 466 |

| Example No. | 618 | 619 | 620 |
|---|---|---|---|
| $R^a$ | (4-(4-fluorobenzoyl)benzyl) | (2'-cyanobiphenyl-4-ylmethyl) | (6-(1H-indol-3-yl)-6-oxohexyl) |
| $R^b$ | H | H | H |
| $[M+H]^+$ | 528 | 507 | 526 |

| Example No. | 621 | 622 | 623 | 624 | 625 |
|---|---|---|---|---|---|
| $R^a$ | (1-phenylethyl) | (1-methyl-2-oxo-2-phenylethyl) | (3-bromobenzyl) | (4-tert-butylbenzyl) | cinnamyl |
| $R^b$ | Me | Me | Me | Me | Me |
| $[M+H]^+$ | 434 | 462 | 498 | 476 | 446 |

TABLE 1-continued

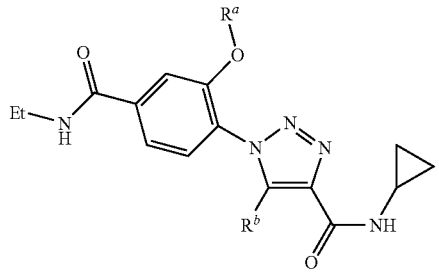

| Example No. | 626 | 627 | 628 | 629 | 630 |
|---|---|---|---|---|---|
| $R^a$ | phenacyl | 3-methoxyphenacyl | 2-phenoxyethyl | 2-phenylethyl | 3-phenoxypropyl |
| $R^b$ | Me | Me | Me | Me | Me |
| $[M+H]^+$ | 448 | 478 | 450 | 434 | 464 |

| Example No. | 631 | 632 | 633 | 634 | 635 |
|---|---|---|---|---|---|
| $R^a$ | ethoxycarbonylpropyl | pent-4-enyl | 2,6-difluorobenzyl | 3-(trifluoromethyl)benzyl | 2-(4-chlorophenoxy)ethyl |
| $R^b$ | Me | Me | Me | Me | Me |
| $[M+H]^+$ | 444 | 398 | 456 | 488 | 484 |

| Example No. | 636 | 637 | 638 | 639 | 640 |
|---|---|---|---|---|---|
| $R^a$ | 3-cyanobenzyl | 4-cyanobutyl | 1-hydroxyindan-2-yl | 2-naphthoylmethyl | 3,4-difluorobenzyl |
| $R^b$ | Me | Me | Me | Me | Me |
| $[M+H]^+$ | 445 | 397 | 462 | 498 | 456 |

| Example No. | 641 | 642 | 643 | 644 | 645 |
|---|---|---|---|---|---|
| $R^a$ | 4-(methoxycarbonyl)benzyl | 1-oxoindan-2-yl | 3,4-dichlorobenzyl | 2,3-difluorobenzyl | 3,4-dichlorophenacyl |
| $R^b$ | Me | Me | Me | Me | Me |
| $[M+H]^+$ | 478 | 460 | 488 | 456 | 516 |

TABLE 1-continued

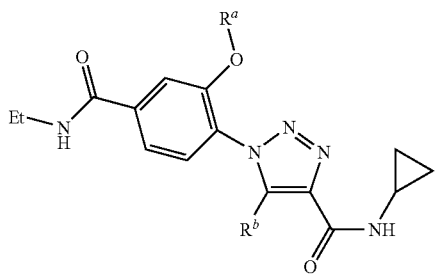

| Example No. | 646 | 647 | 648 | 649 |
|---|---|---|---|---|
| R$^a$ | CH$_2$CH$_2$OEt | 4-CN-C$_6$H$_4$-C(O)CH$_2$- | PhC(O)OCH$_2$CH$_2$- | 3-(4-F-benzyl)benzyl |
| R$^b$ | Me | Me | Me | Me |
| [M + H]$^+$ | 402 | 473 | 478 | 530 |

| Example No. | 650 | 651 | 652 | 653 |
|---|---|---|---|---|
| R$^a$ | 4-OCF$_3$-benzyl | 4-benzoylbenzyl | 2-(1H-indol-3-yl)ethyl | 4-(benzyloxy)butyl |
| R$^b$ | Me | Me | Me | Me |
| [M + H]$^+$ | 504 | 524 | 473 | 492 |

| Example No. | 654 | 655 | 656 | 657 | 658 |
|---|---|---|---|---|---|
| R$^a$ | 4-SO$_2$Me-benzyl | 2-(1H-pyrrol-1-yl)ethyl | 3-(1H-pyrrol-1-yl)propyl | benzothiazol-2-ylmethyl | 2-(benzyloxy)ethyl |
| R$^b$ | Me | Me | Me | Me | Me |
| [M + H]$^+$ | 423 | 437 | 477 | 464 | 498 |

| Example No. | 659 | 660 | 661 | 662 |
|---|---|---|---|---|
| R$^a$ | (6-(hydroxymethyl)pyridin-2-yl)methyl | (5-methylisoxazol-3-yl)methyl | 2-(4-fluorophenoxy)ethyl | (biphenyl-4-yl)C(O)CH$_2$- |
| R$^b$ | Me | Me | Me | Me |
| [M + H]$^+$ | 451 | 425 | 468 | 524 |

TABLE 1-continued
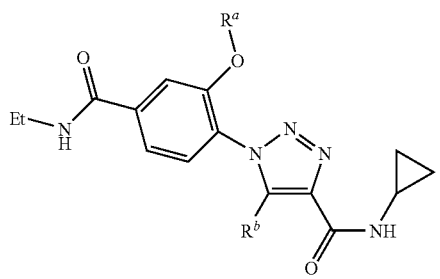
| Example No. | 663 | 664 | 665 |
|---|---|---|---|
| $R^a$ | | | |
| $R^b$ | Me | Me | Me |
| $[M + H]^+$ | 510 | 530 | 567 |
| Example No. | 666 | 667 | 668 | 669 |
|---|---|---|---|---|
| $R^a$ | | | | |
| $R^b$ | Me | Me | Me | Me |
| $[M + H]^+$ | 568 | 556 | 513 | 539 |
| Example No. | 670 | 671 | 672 | 673 |
|---|---|---|---|---|
| $R^a$ | | | | |
| $R^b$ | Me | Me | Me | Me |
| $[M + H]^+$ | 545 | 517 | 532 | 480 |
| Example No. | 674 | 675 | 676 |
|---|---|---|---|
| $R^a$ | | | |
| $R^b$ | Me | Me | Me |
| $[M + H]^+$ | 542 | 521 | 543 |

Example 677

1-(2-[(6-fluorohexyl)oxy]-4-{[(2,2,2-trifluoroethyl)amino]carbonyl}phenyl)-N-isopropyl-1H-1,2,3-triazole-4-carboxamide

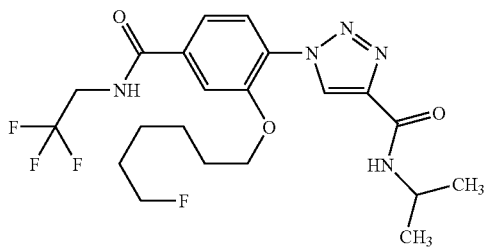

To a solution of 1-(2-[(6-fluorohexyl)oxy]-4-{[(2,2,2-trifluoroethyl)amino]carbonyl}phenyl)-1H-1,2,3-triazole-4-carboxylic acid (26 mg, 0.06 mmol) obtained in Reference Example in N,N-dimethylformamide (0.5 mL) were added a solution of isopropylamine (6 mg, 0.10 mmol) in N,N-dimethylformamide (0.5 mL), and further, 1-ethyl-3-(3-dimethylaminopropyl)carbodiimide hydrochloride (19 mg, 0.10 mmol) and a solution of 1-hydroxybenzotriazole (14 mg, 0.10 mmol) in N,N-dimethylformamide (0.5 mL), and the mixture was stirred at room temperature for 3 days. Dichloromethane (3 mL) and saturated aqueous sodium hydrogen carbonate solution (2 mL) were added to the reaction mixture and, after stirring for 10 min, the aqueous layer was removed. Water (2 mL) was added and, after stirring for 10 min, the organic layer was passed through a PTFE tube (polytetrafluoroethylene membrane tube) to give a solution containing the object compound. The solvent was evaporated under reduced pressure, and the residue was dissolved in DMSO (1 ml), and purified by preparative HPLC (Gilson, Inc., high-throughput purification system, column: YMC CombiPrep ODS-A S-5 μm, 50×20 mm, solvent: solution A; 0.1% formic acid aqueous solution, solution B; 0.1% formic acid acetonitrile solution, gradient cycle: 0 min (solution A/solution B=95/5), 1.00 min (solution A/solution B=95/5), 5.20 min (solution A/solution B=5/95), 6.40 min (solution A/solution B=5/95), 6.50 min (solution A/solution B=95/5), 6.60 min (solution A/solution B=95/5), flow rate: 25 ml/min, detection method: UV 220 nm) to give the title compound (17.4 mg) (LC/MS purity 100%, ESI+:474 [M+H]$^+$).

In the same manner as in Example 677, the compounds described in Table 2 (Examples 678 to 1189) were obtained.

TABLE 2

| Example No. | Compound name | yield | [M + H]$^+$ |
|---|---|---|---|
| 678 | 1-(2-[(6-fluorohexyl)oxy]-4-{[(2,2,2-trifluoroethyl)amino]carbonyl}phenyl)-N-(2-phenoxyethyl)-1H-1,2,3-triazole-4-carboxamide | 24.3 mg | 552 |
| 679 | N-(tert-butyl)-1-(2-[(6-fluorohexyl)oxy]-4-{[(2,2,2-trifluoroethyl)amino]carbonyl}phenyl)-1H-1,2,3-triazole-4-carboxamide | 18.3 mg | 488 |
| 680 | 1-(2-[(6-fluorohexyl)oxy]-4-{[(2,2,2-trifluoroethyl)amino]carbonyl}phenyl)-N-(3-hydroxypropyl)-1H-1,2,3-triazole-4-carboxamide | 19.7 mg | 490 |
| 681 | 1-(2-[(6-fluorohexyl)oxy]-4-{[(2,2,2-trifluoroethyl)amino]carbonyl}phenyl)-N-(2-hydroxy-1-methylethyl)-1H-1,2,3-triazole-4-carboxamide | 19 mg | 490 |
| 682 | N-cyclopentyl-1-(2-[(6-fluorohexyl)oxy]-4-{[(2,2,2-trifluoroethyl)amino]carbonyl}phenyl)-1H-1,2,3-triazole-4-carboxamide | 12.9 mg | 500 |
| 683 | N-(2-ethoxyethyl)-1-(2-[(6-fluorohexyl)oxy]-4-{[(2,2,2-trifluoroethyl)amino]carbonyl}phenyl)-1H-1,2,3-triazole-4-carboxamide | 22.6 mg | 504 |
| 684 | 1-(2-[(6-fluorohexyl)oxy]-4-{[(2,2,2-trifluoroethyl)amino]carbonyl}phenyl)-N-(2-hydroxy-1,1-dimethylethyl)-1H-1,2,3-triazole-4-carboxamide | 18.7 mg | 504 |
| 685 | 1-(2-[(6-fluorohexyl)oxy]-4-{[(2,2,2-trifluoroethyl)amino]carbonyl}phenyl)-N-(4-hydroxybutyl)-1H-1,2,3-triazole-4-carboxamide | 17.3 mg | 504 |
| 686 | 1-(2-[(6-fluorohexyl)oxy]-4-{[(2,2,2-trifluoroethyl)amino]carbonyl}phenyl)-N-(tetrahydrofuran-2-ylmethyl)-1H-1,2,3-triazole-4-carboxamide | 15.7 mg | 516 |
| 687 | N-[2-(acetylamino)ethyl]-1-(2-[(6-fluorohexyl)oxy]-4-{[(2,2,2-trifluoroethyl)amino]carbonyl}phenyl)-1H-1,2,3-triazole-4-carboxamide | 18.4 mg | 517 |
| 688 | 1-(2-[(6-fluorohexyl)oxy]-4-{[(2,2,2-trifluoroethyl)amino]carbonyl}phenyl)-N-[1-(methoxymethyl)propyl]-1H-1,2,3-triazole-4-carboxamide | 21.6 mg | 518 |

TABLE 2-continued

| Example No. | Compound name | yield | [M + H]+ |
|---|---|---|---|
| 689 | N-(3-ethoxypropyl)-1-(2-[(6-fluorohexyl)oxy]-4-{[(2,2,2-trifluoroethyl)amino]carbonyl}phenyl)-1H-1,2,3-triazole-4-carboxamide | 22.6 mg | 518 |
| 690 | 1-(2-[(6-fluorohexyl)oxy]-4-{[(2,2,2-trifluoroethyl)amino]carbonyl}phenyl)-N-[2-(2-hydroxyethoxy)ethyl]-1H-1,2,3-triazole-4-carboxamide | 20.3 mg | 520 |
| 691 | N-(3-amino-3-oxopropyl)-1-(2-[(6-fluorohexyl)oxy]-4-{[(2,2,2-trifluoroethyl)amino]carbonyl}phenyl)-1H-1,2,3-triazole-4-carboxamide | 9.9 mg | 503 |
| 692 | N-(3-fluorobenzyl)-1-(2-[(6-fluorohexyl)oxy]-4-{[(2,2,2-trifluoroethyl)amino]carbonyl}phenyl)-1H-1,2,3-triazole-4-carboxamide | 20.5 mg | 540 |
| 693 | 1-(2-[(6-fluorohexyl)oxy]-4-{[(2,2,2-trifluoroethyl)amino]carbonyl}phenyl)-N-[2-(2-thienyl)ethyl]-1H-1,2,3-triazole-4-carboxamide | 24.5 mg | 542 |
| 694 | 1-(2-[(6-fluorohexyl)oxy]-4-{[(2,2,2-trifluoroethyl)amino]carbonyl}phenyl)-N-(2-oxoazepan-3-yl)-1H-1,2,3-triazole-4-carboxamide | 24.8 mg | 543 |
| 695 | 1-(2-[(6-fluorohexyl)oxy]-4-{[(2,2,2-trifluoroethyl)amino]carbonyl}phenyl)-N-(3-phenylpropyl)-1H-1,2,3-triazole-4-carboxamide | 26.9 mg | 550 |
| 696 | 1-(2-[(6-fluorohexyl)oxy]-4-{[(2,2,2-trifluoroethyl)amino]carbonyl}phenyl)-N-[3-(2-oxopyrrolidin-1-yl)propyl]-1H-1,2,3-triazole-4-carboxamide | 28.4 mg | 557 |
| 697 | N-[(3S,5S,7S)-1-adamantyl]-1-(2-[(6-fluorohexyl)oxy]-4-{[(2,2,2-trifluoroethyl)amino]carbonyl}phenyl)-1H-1,2,3-triazole-4-carboxamide | 24.6 mg | 566 |
| 698 | N-(benzyloxy)-1-(2-[(6-fluorohexyl)oxy]-4-{[(2,2,2-trifluoroethyl)amino]carbonyl}phenyl)-1H-1,2,3-triazole-4-carboxamide | 8.7 mg | 538 |
| 699 | 1-(2-[(6-fluorohexyl)oxy]-4-{[(2,2,2-trifluoroethyl)amino]carbonyl}phenyl)-N-[4-(methylsulfonyl)benzyl]-1H-1,2,3-triazole-4-carboxamide | 6.6 mg | 600 |
| 700 | 3-[(6-fluorohexyl)oxy]-4-{4-[(4-hydroxypiperidin-1-yl)carbonyl]-1H-1,2,3-triazol-1-yl}-N-(2,2,2-trifluoroethyl)benzamide | 24.4 mg | 516 |
| 701 | 3-[(6-fluorohexyl)oxy]-4-{4-[(3-hydroxypyrrolidin-1-yl)carbonyl]-1H-1,2,3-triazol-1-yl}-N-(2,2,2-trifluoroethyl)benzamide | 20.2 mg | 502 |
| 702 | 1-(2-[(6-fluorohexyl)oxy]-4-{[(2,2,2-trifluoroethyl)amino]carbonyl}phenyl)-N-(2-methoxyethyl)-N-methyl-1H-1,2,3-triazole-4-carboxamide | 18.1 mg | 504 |
| 703 | 1-(2-[(6-fluorohexyl)oxy]-4-{[(2,2,2-trifluoroethyl)amino]carbonyl}phenyl)-N-methoxy-N-methyl-1H-1,2,3-triazole-4-carboxamide | 14.9 mg | 476 |
| 704 | 3-[(6-fluorohexyl)oxy]-4-(4-{[(2S)-2-(methoxymethyl)pyrrolidin-1-yl]carbonyl}-1H-1,2,3-triazol-1-yl)-N-(2,2,2-trifluoroethyl)benzamide | 18.4 mg | 530 |
| 705 | 1-{1-(2-[(6-fluorohexyl)oxy]-4-{[(2,2,2-trifluoroethyl)amino]carbonyl}phenyl-1H-1,2,3-triazol-4-yl]carbonyl}piperidine-4-carboxamide | 22.1 mg | 543 |
| 706 | 4-(4-{[4-(ethylsulfonyl)piperazin-1-yl]carbonyl}-1H-1,2,3-triazol-1-yl)-3-[(6-fluorohexyl)oxy]-N-(2,2,2-trifluoroethyl)benzamide | 25.8 mg | 593 |
| 707 | N-[2-(dimethylamino)ethyl]-1-(2-[(6-fluorohexyl)oxy]-4-{[(2,2,2-trifluoroethyl)amino]carbonyl}phenyl)-1H-1,2,3-triazole-4-carboxamide | 1.8 mg | 503 |

TABLE 2-continued

| Example No. | Compound name | yield | [M + H]+ |
|---|---|---|---|
| 708 | 1-(2-[(6-fluorohexyl)oxy]-4-{[(2,2,2-trifluoroethyl)amino]carbonyl}phenyl)-N-(pyridin-2-ylmethyl)-1H-1,2,3-triazole-4-carboxamide | 20.8 mg | 523 |
| 709 | 1-(2-[(6-fluorohexyl)oxy]-4-{[(2,2,2-trifluoroethyl)amino]carbonyl}phenyl)-N-[2-(pyrrolidin-1-yl)ethyl]-1H-1,2,3-triazole-4-carboxamide | 10.4 mg | 529 |
| 710 | 1-(2-[(6-fluorohexyl)oxy]-4-{[(2,2,2-trifluoroethyl)amino]carbonyl}phenyl)-N-[2-(pyridin-2-yl)ethyl]-1H-1,2,3-triazole-4-carboxamide | 14.7 mg | 537 |
| 711 | 1-(2-[(6-fluorohexyl)oxy]-4-{[(2,2,2-trifluoroethyl)amino]carbonyl}phenyl)-N-[3-(1H-imidazol-1-yl)propyl]-1H-1,2,3-triazole-4-carboxamide | 18.4 mg | 540 |
| 712 | 1-(2-[(6-fluorohexyl)oxy]-4-{[(2,2,2-trifluoroethyl)amino]carbonyl}phenyl)-N-[2-(morpholin-4-yl)ethyl]-1H-1,2,3-triazole-4-carboxamide | 20.1 mg | 545 |
| 713 | N-[2-(diisopropylamino)ethyl]-1-(2-[(6-fluorohexyl)oxy]-4-{[(2,2,2-trifluoroethyl)amino]carbonyl}phenyl)-1H-1,2,3-triazole-4-carboxamide | 27.1 mg | 559 |
| 714 | 1-(2-[(6-fluorohexyl)oxy]-4-{[(2,2,2-trifluoroethyl)amino]carbonyl}phenyl)-N-(pyridin-2-yl)-1H-1,2,3-triazole-4-carboxamide | 3.6 mg | 509 |
| 715 | 1-(2-[(6-fluorohexyl)oxy]-4-{[(2,2,2-trifluoroethyl)amino]carbonyl}phenyl)-N-(5-methylisoxazol-3-yl)-1H-1,2,3-triazole-4-carboxamide | 1.5 mg | 513 |
| 716 | 3-[(6-fluorohexyl)oxy]-4-(4-{[4-(2-hydroxyethyl)piperazin-1-yl]carbonyl}-1H-1,2,3-triazol-1-yl)-N-(2,2,2-trifluoroethyl)benzamide | 6.4 mg | 545 |
| 717 | 4-{4-[(1,4'-bipiperidin-1'-yl)carbonyl]-1H-1,2,3-triazol-1-yl}-3-[(6-fluorohexyl)oxy]-N-(2,2,2-trifluoroethyl)benzamide | 28.6 mg | 583 |
| 718 | 4-(4-{[4-(2-ethoxyphenyl)piperazin-1-yl]carbonyl}-1H-1,2,3-triazol-1-yl)-3-[(6-fluorohexyl)oxy]-N-(2,2,2-trifluoroethyl)benzamide | 26.1 mg | 621 |
| 719 | N-[2-(ethylthio)ethyl]-1-(2-[(6-fluorohexyl)oxy]-4-{[(2,2,2-trifluoroethyl)amino]carbonyl}phenyl)-1H-1,2,3-triazole-4-carboxamide | 28.6 mg | 520 |
| 720 | 1-(2-[(6-fluorohexyl)oxy]-4-{[(2,2,2-trifluoroethyl)amino]carbonyl}phenyl)-N-(tetrahydro-2H-pyran-4-yl)-1H-1,2,3-triazole-4-carboxamide | 21.9 mg | 516 |
| 721 | 1-(2-[(6-fluorohexyl)oxy]-4-{[(2,2,2-trifluoroethyl)amino]carbonyl}phenyl)-N-[2-(methylsulfonyl)ethyl]-1H-1,2,3-triazole-4-carboxamide | 18.1 mg | 538 |
| 722 | 4-{4-[(1,1-dioxide-1,3-thiazolidin-3-yl)carbonyl]-1H-1,2,3-triazol-1-yl}-3-[(6-fluorohexyl)oxy]-N-(2,2,2-trifluoroethyl)benzamide | 5 mg | 536 |
| 723 | 1-{4-[(ethylamino)carbonyl]-2-[(6-fluorohexyl)oxy]phenyl}-N-isopropyl-1H-1,2,3-triazole-4-carboxamide | 13.1 mg | 420 |
| 724 | 1-{4-[(ethylamino)carbonyl]-2-[(6-fluorohexyl)oxy]phenyl}-N-(2-phenoxyethyl)-1H-1,2,3-triazole-4-carboxamide | 18.1 mg | 498 |
| 725 | N-(tert-butyl)-1-{4-[(ethylamino)carbonyl]-2-[(6-fluorohexyl)oxy]phenyl}-1H-1,2,3-triazole-4-carboxamide | 14.7 mg | 434 |
| 726 | 1-{4-[(ethylamino)carbonyl]-2-[(6-fluorohexyl)oxy]phenyl}-N-(3-hydroxypropyl)-1H-1,2,3-triazole-4-carboxamide | 15.1 mg | 436 |
| 727 | 1-{4-[(ethylamino)carbonyl]-2-[(6-fluorohexyl)oxy]phenyl}-N-(2-hydroxy-1- | 13.3 mg | 436 |

TABLE 2-continued

| Example No. | Compound name | yield | [M + H]+ |
|---|---|---|---|
| | methylethyl)-1H-1,2,3-triazole-4-carboxamide | | |
| 728 | N-cyclopentyl-1-{4-[(ethylamino)carbonyl]-2-[(6-fluorohexyl)oxy]phenyl}-1H-1,2,3-triazole-4-carboxamide | 13.8 mg | 446 |
| 729 | N-(2-ethoxyethyl)-1-{4-[(ethylamino)carbonyl]-2-[(6-fluorohexyl)oxy]phenyl}-1H-1,2,3-triazole-4-carboxamide | 15.2 mg | 450 |
| 730 | 1-{4-[(ethylamino)carbonyl]-2-[(6-fluorohexyl)oxy]phenyl}-N-(2-hydroxy-1,1-dimethylethyl)-1H-1,2,3-triazole-4-carboxamide | 14.1 mg | 450 |
| 731 | 1-{4-[(ethylamino)carbonyl]-2-[(6-fluorohexyl)oxy]phenyl}-N-(4-hydroxybutyl)-1H-1,2,3-triazole-4-carboxamide | 16.7 mg | 450 |
| 732 | 1-{4-[(ethylamino)carbonyl]-2-[(6-fluorohexyl)oxy]phenyl}-N-(tetrahydrofuran-2-ylmethyl)-1H-1,2,3-triazole-4-carboxamide | 16.1 mg | 462 |
| 733 | N-[2-(acetylamino)ethyl]-1-{4-[(ethylamino)carbonyl]-2-[(6-fluorohexyl)oxy]phenyl}-1H-1,2,3-triazole-4-carboxamide | 14.1 mg | 463 |
| 734 | 1-{4-[(ethylamino)carbonyl]-2-[(6-fluorohexyl)oxy]phenyl}-N-[1-(methoxymethyl)propyl]-1H-1,2,3-triazole-4-carboxamide | 15.7 mg | 464 |
| 735 | N-(3-ethoxypropyl)-1-{4-[(ethylamino)carbonyl]-2-[(6-fluorohexyl)oxy]phenyl}-1H-1,2,3-triazole-4-carboxamide | 16.9 mg | 464 |
| 736 | 1-{4-[(ethylamino)carbonyl]-2-[(6-fluorohexyl)oxy]phenyl}-N-[2-(2-hydroxyethoxy)ethyl]-1H-1,2,3-triazole-4-carboxamide | 13.4 mg | 466 |
| 737 | N-(3-amino-3-oxopropyl)-1-{4-[(ethylamino)carbonyl]-2-[(6-fluorohexyl)oxy]phenyl}-1H-1,2,3-triazole-4-carboxamide | 8.2 mg | 449 |
| 738 | 1-{4-[(ethylamino)carbonyl]-2-[(6-fluorohexyl)oxy]phenyl}-N-(3-fluorobenzyl)-1H-1,2,3-triazole-4-carboxamide | 14.8 mg | 486 |
| 739 | 1-{4-[(ethylamino)carbonyl]-2-[(6-fluorohexyl)oxy]phenyl}-N-[2-(2-thienyl)ethyl]-1H-1,2,3-triazole-4-carboxamide | 17.8 mg | 488 |
| 740 | 1-{4-[(ethylamino)carbonyl]-2-[(6-fluorohexyl)oxy]phenyl}-N-(2-oxoazepan-3-yl)-1H-1,2,3-triazole-4-carboxamide | 21.8 mg | 489 |
| 741 | 1-{4-[(ethylamino)carbonyl]-2-[(6-fluorohexyl)oxy]phenyl}-N-(3-phenylpropyl)-1H-1,2,3-triazole-4-carboxamide | 15.5 mg | 496 |
| 742 | 1-{4-[(ethylamino)carbonyl]-2-[(6-fluorohexyl)oxy]phenyl}-N-[3-(2-oxopyrrolidin-1-yl)propyl]-1H-1,2,3-triazole-4-carboxamide | 16.2 mg | 503 |
| 743 | N-[(3S,5S,7S)-1-adamantyl]-1-{4-[(ethylamino)carbonyl]-2-[(6-fluorohexyl)oxy]phenyl}-1H-1,2,3-triazole-4-carboxamide | 19.2 mg | 512 |
| 744 | N-(benzyloxy)-1-{4-[(ethylamino)carbonyl]-2-[(6-fluorohexyl)oxy]phenyl}-1H-1,2,3-triazole-4-carboxamide | 4.8 mg | 484 |
| 745 | 1-{4-[(ethylamino)carbonyl]-2-[(6-fluorohexyl)oxy]phenyl}-N-[4-(methylsulfonyl)benzyl]-1H-1,2,3-triazole-4-carboxamide | 14.6 mg | 546 |
| 746 | N-ethyl-3-[(6-fluorohexyl)oxy]-4-{4-[(4-hydroxypiperidin-1-yl)carbonyl]-1H-1,2,3-triazol-1-yl}benzamide | 16.2 mg | 462 |

TABLE 2-continued

| Example No. | Compound name | yield | [M + H]+ |
|---|---|---|---|
| 747 | N-ethyl-3-[(6-fluorohexyl)oxy]-4-{4-[(3-hydroxypyrrolidin-1-yl)carbonyl]-1H-1,2,3-triazol-1-yl}benzamide | 16.3 mg | 448 |
| 748 | 1-{4-[(ethylamino)carbonyl]-2-[(6-fluorohexyl)oxy]phenyl}-N-(2-methoxyethyl)-N-methyl-1H-1,2,3-triazole-4-carboxamide | 15.5 mg | 450 |
| 749 | 1-{4-[(ethylamino)carbonyl]-2-[(6-fluorohexyl)oxy]phenyl}-N-methoxy-N-methyl-1H-1,2,3-triazole-4-carboxamide | 9.4 mg | 422 |
| 750 | N-ethyl-3-[(6-fluorohexyl)oxy]-4-(4-{[(2S)-2-(methoxymethyl)pyrrolidin-1-yl]carbonyl}-1H-1,2,3-triazol-1-yl)benzamide | 15.3 mg | 476 |
| 751 | 1-[(1-{4-[(ethylamino)carbonyl]-2-[(6-fluorohexyl)oxy]phenyl}-1H-1,2,3-triazol-4-yl)carbonyl]piperidine-4-carboxamide | 15.9 mg | 489 |
| 752 | N-ethyl-4-(4-{[4-(ethylsulfonyl)piperazin-1-yl]carbonyl}-1H-1,2,3-triazol-1-yl)-3-[(6-fluorohexyl)oxy]benzamide | 18.7 mg | 539 |
| 753 | 1-{4-[(ethylamino)carbonyl]-2-[(6-fluorohexyl)oxy]phenyl}-N-(pyridin-2-ylmethyl)-1H-1,2,3-triazole-4-carboxamide | 15 mg | 469 |
| 754 | 1-{4-[(ethylamino)carbonyl]-2-[(6-fluorohexyl)oxy]phenyl}-N-[2-(pyridin-2-yl)ethyl]-1H-1,2,3-triazole-4-carboxamide | 14.4 mg | 483 |
| 755 | 1-{4-[(ethylamino)carbonyl]-2-[(6-fluorohexyl)oxy]phenyl}-N-[2-(morpholin-4-yl)ethyl]-1H-1,2,3-triazole-4-carboxamide | 2.8 mg | 491 |
| 756 | N-[2-(diisopropylamino)ethyl]-1-{4-[(ethylamino)carbonyl]-2-[(6-fluorohexyl)oxy]phenyl}-1H-1,2,3-triazole-4-carboxamide | 11.1 mg | 505 |
| 757 | N-ethyl-3-[(6-fluorohexyl)oxy]-4-(4-{[4-(2-hydroxyethyl)piperazin-1-yl]carbonyl}-1H-1,2,3-triazol-1-yl)benzamide | 1.1 mg | 491 |
| 758 | 4-{4-[(1,4'-bipiperidin-1'-yl)carbonyl]-1H-1,2,3-triazol-1-yl}-N-ethyl-3-[(6-fluorohexyl)oxy]benzamide | 9 mg | 529 |
| 759 | 4-(4-{[4-(2-ethoxyphenyl)piperazin-1-yl]carbonyl}-1H-1,2,3-triazol-1-yl)-N-ethyl-3-[(6-fluorohexyl)oxy]benzamide | 20.7 mg | 567 |
| 760 | 1-{4-[(ethylamino)carbonyl]-2-[(6-fluorohexyl)oxy]phenyl}-N-[2-(ethylthio)ethyl]-1H-1,2,3-triazole-4-carboxamide | 15.5 mg | 466 |
| 761 | 1-{4-[(ethylamino)carbonyl]-2-[(6-fluorohexyl)oxy]phenyl}-N-(tetrahydro-2H-pyran-4-yl)-1H-1,2,3-triazole-4-carboxamide | 14.2 mg | 462 |
| 762 | 1-{4-[(ethylamino)carbonyl]-2-[(6-fluorohexyl)oxy]phenyl}-N-[2-(methylsulfonyl)ethyl]-1H-1,2,3-triazole-4-carboxamide | 14.2 mg | 484 |
| 763 | N-isopropyl-1-(2-(pent-4-en-1-yloxy)-4-{[(2,2,2-trifluoroethyl)amino]carbonyl}phenyl)-1H-1,2,3-triazole-4-carboxamide | 17.2 mg | 440 |
| 764 | 1-(2-(pent-4-en-1-yloxy)-4-{[(2,2,2-trifluoroethyl)amino]carbonyl}phenyl)-N-(2-phenoxyethyl)-1H-1,2,3-triazole-4-carboxamide | 20.7 mg | 518 |
| 765 | N-(tert-butyl)-1-(2-(pent-4-en-1-yloxy)-4-{[(2,2,2-trifluoroethyl)amino]carbonyl}phenyl)-1H-1,2,3-triazole-4-carboxamide | 16.2 mg | 454 |
| 766 | N-(3-hydroxypropyl)-1-(2-(pent-4-en-1-yloxy)-4-{[(2,2,2-trifluoroethyl)amino]carbonyl}phenyl)-1H-1,2,3-triazole-4-carboxamide | 16.9 mg | 456 |

TABLE 2-continued

| Example No. | Compound name | yield | [M + H]⁺ |
|---|---|---|---|
| 767 | N-(2-hydroxy-1-methylethyl)-1-(2-(pent-4-en-1-yloxy)-4-{[(2,2,2-trifluoroethyl)amino]carbonyl}phenyl)-1H-1,2,3-triazole-4-carboxamide | 17.1 mg | 456 |
| 768 | N-cyclopentyl-1-(2-(pent-4-en-1-yloxy)-4-{[(2,2,2-trifluoroethyl)amino]carbonyl}phenyl)-1H-1,2,3-triazole-4-carboxamide | 16.2 mg | 466 |
| 769 | N-(2-ethoxyethyl)-1-(2-(pent-4-en-1-yloxy)-4-{[(2,2,2-trifluoroethyl)amino]carbonyl}phenyl)-1H-1,2,3-triazole-4-carboxamide | 15.7 mg | 470 |
| 770 | N-(2-hydroxy-1,1-dimethylethyl)-1-(2-(pent-4-en-1-yloxy)-4-{[(2,2,2-trifluoroethyl)amino]carbonyl}phenyl)-1H-1,2,3-triazole-4-carboxamide | 18.4 mg | 470 |
| 771 | N-(4-hydroxybutyl)-1-(2-(pent-4-en-1-yloxy)-4-{[(2,2,2-trifluoroethyl)amino]carbonyl}phenyl)-1H-1,2,3-triazole-4-carboxamide | 18.8 mg | 470 |
| 772 | 1-(2-(pent-4-en-1-yloxy)-4-{[(2,2,2-trifluoroethyl)amino]carbonyl}phenyl)-N-(tetrahydrofuran-2-ylmethyl)-1H-1,2,3-triazole-4-carboxamide | 15.5 mg | 482 |
| 773 | N-[2-(acetylamino)ethyl]-1-(2-(pent-4-en-1-yloxy)-4-{[(2,2,2-trifluoroethyl)amino]carbonyl}phenyl)-1H-1,2,3-triazole-4-carboxamide | 16.8 mg | 483 |
| 774 | N-[1-(methoxymethyl)propyl]-1-(2-(pent-4-en-1-yloxy)-4-{[(2,2,2-trifluoroethyl)amino]carbonyl}phenyl)-1H-1,2,3-triazole-4-carboxamide | 17 mg | 484 |
| 775 | N-(3-ethoxypropyl)-1-(2-(pent-4-en-1-yloxy)-4-{[(2,2,2-trifluoroethyl)amino]carbonyl}phenyl)-1H-1,2,3-triazole-4-carboxamide | 19.7 mg | 484 |
| 776 | N-[2-(2-hydroxyethoxy)ethyl]-1-(2-(pent-4-en-1-yloxy)-4-{[(2,2,2-trifluoroethyl)amino]carbonyl}phenyl)-1H-1,2,3-triazole-4-carboxamide | 19 mg | 486 |
| 777 | N-(3-amino-3-oxopropyl)-1-(2-(pent-4-en-1-yloxy)-4-{[(2,2,2-trifluoroethyl)amino]carbonyl}phenyl)-1H-1,2,3-triazole-4-carboxamide | 9.2 mg | 469 |
| 778 | N-(3-fluorobenzyl)-1-(2-(pent-4-en-1-yloxy)-4-{[(2,2,2-trifluoroethyl)amino]carbonyl}phenyl)-1H-1,2,3-triazole-4-carboxamide | 18.7 mg | 506 |
| 779 | 1-(2-(pent-4-en-1-yloxy)-4-{[(2,2,2-trifluoroethyl)amino]carbonyl}phenyl)-N-[2-(2-thienyl)ethyl]-1H-1,2,3-triazole-4-carboxamide | 21.9 mg | 508 |
| 780 | N-(2-oxoazepan-3-yl)-1-(2-(pent-4-en-1-yloxy)-4-{[(2,2,2-trifluoroethyl)amino]carbonyl}phenyl)-1H-1,2,3-triazole-4-carboxamide | 21.4 mg | 509 |
| 781 | 1-(2-(pent-4-en-1-yloxy)-4-{[(2,2,2-trifluoroethyl)amino]carbonyl}phenyl)-N-(3-phenylpropyl)-1H-1,2,3-triazole-4-carboxamide | 18.7 mg | 516 |
| 782 | N-[3-(2-oxopyrrolidin-1-yl)propyl]-1-(2-(pent-4-en-1-yloxy)-4-{[(2,2,2-trifluoroethyl)amino]carbonyl}phenyl)-1H-1,2,3-triazole-4-carboxamide | 20.9 mg | 523 |
| 783 | N-[(3S,5S,7S)-1-adamantyl]-1-(2-(pent-4-en-1-yloxy)-4-{[(2,2,2-trifluoroethyl)amino]carbonyl}phenyl)-1H-1,2,3-triazole-4-carboxamide | 21.6 mg | 532 |
| 784 | N-(benzyloxy)-1-(2-(pent-4-en-1-yloxy)-4-{[(2,2,2-trifluoroethyl)amino]carbonyl}phenyl)-1H-1,2,3-triazole-4-carboxamide | 6.9 mg | 504 |
| 785 | N-(4-methylsulfonylbenzyl)-1-(2-(pent-4-en-1-yloxy)-4-{[(2,2,2-trifluoroethyl)amino]carbonyl}phenyl)-1H-1,2,3-triazole-4-carboxamide | 18.5 mg | 566 |

TABLE 2-continued

| Example No. | Compound name | yield | [M + H]+ |
|---|---|---|---|
| 786 | 4-{4-[(4-hydroxypiperidin-1-yl)carbonyl]-1H-1,2,3-triazol-1-yl}-3-(pent-4-en-1-yloxy)-N-(2,2,2-trifluoroethyl)benzamide | 18.9 mg | 482 |
| 787 | 4-{4-[(3-hydroxypyrrolidin-1-yl)carbonyl]-1H-1,2,3-triazol-1-yl}-3-(pent-4-en-1-yloxy)-N-(2,2,2-trifluoroethyl)benzamide | 19.2 mg | 468 |
| 788 | N-(2-methoxyethyl)-N-methyl-1-(2-(pent-4-en-1-yloxy)-4-{[(2,2,2-trifluoroethyl)amino]carbonyl}phenyl)-1H-1,2,3-triazole-4-carboxamide | 20.5 mg | 470 |
| 789 | N-methoxy-N-methyl-1-(2-(pent-4-en-1-yloxy)-4-{[(2,2,2-trifluoroethyl)amino]carbonyl}phenyl)-1H-1,2,3-triazole-4-carboxamide | 14.7 mg | 442 |
| 790 | 4-(4-{[(2S)-2-(methoxymethyl)pyrrolidin-1-yl]carbonyl}-1H-1,2,3-triazol-1-yl)-3-(pent-4-en-1-yloxy)-N-(2,2,2-trifluoroethyl)benzamide | 20.6 mg | 496 |
| 791 | 1-{1-(2-(pent-4-en-1-yloxy)-4-{[(2,2,2-trifluoroethyl)amino]carbonyl}phenyl)-1H-1,2,3-triazol-4-yl]carbonyl}piperidine-4-carboxamide | 21 mg | 509 |
| 792 | 4-(4-{[4-(ethylsulfonyl)piperazin-1-yl]carbonyl}-1H-1,2,3-triazol-1-yl)-3-(pent-4-en-1-yloxy)-N-(2,2,2-trifluoroethyl)benzamide | 20.4 mg | 559 |
| 793 | N-[2-(dimethylamino)ethyl]-1-(2-(pent-4-en-1-yloxy)-4-{[(2,2,2-trifluoroethyl)amino]carbonyl}phenyl)-1H-1,2,3-triazole-4-carboxamide | 9.1 mg | 469 |
| 794 | 1-(2-(pent-4-en-1-yloxy)-4-{[(2,2,2-trifluoroethyl)amino]carbonyl}phenyl)-N-(pyridin-2-ylmethyl)-1H-1,2,3-triazole-4-carboxamide | 18.8 mg | 489 |
| 795 | 1-(2-(pent-4-en-1-yloxy)-4-{[(2,2,2-trifluoroethyl)amino]carbonyl}phenyl)-N-[2-(pyridin-2-yl)ethyl]-1H-1,2,3-triazole-4-carboxamide | 14.8 mg | 503 |
| 796 | N-[3-(1H-imidazol-1-yl)propyl]-1-(2-(pent-4-en-1-yloxy)-4-{[(2,2,2-trifluoroethyl)amino]carbonyl}phenyl)-1H-1,2,3-triazole-4-carboxamide | 4.9 mg | 506 |
| 797 | N-[2-(diisopropylamino)ethyl]-1-(2-(pent-4-en-1-yloxy)-4-{[(2,2,2-trifluoroethyl)amino]carbonyl}phenyl)-1H-1,2,3-triazole-4-carboxamide | 13.3 mg | 525 |
| 798 | 1-(2-(pent-4-en-1-yloxy)-4-{[(2,2,2-trifluoroethyl)amino]carbonyl}phenyl)-N-(pyridin-2-yl)-1H-1,2,3-triazole-4-carboxamide | 3.3 mg | 475 |
| 799 | 4-(4-{[4-(2-hydroxyethyl)piperazin-1-yl]carbonyl}-1H-1,2,3-triazol-1-yl)-3-(pent-4-en-1-yloxy)-N-(2,2,2-trifluoroethyl)benzamide | 10.1 mg | 511 |
| 800 | 4-{4-[(1,4'-bipiperidin-1'-yl)carbonyl]-1H-1,2,3-triazol-1-yl}-3-(pent-4-en-1-yloxy)-N-(2,2,2-trifluoroethyl)benzamide | 17.3 mg | 549 |
| 801 | 4-(4-{[4-(2-ethoxyphenyl)piperazin-1-yl]carbonyl}-1H-1,2,3-triazol-1-yl)-3-(pent-4-en-1-yloxy)-N-(2,2,2-trifluoroethyl)benzamide | 23.6 mg | 587 |
| 802 | N-[2-(ethylthio)ethyl]-1-(2-(pent-4-en-1-yloxy)-4-{[(2,2,2-trifluoroethyl)amino]carbonyl}phenyl)-1H-1,2,3-triazole-4-carboxamide | 19.2 mg | 486 |
| 803 | 1-(2-(pent-4-en-1-yloxy)-4-{[(2,2,2-trifluoroethyl)amino]carbonyl}phenyl)-N-(tetrahydro-2H-pyran-4-yl)-1H-1,2,3-triazole-4-carboxamide | 18.3 mg | 482 |
| 804 | N-[2-(methylsulfonyl)ethyl]-1-(2-(pent-4-en-1-yloxy)-4-{[(2,2,2-trifluoroethyl)amino]carbonyl}phenyl)-1H-1,2,3-triazole-4-carboxamide | 19.6 mg | 504 |

TABLE 2-continued

| Example No. | Compound name | yield | [M + H]+ |
|---|---|---|---|
| 805 | 4-{4-[(1,1-dioxide-1,3-thiazolidin-3-yl)carbonyl]-1H-1,2,3-triazol-1-yl}-3-(pent-4-en-1-yloxy)-N-(2,2,2-trifluoroethyl)benzamide | 4.4 mg | 502 |
| 806 | 1-[4-[(ethylamino)carbonyl]-2-(pent-4-en-1-yloxy)phenyl]-N-isopropyl-1H-1,2,3-triazole-4-carboxamide | 10.7 mg | 386 |
| 807 | 1-[4-[(ethylamino)carbonyl]-2-(pent-4-en-1-yloxy)phenyl]-N-(2-phenoxyethyl)-1H-1,2,3-triazole-4-carboxamide | 14.8 mg | 464 |
| 808 | N-(tert-butyl)-1-[4-[(ethylamino)carbonyl]-2-(pent-4-en-1-yloxy)phenyl]-1H-1,2,3-triazole-4-carboxamide | 17.5 mg | 400 |
| 809 | 1-[4-[(ethylamino)carbonyl]-2-(pent-4-en-1-yloxy)phenyl]-N-(3-hydroxypropyl)-1H-1,2,3-triazole-4-carboxamide | 15 mg | 402 |
| 810 | 1-[4-[(ethylamino)carbonyl]-2-(pent-4-en-1-yloxy)phenyl]-N-(2-hydroxy-1-methylethyl)-1H-1,2,3-triazole-4-carboxamide | 14.2 mg | 402 |
| 811 | N-cyclopentyl-1-[4-[(ethylamino)carbonyl]-2-(pent-4-en-1-yloxy)phenyl]-1H-1,2,3-triazole-4-carboxamide | 14.2 mg | 412 |
| 812 | N-(2-ethoxyethyl)-1-[4-[(ethylamino)carbonyl]-2-(pent-4-en-1-yloxy)phenyl]-1H-1,2,3-triazole-4-carboxamide | 17.3 mg | 416 |
| 813 | 1-[4-[(ethylamino)carbonyl]-2-(pent-4-en-1-yloxy)phenyl]-N-(2-hydroxy-1,1-dimethylethyl)-1H-1,2,3-triazole-4-carboxamide | 17 mg | 416 |
| 814 | 1-[4-[(ethylamino)carbonyl]-2-(pent-4-en-1-yloxy)phenyl]-N-(4-hydroxybutyl)-1H-1,2,3-triazole-4-carboxamide | 17.3 mg | 416 |
| 815 | 1-[4-[(ethylamino)carbonyl]-2-(pent-4-en-1-yloxy)phenyl]-N-(tetrahydrofuran-2-ylmethyl)-1H-1,2,3-triazole-4-carboxamide | 18 mg | 428 |
| 816 | N-[2-(acetylamino)ethyl]-1-[4-[(ethylamino)carbonyl]-2-(pent-4-en-1-yloxy)phenyl]-1H-1,2,3-triazole-4-carboxamide | 13.6 mg | 429 |
| 817 | 1-[4-[(ethylamino)carbonyl]-2-(pent-4-en-1-yloxy)phenyl]-N-[1-(methoxymethyl)propyl]-1H-1,2,3-triazole-4-carboxamide | 18.3 mg | 430 |
| 818 | N-(3-ethoxypropyl)-1-[4-[(ethylamino)carbonyl]-2-(pent-4-en-1-yloxy)phenyl]-1H-1,2,3-triazole-4-carboxamide | 16.6 mg | 430 |
| 819 | 1-[4-[(ethylamino)carbonyl]-2-(pent-4-en-1-yloxy)phenyl]-N-[2-(2-hydroxyethoxy)ethyl]-1H-1,2,3-triazole-4-carboxamide | 17.3 mg | 432 |
| 820 | N-(3-amino-3-oxopropyl)-1-[4-[(ethylamino)carbonyl]-2-(pent-4-en-1-yloxy)phenyl]-1H-1,2,3-triazole-4-carboxamide | 6.8 mg | 415 |
| 821 | 1-[4-[(ethylamino)-carbonyl]-2-(pent-4-en-1-yloxy)phenyl]-N-(3-fluorobenzyl)-1H-1,2,3-triazole-4-carboxamide | 16 mg | 452 |
| 822 | 1-[4-[(ethylamino)carbonyl]-2-(pent-4-en-1-yloxy)phenyl]-N-[2-(2-thienyl)ethyl]-1H-1,2,3-triazole-4-carboxamide | 14.4 mg | 454 |
| 823 | 1-[4-[(ethylamino)carbonyl]-2-(pent-4-en-1-yloxy)phenyl]-N-(2-oxoazepan-3-yl)-1H-1,2,3-triazole-4-carboxamide | 18.1 mg | 455 |
| 824 | 1-[4-[(ethylamino)carbonyl]-2-(pent-4-en-1-yloxy)phenyl]-N-(3-phenylpropyl)-1H-1,2,3-triazole-4-carboxamide | 19 mg | 462 |
| 825 | 1-[4-[(ethylamino)carbonyl]-2-(pent-4-en-1-yloxy)phenyl]-N-[3-(2-oxopyrrolidin-1-yl)propyl]-1H-1,2,3-triazole-4-carboxamide | 19.2 mg | 469 |

TABLE 2-continued

| Example No. | Compound name | yield | [M + H]+ |
|---|---|---|---|
| 826 | N-[(3S,5S,7S)-1-adamantyl]-1-[4-[(ethylamino)carbonyl]-2-(pent-4-en-1-yloxy)phenyl]-1H-1,2,3-triazole-4-carboxamide | 21.3 mg | 478 |
| 827 | N-(benzyloxy)-1-[4-[(ethylamino)carbonyl]-2-(pent-4-en-1-yloxy)phenyl]-1H-1,2,3-triazole-4-carboxamide | 5.4 mg | 450 |
| 828 | 1-[4-[(ethylamino)carbonyl]-2-(pent-4-en-1-yloxy)phenyl]-N-[4-(methylsulfonyl)benzyl]-1H-1,2,3-triazole-4-carboxamide | 22.6 mg | 512 |
| 829 | N-ethyl-4-{4-[(4-hydroxypiperidin-1-yl)carbonyl]-1H-1,2,3-triazol-1-yl}-3-(pent-4-en-1-yloxy)benzamide | 18.3 mg | 428 |
| 830 | N-ethyl-4-{4-[(3-hydroxypyrrolidin-1-yl)carbonyl]-1H-1,2,3-triazol-1-yl}-3-(pent-4-en-1-yloxy)benzamide | 15.5 mg | 414 |
| 831 | 1-[4-[(ethylamino)carbonyl]-2-(pent-4-en-1-yloxy)phenyl]-N-(2-methoxyethyl)-N-methyl-1H-1,2,3-triazole-4-carboxamide | 16.8 mg | 416 |
| 832 | 1-[4-[(ethylamino)carbonyl]-2-(pent-4-en-1-yloxy)phenyl]-N-methoxy-N-methyl-1H-1,2,3-triazole-4-carboxamide | 12.9 mg | 388 |
| 833 | N-ethyl-4-(4-{[(2S)-2-(methoxymethyl)pyrrolidin-1-yl]carbonyl}-1H-1,2,3-triazol-1-yl)-3-(pent-4-en-1-yloxy)benzamide | 19.1 mg | 442 |
| 834 | 1-({1-[4-[(ethylamino)carbonyl]-2-(pent-4-en-1-yloxy)phenyl]-1H-1,2,3-triazol-4-yl}carbonyl)piperidine-4-carboxamide | 16.4 mg | 455 |
| 835 | N-ethyl-4-(4-{[4-(ethylsulfonyl)piperazin-1-yl]carbonyl}-1H-1,2,3-triazol-1-yl)-3-(pent-4-en-1-yloxy)benzamide | 19.8 mg | 505 |
| 836 | N-[2-(dimethylamino)ethyl]-1-[4-[(ethylamino)carbonyl]-2-(pent-4-en-1-yloxy)phenyl]-1H-1,2,3-triazole-4-carboxamide trifluoroacetate | 26.5 mg | 415 |
| 837 | 1-[4-[(ethylamino)carbonyl]-2-(pent-4-en-1-yloxy)phenyl]-N-(pyridin-2-ylmethyl)-1H-1,2,3-triazole-4-carboxamide trifluoroacetate | 22.9 mg | 435 |
| 838 | 1-[4-[(ethylamino)carbonyl]-2-(pent-4-en-1-yloxy)phenyl]-N-[2-(pyrrolidin-1-yl)ethyl]-1H-1,2,3-triazole-4-carboxamide trifluoroacetate | 25.9 mg | 441 |
| 839 | 1-[4-[(ethylamino)carbonyl]-2-(pent-4-en-1-yloxy)phenyl]-N-[2-(pyridin-2-yl)ethyl]-1H-1,2,3-triazole-4-carboxamide | 10.6 mg | 449 |
| 840 | 1-[4-[(ethylamino)carbonyl]-2-(pent-4-en-1-yloxy)phenyl]-N-[3-(1H-imidazol-1-yl)propyl]-1H-1,2,3-triazole-4-carboxamide trifluoroacetate | 23.6 mg | 452 |
| 841 | 1-[4-[(ethylamino)carbonyl]-2-(pent-4-en-1-yloxy)phenyl]-N-[2-(morpholin-4-yl)ethyl]-1H-1,2,3-triazole-4-carboxamide trifluoroacetate | 27.4 mg | 457 |
| 842 | N-[2-(diisopropylamino)ethyl]-1-[4-[(ethylamino)carbonyl]-2-(pent-4-en-1-yloxy)phenyl]-1H-1,2,3-triazole-4-carboxamide trifluoroacetate | 26.6 mg | 471 |
| 843 | 1-[4-[(ethylamino)carbonyl]-2-(pent-4-en-1-yloxy)phenyl]-N-(pyridin-2-yl)-1H-1,2,3-triazole-4-carboxamide trifluoroacetate | 5.9 mg | 421 |
| 844 | N-ethyl-4-(4-{[4-(2-hydroxyethyl)piperazin-1-yl]carbonyl}-1H-1,2,3-triazol-1-yl)-3-(pent-4-en-1-yloxy)benzamide trifluoroacetate | 26.5 mg | 457 |
| 845 | 4-{4-[(1,4'-bipiperidin-1'-yl)carbonyl]-1H-1,2,3-triazol-1-yl}-N-ethyl-3-(pent-4-en-1-yloxy)benzamide trifluoroacetate | 28.1 mg | 495 |

TABLE 2-continued

| Example No. | Compound name | yield | [M + H]+ |
|---|---|---|---|
| 846 | 4-(4-{[4-(2-ethoxyphenyl)piperazin-1-yl]carbonyl}-1H-1,2,3-triazol-1-yl)-N-ethyl-3-(pent-4-en-1-yloxy)benzamide | 22.4 mg | 533 |
| 847 | 1-[4-[(ethylamino)carbonyl]-2-(pent-4-en-1-yloxy)phenyl]-N-[2-(ethylthio)ethyl]-1H-1,2,3-triazole-4-carboxamide | 14.8 mg | 432 |
| 848 | 1-[4-[(ethylamino)carbonyl]-2-(pent-4-en-1-yloxy)phenyl]-N-(tetrahydro-2H-pyran-4-yl)-1H-1,2,3-triazole-4-carboxamide | 15.5 mg | 428 |
| 849 | 1-[4-[(ethylamino)carbonyl]-2-(pent-4-en-1-yloxy)phenyl]-N-[2-(methylsulfonyl)ethyl]-1H-1,2,3-triazole-4-carboxamide | 17.8 mg | 450 |
| 850 | 5-(5-fluoropentyl)-N-isopropyl-1-(4-{[(2,2,2-trifluoroethyl)amino]carbonyl}phenyl)-1H-1,2,3-triazole-4-carboxamide | 5.7 mg | 444 |
| 851 | 5-(5-fluoropentyl)-N-(2-phenoxyethyl)-1-(4-{[(2,2,2-trifluoroethyl)amino]carbonyl}phenyl)-1H-1,2,3-triazole-4-carboxamide | 18.4 mg | 522 |
| 852 | N-(tert-butyl)-5-(5-fluoropentyl)-1-(4-{[(2,2,2-trifluoroethyl)amino]carbonyl}phenyl)-1H-1,2,3-triazole-4-carboxamide | 16.9 mg | 458 |
| 853 | 5-(5-fluoropentyl)-N-(3-hydroxypropyl)-1-(4-{[(2,2,2-trifluoroethyl)amino]carbonyl}phenyl)-1H-1,2,3-triazole-4-carboxamide | 20.7 mg | 460 |
| 854 | 5-(5-fluoropentyl)-N-(2-hydroxy-1-methylethyl)-1-(4-{[(2,2,2-trifluoroethyl)amino]carbonyl}phenyl)-1H-1,2,3-triazole-4-carboxamide | 20.8 mg | 460 |
| 855 | N-cyclopentyl-5-(5-fluoropentyl)-1-(4-{[(2,2,2-trifluoroethyl)amino]carbonyl}phenyl)-1H-1,2,3-triazole-4-carboxamide | 20.2 mg | 470 |
| 856 | N-(2-ethoxyethyl)-5-(5-fluoropentyl)-1-(4-{[(2,2,2-trifluoroethyl)amino]carbonyl}phenyl)-1H-1,2,3-triazole-4-carboxamide | 19.6 mg | 474 |
| 857 | 5-(5-fluoropentyl)-N-(2-hydroxy-1,1-dimethylethyl)-1-(4-{[(2,2,2-trifluoroethyl)amino]carbonyl}phenyl)-1H-1,2,3-triazole-4-carboxamide | 21.3 mg | 474 |
| 858 | 5-(5-fluoropentyl)-N-(4-hydroxybutyl)-1-(4-{[(2,2,2-trifluoroethyl)amino]carbonyl}phenyl)-1H-1,2,3-triazole-4-carboxamide | 21 mg | 474 |
| 859 | 5-(5-fluoropentyl)-N-(tetrahydrofuran-2-ylmethyl)-1-(4-{[(2,2,2-trifluoroethyl)amino]carbonyl}phenyl)-1H-1,2,3-triazole-4-carboxamide | 22.2 mg | 486 |
| 860 | N-[2-(acetylamino)ethyl]-5-(5-fluoropentyl)-1-(4-{[(2,2,2-trifluoroethyl)amino]carbonyl}phenyl)-1H-1,2,3-triazole-4-carboxamide | 18.7 mg | 487 |
| 861 | 5-(5-fluoropentyl)-N-[1-(methoxymethyl)propyl]-1-(4-{[(2,2,2-trifluoroethyl)amino]carbonyl}phenyl)-1H-1,2,3-triazole-4-carboxamide | 19.6 mg | 488 |
| 862 | N-(3-ethoxypropyl)-5-(5-fluoropentyl)-1-(4-{[(2,2,2-trifluoroethyl)amino]carbonyl}phenyl)-1H-1,2,3-triazole-4-carboxamide | 17.1 mg | 488 |
| 863 | 5-(5-fluoropentyl)-N-[2-(2-hydroxyethoxy)ethyl]-1-(4-{[(2,2,2-trifluoroethyl)amino]carbonyl}phenyl)-1H-1,2,3-triazole-4-carboxamide | 21.6 mg | 490 |
| 864 | N-(3-amino-3-oxopropyl)-5-(5-fluoropentyl)-1-(4-{[(2,2,2-trifluoroethyl)amino]carbonyl}phenyl)-1H-1,2,3-triazole-4-carboxamide | 10.4 mg | 473 |

TABLE 2-continued

| Example No. | Compound name | yield | [M + H]+ |
|---|---|---|---|
| 865 | N-(3-fluorobenzyl)-5-(5-fluoropentyl)-1-(4-{[(2,2,2-trifluoroethyl)amino]carbonyl}phenyl)-1H-1,2,3-triazole-4-carboxamide | 18.5 mg | 510 |
| 866 | 5-(5-fluoropentyl)-N-[2-(2-thienyl)ethyl]-1-(4-{[(2,2,2-trifluoroethyl)amino]carbonyl}phenyl)-1H-1,2,3-triazole-4-carboxamide | 23 mg | 512 |
| 867 | 5-(5-fluoropentyl)-N-(2-oxoazepan-3-yl)-1-(4-{[(2,2,2-trifluoroethyl)amino]carbonyl}phenyl)-1H-1,2,3-triazole-4-carboxamide | 23.9 mg | 513 |
| 868 | 5-(5-fluoropentyl)-N-(3-phenylpropyl)-1-(4-{[(2,2,2-trifluoroethyl)amino]carbonyl}phenyl)-1H-1,2,3-triazole-4-carboxamide | 23.9 mg | 520 |
| 869 | 5-(5-fluoropentyl)-N-[3-(2-oxopyrrolidin-1-yl)propyl]-1-(4-{[(2,2,2-trifluoroethyl)amino]carbonyl}phenyl)-1H-1,2,3-triazole-4-carboxamide | 24.9 mg | 527 |
| 870 | N-[(3S,5S,7S)-1-adamantyl]-5-(5-fluoropentyl)-1-(4-{[(2,2,2-trifluoroethyl)amino]carbonyl}phenyl)-1H-1,2,3-triazole-4-carboxamide | 24.3 mg | 536 |
| 871 | N-(benzyloxy)-5-(5-fluoropentyl)-1-(4-{[(2,2,2-trifluoroethyl)amino]carbonyl}phenyl)-1H-1,2,3-triazole-4-carboxamide | 9 mg | 508 |
| 872 | 5-(5-fluoropentyl)-N-[4-(methylsulfonyl)benzyl]-1-(4-{[(2,2,2-trifluoroethyl)amino]carbonyl}phenyl)-1H-1,2,3-triazole-4-carboxamide | 21.5 mg | 570 |
| 873 | 4-{5-(5-fluoropentyl)-4-[(4-hydroxypiperidin-1-yl)carbonyl]-1H-1,2,3-triazol-1-yl}-N-(2,2,2-trifluoroethyl)benzamide | 21.6 mg | 486 |
| 874 | 4-{5-(5-fluoropentyl)-4-[(3-hydroxypyrrolidin-1-yl)carbonyl]-1H-1,2,3-triazol-1-yl}-N-(2,2,2-trifluoroethyl)benzamide | 21.3 mg | 472 |
| 875 | 5-(5-fluoropentyl)-N-(2-methoxyethyl)-N-methyl-1-(4-{[(2,2,2-trifluoroethyl)amino]carbonyl}phenyl)-1H-1,2,3-triazole-4-carboxamide | 22.2 mg | 474 |
| 876 | 5-(5-fluoropentyl)-N-methoxy-N-methyl-1-(4-{[(2,2,2-trifluoroethyl)amino]carbonyl}phenyl)-1H-1,2,3-triazole-4-carboxamide | 15.4 mg | 446 |
| 877 | 4-(5-(5-fluoropentyl)-4-{[(2S)-2-(methoxymethyl)pyrrolidin-1-yl]carbonyl}-1H-1,2,3-triazol-1-yl)-N-(2,2,2-trifluoroethyl)benzamide | 23.8 mg | 500 |
| 878 | 1-{[5-(5-fluoropentyl)-1-(4-{[(2,2,2-trifluoroethyl)amino]carbonyl}phenyl)-1H-1,2,3-triazol-4-yl]carbonyl}piperidine-4-carboxamide | 22.6 mg | 513 |
| 879 | 4-[4-{[4-(ethylsulfonyl)piperazin-1-yl]carbonyl}-5-(5-fluoropentyl)-1H-1,2,3-triazol-1-yl]-N-(2,2,2-trifluoroethyl)benzamide | 25.6 mg | 563 |
| 880 | N-[2-(dimethylamino)ethyl]-5-(5-fluoropentyl)-1-(4-{[(2,2,2-trifluoroethyl)amino]carbonyl}phenyl)-1H-1,2,3-triazole-4-carboxamide trifluoroacetate | 27.8 mg | 473 |
| 881 | 5-(5-fluoropentyl)-N-(pyridin-2-ylmethyl)-1-(4-{[(2,2,2-trifluoroethyl)amino]carbonyl}phenyl)-1H-1,2,3-triazole-4-carboxamide trifluoroacetate | 26.2 mg | 493 |
| 882 | 5-(5-fluoropentyl)-N-[2-(pyrrolidin-1-yl)ethyl]-1-(4-{[(2,2,2-trifluoroethyl)amino]carbonyl}phenyl)-1H-1,2,3-triazole-4-carboxamide trifluoroacetate | 29 mg | 499 |

TABLE 2-continued

| Example No. | Compound name | yield | [M + H]+ |
|---|---|---|---|
| 883 | 5-(5-fluoropentyl)-N-[2-(pyridin-2-yl)ethyl]-1-(4-{[(2,2,2-trifluoroethyl)amino]carbonyl}phenyl)-1H-1,2,3-triazole-4-carboxamide | 18.3 mg | 507 |
| 884 | 5-(5-fluoropentyl)-N-[3-(1H-imidazol-1-yl)propyl]-1-(4-{[(2,2,2-trifluoroethyl)amino]carbonyl}phenyl)-1H-1,2,3-triazole-4-carboxamide trifluoroacetate | 27.6 mg | 510 |
| 885 | 5-(5-fluoropentyl)-N-[2-(morpholin-4-yl)ethyl]-1-(4-{[(2,2,2-trifluoroethyl)amino]carbonyl}phenyl)-1H-1,2,3-triazole-4-carboxamide trifluoroacetate | 30.7 mg | 515 |
| 886 | N-[2-(diisopropylamino)ethyl]-5-(5-fluoropentyl)-1-(4-{[(2,2,2-trifluoroethyl)amino]carbonyl}phenyl)-1H-1,2,3-triazole-4-carboxamide | 9 mg | 529 |
| 887 | 5-(5-fluoropentyl)-N-(pyridin-2-yl)-1-(4-{[(2,2,2-trifluoroethyl)amino]carbonyl}phenyl)-1H-1,2,3-triazole-4-carboxamide | 3.5 mg | 479 |
| 888 | 5-(5-fluoropentyl)-N-(5-methylisoxazol-3-yl)-1-(4-{[(2,2,2-trifluoroethyl)amino]carbonyl}phenyl)-1H-1,2,3-triazole-4-carboxamide | 1.7 mg | 483 |
| 889 | 4-(5-(5-fluoropentyl)-4-{[4-(2-hydroxyethyl)piperazin-1-yl]carbonyl}-1H-1,2,3-triazol-1-yl)-N-(2,2,2-trifluoroethyl)benzamide trifluoroacetate | 32 mg | 515 |
| 890 | 4-{4-[(1,4'-bipiperidine-1'-yl)carbonyl]-5-(5-fluoropentyl)-1H-1,2,3-triazol-1-yl}-N-(2,2,2-trifluoroethyl)benzamide trifluoroacetate | 34.2 mg | 553 |
| 891 | 4-[4-{[4-(2-ethoxyphenyl)piperazin-1-yl]carbonyl}-5-(5-fluoropentyl)-1H-1,2,3-triazol-1-yl]-N-(2,2,2-trifluoroethyl)benzamide | 20.1 mg | 591 |
| 892 | N-[2-(ethylthio)ethyl]-5-(5-fluoropentyl)-1-(4-{[(2,2,2-trifluoroethyl)amino]carbonyl}phenyl)-1H-1,2,3-triazole-4-carboxamide | 17.7 mg | 490 |
| 893 | 5-(5-fluoropentyl)-N-(tetrahydro-2H-pyran-4-yl)-1-(4-{[(2,2,2-trifluoroethyl)amino]carbonyl}phenyl)-1H-1,2,3-triazole-4-carboxamide | 17.5 mg | 486 |
| 894 | 5-(5-fluoropentyl)-N-[2-(methylsulfonyl)ethyl]-1-(4-{[(2,2,2-trifluoroethyl)amino]carbonyl}phenyl)-1H-1,2,3-triazole-4-carboxamide | 19.6 mg | 508 |
| 895 | N-[2-(dimethylamino)ethyl]-1-{4-[(ethylamino)carbonyl]-2-[(6-fluorohexyl)oxy]phenyl}-1H-1,2,3-triazole-4-carboxamide trifluoroacetate | 36.6 mg | 449 |
| 896 | 1-{4-[(ethylamino)carbonyl]-2-[(6-fluorohexyl)oxy]phenyl}-N-[2-(pyrrolidin-1-yl)ethyl]-1H-1,2,3-triazole-4-carboxamide trifluoroacetate | 23.7 mg | 475 |
| 897 | 1-{4-[(ethylamino)carbonyl]-2-[(6-fluorohexyl)oxy]phenyl}-N-[3-(1H-imidazol-1-yl)propyl]-1H-1,2,3-triazole-4-carboxamide | 29.3 mg | 486 |
| 898 | 4-{4-[(1,1-dioxide-1,3-thiazolidin-3-yl)carbonyl]-1H-1,2,3-triazol-1-yl}-N-ethyl-3-[(6-fluorohexyl)oxy]benzamide | 3.6 mg | 482 |
| 899 | 1-(2-(pent-4-en-1-yloxy)-4-{[(2,2,2-trifluoroethyl)amino]carbonyl}phenyl)-N-[2-(pyrrolidin-1-yl)ethyl]-1H-1,2,3-triazole-4-carboxamide trifluoroacetate | 38 mg | 495 |
| 900 | N-[2-(morpholin-4-yl)ethyl]-1-(2-(pent-4-en-1-yloxy)-4-{[(2,2,2-trifluoroethyl)amino]carbonyl}phenyl)-1H-1,2,3-triazole-4-carboxamide trifluoroacetate | 43.9 mg | 511 |

TABLE 2-continued

| Example No. | Compound name | yield | [M + H]+ |
|---|---|---|---|
| 901 | 4-{4-[(1,1-dioxide-1,3-thiazolidin-3-yl)carbonyl]-1H-1,2,3-triazol-1-yl}-N-ethyl-3-(pent-4-en-1-yloxy)benzamide | 4.8 mg | 448 |
| 902 | 4-[4-[(1,1-dioxide-1,3-thiazolidin-3-yl)carbonyl]-5-(5-fluoropentyl)-1H-1,2,3-triazol-1-yl]-N-(2,2,2-trifluoroethyl)benzamide | 3.1 mg | 506 |
| 903 | N-{[5-(4-chlorophenyl)-2-thienyl]methyl}-1-{4-[(ethylamino)carbonyl]-2-[2-(2-fluoroethoxy)ethoxy]phenyl}-1H-1,2,3-triazole-4-carboxamide | 18 mg | 572 |
| 904 | 1-{4-[(ethylamino)carbonyl]-2-[2-(2-fluoroethoxy)ethoxy]phenyl}-N-{[2-(2-thienyl)-1,3-thiazol-4-yl]methyl}-1H-1,2,3-triazole-4-carboxamide | 20.3 mg | 545 |
| 905 | N-(1-benzothien-2-ylmethyl)-1-{4-[(ethylamino)carbonyl]-2-[2-(2-fluoroethoxy)ethoxy]phenyl}-1H-1,2,3-triazole-4-carboxamide | 18.4 mg | 512 |
| 906 | N-{[2-(benzyloxy)pyridin-4-yl]methyl}-1-{4-[(ethylamino)carbonyl]-2-[2-(2-fluoroethoxy)ethoxy]phenyl}-1H-1,2,3-triazole-4-carboxamide | 20.8 mg | 563 |
| 907 | 1-{4-[(ethylamino)carbonyl]-2-[2-(2-fluoroethoxy)ethoxy]phenyl}-N-{[2-(tetrahydro-2H-pyran-4-ylmethoxy)pyridin-4-yl]methyl}-1H-1,2,3-triazole-4-carboxamide trifluoroacetate | 24.3 mg | 571 |
| 908 | N-(2-{[(5-chloroimidazo[1,2-a]pyridin-2-yl)methyl]thio}ethyl)-1-{4-[(ethylamino)carbonyl]-2-[2-(2-fluoroethoxy)ethoxy]phenyl}-1H-1,2,3-triazole-4-carboxamide | 27.4 mg | 591 |
| 909 | 1-{4-[(ethylamino)carbonyl]-2-[2-(2-fluoroethoxy)ethoxy]phenyl}-N-[(4'-fluorobiphenyl-3-yl)methyl]-1H-1,2,3-triazole-4-carboxamide | 20.1 mg | 550 |
| 910 | 1-{4-[(ethylamino)carbonyl]-2-[2-(2-fluoroethoxy)ethoxy]phenyl}-N-[3-(pyridin-2-yloxy)benzyl]-1H-1,2,3-triazole-4-carboxamide | 23.1 mg | 549 |
| 911 | 1-{4-[(ethylamino)carbonyl]-2-[2-(2-fluoroethoxy)ethoxy]phenyl}-N-[(5-methyl-2-phenyl-2H-1,2,3-triazol-4-yl)methyl]-1H-1,2,3-triazole-4-carboxamide | 16.7 mg | 537 |
| 912 | 1-{4-[(ethylamino)carbonyl]-2-[2-(2-fluoroethoxy)ethoxy]phenyl}-N-[(1-methyl-1H-1,2,3-benzotriazol-5-yl)methyl]-1H-1,2,3-triazole-4-carboxamide | 18.5 mg | 511 |
| 913 | 1-{4-[(ethylamino)carbonyl]-2-[2-(2-fluoroethoxy)ethoxy]phenyl}-N-[3-(methylthio)benzyl]-1H-1,2,3-triazole-4-carboxamide | 18.7 mg | 502 |
| 914 | N-[(2-ethoxypyridin-4-yl)methyl]-1-{4-[(ethylamino)carbonyl]-2-[2-(2-fluoroethoxy)ethoxy]phenyl}-1H-1,2,3-triazole-4-carboxamide | 25.7 mg | 501 |
| 915 | N-(3-ethoxybenzyl)-1-{4-[(ethylamino)carbonyl]-2-[2-(2-fluoroethoxy)ethoxy]phenyl}-1H-1,2,3-triazole-4-carboxamide | 17.7 mg | 500 |
| 916 | 1-{4-[(ethylamino)carbonyl]-2-[2-(2-fluoroethoxy)ethoxy]phenyl}-N-[1-(2-thienyl)ethyl]-1H-1,2,3-triazole-4-carboxamide | 18.1 mg | 476 |
| 917 | N-[1-(3-chloro-4-fluorophenyl)-3-methyl-1H-pyrazol-5-yl]-1-{4-[(ethylamino)carbonyl]-2-[2-(2-fluoroethoxy)ethoxy]phenyl}-1H-1,2,3-triazole-4-carboxamide | 2.4 mg | 574 |
| 918 | 1-{4-[(ethylamino)carbonyl]-2-[2-(2-fluoroethoxy)ethoxy]phenyl}-N-[3-(methylthio)propyl]-1H-1,2,3-triazole-4-carboxamide | 17.6 mg | 454 |

TABLE 2-continued

| Example No. | Compound name | yield | [M + H]+ |
|---|---|---|---|
| 919 | N-benzyl-1-{4-[(ethylamino)carbonyl]-2-[2-(2-fluoroethoxy)ethoxy]phenyl}-1H-1,2,3-triazole-4-carboxamide | 17.6 mg | 456 |
| 920 | 1-{4-[(ethylamino)carbonyl]-2-[2-(2-fluoroethoxy)ethoxy]phenyl}-N-(3-fluorobenzyl)-1H-1,2,3-triazole-4-carboxamide | 18.5 mg | 474 |
| 921 | N-(2,3-dihydro-1H-inden-2-yl)-1-{4-[(ethylamino)carbonyl]-2-[2-(2-fluoroethoxy)ethoxy]phenyl}-1H-1,2,3-triazole-4-carboxamide | 17.7 mg | 482 |
| 922 | N-(1,3-benzodioxol-5-ylmethyl)-1-{4-[(ethylamino)carbonyl]-2-[2-(2-fluoroethoxy)ethoxy]phenyl}-1H-1,2,3-triazole-4-carboxamide | 19.2 mg | 500 |
| 923 | N-(4-tert-butylcyclohexyl)-1-{4-[(ethylamino)carbonyl]-2-[2-(2-fluoroethoxy)ethoxy]phenyl}-1H-1,2,3-triazole-4-carboxamide | 20.3 mg | 504 |
| 924 | 1-{4-[(ethylamino)carbonyl]-2-[2-(2-fluoroethoxy)ethoxy]phenyl}-N-[2-(1H-indol-3-yl)ethyl]-1H-1,2,3-triazole-4-carboxamide | 18.8 mg | 509 |
| 925 | 1-{4-[(ethylamino)carbonyl]-2-[2-(2-fluoroethoxy)ethoxy]phenyl}-N-[4-(trifluoromethyl)benzyl]-1H-1,2,3-triazole-4-carboxamide | 18.2 mg | 524 |
| 926 | N-(3,4-dichlorobenzyl)-1-{4-[(ethylamino)carbonyl]-2-[2-(2-fluoroethoxy)ethoxy]phenyl}-1H-1,2,3-triazole-4-carboxamide | 16.2 mg | 525 |
| 927 | 1-{4-[(ethylamino)carbonyl]-2-[2-(2-fluoroethoxy)ethoxy]phenyl}-N-[2-(5-methoxy-1H-indol-3-yl)ethyl]-1H-1,2,3-triazole-4-carboxamide | 20.1 mg | 539 |
| 928 | N-[3,5-bis(trifluoromethyl)benzyl]-1-{4-[(ethylamino)carbonyl]-2-[2-(2-fluoroethoxy)ethoxy]phenyl}-1H-1,2,3-triazole-4-carboxamide | 14.7 mg | 592 |
| 929 | 1-{4-[(ethylamino)carbonyl]-2-[2-(2-fluoroethoxy)ethoxy]phenyl}-N-[1-(methoxymethyl)propyl]-1H-1,2,3-triazole-4-carboxamide | 16.9 mg | 452 |
| 930 | 1-{4-[(ethylamino)carbonyl]-2-[2-(2-fluoroethoxy)ethoxy]phenyl}-N-[2-(2-thienyl)ethyl]-1H-1,2,3-triazole-4-carboxamide | 18.6 mg | 476 |
| 931 | 1-{4-[(ethylamino)carbonyl]-2-[2-(2-fluoroethoxy)ethoxy]phenyl}-N-(3-methoxybenzyl)-1H-1,2,3-triazole-4-carboxamide | 18.9 mg | 486 |
| 932 | N-(3-chlorobenzyl)-1-{4-[(ethylamino)carbonyl]-2-[2-(2-fluoroethoxy)ethoxy]phenyl}-1H-1,2,3-triazole-4-carboxamide | 18 mg | 490 |
| 933 | N-(2,5-difluorobenzyl)-1-{4-[(ethylamino)carbonyl]-2-[2-(2-fluoroethoxy)ethoxy]phenyl}-1H-1,2,3-triazole-4-carboxamide | 18.7 mg | 492 |
| 934 | N-(2,4-difluorobenzyl)-1-{4-[(ethylamino)carbonyl]-2-[2-(2-fluoroethoxy)ethoxy]phenyl}-1H-1,2,3-triazole-4-carboxamide | 18.8 mg | 492 |
| 935 | N-(3,5-difluorobenzyl)-1-{4-[(ethylamino)carbonyl]-2-[2-(2-fluoroethoxy)ethoxy]phenyl}-1H-1,2,3-triazole-4-carboxamide | 13.4 mg | 492 |
| 936 | N-(2,3-difluorobenzyl)-1-{4-[(ethylamino)carbonyl]-2-[2-(2-fluoroethoxy)ethoxy]phenyl}-1H-1,2,3-triazole-4-carboxamide | 18.4 mg | 492 |
| 937 | N-(4-tert-butylbenzyl)-1-{4-[(ethylamino)carbonyl]-2-[2-(2-fluoroethoxy)ethoxy]phenyl}-1H-1,2,3-triazole-4-carboxamide | 20.8 mg | 512 |

TABLE 2-continued

| Example No. | Compound name | yield | [M + H]+ |
|---|---|---|---|
| 938 | 1-{4-[(ethylamino)carbonyl]-2-[2-(2-fluoroethoxy)ethoxy]phenyl}-N-[3-(trifluoromethyl)benzyl]-1H-1,2,3-triazole-4-carboxamide | 15.8 mg | 524 |
| 939 | 1-{4-[(ethylamino)carbonyl]-2-[2-(2-fluoroethoxy)ethoxy]phenyl}-N-[4-(trifluoromethoxy)benzyl]-1H-1,2,3-triazole-4-carboxamide | 16.7 mg | 540 |
| 940 | 1-{4-[(ethylamino)carbonyl]-2-[2-(2-fluoroethoxy)ethoxy]phenyl}-N-[3-fluoro-5-(trifluoromethyl)benzyl]-1H-1,2,3-triazole-4-carboxamide | 13.9 mg | 542 |
| 941 | N-[2-(benzylthio)ethyl]-1-{4-[(ethylamino)carbonyl]-2-[2-(2-fluoroethoxy)ethoxy]phenyl}-1H-1,2,3-triazole-4-carboxamide | 19.8 mg | 516 |
| 942 | 1-{4-[(ethylamino)carbonyl]-2-[2-(2-fluoroethoxy)ethoxy]phenyl}-N-[(pentafluorobenzyl)oxy]-1H-1,2,3-triazole-4-carboxamide | 3.7 mg | 562 |
| 943 | 1-{4-[(ethylamino)carbonyl]-2-[2-(2-fluoroethoxy)ethoxy]phenyl}-N-(pyridin-3-ylmethyl)-1H-1,2,3-triazole-4-carboxamide trifluoroacetate | 22.1 mg | 457 |
| 944 | 1-{4-[(ethylamino)carbonyl]-2-[2-(2-fluoroethoxy)ethoxy]phenyl}-N-(pyridin-2-ylmethyl)-1H-1,2,3-triazole-4-carboxamide trifluoroacetate | 24.9 mg | 457 |
| 945 | 1-{4-[(ethylamino)carbonyl]-2-[2-(2-fluoroethoxy)ethoxy]phenyl}-N-(pyridin-4-ylmethyl)-1H-1,2,3-triazole-4-carboxamide trifluoroacetate | 26 mg | 457 |
| 946 | 1-{4-[(ethylamino)carbonyl]-2-[2-(2-fluoroethoxy)ethoxy]phenyl}-N-[2-(pyridin-2-yl)ethyl]-1H-1,2,3-triazole-4-carboxamide trifluoroacetate | 26.8 mg | 471 |
| 947 | 1-{4-[(ethylamino)carbonyl]-2-[2-(2-fluoroethoxy)ethoxy]phenyl}-N-[(5-methylpyrazin-2-yl)methyl]-1H-1,2,3-triazole-4-carboxamide | 17.4 mg | 472 |
| 948 | N-(2-anilinoethyl)-1-{4-[(ethylamino)carbonyl]-2-[2-(2-fluoroethoxy)ethoxy]phenyl}-1H-1,2,3-triazole-4-carboxamide | 21.5 mg | 485 |
| 949 | N-(1-benzylpyrrolidin-3-yl)-1-{4-[(ethylamino)carbonyl]-2-[2-(2-fluoroethoxy)ethoxy]phenyl}-1H-1,2,3-triazole-4-carboxamide trifluoroacetate | 26.5 mg | 525 |
| 950 | N-(1-benzylpiperidin-4-yl)-1-{4-[(ethylamino)carbonyl]-2-[2-(2-fluoroethoxy)ethoxy]phenyl}-1H-1,2,3-triazole-4-carboxamide trifluoroacetate | 26.2 mg | 539 |
| 951 | 1-{4-[(ethylamino)carbonyl]-2-[2-(2-fluoroethoxy)ethoxy]phenyl}-N-(2-thienylmethyl)-1H-1,2,3-triazole-4-carboxamide | 16.9 mg | 462 |
| 952 | 1-{4-[(ethylamino)carbonyl]-2-[2-(2-fluoroethoxy)ethoxy]phenyl}-N-[(3-methyl-2-thienyl)methyl]-1H-1,2,3-triazole-4-carboxamide | 14.1 mg | 476 |
| 953 | 1-{4-[(ethylamino)carbonyl]-2-[2-(2-fluoroethoxy)ethoxy]phenyl}-N-(3-thienylmethyl)-1H-1,2,3-triazole-4-carboxamide | 17.6 mg | 462 |
| 954 | 1-{4-[(ethylamino)carbonyl]-2-[2-(2-fluoroethoxy)ethoxy]phenyl}-N-(2-fluorobenzyl)-1H-1,2,3-triazole-4-carboxamide | 19 mg | 474 |
| 955 | 1-{4-[(ethylamino)carbonyl]-2-[2-(2-fluoroethoxy)ethoxy]phenyl}-N-(4-fluorobenzyl)-1H-1,2,3-triazole-4-carboxamide | 18.2 mg | 474 |
| 956 | N-(3-bromobenzyl)-1-{4-[(ethylamino)carbonyl]-2-[2-(2-fluoroethoxy)ethoxy]phenyl}-1H-1,2,3-triazole-4-carboxamide | 19.7 mg | 535 |

TABLE 2-continued

| Example No. | Compound name | yield | [M + H]+ |
|---|---|---|---|
| 957 | N-(2,6-difluorobenzyl)-1-{4-[(ethylamino)carbonyl]-2-[2-(2-fluoroethoxy)ethoxy]phenyl}-1H-1,2,3-triazole-4-carboxamide | 29.7 mg | 492 |
| 958 | N-(3,4-difluorobenzyl)-1-{4-[(ethylamino)carbonyl]-2-[2-(2-fluoroethoxy)ethoxy]phenyl}-1H-1,2,3-triazole-4-carboxamide | 12.2 mg | 492 |
| 959 | N-(3-chloro-4-fluorobenzyl)-1-{4-[(ethylamino)carbonyl]-2-[2-(2-fluoroethoxy)ethoxy]phenyl}-1H-1,2,3-triazole-4-carboxamide | 18.5 mg | 508 |
| 960 | 1-{4-[(ethylamino)carbonyl]-2-[2-(2-fluoroethoxy)ethoxy]phenyl}-N-(2,3,6-trifluorobenzyl)-1H-1,2,3-triazole-4-carboxamide | 17.9 mg | 510 |
| 961 | N-(1H-benzimidazol-2-ylmethyl)-1-{4-[(ethylamino)carbonyl]-2-[2-(2-fluoroethoxy)ethoxy]phenyl}-1H-1,2,3-triazole-4-carboxamide trifluoroacetate | 8.5 mg | 496 |
| 962 | 1-{4-[(ethylamino)carbonyl]-2-[2-(2-fluoroethoxy)ethoxy]phenyl}-N-[2-(6-fluoro-1H-indol-3-yl)ethyl]-1H-1,2,3-triazole-4-carboxamide | 21.9 mg | 527 |
| 963 | 1-{4-[(ethylamino)carbonyl]-2-[2-(2-fluoroethoxy)ethoxy]phenyl}-N-[2-(pyridin-2-ylamino)ethyl]-1H-1,2,3-triazole-4-carboxamide trifluoroacetate | 16.5 mg | 486 |
| 964 | N-[(5-chloro-2-thienyl)methyl]-1-{4-[(ethylamino)carbonyl]-2-[2-(2-fluoroethoxy)ethoxy]phenyl}-1H-1,2,3-triazole-4-carboxamide | 10.8 mg | 496 |
| 965 | N-[2-(5-chloro-2-thienyl)ethyl]-1-{4-[(ethylamino)carbonyl]-2-[2-(2-fluoroethoxy)ethoxy]phenyl}-1H-1,2,3-triazole-4-carboxamide | 13.2 mg | 510 |
| 966 | 1-{4-[(ethylamino)carbonyl]-2-[2-(2-fluoroethoxy)ethoxy]phenyl}-N-[5-fluoro-2-(trifluoromethyl)benzyl]-1H-1,2,3-triazole-4-carboxamide | 18.6 mg | 542 |
| 967 | 1-{4-[(ethylamino)carbonyl]-2-[2-(2-fluoroethoxy)ethoxy]phenyl}-N-[3-fluoro-4-(trifluoromethyl)benzyl]-1H-1,2,3-triazole-4-carboxamide | 18.2 mg | 542 |
| 968 | N-[3-(difluoromethoxy)benzyl]-1-{4-[(ethylamino)carbonyl]-2-[2-(2-fluoroethoxy)ethoxy]phenyl}-1H-1,2,3-triazole-4-carboxamide | 20.6 mg | 522 |
| 969 | 1-{4-[(ethylamino)carbonyl]-2-[2-(2-fluoroethoxy)ethoxy]phenyl}-N-[3-(1H-pyrrol-1-yl)benzyl]-1H-1,2,3-triazole-4-carboxamide | 20.7 mg | 521 |
| 970 | N-(2-chloro-6-fluorobenzyl)-1-{4-[(ethylamino)carbonyl]-2-[2-(2-fluoroethoxy)ethoxy]phenyl}-1H-1,2,3-triazole-4-carboxamide | 18.9 mg | 508 |
| 971 | 1-{4-[(ethylamino)carbonyl]-2-[2-(2-fluoroethoxy)ethoxy]phenyl}-N-[(1-methyl-1H-benzimidazol-2-yl)methyl]-1H-1,2,3-triazole-4-carboxamide trifluoroacetate | 7.5 mg | 510 |
| 972 | 1-{4-[(ethylamino)carbonyl]-2-[2-(2-fluoroethoxy)ethoxy]phenyl}-N-[3-(trifluoromethoxy)benzyl]-1H-1,2,3-triazole-4-carboxamide | 21.3 mg | 540 |
| 973 | 1-{4-[(ethylamino)carbonyl]-2-[2-(2-fluoroethoxy)ethoxy]phenyl}-N-[2-(3-fluorophenyl)ethyl]-1H-1,2,3-triazole-4-carboxamide | 15 mg | 488 |
| 974 | 1-{4-[(ethylamino)carbonyl]-2-[2-(2-fluoroethoxy)ethoxy]phenyl}-N-[(1-methyl-1H-pyrrol-2-yl)methyl]-1H-1,2,3-triazole-4-carboxamide | 22.2 mg | 459 |
| 975 | N-{[5-(4-chlorophenyl)-2-thienyl]methyl}-1-(2-[2-(2-fluoroethoxy)ethoxy]-4-{[(2,2,2- | 18.6 mg | 626 |

TABLE 2-continued

| Example No. | Compound name | yield | [M + H]+ |
|---|---|---|---|
| | trifluoroethyl)amino]carbonyl}phenyl)-1H-1,2,3-triazole-4-carboxamide | | |
| 976 | 1-(2-[2-(2-fluoroethoxy)ethoxy]-4-{[(2,2,2-trifluoroethyl)amino]carbonyl}phenyl)-N-{[2-(2-thienyl)-1,3-thiazol-4-yl]methyl}-1H-1,2,3-triazole-4-carboxamide | 21.3 mg | 599 |
| 977 | N-(1-benzothien-2-ylmethyl)-1-(2-[2-(2-fluoroethoxy)ethoxy]-4-{[(2,2,2-trifluoroethyl)amino]carbonyl}phenyl)-1H-1,2,3-triazole-4-carboxamide | 12.5 mg | 566 |
| 978 | N-{[2-(benzyloxy)pyridin-4-yl]methyl}-1-(2-[2-(2-fluoroethoxy)ethoxy]-4-{[(2,2,2-trifluoroethyl)amino]carbonyl}phenyl)-1H-1,2,3-triazole-4-carboxamide | 21.7 mg | 617 |
| 979 | 1-(2-[2-(2-fluoroethoxy)ethoxy]-4-{[(2,2,2-trifluoroethyl)amino]carbonyl}phenyl)-N-{[2-(tetrahydro-2H-pyran-4-ylmethoxy)pyridin-4-yl]methyl}-1H-1,2,3-triazole-4-carboxamide | 28.6 mg | 625 |
| 980 | N-(2-{[(5-chloroimidazo[1,2-a]pyridin-2-yl)methyl]thio}ethyl)-1-(2-[2-(2-fluoroethoxy)ethoxy]-4-{[(2,2,2-trifluoroethyl)amino]carbonyl}phenyl)-1H-1,2,3-triazole-4-carboxamide trifluoroacetate | 25.7 mg | 645 |
| 981 | N-[(4'-fluorobiphenyl-3-yl)methyl]-1-(2-[2-(2-fluoroethoxy)ethoxy]-4-{[(2,2,2-trifluoroethyl)amino]carbonyl}phenyl)-1H-1,2,3-triazole-4-carboxamide | 21.9 mg | 604 |
| 982 | 1-(2-[2-(2-fluoroethoxy)ethoxy]-4-{[(2,2,2-trifluoroethyl)amino]carbonyl}phenyl)-N-[3-(pyridin-2-yloxy)benzyl]-1H-1,2,3-triazole-4-carboxamide | 20.3 mg | 603 |
| 983 | 1-(2-[2-(2-fluoroethoxy)ethoxy]-4-{[(2,2,2-trifluoroethyl)amino]carbonyl}phenyl)-N-[(5-methyl-2-phenyl-2H-1,2,3-triazol-4-yl)methyl]-1H-1,2,3-triazole-4-carboxamide | 21.6 mg | 591 |
| 984 | 1-(2-[2-(2-fluoroethoxy)ethoxy]-4-{[(2,2,2-trifluoroethyl)amino]carbonyl}phenyl)-N-[(1-methyl-1H-1,2,3-benzotriazol-5-yl)methyl]-1H-1,2,3-triazole-4-carboxamide | 19.3 mg | 565 |
| 985 | 1-(2-[2-(2-fluoroethoxy)ethoxy]-4-{[(2,2,2-trifluoroethyl)amino]carbonyl}phenyl)-N-[3-(methylthio)benzyl]-1H-1,2,3-triazole-4-carboxamide | 19.1 mg | 556 |
| 986 | N-[(2-ethoxypyridin-4-yl)methyl]-1-(2-[2-(2-fluoroethoxy)ethoxy]-4-{[(2,2,2-trifluoroethyl)amino]carbonyl}phenyl)-1H-1,2,3-triazole-4-carboxamide | 23.9 mg | 555 |
| 987 | N-(3-ethoxybenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 15.1 mg | 554 |
| 988 | 1-(2-[2-(2-fluoroethoxy)ethoxy]-4-{[(2,2,2-trifluoroethyl)amino]carbonyl}phenyl)-N-[1-(2-thienyl)ethyl]-1H-1,2,3-triazole-4-carboxamide | 18.5 mg | 530 |
| 989 | N-[1-(3-chloro-4-fluorophenyl)-3-methyl-1H-pyrazol-5-yl]-1-(2-[2-(2-fluoroethoxy)ethoxy]-4-{[(2,2,2-trifluoroethyl)amino]carbonyl}phenyl)-1H-1,2,3-triazole-4-carboxamide | 2.2 mg | 628 |
| 990 | 1-(2-[2-(2-fluoroethoxy)ethoxy]-4-{[(2,2,2-trifluoroethyl)amino]carbonyl}phenyl)-N- | 17.9 mg | 508 |

TABLE 2-continued

| Example No. | Compound name | yield | [M + H]+ |
|---|---|---|---|
| | [3-(methylthio)propyl]-1H-1,2,3-triazole-4-carboxamide | | |
| 991 | N-benzyl-1-(2-[2-(2-fluoroethoxy)ethoxy]-4-{[(2,2,2-trifluoroethyl)amino]carbonyl}phenyl)-1H-1,2,3-triazole-4-carboxamide | 17.7 mg | 510 |
| 992 | N-(2,3-dihydro-1H-inden-2-yl)-1-(2-[2-(2-fluoroethoxy)ethoxy]-4-{[(2,2,2-trifluoroethyl)amino]carbonyl}phenyl)-1H-1,2,3-triazole-4-carboxamide | 18 mg | 536 |
| 993 | N-(1,3-benzodioxol-5-ylmethyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.8 mg | 554 |
| 994 | N-(4-tert-butylcyclohexyl)-1-(2-[2-(2-fluoroethoxy)ethoxy]-4-{[(2,2,2-trifluoroethyl)amino]carbonyl}phenyl)-1H-1,2,3-triazole-4-carboxamide | 21 mg | 558 |
| 995 | 1-(2-[2-(2-fluoroethoxy)ethoxy]-4-{[(2,2,2-trifluoroethyl)amino]carbonyl}phenyl)-N-[2-(1H-indol-3-yl)ethyl]-1H-1,2,3-triazole-4-carboxamide | 20.3 mg | 563 |
| 996 | 1-(2-[2-(2-fluoroethoxy)ethoxy]-4-{[(2,2,2-trifluoroethyl)amino]carbonyl}phenyl)-N-[4-(trifluoromethyl)benzyl]-1H-1,2,3-triazole-4-carboxamide | 14.8 mg | 578 |
| 997 | N-(3,4-dichlorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 20 mg | 579 |
| 998 | 1-(2-[2-(2-fluoroethoxy)ethoxy]-4-{[(2,2,2-trifluoroethyl)amino]carbonyl}phenyl)-N-[2-(5-methoxy-1H-indol-3-yl)ethyl]-1H-1,2,3-triazole-4-carboxamide | 21.2 mg | 593 |
| 999 | N-[3,5-bis(trifluoromethyl)benzyl]-1-(2-[2-(2-fluoroethoxy)ethoxy]-4-{[(2,2,2-trifluoroethyl)amino]carbonyl}phenyl)-1H-1,2,3-triazole-4-carboxamide | 21.2 mg | 646 |
| 1000 | 1-(2-[2-(2-fluoroethoxy)ethoxy]-4-{[(2,2,2-trifluoroethyl)amino]carbonyl}phenyl)-N-[1-(methoxymethyl)propyl]-1H-1,2,3-triazole-4-carboxamide | 18.7 mg | 506 |
| 1001 | 1-(2-[2-(2-fluoroethoxy)ethoxy]-4-{[(2,2,2-trifluoroethyl)amino]carbonyl}phenyl)-N-[2-(2-thienyl)ethyl]-1H-1,2,3-triazole-4-carboxamide | 19 mg | 530 |
| 1002 | 1-(2-[2-(2-fluoroethoxy)ethoxy]-4-{[(2,2,2-trifluoroethyl)amino]carbonyl}phenyl)-N-(3-methoxybenzyl)-1H-1,2,3-triazole-4-carboxamide | 18.9 mg | 540 |
| 1003 | N-(3-chlorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.1 mg | 544 |
| 1004 | N-(2,5-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 21.4 mg | 546 |
| 1005 | N-(2,4-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.8 mg | 546 |
| 1006 | N-(3,5-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 20 mg | 546 |
| 1007 | N-(2,3-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 28.6 mg | 546 |

TABLE 2-continued

| Example No. | Compound name | yield | [M + H]+ |
|---|---|---|---|
| 1008 | N-(4-tert-butylbenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 21 mg | 566 |
| 1009 | 1-(2-[2-(2-fluoroethoxy)ethoxy]-4-{[(2,2,2-trifluoroethyl)amino]carbonyl}phenyl)-N-[3-(trifluoromethyl)benzyl]-1H-1,2,3-triazole-4-carboxamide | 23.3 mg | 578 |
| 1010 | 1-(2-[2-(2-fluoroethoxy)ethoxy]-4-{[(2,2,2-trifluoroethyl)amino]carbonyl}phenyl)-N-[4-(trifluoromethoxy)benzyl]-1H-1,2,3-triazole-4-carboxamide | 12.1 mg | 594 |
| 1011 | 1-(2-[2-(2-fluoroethoxy)ethoxy]-4-{[(2,2,2-trifluoroethyl)amino]carbonyl}phenyl)-N-[3-fluoro-5-(trifluoromethyl)benzyl]-1H-1,2,3-triazole-4-carboxamide | 20.8 mg | 596 |
| 1012 | N-[2-(benzylthio)ethyl]-1-(2-[2-(2-fluoroethoxy)ethoxy]-4-{[(2,2,2-trifluoroethyl)amino]carbonyl}phenyl)-1H-1,2,3-triazole-4-carboxamide | 20.2 mg | 570 |
| 1013 | 1-(2-[2-(2-fluoroethoxy)ethoxy]-4-{[(2,2,2-trifluoroethyl)amino]carbonyl}phenyl)-N-[(pentafluorobenzyl)oxy]-1H-1,2,3-triazole-4-carboxamide | 5 mg | 616 |
| 1014 | 1-(2-[2-(2-fluoroethoxy)ethoxy]-4-{[(2,2,2-trifluoroethyl)amino]carbonyl}phenyl)-N-(pyridin-3-ylmethyl)-1H-1,2,3-triazole-4-carboxamide trifluoroacetate | 24.3 mg | 511 |
| 1015 | 1-(2-[2-(2-fluoroethoxy)ethoxy]-4-{[(2,2,2-trifluoroethyl)amino]carbonyl}phenyl)-N-(pyridin-2-ylmethyl)-1H-1,2,3-triazole-4-carboxamide trifluoroacetate | 22 mg | 511 |
| 1016 | 1-(2-[2-(2-fluoroethoxy)ethoxy]-4-{[(2,2,2-trifluoroethyl)amino]carbonyl}phenyl)-N-(pyridin-4-ylmethyl)-1H-1,2,3-triazole-4-carboxamide trifluoroacetate | 27.1 mg | 511 |
| 1017 | 1-(2-[2-(2-fluoroethoxy)ethoxy]-4-{[(2,2,2-trifluoroethyl)amino]carbonyl}phenyl)-N-[2-(pyridin-2-yl)ethyl]-1H-1,2,3-triazole-4-carboxamide trifluoroacetate | 16.1 mg | 525 |
| 1018 | 1-(2-[2-(2-fluoroethoxy)ethoxy]-4-{[(2,2,2-trifluoroethyl)amino]carbonyl}phenyl)-N-[(5-methylpyrazin-2-yl)methyl]-1H-1,2,3-triazole-4-carboxamide | 19 mg | 526 |
| 1019 | N-(2-anilinoethyl)-1-(2-[2-(2-fluoroethoxy)ethoxy]-4-{[(2,2,2-trifluoroethyl)amino]carbonyl}phenyl)-1H-1,2,3-triazole-4-carboxamide | 20.8 mg | 539 |
| 1020 | N-(1-benzylpyrrolidin-3-yl)-1-(2-[2-(2-fluoroethoxy)ethoxy]-4-{[(2,2,2-trifluoroethyl)amino]carbonyl}phenyl)-1H-1,2,3-triazole-4-carboxamide trifluoroacetate | 26.9 mg | 579 |
| 1021 | N-(1-benzylpiperidin-4-yl)-1-(2-[2-(2-fluoroethoxy)ethoxy]-4-{[(2,2,2-trifluoroethyl)amino]carbonyl}phenyl)-1H-1,2,3-triazole-4-carboxamide | 17.1 mg | 593 |
| 1022 | 1-(2-[2-(2-fluoroethoxy)ethoxy]-4-{[(2,2,2-trifluoroethyl)amino]carbonyl}phenyl)-N-(2-thienylmethyl)-1H-1,2,3-triazole-4-carboxamide | 17.5 mg | 516 |
| 1023 | 1-(2-[2-(2-fluoroethoxy)ethoxy]-4-{[(2,2,2-trifluoroethyl)amino]carbonyl}phenyl)-N-[(3-methyl-2-thienyl)methyl]-1H-1,2,3-triazole-4-carboxamide | 12.1 mg | 530 |

TABLE 2-continued

| Example No. | Compound name | yield | [M + H]+ |
|---|---|---|---|
| 1024 | 1-(2-[2-(2-fluoroethoxy)ethoxy]-4-{[(2,2,2-trifluoroethyl)amino]carbonyl}phenyl)-N-(3-thienylmethyl)-1H-1,2,3-triazole-4-carboxamide | 17.8 mg | 516 |
| 1025 | N-(2-fluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 18.4 mg | 528 |
| 1026 | N-(4-fluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 18.9 mg | 528 |
| 1027 | N-(3-bromobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 26 mg | 589 |
| 1028 | N-(2,6-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.1 mg | 546 |
| 1029 | N-(3,4-difluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19 mg | 546 |
| 1030 | N-(3-chloro-4-fluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.6 mg | 562 |
| 1031 | 1-(2-[2-(2-fluoroethoxy)ethoxy]-4-{[(2,2,2-trifluoroethyl)amino]carbonyl}phenyl)-N-(2,3,6-trifluorobenzyl)-1H-1,2,3-triazole-4-carboxamide | 19.4 mg | 564 |
| 1032 | N-(1H-benzimidazol-2-ylmethyl)-1-(2-[2-(2-fluoroethoxy)ethoxy]-4-{[(2,2,2-trifluoroethyl)amino]carbonyl}phenyl)-1H-1,2,3-triazole-4-carboxamide trifluoroacetate | 8 mg | 550 |
| 1033 | 1-(2-[2-(2-fluoroethoxy)ethoxy]-4-{[(2,2,2-trifluoroethyl)amino]carbonyl}phenyl)-N-[2-(6-fluoro-1H-indol-3-yl)ethyl]-1H-1,2,3-triazole-4-carboxamide | 23 mg | 581 |
| 1034 | 1-(2-[2-(2-fluoroethoxy)ethoxy]-4-{[(2,2,2-trifluoroethyl)amino]carbonyl}phenyl)-N-[2-(pyridin-2-ylamino)ethyl]-1H-1,2,3-triazole-4-carboxamide trifluoroacetate | 20.6 mg | 540 |
| 1035 | N-[(5-chloro-2-thienyl)methyl]-1-(2-[2-(2-fluoroethoxy)ethoxy]-4-{[(2,2,2-trifluoroethyl)amino]carbonyl}phenyl)-1H-1,2,3-triazole-4-carboxamide | 10.1 mg | 550 |
| 1036 | N-[2-(5-chloro-2-thienyl)ethyl]-1-(2-[2-(2-fluoroethoxy)ethoxy]-4-{[(2,2,2-trifluoroethyl)amino]carbonyl}phenyl)-1H-1,2,3-triazole-4-carboxamide | 11.8 mg | 564 |
| 1037 | 1-(2-[2-(2-fluoroethoxy)ethoxy]-4-{[(2,2,2-trifluoroethyl)amino]carbonyl}phenyl)-N-[5-fluoro-2-(trifluoromethyl)benzyl]-1H-1,2,3-triazole-4-carboxamide | 18.3 mg | 596 |
| 1038 | 1-(2-[2-(2-fluoroethoxy)ethoxy]-4-{[(2,2,2-trifluoroethyl)amino]carbonyl}phenyl)-N-[3-fluoro-4-(trifluoromethyl)benzyl]-1H-1,2,3-triazole-4-carboxamide | 22.2 mg | 596 |
| 1039 | N-[3-(difluoromethoxy)benzyl]-1-(2-[2-(2-fluoroethoxy)ethoxy]-4-{[(2,2,2-trifluoroethyl)amino]carbonyl}phenyl)-1H-1,2,3-triazole-4-carboxamide | 25 mg | 576 |
| 1040 | 1-(2-[2-(2-fluoroethoxy)ethoxy]-4-{[(2,2,2-trifluoroethyl)amino]carbonyl}phenyl)-N-[3-(1H-pyrrol-1-yl)benzyl]-1H-1,2,3-triazole-4-carboxamide | 20.7 mg | 575 |

TABLE 2-continued

| Example No. | Compound name | yield | [M + H]+ |
|---|---|---|---|
| 1041 | N-(2-chloro-6-fluorobenzyl)-1-(2-[2-(2-fluoroethoxy)ethoxy]-4-{[(2,2,2-trifluoroethyl)amino]carbonyl}phenyl)-1H-1,2,3-triazole-4-carboxamide | 19.7 mg | 562 |
| 1042 | 1-(2-[2-(2-fluoroethoxy)ethoxy]-4-{[(2,2,2-trifluoroethyl)amino]carbonyl}phenyl)-N-[(1-methyl-1H-benzimidazol-2-yl)methyl]-1H-1,2,3-triazole-4-carboxamide trifluoroacetate | 15.9 mg | 564 |
| 1043 | 1-(2-[2-(2-fluoroethoxy)ethoxy]-4-{[(2,2,2-trifluoroethyl)amino]carbonyl}phenyl)-N-[3-(trifluoromethoxy)benzyl]-1H-1,2,3-triazole-4-carboxamide | 20.8 mg | 594 |
| 1044 | 1-(2-[2-(2-fluoroethoxy)ethoxy]-4-{[(2,2,2-trifluoroethyl)amino]carbonyl}phenyl)-N-[2-(3-fluorophenyl)ethyl]-1H-1,2,3-triazole-4-carboxamide | 19 mg | 542 |
| 1045 | 1-(2-[2-(2-fluoroethoxy)ethoxy]-4-{[(2,2,2-trifluoroethyl)amino]carbonyl}phenyl)-N-[(1-methyl-1H-pyrrol-2-yl)methyl]-1H-1,2,3-triazole-4-carboxamide | 17.7 mg | 513 |
| 1046 | N-{[5-(4-chlorophenyl)-2-thienyl]methyl}-1-{4-[(ethylamino)carbonyl]phenyl}-5-[(methylthio)methyl]-1H-1,2,3-triazole-4-carboxamide | 17.7 mg | 526 |
| 1047 | 1-{4-[(ethylamino)carbonyl]phenyl}-5-[(methylthio)methyl]-N-{[2-(2-thienyl)-1,3-thiazol-4-yl]methyl}-1H-1,2,3-triazole-4-carboxamide | 22.3 mg | 499 |
| 1048 | N-(1-benzothien-2-ylmethyl)-1-{4-[(ethylamino)carbonyl]phenyl}-5-[(methylthio)methyl]-1H-1,2,3-triazole-4-carboxamide | 20.4 mg | 466 |
| 1049 | N-{[2-(benzyloxy)pyridin-4-yl]methyl}-1-{4-[(ethylamino)carbonyl]phenyl}-5-[(methylthio)methyl]-1H-1,2,3-triazole-4-carboxamide | 23 mg | 517 |
| 1050 | 1-{4-[(ethylamino)carbonyl]phenyl}-5-[(methylthio)methyl]-N-{[2-(tetrahydro-2H-pyran-4-ylmethoxy)pyridin-4-yl]methyl}-1H-1,2,3-triazole-4-carboxamide | 29.4 mg | 525 |
| 1051 | N-(2-{[(5-chloroimidazo[1,2-a]pyridin-2-yl)methyl]thio}ethyl)-1-{4-[(ethylamino)carbonyl]phenyl}-5-[(methylthio)methyl]-1H-1,2,3-triazole-4-carboxamide trifluoroacetate | 27.5 mg | 545 |
| 1052 | 1-{4-[(ethylamino)carbonyl]phenyl}-N-[(4'-fluorobiphenyl-3-yl)methyl]-5-[(methylthio)methyl]-1H-1,2,3-triazole-4-carboxamide | 22.9 mg | 504 |
| 1053 | 1-{4-[(ethylamino)carbonyl]phenyl}-5-[(methylthio)methyl]-N-[3-(pyridin-2-yloxy)benzyl]-1H-1,2,3-triazole-4-carboxamide | 25 mg | 503 |
| 1054 | 1-{4-[(ethylamino)carbonyl]phenyl}-N-[(5-methyl-2-phenyl-2H-1,2,3-triazol-4-yl)methyl]-5-[(methylthio)methyl]-1H-1,2,3-triazole-4-carboxamide | 19.2 mg | 491 |
| 1055 | 1-{4-[(ethylamino)carbonyl]phenyl}-N-[(1-methyl-1H-1,2,3-benzotriazol-5-yl)methyl]-5-[(methylthio)methyl]-1H-1,2,3-triazole-4-carboxamide | 20.2 mg | 465 |
| 1056 | 1-{4-[(ethylamino)carbonyl]phenyl}-N-[3-(methylthio)benzyl]-5-[(methylthio)methyl]-1H-1,2,3-triazole-4-carboxamide | 19.1 mg | 456 |
| 1057 | N-[(2-ethoxypyridin-4-yl)methyl]-1-{4-[(ethylamino)carbonyl]phenyl}-5-[(methylthio)methyl]-1H-1,2,3-triazole-4-carboxamide | 26.9 mg | 455 |

TABLE 2-continued

| Example No. | Compound name | yield | [M + H]+ |
|---|---|---|---|
| 1058 | N-(3-ethoxybenzyl)-1-{4-[(ethylamino)carbonyl]phenyl}-5-[(methylthio)methyl]-1H-1,2,3-triazole-4-carboxamide | 17.6 mg | 454 |
| 1059 | 1-{4-[(ethylamino)carbonyl]phenyl}-5-[(methylthio)methyl]-N-[1-(2-thienyl)ethyl]-1H-1,2,3-triazole-4-carboxamide | 17.8 mg | 430 |
| 1060 | N-[1-(3-chloro-4-fluorophenyl)-3-methyl-1H-pyrazol-5-yl]-1-{4-[(ethylamino)carbonyl]phenyl}-5-[(methylthio)methyl]-1H-1,2,3-triazole-4-carboxamide | 2.3 mg | 528 |
| 1061 | 1-{4-[(ethylamino)carbonyl]phenyl}-5-[(methylthio)methyl]-N-[3-(methylthio)propyl]-1H-1,2,3-triazole-4-carboxamide | 16.4 mg | 408 |
| 1062 | N-benzyl-1-{4-[(ethylamino)carbonyl]phenyl}-5-[(methylthio)methyl]-1H-1,2,3-triazole-4-carboxamide | 17.8 mg | 410 |
| 1063 | 1-{4-[(ethylamino)carbonyl]phenyl}-N-(3-fluorobenzyl)-5-[(methylthio)methyl]-1H-1,2,3-triazole-4-carboxamide | 18.3 mg | 428 |
| 1064 | N-(2,3-dihydro-1H-inden-2-yl)-1-{4-[(ethylamino)carbonyl]phenyl}-5-[(methylthio)methyl]-1H-1,2,3-triazole-4-carboxamide | 18 mg | 436 |
| 1065 | N-(1,3-benzodioxol-5-ylmethyl)-1-{4-[(ethylamino)carbonyl]phenyl}-5-[(methylthio)methyl]-1H-1,2,3-triazole-4-carboxamide | 20.5 mg | 454 |
| 1066 | N-(4-tert-butylcyclohexyl)-1-{4-[(ethylamino)carbonyl]phenyl}-5-[(methylthio)methyl]-1H-1,2,3-triazole-4-carboxamide | 21.3 mg | 458 |
| 1067 | 1-{4-[(ethylamino)carbonyl]phenyl}-N-[2-(1H-indol-3-yl)ethyl]-5-[(methylthio)methyl]-1H-1,2,3-triazole-4-carboxamide | 21.8 mg | 463 |
| 1068 | 1-{4-[(ethylamino)carbonyl]phenyl}-5-[(methylthio)methyl]-N-[4-(trifluoromethyl)benzyl]-1H-1,2,3-triazole-4-carboxamide | 24.7 mg | 478 |
| 1069 | N-(3,4-dichlorobenzyl)-1-{4-[(ethylamino)carbonyl]phenyl}-5-[(methylthio)methyl]-1H-1,2,3-triazole-4-carboxamide | 20.7 mg | 479 |
| 1070 | 1-{4-[(ethylamino)carbonyl]phenyl}-N-[2-(5-methoxy-1H-indol-3-yl)ethyl]-5-[(methylthio)methyl]-1H-1,2,3-triazole-4-carboxamide | 20.9 mg | 493 |
| 1071 | N-[3,5-bis(trifluoromethyl)benzyl]-1-{4-[(ethylamino)carbonyl]phenyl}-5-[(methylthio)methyl]-1H-1,2,3-triazole-4-carboxamide | 19.7 mg | 546 |
| 1072 | 1-{4-[(ethylamino)carbonyl]phenyl}-N-[1-(methoxymethyl)propyl]-5-[(methylthio)methyl]-1H-1,2,3-triazole-4-carboxamide | 16.4 mg | 406 |
| 1073 | 1-{4-[(ethylamino)carbonyl]phenyl}-5-[(methylthio)methyl]-N-[2-(2-thienyl)ethyl]-1H-1,2,3-triazole-4-carboxamide | 17.6 mg | 430 |
| 1074 | 1-{4-[(ethylamino)carbonyl]phenyl}-N-(3-methoxybenzyl)-5-[(methylthio)methyl]-1H-1,2,3-triazole-4-carboxamide | 19.4 mg | 440 |
| 1075 | N-(3-chlorobenzyl)-1-{4-[(ethylamino)carbonyl]phenyl}-5-[(methylthio)methyl]-1H-1,2,3-triazole-4-carboxamide | 19.9 mg | 445 |
| 1076 | N-(2,5-difluorobenzyl)-1-{4-[(ethylamino)carbonyl]phenyl}-5-[(methylthio)methyl]-1H-1,2,3-triazole-4-carboxamide | 18.4 mg | 446 |

TABLE 2-continued

| Example No. | Compound name | yield | [M + H]+ |
|---|---|---|---|
| 1077 | N-(2,4-difluorobenzyl)-1-{4-[(ethylamino)carbonyl]phenyl}-5-[(methylthio)methyl]-1H-1,2,3-triazole-4-carboxamide | 22.4 mg | 446 |
| 1078 | N-(3,5-difluorobenzyl)-1-{4-[(ethylamino)carbonyl]phenyl}-5-[(methylthio)methyl]-1H-1,2,3-triazole-4-carboxamide | 19.4 mg | 446 |
| 1079 | N-(2,3-difluorobenzyl)-1-{4-[(ethylamino)carbonyl]phenyl}-5-[(methylthio)methyl]-1H-1,2,3-triazole-4-carboxamide | 18.6 mg | 446 |
| 1080 | N-(4-tert-butylbenzyl)-1-{4-[(ethylamino)carbonyl]phenyl}-5-[(methylthio)methyl]-1H-1,2,3-triazole-4-carboxamide | 20.6 mg | 466 |
| 1081 | 1-{4-[(ethylamino)carbonyl]phenyl}-5-[(methylthio)methyl]-N-[3-(trifluoromethyl)benzyl]-1H-1,2,3-triazole-4-carboxamide | 20.3 mg | 478 |
| 1082 | 1-{4-[(ethylamino)carbonyl]phenyl}-5-[(methylthio)methyl]-N-[4-(trifluoromethoxy)benzyl]-1H-1,2,3-triazole-4-carboxamide | 19.7 mg | 494 |
| 1083 | 1-{4-[(ethylamino)carbonyl]phenyl}-N-[3-fluoro-5-(trifluoromethyl)benzyl]-5-[(methylthio)methyl]-1H-1,2,3-triazole-4-carboxamide | 20.9 mg | 496 |
| 1084 | N-[2-(benzylthio)ethyl]-1-{4-[(ethylamino)carbonyl]phenyl}-5-[(methylthio)methyl]-1H-1,2,3-triazole-4-carboxamide | 19.3 mg | 470 |
| 1085 | 1-{4-[(ethylamino)carbonyl]phenyl}-5-[(methylthio)methyl]-N-[(pentafluorobenzyl)oxy]-1H-1,2,3-triazole-4-carboxamide | 4.9 mg | 516 |
| 1086 | 1-{4-[(ethylamino)carbonyl]phenyl}-5-[(methylthio)methyl]-N-(pyridin-3-ylmethyl)-1H-1,2,3-triazole-4-carboxamide trifluoroacetate | 25.4 mg | 411 |
| 1087 | 1-{4-[(ethylamino)carbonyl]phenyl}-5-[(methylthio)methyl]-N-(pyridin-2-ylmethyl)-1H-1,2,3-triazole-4-carboxamide trifluoroacetate | 29 mg | 411 |
| 1088 | 1-{4-[(ethylamino)carbonyl]phenyl}-5-[(methylthio)methyl]-N-(pyridin-4-ylmethyl)-1H-1,2,3-triazole-4-carboxamide trifluoroacetate | 25.9 mg | 411 |
| 1089 | 1-{4-[(ethylamino)carbonyl]phenyl}-5-[(methylthio)methyl]-N-[2-(pyridin-2-yl)ethyl]-1H-1,2,3-triazole-4-carboxamide trifluoroacetate | 25.4 mg | 425 |
| 1090 | 1-{4-[(ethylamino)carbonyl]phenyl}-N-[(5-methylpyrazin-2-yl)methyl]-5-[(methylthio)methyl]-1H-1,2,3-triazole-4-carboxamide | 16.9 mg | 426 |
| 1091 | N-(2-anilinoethyl)-1-{4-[(ethylamino)carbonyl]phenyl}-5-[(methylthio)methyl]-1H-1,2,3-triazole-4-carboxamide | 23.4 mg | 439 |
| 1092 | N-(1-benzylpyrrolidin-3-yl)-1-{4-[(ethylamino)carbonyl]phenyl}-5-[(methylthio)methyl]-1H-1,2,3-triazole-4-carboxamide trifluoroacetate | 26.3 mg | 479 |
| 1093 | N-(1-benzylpiperidin-4-yl)-1-{4-[(ethylamino)carbonyl]phenyl}-5-[(methylthio)methyl]-1H-1,2,3-triazole-4-carboxamide | 27.3 mg | 493 |
| 1094 | 1-{4-[(ethylamino)carbonyl]phenyl}-5-[(methylthio)methyl]-N-(2-thienylmethyl)-1H-1,2,3-triazole-4-carboxamide | 17.7 mg | 416 |
| 1095 | 1-{4-[(ethylamino)carbonyl]phenyl}-N-[(3-methyl-2-thienyl)methyl]-5-[(methylthio)methyl]-1H-1,2,3-triazole-4-carboxamide | 13.1 mg | 430 |

TABLE 2-continued

| Example No. | Compound name | yield | [M + H]+ |
|---|---|---|---|
| 1096 | 1-{4-[(ethylamino)carbonyl]phenyl}-5-[(methylthio)methyl]-N-(3-thienylmethyl)-1H-1,2,3-triazole-4-carboxamide | 16.4 mg | 416 |
| 1097 | 1-{4-[(ethylamino)carbonyl]phenyl}-N-(2-fluorobenzyl)-5-[(methylthio)methyl]-1H-1,2,3-triazole-4-carboxamide | 26.4 mg | 428 |
| 1098 | 1-{4-[(ethylamino)carbonyl]phenyl}-N-(4-fluorobenzyl)-5-[(methylthio)methyl]-1H-1,2,3-triazole-4-carboxamide | 16.9 mg | 428 |
| 1099 | N-(3-bromobenzyl)-1-{4-[(ethylamino)carbonyl]phenyl}-5-[(methylthio)methyl]-1H-1,2,3-triazole-4-carboxamide | 21.3 mg | 489 |
| 1100 | N-(2,6-difluorobenzyl)-1-{4-[(ethylamino)carbonyl]phenyl}-5-[(methylthio)methyl]-1H-1,2,3-triazole-4-carboxamide | 12.6 mg | 446 |
| 1101 | N-(3,4-difluorobenzyl)-1-{4-[(ethylamino)carbonyl]phenyl}-5-[(methylthio)methyl]-1H-1,2,3-triazole-4-carboxamide | 19.1 mg | 446 |
| 1102 | N-(3-chloro-4-fluorobenzyl)-1-{4-[(ethylamino)carbonyl]phenyl}-5-[(methylthio)methyl]-1H-1,2,3-triazole-4-carboxamide | 18.5 mg | 462 |
| 1103 | 1-{4-[(ethylamino)carbonyl]phenyl}-5-[(methylthio)methyl]-N-(2,3,6-trifluorobenzyl)-1H-1,2,3-triazole-4-carboxamide | 15.5 mg | 464 |
| 1104 | N-(1H-benzimidazol-2-ylmethyl)-1-{4-[(ethylamino)carbonyl]phenyl}-5-[(methylthio)methyl]-1H-1,2,3-triazole-4-carboxamide trifluoroacetate | 9.1 mg | 450 |
| 1105 | 1-{4-[(ethylamino)carbonyl]phenyl}-N-[2-(6-fluoro-1H-indol-3-yl)ethyl]-5-[(methylthio)methyl]-1H-1,2,3-triazole-4-carboxamide | 22.2 mg | 481 |
| 1106 | 1-{4-[(ethylamino)carbonyl]phenyl}-5-[(methylthio)methyl]-N-[2-(pyridin-2-ylamino)ethyl]-1H-1,2,3-triazole-4-carboxamide trifluoroacetate | 20.5 mg | 440 |
| 1107 | N-[(5-chloro-2-thienyl)methyl]-1-{4-[(ethylamino)carbonyl]phenyl}-5-[(methylthio)methyl]-1H-1,2,3-triazole-4-carboxamide | 10.7 mg | 450 |
| 1108 | N-[2-(5-chloro-2-thienyl)ethyl]-1-{4-[(ethylamino)carbonyl]phenyl}-5-[(methylthio)methyl]-1H-1,2,3-triazole-4-carboxamide | 12.2 mg | 464 |
| 1109 | 1-{4-[(ethylamino)carbonyl]phenyl}-N-[5-fluoro-2-(trifluoromethyl)benzyl]-5-[(methylthio)methyl]-1H-1,2,3-triazole-4-carboxamide | 18.4 mg | 496 |
| 1110 | 1-{4-[(ethylamino)carbonyl]phenyl}-N-[3-fluoro-4-(trifluoromethyl)benzyl]-5-[(methylthio)methyl]-1H-1,2,3-triazole-4-carboxamide | 20.4 mg | 496 |
| 1111 | N-[3-(difluoromethoxy)benzyl]-1-{4-[(ethylamino)carbonyl]phenyl}-5-[(methylthio)methyl]-1H-1,2,3-triazole-4-carboxamide | 21.4 mg | 476 |
| 1112 | 1-{4-[(ethylamino)carbonyl]phenyl}-5-[(methylthio)methyl]-N-[3-(1H-pyrrol-1-yl)benzyl]-1H-1,2,3-triazole-4-carboxamide | 20.2 mg | 475 |
| 1113 | N-(2-chloro-6-fluorobenzyl)-1-{4-[(ethylamino)carbonyl]phenyl}-5-[(methylthio)methyl]-1H-1,2,3-triazole-4-carboxamide | 18.8 mg | 462 |
| 1114 | 1-{4-[(ethylamino)carbonyl]phenyl}-N-[(1-methyl-1H-benzimidazol-2-yl)methyl]-5-[(methylthio)methyl]-1H-1,2,3-triazole-4-carboxamide trifluoroacetate | 24.5 mg | 464 |
| 1115 | 1-{4-[(ethylamino)carbonyl]phenyl}-5-[(methylthio)methyl]-N-[3- | 20.1 mg | 494 |

TABLE 2-continued

| Example No. | Compound name | yield | [M + H]+ |
|---|---|---|---|
| | (trifluoromethoxy)benzyl]-1H-1,2,3-triazole-4-carboxamide | | |
| 1116 | 1-{4-[(ethylamino)carbonyl]phenyl}-N-[2-(3-fluorophenyl)ethyl]-5-[(methylthio)methyl]-1H-1,2,3-triazole-4-carboxamide | 18.7 mg | 442 |
| 1117 | 1-{4-[(ethylamino)carbonyl]phenyl}-N-[(1-methyl-1H-pyrrol-2-yl)methyl]-5-[(methylthio)methyl]-1H-1,2,3-triazole-4-carboxamide | 16.3 mg | 413 |
| 1118 | 5-[(benzyloxy)methyl]-N-{[5-(4-chlorophenyl)-2-thienyl]methyl}-1-(4-{[(2,2,2-trifluoroethyl)amino]carbonyl}phenyl)-1H-1,2,3-triazole-4-carboxamide | 16.9 mg | 640 |
| 1119 | 5-[(benzyloxy)methyl]-N-{[2-(2-thienyl)-1,3-thiazol-4-yl]methyl}-1-(4-{[(2,2,2-trifluoroethyl)amino]carbonyl}phenyl)-1H-1,2,3-triazole-4-carboxamide | 22.6 mg | 613 |
| 1120 | N-(1-benzothien-2-ylmethyl)-5-[(benzyloxy)methyl]-1-(4-{[(2,2,2-trifluoroethyl)amino]carbonyl}phenyl)-1H-1,2,3-triazole-4-carboxamide | 20.9 mg | 580 |
| 1121 | 5-[(benzyloxy)methyl]-N-{[2-(benzyloxy)pyridin-4-yl]methyl}-1-(4-{[(2,2,2-trifluoroethyl)amino]carbonyl}phenyl)-1H-1,2,3-triazole-4-carboxamide | 25.5 mg | 631 |
| 1122 | 5-[(benzyloxy)methyl]-N-{[2-(tetrahydro-2H-pyran-4-ylmethoxy)pyridin-4-yl]methyl}-1-(4-{[(2,2,2-trifluoroethyl)amino]carbonyl}phenyl)-1H-1,2,3-triazole-4-carboxamide | 25.9 mg | 639 |
| 1123 | 5-[(benzyloxy)methyl]-N-(2-{[(5-chloroimidazo[1,2-a]pyridin-2-yl)methyl]thio}ethyl)-1-(4-{[(2,2,2-trifluoroethyl)amino]carbonyl}phenyl)-1H-1,2,3-triazole-4-carboxamide trifluoroacetate | 24.6 mg | 658 |
| 1124 | 5-[(benzyloxy)methyl]-N-[(4'-fluorobiphenyl-3-yl)methyl]-1-(4-{[(2,2,2-trifluoroethyl)amino]carbonyl}phenyl)-1H-1,2,3-triazole-4-carboxamide | 19.5 mg | 618 |
| 1125 | 5-[(benzyloxy)methyl]-N-[3-(pyridin-2-yloxy)benzyl]-1-(4-{[(2,2,2-trifluoroethyl)amino]carbonyl}phenyl)-1H-1,2,3-triazole-4-carboxamide | 21.2 mg | 617 |
| 1126 | 5-[(benzyloxy)methyl]-N-[(5-methyl-2-phenyl-2H-1,2,3-triazol-4-yl)methyl]-1-(4-{[(2,2,2-trifluoroethyl)amino]carbonyl}phenyl)-1H-1,2,3-triazole-4-carboxamide | 18 mg | 605 |
| 1127 | 5-[(benzyloxy)methyl]-N-[(1-methyl-1H-1,2,3-benzotriazol-5-yl)methyl]-1-(4-{[(2,2,2-trifluoroethyl)amino]carbonyl}phenyl)-1H-1,2,3-triazole-4-carboxamide | 14.6 mg | 579 |
| 1128 | 5-[(benzyloxy)methyl]-N-[3-(methylthio)benzyl]-1-(4-{[(2,2,2-trifluoroethyl)amino]carbonyl}phenyl)-1H-1,2,3-triazole-4-carboxamide | 18.7 mg | 570 |
| 1129 | 5-[(benzyloxy)methyl]-N-[(2-ethoxypyridin-4-yl)methyl]-1-(4-{[(2,2,2-trifluoroethyl)amino]carbonyl}phenyl)-1H-1,2,3-triazole-4-carboxamide | 25 mg | 569 |
| 1130 | 5-[(benzyloxy)methyl]-N-(3-ethoxybenzyl)-1-(4-{[(2,2,2-trifluoroethyl)amino]carbonyl}phenyl)-1H-1,2,3-triazole-4-carboxamide | 15.5 mg | 568 |
| 1131 | 5-[(benzyloxy)methyl]-N-[1-(2-thienyl)ethyl]-1-(4-{[(2,2,2-trifluoroethyl)amino]carbonyl}phenyl)-1H-1,2,3-triazole-4-carboxamide | 15.6 mg | 544 |

TABLE 2-continued

| Example No. | Compound name | yield | [M + H]+ |
|---|---|---|---|
| 1132 | 5-[(benzyloxy)methyl]-N-[1-(3-chloro-4-fluorophenyl)-3-methyl-1H-pyrazol-5-yl]-1-(4-{[(2,2,2-trifluoroethyl)amino]carbonyl}phenyl)-1H-1,2,3-triazole-4-carboxamide | 3.6 mg | 642 |
| 1133 | 5-[(benzyloxy)methyl]-N-[3-(methylthio)propyl]-1-(4-{[(2,2,2-trifluoroethyl)amino]carbonyl}phenyl)-1H-1,2,3-triazole-4-carboxamide | 14.4 mg | 522 |
| 1134 | N-benzyl-5-[(benzyloxy)methyl]-1-(4-{[(2,2,2-trifluoroethyl)amino]carbonyl}phenyl)-1H-1,2,3-triazole-4-carboxamide | 16.4 mg | 524 |
| 1135 | 5-[(benzyloxy)methyl]-N-(3-fluorobenzyl)-1-(4-{[(2,2,2-trifluoroethyl)amino]carbonyl}phenyl)-1H-1,2,3-triazole-4-carboxamide | 15 mg | 542 |
| 1136 | 5-[(benzyloxy)methyl]-N-(2,3-dihydro-1H-inden-2-yl)-1-(4-{[(2,2,2-trifluoroethyl)amino]carbonyl}phenyl)-1H-1,2,3-triazole-4-carboxamide | 17.1 mg | 550 |
| 1137 | N-(1,3-benzodioxol-5-ylmethyl)-5-[(benzyloxy)methyl]-1-(4-{[(2,2,2-trifluoroethyl)amino]carbonyl}phenyl)-1H-1,2,3-triazole-4-carboxamide | 22.2 mg | 568 |
| 1138 | 5-[(benzyloxy)methyl]-N-(4-tert-butylcyclohexyl)-1-(4-{[(2,2,2-trifluoroethyl)amino]carbonyl}phenyl)-1H-1,2,3-triazole-4-carboxamide | 11.7 mg | 572 |
| 1139 | 5-[(benzyloxy)methyl]-N-[2-(1H-indol-3-yl)ethyl]-1-(4-{[(2,2,2-trifluoroethyl)amino]carbonyl}phenyl)-1H-1,2,3-triazole-4-carboxamide | 22 mg | 577 |
| 1140 | 5-[(benzyloxy)methyl]-1-(4-{[(2,2,2-trifluoroethyl)amino]carbonyl}phenyl)-N-[4-(trifluoromethyl)benzyl]-1H-1,2,3-triazole-4-carboxamide | 20.2 mg | 592 |
| 1141 | 5-[(benzyloxy)methyl]-N-(3,4-dichlorobenzyl)-1-(4-{[(2,2,2-trifluoroethyl)amino]carbonyl}phenyl)-1H-1,2,3-triazole-4-carboxamide | 20.4 mg | 592 |
| 1142 | 5-[(benzyloxy)methyl]-N-[2-(5-methoxy-1H-indol-3-yl)ethyl]-1-(4-{[(2,2,2-trifluoroethyl)amino]carbonyl}phenyl)-1H-1,2,3-triazole-4-carboxamide | 20.4 mg | 607 |
| 1143 | 5-[(benzyloxy)methyl]-N-[3,5-bis(trifluoromethyl)benzyl]-1-(4-{[(2,2,2-trifluoroethyl)amino]carbonyl}phenyl)-1H-1,2,3-triazole-4-carboxamide | 21.6 mg | 660 |
| 1144 | 5-[(benzyloxy)methyl]-N-[1-(methoxymethyl)propyl]-1-(4-{[(2,2,2-trifluoroethyl)amino]carbonyl}phenyl)-1H-1,2,3-triazole-4-carboxamide | 14.3 mg | 520 |
| 1145 | 5-[(benzyloxy)methyl]-N-[2-(2-thienyl)ethyl]-1-(4-{[(2,2,2-trifluoroethyl)amino]carbonyl}phenyl)-1H-1,2,3-triazole-4-carboxamide | 16.1 mg | 544 |
| 1146 | 5-[(benzyloxy)methyl]-N-(3-methoxybenzyl)-1-(4-{[(2,2,2-trifluoroethyl)amino]carbonyl}phenyl)-1H-1,2,3-triazole-4-carboxamide | 14.8 mg | 554 |
| 1147 | 5-[(benzyloxy)methyl]-N-(3-chlorobenzyl)-1-(4-{[(2,2,2-trifluoroethyl)amino]carbonyl}phenyl)-1H-1,2,3-triazole-4-carboxamide | 17.4 mg | 558 |
| 1148 | 5-[(benzyloxy)methyl]-N-(2,5-difluorobenzyl)-1-(4-{[(2,2,2-trifluoroethyl)amino]carbonyl}phenyl)-1H-1,2,3-triazole-4-carboxamide | 14.6 mg | 560 |
| 1149 | 5-[(benzyloxy)methyl]-N-(2,4-difluorobenzyl)-1-(4-{[(2,2,2-trifluoroethyl)amino]carbonyl}phenyl)-1H-1,2,3-triazole-4-carboxamide | 23.3 mg | 560 |
| 1150 | 5-[(benzyloxy)methyl]-N-(3,5-difluorobenzyl)-1-(4-{[(2,2,2- | 17.4 mg | 560 |

TABLE 2-continued

| Example No. | Compound name | yield | [M + H]+ |
|---|---|---|---|
|  | trifluoroethyl)amino]carbonyl}phenyl)-1H-1,2,3-triazole-4-carboxamide | | |
| 1151 | 5-[(benzyloxy)methyl]-N-(2,3-difluorobenzyl)-1-(4-{[(2,2,2-trifluoroethyl)amino]carbonyl}phenyl)-1H-1,2,3-triazole-4-carboxamide | 16 mg | 560 |
| 1152 | 5-[(benzyloxy)methyl]-N-(4-tert-butylbenzyl)-1-(4-{[(2,2,2-trifluoroethyl)amino]carbonyl}phenyl)-1H-1,2,3-triazole-4-carboxamide | 18.9 mg | 580 |
| 1153 | 5-[(benzyloxy)methyl]-1-(4-{[(2,2,2-trifluoroethyl)amino]carbonyl}phenyl)-N-[3-(trifluoromethyl)benzyl]-1H-1,2,3-triazole-4-carboxamide | 17.1 mg | 592 |
| 1154 | 5-[(benzyloxy)methyl]-1-(4-{[(2,2,2-trifluoroethyl)amino]carbonyl}phenyl)-N-[4-(trifluoromethoxy)benzyl]-1H-1,2,3-triazole-4-carboxamide | 20.1 mg | 608 |
| 1155 | 5-[(benzyloxy)methyl]-N-[3-fluoro-5-(trifluoromethyl)benzyl]-1-(4-{[(2,2,2-trifluoroethyl)amino]carbonyl}phenyl)-1H-1,2,3-triazole-4-carboxamide | 18.2 mg | 610 |
| 1156 | 5-[(benzyloxy)methyl]-N-[2-(benzylthio)ethyl]-1-(4-{[(2,2,2-trifluoroethyl)amino]carbonyl}phenyl)-1H-1,2,3-triazole-4-carboxamide | 17.5 mg | 584 |
| 1157 | 5-[(benzyloxy)methyl]-N-[(pentafluorobenzyl)oxy]-1-(4-{[(2,2,2-trifluoroethyl)amino]carbonyl}phenyl)-1H-1,2,3-triazole-4-carboxamide | 3.7 mg | 630 |
| 1158 | 5-[(benzyloxy)methyl]-N-(pyridin-3-ylmethyl)-1-(4-{[(2,2,2-trifluoroethyl)amino]carbonyl}phenyl)-1H-1,2,3-triazole-4-carboxamide trifluoroacetate | 24.9 mg | 525 |
| 1159 | 5-[(benzyloxy)methyl]-N-(pyridin-2-ylmethyl)-1-(4-{[(2,2,2-trifluoroethyl)amino]carbonyl}phenyl)-1H-1,2,3-triazole-4-carboxamide trifluoroacetate | 19.4 mg | 525 |
| 1160 | 5-[(benzyloxy)methyl]-N-(pyridin-4-ylmethyl)-1-(4-{[(2,2,2-trifluoroethyl)amino]carbonyl}phenyl)-1H-1,2,3-triazole-4-carboxamide trifluoroacetate | 22.6 mg | 525 |
| 1161 | 5-[(benzyloxy)methyl]-N-[2-(pyridin-2-yl)ethyl]-1-(4-{[(2,2,2-trifluoroethyl)amino]carbonyl}phenyl)-1H-1,2,3-triazole-4-carboxamide trifluoroacetate | 29.9 mg | 539 |
| 1162 | 5-[(benzyloxy)methyl]-N-[(5-methylpyrazin-2-yl)methyl]-1-(4-{[(2,2,2-trifluoroethyl)amino]carbonyl}phenyl)-1H-1,2,3-triazole-4-carboxamide | 18.8 mg | 540 |
| 1163 | N-(2-anilinoethyl)-5-[(benzyloxy)methyl]-1-(4-{[(2,2,2-trifluoroethyl)amino]carbonyl}phenyl)-1H-1,2,3-triazole-4-carboxamide | 20.5 mg | 553 |
| 1164 | 5-[(benzyloxy)methyl]-N-(1-benzylpyrrolidin-3-yl)-1-(4-{[(2,2,2-trifluoroethyl)amino]carbonyl}phenyl)-1H-1,2,3-triazole-4-carboxamide trifluoroacetate | 20.2 mg | 593 |
| 1165 | 5-[(benzyloxy)methyl]-N-(1-benzylpiperidin-4-yl)-1-(4-{[(2,2,2-trifluoroethyl)amino]carbonyl}phenyl)-1H-1,2,3-triazole-4-carboxamide trifluoroacetate | 20.6 mg | 607 |
| 1166 | 5-[(benzyloxy)methyl]-N-(2-thienylmethyl)-1-(4-{[(2,2,2-trifluoroethyl)amino]carbonyl}phenyl)-1H-1,2,3-triazole-4-carboxamide | 15.4 mg | 530 |

TABLE 2-continued

| Example No. | Compound name | yield | [M + H]⁺ |
|---|---|---|---|
| 1167 | 5-[(benzyloxy)methyl]-N-[(3-methyl-2-thienyl)methyl]-1-(4-{[(2,2,2-trifluoroethyl)amino]carbonyl}phenyl)-1H-1,2,3-triazole-4-carboxamide | 12.6 mg | 544 |
| 1168 | 5-[(benzyloxy)methyl]-N-(3-thienylmethyl)-1-(4-{[(2,2,2-trifluoroethyl)amino]carbonyl}phenyl)-1H-1,2,3-triazole-4-carboxamide | 18.1 mg | 530 |
| 1169 | 5-[(benzyloxy)methyl]-N-(2-fluorobenzyl)-1-(4-{[(2,2,2-trifluoroethyl)amino]carbonyl}phenyl)-1H-1,2,3-triazole-4-carboxamide | 15.4 mg | 542 |
| 1170 | 5-[(benzyloxy)methyl]-N-(4-fluorobenzyl)-1-(4-{[(2,2,2-trifluoroethyl)amino]carbonyl}phenyl)-1H-1,2,3-triazole-4-carboxamide | 13 mg | 542 |
| 1171 | 5-[(benzyloxy)methyl]-N-(3-bromobenzyl)-1-(4-{[(2,2,2-trifluoroethyl)amino]carbonyl}phenyl)-1H-1,2,3-triazole-4-carboxamide | 19.5 mg | 603 |
| 1172 | 5-[(benzyloxy)methyl]-N-(2,6-difluorobenzyl)-1-(4-{[(2,2,2-trifluoroethyl)amino]carbonyl}phenyl)-1H-1,2,3-triazole-4-carboxamide | 11.3 mg | 560 |
| 1173 | 5-[(benzyloxy)methyl]-N-(3,4-difluorobenzyl)-1-(4-{[(2,2,2-trifluoroethyl)amino]carbonyl}phenyl)-1H-1,2,3-triazole-4-carboxamide | 13.9 mg | 560 |
| 1174 | 5-[(benzyloxy)methyl]-N-(3-chloro-4-fluorobenzyl)-1-(4-{[(2,2,2-trifluoroethyl)amino]carbonyl}phenyl)-1H-1,2,3-triazole-4-carboxamide | 16.1 mg | 577 |
| 1175 | 5-[(benzyloxy)methyl]-N-(2,3,6-trifluorobenzyl)-1-(4-{[(2,2,2-trifluoroethyl)amino]carbonyl}phenyl)-1H-1,2,3-triazole-4-carboxamide | 14.4 mg | 578 |
| 1176 | 5-[(benzyloxy)methyl]-N-[(1H-benzimidazol-2-ylmethyl)]-1-(4-{[(2,2,2-trifluoroethyl)amino]carbonyl}phenyl)-1H-1,2,3-triazole-4-carboxamide trifluoroacetate | 6.5 mg | 564 |
| 1177 | 5-[(benzyloxy)methyl]-N-[2-(6-fluoro-1H-indol-3-yl)ethyl]-1-(4-{[(2,2,2-trifluoroethyl)amino]carbonyl}phenyl)-1H-1,2,3-triazole-4-carboxamide | 20.6 mg | 595 |
| 1178 | 5-[(benzyloxy)methyl]-N-[2-(pyridin-2-ylamino)ethyl]-1-(4-{[(2,2,2-trifluoroethyl)amino]carbonyl}phenyl)-1H-1,2,3-triazole-4-carboxamide trifluoroacetate | 15 mg | 554 |
| 1179 | 5-[(benzyloxy)methyl]-N-[(5-chloro-2-thienyl)methyl]-1-(4-{[(2,2,2-trifluoroethyl)amino]carbonyl}phenyl)-1H-1,2,3-triazole-4-carboxamide | 10 mg | 565 |
| 1180 | 5-[(benzyloxy)methyl]-N-[2-(5-chloro-2-thienyl)ethyl]-1-(4-{[(2,2,2-trifluoroethyl)amino]carbonyl}phenyl)-1H-1,2,3-triazole-4-carboxamide | 9 mg | 579 |
| 1181 | 5-[(benzyloxy)methyl]-N-[5-fluoro-2-(trifluoromethyl)benzyl]-1-(4-{[(2,2,2-trifluoroethyl)amino]carbonyl}phenyl)-1H-1,2,3-triazole-4-carboxamide | 19.3 mg | 610 |
| 1182 | 5-[(benzyloxy)methyl]-N-[3-fluoro-4-(trifluoromethyl)benzyl]-1-(4-{[(2,2,2-trifluoroethyl)amino]carbonyl}phenyl)-1H-1,2,3-triazole-4-carboxamide | 25.7 mg | 610 |
| 1183 | 5-[(benzyloxy)methyl]-N-[3-(difluoromethoxy)benzyl]-1-(4-{[(2,2,2-trifluoroethyl)amino]carbonyl}phenyl)-1H-1,2,3-triazole-4-carboxamide | 17.9 mg | 590 |
| 1184 | 5-[(benzyloxy)methyl]-N-[3-(1H-pyrrol-1-yl)benzyl]-1-(4-{[(2,2,2-trifluoroethyl)amino]carbonyl}phenyl)-1H-1,2,3-triazole-4-carboxamide | 21.1 mg | 589 |
| 1185 | 5-[(benzyloxy)methyl]-N-(2-chloro-6-fluorobenzyl)-1-(4-{[(2,2,2- | 17.3 mg | 577 |

TABLE 2-continued

| Example No. | Compound name | yield | [M + H]+ |
|---|---|---|---|
| | trifluoroethyl)amino]carbonyl}phenyl)-1H-1,2,3-triazole-4-carboxamide | | |
| 1186 | 5-[(benzyloxy)methyl]-N-[(1-methyl-1H-benzimidazol-2-yl)methyl]-1-(4-{[(2,2,2-trifluoroethyl)amino]carbonyl}phenyl)-1H-1,2,3-triazole-4-carboxamide trifluoroacetate | 22.2 mg | 578 |
| 1187 | 5-[(benzyloxy)methyl]-N-(3-trifluoromethoxybenzyl)-1-(4-{[(2,2,2-trifluoroethyl)amino]carbonyl}phenyl)-1H-1,2,3-triazole-4-carboxamide | 16.6 mg | 608 |
| 1188 | 5-[(benzyloxy)methyl]-N-[2-(3-fluorophenyl)ethyl]-1-(4-{[(2,2,2-trifluoroethyl)amino]carbonyl}phenyl)-1H-1,2,3-triazole-4-carboxamide | 16.3 mg | 556 |
| 1189 | 5-[(benzyloxy)methyl]-N-[(1-methyl-1H-pyrrol-2-yl)methyl]-1-(4-{[(2,2,2-trifluoroethyl)amino]carbonyl}phenyl)-1H-1,2,3-triazole-4-carboxamide | 13 mg | 527 |

Example 1190

N-cyclopropyl-1-{4-[(ethylamino)carbonyl]phenyl}-5-{[(4-fluorobenzyl)amino]methyl}-1H-1,2,3-triazole-4-carboxamide

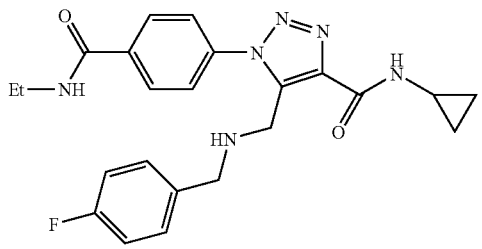

In the same manner as in Example 126, the title compound was obtained as a white powder (115 mg, 53%).

NMR (300 MHz, CDCl$_3$) δ: 0.67-0.72 (2H, m), 0.87-0.94 (2H, m), 1.30 (3H, t, J=7.2 Hz), 2.69 (1H, brs), 2.67-2.95 (1H, m), 3.50-3.59 (2H, m), 3.78 (2H, s), 3.96 (2H, s), 6.22 (1H, brs), 6.95-7.02 (2H, m), 7.23-7.28 (2H, m), 7.39 (1H, brs), 7.64 (2H, d, J=8.7 Hz) 7.86 (2H, d, J=8.7 Hz).

Example 1191

5-(anilinomethyl)-N-cyclopropyl-1-{4-[(ethylamino)carbonyl]phenyl}-1H-1,2,3-triazole-4-carboxamide

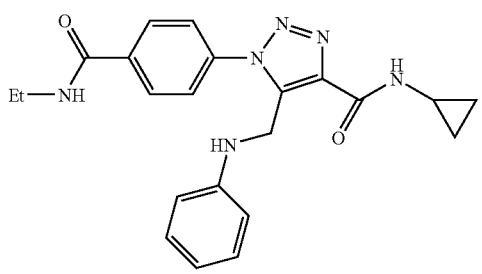

In the same manner as in Example 126, the title compound was obtained as a white powder (98 mg, 49%).

NMR (300 MHz, CDCl$_3$) δ: 0.67-0.73 (2H, m), 0.86-0.95 (2H, m), 1.30 (3H, t, J=7.2 Hz), 2.92-2.95 (1H, m), 3.51-3.60 (2H, m), 4.59 (2H, d, J=6.8 Hz), 5.15 (1H, t, J=6.8 Hz), 6.24 (1H, brs), 6.44 (2H, d, J=7.5 Hz), 6.71 (1H, t, J=7.5 Hz), 7.07 (2H, t, J=7.5 Hz), 7.39 (1H, brs) 7.56 (2H, d, J=8.7 Hz), 7.99 (2H, d, J=8.7 Hz).

Example 1192

N-cyclopropyl-1-{4-[(ethylamino)carbonyl]phenyl}-5-{[(2-phenylethyl)amino]methyl}-1H-1,2,3-triazole-4-carboxamide

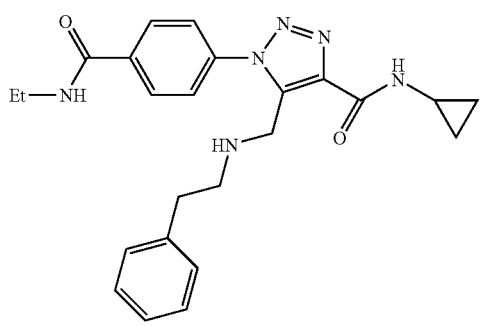

In the same manner as in Example 126, the title compound was obtained as a white powder (145 mg, 67%).

NMR (300 MHz, CDCl$_3$) δ: 0.66-0.71 (2H, m), 0.87-0.93 (2H, m), 1.30 (3H, t, J=7.1 Hz), 2.07 (1H, brs), 2.78 (2H, t, J=4.0 Hz), 2.86-2.94 (1H, m), 2.88 (2H, t, J=4.0 Hz), 3.50-3.59 (2H, m), 4.02 (2H, s), 6.19 (1H, brs), 7.16-7.32 (5H, m), 7.39 (1H, brs), 7.69 (2H, d, J=8.7 Hz), 7.87 (2H, d, J=8.7 Hz).

Example 1193

N-cyclopropyl-1-{4-[(ethylamino)carbonyl]phenyl}-5-{[(3-phenylpropyl)amino]methyl}-1H-1,2,3-triazole-4-carboxamide

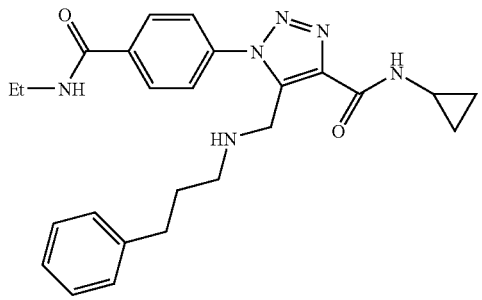

In the same manner as in Example 126, the title compound was obtained as a white powder (110 mg, 49%).

NMR (300 MHz, CDCl$_3$) δ: 0.66-0.72 (2H, m), 0.87-0.93 (2H, m), 1.29 (3H, t, J=7.2 Hz), 1.75-1.84 (2H, m), 2.17 (1H, brs), 2.61-2.68 (4H, m), 2.87-2.94 (1H, m), 3.49-3.58 (2H, m), 3.97 (2H, s), 6.19 (1H, brs), 7.14-7.21 (3H, m), 7.25-7.30 (2H, m), 7.75 (2H, d, J=8.7 Hz), 7.92 (2H, d, J=8.7 Hz).

Example 1194

N-cyclopropyl-1-{4-[(ethylamino)carbonyl]phenyl}-5-{[(2-fluorobenzyl)amino]methyl}-1H-1,2,3-triazole-4-carboxamide

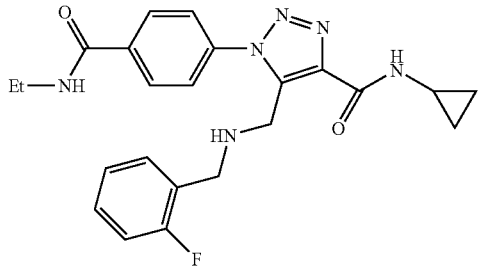

In the same manner as in Example 126, the title compound was obtained as a white powder (110 mg, 50%).

NMR (300 MHz, CDCl$_3$) δ: 0.66-0.72 (2H, m), 0.87-0.93 (2H, m), 1.30 (3H, t, J=7.2 Hz), 2.62 (1H, brs), 2.88-2.94 (1H, m), 3.50-3.59 (2H, m), 3.87 (2H, s), 4.03 (2H, s), 6.17 (1H, brs), 7.00-7.12 (2H, m), 7.21-7.34 (2H, m), 7.36 (1H, brs), 7.72 (2H, d, J=8.7 Hz) 7.88 (2H, d, J=8.7 Hz).

Example 1195

N-cyclopropyl-1-{4-[(ethylamino)carbonyl]phenyl}-5-{[(3-fluorobenzyl)amino]methyl}-1H-1,2,3-triazole-4-carboxamide

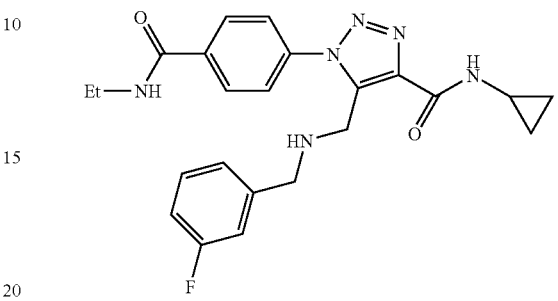

In the same manner as in Example 126, the title compound was obtained as a white powder (110 mg, 50%).

NMR (300 MHz, CDCl$_3$) δ: 0.67-0.72 (2H, m), 0.88-0.94 (2H, m), 1.30 (3H, t, J=7.1 Hz), 2.69 (1H, brs), 2.90-2.93 (1H, m), 3.50-3.59 (2H, m), 3.82 (2H, s), 3.96 (2H, s), 6.18 (1H, brs), 6.92-7.06 (3H, m), 7.21-7.29 (1H, m), 7.38 (1H, brs), 7.69 (2H, d, J=8.7 Hz) 7.88 (2H, d, J=8.7 Hz).

Example 1196

N-cyclopropyl-5-[(1,3-dioxo-1,3-dihydro-2H-isoindol-2-yl)methyl]-1-{4-[(ethylamino)carbonyl]phenyl}-1H-1,2,3-triazole-4-carboxamide

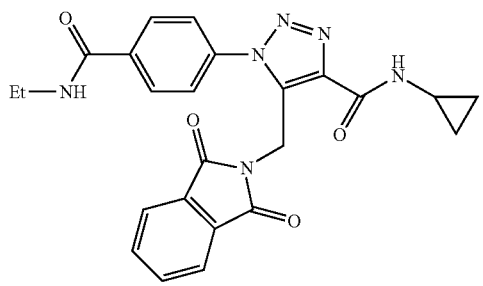

(4-[(Cyclopropylamino)carbonyl]-1-{4-[(ethylamino)carbonyl]phenyl}-1H-1,2,3-triazol-5-yl)methyl methanesulfonate (1.02 g, 2.5 mmol) obtained in Example 126a) and potassium 1,3-dioxo-1,3-dihydroisoindol-2-ide (463 mg, 2.5 mmol, 1.0 eq.) were dissolved in DMF (10 ml), and the mixture was stirred at 50° C. for 30 min. The reaction mixture was diluted with ethyl acetate (20 ml), and the precipitate was collected by filtration, washed with water and dried to give the title compound as a white powder (1.0 g, 87.7%).

NMR (300 MHz, DMSO-d$_6$) δ: 0.57-0.68 (4H, m), 1.13 (3H, t, J=7.1 Hz), 2.78-2.85 (1H, m), 3.24-3.32 (2H, m), 5.25 (2H, s), 7.64 (2H, d, J=8.6 Hz), 7.69-7.78 (4H, m), 7.90 (2H, d, J=8.6 Hz) 8.55 (1H, t, J=5.7 Hz), 8.73 (1H, t, J=5.0 Hz).

Example 1197

5-(aminomethyl)-N-cyclopropyl-1-{4-[(ethylamino)carbonyl]phenyl}-1H-1,2,3-triazole-4-carboxamide

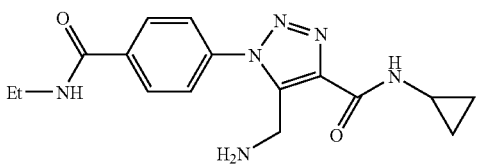

A solution of N-cyclopropyl-5-[(1,3-dioxo-1,3-dihydro-2H-isoindol-2-yl)methyl]-1-{4-[(ethylamino)carbonyl]phenyl}-1H-1,2,3-triazole-4-carboxamide (0.9 g, 2.0 mmol) obtained in Example 1196 and hydrazine hydrate (200 mg, 4.0 mmol) in ethanol (20 ml) was boiled under reflux for 1 hr, and precipitated insoluble material was filtered off. The filtrate was concentrated to dryness to give the title compound as a white powder (0.65 g, 99%).

NMR (300 MHz, CDCl$_3$) δ: 0.67-0.72 (2H, m), 0.87-0.93 (2H, m), 1.29 (3H, t, J=7.1 Hz), 2.15 (2H, brs), 2.88-2.96 (1H, m), 3.49-3.59 (2H, m), 4.12 (2H, s), 6.31 (1H, brs), 7.40 (1H, brs), 7.69 (2H, d, J=8.6 Hz) 7.98 (2H, d, J=8.6 Hz).

Example 1198

N-cyclopropyl-1-{4-[(ethylamino)carbonyl]phenyl}-5-({[(1-trityl-1H-imidazol-2-yl)methyl]amino}methyl)-1H-1,2,3-triazole-4-carboxamide

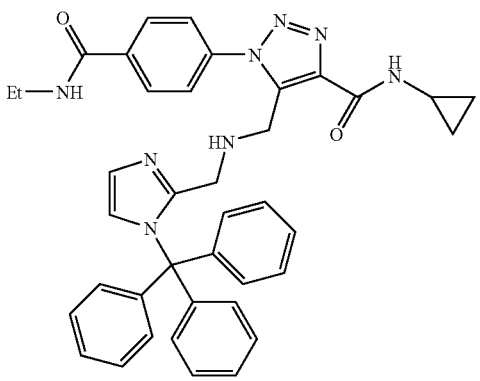

To a solution of 5-(aminomethyl)-N-cyclopropyl-1-{4-[(ethylamino)carbonyl]phenyl}-1H-1,2,3-triazole-4-carboxamide (164 mg, 0.5 mmol) obtained in Example 1197 in dichloroethane (10 ml) were successively added 1-trityl-1H-imidazole-2-carbaldehyde (169 mg, 0.5 mmol), acetic acid (30 mg, 0.5 mmol) and sodium triacetoxyborohydride (138 mg, 0.65 mmol) at 0° C., and the mixture was stirred at room temperature for 48 hr. The reaction mixture was neutralized with saturated aqueous sodium hydrogen carbonate solution (5 ml) and, after partitioning, the organic layer was dried over magnesium sulfate and concentrated. The residue was purified by silica gel column (hexane/ethyl acetate=1/1 to ethyl acetate/methanol=4/1) to give the title compound as a colorless powder (130 mg, 40%).

NMR (300 MHz, CDCl$_3$) δ: 0.67-0.72 (2H, m), 0.83-0.89 (2H, m), 1.31 (3H, t, J=7.1 Hz), 2.86-2.90 (1H, m), 3.04 (2H, s), 3.51-3.61 (2H, m), 3.76 (2H, s), 6.18 (1H, brs), 6.99 (1H, d, J=1.5 Hz), 7.08-7.11 (6H, m), 7.28-7.30 (9H, m), 7.34 (1H, brs), 7.70 (2H, d, J=8.7 Hz) 7.86 (2H, d, J=8.7 Hz).

Example 1199

N-cyclopropyl-1-{4-[(ethylamino)carbonyl]phenyl}-5-{[(1H-imidazol-2-ylmethyl)amino]methyl}-1H-1,2,3-triazole-4-carboxamide

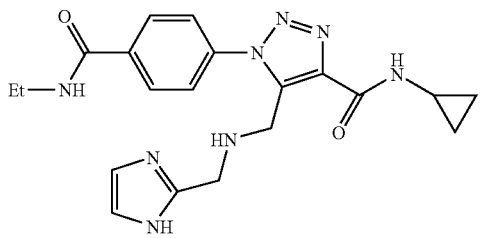

Trifluoroacetic acid (0.5 ml) was added to N-cyclopropyl-1-{4-[(ethylamino)carbonyl]phenyl}-5-({[(1-trityl-1H-imidazol-2-yl)methyl]amino}methyl)-1H-1,2,3-triazole-4-carboxamide (78 mg, 0.12 mmol) obtained in Example 1198, and the mixture was stirred at room temperature for 1 hr. The reaction mixture was concentrated, water (2 ml) was added to the residue, and precipitated crystals were filtered off. The filtrate was neutralized with 1N aqueous sodium hydroxide solution and concentrated to dryness. The residue was purified by silica gel column (hexane/ethyl acetate=1/1 to ethyl acetate/methanol=4/1) to give the title compound as a colorless powder (30 mg, 61%).

NMR (300 MHz, DMSO-d$_6$) δ: 0.64-0.70 (4H, m), 1.15 (3H, t, J=7.2 Hz), 2.88-2.95 (1H, m), 2.95 (1H, brs), 3.28-3.37 (2H, m), 3.65 (2H, s), 3.92 (2H, s), 6.75 (1H, brs), 7.00 (1H, brs), 7.77 (2H, d, J=8.7 Hz), 8.04 (2H, d, J=8.7 Hz) 8.68 (1H, t, J=5.7 Hz), 8.95 (1H, d, J=4.6 Hz), 11.79 (1H, brs).

Example 1200

N-cyclopropyl-1-{4-[(ethylamino)carbonyl]phenyl}-5-{[(1,3-thiazol-2-ylmethyl)amino]methyl}-1H-1,2,3-triazole-4-carboxamide

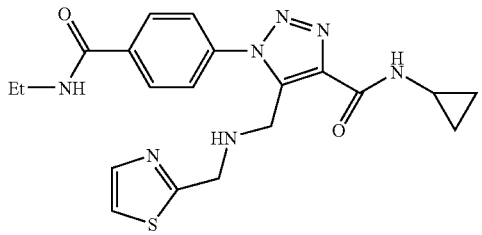

In the same manner as in Example 1198, the title compound was obtained as a white powder (78 mg, 37%).

$^1$H NMR (300 MHz, CDCl$_3$) δ: 0.67-0.73 (2H, m), 0.87-0.94 (2H, m), 1.29 (3H, t, J=7.2 Hz), 2.88-2.94 (1H, m), 3.15 (1H, brs), 3.49-3.59 (2H, m), 4.11 (2H, s), 4.15 (2H, s), 6.19

(1H, brs), 7.27 (1H, d, J=3.2 Hz), 7.38 (1H, brs), 7.67 (1H, d, J=3.2 Hz), 7.68 (2H, d, J=8.6 Hz) 7.90 (2H, d, J=8.6 Hz).

Example 1201

N-cyclopropyl-5-[3-(1,3-dioxo-1,3-dihydro-2H-isoindol-2-yl)propyl]-1-{4-[(ethylamino)carbonyl]phenyl}-1H-1,2,3-triazole-4-carboxamide

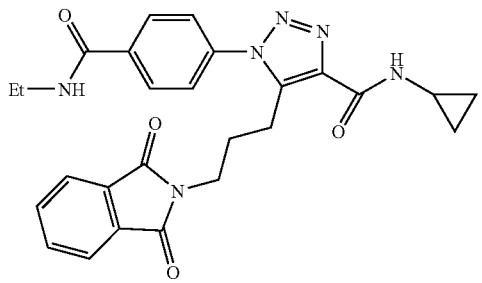

1201a) (4-[(cyclopropylamino)carbonyl]-1-{4-[(ethylamino)carbonyl]phenyl}-1H-1,2,3-triazol-5-yl)propyl methanesulfonate N-Cyclopropyl-1-{4-[(ethylamino)carbonyl]phenyl}-5-(3-hydroxypropyl)-1H-1,2,3-triazole-4-carboxamide (3.57 g, 10 mmol) obtained in Example 113 and mesyl chloride (1.37 g, 12 mmol, 1.2 eq.) were dissolved in dichloromethane (50 ml) and triethylamine (1.21 g, 12 mmol, 1.2 eq.) was added dropwise over 10 min while stirring at 0° C. The reaction mixture was stirred at 0° C. for 1 hr. The reaction mixture was washed with 10% brine and saturated brine, dried over anhydrous sodium sulfate and concentrated. Diethyl ether was added and the precipitate was collected by filtration, washed with diethyl ether and dried to give the title compound as a white powder (4.25 g, 97.6%).

NMR (300 MHz, CDCl$_3$) δ: 0.66-0.71 (2H, m), 0.86-0.92 (2H, m), 1.29 (3H, t, J=7.2 Hz), 2.04-2.13 (2H, m), 2.85-2.92 (1H, m), 2.94 (3H, s), 3.15-3.20 (2H, m), 3.49-3.58 (2H, m), 4.20 (2H, t, J=5.7 Hz), 6.35 (1H, brs), 7.37 (1H, brs), 7.52 (2H, d, J=8.7 Hz), 7.98 (2H, d, J=8.7 Hz).

1201b) N-cyclopropyl-5-[3-(1,3-dioxo-1,3-dihydro-2H-isoindol-2-yl)propyl]-1-{4-[(ethylamino)carbonyl]phenyl}-1H-1,2,3-triazole-4-carboxamide (4-[(Cyclopropylamino)carbonyl]-1-{4-[(ethylamino)carbonyl]phenyl}-1H-1,2,3-triazol-5-yl)propyl methanesulfonate (1.31 g, 3 mmol) obtained in Example 1201a) and potassium 1,3-dioxo-1,3-dihydroisoindol-2-ide (556 mg, 3 mmol, 1.0 eq.) were dissolved in DMF (20 ml) and the mixture was stirred at 60° C. for 3 hr. The reaction mixture was diluted with water (20 ml), and the precipitate was collected by filtration, washed with water and dried to give the title compound as a white powder (1.32 g, 90.4%).

NMR (300 MHz, DMSO-d$_6$) δ: 0.64-0.66 (4H, m), 1.17 (3H, t, J=7.2 Hz), 1.72-1.78 (2H, m), 2.80-2.86 (1H, m), 2.98-3.03 (2H, m), 3.29-3.38 (2H, m), 3.47 (2H, t, J=6.8 Hz), 7.64 (2H, d, J=8.7 Hz), 7.81 (4H, m), 7.96 (2H, d, J=8.6 Hz) 8.62-8.66 (2H, m).

Example 1202

5-(3-aminopropyl)-N-cyclopropyl-1-{4-[(ethylamino)carbonyl]phenyl}-1H-1,2,3-triazole-4-carboxamide

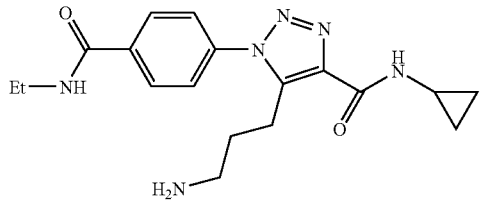

A solution of N-cyclopropyl-5-[3-(1,3-dioxo-1,3-dihydro-2H-isoindol-2-yl)propyl]-1-{4-[(ethylamino)carbonyl]phenyl}-1H-1,2,3-triazole-4-carboxamide (1.27 g, 2.6 mmol) obtained in Example 1201 and hydrazine hydrate (261 mg, 5.2 mmol) in ethanol (20 ml) was boiled under reflux for 3 hr, and the precipitated insoluble material was filtered off. The filtrate was concentrated to dryness to give the title compound as a white powder (0.9 g, 97%).

NMR (300 MHz, CDCl$_3$) δ: 0.65-0.71 (2H, m), 0.85-0.92 (2H, m), 1.29 (3H, t, J=7.2 Hz), 1.67-1.71 (2H, m), 2.64 (2H, t, J=6.8 Hz), 2.87-2.93 (1H, m), 3.12 (2H, t, J=6.8 Hz), 3.50-3.59 (2H, m), 6.33 (1H, brs), 7.38 (1H, brs), 7.53 (2H, d, J=8.7 Hz) 7.98 (2H, d, J=8.7 Hz).

Example 1203

5-[3-({[(2-chloroethyl)amino]carbonyl}amino)propyl]-N-cyclopropyl-1-{4-[(ethylamino)carbonyl]phenyl}-1H-1,2,3-triazole-4-carboxamide

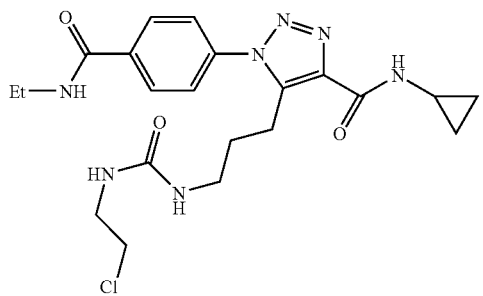

To a solution of 5-(3-aminopropyl)-N-cyclopropyl-1-{4-[(ethylamino)carbonyl]phenyl}-1H-1,2,3-triazole-4-carboxamide (356 mg, 1 mmol) obtained in Example 1202 in THF (5 ml) was added 1-chloro-2-isocyanatoethane (106 mg, 1 mmol) at room temperature, and the mixture was stirred at room temperature for 30 min. The precipitated crystals were collected by filtration and dried to give the title compound as a white powder (450 mg, 97.4%).

NMR (300 MHz, CDCl$_3$) δ: 0.67-0.72 (2H, m), 0.87-0.93 (2H, m), 1.29 (3H, t, J=7.2 Hz), 1.59-1.68 (2H, m), 2.89-2.94 (1H, m), 3.03-3.11 (4H, m), 3.49-3.62 (6H, m), 5.10 (1H, brt, J=5.7 Hz), 5.87 (1H, brt, J=5.3 Hz), 6.53 (1H, t, J=5.7 Hz), 7.45 (1H, brs), 7.49 (2H, d, J=8.3 Hz) 7.98 (2H, d, J=8.3 Hz).

Example 1204

4-(5-cyclopropyl-4-oxo-5,6,7,8-tetrahydro[1,2,3]triazolo[4,5-c]azepin-1(4H)-yl)-N-ethylbenzamide

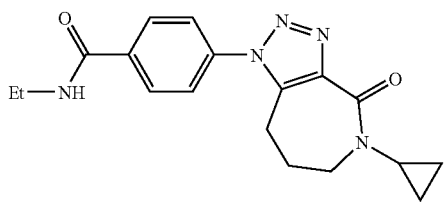

(4-[(Cyclopropylamino)carbonyl]-1-{4-[(ethylamino)carbonyl]phenyl}-1H-1,2,3-triazol-5-yl)propyl methanesulfonate (218 mg, 0.5 mmol) obtained in Example 1201a) and 60% sodium hydride (24 mg, 0.6 mmol, 1.2 eq.) were dissolved in DMF (5 ml) and the mixture was stirred at 60° C. for 3 hr. The reaction mixture was diluted with water (10 ml), and the precipitate was collected by filtration, washed with water and dried to give the title compound as a white powder (85 mg, 50.1%).

NMR (300 MHz, DMSO-$d_6$) δ: 0.70-0.75 (2H, m), 0.90-0.96 (2H, m), 1.31 (3H, t, J=7.2 Hz), 2.05-2.13 (2H, m), 2.85 (2H, t, J=7.0 Hz), 2.88-2.95 (1H, m), 3.51-3.60 (4H, m), 6.80 (1H, t, J=5.3 Hz), 7.45 (2H, d, J=8.7 Hz), 7.99 (2H, d, J=8.7 Hz).

Example 1205

N-cyclopropyl-1-{4-[(ethylamino)carbonyl]phenyl}-5-[3-(1H-imidazol-1-yl)propyl]-1H-1,2,3-triazole-4-carboxamide

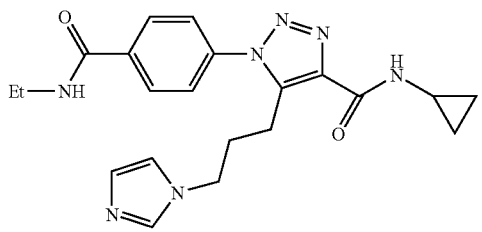

(4-[(Cyclopropylamino)carbonyl]-1-{4-[(ethylamino)carbonyl]phenyl}-1H-1,2,3-triazol-5-yl)propyl methanesulfonate (218 mg, 0.5 mmol) obtained in Example 1201a), potassium carbonate (83 mg, 0.6 mmol, 1.2 eq.) and imidazole (41 mg, 0.6 mmol, 1.2 eq.) were suspended in acetonitrile (5.0 ml) and the mixture was stirred at 80° C. for 10 hr. The mixture was concentrated to dryness, and the residue was purified by silica gel column (hexane/ethyl acetate=1/1 to ethyl acetate/methanol=4/1) to give the title compound as a colorless powder (42 mg, 21%).

NMR (300 MHz, CDCl$_3$) δ: 0.66-0.72 (2H, m), 0.87-0.93 (2H, m), 1.33 (3H, t, J=7.2 Hz), 1.91-2.01 (2H, m), 2.87-2.93 (1H, m), 2.97-3.02 (2H, m), 3.51-3.60 (2H, m), 3.93 (2H, t, J=6.0 Hz), 6.79 (1H, s), 6.97 (1H, s), 7.10 (1H, s), 7.27 (2H, d, J=8.7 Hz) 7.32-7.36 (2H, m), 7.83 (2H, d, J=8.7 Hz).

Example 1206

N-cyclopropyl-1-{4-[(ethylamino)carbonyl]phenyl}-5-[3-(1H-pyrazol-1-yl)propyl]-1H-1,2,3-triazole-4-carboxamide

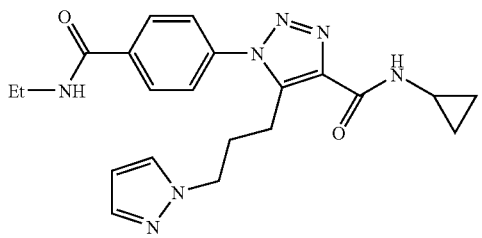

In the same manner as in Example 1205, the title compound was obtained as a white powder (30 mg, 15%).

NMR (300 MHz, CDCl$_3$) δ: 0.67-0.72 (2H, m), 0.86-0.94 (2H, m), 1.31 (3H, t, J=7.2 Hz), 2.19-2.28 (2H, m), 2.88-2.94 (1H, m), 2.99-3.04 (2H, m), 3.52-3.61 (2H, m), 4.17 (2H, t, J=6.6 Hz), 6.18 (1H, t, J=2.0 Hz), 6.23 (1H, brs), 7.32 (1H, d, J=2.0 Hz), 7.36 (1H, brs), 7.43 (2H, d, J=8.5 Hz) 7.45 (1H, brs), 7.91 (2H, d, J=8.5 Hz).

Example 1207

5-(3-cyanopropyl)-N-cyclopropyl-1-{4-[(ethylamino)carbonyl]phenyl}-1H-1,2,3-triazole-4-carboxamide

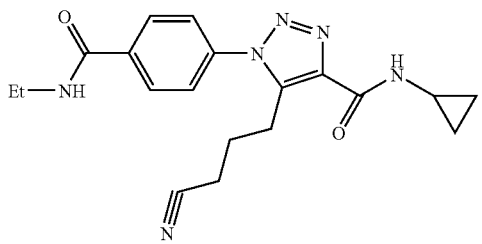

A solution of (4-[(cyclopropylamino)carbonyl]-1-{4-[(ethylamino)carbonyl]phenyl}-1H-1,2,3-triazol-5-yl)propyl methanesulfonate (1.31 g, 3 mmol) obtained in Example 1201a) and potassium cyanide (235 mg, 3.6 mmol, 1.2 eq.) in DMSO (10 ml) was stirred for 15 hr, ice water (20 ml) was added, and the precipitated crystals were collected by filtration and dried to give the title compound as a colorless powder (925 mg, 84%).

NMR (300 MHz, CDCl$_3$) δ: 0.66-0.71 (2H, m), 0.86-0.93 (2H, m), 1.29 (3H, t, J=7.2 Hz), 1.92-2.02 (2H, m), 2.39 (2H, t, J=7.2 Hz), 2.86-2.92 (1H, m), 3.15-3.21 (2H, m), 3.49-3.58 (2H, m), 6.40 (1H, brt, J=5.3 Hz), 7.38 (1H, brs), 7.52 (2H, d, J=8.7 Hz), 8.01 (2H, d, J=8.7 Hz).

Example 1208

N-cyclopropyl-1-{4-[(ethylamino)carbonyl]phenyl}-5-[3-(1H-tetrazol-5-yl)propyl]-1H-1,2,3-triazole-4-carboxamide

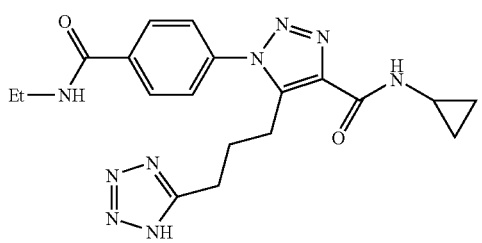

A solution of 5-(3-cyanopropyl)-N-cyclopropyl-1-{4-[(ethylamino)carbonyl]phenyl}-1H-1,2,3-triazole-4-carboxamide (183 mg, 0.5 mmol) obtained in Example 1207, trimethylsilyl azide (58 mg, 0.5 mmol) and di-N-butyltin oxide (12.5 mg, 0.05 mmol) in toluene (5 ml) was boiled under reflux for 24 hr and the solvent was evaporated. Methanol (5 ml) was added to the residue, and the solvent was evaporated again. Ethyl acetate (10 ml) and 6% aqueous sodium bicarbonate solution (10 ml) were added to the residue and, after partitioning, the aqueous layer was adjusted to pH 4-5 with 1N hydrochloric acid, and the precipitated crystals were collected by filtration and dried to give the title compound as a colorless powder (55 mg, 27%).

NMR (300 MHz, CDCl$_3$) δ: 0.71-0.76 (2H, m), 0.94-1.00 (2H, m), 1.31 (3H, t, J=7.2 Hz), 2.05-2.14 (2H, m), 2.96-3.04 (5H, m), 3.51-3.61 (2H, m), 6.52 (1H, brt, J=5.7 Hz), 7.48 (2H, d, J=8.7 Hz), 7.63 (1H, brd, J=3.8 Hz), 7.98 (2H, d, J=8.7 Hz).

Example 1209

5-[(4Z)-4-amino-4-(hydroxyimino)butyl]-N-cyclopropyl-1-{4-[(ethylamino)carbonyl]phenyl}-1H-1,2,3-triazole-4-carboxamide

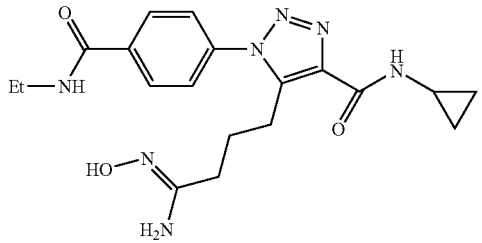

A solution of 5-(3-cyanopropyl)-N-cyclopropyl-1-{4-[(ethylamino)carbonyl]phenyl}-1H-1,2,3-triazole-4-carboxamide (366 mg, 1.0 mmol) obtained in Example 1207, hydroxyammonium chloride (139 mg, 2.0 mmol, 2.0 eq.) and sodium hydrogen carbonate (168 mg, 2.0 mmol, 2.0 eq.) in DMSO (5 ml) was stirred at 90° C. for 5 hr. Saturated brine (10 ml) was added to the reaction mixture, and the mixture was extracted with ethyl acetate (30 ml×3), and dried over anhydrous sodium sulfate. The solvent was evaporated and the residue was purified by silica gel column (hexane/ethyl acetate=1/1 to ethyl acetate/methanol=4/1) to give the title compound as a colorless powder (315 mg, 79%).

NMR (300 MHz, DMSO-d$_6$) δ: 0.64-0.69 (4H, m), 1.16 (3H, t, J=7.2 Hz), 1.61-1.71 (2H, m), 1.86 (2H, t, J=7.2 Hz), 2.86-2.92 (2H, m), 2.97 (2H, t, J=7.2 Hz), 3.29-3.37 (2H, m), 5.29 (2H, s), 7.70 (2H, d, J=8.7 Hz), 8.08 (2H, d, J=8.7 Hz), 8.66 (1H, brd, J=4.9 Hz), 8.67 (1H, s), 8.70 (1H, brt, J=5.7 Hz).

Example 1210

N-cyclopropyl-1-{4-[(ethylamino)carbonyl]phenyl}-5-[3-(5-oxo-4,5-dihydro-1,2,4-oxadiazol-3-yl)propyl]-1H-1,2,3-triazole-4-carboxamide

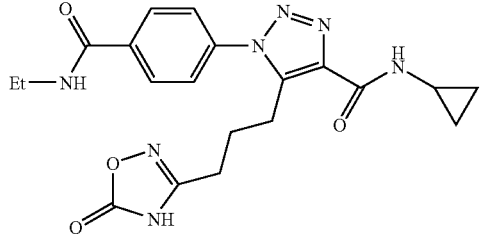

To a solution of 5-[(4Z)-4-amino-4-(hydroxyimino)butyl]-N-cyclopropyl-1-{4-[(ethylamino)carbonyl]phenyl}-1H-1,2,3-triazole-4-carboxamide (240 mg, 0.6 mmol) obtained in Example 1209 and 1,1'-carbonyldiimidazole (97 mg, 0.6 mmol) in THF (5 ml) was added DBU (91 mg, 0.6 mmol) at room temperature and the mixture was stirred at 50° C. for 3 hr and concentrated. The residue was dissolved in water (10 ml), adjusted to pH 4-5 with 1N hydrochloric acid and liberated oil was extracted with ethyl acetate (30 ml×2). The extract was dried over anhydrous sodium sulfate, and the solvent was evaporated. The residue was purified by silica gel column (hexane/ethyl acetate=1/1 to ethyl acetate/methanol=4/1) to give the title compound as a colorless powder (150 mg, 59%).

NMR (300 MHz, DMSO-d$_6$) δ: 0.64-0.69 (4H, m), 1.16 (3H, t, J=7.2 Hz), 1.72-1.82 (2H, m), 2.40 (2H, t, J=7.2 Hz), 2.84-2.93 (1H, m), 3.06 (2H, t, J=7.2 Hz), 3.29-3.40 (2H, m), 7.71 (2H, d, J=8.7 Hz), 8.08 (2H, d, J=8.7 Hz), 8.67-8.70 (2H, m), 12.09 (1H, brs).

Example 1211

N-cyclopropyl-1-{4-[(ethylamino)carbonyl]phenyl}-5-(3-phenylpropoxy)-1H-1,2,3-triazole-4-carboxamide

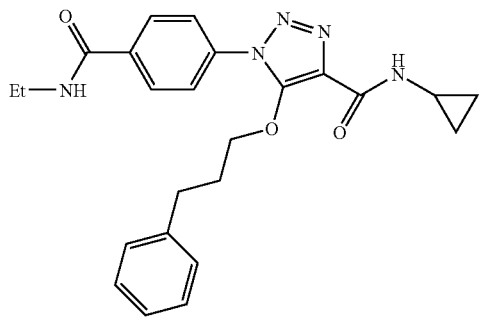

1211a) methyl 1-{4-[(ethylamino)carbonyl]phenyl}-5-hydroxy-1H-1,2,3-triazole-4-carboxylate To a solution of 4-azido-N-ethylbenzamide (3.8 g, 20 mmol) obtained in Example 43a) in methanol (200 ml) was added dimethyl malonate (3.96 g, 30 mmol) at 0-5° C., and then 28% sodium methoxide in methanol solution (5.79 g, 30 mmol) was added. The mixture was stirred at room temperature for 3 days. The reaction mixture was concentrated, and the residue was dissolved in water (50 ml) and adjusted to pH 2-3 with 1N hydrochloric acid. The precipitated crystals were filtered off, and the filtrate was neutralized with 6% aqueous sodium hydrogen carbonate solution. The mixture was concentrated to dryness, methanol (100 ml) was added to the residue, and the insoluble material was filtered off. The filtrate was concentrated to dryness. Ethanol (50 ml) was added to the residue and the precipitated crystals were collected by filtration, and dried to give the title compound as a white powder (2.5 g, 43%).

NMR (300 MHz, DMSO-$d_6$) δ: 1.13 (3H, t, J=7.2 Hz), 3.25-3.34 (2H, m), 3.68 (3H, s), 7.94 (2H, d, J=8.7 Hz), 8.16 (2H, d, J=8.7 Hz), 8.51 (1H, t, J=5.7 Hz).

1211b) methyl 1-{4-[(ethylamino)carbonyl]phenyl}-5-(3-phenylpropoxy)-1H-1,2,3-triazole-4-carboxylate A solution of methyl 1-{4-[(ethylamino)carbonyl]phenyl}-5-hydroxy-1H-1,2,3-triazole-4-carboxylate (580 mg, 2 mmol) obtained in Example 1211a), (3-bromopropyl)benzene (438 mg, 2.2 mmol, 1.1 eq.) and potassium carbonate (332 mg, 2.4 mmol, 1.2 eq.) in DMF (5 ml) was stirred at 90° C. for 15 hr. The reaction mixture was concentrated under reduced pressure, and the residue was dissolved in chloroform (20 ml), washed with water (10 ml×2) and dried over anhydrous sodium sulfate. The solvent was evaporated and the residue was purified by silica gel column (hexane/ethyl acetate=1/1 to ethyl acetate/methanol=4/1) to give the title compound as a colorless powder (150 mg, 18%).

NMR (300 MHz, CDCl$_3$) δ: 1.27 (3H, t, J=7.2 Hz), 2.28-2.38 (2H, m), 2.76 (2H, t, J=7.2 Hz), 3.47-3.56 (2H, m), 3.95 (3H, s), 4.74 (2H, t, J=7.2 Hz), 6.31 (1H, brt, J=4.2 Hz), 7.18-7.32 (5H, m), 7.91 (2H, d, J=9.0 Hz), 8.13 (2H, d, J=9.0 Hz).

1211c) N-cyclopropyl-1-{4-[(ethylamino)carbonyl]phenyl}-5-(3-phenylpropoxy)-1H-1,2,3-triazole-4-carboxamide To a solution of methyl 1-{4-[(ethylamino)carbonyl]phenyl}-5-(3-phenylpropoxy)-1H-1,2,3-triazole-4-carboxylate (106 mg, 0.26 mmol) obtained in Example 1211b) in methanol (3 ml) was added 1N sodium hydroxide (1 ml), the mixture was stirred at 60° C. for 30 min, and the solvent was evaporated. The residue was adjusted to pH 2-3 with 1N hydrochloric acid. The precipitated crystals were collected by filtration, dried and dissolved in DMF (3 ml). Cyclopropylamine (15 mg, 0.26 mmol), HOBt (44 mg, 0.26 mmol) and WSC (55 mg, 0.29 mmol) were successively added, and the reaction mixture was stirred at room temperature overnight. The solvent was evaporated under reduced pressure, and the residue was dissolved in ethyl acetate and washed with saturated aqueous sodium hydrogen carbonate solution. The organic layer was dried over anhydrous sodium sulfate, and the solvent was evaporated under reduced pressure. The residue was purified by silica gel column (ethyl acetate/hexane=1/1 to ethyl acetate) to give the title compound as a white powder (88 mg, 78%).

NMR (300 MHz, CDCl$_3$) δ: 0.62-0.67 (2H, m), 0.83-0.89 (2H, m), 1.28 (3H, t, J=7.2 Hz), 2.33-2.43 (2H, m), 2.78 (2H, t, J=7.2 Hz), 2.83-2.91 (1H, m), 3.48-3.57 (2H, m), 4.85 (2H, t, J=7.2 Hz), 6.17 (1H, brt, J=4.9 Hz), 7.17-7.30 (5H, m), 7.90 (2H, d, J=9.0 Hz), 8.12 (2H, d, J=9.0 Hz) 8.42 (1H, brd, J=3.0 Hz).

Example 1212

N-cyclopropyl-5-ethoxy-1-{4-[(ethylamino)carbonyl]phenyl}-1H-1,2,3-triazole-4-carboxamide

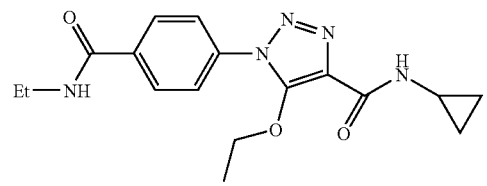

1212a) methyl 5-ethoxy-1-{4-[(ethylamino)carbonyl]phenyl}-1H-1,2,3-triazole-4-carboxylate A solution of methyl 1-{4-[(ethylamino)carbonyl]phenyl}-5-hydroxy-1H-1,2,3-triazole-4-carboxylate (580 mg, 2 mmol) obtained in Example 1211a) and diethyl sulfate (339 mg, 2.2 mmol, 1.1 eq.) in DMF (5 ml) was stirred at 90° C. for 15 hr. The reaction mixture was concentrated to dryness, and chloroform (20 ml) and water (10 ml) were added to the residue. After partitioning, the organic layer was dried over anhydrous sodium sulfate, and the solvent was evaporated under reduced pressure. The residue was purified by silica gel column (hexane/ethyl acetate=1/1 to ethyl acetate/methanol=4/1) to give the title compound as a white powder (210 mg, 33%).

NMR (300 MHz, CDCl$_3$) δ: 1.27 (3H, t, J=7.2 Hz), 1.62 (3H, t, J=7.2 Hz), 3.47-3.56 (2H, m), 3.96 (3H, s), 4.78 (2H, t, J=7.2 Hz), 6.38 (1H, brs), 7.92 (2H, d, J=8.7 Hz), 8.14 (2H, d, J=8.7 Hz).

1212b) N-cyclopropyl-5-ethoxy-1-{4-[(ethylamino)carbonyl]phenyl}-1H-1,2,3-triazole-4-carboxamide To a solution of methyl 5-ethoxy-1-{4-[(ethylamino)carbonyl]phenyl}-1H-1,2,3-triazole-4-carboxylate (159 mg, 0.5 mmol) obtained in Example 1212a) in methanol (5 ml) was added 1N sodium hydroxide (2 ml) and the mixture was stirred at 60° C. for 30 min. The solvent was evaporated, and the residue was adjusted to pH 2-3 with 1N hydrochloric acid. The precipitated crystals were collected by filtration, dried and dissolved in DMF (5 ml). Cyclopropylamine (29 mg, 0.5 mmol), HOBt (84 mg, 0.55 mmol) and WSC (105 mg, 0.55 mmol) were successively added, and the reaction mixture was stirred at room temperature overnight. The solvent was evaporated under reduced pressure, water (5 ml) was added to the residue, and the precipitated crystals were collected by filtration and dried to give the title compound as a white powder (140 mg, 82%).

NMR (300 MHz, CDCl$_3$) δ: 0.62-0.67 (2H, m), 0.82-0.89 (2H, m), 1.28 (3H, t, J=7.2 Hz), 1.63 (3H, t, J=7.2 Hz), 2.85-2.91 (1H, m), 3.48-3.57 (2H, m), 4.88 (2H, t, J=7.2 Hz), 6.20 (1H, brt, J=4.9 Hz), 7.91 (2H, d, J=9.0 Hz), 8.14 (2H, d, J=9.0 Hz), 8.43 (1H, brs).

Example 1213

N-cyclopropyl-5-[(2,2-difluoroethoxy)methyl]-1-{4-[(ethylamino)carbonyl]phenyl}-1H-1,2,3-triazole-4-carboxamide

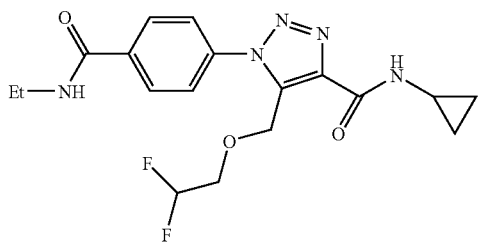

(4-[(Cyclopropylamino)carbonyl]-1-{4-[(ethylamino)carbonyl]phenyl}-1H-1,2,3-triazol-5-yl)methyl methanesulfonate (204 mg, 0.5 mmol) obtained in Example 126a), potassium carbonate (69 mg, 0.5 mmol, 1.0 eq.) and 2,2-difluoroethanol (0.5 ml) were suspended in acetonitrile (3 ml), and the suspension was stirred at room temperature for 12 hr. The reaction mixture was diluted with ethyl acetate (30 ml), washed with saturated aqueous sodium hydrogen carbonate solution and saturated brine, dried over anhydrous sodium sulfate, and concentrated. Diethyl ether was added and the precipitate was collected by filtration, washed with diethyl ether and dried to give the title compound as a white powder (160 mg, 83%).

NMR (300 MHz, CDCl$_3$) δ: 0.67-0.73 (2H, m), 0.88-0.94 (2H, m), 1.29 (3H, t, J=7.2 Hz), 2.88-2.96 (1H, m), 3.50-3.59 (2H, m), 3.89 (2H, td, J=14.3, 3.8 Hz), 5.00 (2H, s), 5.88 (1H, tt, J=55.0, 3.8 Hz), 6.23 (1H, brt, J=4.9 Hz), 7.42 (1H, brd, J=3.0 Hz), 7.79 (2H, d, J=8.3 Hz), 7.98 (2H, d, J=8.3 Hz).

Example 1214

N-cyclopropyl-5-[3-(2,2-difluoroethoxy)propyl]-1-{4-[(ethylamino)carbonyl]phenyl}-1H-1,2,3-triazole-4-carboxamide

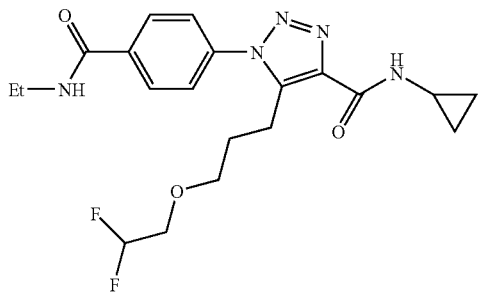

(4-[(Cyclopropylamino)carbonyl]-1-{4-[(ethylamino)carbonyl]phenyl}-1H-1,2,3-triazol-5-yl)propyl methanesulfonate (218 mg, 0.5 mmol) obtained in Example 1201a), potassium carbonate (69 mg, 0.5 mmol, 1.0 eq.) and 2,2-difluoroethanol (0.5 ml) were suspended in acetonitrile (3 ml) and the mixture was stirred at 80° C. for 8 hr. The reaction mixture was concentrated, and chloroform (10 ml) and water (10 ml) were added to the residue. After partitioning, the organic layer was dried over anhydrous sodium sulfate, and the solvent was evaporated under reduced pressure. The residue was purified by silica gel column (hexane/ethyl acetate=1/1 to ethyl acetate) to give the title compound as a white powder (50 mg, 24%).

NMR (300 MHz, CDCl$_3$) δ: 0.65-0.70 (2H, m), 0.85-0.92 (2H, m), 1.29 (3H, t, J=7.2 Hz), 1.86-1.95 (2H, m), 2.85-2.94 (1H, m), 3.15 (2H, t, J=6.0 Hz), 3.45-3.59 (6H, m), 5.72 (1H, tt, J=55.4, 4.1 Hz), 6.23 (1H, brt, J=4.9 Hz), 7.35 (1H, brd, J=2.6 Hz), 7.54 (2H, d, J=8.3 Hz), 7.97 (2H, d, J=8.3 Hz).

Example 1215

N-cyclopropyl-5-[(1E)-prop-1-en-1-yl]-1-(4-{[(2,2,2-trifluoroethyl)amino]carbonyl}phenyl)-1H-1,2,3-triazole-4-carboxamide 1215a) 5-[(1E)-prop-1-en-1-yl]-1-(4-{[(2,2,2-trifluoroethyl)amino]carbonyl}phenyl)-1H-1,2,3-triazole-4-carboxylic acid To a solution of 4-azido-N-(2,2,2-trifluoroethyl)benzamide (2.44 g) obtained in Example 46a) in ethanol (40 ml) were added ethyl 3-oxohex-5-enoate (Tetrahedron Lett., 41, 8803-8806 (2000)) (2.10 g) synthesized separately and 20% sodium ethoxide in ethanol solution (4.6 ml), and the mixture was stirred at room temperature overnight. The solvent was evaporated under reduced pressure, and the residue was diluted with water and washed with ether. The aqueous layer was acidified with 1N hydrochloric acid, and the mixture was extracted with ethyl acetate. The extract was dried over anhydrous magnesium sulfate and the solvent was evaporated under reduced pressure to give the title compound as a yellow amorphous substance (1.96 g, 55%).

NMR (DMSO-d$_6$) δ: 1.78 (3H, dd, J=6.6, 1.7), 4.15 (2H, qd, J=9.7, 6.4), 6.27 (1H, brs), 6.55 (1H, dd, J=16.6, 1.5), 7.73 (2H, d, J=8.7), 8.12 (2H, d, J=8.7), 9.34 (1H, t, J=6.2), 13.19 (1H, brs).

1215b) N-cyclopropyl-5-[(1E)-prop-1-en-1-yl]-1-(4-{[(2,2,2-trifluoroethyl)amino]carbonyl}phenyl)-1H-1,2,3-triazole-4-carboxamide To a solution of 5-[(1E)-prop-1-en-1-yl]-1-(4-{[(2,2,2-trifluoroethyl)amino]carbonyl}phenyl)-1H-1,2,3-triazole-4-carboxylic acid (1.96 g) obtained in Example 1215a) in DMF (22 ml) were successively added cyclopropylamine (0.46 ml), triethylamine (0.92 ml), HOBt (1.01 g) and WSC (1.27 g), and the reaction mixture was stirred at room temperature for 2.5 hr. Water and ethyl acetate were added to the reaction mixture and the organic layer was separated. The organic layer was dried over anhydrous sodium sulfate, and the solvent was evaporated under reduced pressure. The residue was purified by silica gel column (ethyl acetate/hexane=1/1 to ethyl acetate) and recrystallized from ethyl acetate-diisopropyl ether to give the title compound as a white powder (1.13 g, 52%).

NMR (CDCl$_3$) δ: 0.65-0.71 (2H, m), 0.85-0.92 (2H, m), 1.85 (3H, dd, J=6.6, 1.8), 2.86-2.93 (1H, m), 4.18 (2H, qd, J=9.0, 2.4), 6.49 (1H, dq, J=16.2, 1.5), 6.63 (1H, t, J=6.6), 6.80 (1H, dq, J=16.2, 6.6), 7.43 (1H, brs), 7.58 (2H, d, J=8.7), 8.00 (2H, d, J=8.7).

Reference Example 1

1-[4-(acetylamino)phenyl]-N-cyclopropyl-5-propyl-1H-1,2,3-triazole-4-carboxamide

1a) N-(4-azidophenyl)acetamide

4-Aminoacetoanilide (15.00 g) was dissolved in 1N hydrochloric acid (400 ml), sodium nitrite (6.89 g) was added under ice-cooling, ice bath was removed and the mixture was stirred for 30 min. The reaction solution was cooled to 5° C., sodium azide (6.49 g) was slowly added while vigorously stirring the mixture, and the mixture was stirred for 10 min. The resulting precipitate was collected by filtration and washed with water. The obtained crude product was recrystallized from methanol-water to give the title compound (13.63 g, 78%).

NMR (CDCl$_3$) δ: 2.16 (3H, s), 6.97 (2H, d, J=8.9), 7.21 (1H, br), 7.48 (2H, d, J=8.9).

1b) N-cyclopropyl-2-hexynamide

A solution of 2-hexynoic acid (5.03 g) and cyclopropylamine (2.70 g) in dichloromethane (75 ml), and a solution of 1-(3-dimethylaminopropyl)-3-ethylcarbodiimide hydrochloride (9.00 g) and 1-hydroxybenzotriazole hydrate (7.19 g) in dichloromethane (75 ml) were mixed, and the mixture was stirred at room temperature for 18 hr. 1N Hydrochloric acid (200 ml) was added, and the mixture was extracted with dichloromethane. The organic layer was washed with 5% aqueous sodium hydrogen carbonate solution, water and saturated brine, dried over anhydrous magnesium sulfate, and purified by silica gel column to give the title compound (6.04 g, 89%).

NMR (CDCl$_3$) δ: 0.55-0.85 (4H, m), 1.01 (3H, t, J=7.3), 1.55-1.66 (2H, m), 2.27 (2H, t, J=7.1), 2.71-2.77 (1H, m), 5.95 (1H, br).

1c) 1-[4-(acetylamino)phenyl]-N-cyclopropyl-5-propyl-1H-1,2,3-triazole-4-carboxamide N-(4-Azidophenyl)acetamide (3.16 g) obtained in Reference Example 1a) and N-cyclopropyl-2-hexynamide (3.04 g) obtained in Reference Example 1b) were dissolved in toluene (60 ml) and the mixture was stirred at 80° C. for 43 hr. After cooling to room temperature, the resulting precipitate was collected by filtration, and washed with toluene. The obtained solid was recrystallized from methanol-diisopropyl ether and dried in vacuo to give a regioisomer 1-[4-(acetylamino)phenyl]-N-cyclopropyl-4-propyl-1H-1,2,3-triazole-5-carboxamide (0.98 g, 17%).

NMR (CDCl$_3$) δ: 0.36-0.41 (2H, m), 0.64-0.70 (2H, m), 0.91 (3H, t, J=7.4), 1.60-1.68 (2H, m), 2.09 (3H, s), 2.66 (2H, t, J=7.4), 2.70-2.78 (1H, m), 7.42 (2H, d, J=8.9), 7.74 (2H, d, J=8.9), 8.77 (1H, d, J=4.0), 10.22 (1H, br).

Separately, the filtrate was purified by silica gel column (elution solvent, ethyl acetate-hexane=3:7-10:0) to give the title compound (1.72 g, 29%).

NMR (CDCl$_3$) δ: 0.62-0.70 (4H, m), 0.73 (3H, t, J=7.4), 1.34-1.47 (2H, m), 2.10 (3H, s), 2.82-2.88 (1H, m), 2.91 (2H, t, J=7.4), 7.49 (2H, d, J=8.9), 7.81 (2H, d, J=8.9), 8.58 (1H, d, J=4.7), 10.28 (1H, br).

Elemental analysis for $C_{17}H_{21}N_5O_2$
Calcd. (%): C, 62.37; H, 6.47; N, 21.39.
Found (%): C, 62.41; H, 6.28; N, 21.13

Compounds 2 and 3 described in Experimental Example 6 below can be produced in the same manner as in Reference Example 1.

Preparation Examples

The pharmaceutical agent and thrombin receptor antagonist of the present invention can be produced, for example, according to the following formulations. In the following formulations, as the ingredients (additives) other than the active ingredient, the products recited in the Japanese Pharmacopoeia, the Japanese Pharmacopoeia Japanese Pharmaceutical Codex or Japanese Pharmaceutical Excipients and the like can be used.

1. Capsule

| | |
|---|---|
| (1) compound obtained in Example 27 | 70 mg |
| (2) lactose | 210 mg |
| (3) microcrystalline cellulose | 27 mg |
| (4) magnesium stearate | 3 mg |
| 1 capsule | 310 mg |

(1), (2), (3) and 1/2 of (4) are blended and granulated. The rest of (4) is added and the whole is encapsulated in a gelatin capsule.

2. Tablet

| | |
|---|---|
| (1) compound obtained in Example 27 | 70 mg |
| (2) lactose | 174 mg |
| (3) cornstarch | 54 mg |
| (4) microcrystalline cellulose | 10.5 mg |
| (5) magnesium stearate | 1.5 mg |
| 1 tablet | 310 mg |

(1), (2), (3), 2/3 of (4) and 1/2 of (5) are blended and granulated. The rest of (4) and (5) is added to the granules and the mixture is compression molded to give tablet.

3. Injection

The compound obtained in Example 27 (50 mg) is dissolved in the Japanese Pharmacopoeia distilled water for injection (50 ml), and the Japanese Pharmacopoeia distilled water for injection is added to 100 ml. The solution is filtered under sterilization conditions, the solution (1 ml) is taken, filled in a vial for injection under sterilization conditions and freeze-dried, and then the vial is sealed.

4. Capsule

| | |
|---|---|
| (1) compound obtained in Example 43 | 70 mg |
| (2) lactose | 210 mg |
| (3) microcrystalline cellulose | 27 mg |
| (4) magnesium stearate | 3 mg |
| 1 capsule | 310 mg |

(1), (2), (3) and 1/2 of (4) are blended and granulated. The rest of (4) is added and the whole is encapsulated in a gelatin capsule.

5. Tablet

| | |
|---|---|
| (1) compound obtained in Example 43 | 70 mg |
| (2) lactose | 174 mg |

-continued

| | |
|---|---|
| (3) cornstarch | 54 mg |
| (4) microcrystalline cellulose | 10.5 mg |
| (5) magnesium stearate | 1.5 mg |
| 1 tablet | 310 mg |

(1), (2), (3), 2/3 of (4) and 1/2 of (5) are blended and granulated. The rest of (4) and (5) is added to the granules and the mixture is compression molded to give tablet.

6. Injection

The compound obtained in Example 43 (50 mg) is dissolved in the Japanese Pharmacopoeia distilled water for injection (50 ml), and the Japanese Pharmacopoeia distilled water for injection is added to 100 ml. The solution is filtered under sterilization conditions, the solution (1 ml) is taken, filled in a vial for injection under sterilization conditions and freeze-dried, and then the vial is sealed.

7. Capsule

| | |
|---|---|
| (1) compound obtained in Reference Example 1 | 70 mg |
| (2) lactose | 210 mg |
| (3) microcrystalline cellulose | 27 mg |
| (4) magnesium stearate | 3 mg |
| 1 capsule | 310 mg |

(1), (2), (3) and 1/2 of (4) are blended and granulated. The rest of (4) is added and the whole is encapsulated in a gelatin capsule.

8. Tablet

| | |
|---|---|
| (1) compound obtained in Reference Example 1 | 70 mg |
| (2) lactose | 174 mg |
| (3) cornstarch | 54 mg |
| (4) microcrystalline cellulose | 10.5 mg |
| (5) magnesium stearate | 1.5 mg |
| 1 tablet | 310 mg |

(1), (2), (3), 2/3 of (4) and 1/2 of (5) are blended and granulated. The rest of (4) and (5) is added to the granules and the mixture is compression molded to give tablet.

9. Injection

The compound obtained in Reference Example 1 (50 mg) is dissolved in the Japanese Pharmacopoeia distilled water for injection (50 ml), and the Japanese Pharmacopoeia distilled water for injection is added to 100 ml. The solution is filtered under sterilization conditions, the solution (1 ml) is taken, filled in a vial for injection under sterilization conditions and freeze-dried, and then the vial is sealed.

The genetic manipulation methods described in the following Experimental Examples followed the method described in the book (Maniatis et al., Molecular Cloning, Cold Spring Harbor Laboratory, 1989) or the method described in the protocol attached to the reagent.

Experimental Example 1

Cloning of cDNA Encoding Human PAR-1 and Preparation of Expression Vector for Animal Cell A method of cloning cDNA encoding human PAR-1 is shown below.

Human PAR-1 was cloned by PCR method using human aorta cDNA (Quick-clone cDNA) as a template and the primer set

```
PAR1-U:
                               (SEQ ID NO: 1)
5'-GCAGGGATCCGCAGAGCCCGGGACAATGGG-3'

PAR1-L:
                               (SEQ ID NO: 2)
5'-TAACTCTAGAGCAGTCCCTTTTCCTAAGTTA-3'
``` prepared in reference to the sequence of PAR-1 gene reported by Thien-Khai et al. (Cell, Vol. 64, 1057-1068 (1991)).

The PCR reaction followed the protocol attached to LA Taq DNA polymerase (Takara Shuzo Co., Ltd.). To the amplified DNA fragment were added BamHI site at the 5' terminal and XbaI site at the 3' terminal. The obtained PCR product was subjected to agarose gel electrophoresis and, after recovering a 1.3 kb DNA fragment containing PAR-1 gene sequence, cleaved with BamHI and XbaI. The DNA fragment was ligated into pCMVflag1 (Sigma Ltd.) previously cleaved with BamHI and XbaI to give plasmid pCMVflag1/PAR1. The nucleotide sequence of the insert fragment was confirmed to verify that it was identical with the object sequence.

Then, pCMVflag1/PAR1 was cleaved with SacI and, after blunting, cleaved with XbaI to give a flag1/PAR1 fragment. The expression vector PMSαneo (prepared by Takeda Pharmaceutical Company Limited) was cleaved with EcoRI and, after blunting, cleaved with XbaI to give a DNA fragment insertion site. flag1/PAR1 fragment was ligated into the site to give an expression vector PMSαneo/flag1/PAR1 for animal cell.

Experimental Example 2

Preparation of Human PAR-1-Expressing CHO Cells

CHO-K1 cells grown in Ham's F-12 medium (Invitrogen) containing 10% fetal calf serum, 10 mM HEPES and 50 µg/mL gentamicin (Invitrogen) in a tissue culture flask (Coaster) were detached by a treatment with 0.5 g/L trypsin-0.2 g/L EDTA (Invitrogen), and the cells were washed with PBS, centrifuged (1000 rpm, 5 min) and suspended in PBS. Using a Gene Pulser (Bio-Rad), transfection by electroporation was performed (conditions: expression vector PMSα-neo obtained in Experimental Example 1/flag1/PAR1 10 µg, $8 \times 10^6$ cells, electrode distance 0.4 cm, voltage 0.25 kV, capacitance 960 µF). Then, the cells were transferred to Ham's F-12 medium containing 10% fetal calf serum and cultured for 24 hr.

Then, the cells were detached again, centrifuged, suspended in Ham's F-12 medium containing 10% fetal calf serum supplemented with Geneticin (Invitrogen) to 500 µg/mL, diluted to $10^4$ cells, plated on a 96 well plate (Coaster 3997 type), and cultivated in a carbon dioxide gas incubator at 37° C. to give a Geneticin-resistant transformant.

Finally, the obtained transformant was plated on a 96 well plate and cultivated in a carbon dioxide gas incubator at 37° C. for 48 hr. Using an anti-flag antibody, ELISA was performed on this plate and transformant flag/trn/CHO-K1 that showed a positive reaction was selected.

Experimental Example 3

Confirmation of Human PAR-1-Expressing Cells by Intracellular Calcium Concentration Variation Assay The transformant flag/trn/CHO-K1 obtained in Experimental Example 2 was plated at $2 \times 10^4$ cells/well on a 96 well white plate (Coaster 3917 type) and cultured for 48 hr. The cells were washed with saline. BSS buffer (50 μL, 130 mM NaCl, 5.4 mM KCl, 2 mM $CaCl_2$, 1 mM $MgCl_2$, 5.5 mM D-glucose, 10 mM HEPES, pH 7.4) containing 5 μM of FuraPE3AM (manufactured by Texas Fluorescence Laboratories) was added to the cells and the mixture was reacted at 37° C. for 1 hr. The cells were washed twice with BSS buffer. The BSS buffer (180 μL) was added, 100 μM human PAR1 agonist peptide SFLLRN—$NH_2$ (20 μL) was added, and the intracellular calcium concentration was measured by fluorometry image-plate reader (FDSS 2000, manufactured by Hamamatsu Photonics K.K.). An increase in the intracellular calcium concentration of transformant flag/trn/CHO-K1 due to the stimulation with human PAR1 agonist peptide SFLLRN—$NH_2$ was confirmed. The transformant flag/trn/CHO-$K^1$ was used as human PAR-1-expressing cells for screening.

Experimental Example 4

Evaluation of PAR-1 Antagonistic Action of Compound by Intracellular Calcium Concentration Variation Assay Human PAR-1-expressing cells was plated at $3 \times 10^4$ cells/well on a 96 well clear bottom plate (Corning 3904 type) and cultured for 16-24 hr. The medium was removed from the wells of the plate, measurement buffer (50 μL, 115 mM NaCl, 5.4 mM KCl, 1.8 mM $CaCl_2$, 0.8 mM $MgCl_2$, 13.8 mM D-glucose, 0.1% BSA, 20 mM HEPES, pH 7.4) containing 2.5 μg/mL of Fluo-3AM (manufactured by Dojindo Laboratories), 0.08% Pluronic F-127 and 2.5 mM Probenecid was added to the cells and the mixture was reacted at 37° C. for 1 hr. The cells were washed twice with the measurement buffer. After addition of the measurement buffer (100 μL), a measurement buffer (50 μL) containing a test compound was added, and the mixture was stood still for 10 min. The plate was moved to a fluorometry image-plate reader (FLIPR-1, manufactured by Molecular Devices). The agonist peptide SFLLRN—$NH_2$ was dissolved in measurement buffer to the final concentration of 0.3 nM and 50 μL thereof was added using a FLIPR injector. The intracellular calcium concentration was measured by FLIPR. The concentration ($IC_{50}$) necessary for inhibiting an increase in the intracellular calcium concentration by 50% was calculated. The results are shown in Table 3.

TABLE 3

| | Example No. | | | | | | | |
|---|---|---|---|---|---|---|---|---|
| | 3 | 4 | 16 | 19 | 25 | 27 | 31 | 41 |
| $IC_{50}$ (μM) | 0.52 | 0.55 | 0.25 | 0.75 | 0.094 | 0.37 | 3.7 | 0.63 |
| | Example No. | | | | | | | |
| | 43 | 46 | 49 | 52 | 53 | 54 | 55 | 72 |
| $IC_{50}$ (μM) | 1.5 | 0.95 | 3.5 | 1.4 | 3.4 | 1.6 | 3.6 | 3.4 |
| | Example No. | | | | | | | |
| | 82 | 83 | 84 | 85 | 86 | 87 | 88 | 89 |
| $IC_{50}$ (μM) | 1.9 | 3.6 | 1.3 | 1.9 | 0.62 | 0.28 | 0.72 | 0.67 |
| | Example No. | | | | | | | |
| | 90 | 91 | 93 | 94 | 96 | 97 | 98 | 99 |
| $IC_{50}$ (μM) | 2.4 | 2.2 | 1.2 | 1.7 | 1.2 | 1.6 | 0.5 | 1.3 |
| | Example No. | | | | | | | |
| | 100 | 101 | 102 | 103 | 105 | 106 | 108 | 109 |
| $IC_{50}$ (μM) | 0.7 | 0.82 | 1.8 | 0.78 | 2.7 | 0.4 | 0.62 | 3.4 |
| | Example No. | | | | | | | |
| | 111 | 113 | 116 | 118 | 122 | 123 | 129 | 130 |
| $IC_{50}$ (μM) | 1.6 | 3.1 | 0.75 | 1.4 | 3.3 | 0.98 | 0.74 | 0.48 |
| | Example No. | | | | | | | |
| | 133 | 399 | 414 | 522 | | | | |
| $IC_{50}$ (μM) | 0.27 | 1.4 | 0.19 | 0.33 | | | | |

From the results shown in Table 3, it is clear that the compound of the present invention has a PAR-1 antagonistic action.

The biochemical activity and pharmacological action (platelet aggregation suppressive action) of a compound contained in the thrombin receptor antagonist of the present invention was evaluated by the following method.

Experimental Example 5

GTPγS Binding Assay

The preparation method of the membrane fraction used for the GTPγS binding assay is shown below.

Human PAR-1-expressing cells were inoculated to an F500 flask at $1.8 \times 10^5$ cells/flask, and the cells were cultured for 2 days. The cells were detached with saline containing 0.02% EDTA. The cells were centrifuged (2000 rpm, 10 min), cell pellets were re-suspended in 12 ml of homogenate buffer (10 mM $NaHCO_3$, 1 mM EDTA, protease inhibitor cocktail, pH 7.4), and homogenized by Polytron™. The residual cells were removed by centrifugation (2000 rpm, 10 min), and the supernatant was ultracentrifuged (Beckman Instruments 70 Ti type rotor, 30000 rpm, 1 hr) to give a membrane fraction of human PAR-1-expressing cells in a sediment, which was preserved at −80° C. and dissolved before use for an assay.

The measurement method of the GTPγS binding activity is shown below.

To an assay buffer (150 μL, 100 mM NaCl, 1 mM $MgCl_2$, 167 g/mL DTT, 5 μM guanosine 5'-diphosphate, 0.4 nM

[35S]-guanosine 5'-(γ-thio)triphosphate ([35S]-GTPγS), 20 mM HEPES, pH 7.4) containing human PAR-1-expressing cell membrane fraction (10-20 μg) were added 25 μL of a test compound solution, and 25 μL of 200-800 nM agonist peptide SFLLRN—NH$_2$ and, after blending, and the mixture was reacted at room temperature for 1 hr. Then, the reaction mixture was filtered through a GF/C filter, washed 4 times with 300 μL of saline, and the radioactivity of the filter was measured by a TopCount scintillation counter. The test compound inhibited binding of [35S]-GTPγS to a membrane fraction in a concentration-dependent manner.

The concentration (IC$_{50}$ value) of the test compound necessary for inhibiting the GTPγS binding activity by 50% was calculated using PRISM3.0 (PraphPad software).

Experimental Example 6

Platelet Aggregation Test (Platelet Rich Plasma)

Using a syringe filled in advance with 3.8% sodium citrate solution (Chitral: Yamanouchi Pharmaceutical Co., Ltd.), its 9-fold volume of venous blood was taken from healthy volunteers. After blood sampling, the blood was centrifuged at room temperature, 2700 G for 5 sec and 15 min to give platelet rich plasma (PRP) and platelet poor plasma (PPP), respectively. PRP was applied to an automated blood cell counter (Sysmex) to adjust the platelet count to 300,000/μL, and fibrin polymerization inhibitory peptide was added thereto to a final concentration of 4 mM. The platelet aggregation rate was measured using an aggregometer (Kowa). To be specific, 200 μL of PRP was placed in a cuvette with a microstirrer, preheated at 37° C. for 2 min, and a test compound solution (20 μL) was added. The mixture was further preheated at 37° C. for 2 min with stirring (1000 rpm), thrombin (20 μL) was added, and changes in the transmittance caused by platelet aggregation were recorded over time. Thrombin was used at a minimum concentration causing maximum aggregation, and the aggregation suppressive rate (%) was calculated from the ratio of the maximum aggregation rate with addition of test compound to the maximum aggregation rate of control group.

The test compound was dissolved in dimethyl sulfoxide and diluted with saline before use.

TABLE 4

Compound 1

Compound 2

Compound 3

|  | Compound 1 | Compound 2 | Compound 3 |
|---|---|---|---|
| GTPγS binding activity (IC$_{50}$ value: μM) | 1.9 | 2.1 | 1.9 |
| aggregation suppressive rate (%) | 66 | 39 | — |

From the results shown in Table 4, it is clear that the thrombin receptor antagonist of the present invention is useful, for example, as a platelet aggregation inhibitor and the like.

This application is based on a patent application No. 2005-110391 filed in Japan, the contents of which are incorporated in full herein by this reference.

The invention claimed is:
1. A compound represented by the formula (I')

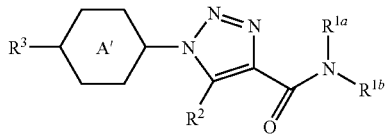

wherein $R^{1a}$ and $R^{1b}$ are each independently a hydrogen atom, an optionally substituted hydrocarbon group, an optionally substituted heterocyclic group, or an optionally substituted alkoxy,
  $R^2$ is a hydrogen atom, an optionally substituted hydrocarbon group, an optionally substituted heterocyclic group, or an optionally substituted alkoxy,
  $R^3$ is a group represented by the formula —NHCOR$^4$, —NHSO$_2$R$^5$, —NHCON(R$^{6a}$)(R$^{6b}$), —NHCOOR$^7$ or —CONHR$^8$
  wherein $R^4$ and $R^7$ are each independently a hydrogen atom, an optionally substituted hydrocarbon group, or an optionally substituted heterocyclic group,
  $R^5$, $R^{6a}$, $R^{6b}$ and $R^8$ are each independently a hydrogen atom, an optionally substituted hydrocarbon group, an optionally substituted heterocyclic group, or an optionally substituted alkoxy,
  $R^{6a}$ and $R^{6b}$ are optionally bonded to each other to form an optionally substituted nitrogen-containing non-aromatic heterocycle,
  ring A' is a benzene ring optionally further having substituent(s) or a 6-membered nitrogen-containing aromatic heterocycle optionally further having substituent(s),
  $R^2$ and the substituent on ring A' other than $R^3$ are optionally bonded to each other to form an optionally substituted ring,
  $R^8$ and the substituent on ring A' are optionally bonded to each other to form an optionally substituted ring,
  $R^{1a}$ and $R^2$ are optionally bonded to each other to form an optionally substituted ring,
  $R^{1a}$ and $R^{1b}$ are optionally bonded to each other to form an optionally substituted nitrogen-containing non-aromatic heterocycle,
  provided that when ring A' is a benzene ring optionally further having substituent(s), $R^4$ is not methyl,
  or a salt thereof.

2. The compound of claim 1, wherein $R^{1a}$ is a hydrogen atom.

3. The compound of claim 2, wherein $R^{1b}$ is a hydrogen atom, an optionally substituted alkyl, or an optionally substituted cycloalkyl.

4. The compound of claim 1, wherein $R^2$ is an optionally substituted chain hydrocarbon group.

5. The compound of claim 4, wherein the chain hydrocarbon group is alkyl or alkenyl.

6. The compound of claim 1, wherein $R^3$ is a group represented by the formula —CONHR$^8$ wherein $R^8$ is as defined in claim 1.

7. The compound of claim 6, wherein $R^8$ is an optionally substituted chain hydrocarbon group.

8. The compound of claim 1, wherein ring A' is a benzene ring optionally further having substituent(s) or a pyridine ring optionally further having substituent(s).

9. The compound of claim 1, which is a compound selected from the group consisting of N-cyclopropyl-1-{4-[(ethylamino)carbonyl]phenyl}-5-propyl-1H-1,2,3-triazole-4-carboxamide,
  N-cyclopropyl-5-propyl-1-(4-{[(2,2,2-trifluoro ethyl)amino]carbonyl} phenyl)-1H-1,2,3-triazole-4-carboxamide,
  N-cyclopropyl-1-{4-[(ethylamino)carbonyl]phenyl}-5-(4-fluorobutyl)-1H-1,2,3-triazole-4-carboxamide,
  N-cyclopropyl-5-[(1E)-prop-1-en-1-yl]-1-(4-{[(2,2,2-trifluoroethyl)amino]carbonyl}phenyl)-1H-1,2,3-triazole-4-carboxamide,
  N-cyclopropyl-1-{4-[(ethylamino)carbonyl]phenyl}-5-[(3-fluorophenoxy)methyl]-1H-1,2,3-triazole-4-carboxamide, and
  N-cyclopropyl-5-propyl-1-{4-[(3,3,3-trifluoropropanoyl)amino]phenyl}-1H-1,2,3-triazole-4-carboxamide,
  or a salt thereof.

10. A pharmaceutical composition comprising the compound of claim 1, and a pharmacologically acceptable carrier.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial
<220> FEATURE:
<223> OTHER INFORMATION: primer for cloning human PAR-1 gene

<400> SEQUENCE: 1
gcagggatcc gcagagcccg ggacaatggg                                        30

<210> SEQ ID NO 2
<211> LENGTH: 31
<212> TYPE: DNA
<213> ORGANISM: Artificial
<220> FEATURE:
<223> OTHER INFORMATION: primer for cloning human PAR-1 gene

<400> SEQUENCE: 2
taactctaga gcagtccctt ttcctaagtt a                                      31